United States Patent
Eickhoff et al.

(10) Patent No.: US 9,567,345 B2
(45) Date of Patent: Feb. 14, 2017

(54) PHARMACEUTICALLY ACTIVE PYRAZOLO-TRIAZINE DERIVATIVES

(71) Applicant: LEAD DISCOVERY CENTER GMBH, Dortmund (DE)

(72) Inventors: Jan Eickhoff, Herdecke (DE); Gunther Zischinsky, Datteln (DE); Uwe Koch, Dortmund (DE)

(73) Assignee: Lead Discovery Center GmbH, Dortmund (DE)

( * ) Notice: Subject to any disclaimer, the term of this patent is extended or adjusted under 35 U.S.C. 154(b) by 0 days.

(21) Appl. No.: 14/381,146

(22) PCT Filed: Mar. 1, 2013

(86) PCT No.: PCT/EP2013/054224
§ 371 (c)(1),
(2) Date: Aug. 26, 2014

(87) PCT Pub. No.: WO2013/128028
PCT Pub. Date: Sep. 6, 2013

(65) Prior Publication Data
US 2015/0018329 A1   Jan. 15, 2015

(30) Foreign Application Priority Data
Mar. 1, 2012   (EP) ..................... 12157751

(51) Int. Cl.
| | | |
|---|---|---|
| *C07D 401/06* | (2006.01) | |
| *C07D 401/12* | (2006.01) | |
| *C07D 401/14* | (2006.01) | |
| *C07D 403/06* | (2006.01) | |
| *C07D 403/12* | (2006.01) | |
| *C07D 403/14* | (2006.01) | |
| *C07D 405/06* | (2006.01) | |
| *C07D 405/12* | (2006.01) | |
| *C07D 405/14* | (2006.01) | |
| *A61K 31/4162* | (2006.01) | |
| *A61K 31/5377* | (2006.01) | |
| *C07D 491/107* | (2006.01) | |
| *C07D 487/04* | (2006.01) | |
| *C07D 471/10* | (2006.01) | |

(52) U.S. Cl.
CPC ......... *C07D 491/107* (2013.01); *C07D 471/10* (2013.01); *C07D 487/04* (2013.01)

(58) Field of Classification Search
CPC ... C07D 205/04; C07D 403/12; C07D 401/12; C07D 409/12; C07D 207/12
USPC .......................................... 544/113; 540/544
See application file for complete search history.

(56) References Cited

U.S. PATENT DOCUMENTS
7,119,200 B2   10/2006   Guzi et al.

FOREIGN PATENT DOCUMENTS
| | | |
|---|---|---|
| CN | 1922185 A | 2/2007 |
| WO | 2005/077954 A2 | 8/2005 |
| WO | 2005/082908 A1 | 9/2005 |
| WO | 2010/103486 A1 | 9/2010 |

OTHER PUBLICATIONS

Popowycz, et al. "Pyrazolo[1,5-a]-1,3,5-triazine as a Purine Bioisostere: Access to Potent Cyclin-Dependent Kinase Inhibitor (R)-Roscovitine Analogue", Journal of Medicinal Chemistry, American Chemical Society, 52 (3), Jan. 2009, pp. 655-663.*
Chinese Office Action dated Sep. 1, 2015, in connection with corresponding CN Application No. 201380011917.5 (21 pgs., including English abstract).
Florence Popowycz, et al., "Synthesis and antiproliferative evaluation of pyrazolo[1,5-a]-1,3,5-triazine myoseverin derivatives", in Bioorganic & Medicinal Chemistry, 17, 2009, pp. 3471-3478 (8 pgs.).
Florence Popowycz, et al., "Pyrazolo[1,5-a]-1,3,5-triazine as a Purine Bioisostere: Access to Potent Cyclin-Dependent Kinase Inhibitor (R)-Roscovitine Analogue", in Journal of Medicinal Chemistry, 52, 2009, pp. 655-663 (9 pgs.).

* cited by examiner

*Primary Examiner* — Alicia L Otton
*Assistant Examiner* — Sagar Patel
(74) *Attorney, Agent, or Firm* — Maier & Maier, PLLC

(57) ABSTRACT

The present invention relates to pyrazolo[1,5-a][1,3,5]triazine derivatives and/or pharmaceutically acceptable salts thereof, the use of these derivatives as pharmaceutically active agents, especially for the prophylaxis and/or treatment of infectious diseases, including opportunistic diseases, immunological diseases, autoimmune diseases, cardiovascular diseases, cell proliferative diseases, inflammation, erectile dysfunction and stroke, and pharmaceutical compositions containing at least one of said pyrazolo[1,5-a][1,3,5]triazine derivatives and/or pharmaceutically acceptable salts thereof. Furthermore, the present invention relates to the use of said pyrazolo[1,5-a][1,3,5]triazine derivatives as inhibitors for a protein kinase.

6 Claims, No Drawings

PHARMACEUTICALLY ACTIVE PYRAZOLO-TRIAZINE DERIVATIVES

The present invention relates to pyrazolo[1,5-a][1,3,5]triazine derivatives and/or pharmaceutically acceptable salts thereof, the use of these derivatives as pharmaceutically active agents, especially for the prophylaxis and/or treatment of cell proliferative diseases, inflammatory and immunological diseases, cardiovascular diseases and infectious diseases. Furthermore, the present invention is directed towards pharmaceutical composition containing at least one of the pyrazolo[1,5-a][1,3,5]triazine derivatives and/or pharmaceutically acceptable salts thereof.

Cyclin-dependent kinase (CDK) family members that trigger passage through the cell cycle are being considered as attractive therapeutic targets, especially for cancer. CDK family members that control other processes such as transcription and RNA processing have caught less attention so far, although experimental evidence for their involvement in different pathological processes is emerging. The CDK-activating kinase, or CAK complex, consists of CDK7, cyclin H, and MAT1. As part of CAK, CDK7 phosphorylates other CDKs, an essential step for their activation. Therefore CDK7 is required for cell cycle progression, which suggests that CDK7 is a target for cancer therapy. As the kinase subunit of TFIIH, CDK7 participates in basal transcription by phosphorylating the carboxy-terminal domain of the largest subunit of RNA polymerase II. As a general regulator of transcription, CDK7 is a therapeutic target for treatment of diseases like inflammation, virus replication such as HIV, EBV, and HCV, cancer and cardiac hypertrophy.

HIV-1 gene expression is regulated by a viral transactivator protein (Tat) which induces transcriptional elongation of HIV-1 long tandem repeat. This induction requires hyperphosphorylation of the C-terminal domain repeats of RNA polymerase II. To achieve said hyperphosphorylation, Tat stimulates CTD kinases associated with general transcription factors of the promoter complex, specifically TFIIH-associated CDK7. (Nekhai et al.; Biochem. J. (2002) 364, 649-657). Also the inventors of U.S. Pat. No. 615,968 describe that Tat binds to CDK7 and that this interaction increases the ability of CAK to phosphorylate CTD. The authors of U.S. Pat. No. 615,968 further disclose that the transcriptional activation by Tat is dependent upon the kinase activity of CDK07. Additionally, Young Kyeung Kim and colleagues conclude that the recruitment and activation of TFIIH represents a rate-limiting step for the emergence of HIV from latency (Young Kyeung Kim, EMBO I (2006) 25, 3596-3604).

Levels of CDK7 and CDK9, as well as other components of the kinase complexes, MAT-1/cyclin H are upregulated during Human cytomegalovirus infection. In addition, there is an increase in the kinase activities of CDK7 and CDK9 (Tamrakar et al., Journal of Virology, 2005, 79; 15477-15493).

Many antiviral drugs target viral proteins. These have the disadvantage that viruses often develop resistance against these drugs. Antiviral drugs targeting cellular proteins essential for viral process, like CDK7, could bypass this disadvantage. These drugs may further be effective in treating several unrelated viruses and their effects should be additive to traditional antiviral agents. Inhibitors of CDK7, which has its dual function of CDK-activating kinase and transcription regulation is very effective in the treatment of several viruses.

It is object of the present invention to provide compounds and/or pharmaceutically acceptable salts thereof which can be used as pharmaceutically active agents, especially for prophylaxis and or treatment of cell proliferative diseases, inflammatory diseases, immunological diseases, cardiovascular diseases and infectious diseases, as well as compositions comprising at least one of those compounds and/or pharmaceutically acceptable salts thereof as pharmaceutically active ingredients.

This object is solved by the compounds and/or their pharmaceutically acceptable salts according to independent claim 1, the compounds of the present invention for use as pharmaceutically active agents, the use of the compounds of the present invention for the preparation of a pharmaceutical composition for the prophylaxis and/or treatment of infectious diseases, including opportunistic diseases, immunological diseases, autoimmune diseases, cardiovascular diseases, cell proliferative diseases, inflammation, erectile dysfunction and stroke according to independent claim 6, the use of compounds according to the present invention as inhibitors for the protein kinase CDK7.

Further advantageous features, aspects and details of the invention are evident from the dependent claims, the description, the examples and the drawings.

The pyrazolotriazine compounds according to the present invention are defined by the general formula (I)

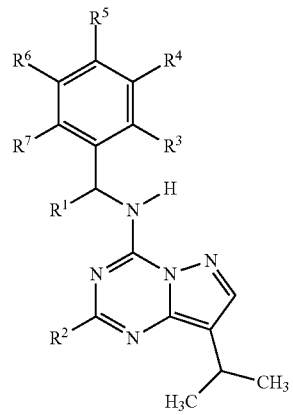

wherein
$R^1$ represents —H or —$CH_3$;
$R^2$ represents —$R^8$, -Q-$R^8$, —$R^9$, -Q-$(CH_2)_n$—$R^9$, —$(CH_2)_n$—$R^9$, —$(CH_2)_n$—NH—$R^8$, —$(CH_2)_m$—NH—$(CH_2)_n$—$R^9$, —CO—NH—$(CH_2)_n$—$NH_2$, —CO—NH—$(CH_2)_n$—$R^9$, —CO—$R^9$, —SO—$R^9$, —$(CH_2)_n$—$NR^{10}$—$R^8$, —$(CH_2)_m$—$NR^{10}$—$(CH_2)_n$—$R^9$, —CO—$NR^{10}$—$(CH_2)_n$—$R^9$, —$(CH_2)_a$-$(Q)_b$-$(CH_2)_c$-$(G^1)_d$-$(CH_2)_e$-$(G^2)_f$-$(CH_2)_g$—$R^8$, -$(Q)_b$-$(CH_2)_m$-$(G^1)_d$-$(CH_2)_e$—$R^8$, -$(Q)_b$-$(CH_2)_m$-$(G^1)_d$-$(CH_2)_n$—$R^9$, —$(CH_2)_a$-$(Q)_b$-$(CH_2)_c$-$(G^1)_d$-$(CH_2)_e$-$(G^2)_f$-$CH_2$—$R^9$, -Q-$R^{10}$, -Q-CH($COOR^{10}$)—$R^8$, -Q-CH($R^{10}$)—$R^8$, —$(CH_2)_n$—OH, —CHO, —OH;
$R^3$ represents —OH, —$NH_2$, —F, —Cl, —Br, —I, —CN, —$OR^{11}$, —$R^{11}$, —CO—O—$R^{11}$, —$NR^{11}$—CO—$OR^{12}$, —$NHR^{11}$, —$NR^{11}R^{12}$, —$CONR^{11}R^{12}$, —O—CO—$NR^{11}R^{12}$, —O—CO—$OR^{11}$, —$CH_3$, —$NR^{11}$—CO—$NR^{12}R^{13}$, —$SO_2NR^{11}R^{12}$, —C(=$NR^{11}$)—$NR^{12}R^{13}$, —C($R^{12}$)=$NR^{11}$, —N=$CR^{11}R^{12}$, —N=S(=O)$R^{11}R^{12}$, —$CR^{11}R^{12}R^{13}$, —$CR^{11}$=$CR^{12}R^{13}$, —C=$CR^{11}$, —$NR^{11}$—C(=$NR^{12}$)—$NR^{13}R^{14}$, —$SR^{11}$, —S(=O)$R^{11}$, —$NR^{11}$—S(=O)$R^{12}$, —O—S(=O)$R^{11}$, —$SO_2$—$R^{11}$, —$NR^{11}$—$SO_2$—$R^{12}$, —O—$SO_2$—$R^{11}$, —SO(=$NR^{11}$)—$R^{12}$, —CO—$R^{11}$, —O—CO—$R^{11}$, —$NR^{11}$—CO—$R^{12}$, —CH₂F, —CHF₂, —CF₃, 3-membered heterocyclyl, 4-membered heterocyclyl, 5-membered heterocyclyl, 6-membered heterocyclyl, monounsaturated 4-membered heterocyclyl, monounsaturated 5-membered heterocyclyl, monounsaturated 6-membered heterocyclyl, 3-membered carbocyclyl, 4-membered carbocyclyl, 5-membered carbocyclyl, 6-membered carbocyclyl, 6-membered aryl, 5-membered heteroaryl, 6-membered heteroaryl, and wherein all afore-mentioned ring systems can be substituted with 1 to 4 substituents selected from $Z^1$, $Z^2$, $Z^3$ and $Z^4$;

$Z^1$ and $Z^2$ if attached to the same carbon atom can together represent =O to form a carbonyl group with the carbon atom to which $Z^1$ and $Z^2$ are attached;

$R^3$ together with $R^4$ can form a carbocyclic or heterocyclic 4-, 5-, 6- or 7-membered ring with the two carbon atoms of the benzo ring to which $R^3$ and $R^4$ are attached and that 4-, 5-, 6- or 7-membered ring can be partly saturated or unsaturated and can be substituted with 1 to 4 substituents selected from $Z^1$, $Z^2$, $Z^3$ and $Z^4$;

$Z^1$ and $Z^2$ if attached to the same carbon atom can together represent =O to form a carbonyl group with the carbon atom to which $Z^1$ and $Z^2$ are attached;

$R^4$-$R^7$ represent independently of each other —H, —F, —Cl, —CH₃;

$R^9$ represents —(CH₂)$_p$—NH₂, —(CH₂)$_p$—N($R^{16}R^{17}$), carbocyclyl, heterocyclyl, spirocarbocyclyl, spiroheterocyclyl, wherein the afore-mentioned carbocyclyl, heterocyclyl, spirocarbocyclyl and spiroheterocyclyl residues are linked through a ring carbon atom and can be substituted with 1 to 3 substituents selected from $Z^5$, $Z^6$ and $Z^7$; $Z^5$ and $Z^6$ if attached to the same carbon atom can together represent =O to form a carbonyl group with the carbon atom to which $Z^5$ and $Z^6$ are attached;

$R^9$ represents —$R^8$, nitrogenheterocyclyl, spironitrogencyclyl, wherein the afore-mentioned nitrogenheterocyclyl and spironitrogencyclyl residues are linked through a ring nitrogen atom and can be substituted with 1 to 3 substituents selected from $Z^5$, $Z^6$ and $Z^7$;

$Z^5$ and $Z^6$ if attached to the same carbon atom can together represent =O to form a carbonyl group with the carbon atom to which $Z^5$ and $Z^6$ are attached;

$R^{11}$, $R^{12}$, $R^{13}$, $R^{14}$ and $R^{15}$ represent independently of each other —H, linear or branched $C_1$-$C_8$-alkyl, $C_3$-$C_8$-cycloalkyl, $C_1$-$C_9$-heterocyclyl, linear or branched $C_2$-$C_8$-alkenyl, linear or branched $C_2$-$C_8$-alkynyl, $C_6$-$C_{14}$-aryl, $C_1$-$C_{10}$-heteroaryl, wherein the afore-mentioned residues can be substituted with 1 to 5 substituents selected from $Z^8$, $Z^9$, $Z^{10}$, $Z^{11}$ and $Z^{12}$;

$R^{11}$ together with $R^{12}$ can form a carbocyclic or heterocyclic 4-, 5- or 6-membered ring and that 4-, 5- or 6-membered ring can be saturated or unsaturated and can be substituted with 1 to 8 substituents selected from $Z^8$, $Z^9$, $Z^{10}$, $Z^{11}$, $Z^{12}$, $Z^{13}$, $Z^{14}$ and $Z^{15}$;

$Z^8$ and $Z^9$ if attached to the same carbon atom can together represent =O to form a carbonyl group with the carbon atom to which $Z^8$ and $Z^9$ are attached;

$R^{10}$, $R^{16}$ and $R^{17}$ represent independently of each other —H, —CH₃, —C₂H₅, —C₃H₇, —CH(CH₃)₂, —CH₂F, —CHF₂, —CF₃,

cyclo-C₃H₅, cyclo-C₄H₇, cyclo-C₅H₉, cyclo-C₆H₁₁, cyclo-C₇H₁₃, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, -Ph, —CH₂-Ph, —CH₂—CH₂-Ph, —CH₂—CH=CH₂, —C(CH₃)=CH₂, —C₂H₄—CH=CH₂, —CH₂—CH=CH—CH₃, —CH₂—C(CH₃)=CH₂, —CH(CH₃)—CH=CH₂, —C(CH₃)=CH—CH₃, —CH₂—C≡CH, —C₂H₄—C≡CH, —CH₂—C≡C—CH₃, —C₂H₄—OCF₃, —C₃H₆—OCF₃, —C₂H₄—OCH₃, —C₃H₆—OCH₃, —C₂H₄—OC₂H₅, —C₃H₆—OC₂H₅;

Q, $G^1$, $G^2$ represent independently of each other —O—, —S—, —NR¹⁵—, —SO—, —NR¹⁵—SO—, —SO—NR¹⁵—, —SO₂—, —O—SO₂—, —SO₂—O—, —SO₂—NR¹⁵—, —NR¹⁵—SO₂—, —O—CO—, —O—CO—O—, —CO—, —CO—NR¹⁵—, —NR¹⁵—CO—, —NR¹⁵—CO—NR¹⁵—, —NR¹⁵—CO—O—, —O—CO—NR¹⁵—, —CO—O—, —(CH₂)$_m$—NR¹⁵—, bridging carbocyclyl-, bridging heterocyclyl-, bridging spirocarbocyclyl-, bridging spiroheterocyclyl-;

$Z^1$-$Z^{15}$ represent independently of each other

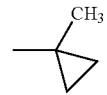

cyclo-C₃H₅, cyclo-C₄H₇, cyclo-C₅H₉, cyclo-C₆H₁₁, cyclo-C₇H₁₃, —H, —OH, —OCH₃, —OC₂H₅, —OC₃H₇, —O-cyclo-C₃H₅, —OCH(CH₃)₂, —OC(CH₃)₃, —OC₄H₉, —OPh, —OCH₂-Ph, —OCPh₃, —CH₂—OCH₃, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —SH, —SCH₃, —SC₂H₅, —SC₃H₇, —S-cyclo-C₃H₅, —SCH(CH₃)₂, —SC(CH₃)₃, —F, —Cl, —Br, —I, —CN, —COCH₃, —COC₂H₅, —COC₃H₇, —CO-cyclo-C₃H₅, —COCH(CH₃)₂, —COC(CH₃)₃, —COOH, —COOCH₃, —COOC₂H₅, —COOC₃H₇, —COO-cyclo-C₃H₅, —COOCH(CH₃)₂, —COOC(CH₃)₃, —OOC—CH₃, —OOC—C₂H₅, —OOC—C₃H₇, —OOC-cyclo-C₃H₅, —OOC—CH(CH₃)₂, —OOC—C(CH₃)₃, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NHCOCH₃, —NHCOC₂H₅, —NHCOC₃H₇, —NHCO-cyclo-C₃H₅, —NHCO—CH(CH₃)₂, —NHCO—C(CH₃)₃, —NHCO—OCH₃, —NHCO—OC₂H₅, —NHCO—OC₃H₇, —NHCO—O-cyclo-C₃H₅, —NHCO—OCH(CH₃)₂, —NHCO—OC(CH₃)₃, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SOC₃H₇, —SO-cyclo-C₃H₅, —SOCH(CH₃)₂, —SOC(CH₃)₃, —SO₂CH₃, —SO₂C₂H₅, —SO₂C₃H₇, —SO₂-cyclo-C₃H₅, —SO₂CH(CH₃)₂, —SO₂C(CH₃)₃, —SO₃H, —SO₃CH₃, —SO₃C₂H₅, —SO₃C₃H₇, —SO₃-cyclo-C₃H₅, —SO₃CH(CH₃)₂, —SO₃C(CH₃)₃, —SO₂NH₂, —SO₂NHCH₃, —SO₂NHC₂H₅, —SO₂NHC₃H₇, —SO₂NH-cyclo-C₃H₅, —SO₂NHCH(CH₃)₂, —SO₂NHC(CH₃)₃, —SO₂N(CH₃)₂, —SO₂N(C₂H₅)₂, —SO₂N(C₃H₇)₂, —SO₂N(cyclo-C₃H₅)₂, —SO₂N[CH(CH₃)₂]₂, —SO₂N[C(CH₃)₃]₂, —O—S(=O)CH₃, —O—S(=O)C₂H₅, —O—S(=O)C₃H₇, —O—S(=O)-cyclo-C₃H₅, —O—S(=O)CH(CH₃)₂, —O—S(=O)C(CH₃)₃, —S(=O)(=NH)CH₃, —S(=O)(=NH)C₂H₅, —S(=O)(=NH)C₃H₇, —S(=O)(=NH)-cyclo-C₃H₅, —S(=O)(=NH)CH(CH₃)₂, —S(=O)(=NH)C(CH₃)₃, —NH—SO₂—CH₃, —NH—SO₂—C₂H₅, —NH—SO₂—C₃H₇, —NH—SO₂-cyclo-C₃H₅, —NH—SO₂—CH(CH₃)₂, —NH—SO₂—C(CH₃)₃, —O—SO₂—CH₃, —O—SO₂—C₂H₅, —O—SO₂—C₃H₇, —O—SO₂-cyclo-C₃H₅, —O—SO₂—CH(CH₃)₂, —O—SO₂—C(CH₃)₃, —OCH₂F, —OCHF₂—OCF₃, —CH₂—OCF₃, —C₂H₄—OCF₃, —C₃H₆—OCF₃, —OC₂F₅, —CH₂—OC₂F₅, —C₂H₄—OC₂F₅, —C₃H₆—OC₂F₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NH₂, —NH—CO—NHCH₃, —NH—CO—NHC₂H₅, —NH—CO—NHC₃H₇, —NH—C(=NH)NH₂, —NH—CO—N(C₃H₇)₂, —NH—CO—NH[CH(CH₃)₂], —NH—CO—NH[C(CH₃)₃], —NH—CO—N(CH₃)₂, —NH—CO—N(C₂H₅)₂, —NH—CO—NH-cyclo-C₃H₅, —NH—CO—N(cyclo-C₃H₅)₂, —NH—CO—N[CH(CH₃)₂]₂, —NH—C(=NH)—NHCH₃, —NH—C(=NH)—NHC₂H₅, —NH—C(=NH)—NHC₃H₇, —O—CO—NH-cyclo-C₃H₅, —NH—C(=NH)—NH-cyclo-C₃H₅, —NH—C(=NH)—NH[CH(CH₃)₂], —O—CO—NH[CH(CH₃)₂], —NH—C(=NH)—NH[C(CH₃)₃], —NH—C(=NH)—N(CH₃)₂, —NH—C(=NH)—N(C₂H₅)₂, —NH—C(=NH)—N(C₃H₇)₂, —NH—C(=NH)—N(cyclo-C₃H₅)₂, —O—CO—NHC₃H₇, —NH—C(=NH)—N[CH(CH₃)₂]₂, —NH—C(=NH)—N[C(CH₃)₃]₂, —O—CO—NH₂, —O—CO—NHCH₃, —O—CO—NHC₂H₅, —O—CO—NH[C(CH₃)₃], —O—CO—N(CH₃)₂, —O—CO—N(C₂H₅)₂, —O—CO—N(C₃H₇)₂, —O—CO—N(cyclo-C₃H₅)₂, —O—CO—N[CH(CH₃)₂]₂, —O—CO—N[C(CH₃)₃]₂, —O—CO—OCH₃, —O—CO—OC₂H₅, —O—CO—OC₃H₇, —O—CO—O-cyclo-C₃H₅, —O—CO—OCH(CH₃)₂, —O—CO—OC(CH₃)₃, —CH₂F, —CHF₂, —CF₃, —CH₂—CH₂F, —CH₂—CHF₂, —CH₂—CF₃, cyclo-C₈H₁₅, -Ph, —CH₂-Ph, —CH₂—CH₂-Ph, —CH=CH-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH₃, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH(CH₃)—CH₂—CH=CH—CH₃, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH=CH—C₂H₄—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH=CH—CH₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—CH=CH₂, —C(CH₃)=C(C₂H₅)—CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —C₃H₆—C≡C—CH₃, —CH₂—CH=CH—CH=CH—CH₃, —CH=CH—CH=CH—C₂H₅, —CH(CH₃)—CH₂—C≡CH, —CH(CH₃)—C≡C—CH₃, —C₂H₄—CH(CH₃)—C≡CH, —CH=CH—CH=C(CH₃)₂, —CH₂—CH(CH₃)—CH₂—C≡CH, —CH=CH—C(CH₃)=CH—CH₃, —CH=C(CH₃)—CH=CH—CH₃, —CH₂—CH(CH₃)—C≡CH, —C(CH₃)=CH—CH=CH—CH₃, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—CH₂—CH(CH₃)₂, —CH(CH₃)—C₂H₄—C≡CH, —CH₂—CH(CH₃)—C≡C—CH₃, —C(CH₃)(C₂H₅)—C≡CH, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —CH₂—C≡C—C≡C—CH₃, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —CH₂—CH(C=CH)₂, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —C≡C—C(CH₃)₃, —C≡C—CH₂—C≡C—CH₃, —C≡C—C≡C—C₂H₅;

a, c, e, g are independently of each other selected from 0, 1, 2, 3 b, d, f are independently of each other 0 or 1 n is an integer selected from 1, 2, 3, 4, 5, 6, 7 or 8, m is an integer selected from 0, 1, 2, 3, 4, 5 or 6, p is an integer selected from 1, 2, 3, 4, 5, 6, 7 or 8 and enantiomers, stereoisomeric forms, mixtures of enantiomers, diastereomers, mixtures of diastereomers, hydrates, solvates, acid salt forms, tautomers, and racemates of the above mentioned compounds and pharmaceutically acceptable salts thereof.

Prodrugs of the compounds related to formula (I) are also within the scope of this invention. These derivatives may have little or no pharmacological activity themselves. The term "prodrug" as used herein describes a precursor of the active ingredient according to general formula (I), wherein said precursor comprises groups which can be cleaved under physiological conditions so that the active agent of formula (I) is formed. Information on the use of prodrugs may be found for example in "Pro-drugs as Novel Drug Delivery Systems" by T. Higuchi and W. Stella, ACS Symposium Series Vol. 14, 1975(ISBN13: 9780841202917).

A person skilled in the art can synthesize prodrugs for example by replacing a functional group in the compounds according to formula (I) with certain moieties. Examples for prodrugs of a compound according to formula (I) containing a primary or secondary amino functionality include but are not limited to moieties like amides, carbamates or alkyl derivatives thereof. More information on the use of prodrugs for amines may be found for example in *Molecules* 2008, 13, 519-547 (A. L. Simplicio et al.) or "Prodrugs of Amines" by J. P. Krise and R. Oliyai (Biotechnology: Pharmaceutical Aspects, 2007, Volume V, Part III, 801-831).

The expression tautomer is defined as an organic compound that is interconvertible by a chemical reaction called tautomerization. Tautomerization can be catalyzed preferably by bases or acids or other suitable compounds.

Preferred are compounds of general formula (I), wherein $R^3$ represents —OH, —$NH_2$, —F, —Cl, —Br, —I, —CN, —$OR^{11}$, —CO—O—$R^{11}$, —$NR^{11}$—CO—$OR^{12}$, —$NHR^{11}$, —$NR^{11}R^{12}$, —$CONR^{11}R^{12}$, —O—CO—$NR^{11}R^{12}$, —O—CO—$OR^{11}$, —$CH_3$, —$NR^{11}CO$—$NR^{12}R^{13}$, —$SO_2NR^{11}R^{12}$, —C(=$NR^{11}$)—$NR^{12}R^{13}$, —C($R^{12}$)=$NR^{11}$, —N=$CR^{11}R^{12}$, —N=S(=O)$R^{11}R^{12}$, —$CR^{11}R^{12}R^{13}$, —$CR^{11}$=$CR^{12}R^{13}$, —C≡$CR^{11}$, —$NR^{11}$—C(=$NR^{12}$)—$NR^{13}R^{14}$, —$SR^{11}$, —S(=O)$R^{11}$, —$NR^{11}$—S(=O)$R^{12}$, —O—S(=O)$R^{11}$, —$SO_2$—$R^{11}$, —$NR^{11}$—$SO_2$—$R^{12}$, —O—$SO_2$—$R^{11}$, —SO(=$NR^{11}$)—$R^{12}$, —CO—$R^{11}$, —O—CO—$R^{11}$, —$NR^{11}$—CO—$R^{12}$, —$CH_2F$, —$CHF_2$, —$CF_3$, pyridyl, pyrimidinyl, pyrazinyl, pyridazinyl, triazinyl, imidazolyl, furyl, dihydrofuryl, tetrahydrofuryl, thienyl, dihydrothienyl, tetrahydrothienyl, 1,3-oxazolyl, dihydro-1,3-oxazolyl, 1,3-oxazolidinyl, isoxazolyl, dihydro-isoxazolyl, isoxazolidinyl, pyrrolyl, dihydropyrrolyl, pyrrolidinyl, imidazolyl, dihydroimidazolyl, imidazolidinyl, triazolyl, dihydrotriazolyl, triazolidinyl, pyrazolyl, dihydropyrazolyl, pyrazolidinyl, oxadiazolyl, dihydrooxadiazolyl, oxadiazolidinyl, thiadiazolyl, dihydrothiadiazolyl, thiadiazolidinyl, 1,3-thiazolyl, dihydro-1,3-thiazolyl, 1,3-thiazolidinyl, isothiazolyl, dihydroisothiazolyl, isothiazolidinyl, tetrazolyl, dihydrotetrazolyl, tetrazolidinyl, aziridinyl, azirenyl, oxiranyl, thiiranyl, azetidinyl, oxetanyl, thietanyl, cyclopentanonyl, cyclohexanonyl, pyrrolidinonyl, pyrrolidindionyl, piperidinonyl, piperidindionyl, 1-oxid-thiopyranyl, 1,1-dioxid-thiopyranyl, dihydro-1-oxid-thiopyranyl, dihydro-1,1-dioxid-thiopyranyl, tetrahydro-1-oxid-thiopyranyl, tetrahydro-1,1-dioxid-thiopyranyl, morpholinyl, thiomorpholinyl, 1,2-dioxanyl, 1,3-dioxanyl, 1,4-dioxanyl, 1,2-dioxolanyl, 1,3-dioxolanyl, 1,4-dioxolanyl, piperazinyl, 2-oxo-azetidinyl, 2-oxo-pyrrolidinyl, 2-oxo-piperidinyl, 2-oxo-oxazolidinyl, 2-oxo-imidazolidinyl, 2-oxo-1,3-oxazinanyl, or 2-oxo-tetrahydropyrimidinyl, wherein the afore-mentioned ring systems can be substituted with one to four substituents selected from $Z^1$, $Z^2$, $Z^3$ and $Z^4$;

$R^8$ represents 4-membered heterocyclyl, 5-membered heterocyclyl, 6-membered heterocyclyl, 4-membered carbocyclyl, 5-membered carbocyclyl, 6-membered carbocyclyl, azaspiro[3,3]heptyl, azaspiro[3,4]octyl, azaspiro[3,5]nonyl, azaspiro[3,6]decyl, azaspiro[4,4]nonyl, azaspiro[4,5]decyl, azaspiro[4,6]undecyl, azaspiro[5,5]undecyl, azaspiro[5,6]dodecyl, azaspiro[6,6]tridecyl, diazaspiro[3,3]heptyl, diazaspiro[3,4]octyl, diazaspiro[3,5]nonyl, diazaspiro[3,6]decyl, diazaspiro[4,4]nonyl, diazaspiro[4,5]decyl, diazaspiro[4,6]undecyl, diazaspiro[5,5]undecyl, diazaspiro[5,6]dodecyl, diazaspiro[6,6]tridecyl, triazaspiro[3,5]nonyl, triazaspiro[3,6]decyl, triazaspiro[4,5]decyl, triazaspiro[4,6]undecyl, triazaspiro[5,5]undecyl, triazaspiro[5,6]dodecyl, triazaspiro[6,6]tridecyl, oxazaspiro[3,3]heptyl, oxazaspiro[3,4]octyl, oxazaspiro[3,5]nonyl, oxazaspiro[3,6]decyl, oxazaspiro[4,4]nonyl, oxazaspiro[4,5]decyl, oxazaspiro[4,6]undecyl, oxazaspiro[5,5]undecyl, oxazaspiro[5,6]dodecyl, oxazaspiro[6,6]tridecyl, oxadiazaspiro[3,5]nonyl, oxadiazaspiro[3,6]decyl, oxadiazaspiro[4,5]decyl, oxadiazaspiro[4,6]undecyl, oxadiazaspiro[5,5]undecyl, oxadiazaspiro[5,6]dodecyl, or oxadiazaspiro[6,6]tridecyl, wherein the afore-mentioned carbocyclyl, heterocyclyl, azaspiro, diazaspiro, triazaspiro, oxazaspiro, oxadiazaspiro residues are linked through a ring carbon atom and wherein the afore-mentioned carbocyclyl, heterocyclyl, azaspiro, diazaspiro, triazaspiro, oxazaspiro, oxadiazaspiro residues are substituted with one to three substituents selected from $Z^5$, $Z^6$ and $Z^7$;

$Z^5$ and $Z^6$ if attached to the same carbon atom can together represent =O to form a carbonyl group with the carbon atom to which $Z^5$ and $Z^6$ are attached;

$R^9$ represents 4-membered nitrogenheterocyclyl, 5-membered nitrogenheterocyclyl, 6-membered nitrogenheterocyclyl, 5-membered dinitrogenheterocyclyl, 6-membered dinitrogenheterocyclyl, spiro[2,3]heterohexyl, spiro[2,4]heteroheptyl, spiro[2,5]heterooctyl, spiro[2,7]heterononyl, spiro[3,3]heteroheptyl, spiro[3,4]heterooctyl, spiro[3,5]heterononyl, spiro[3,6]heterodecyl, spiro[4,4]heterononyl, spiro[4,5]heterodecyl, spiro[4,6]heteroundecyl, spiro[5,5]heteroundecyl, spiro[5,6]heterododecyl, or spiro[6,6]heterotridecyl, wherein the afore-mentioned nitrogenheterocyclyl, dinitrogenheterocyclyl and spiro residues are linked through the or a ring nitrogen atom and wherein the afore-mentioned nitrogenheterocyclyl, dinitrogenheterocyclyl and spiro residues are substituted with one to three substituents selected from $Z^5$, $Z^6$ and $Z^7$;

$Z^5$ and $Z^6$ if attached to the same carbon atom can together represent =O to form a carbonyl group with the carbon atom to which $Z^5$ and $Z^6$ are attached; and the residues $R^1$, $R^2$, $R^4$-$R^7$, $R^{10}$-$R^{17}$, a, b, c, d, e, f, g, m, n, p, Q, $G^1$, $G^2$ and $Z^1$-$Z^{15}$ have the meanings as defined herein.

Further preferred compounds of general formula (I) are these compounds, wherein $R^2$ represents —$R^8$, -Q-$R^8$, —$R^9$, -Q-$(CH_2)_n$—$R^8$, -Q-$(CH_2)_n$—$R^9$, —$(CH_2)_n$—$R^9$, —$(CH_2)_n$—NH—$R^8$, —$(CH_2)_m$—NH—$(CH_2)_n$—$R^9$, —CO—NH—$(CH_2)_n$—$NH_2$, —CO—NH—$(CH_2)_n$—$R^9$, —CO—$NR^{10}$—$(CH_2)_n$—$R^9$, —CO—$R^9$, —SO—$R^9$, -Q-$R^{10}$, —$(CH_2)_n$—$NR^{10}$—$R^8$, —$(CH_2)_m$—$NR^{10}$—$(CH_2)_n$—$R^9$, -(Q)$_b$-$(CH_2)_m$-($G^1$)$_d$-(CH_2)_e$—$R^8$, -(Q)$_b$-$(CH_2)_m$-($G^1$)$_d$-$(CH_2)_n$—$R^9$, -Q-CH(COO$R^{10}$)—$R^8$, or -Q-CH($R^{10}$)—$R^8$, Q, represents —O—, —S—, —$NR^{15}$—, —SO—, —$SO_2$—, —$(CH_2)_m$—$NR^{15}$—, bridging carbocyclyl, bridging heterocyclyl, bridging spirocarbocyclyl, or bridging spiroheterocyclyl;

$R^4$-$R^7$ represent independently of each other —H or —F; and the residues $R^1$, $R^3$, $R^8$-$R^{17}$, a, b, c, d, e, f, g, m, n, p, $G^1$, $G^2$ and $Z^1$-$Z^{15}$ have the meanings as defined herein.

It was surprisingly found that the substituent $R^3$ being a residue different from hydrogen is essential in order to obtain the desired activity and selectivity of the compounds of general formula (I). Consequently, the possibility that $R^3$ is hydrogen is excluded from the scope of the present invention. The other substituents $R^4$-$R^7$ can be hydrogen or any other of the substituents defined herein for these groups. Further, $R^1$ is limited to hydrogen or methyl in order to best obtain the surprising effects of the compounds of the present invention.

Moreover, it is particularly advantageous if $R^1$ represents hydrogen.

$R^2$ represents preferably a moiety containing a group able to form hydrogen bridges such as —$NH_2$, or a secondary or tertiary amino group [such as —NH-(carbon linked substituent), —N(carbon linked substituent1)(carbon linked substituent2), —NH-(sulfur linked substituent) or —N(sulfur linked substituent1)(carbon linked substituent2)], wherein the carbon or sulfur linked substituents are the $C_1$-$C_8$-alkylamines, carbocyclyl, heterocyclyl, nitrogenheterocyclyl, spirocarbocyclyl, spiroheterocyclyl, $C_1$-$C_8$-alkyl, $C_3$-$C_8$-cycloalkyl, $C_1$-$C_8$-fluoroalkyl, $C_6$-$C_{14}$-aryl, $C_7$-$C_{20}$-alkylaryl, $C_8$-$C_{20}$-alkenylaryl, $C_2$-$C_8$-alkenyl, $C_2$-$C_8$-alkynyl, $C_2$-$C_8$-alkoxyalkyl, CO—$C_1$-$C_8$-alkyl, $SO_2$—$C_1$-$C_8$-alkyl, SO—$C_1$-$C_8$-alkyl and $C_2$-$C_8$-fluoroalkoxyalkyl residues as defined herein for the substituents $R^8$, $R^9$, $R^{10}$ and $R^{15}$. Further, the group which is able to form hydrogen bridges is preferably linked through a linker to the pyrazolo[1,5-a][1,3,5]triazine ring system. Furthermore, the group which is able to form hydrogen bridges can also be part of a cyclic ring preferably a nitrogen heterocyclic ring (=nitrogenheterocyclyl) such as the nitrogen in piperidinyl, piperazinyl, hexahydropyrimidinyl, morpholinyl, hexahydropyridazinyl, pyrrolidinyl, pyrazolidinyl, imidazolidinyl, 1,3-oxazolidinyl, isoxazolidinyl or can be part of a spiro residue preferably a nitrogen spiro residue (=spironitrogencyclyl) such as the nitrogen in azaspiro, diazaspiro, triazaspiro, oxazaspiro or oxadiazaspiro residues. Also, the group which is able to form hydrogen bridges, especially in case it is an amino group is further preferably attached to a carbocyclic or heterocyclic ring. Examples for such residues are aminocyclohexyl, aminocyclopentyl, aminocyclobutyl, aminopiperidinyl, or an amino spiro residue, amino azaspiro residue, amino diazaspiro residue, amino triazaspiro residue, amino oxazaspiro residue or amino oxadiazaspiro residue.

Thus, it is preferred that $R^2$ represents -Q-$R^8$, —$R^9$, -Q-$(CH_2)_n$—$R^9$, —$(CH_2)_n$—$R^9$, —$(CH_2)_n$—NH—$R^8$, —$(CH_2)_n$—NH—$(CH_2)_m$—$R^9$, —CO—NH—$R^8$, —CO—$R^9$, —$(CH_2)_n$—$NR^{15}$—$R^8$, —$(CH_2)_n$—$NR^{15}$—$(CH_2)_m$—$R^9$, —CO—$NR^{15}$—$R^8$, —CO—$NR^{15}$—$(CH_2)_n$—$N(R^{16})(R^{17})$, or —CO—$NR^{15}$—$(CH_2)_n$—$R^9$, and it is more preferred that $R^2$ represents -Q-$R^8$, —$R^9$, -Q-$(CH_2)_n$—$R^9$, —$(CH_2)_n$—$R^9$, —$(CH_2)_n$—NH—$R^8$, —$(CH_2)_n$—NH—$(CH_2)_m$—$R^9$, —CO—NH—$R^8$, —CO—$R^9$, —$(CH_2)_n$—$NR^{15}$—$R^8$, or —$(CH_2)_n$—$NR^{15}$—$(CH_2)_m$—$R^9$, and it is most preferred that $R^2$ represents -Q-$R^8$, —$R^9$, -Q-$(CH_2)_n$—$R^9$, —$(CH_2)_n$—$R^9$, —$(CH_2)_n$—NH—$R^8$, —$(CH_2)_n$—NH—$(CH_2)_m$—$R^9$, or —CO—NH—$R^8$, wherein n is an integer selected from 1, 2, 3, 4, 5, 6, 7 or 8,
m is an integer selected from 0, 1, 2, 3, 4, 5 or 6.

Q represents preferably —O—, —S—, —$NR^{15}$—, —SO—, —$NR^{15}$—SO—, —SO—$NR^{15}$—, —$SO_2$—, —O—$SO_2$—, —$SO_2$—O—, —$SO_2$—$NR^{15}$—, —$NR^{15}$—$SO_2$—, —O—CO—, —O—CO—O—, —CO—, —CO—$NR^{15}$—, —$NR^{15}$—CO—, —$NR^{15}$—CO—$NR^{15}$—, —$NR^{15}$—CO—O—, —O—CO—$NR^{15}$—, —CO—O—, —$(CH_2)_m$—$NR^{15}$—, bridging carbocyclyl, bridging heterocyclyl, bridging spirocarbocyclyl, bridging spiroheterocyclyl;

n is an integer selected from 1, 2, 3, 4, 5, 6, 7 or 8,
m is an integer selected from 0, 1, 2, 3, 4, 5 or 6, More preferably, Q represents —O—, —S—, —$NR^{15}$—, —SO—, —$SO_2$—, —O—CO—, —CO—, —CO—$NR^{15}$—, —$NR^{15}$—CO—, —CO—O—, —$(CH_2)_m$—$NR^{15}$—, and even more preferably Q represents —O—, —S—, —$NR^{15}$—, —SO—, —$SO_2$—, —$(CH_2)_m$—$NR^{15}$—, and most preferably Q represents —O—, —NH—, —SO—, —CO—$NR^{15}$— or —$(CH_2)_m$—$NR^{15}$—.

The substituent -Q-$R^{10}$ represents preferably —S—$R^{10}$. More preferably —$R^{10}$ in —S—$R^{10}$ is selected from —$CH_3$, —$C_2H_5$, —$C_3H_7$, —$CH(CH_3)_2$, —$CH_2F$, —$CHF_2$, —$CF_3$,

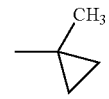

cyclo-$C_3H_5$, cyclo-$C_4H_7$, cyclo-$C_5H_9$, cyclo-$C_6H_{11}$, cyclo-$C_7H_{13}$, —$C_4H_9$, —$CH_2$—$CH(CH_3)_2$, —$CH(CH_3)$—$C_2H_5$, —$C(CH_3)_3$, —$C_5H_{11}$, —$CH(CH_3)$—$C_3H_7$, —$CH_2$—CH $(CH_3)$—$C_2H_5$, —$CH(CH_3)$—$CH(CH_3)_2$, —$C(CH_3)_2$—$C_2H_5$, —$CH_2$—$C(CH_3)_3$, —$CH(C_2H_5)_2$, —$C_2H_4$—CH $(CH_3)_2$, —$C_6H_{13}$, -Ph, —$CH_2$Ph, —$CH_2$—$CH_2$-Ph, —$CH_2$—CH=$CH_2$, —$C(CH_3)$=$CH_2$, —$C_2H_4$—CH=$CH_2$, or —$CH_2$CH=CH—$CH_3$.

In one embodiment of the compounds of the present invention $R^2$ represents a linking moiety —$(CH_2)_a$-$(Q)_b$-$(CH_2)_c$-$(G^1)_d$-$(CH_2)_e$-$(G^2)_f$-$(CH_2)_g$—$R^8$ or —$(CH_2)_a$-$(Q)_b$-$(CH_2)_c$-$(G^1)_d$-$(CH_2)_e$-$(G^2)_f$-$CH_2$—$R^9$, with $R^8$ and $R^9$ as defined herein and Q is defined as discloses herein and $G^1$ and $G^2$ represent independently of each other:
bifunctional carbocyclic or heterocyclic 4-, 5-, 6- or 7-membered ring, wherein the term "bifunctional" refers to the fact that this ring is within the chain or carbon chain and consequently is linked through two ring atoms and is thus a "diyl" residue. Preferred residues for Q, $G^1$ and/or $G^2$ and especially for $G^1$ and/or $G^2$ are:
piperidindiyl, piperazindiyl, pyrimidindiyl, morpholindiyl, pyrrolidindiyl, pyrazolidinyl, and even more preferably at least $G^1$ or $G^2$ represents independently one of the following linking structures, wherein the lines are not methyl groups and indicate the linking bonds:

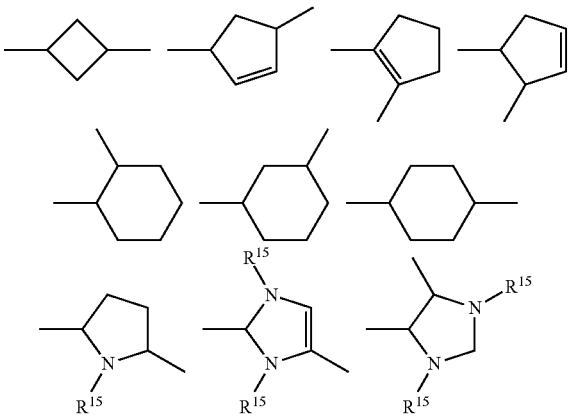

-continued

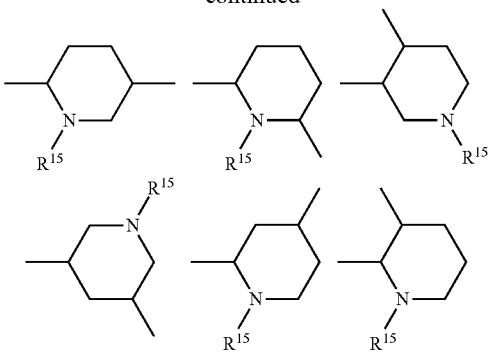

a, c, e, g are independently of each other selected from 0, 1, 2, 3
b, d, f are independently of each other 0 or 1
n is an integer selected from 1, 2, 3, 4, 5, 6, 7 or 8,
m is an integer selected from 0, 1, 2, 3, 4, 5 or 6,
p is an integer selected from 1, 2, 3, 4, 5, 6, 7 or 8;
$R^3$ represents —OH, —$NH_2$, —F, —Cl, —Br, —I, —CN, —$OR^{11}$, —CO—O—$R^{11}$, —$NR^{11}$—CO—$OR^{12}$, —$NHR^{11}$, —$NR^{11}R^{12}$, —$CONR^{11}R^{12}$, —O—CO—$NR^{11}R^{12}$, —O—CO—$OR^{11}$, —$NR^{11}$—CO—$NR^{12}R^{13}$, —$SO_2NR^{11}R^{12}$, —C(=$NR^{11}$)—$NR^{12}R^{13}$, —C($R^{12}$)=$NR^{11}$, —N=$CR^{11}R^{12}$, —$CR^{11}R^{12}R^{13}$, —$CR^{11}$=$CR^{12}R^{13}$, —C≡$CR^{11}$, —$NR^{11}$—C(=$NR^{12}$)—$NR^{13}R^{14}$, —$SR^{11}$, —S(=O)$R^{11}$, —N=S(=O)$R^{11}R^{12}$, —$NR^{11}$—S(=O)$R^{12}$, —O—S(=O)$R^{11}$, —$SO_2$—$R^{11}$, —$NR^{11}$—$SO_2$—$R^{12}$, —O—$SO_2$—$R^{11}$, —SO(=$NR^{11}$)—$R^{12}$, —CO—$R^{11}$, —O—CO—$R^{11}$, —$NR^{11}$—CO—$R^{12}$, 3-membered heterocyclyl, 4-membered heterocyclyl, 5-membered heterocyclyl, 6-membered heterocyclyl, monounsaturated 4-membered heterocyclyl, monounsaturated 5-membered heterocyclyl, monounsaturated 6-membered heterocyclyl, 3-membered carbocyclyl, 4-membered carbocyclyl, 5-membered carbocyclyl, 6-membered carbocyclyl, 6-membered aryl, 5-membered heteroaryl, 6-membered heteroaryl,
and
wherein all afore-mentioned ring systems can be substituted with 1 to 4 substituents selected from $Z^1$, $Z^2$, $Z^3$ and $Z^4$, wherein $Z^1$ and $Z^2$ if attached to the same carbon atom can together represent =O to form a carbonyl group with the carbon atom to which $Z^1$ and $Z^2$ are attached. That means, the afore-mentioned ring systems can comprise a carbonyl group in the ring system, namely where $Z^1$ and $Z^2$ are attached to the same ring carbon atom and form together an oxygen (=O) in addition to two further substituents $Z^3$ and $Z^4$ which are not defined as a carbonyl group together. The same definition applies where $Z^5$ and $Z^6$ or where $Z^8$ and $Z^9$ can form together a carbonyl group.

Preferably the residue $R^3$ represents independently of each other —$OR^{11}$, —F, —Cl, pyridyl, pyrimidinyl, pyrazinyl, pyridazinyl, triazinyl, imidazolyl, furyl, dihydrofuryl, tetrahydrofuryl, thienyl, dihydrothienyl, tetrahydrothienyl, 1,3-oxazolyl, dihydro-1,3-oxazolyl, 1,3-oxazolidinyl, isoxazolyl, dihydro-isoxazolyl, isoxazolidinyl, pyrrolyl, dihydropyrrolyl, pyrrolidinyl, imidazolyl, dihydroimidazolyl, imidazolidinyl, triazolyl, dihydrotriazolyl, triazolidinyl, pyrazolyl, dihydropyrazolyl, pyrazolidinyl, oxadiazolyl, dihydrooxadiazolyl, oxadiazolidinyl, thiadiazolyl, dihydrothiadiazolyl, thiadiazolidinyl, 1,3-thiazolyl, dihydro-1,3-thiazolyl, 1,3-thiazolidinyl, isothiazolyl, dihydroisothiazolyl, isothiazolidinyl, tetrazolyl, dihydrotetrazolyl, tetrazolidinyl, aziridinyl, azirenyl, oxiranyl, thiiranyl, azetidinyl, oxetanyl, thietanyl, cyclopentanonyl, cyclohexanonyl, pyrrolidinonyl, pyrrolidindionyl, piperidinonyl, piperidinyl, 1-oxid-thiopyranyl, 1,1-dioxid-thiopyranyl, dihydro-1-oxid-thiopyranyl, dihydro-1,1-dioxid-thiopyranyl, tetrahydro-1-oxid-thiopyranyl, tetrahydro-1,1-dioxid-thiopyranyl, morpholinyl, thiomorpholinyl, 1,2-dioxanyl, 1,3-dioxanyl, 1,4-dioxanyl, 1,2-dioxolanyl, 1,3-dioxolanyl, 1,4-dioxolanyl, piperazinyl, 2-oxo-azetidinyl, 2-oxo-pyrrolidinyl, 2-oxo-piperidinyl, 2-oxo-oxazolidinyl, 2-oxo-imidazolidinyl, 2-oxo-1,3-oxazinanyl, 2-oxo-tetrahydropyrimidinyl, wherein the afore-mentioned ring systems can be substituted with one to four substituents selected from $Z^1$, $Z^2$, $Z^3$ and $Z^4$. More preferably the afore-mentioned ring systems can be substituted with one to three substituents selected from $Z^1$, $Z^2$ and $Z^3$ and most preferably the afore-mentioned ring systems can be substituted with one or two substituents selected from $Z^1$ and $Z^2$.

$OR^{11}$ is preferably selected from —$OCH_3$, —$OC_2H_5$, and, —$OCF_3$,

Further preferred substituents $R^3$ are the following nitrogen heteroaromatic residues:

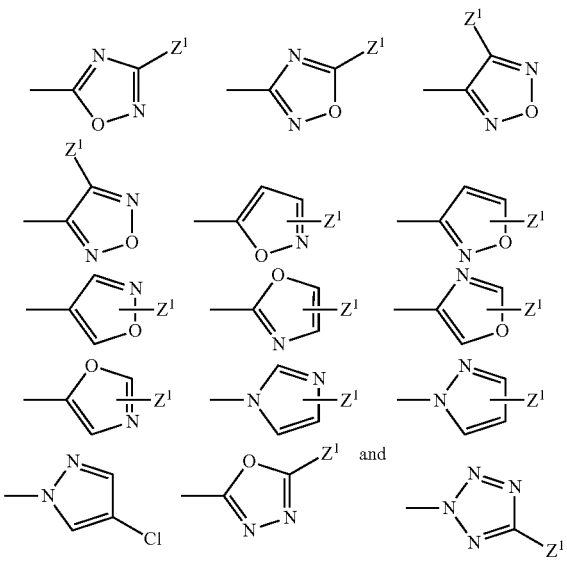

Further, it is also possible that the substituents $R^{11}$ and $R^{12}$ are not single substituent and that $R^{11}$ together with $R^{12}$ can form a carbocyclic or heterocyclic ring, preferably 4-, 5- or 6-membered ring, more preferably a 5- or 6-membered heterocyclic ring, and that 4-, 5- or 6-membered ring can be saturated or unsaturated and can be substituted with 1 to 8 substituents selected from $Z^8$, $Z^9$, $Z^{10}$, $Z^{11}$, $Z^{12}$, $Z^{13}$, $Z^{14}$ and $Z^{15}$, wherein $Z^8$ and $Z^9$ if attached to the same carbon atom can together represent =O to form a carbonyl group with the carbon atom to which $Z^8$ and $Z^9$ are attached. That means, the afore-mentioned ring systems can comprise a carbonyl group in the ring system, namely where $Z^8$ and $Z^9$ are attached to the same ring carbon atom and form together an oxygen (=O) in addition to six further substituents $Z^{10}$, $Z^{11}$, $Z^{12}$, $Z^{13}$, $Z^{14}$ and $Z^{15}$ which are not defined as a carbonyl group together.

Specifically in one preferred embodiment, wherein the substituents $R^{11}$ and $R^{12}$ are attached to different atoms and $R^3$ represents one of the residues —C($R^{12}$)=$NR^{11}$, —$CR^{11}$=$CR^{12}R^{13}$, —$NR^{11}$—S(O)$R^{12}$, —$NR^{11}$—$SO_2$—$R^{12}$, —SO(=$NR^{11}$)—$R^{12}$, or —$NR^{11}$—CO—$R^{12}$ the substituents $R^{11}$ and $R^{12}$ can be joined together and represent one of the following ring fragments:
—$CZ^8Z^9$—$CZ^{10}Z^{11}$—$CZ^{12}Z^{13}$—, —$CZ^8$=$CZ^9$—$CZ^{10}$=$CZ^{11}$—, —$CZ^8Z^9$—$CZ^{10}Z^{11}$—$CZ^{12}Z^{13}$—$CZ^{14}Z^{15}$—, —$CZ^8Z^9$—$CZ^{10}$=$CZ^{11}$—, —$CZ^8$=$CZ^9$—$CZ^{10}Z^{11}$—, —$CZ^8Z^9$—$CZ^{10}Z^{11}$—$CZ^{12}$=$CZ^{13}$—, —$CZ^8Z^9$—$CZ^{10}$=$CZ^{11}$—$CZ^{12}Z^{13}$—, —$CZ^8$=$CZ^9$—$CZ^{10}Z^{11}$—$CZ^{12}Z^{13}$—, —$CZ^8Z^9$—O—$CZ^{10}Z^{11}$—, —$CZ^8Z^9$—$CZ^{10}Z^{11}$—O—$CZ^{12}Z^{13}$—, —$CZ^8Z^9$—O—$CZ^{10}Z^{11}$—$CZ^{12}Z^{13}$—, —$CZ^8$=$CZ^9$—O—$CZ^{10}Z^{11}$—, —$CZ^8Z^9$—O—$CZ^{10}$=$CZ^{11}$—, —O—$CZ^8Z^9$—$CZ^{10}Z^{11}$—, —$CZ^8Z^9$—$CZ^{10}Z^{11}$—O—, —O—$CZ^8$=$CZ^9$—, —$CZ^8$=$CZ^9$—O—, —O—$CZ^8Z^9$—$CZ^{10}Z^{11}$—$CZ^{12}Z^{13}$—, —$CZ^8Z^9$—$CZ^{10}Z^{11}$—$CZ^{12}Z^{13}$—O—, —O—$CZ^8$=$CZ^9$—$CZ^{10}Z^{11}$—, —O—$CZ^8Z^9$—$CZ^{10}$=$CZ^{11}$—, —$CZ^8Z^9$—$CZ^{10}$=$CZ^{11}$—O—, —$CZ^8$=$CZ^9CZ^{10}Z^{11}$—O—, —CO—$CZ^8Z^9$—$CZ^{10}Z^{11}$—, —$CZ^8Z^9$—CO—$CZ^{10}Z^{11}$—, —$CZ^8Z^9$—$CZ^{10}Z^{11}$—CO—, —CO—$CZ^8$=$CZ^9$—, —$CZ^8$=$Z^9$—CO—, —CO—$CZ^8Z^9$—$CZ^{10}Z^{11}$—$CZ^{12}Z^{13}$—, —$CZ^8Z^9$—CO—$CZ^{10}Z^{11}$—$Z^{12}Z^{13}$—, —$CZ^8Z^9$—$CZ^{10}Z^{11}$—CO—$CZ^{12}Z^{13}$—, —$CZ^8Z^9$—$CZ^{10}Z^{11}$—$CZ^{12}Z^{13}$—CO—, —CO—$CZ^8$=$CZ^9CZ^{10}Z^{11}$—, —$CZ^8Z^9$—CO—$CZ^{10}$=$CZ^{11}$—, —$CZ^8$=$CZ^9$—CO—$CZ^{10}Z^{11}$—, —$CZ^8$=$CZ^9$—$CZ^{10}Z^{11}$—CO—, —$CZ^8Z^9$—$CZ^{10}$=$CZ^{11}$—CO—, —CO—O—$CZ^8Z^9$—, —$CZ^8Z^9$—CO—O—, —CO—O—$CZ^8Z^9$—$CZ^{10}Z^{11}$—, —$CZ^8Z^9$—CO—O—$CZ^{10}Z^{11}$—, —$CZ^8Z^9$—$CZ^{10}Z^{11}$—CO—O—, —CO—O—$CZ^8$=$CZ^9$—, —$CZ^8$=$CZ^9$—CO—O—, —O—CO—$CZ^8Z^9$—, —$CZ^8Z^9$—O—CO—, —O—CO—$CZ^8Z^9$—$CZ^{10}Z^{11}$—, —$CZ^8Z^9$—O—CO—$CZ^{10}Z^{11}$—, —$CZ^8Z^9$—$CZ^{10}Z^{11}$—O—CO—, —O—CO—$CZ^8$=$CZ^9$—, —$CZ^8$=$CZ^9$—O—CO—, —CO—$NR^{14}$—$CZ^9Z^{10}$—, —CO—$CZ^8Z^9$—$NR^{14}$—, —CO—N=$CZ^8$—, —CO—$CZ^8$=N—, —CO—$NZ^8$—$CZ^9Z^{10}$—$CZ^{11}Z^{12}$—, —CO—$CZ^8Z^9$—$NR^{14}$—$CZ^{11}Z^{12}$, —CO—$CZ^8Z^9$—$CZ^{10}Z^{11}$—$NR^{14}$—, —CO—$NR^{14}$—$CZ^9$=$CZ^{10}$—, —CO—$CZ^8$=$CZ^9$—$NR^{14}$—, —CO—N=$CZ^8$—$CZ^9Z^{10}$—, —CO—$CZ^8$=N—$CZ^9Z^{10}$—, —CO—$CZ^8Z^9$—N=$CZ^{10}$—, —CO—$CZ^8Z^9$—$CZ^{10}$=N—, —$NR^{14}$—CO—$CZ^9Z^{10}$—, —$NR^{14}$—$CZ^9Z^{10}$—CO—, —N=$CZ^8$—CO—, —$NR^{14}$—CO—$CZ^9Z^{10}$—$Z^{11}Z^{12}$—, —$NR^{14}$—$CZ^9Z^{10}$—CO—$CZ^{11}Z^{12}$—, —$NR^{14}$—$Z^9Z^{10}$—$Z^{11}Z^{12}$—CO—, —$NR^{14}$—CO—$CZ^9$=$Z^{10}$—, —$NR^{14}$—$CZ^9$=$CZ^{10}$—CO—, —N=$CZ^8$—CO—$CZ^9Z^{10}$—, —N=$CZ^8$—$CZ^{10}Z^{11}$—CO—, —$NR^{14}$—CO—O—$CZ^9Z^{10}$—, —$NR^{14}$—$Z^9Z^{10}$—CO—O—, —CO—O—$NR^{14}$—$CZ^9Z^{10}$—, —N=$CZ^8$—CO—O—, —CO—O—N=$CZ^8$—, —$NR^{14}$—O—CO—$CZ^9Z^{10}$—, —$NR^{14}$—$Z^9Z^{10}$—O—CO—, —O—CO—$NR^{14}$—$CZ^9Z^{10}$—, —$NR^{14}$—O—$CZ^9Z^{10}$—CO—, —N=$CZ^8$—O—CO—, —O—CO—N=$Z^8$—, —$NR^{14}$—$CZ^9Z^{10}$—$CZ^{11}Z^{12}$—, —$CZ^8Z^9$—$NR^{14}$—$CZ^{11}$—$Z^{12}$—, —$CZ^8Z^9$—$CZ^{10}CZ^{11}$—$NR^{14}$—, —$CZ^8Z^9$—$CZ^{10}Z^{11}$—$NR^{14}$—$CZ^{13}Z^{14}$, —$CZ^8Z^9$—$CZ^{10}Z^{11}$—$CZ^{12}Z^{13}$—$NR^{14}$—, —$NR^{14}$—$CZ^9$=$CZ^{10}CZ^{11}Z^{12}$—, —$CZ^8Z^9$—$NR^{14}$—$CZ^{11}$=$CZ^{12}$—, —$CZ^8$=$CZ^9$—$NR^{14}$—$CZ^{11}Z^{12}$—, —$CZ^8CZ^9$—$CZ^{10}Z^{11}$—$NR^{14}$—, —$CZ^8Z^9$—$CZ^{10}$=$CZ^{11}Z^{12}$—$NR^{14}$—, —N=$CZ^8$—$CZ^9Z^{10}$—$CZ^{11}Z^{12}$—, —$CZ^8Z^9$—N=$CZ^{10}$—$CZ^{11}Z^{12}$—, —$CZ^8Z^9$—$CZ^{10}Z^{11}$—N=$CZ^{12}$—, —$CZ^8Z^9$—$CZ^{10}Z^{11}$—$CZ^{12}$=N—, —$CZ^8$=N—$CZ^9$=$CZ^{10}$—, —$CZ^8$=$CZ^9$—N=$CZ^{10}$—, —$CZ^8$=$CZ^9$—$CZ^{10}$=N—, —$NR^{13}$—CO—$NR^{14}$—, —$NR^{13}$—CO—$NR^{14}$—$CZ^{10}Z^{11}$—, —$CZ^8Z^9$—$NR^{13}$—O—$NR^{14}$—, —$NR^{14}CO$—N=$CZ^9$—, —$Z^8$=N—O—$NR^{14}$—, —$NR^{13}$—$CZ^9Z^{10}$—CO—$NR^{14}$—, —$NR^{13}$—CO—$CZ^9Z^{10}$—$NR^{14}$—, —N=$CZ^8$—CO—$NR^{14}$—, —O—CO—$NR^{14}$—, —CO—

O—$NR^{14}$—, —$NR^{14}$—O—CO—, —$NR^{14}$—CO—O—, —CO—$NR^{14}$—O—, —O—CO—$NR^{14}$—$CZ^9Z^{10}$—, —O—CO—$CZ^8Z^9$—$NR^{14}$—, —CO—O—$NR^{14}$—$CZ^9Z^{10}$—, —CO—O—$CZ^8Z^9$—$NR^{14}$—, —$CZ^8Z^9$—$NR^{14}$—O—CO—, —$CZ^8Z^9$—$NR^{14}$—CO—O—, —NH—C(=$NR^{13}$)—$NR^{14}$—, or —O—CO—N=$CZ^8$—.

Also in another preferred embodiment, wherein the substituents $R^{11}$ and $R^{12}$ are attached to different atoms and $R^3$ represents one of the substituents —$NR^{11}$—CO—$OR^{12}$, —$NR^{11}$—CO—$NR^{12}R^{13}$, —C(=$NR^{11}$)—$NR^{12}R^{13}$ or —$NR^{11}$—C(=$NR^{12}$)—$NR^{13}R^{14}$, $R^{11}$ and $R^{12}$ can be joined together and represent one of the following ring fragments:
—$CZ^8Z^9$—$CZ^{10}Z^{11}$—$CZ^{12}Z^{13}$—, —$CZ^8Z^9$—$CZ^{10}$=$Z^{11}$—, —$CZ^8$=$CZ^9$—$CZ^{10}Z^{11}$—, —$CZ^8Z^9$—$CZ^{10}Z^{11}$—, —$CZ^8$=$CZ^9$—, —$CZ^8Z^9$—O—$CZ^{10}Z^{11}$—, —O—$CZ^8Z^9CZ^{10}Z^{11}$—, —$CZ^8Z^9$—$CZ^{10}Z^{11}$—O—, —O—$CZ^8$=$CZ^9$—, —$CZ^8$=$CZ^9$—O—, —O—$CZ^8Z^9$—, —$CZ^8Z^9$—O—, —CO—$CZ^8Z^9$—$CZ^{10}Z^{11}$—, —$CZ^8Z^9$—CO—$CZ^{10}Z^{11}$—, —$CZ^8Z^9$—$CZ^{10}Z^{11}$—CO—, —CO—$CZ^8$=$CZ^9$—, —$CZ^8$=$CZ^9$—CO—, —CO—$CZ^8Z^9$—, —$CZ^8Z^9$—CO—, —CO—O—$CZ^8Z^9$—, —$CZ^8Z^9$—CO—O—, —CO—O—, —O—CO—$CZ^8Z^9$—, —$CZ^8Z^9$—O—CO—, —$CZ^8Z^9$—$NR^{14}$—, —CO—N=$CZ^8$—, —CO—$CZ^8$=N—, —CO—$NR^{14}$—, —$NR^{14}$—CO—$CZ^9Z^{10}$, —$NR^{14}$—$CZ^9Z^{10}$—CO—, —N=$CZ^8$—CO—, —$NR^{14}$—CO—, —$NR^{14}$—$CZ^9Z^{10}$—$CZ^{11}Z^{12}$—, —$CZ^8Z^9$—$NR^{14}$—$CZ^{11}Z^{12}$—, —$CZ^8Z^9$—$CZ^{10}Z^{11}$—$NR^{14}$—, —$NR^{14}$—$CZ^9$=$CZ^{10}$—, —$CZ^8$=$CZ^9$—$NR^{14}$—, —N=$CZ^8$—$CZ^9Z^{10}$—, —$CZ^8Z^9$—N=$CZ^{10}$—, —$CZ^8Z^9$—$CZ^{10}$=N—, —$NR^{14}$—$CZ^9$=$CZ^{10}$—, —$CZ^8$=$CZ^9$—$NR^{14}$—, —$NR^{14}$—$CZ^9Z^{10}$—, —$CZ^8Z^9$—$NR^{14}$—, —N=$CZ^8$—, —N=$CZ^8$—, —$NR^{14}$—CO—$NR^{14}$—, —O—CO—$NR^{14}$—, —$NR^{14}$—CO—O—, or —NH—C(=$NR^{14}$)—$NR^{14}$—.

Specifically in one preferred embodiment, wherein the substituents $R^{11}$ and $R^{12}$ are attached to the same atom, in that $R^3$ represents one of the residues —$NR^{11}R^{12}$, —$CONR^{11}R^{12}$, —O—CO—$NR^{11}R^{12}$, —$SO_2NR^{11}R^{12}$, —N=$CR^{11}R^{12}$, —N=S(=O)$R^{11}R^{12}$, —$CR^{11}R^{12}R^{13}$, the substituents $R^{11}$ and $R^{12}$ can be joined together and represent one of the following ring fragments:
—$CZ^8Z^9$—$CZ^{10}Z^{11}$—$CZ^{12}Z^{13}$—, —$CZ^8$=$CZ^9$—$CZ^{10}$=$CZ^{11}$—, —$CZ^8Z^9$—$CZ^{10}Z^{11}$—$CZ^{12}Z^{13}$—$CZ^{14}Z^{15}$—, —$CZ^8Z^9$—$CZ^{10}$=$CZ^{11}$—, —$CZ^8$=$CZ^9$—$CZ^{10}Z^{11}$—, —$CZ^8Z^9$—$CZ^{10}Z^{11}$—$CZ^{12}$=$CZ^{13}$—, —$CZ^8Z^9$—$CZ^{19}$=$CZ^{11}$—$CZ^{12}Z^{13}$—, —$CZ^8$=$CZ^9$—$CZ^{10}Z^{11}$—$CZ^{12}Z^{13}$—$CZ^8Z^9$—O—$CZ^{19}Z^{11}$—, —$CZ^8Z^9$—$CZ^{10}Z^{11}$—O—$CZ^{12}Z^{13}$—, —$CZ^8Z^9$—O—$CZ^{10}Z^{11}$—$CZ^{12}Z^{13}$—$CZ^8$=$CZ^9$—O—$CZ^{19}Z^{11}$—, —$CZ^8Z^9$—O—$CZ^{10}$=$CZ^{11}$—, —O—$CZ^8Z^9$—$CZ^{11}Z^{12}$—$CZ^8Z^9$—$CZ^{10}Z^{11}$—O—, —O—$CZ^8$=$CZ^9$—, —$CZ^8$=$CZ^9$—O—, —O—$CZ^8Z^9$—$CZ^{11}Z^{11}$—$CZ^{12}Z^{13}$—$CZ^8Z^9$—$CZ^{11}Z^{12}$—$CZ^{12}Z^{13}$—O—, —O—$CZ^8$=$CZ^9$—$CZ^{10}Z^{11}$—, —O—$CZ^8Z^9$—$CZ^{11}$=$CZ^{11}$—, —$CZ^8Z^9$—$CZ^{11}$=$CZ^{11}$—O—, —$CZ^8$=$CZ^9$—$CZ^{10}Z^{11}$—O—, —CO—$CZ^8Z^9$—$CZ^{10}Z^{11}$—$CZ^8Z^9$—CO—$CZ^{10}Z^{11}$—, —$CZ^8Z^9$—$CZ^{10}Z^{11}$—CO—, —CO—$CZ^8$=$CZ^9$—, —$CZ^8$=$CZ^9$—CO—, —CO—$CZ^8Z^9$—$CZ^{10}CZ^{11}$—$CZ^{12}Z^{13}$—, —$CZ^8Z^9$—CO—$CZ^{10}Z^{11}$—$CZ^{12}Z^{13}$—, —$CZ^8Z^9$—$CZ^{11}Z^{12}$—CO—$CZ^{12}Z^{13}$—, —$CZ^8Z^9$—$CZ^{11}Z^{12}$—$CZ^{12}Z^{13}$—O—, —CO—$CZ^8$=$CZ^9$—$CZ^{11}Z^{12}$—, —$CZ^8Z^9$—CO—$CZ^{10}$=$CZ^{11}$—, —$CZ^8$=$CZ^9$—CO—$CZ^{10}Z^{11}$—, —$CZ^8$=$CZ^9$—$CZ^{10}Z^{11}$—CO—, —$CZ^8Z^9$—$CZ^{10}$=$CZ^{11}$—CO—, —$CZ^8Z^9$—CO—O—, —CO—O—$CZ^8Z^9$—$CZ^{10}Z^{11}$—, —$CZ^8Z^9$—CO—O—$CZ^{10}Z^{11}$—, —CO—O—CZ⁸=CZ⁹—, —CZ⁸=CZ⁹—CO—O—, —O—CO—CZ⁸Z⁹—, —CZ⁸Z⁹—O—CO—, —O—CO—CZ⁸Z⁹—CZ¹⁰Z¹¹—, —CZ⁸Z⁹—O—CO—CZ¹⁰Z¹¹—, —CZ⁸Z⁹—CZ¹⁰Z¹¹—O—CO—, —O—CO—CZ⁸=CZ⁹—, —CZ⁸=CZ⁹—O—CO—, —CO—NR¹⁴—CZ⁹Z¹⁰—, —CO—CZ⁸Z⁹—NR¹⁴—, —CO—N=CZ⁸—, —CO—CZ⁸=N—, —CO—NZ⁸—CZ⁹Z¹⁰—CZ¹¹Z¹²—, —CO—CZ⁸Z⁹—NR¹⁴—CZ¹¹Z¹²—, —CO—CZ⁸Z⁹—CZ¹⁰Z¹¹—NR¹⁴—, —CO—NR¹⁴—CZ⁹=CZ¹⁰—, —CO—CZ⁸=CZ⁹—NR¹⁴—, —CO—N=CZ⁸—CZ⁹Z¹⁰—, —CO—CZ⁸=N—CZ⁹Z¹⁰—, —CO—CZ⁸Z⁹—N=CZ¹⁰—, —CO—CZ⁸Z⁹—CZ¹⁰=N—, —NR¹⁴—CO—CZ⁹Z¹⁰—, —NR¹⁴—CZ⁹Z¹⁰—CO—, —N=CZ⁸—CO—, —NR¹⁴—CO—CZ⁹Z¹⁰—CZ¹¹Z¹²—, —NR¹⁴—CZ⁹Z¹⁰—CO—CZ¹¹Z¹²—, —NR¹⁴—CZ⁹Z¹⁰—CZ¹¹Z¹²—CO—, —NR¹⁴—CO—CZ⁹=CZ¹⁰—, —NR¹⁴—CZ⁹=CZ¹⁰—CO—, —N=CZ⁸—CO—CZ⁹Z¹⁰—, —N=CZ⁸—CZ¹⁰Z¹¹—CO—, —NR¹⁴—CO—O—CZ⁹Z¹⁰—, —NR¹⁴—CZ⁹Z¹⁰—CO—O—, —O—CO—NR¹⁴—CZ⁹Z¹⁰—, —N=CZ⁸—CO—O—, —CO—O—N=CZ⁸—, —NR¹⁴—O—CO—CZ⁹Z¹⁰—, —NR¹⁴—CZ⁹Z¹⁰—O—CO—, —O—CO—NR¹⁴—CZ⁹Z¹⁰—, —NR¹⁴—O—CO—N=CZ⁸—, —N=CZ⁸—O—CO—, —O—CO—N=CZ⁸—, —NR¹⁴—CZ⁹Z¹⁰—CZ¹¹Z¹²—CZ⁸Z⁹—NR¹⁴—CZ¹¹Z¹²—, —CZ⁸Z⁹—CZ¹⁰Z¹¹—NR¹⁴—, —NR¹⁴—CZ⁹=CZ¹⁰—, —CZ⁸=CZ¹⁰—NR¹⁴—, —N=CZ⁸—CZ⁹Z¹⁰—, —CZ⁸Z⁹—N=CZ¹⁰—, —CZ⁸Z⁹—CZ¹⁰=N—, —NR¹⁴—CZ⁹=CZ¹⁰—, —CZ⁸=CZ⁹—NR¹⁴—, —NR¹⁴—CZ⁹Z¹⁰—CZ¹¹Z¹²—CZ¹³Z¹⁴—, —CZ⁸Z⁹—NR¹⁴—CZ¹¹Z¹²—Z¹³Z¹⁴—, —CZ⁸Z⁹—CZ¹⁰Z¹¹—NR¹⁴—CZ¹³Z¹⁴—, —CZ⁸Z⁹—CZ¹⁰Z¹¹—CZ¹²Z¹³—NR¹⁴—, —NR¹⁴—CZ⁹=CZ¹⁰—CZ¹¹Z¹²—, —CZ⁸Z⁹—NR¹⁴—CZ¹¹=CZ¹²—, —CZ⁸=CZ⁹—NR¹⁴—CZ¹¹Z¹²—, —CZ⁸=CZ⁹—CZ¹⁰Z¹¹—NR¹⁴—, —CZ⁸Z⁹—CZ¹⁰=CZ¹¹Z¹²—NR¹⁴—, —N=CZ⁸—CZ⁹Z¹⁰—CZ¹¹Z¹²—, —CZ⁸Z⁹—N=CZ¹⁰—CZ¹¹Z¹²—, —CZ⁸Z⁹—CZ¹⁰Z¹¹—N=Z¹²—, —CZ⁸Z⁹—CZ¹⁰Z¹¹—Z¹²=N—, —CZ⁸=N—CZ⁹=CZ¹⁰—, —CZ⁸=CZ⁹—N=CZ¹⁰—, —CZ⁸=CZ⁹—CZ¹⁰=N—, —NR¹³—CO—NR¹⁴—, —NR¹³—CO—NR¹⁴—CZ¹⁰Z¹¹—, —CZ⁸Z⁹—NR¹³—CO—NR¹⁴—, —NR¹⁴—CO—N=CZ⁹—, —CZ⁸=N—CO—NR¹⁴—, —NR¹³—CZ⁹Z¹⁰—CO—NR¹⁴—, —NR¹³—CO—CZ⁹Z¹⁰—NR¹⁴—, —N=CZ⁸—CO—NR¹⁴—, —O—CO—NR¹⁴—, —CO—O—NR¹⁴—, —NR¹⁴—O—CO—, —NR¹⁴—CO—O—, —CO—O—, —CO—NR¹⁴—O—, —O—CO—NR¹⁴—CZ⁹Z¹⁰—, —O—CO—CZ⁸Z⁹—NR¹⁴—, —CO—O—NR¹⁴—CZ⁹Z¹⁰—, —CO—O—CZ⁸Z⁹—NR¹⁴—, —CZ⁸Z⁹—NR¹⁴—O—CO—, —CZ⁸Z⁹—CO—O—, —NH—C(=NR¹³)—NR¹⁴—, —O—CO—N=CZ⁸—, —CH₂—CZ⁸Z⁹—CZ¹⁰Z¹¹—CZ¹²Z¹³—, —CH₂—CZ⁸=CZ⁹CZ¹⁰=CZ¹¹—, —CH₂—CZ⁸Z⁹—CZ¹⁰Z¹¹—CZ¹²Z¹³—CZ¹⁴Z¹⁵—, —CH₂—CZ⁸Z⁹—CZ¹⁰=CZ¹¹—, —CH₂—CZ⁸=CZ⁹—CZ¹⁰—Z¹¹—, —CH₂—CZ⁸Z⁹—CZ¹⁰Z¹¹—CZ¹²=CZ¹³—, —CH₂—CZ⁸Z⁹—CZ¹⁰=CZ¹¹—CZ¹²Z¹³—, —CH₂—CZ⁸=CZ⁹—CZ¹⁰Z¹¹—CZ¹²Z¹³—, —CH₂—CZ⁸Z⁹—O—CZ¹⁰Z¹¹—, —CH₂—CZ⁸Z⁹—CZ¹⁰Z¹¹—O—CZ¹²Z¹³—, —CH₂—CZ⁸Z⁹—O—CZ¹⁰Z¹¹—CZ¹²Z¹³—, —CH₂—CZ⁸=Z⁹—O—CZ¹⁰Z¹¹—, —CH₂—CZ⁸Z⁹—O—CZ¹⁰Z¹¹—, —CH₂—O—CZ⁸Z⁹—CZ¹⁰Z¹¹—, —CH₂—CZ⁸Z⁹—CZ¹⁰Z¹¹—O—, —CH₂—O—CZ⁸Z⁹—CZ¹⁰=CZ¹¹—, —CH₂—CZ⁸=CZ⁹CZ¹⁰Z¹¹—O—, —CH₂—CZ⁸=CZ⁹CZ¹⁰Z¹¹—O—, —CH₂CO—CZ⁸Z⁹—CZ¹⁰Z¹¹—, —CH₂—CZ⁸Z⁹—CO—CZ¹⁰Z¹¹—, —CH₂—CZ⁸Z⁹—CZ¹⁰Z¹¹—CO—, —CH₂CO—CZ⁸=CZ⁹—, —CH₂—CZ⁸=Z⁹—CO—, —CH₂—CO—CZ⁸Z⁹—CZ¹⁰Z¹¹—Z¹²Z¹³—, —CH₂—CZ⁸Z⁹—CO—CZ¹⁰Z¹¹—Z¹²Z¹³—, —CH₂—CZ⁸Z⁹—CZ¹⁰Z¹¹—CO—CZ¹²Z¹³—, —CH₂—CZ⁸Z⁹—CZ¹⁰Z¹¹—CZ¹²Z¹³—CO—, —CH₂—CO—CZ⁸=CZ⁹—CZ¹⁰Z¹¹—, —CH₂—CZ⁸Z⁹—CO—CZ¹⁰Z¹¹—, —CH₂—CZ⁸=CZ⁹—CO—CZ¹⁰Z¹¹—, —CH₂—CZ⁸=CZ⁹—CZ¹⁰Z¹¹—CO—, —CH₂—CZ⁸Z⁹—Z¹⁰=CZ¹¹—CO—, —CH₂—CO—O—CZ⁸Z⁹—, —CH₂—CZ⁸Z⁹—CO—O—, —CH₂—CO—O—CZ⁸Z⁹—CZ¹⁰Z¹¹—, —CH₂—CZ⁸Z⁹—CO—O—CZ¹⁰Z¹¹—, —CH₂—CZ⁸Z⁹—CZ¹⁰Z¹¹—CO—O—, —CH₂—CO—O—CZ⁸=CZ⁹—, —CH₂—CZ⁸=CZ⁹—CO—O—, —CH₂—O—CO—CZ⁸Z⁹—, —CH₂—CZ⁸Z⁹—O—CO—, —CH₂—O—CO—CZ⁸Z⁹—CZ¹⁰Z¹¹—, —CH₂—CZ⁸Z⁹—O—CO—CZ¹⁰Z¹¹—, —CH₂—CZ⁸Z⁹—CZ¹⁰Z¹¹—O—CO—, —CH₂—CO—N=CZ⁸—, —CH₂—CZ⁸=CZ⁹—O—CO—, —CH₂—CO—NR¹⁴—CZ⁹Z¹⁰—, —CH₂—CO—CZ⁸Z⁹—NR¹⁴—, —CH₂—CO—CZ⁸=N—, —CH₂—CO—NZ⁸—CZ⁹Z¹⁰—CZ¹¹Z¹²—, —CH₂—CO—CZ⁸Z⁹—NR¹⁴—CZ¹¹Z¹²—, —CH₂—CO—CZ⁸Z⁹—CZ¹⁰Z¹¹—NR¹⁴—, —CH₂—CO—NR¹⁴—CZ⁹=CZ¹⁰—, —CH₂—NR¹⁴—CO—CZ⁹=CZ¹⁰—CO—, —CH₂—CO—CZ⁸=CZ⁹—NR¹⁴—, —CH₂—CO—N=CZ⁸—CZ⁹Z¹⁰—, —CH₂—CO—CZ⁸=N—CZ⁹Z¹⁰—, —CH₂—CO—CZ⁸Z⁹—N=CZ¹⁰—, —CH₂—CO—CZ⁸Z⁹—CZ¹⁰=N—, —CH₂—NR¹⁴—CO—CZ⁹Z¹⁰—, —CH₂—NR¹⁴—CZ⁹Z¹⁰—CO—, —CH₂—N=CZ⁸—CO—, —CH₂—NR¹⁴—CO—CZ⁹Z¹⁰—CZ¹¹Z¹²—, —CH₂—NR¹⁴—CZ⁹Z¹⁰—CO—CZ¹¹Z¹²—, —CH₂—NR¹⁴—CZ⁹Z¹⁰—CZ¹¹Z¹²—CO—, —CH₂—N=CZ⁸—CO—CZ⁹Z¹⁰—, —CH₂—N=CZ⁸—CZ¹⁰Z¹¹—CO—, —CH₂—NR¹⁴—CO—O—CZ⁹Z¹⁰—, —CH₂—NR¹⁴—CZ⁹Z¹⁰—CO—O—, —CH₂—CO—O—NR¹⁴—CZ⁹Z¹⁰—, —CH₂—N=CZ⁸—CO—O—, —CH₂—CO—O—N=CZ⁸—, —CH₂—NR¹⁴—O—CO—CZ⁹Z¹⁰—, —CH₂—NR¹⁴—CZ⁹Z¹⁰—O—CO—, —CH₂—O—CO—NR¹⁴—CZ⁹Z¹⁰—, —CH₂—NR¹⁴—O—CZ⁹Z¹⁰—CO—, —CH₂—N=CZ⁸—O—CO—, —CH₂—O—CO—N=CZ⁸—, —CH₂—NR¹⁴—CZ⁹Z¹⁰—CZ¹¹Z¹²—, —CH₂—CZ⁸Z⁹—NR¹⁴—CZ¹¹Z¹²—, —CH₂—CZ⁸Z⁹—CZ¹⁰Z¹¹—NR¹⁴—, —CH₂—NR¹⁴—CZ⁹=CZ¹⁰—, —CH₂—CZ⁸=CZ⁹—NR¹⁴—, —CH₂—N=CZ⁸—CZ⁹Z¹⁰—, —CH₂—CZ⁸Z⁹—N=CZ¹⁰—, —CH₂—CZ⁸Z⁹—CZ¹⁰=N—, —CH₂—NR¹⁴—CZ⁹=CZ¹⁰—, —CH₂—CZ⁸=CZ⁹—NR¹⁴—, —CH₂—NR¹⁴—CZ⁹Z¹⁰—CZ¹¹Z¹²—CZ¹³Z¹⁴—, —CH₂—CZ⁸Z⁹—NR¹⁴—CZ¹¹Z¹²—CZ¹³Z¹⁴—, —CH₂—CZ⁸Z⁹—CZ¹⁰Z¹¹—NR¹⁴—CZ¹³Z¹⁴—, —CH₂—NR¹⁴—CZ⁹=CZ¹⁰—, —CH₂CZ⁸=CZ⁹—NR¹⁴—, —CH₂—NR¹⁴—CZ⁹Z¹⁰—CZ¹¹Z¹²—CH₂—CZ⁸Z⁹—CZ¹⁰Z¹¹—CZ¹²Z¹³—NR¹⁴—, —CH₂—NR¹⁴—CZ⁹=CZ¹⁰—CZ¹¹Z¹²—, —CH₂—CZ⁸Z⁹—NR¹⁴—CZ¹¹=CZ¹²—, —CH₂—CZ⁸=CZ⁹—NR¹⁴—CZ¹¹Z¹²—, —CH₂—CZ⁸=CZ⁹—CZ¹⁰Z¹¹—NR¹⁴—, —CH₂—CZ⁸Z⁹—CZ¹⁰=CZ¹¹Z¹²—NR¹⁴—, —CH₂—N=CZ⁸—CZ⁹Z¹⁰—CZ¹¹Z¹²—, —CH₂—CZ⁸Z⁹—N=CZ¹⁰—CZ¹¹Z¹²—, —CH₂—N=CZ⁸—CO—NR¹⁴—, —CH₂—CZ⁸Z⁹—CZ¹⁰Z¹¹—N=CZ¹²—, —CH₂—CZ⁸Z⁹—CZ¹⁰Z¹¹—CZ¹²=N—, —CH₂—CZ⁸=N—CZ⁹=CZ¹⁰—, —CH₂—CZ⁸=CZ⁹N=CZ¹⁰—, —CH₂—CZ⁸=CZ⁹—N—, —CH₂—NR¹³—CO—NR¹⁴—, —CH₂—NR¹³—CO—NR¹⁴—CZ¹⁰Z¹¹—, —CH₂—CZ⁸Z⁹—NR¹³—CO—NR¹⁴—, —CH₂—NR¹⁴—CO—N=CZ⁹—, —CH₂—CZ⁸=N—CO—NR¹⁴—, —CH₂—NR¹³—CZ⁹Z¹⁰—CO—NR¹⁴—, —CH$_2$—O—CO—NR$^{14}$—, —CH$_2$—NR$^{13}$—CO—CZ$^9$Z$^{10}$—NR$^{14}$—, —CH$_2$—CO—O—NR$^{14}$—, —CH$_2$—NR$^{14}$—CO—, —CH$_2$—NR$^{14}$—CO—O—, —CH$_2$—CO—NR$^{14}$—O—, —CH$_2$—O—CO—NR$^{14}$—CZ$^9$Z$^{10}$—, —CH$_2$—O—CO—CZ$^8$Z$^9$—NR$^{14}$—, —CH$_2$—CO—O—NR$^{14}$—CZ$^9$Z$^{10}$—, —CH$_2$—CO—O—CZ$^8$Z$^9$—NR$^{14}$—, —CH$_2$—CZ$^8$Z$^9$—NR$^{14}$—O—CO—, —CH$_2$—CZ$^8$Z$^9$—NR$^{14}$—CO—O—, —CH$_2$NH—C(=NR$^{13}$)—NR$^{14}$—, —CH$_2$—O—CO—N=CZ$^8$—, —CZ$^8$Z$^9$—CZ$^{10}$Z$^{11}$—CZ$^{12}$Z$^{13}$—CH$_2$—, —CZ$^8$=CZ$^9$—CZ$^{10}$=CZ$^{11}$—CH$_2$—, —CZ$^8$Z$^9$—CZ$^{10}$Z$^{11}$—CZ$^{12}$Z$^{13}$—CZ$^{14}$Z$^{15}$—CH$_2$—, —CZ$^8$Z$^9$—CZ$^{10}$=CZ$^{11}$—CH$_2$—, —CZ$^8$=CZ$^9$—CZ$^{10}$Z$^{11}$—CH$_2$—, —CZ$^8$Z$^9$—CZ$^{10}$Z$^{11}$—CZ$^{12}$=CZ$^{13}$—CH$_2$—, —CZ$^8$Z$^9$—CZ$^{10}$=CZ$^{11}$—CZ$^{12}$Z$^{13}$—CH$_2$—, —CZ$^8$=CZ$^9$—CZ$^{10}$Z$^{11}$—CZ$^{12}$Z$^{13}$—CH$_2$—, —CZ$^8$Z$^9$—O—CZ$^{10}$Z$^{11}$—CH$_2$—, —CZ$^8$Z$^9$—CZ$^{10}$Z$^{11}$—O—CZ$^{12}$Z$^{13}$—CH$_2$—, —CZ$^8$Z$^9$—O—CZ$^{10}$Z$^{11}$—CZ$^{12}$Z$^{13}$—CH$_2$—, —CZ$^8$=CZ$^9$—O—CH$_2$—, —CZ$^8$=CZ$^9$—O—CZ$^{10}$Z$^{11}$—CH$_2$—, —CZ$^8$Z$^9$—O—CZ$^{10}$=CZ$^{11}$—CH$_2$—, —O—CZ$^8$Z$^9$—CZ$^{10}$Z$^{11}$—CH$_2$—, —CZ$^8$Z$^9$—CZ$^{10}$Z$^{11}$—O—CH$_2$—, —O—CZ$^8$=CZ$^9$—CH$_2$—, —O—CZ$^8$Z$^9$—CZ$^{10}$Z$^{11}$—CZ$^{12}$Z$^{13}$—CH$_2$—, —CZ$^8$Z$^9$—CZ$^{10}$Z$^{11}$—CZ$^{12}$Z$^{13}$—O—CH$_2$—, —O—CZ$^8$Z$^9$—CZ$^{10}$Z$^{11}$—CH$_2$—, —CZ$^8$Z$^9$—O—CZ$^{10}$=CZ$^{11}$—CH$_2$—, —CZ$^8$Z$^9$—CZ$^{10}$=CZ$^{11}$—O—CH$_2$—, —CZ$^8$Z$^9$—CZ$^{10}$Z$^{11}$—CO—CH$_2$—, —CO—CZ$^8$=CZ$^9$—CH$_2$—, —CZ$^8$=CZ$^9$—CZ$^{10}$Z$^{11}$—O—CH$_2$—, —CO—CZ$^8$Z$^9$—CZ$^{10}$Z$^{11}$—CH$_2$—, —CZ$^8$Z$^9$—CO—CZ$^{10}$Z$^{11}$—CH$_2$—, —CZ$^8$=CZ$^9$—CO—CH$_2$—, —CO—CZ$^8$Z$^9$—CZ$^{10}$Z$^{11}$—CZ$^{12}$Z$^{13}$—CH$_2$—, —CZ$^8$Z$^9$—CO—CZ$^{10}$Z$^{11}$—CZ$^{12}$Z$^{13}$—CH$_2$—, —CZ$^8$Z$^9$—CZ$^{10}$Z$^{11}$—CO—CZ$^{12}$Z$^{13}$—CH$_2$—, —CZ$^8$Z$^9$—CZ$^{10}$Z$^{11}$—CZ$^{12}$Z$^{13}$—CO—CH$_2$—, —CO—CZ$^8$=CZ$^9$—CZ$^{10}$Z$^{11}$—CH$_2$—, —CZ$^8$Z$^9$—CO—CZ$^{10}$=CZ$^{11}$—CH$_2$—, —CZ$^8$=CZ$^9$—CO—CZ$^{10}$Z$^{11}$—CH$_2$—, —CZ$^8$=CZ$^9$—CZ$^{10}$Z$^{11}$—CO—CH$_2$—, —CZ$^8$Z$^9$—CZ$^{10}$=CZ$^{11}$—CO—CH$_2$—, —CO—O—CZ$^8$Z$^9$—CH$_2$—, —CZ$^8$Z$^9$—CO—O—CH$_2$—, —CO—O—CZ$^8$Z$^9$CZ$^{10}$Z$^{11}$—CH$_2$—, —CZ$^8$Z$^9$—CO—O—CZ$^{10}$Z$^{11}$—CH$_2$—, —CZ$^8$Z$^9$—O—CO—CH$_2$—, —O—CO—CZ$^8$Z$^9$—CZ$^{10}$Z$^{11}$—CH$_2$—, —CZ$^8$Z$^9$—CZ$^{10}$Z$^{11}$—CO—O—CH$_2$—, —CO—O—CZ$^8$=CZ$^9$—CH$_2$—, —Z$^8$=CZ$^9$—CO—O—CH$_2$—, —O—CO—CZ$^8$Z$^9$—CH$_2$—, —CZ$^8$Z$^9$—O—CO—CZ$^{10}$Z$^{11}$—CH$_2$—, —CZ$^8$Z$^9$—CZ$^{10}$Z$^{11}$—O—CO—CH$_2$—, —O—CO—CZ$^8$=CZ$^9$—CH$_2$—, —CZ$^8$=CZ$^9$—O—CO—CH$_2$—, —CO—NR$^{14}$—CZ$^9$Z$^{10}$—CH$_2$—, —CO—CZ$^8$Z$^9$—NR$^{14}$—CH$_2$—, —CO—N=CZ$^8$—CH$_2$—, —CO—CZ$^8$=N—CH$_2$—, —CO—NZ$^8$—CZ$^9$Z$^{10}$—CZ$^{11}$Z$^{12}$—CH$_2$—, —CO—CZ$^8$Z$^9$—NR$^{14}$—CZ$^{11}$Z$^{12}$—CH$_2$—, —CO—CZ$^8$Z$^9$—CZ$^{10}$Z$^{11}$—NR$^{14}$—CH$_2$—, —NR$^{14}$—CZ$^9$Z$^{10}$—CO—CZ$^{11}$Z$^{12}$—CH$_2$—, —CO—NR$^{14}$—CZ$^9$=CZ$^{10}$—CH$_2$—, —CO—CZ$^8$=CZ$^9$—NR$^{14}$—CH$_2$—, —CO—N=CZ$^8$—CZ$^9$Z$^{10}$—CH$_2$—, —CO—CZ$^8$=N—CZ$^9$Z$^{10}$—CH$_2$—, —CO—CZ$^8$Z$^9$—N=CZ$^{10}$—CH$_2$—, —CO—CZ$^8$Z$^9$—CZ$^{10}$=N—CH$_2$—, —NR$^{14}$—CO—CZ$^9$Z$^{10}$—CH$_2$—, —NR$^{14}$—CZ$^9$Z$^{10}$—CO—CH$_2$—, —N=CZ$^8$—CO—CH$_2$—, —NR$^{14}$—CO—CZ$^9$Z$^{10}$—CZ$^{11}$Z$^{12}$—CH$_2$—, —NR$^{14}$—CZ$^9$Z$^{10}$—CZ$^{11}$Z$^{12}$—CO—CH$_2$—, —NR$^{14}$—CZ$^9$Z$^{10}$—CZ$^{11}$Z$^{12}$—CO—CH$_2$—, —NR$^{14}$—CO—CZ$^9$=CZ$^{10}$—CH$_2$—, —NR$^{14}$—CZ$^9$=CZ$^{10}$—CO—CH$_2$—, —N=CZ$^8$—CO—CZ$^9$Z$^{10}$—CH$_2$—, —N=CZ$^8$—CZ$^9$Z$^{10}$—CO—CH$_2$—, —NR$^{14}$—CO—O—CZ$^9$Z$^{10}$—CH$_2$—, —NR$^{14}$—CZ$^9$Z$^{10}$—CO—O—CH$_2$—, —N=CZ$^8$—CO—O—CH$_2$—, —CO—O—N=CZ$^8$—CH$_2$—, —NR$^{14}$—O—CO—CZ$^9$Z$^{10}$—CH$_2$—, —NR$^{14}$—CZ$^9$Z$^{10}$—O—CO—CH$_2$—, —O—CO—NR$^{14}$—CZ$^9$Z$^{10}$—CH$_2$—, —NR$^{14}$—O—CZ$^9$Z$^{10}$—CO—CH$_2$—, —N=CZ$^8$—O—CO—CH$_2$—, —O—CO—N=CZ$^8$—CH$_2$—, —NR$^{14}$—CZ$^9$Z$^{10}$—CZ$^{11}$Z$^{12}$—CH$_2$—, —CZ$^8$Z$^9$—NR$^{14}$—CZ$^{11}$Z$^{12}$—CH$_2$—, —CZ$^8$Z$^9$—CZ$^{10}$Z$^{11}$—NR$^{14}$—CH$_2$—, —NR$^{14}$—CZ$^9$=CZ$^{10}$—CH$_2$—, —CZ$^8$=CZ$^9$—NR$^{14}$—CH$_2$—, —N=CZ$^8$—CZ$^9$Z$^{10}$—CH$_2$—, —CZ$^8$Z$^9$—N=CZ$^{10}$—CH$_2$—, —CZ$^8$Z$^9$—CZ$^{10}$=N—CH$_2$—, —NR$^{14}$—CZ$^9$=CZ$^{10}$—CH$_2$—, —CZ$^{11}$Z$^{12}$—CZ$^{13}$Z$^{14}$—CH$_2$—, —CZ$^8$Z$^9$—CZ$^{10}$Z$^{11}$—NR$^{14}$—CZ$^{13}$Z$^{14}$—CH$_2$—, —CZ$^8$Z$^9$—CZ$^{10}$Z$^{11}$—CZ$^{12}$Z$^{13}$—NR$^{14}$—CH$_2$—, —NR$^{14}$—CZ$^9$=CZ$^{10}$—CZ$^{11}$Z$^{12}$—CH$_2$—, —CZ$^8$Z$^9$—NR$^{14}$—CZ$^{11}$=CZ$^{12}$—CH$_2$—, —CZ$^8$=CZ$^9$—NR$^{14}$—CZ$^{11}$Z$^{12}$—CH$_2$—, —CZ$^8$=CZ$^9$—CZ$^{10}$Z$^{11}$—NR$^{14}$—CH$_2$—, —CZ$^8$Z$^9$—CZ$^{10}$=CZ$^{11}$Z$^{12}$—CH$_2$—, —N=CZ$^8$—CZ$^9$Z$^{10}$—CZ$^{11}$Z$^{12}$—CH$_2$—, —CZ$^8$Z$^9$—N=CZ$^{10}$—CZ$^{11}$Z$^{12}$—CH$_2$—, —CZ$^8$Z$^9$—CZ$^{10}$Z$^{11}$—N=CZ$^{12}$—CH$_2$—, —NR$^{13}$—CO—CZ$^9$Z$^{10}$—NR$^{14}$—CH$_2$—, —CZ$^8$Z$^9$—CZ$^{10}$Z$^{11}$—CZ$^{12}$=N—CH$_2$—, —CZ$^8$=N—CZ$^9$=CZ$^{10}$—CH$_2$—, —CZ$^8$=CZ$^9$—N=CZ$^{10}$—CH$_2$—, —CZ$^8$=CZ$^9$—CZ$^{10}$=N—CH$_2$—, —NR$^{13}$—CO—NR$^{14}$—CH$_2$—, —NR$^{14}$—CO—O—CH$_2$—, —NR$^{13}$—CO—NR$^{14}$—CZ$^{10}$Z$^{11}$—CH$_2$—, —CZ$^8$Z$^9$—NR$^{13}$—CO—NR$^{14}$—CH$_2$—, —NR$^{14}$—CO—N=CZ$^9$—CH$_2$—, —CZ$^8$=N—CO—NR$^{14}$—CH$_2$—, —NR$^{13}$—CZ$^9$Z$^{10}$—CO—NR$^{14}$—CH$_2$—, —N=CZ$^8$—CO—NR$^{14}$—CH$_2$—, —O—CO—NR$^{14}$—CH$_2$—, —CO—O—NR$^{14}$—CH$_2$—, —NR$^{14}$—O—CO—CH$_2$—, —CO—NR$^{14}$—O—CH$_2$—, —O—CO—NR$^{14}$—CZ$^9$Z$^{10}$—CH$_2$—, —O—CO—CZ$^8$Z$^9$—NR$^{14}$—CH$_2$—, —CO—O—NR$^{14}$—CZ$^9$Z$^{10}$—CH$_2$—, —CO—O—CZ$^8$Z$^9$—NR$^{14}$—CH$_2$—, —CZ$^8$Z$^9$—NR$^{14}$—O—CO—CH$_2$—, —CZ$^8$Z$^9$—NR$^{14}$—CO—O—CH$_2$—, —NH—C(=NR$^{13}$)—NR$^{14}$—CH$_2$—, or —O—CO—N=CZ$^8$CH$_2$—.

If R$^{11}$ and R$^{12}$ are joined together, they form a ring system and especially a four-membered, five-membered or a six-membered ring system together with the atoms to which they are attached. Preferred ring systems are five-membered cyclocarbamates, five-membered cyclic ureas, five-membered cyclic guanidines, six-membered cyclocarbamates, six-membered cyclic ureas, six-membered cyclic guanidines, pyrrolidones, pyridones, piperidinones, imidazoles, imidazolines, pyrrolines, imidazolidin-2-ones.

R$^3$ together with R$^4$ can form a carbocyclic or heterocyclic 4-, 5-, 6- or 7-membered ring with the two carbon atoms of the benzo ring to which R$^3$ and R$^4$ are attached and that 4-, 5-, 6- or 7-membered ring can be partly saturated or unsaturated and can be substituted with 1 to 4 substituents selected from Z$^1$, Z$^2$, Z$^3$ and Z$^4$. Z$^1$ and Z$^2$ if attached to the same carbon atom can together represent =O to form a carbonyl group with the carbon atom to which Z$^1$ and Z$^2$ are attached, so that so a ring has one carbonyl group and may comprise one or two further residues which are not allowed to form a carbonyl group together.

Partly saturated as used herein means that the ring system additionally formed by joining R$^3$ with R$^4$ when taken alone already bears one double bond originated in the phenyl ring to which R$^3$ and R$^4$ are attached. Thus, since R$^3$ and R$^4$ are attached to a phenyl ring a double bond equivalent exists between the two carbonatoms that bear R$^3$ and R$^4$, respectively. Therefore, the person skilled in the art will understand that the ring system formed when R$^3$ and R$^4$ are joined together can not be a saturated ring system, but a partly saturated ring system when the moiety introduces at least one saturated atom or two subsequent saturated bonds.

Preferably R$^{10}$, R$^{16}$ and R$^{17}$ are selected from the following group of substituents: —H, —CH$_3$, —C$_2$H$_5$, —C$_3$H$_7$, —CF$_3$,

cyclo-$C_3H_5$, cyclo-$C_4H_7$, cyclo-$C_5H_9$, cyclo-$C_6H_{11}$, cyclo-$C_7H_{13}$, —CH($CH_3$)$_2$, —$C_4H_9$, —$CH_2$—CH($CH_3$)$_2$, —CH($CH_3$)—$C_2H_5$, —C($CH_3$)$_3$, —$C_5H_{11}$, —CH($CH_3$)—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —CH($C_2H_5$)$_2$, —$C_2H_4$—CH($CH_3$)$_2$, —$C_6H_{13}$, —$C_7H_{15}$, —$C_8H_{17}$, -Ph, —$CH_2$-Ph, —$CH_2$—$CH_2$-Ph, —$CH_2$—CH=$CH_2$, —C($CH_3$)=$CH_2$, —$C_2H_4$—CH=$CH_2$, —$CH_2$—CH=CH—$CH_3$, —$CH_2$—C($CH_3$)=$CH_2$, —CH($CH_3$)—CH=CH, —C($CH_3$)=CH—$CH_3$, —$CH_2$—C≡CH, —$C_2H_4$—C≡CH, —$CH_2$—C≡C—$CH_3$, —$C_2H_4$—$OCF_3$, —$C_3H_6$—$OCF_3$, —$C_2H_4$—$OCH_3$, —$C_3H_6$—$OCH_3$, —$CH_2$—$OC_2H_5$, —$C_3H_6$—$OC_2H_5$, and also preferably from the following group of substituents: —$C_2H_5$,

cyclo-$C_3H_5$, cyclo-$C_4H_7$, cyclo-$C_5H_9$, cyclo-$C_6H_{11}$, —$C_3H_7$, —$CF_3$, —CH($CH_3$)$_2$, —$C_4H_9$, —$CH_2$—CH($CH_3$)$_2$, —CH($CH_3$)—$C_2H_5$, —C($CH_3$)$_3$, —$C_5H_{11}$, —CH($CH_3$)—$C_3H_7$, —CH($CH_3$)—CH($CH_3$)$_2$, —C($CH_3$)$_2$—$C_2H_5$, —$CH_2$—CH=$CH_2$, —C($CH_3$)=$CH_2$, —CH($CH_3$)—CH=CH, —C($CH_3$)=CH—$CH_3$, —$CH_2$—C≡CH, and more preferably from the following group of substituents: —$C_2H_5$, —$C_3H_7$, —CH($CH_3$)$_2$, —$C_4H_9$, —CH($CH_3$)—$C_2H_5$, —C($CH_3$)$_3$,

cyclo-$C_3H_5$, cyclo-$C_4H_7$, cyclo-$C_5H_9$, cyclo-$C_6H_{11}$, —CH($CH_3$)—$C_3H_7$, —CH($CH_3$)—CH($CH_3$)$_2$, —C($CH_3$)$_2$—$C_2H_5$, —$CH_2$—CH=$CH_2$, —C($CH_3$)=$CH_2$, —CH($CH_3$)—CH=CH, —C($CH_3$)=CH—$CH_3$, —$CH_2$—C≡CH, and still more preferably from the following group of substituents: —$C_2H_5$, —$C_3H_7$, —CH($CH_3$)$_2$, —CH($CH_3$)—$C_2H_5$, —C($CH_3$)$_3$, cyclo-$C_4H_7$, cyclo-$C_5H_9$, cyclo-$C_6H_{11}$,

—C($CH_3$)$_2$—$C_2H_5$, —C($CH_3$)=$CH_2$, —CH($CH_3$)—CH=CH, —C($CH_3$)=CH—$CH_3$, and even still more preferably from the following group of substituents: —$C_2H_5$, —CH($CH_3$)$_2$, —CH($CH_3$)—$C_2H_5$, —C($CH_3$)$_3$, cyclo-$C_4H_7$, cyclo-$C_5H_9$, cyclo-$C_6H_{11}$, —C($CH_3$)$_2$—$C_2H_5$, and most preferably from the following group of substituents: —CH($CH_3$)$_2$, cyclo-$C_4H_7$, cyclo-$C_5H_9$.

$R^4$-$R^7$ represent independently of each other —H, —F, —Cl, —$CH_3$; preferably —H or —F.

$R^8$ represents preferably —($CH_2$)$_p$—$NH_2$, —($CH_2$)$_p$—N($R^{16}R^{17}$), $C_3$-$C_8$-cycloalkyl, $C_7$-$C_{16}$-spiroalkyl, $C_1$-$C_9$-heterocyclyl, $C_5$-$C_{14}$-spiroheterocyclyl, wherein the afore-mentioned residues are linked through a ring carbon atom and can be substituted with 1 to 3 substituents selected from $Z^5$, $Z^6$ and $Z^7$;

$R^8$ represents more preferably $C_3$-$C_8$-cycloalkyl, substituted $C_3$-$C_8$-cycloalkyl, $C_7$-$C_{16}$-spiroalkyl, substituted $C_7$-$C_{16}$-spiroalkyl, $C_1$-$C_9$-heterocyclyl, substituted $C_1$-$C_9$-heterocyclyl, $C_5$-$C_{14}$-spiroheterocyclyl, substituted $C_5$-$C_{14}$-spiroheterocyclyl, wherein the afore-mentioned substituted residues are linked through a ring carbon atom and can be substituted with 1 to 3 substituents selected from $Z^5$, $Z^6$ and $Z^7$, $R^8$ represents most preferably piperidinyl, morpholinyl, piperazinyl, pyranyl, pyrrolidinyl, iminopropylenyl, pyridyl and cyclohexyl, wherein the afore-mentioned substituted residues are linked through a ring carbon atom and can be substituted with 1 to 3 substituents selected from $Z^5$, $Z^6$ and $Z^7$.

$R^9$ represents preferably —$R^8$, $C_1$-$C_9$-nitrogenheterocyclyl, $C_5$-$C_{14}$-spironitrogenheterocyclyl, wherein the afore-mentioned nitrogenheterocyclyl and spironitrogencyclyl residues are linked through a ring nitrogen atom and can be substituted with 1 to 3 substituents selected from $Z^5$, $Z^6$ and $Z^7$.

$R^9$ represents more preferably $C_1$-$C_9$-nitrogenheterocyclyl, substituted $C_1$-$C_9$-nitrogenheterocyclyl, $C_5$-$C_{14}$-spironitrogenheterocyclyl, substituted $C_5$-$C_{14}$-spironitrogenheterocyclyl, wherein the afore-mentioned nitrogenheterocyclyl and spironitrogencyclyl residues are linked through a ring nitrogen atom and can be substituted with 1 to 3 substituents selected from $Z^5$, $Z^6$ and $Z^7$.

$R^9$ represents most preferably piperidinyl, morpholinyl, piperazinyl, pyrrolidinyl and iminopropylenyl, wherein the afore-mentioned nitrogenheterocyclyl and spironitrogencyclyl residues are linked through a ring nitrogen atom and can be substituted with 1 to 3 substituents selected from $Z^5$, $Z^6$ and $Z^7$.

In another preferred embodiment of the present invention substituent $R^2$ represents -Q-($CH_2$)$_n$—$R^8$, —($CH_2$)$_m$—NH—($CH_2$)$_n$—$R^8$, —($CH_2$)$_m$—NH—($CH_2$)$_n$—$R^9$, -Q-($CH_2$)$_n$—$R^8$, —($CH_2$)$_n$—$R^8$, —CO—NH—($CH_2$)$_n$—$R^8$, —($CH_2$)$_n$—$NR^{10}$—($CH_2$)$_n$—$R^8$, —CO—$NR^{10}$—($CH_2$)$_n$—$R^8$, —$R^8$, -Q-$R^8$, —$R^9$, -Q-($CH_2$)$_n$—$R^9$, —($CH_2$)$_n$—$R^9$, —($CH_2$)$_n$—NH—$R^8$, —($CH_2$)$_m$—NH—($CH_2$)$_n$—$R^9$, —CO—NH—($CH_2$)$_n$—$NH_2$, —CO—NH—($CH_2$)$_n$—$R^9$, —CO—$R^9$, —SO—$R^9$, —($CH_2$)$_n$—$NR^{10}$—$R^8$, —($CH_2$)$_m$—$NR^{10}$—($CH_2$)$_n$—$R^9$, —CO—$NR^{10}$—($CH_2$)$_n$—$R^9$, —($CH_2$)$_a$-(Q)$_b$-($CH_2$)$_c$-($G^1$)$_d$-($CH_2$)$_e$-($G^2$)$_f$-($CH_2$)$_g$—$R^8$, —($CH_2$)$_a$-(Q)$_b$-($CH_2$)$_c$-($G^1$)$_d$-($CH_2$)$_e$-($G^2$)$_f$-$CH_2$—$R^9$; and more preferably $R^2$ represents -Q-($CH_2$)$_n$—$R^8$, —($CH_2$)$_m$—NH—($CH_2$)$_n$—$R^8$, —($CH_2$)$_m$—NH—($CH_2$)$_n$—$R^8$, -Q-($CH_2$)$_n$—$R^8$, —($CH_2$)$_n$—$R^8$, —CO—NH—($CH_2$)$_n$—$R^8$, —($CH_2$)$_m$—$NR^{10}$—($CH_2$)$_n$—$R^8$, —CO—$NR^{10}$—($CH_2$)$_n$—$R^8$, —$R^8$, -Q-$R^8$, —$R^9$, -Q-($CH_2$)$_n$—$R^9$, —($CH_2$)$_n$—$R^9$, —($CH_2$)$_n$—NH—$R^8$, —($CH_2$)$_m$—NH—($CH_2$)$_n$—$R^9$, —CO—NH—($CH_2$)$_n$—$NH_2$, —CO—NH—($CH_2$)$_n$—$R^9$, —CO—$R^9$, —SO—$R^9$, —($CH_2$)$_n$—$NR^{10}$—$R^8$, —($CH_2$)$_m$—$NR^{10}$—($CH_2$)$_n$—$R^9$, —CO—$NR^{10}$—($CH_2$)$_n$—$R^9$. This is especially the case, if substituent $R^9$ does not include the substituent $R^8$.

$R^{11}$, $R^{12}$, $R^{13}$, $R^{14}$ and $R^{15}$ represent independently of each other —H, linear or branched $C_1$-$C_8$-alkyl, $C_3$-$C_8$-cycloalkyl, $C_1$-$C_9$-heterocyclyl, linear or branched $C_2$-$C_8$-alkenyl, linear or branched $C_2$-$C_8$-alkynyl, $C_6$-$C_{14}$-aryl, $C_1$-$C_{10}$-heteroaryl, wherein the afore-mentioned residues can be substituted with 1 to 5 substituents selected from $Z^8$, $Z^9$, $Z^{10}$, $Z^{11}$ and $Z^{12}$.

$R^{11}$, $R^{12}$, $R^{13}$, $R^{14}$ and $R^{15}$ preferably represent independently of each other —H, methyl, isopropyl and pyrrolidinyl.

As used herein linear $C_1$-$C_8$-alkyl refers to —$CH_3$, —$C_2H_5$, —$C_3H_7$, —$C_4H_9$, —$C_5H_{11}$, —$C_6H_{13}$, —$C_7H_{15}$, —$C_8H_{17}$, —$CH_2$-Ph, —$CH_2$—$CH_2$-Ph, wherein these residues can be substituted with 1 to 5 substituents selected from $Z^8$, $Z^9$, $Z^{10}$, $Z^{11}$ and $Z^{12}$. However it is clear to a skilled person that the term "can be substituted" refers to the replacement of a hydrogen atom by one of the substituents $Z^8$, $Z^9$, $Z^{10}$, $Z^{11}$ or $Z^{12}$. Moreover it is clear to a skilled person that only these hydrogen atoms which are present in the residue can be replaced by the substituents $Z^8$, $Z^9$, $Z^{10}$, $Z^{11}$ and $Z^{12}$. Thus, since the methyl group has only three hydrogen atoms, only three hydrogen atoms can be replaced by three substituents selected from $Z^8$, $Z^9$, $Z^{10}$, $Z^{11}$ and $Z^{12}$. For the definitions used herein the alkylaryl group —$CH_2$-Ph (benzyl group) and the —$CH_2$—$CH_2$-Ph group should fall under the definition "linear $C_1$-$C_8$-alkyl".

The term "substituted" as used herein further indicates that the substituted residue like "substituted linear $C_1$-$C_8$-alkyl" does definitely have at least one substituent (at least one Z substituent) while the residue without the term "substituted" like "linear $C_1$-$C_8$-alkyl" can have at least one substituent. Consequently, if the term "substituted" is not used in relation to a residue this does not indicate that this residue is unsubstituted.

Examples of preferred substituted linear $C_1$-$C_8$-alkyl residues are —$CH_2$—OH, —$CH_2$—O—$CH_3$, —$CH_2$—$OCF_3$, —$CF_3$, —$CH_2Cl$, —$CH_2CH_2Cl$, —$CH_2CH_2$—$OCF_3$, and —$CH_2$-Ph.

As used herein branched $C_1$-$C_8$-alkyl or preferably branched $C_3$-$C_8$-alkyl refers to —$CH(CH_3)_2$, —$CH_2$—$CH(CH_3)_2$, —$CH(CH_3)$—$C_2H_5$, —$C(CH_3)_3$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$CH(C_2H_5)_2$, —$C_2H_4$—$CH(CH_3)_2$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —$C_4H_8$—$CH(CH_3)_2$, —$C_3H_6$—$CH(CH_3)$—$C_2H_5$, —$C_3H_6$—$CH(CH_3)$—$C_2H_5$, —$C_2H_4$—$CH(CH_3)$—$C_3H_7$, —$CH_2$—$CH(CH_3)$—$C_4H_9$, —$CH(CH_3)$—$C_5H_{11}$, —$CH(C_2H_5)$—$C_4H_9$, —$C_2H_4$—$CH(CH_3)$—$C_3H_7$, —$CH_2$—$CH(C_2H_5)$—$C_3H_7$, —$CH_2$—$CH(CH_3)$—$C_4H_9$, —$CH_2$—$CH(CH_3)$—$CH_2$—$CH(CH_3)_2$, —$CH(C_2H_5)$—$CH_2$—$CH(CH_3)_2$, —$CH(CH_3)$—$C_2H_4$—$CH(CH_3)_2$, —$CH(CH_3)$—$CH_2$—$CH(CH_3)$—$C_2H_5$, —$CH_2$—$CH(CH_3)$—$CH(CH_3)$—$C_2H_5$, —$CH(CH_3)$—$CH_2$—$CH(CH_3)$—$C_2H_5$, —$CH(CH_3)$—$CH(C_2H_5)$—$C_2H_5$, —$CH(C_2H_5)$—$CH$ ($CH_3$)—$C_2H_5$, —$CH(CH_3)$—$CH(CH_3)$—$C_3H_7$, —$C_2H_4$—$CH(CH_3)$—$CH(CH_3)_2$, —$CH_2$—$CH(CH_3)$—$CH_2$—$CH(CH_3)_2$, —$CH_2$—$CH(CH_3)$—$CH_2$—$CH$ ($CH_3$)—$CH(CH_3)_2$, —$CH_2$—$CH$ ($CH_3$)—$C_2H_5$, —$CH_2$—$C(CH_3)(C_2H_5)_2$, —$CH_2$—$C(CH_3)_2$—$C_3H_7$, —$CH_2$—$C(CH_3)_2$—$C_3H_7$, —$C(CH_3)(C_2H_5)$—$C_3H_7$, —$C(CH_3)_2$—$C_4H_9$, —$CH_2$—$C(CH_3)_2$—$CH(CH_3)_2$, —$C(CH_3)(C_2H_5)$—$CH(CH_3)_2$, —$C(CH_3)_2$—$CH_2$—$CH$ ($CH_3$)$_2$, —$C(CH_3)_2$—$C(CH_3)_3$, —$C(CH_3)_2$—$CH(CH_3)$—$C_2H_5$, —$C_2H_4$—$C(CH_3)_2$—$C_2H_5$, —$CH_2$—$CH(CH_3)$—$C(CH_3)_3$, —$C(C_2H_5)_3$—$C(CH_3)_3$, —$CH(CH_3)$—$CH_2$—$C(CH_3)_3$, —$CH(CH_3)$—$C(CH_3)_2$—

—$C_2H_5$, —$C_5H_{10}$—$CH(CH_3)_2$, —$C_4H_8$—$C(CH_3)_3$, —$C_4H_8$—$CH(CH_3)$—$C_2H_5$, —$C_4H_8$—$CH(CH_3)$—$C_2H_5$, —$C_4H_8$—$C(CH_3)_2$—$C_2H_5$, —$C_3H_6$—$CH(C_2H_5)$—$C_2H_5$, —$C_3H_6$—$C(CH_3)_2$—$C_2H_5$, —$C_3H_6$—$CH(C_2H_5)$—$C_2H_5$, —$C_3H_6$—$CH(CH_3)$—$C_3H_7$, —$C_2H_4$—$C(CH_3)_2$—$C_3H_7$, —$C_2H_4$—$CH(C_2H_5)$—$C_3H_7$, —$C_2H_4$—$CH(CH_3)$—$C_4H_9$, —$CH_2$—$C(CH_3)_2$—$C_4H_9$, —$CH_2$—$CH(C_2H_5)$—$C_4H_9$, —$CH_2$—$CH(CH_3)$—$C_5H_{11}$, —$C(CH_3)_2$—$C_5H_{11}$, —$CH$ ($CH_3$)—$C_6H_{13}$, —$CH(C_3H_7)$—$C_4H_9$, —$CH(C_2H_5)$—$C_5H_{11}$, —$CH_2$—$C(CH_3)(C_2H_5)$—$C_3H_7$, —$C_2H_4$—$CH$ ($CH_3$)—$CH_2$—$CH(CH_3)_2$, —$CH_2$—$C(CH_3)_2$—$CH_2$—$CH$ ($CH_3$)$_2$, —$CH_2$—$CH(C_2H_5)$—$CH_2$—$CH(CH_3)_2$, —$CH_2$—$CH(CH_3)$—$C_2H_4$—$CH(CH_3)_2$, —$CH_2$—$CH(CH_3)$—$CH_2$—$CH(CH_3)$—$C_2H_5$, —$C(CH_3)(C_2H_5)$—$CH_2$—$CH(CH_3)_2$, —$CH$ ($C_3H_7$)—$CH_2$—$CH(CH_3)_2$, —$CH(C_2H_5)$—$C_2H_4$—$CH$ ($CH_3$)$_2$, —$CH(C_2H_5)$—$CH_2$—$C(CH_3)_3$, —$CH(C_2H_5)$—$CH_2$—$CH(CH_3)$—$C_2H_5$, —$CH_2$—$CH(CH_3)$—$C_2H_4$—$CH$ ($CH_3$)$_2$, —$C(CH_3)_2$—$C_2H_4$—$CH(CH_3)_2$, —$CH(C_2H_5)$—$C_2H_4$—$CH(CH_3)_2$, —$CH(CH_3)$—$C_3H_6$—$CH(CH_3)_2$, —$CH$ ($CH_3$)—$C_2H_4$—$C(CH_3)_3$, —$CH(CH_3)$—$C_2H_4$—$CH$ ($CH_3$)—$C_2H_5$, —$CH_2$—$CH(CH_3)$—$CH_2$—$CH(CH_3)$—$C_2H_5$, —$C(CH_3)_2$—$CH_2$—$CH(CH_3)$—$C_2H_5$, —$CH$ ($CH_3$)—$C_2H_4$—$CH(CH_3)$—$C_2H_5$, —$CH(CH_3)$—$CH_2$—$C(CH_3)_2$—$C_2H_5$, —$CH(CH_3)$—$CH_2$—$CH(CH_3)$—$C_3H_7$, —$C_2H_4$—$CH(CH_3)$—$CH(CH_3)$—$C_2H_5$, —$CH_2$—$C(CH_3)_2$—$CH(CH_3)$—$C_2H_5$, —$CH_2$—$CH(C_2H_5)$—$CH(CH_3)_2$, —$CH(CH_3)$—$CH_2$—$CH(CH_3)$—$CH(CH_3)$—$C_2H_5$, —$CH_2$—$CH(CH_3)$—$C(CH_3)_2$—$C_2H_5$, —$CH_2$—$CH$ ($CH_3$)—$CH(C_2H_5)_2$, —$C_3H_6$—$CH(CH_3)$—$CH(CH_3)_2$, —$C_2H_4$—$C(CH_3)_2$—$CH(CH_3)_2$, —$C_2H_4$—$CH(C_2H_5)$—$CH(CH_3)_2$, —$C_2H_4$—$CH(CH_3)$—$C(CH_3)_3$, —$C_2H_4$—$CH$ ($CH_3$)—$CH(CH_3)$—$C_2H_5$, —$C_3H_6$—$C(CH_3)_2$—$C_2H_5$, —$C_2H_4$—$C(CH_3)_2$—$C_3H_7$, —$CH_2$—$C(CH_3)(C_2H_5)_2$, —$C_2H_4$—$C(C_2H_5)_3$, —$C_2H_4$—$C(CH_3)_2$—$C_3H_7$, —$CH_2$—$C(CH_3)_2$—$C_4H_9$, —$C(C_2H_5)_2$—$C_3H_7$, —$C(CH_3)(C_3H_7)$—$C_3H_7$, —$C(CH_3)(C_2H_5)$—$C_4H_9$, —$C(CH_3)(C_2H_5)$—$C_4H_9$, —$C(CH_3)_2$—$C_5H_{11}$, —$C_2H_4$—$C(CH_3)_2$—$CH(CH_3)_2$, —$CH_2$—$C(CH_3)_2$—$C(CH_3)_3$, —$C(C_2H_5)_2$—$CH(CH_3)_2$, —$C(CH_3)(C_3H_7)$—$CH(CH_3)_2$, —$C(CH_3)(C_2H_5)$—$C(CH_3)_3$, —$CH_2$—$C(CH_3)_2$—$CH_2$—$CH(CH_3)_2$, —$C(CH_3)_2$—$C_2H_4$—$CH(CH_3)_2$, —$C(CH_3)_2$—$CH_2$—$C$ ($CH_3$)$_3$, —$CH_2$—$C(CH_3)_2$—$C(CH_3)_3$, —$C_4H_8$—$C(CH_3)_3$, —$C_3H_6$—$C(CH_3)_2$—$C_2H_5$, —$C_2H_4$—$C(CH_3)_2$—$C_3H_7$, —$C_2H_4$—$CH(CH_3)$—$C(CH_3)_3$, —$CH_2$—$C(CH_3)_2$—$C$ ($CH_3$)$_3$, wherein these residues can be substituted with 1 to 5 substituents selected from $Z^8$, $Z^9$, $Z^{10}$, $Z^{11}$ and $Z^{12}$. However it is clear to a skilled person that the term "can be substituted" refers to the replacement of a hydrogen atom by one of the substituents $Z^8$, $Z^9$, $Z^{10}$, $Z^{11}$ or $Z^{12}$. The carbon atom number of $C_1$-$C_8$ refers only to the carbon atoms of the alkyl residue and does not include the carbon atoms of the substituents $Z^8$ to $Z^{12}$.

Examples of preferred substituted branched $C_1$-$C_8$-alkyl or preferably branched $C_3$-$C_8$-alkyl residues are —$CH(CH_2Cl)_2$, —$CH(CH_3)$—$C_2H_4$—$OCF_3$, —$C(CH_3)_2$—$CF_3$, —$COCH_3(CH_3)_2$—, —$CHCH_3Cl$, —$CH_2$—$CHCH_3NH_2$, —$CClCH_3$—$C_2H_5$, —$C(CH_3)_2OH$, —$CClCH_3$—$C_3H_7$, —$CH_2$—$C(OH)(CH_3)$—$C_2H_5$, —$CH(CH_3)$—$CHCH_3Cl$, —$C(CH_3)_2$—$C_2H_4NH_2$, —$CH_2$—$C(CH_3)_2O$ H, —$CNH_2$ ($C_2H_5)_2$, —$C_2H_4$—$COH(CH_3)_2$, —$C_3H_6$—$CON(CH_3)_2$.

As defined above, the term "substituted" in "substituted branched $C_3$-$C_8$-alkyl" indicated that definitely at least one substituent is present while the term "branched $C_3$-$C_8$-alkyl" only defines that the carbon chain is branched but does not exclude further substituents. Consequently it is stated above that the "branched $C_3$-$C_8$-alkyl" residues can be substituted with 1 to 5 substituents selected from $Z^8$, $Z^9$, $Z^{10}$, $Z^{11}$ and $Z^{12}$. Thus, for instance, the "substituted branched $C_3$-$C_8$- alkyl" residues are a subgroup of the "branched $C_3$-$C_8$-alkyl" residues. The same applies to the other residues which are mentioned with the term "substituted" and without the term "substituted".

As used herein, $C_3$-$C_8$-cycloalkyl refers to cyclo-$C_3H_5$, cyclo-$C_4H_7$, cyclo-$C_5H_9$, cyclo-$C_6H_{11}$, cyclo-$C_7H_{13}$, and cyclo-$C_8H_{15}$, wherein these residues can be substituted with 1 to 5 substituents selected from $Z^8$, $Z^9$, $Z^{10}$, $Z^{11}$ and $Z^{12}$. However it is clear to a skilled person that the term "can be substituted" refers to the replacement of a hydrogen atom by one of the substituents $Z^8$, $Z^9$, $Z^{10}$, $Z^{11}$ or $Z^{12}$. The carbon atom number of $C_3$-$C_8$ refers only to the carbon atoms of the cycloalkyl residue and does not include the carbon atoms of the substituents $Z^8$ to $Z^{12}$.

Examples of preferred substituted $C_3$-$C_8$-cycloalkyl residues are

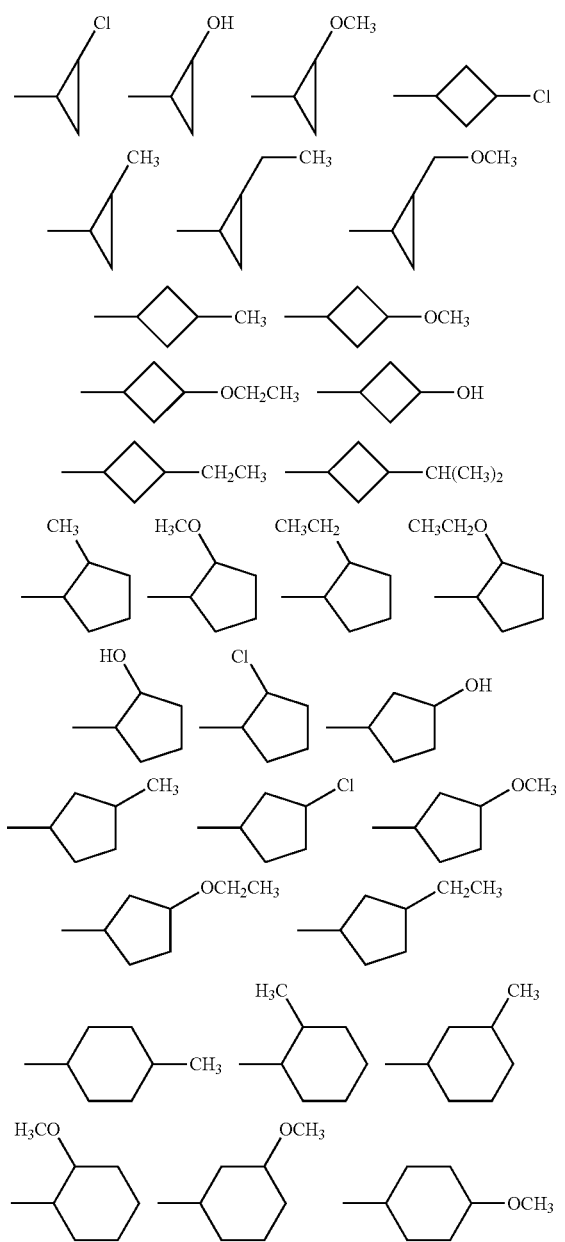

-continued

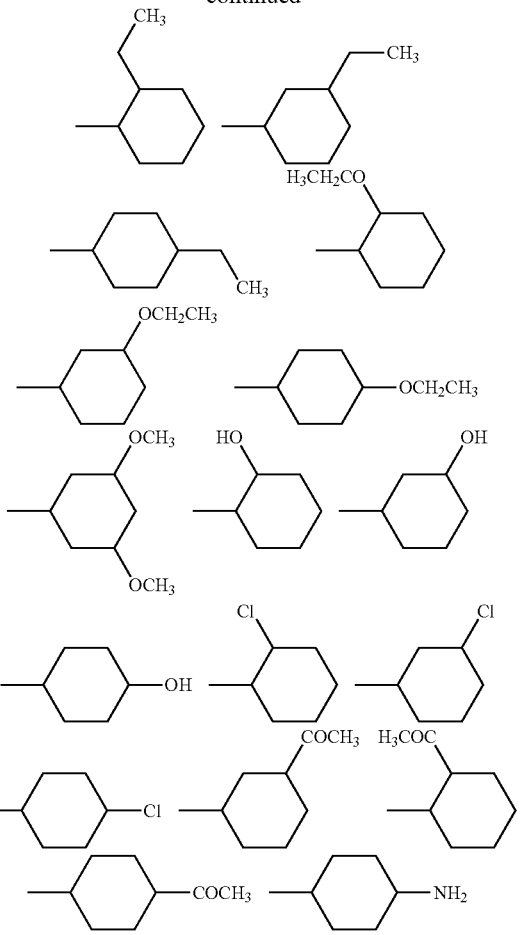

As used herein, the term "linear or branched $C_2$-$C_8$-alkenyl" refers to —CH=$CH_2$, —$CH_2$—CH=$CH_2$, —C($CH_3$)=$CH_2$, —CH=CH—$CH_3$, —$C_2H_4$—CH=$CH_2$, —CH=CH—$C_2H_5$, —$CH_2$—C($CH_3$)=$CH_2$, —CH($CH_3$)—CH=CH, —CH=C($CH_3$)$_2$, —C($CH_3$)=CH—$CH_3$, —CH=CH—CH=$CH_2$, —$C_3H_6$—CH=$CH_2$, —$C_2H_4$—CH=CH—$CH_3$, —$CH_2$—CH=CH—$C_2H_5$, —CH=CH—$C_3H_7$, —$CH_2$—CH=CH—CH=$CH_2$, —CH=CH—CH=CH—$CH_3$, —CH=CH—$CH_2$—CH=$CH_2$, —C($CH_3$)=CH—CH=$CH_2$, —CH=C($CH_3$)—CH=$CH_2$, —CH=CH—C($CH_3$)=$CH_2$, —$C_2H_4$—C($CH_3$)=$CH_2$, —$CH_2$—CH($CH_3$)—CH=$CH_2$, —CH($CH_3$)—$CH_2$—CH=$CH_2$, —$CH_2$—CH=C($CH_3$)$_2$, —$CH_2$—C($CH_3$)=CH—$CH_3$, —CH($CH_3$)—CH=CH—$CH_3$, —CH=CH—CH($CH_3$)$_2$, —CH=C($CH_3$)—$C_2H_5$, —C($CH_3$)=CH—$C_2H_5$, —C($CH_3$)=C($CH_3$)$_2$, —C($CH_3$)$_2$—CH=$CH_2$, —CH($CH_3$)—C($CH_3$)=$CH_2$, —C($CH_3$)=CH—CH=$CH_2$, —CH=C($CH_3$)—CH=$CH_2$, —CH=CH—C($CH_3$)=$CH_2$, —$C_4H_8$—CH=$CH_2$, —$C_3H_6$—CH=CH—$CH_3$, —$C_2H_4$—CH=CH—$C_2H_5$, —$CH_2$—CH=CH—$C_3H_7$, —CH=CH—$C_4H_9$, —$C_3H_6$—C($CH_3$)=$CH_2$, —$C_2H_4$—CH($CH_3$)—CH=$CH_2$, —$CH_2$—CH($CH_3$)—$CH_2$—CH=$CH_2$, —$CH_2$—CH=CH—$CH_3$, —CH($CH_3$)—$C_2H_4$—CH=$CH_2$, —$C_2H_4$—CH=C($CH_3$)$_2$, —$C_2H_4$—C($CH_3$)=CH—$CH_3$, —$CH_2$—CH($CH_3$)—CH=CH—$CH_3$, —CH($CH_3$)—$CH_2$—CH=CH—$CH_3$, —C($C_4H_9$)=$CH_2$, —$CH_2$—CH=CH—CH($CH_3$)$_2$, —$CH_2$—CH=C($CH_3$)—$C_2H_5$, —$CH_2$—C($CH_3$)=CH—$C_2H_5$, —CH($CH_3$)—

—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —CH(CH$_3$)—CH$_2$—C(CH$_3$)=CH$_2$, —CH(CH$_3$)—CH(CH$_3$)—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_3$H$_7$)=CH—CH$_3$, —C(C$_2$H$_5$)=CH—C$_2$H$_5$, —C(C$_2$H$_5$)=C(CH$_3$)$_2$, —C[C(CH$_3$)$_3$]=CH$_2$, —C[CH(CH$_3$)(C$_2$H$_5$)]=CH$_2$, —C[CH$_2$—CH(CH$_3$)$_2$]=CH$_2$, —C$_2$H$_4$—CH=CH—CH=CH$_2$, —CH$_2$—CH=CH—CH$_2$—CH=CH$_2$, —CH=CH—C$_2$H$_4$—CH=CH$_2$, —CH$_2$—CH=CH—CH=CH—CH$_3$, —CH=CH—CH$_2$—CH=CH—CH$_3$, —CH=CH—CH=CH—C$_2$H$_5$, —CH$_2$—CH=CH—C(CH$_3$)=CH$_2$, —CH$_2$—CH=C(CH$_3$)—CH=CH$_2$, —CH$_2$—C(CH$_3$)=CH—CH=CH$_2$, —CH(CH$_3$)—CH=CH—CH=CH$_2$, —CH$_2$—C(CH$_3$)=CH$_2$, —CH=CH—CH(CH$_3$)—CH=CH$_2$, —CH=C(CH$_3$)—CH$_2$—CH=CH$_2$, —C(CH$_3$)=CH—CH$_2$—CH=CH$_2$, —CH=CH—CH=C(CH$_3$)$_2$, —CH=CH—C(CH$_3$)=CH—CH$_3$, —CH=C(CH$_3$)—CH=CH—CH$_3$, —C(CH$_3$)=CH—CH=CH—CH$_3$, —CH=C(CH$_3$)—C(CH$_3$)=CH$_2$, —C(CH$_3$)=CH—C(CH$_3$)=CH$_2$, —C(CH$_3$)=C(CH$_3$)—CH=CH$_2$, —CH=CH—CH=CH—CH=CH$_2$, —C$_5$H$_{10}$—CH=CH$_2$, —C$_4$H$_8$—CH=CH—CH$_3$, —C$_3$H$_6$—CH=CH—C$_2$H$_5$, —C$_2$H$_4$—CH=CH—C$_3$H$_7$, —CH$_2$—CH=CH—C$_4$H$_9$, —C$_4$H$_8$—C(CH$_3$)=CH$_2$, —C$_3$H$_6$—CH(CH$_3$)—CH=CH$_2$, —C$_2$H$_4$—CH(CH$_3$)—CH$_2$—CH=CH$_2$, —C$_3$H$_6$—CH=C(CH$_3$)$_2$, —C$_3$H$_6$—C(CH$_3$)=CH—CH$_3$, —C$_2$H$_4$—CH(CH$_3$)—CH=CH—CH$_3$, —CH$_2$—CH(CH$_3$)—CH$_2$—CH=CH—CH$_3$, —C$_2$H$_4$—CH=CH—CH(CH$_3$)$_2$, —C$_2$H$_4$—CH=C(CH$_3$)—C$_2$H$_5$, —C$_2$H$_4$—C(CH$_3$)=CH—C$_2$H$_5$, —CH$_2$—CH(CH$_3$)—CH=CH—C$_2$H$_5$, —CH$_2$—CH=CH—CH$_2$—CH(CH$_3$)$_2$, —CH$_2$—CH=CH—CH(CH$_3$)—C$_2$H$_5$, —CH$_2$—CH=C(CH$_3$)—C$_3$H$_7$, —C$_2$H$_4$—CH(CH$_3$)—C(CH$_3$)=CH$_2$, —CH$_2$—CH(CH$_3$)—CH$_2$—C(CH$_3$)=CH$_2$, —CH$_2$—CH(CH$_3$)—CH(CH$_3$)—CH=CH$_2$, —C$_2$H$_4$—C(CH$_3$)$_2$—CH=CH$_2$, —CH$_2$—C(CH$_3$)$_2$—CH$_2$—CH=CH$_2$, —C$_2$H$_4$—C(CH$_3$)=C(CH$_3$)$_2$, —CH$_2$—CH(CH$_3$)—CH=C(CH$_3$)$_2$, —CH$_2$—C(CH$_3$)$_2$—CH=CH—CH$_3$, —CH$_2$—CH(CH$_3$)—C(CH$_3$)=CH—CH$_3$, —CH$_2$—CH=C(CH$_3$)—CH(CH$_3$)$_2$, —CH$_2$—C(CH$_3$)=CH—CH(CH$_3$)$_2$, —CH$_2$—C(CH$_3$)=C(CH$_3$)—C$_2$H$_5$, —CH$_2$—CH=CH—C(CH$_3$)$_3$, —CH$_2$—C(CH$_3$)$_2$—C(CH$_3$)=CH$_2$, —CH$_2$—CH(C$_2$H$_5$)—C(CH$_3$)=CH$_2$, —CH$_2$—C(CH$_3$)(C$_2$H$_5$)—CH=CH$_2$, —CH$_2$—CH(CH$_3$)—C(C$_2$H$_5$)=CH$_2$, —C$_3$H$_6$—C(C$_3$H$_7$)=CH$_2$, —C$_3$H$_6$—C(C$_2$H$_5$)=CH—CH$_3$, —C$_2$H$_4$—CH(C$_2$H$_5$)—CH=CH—CH$_3$, —C$_2$H$_4$—C(C$_4$H$_9$)=CH$_2$, —C$_2$H$_4$—C(C$_3$H$_7$)=CH—CH$_3$, —C$_2$H$_4$—C(C$_2$H$_5$)=CH—C$_2$H$_5$, —C$_2$H$_4$—C(C$_2$H$_5$)=C(CH$_3$)$_2$, —C$_2$H$_4$—C[C(CH$_3$)$_3$]=CH$_2$, —C$_2$H$_4$—C[CH(CH$_3$)(C$_2$H$_5$)]=CH$_2$, —C$_2$H$_4$—C[CH$_2$—CH(CH$_3$)$_2$]=CH$_2$, —C$_4$H$_8$—CH=CH—CH=CH$_2$, —C$_3$H$_6$—CH=CH—CH$_2$—CH=CH$_2$, —C$_2$H$_4$—CH=CH—C$_2$H$_4$—CH=CH$_2$, —C$_3$H$_6$—CH=CH—CH=CH—CH$_3$, —C$_2$H$_4$—CH=CH—CH=CH—C$_2$H$_5$, —C$_3$H$_6$—CH=CH—C(CH$_3$)=CH$_2$, —C$_3$H$_6$—CH=C(CH$_3$)—CH=CH$_2$, —C$_3$H$_6$—C(CH$_3$)=CH—CH=CH$_2$, —C$_2$H$_4$—CH(CH$_3$)—CH=CH—CH=CH$_2$, —C$_2$H$_4$—CH=CH—CH$_2$—C(CH$_3$)=CH$_2$, —C$_2$H$_4$—CH=CH—CH(CH$_3$)—CH=CH$_2$, —C$_2$H$_4$—CH=C(CH$_3$)—CH$_2$—CH=CH$_2$, —C$_2$H$_4$—C(CH$_3$)=CH—CH$_2$—CH=CH$_2$, —C$_2$H$_4$—CH=CH—CH=C(CH$_3$)$_2$, —C$_2$H$_4$—CH=CH—C(CH$_3$)=CH—CH$_3$, —C$_2$H$_4$—CH=C(CH$_3$)—CH=CH—CH$_3$, —C$_2$H$_4$—C(CH$_3$)=CH—CH=CH—CH$_3$, —C$_2$H$_4$—CH=C(CH$_3$)—C(CH$_3$)=CH$_2$, —C$_2$H$_4$—C(CH$_3$)=C(CH$_3$)—CH=CH$_2$, —C$_2$H$_4$—C(CH$_3$)=C(CH$_3$)—CH=CH$_2$, —CH=CH-Ph and —C$_2$H$_4$—CH=CH—CH=CH—CH=CH$_2$, wherein these residues can be substituted with 1 to 5 substituents selected from $Z^8$, $Z^9$, $Z^{10}$, $Z^{11}$ and $Z^{12}$. However it is clear to a skilled person that the term "can be substituted" refers to the replacement of a hydrogen atom by one of the substituents $Z^8$, $Z^9$, $Z^{10}$, $Z^{11}$ or $Z^{12}$. Moreover, it is clear to a skilled person that only these hydrogen atoms which are present in the residue can be replaced by the substituents $Z^8$, $Z^9$, $Z^{10}$, $Z^{11}$ and $Z^{12}$. Thus, since the vinyl group has only three hydrogen atoms, only three hydrogen atoms can be replaced by three substituents selected from $Z^8$, $Z^9$, $Z^{10}$, $Z^{11}$ and $Z^{12}$. The carbon atom number of $C_2$-$C_8$ refers only to the carbon atoms of the alkenyl residue and does not include the carbon atoms of the substituents $Z^8$ to $Z^{12}$. For the definitions used herein, the group —CH=CH-Ph should fall under the term "linear or branched $C_2$-$C_8$-alkenyl".

Preferred are —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$. Especially preferred are —CH=CH$_2$, —CH$_2$—CH=CH$_2$, and —CH=CH—CH$_3$.

Examples of preferred substituted linear or branched $C_2$-$C_8$-alkenyl residues are —CF=CF$_2$, —CCl=C$_{12}$, —CH=CH—OH, —CH=CH—NH$_2$, —CH=CH—C$_1$, —CH=CH—CF$_3$, —C(CH$_3$)=CH—NH$_2$, —C(CH$_3$)=CH—OH, —C(CH$_3$)=CH—CF$_3$, —C(CH$_3$)=CH—Cl, —CH$_2$—CH=CF$_2$, —CF$_2$—CH=CH$_2$, —CH(OH)—CH=CH$_2$, —CH(NH$_2$)—CH=CH$_2$, —CHCl—CH=CH$_2$, —CH(CF$_3$)—CH=CH$_2$, —CH=CCl—CH$_3$, —CH=C(OH)—CH$_3$, —CH=C(NH$_2$)—CH$_3$, —CH=C(CF$_3$)—CH$_3$, —C(OH)=CH—CH$_3$, —CCl=CH—CH$_3$, —C(NH$_2$)=CH—CH$_3$, —C(CF$_3$)=CH—CH$_3$, —C$_2$H$_4$—CH=CH—OH, —C$_2$H$_4$—CH=CH—NH$_2$, —C$_2$H$_4$—CH=CHCl, —C$_2$H$_4$—CH=CH—CF$_3$, —C$_2$H$_4$—C(OH)=CH$_2$, —C$_2$H$_4$—CCl=CH$_2$, —C$_2$H$_4$—C(NH$_2$)=CH$_2$, —C$_2$H$_4$—C(CF$_3$)=CH$_2$, —C$_2$H$_4$—CH=CF$_2$, —C$_2$H$_4$—CF=CF$_2$, —C$_2$H$_4$—CCl=CH$_2$, —C$_2$H$_4$—CCl=CCl$_2$, —CH$_2$—COH=CH—CH$_3$, —CH$_2$—CCl=CH—CH$_3$, —CH$_2$—C(NH$_2$)=CH—CH$_3$, —CH$_2$—C(CF$_3$)=CH—CH$_3$, —CH$_2$—CH=C(OH)—CH$_3$, —CH$_2$—CH=CCl—CH$_3$, —CH$_2$—CH=C(NH$_2$)—CH$_3$, and —CH$_2$—CH=C(CF$_3$)—CH$_3$.

As used herein, the term "linear or branched $C_2$-$C_8$-alkynyl" refers to —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_2$H$_4$—C≡C—CH$_3$, —CH$_2$—C≡C—C$_2$H$_5$, —C≡C—C$_3$H$_7$, —CH(CH$_3$)—C≡CH, —CH$_2$—CH(CH$_3$)—C≡CH, —CH(CH$_3$)—CH$_2$—C≡CH, —CH(CH$_3$)—C≡C—CH$_3$, —C$_4$H$_8$—C≡CH, —C$_3$H$_6$—C≡C—CH$_3$, —C$_2$H$_4$—C≡C—C$_2$H$_5$, —CH$_2$—C≡C—C$_3$H$_7$, —C≡C—C$_4$H$_9$, —C$_2$H$_4$—CH(CH$_3$)—C≡CH, —CH$_2$—CH(CH$_3$)—CH$_2$—C≡CH, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH$_2$—C≡C—CH(CH$_3$), —CH(CH$_3$)—C≡C—C$_2$H$_5$, —CH$_2$—C≡C—CH(CH$_3$)$_2$, —C≡C—CH(CH$_3$)—C$_2$H$_5$, —C≡C—CH$_2$—CH(CH$_3$)$_2$, —C≡C—C(CH$_3$)$_3$, —C$_3$H$_6$—C≡CH, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —C≡C—C≡CH, —CH$_2$—C≡C—C≡CH, —C≡C—C≡C—CH$_3$, —CH(C≡CH)$_2$, —C$_2$H$_4$—C≡C—C≡CH, —CH$_2$—C≡C—CH$_2$—C≡CH, —C≡C—C$_2$H$_4$—C≡CH, —CH$_2$—C≡C—C≡C—CH$_3$, —C≡C—CH$_2$—C≡C—CH$_3$, —C≡C—CH$_2$—C≡C—CH$_3$, —C≡C—C≡C—C$_2$H$_5$, —C≡C—CH(CH$_3$)—C≡CH, —CH(CH$_3$)—C≡C—C≡CH, —CH(C≡CH)—CH$_2$—C≡CH, —C$_5$H$_{10}$—C≡CH, —C$_4$H$_8$—C≡C—CH$_3$, —C$_3$H$_6$—C≡C—C$_2$H$_5$, —C$_2$H$_4$—C≡C—C$_3$H$_7$, —CH$_2$—C≡C—C$_4$H$_9$, —C$_3$H$_6$—CH(CH$_3$)—C≡CH, —C$_2$H$_4$—CH(CH$_3$)—CH$_2$—C≡CH, —CH$_2$—CH(CH$_3$)—C$_2$H$_4$—C≡CH, —C$_2$H$_4$—CH(CH$_3$)—C≡C—CH$_3$, —CH$_2$—CH(CH$_3$)—CH$_2$—C≡C—CH$_3$, —CH$_2$—CH(CH$_3$)—C$_2$H$_5$, —CH$_2$—C≡C—CH(CH$_3$)—C$_2$H$_5$, —CH$_2$—C≡C—CH$_2$—CH(CH$_3$)$_2$, —CH$_2$—C≡C—C(CH$_3$)$_3$, —CH$_2$—CH(C$_2$H$_5$)—C≡C—CH$_3$, —CH$_2$—C(CH$_3$)$_2$—C≡C—CH$_3$, —CH$_2$—CH(C$_2$H$_5$)—CH$_2$—C≡CH, —CH$_2$—C(CH$_3$)$_2$—CH$_2$—C≡CH, —CH$_2$—C(CH$_3$)$_2$—C≡CH, —CH$_2$—CH(CH$_3$)—CH(CH$_3$)—C≡CH, —CH$_2$—CH(CH$_3$)—C≡CH, —CH$_2$—CH(C$_3$H$_7$)—C≡CH, —CH$_2$—C(CH$_3$)(C$_2$H$_5$)—C≡CH, —C$_4$H$_8$—C≡C—CH, —C$_3$H$_6$—C≡C—CH$_2$—C≡CH, —C$_2$H$_4$—C≡C—C$_2$H$_4$—C≡CH, —C$_3$H$_6$—C≡C—C≡C—CH$_3$, —C$_2$H$_4$—C≡C—CH$_2$—C≡C—CH$_3$, —C$_2$H$_4$—C≡C—C≡C—C$_2$H$_5$, —C$_2$H$_4$—C≡C—CH(CH$_3$)—C≡CH, —C≡C-Ph, —C$_2$H$_4$—CH(CH$_3$)—C≡C—C≡CH, —C$_2$H$_4$—CH(C≡CH)—CH$_2$—C≡CH, —C$_2$H$_4$—C(C≡CH)$_2$—CH$_3$, —C$_3$H$_6$—CH(C≡CH)$_2$, —C$_2$H$_4$—CH(C≡CH)—C≡C—CH$_3$, wherein these residues can be substituted with 1 to 5 substituents selected from $Z^8$, $Z^9$, $Z^{10}$, $Z^{11}$ and $Z^{12}$. However it is clear to a skilled person that the term "can be substituted" refers to the replacement of a hydrogen atom by one of the substituents $Z^8$, $Z^9$, $Z^{10}$, $Z^{11}$ or $Z^{12}$. Moreover it is clear to a skilled person that only these hydrogen atoms which are present in the residue can be replaced by the substituents $Z^8$, $Z^9$, $Z^{10}$, $Z^{11}$ and $Z^{12}$. Thus, since the acetylenyl group has only one hydrogen atom, only one hydrogen atom can be replaced by one substituent selected from $Z^8$, $Z^9$, $Z^{10}$, $Z^{11}$ and $Z^{12}$. The carbon atom number of $C_2$-$C_8$ refers only to the carbon atoms of the alkynyl residue and does not include the carbon atoms of the substituents $Z^8$ to $Z^{12}$. For the definitions used herein, the group —C≡C-Ph should fall under the term "linear or branched $C_2$-$C_8$-alkynyl".

Preferred are —C≡CH, —C≡C—CH$_3$.

Examples of preferred substituted linear or branched $C_2$-$C_8$-alkynyl residues are —C≡C—OH, —C≡C—Cl, —C≡C—NH$_2$, —C≡C—CF$_3$, —C≡C—CH$_2$Cl, —C≡C—CHCl$_2$, —C≡C—CCl$_3$, —C≡C—CF$_3$, —CH$_2$—C≡C—CO—CH$_3$, As used herein, the term "$C_1$-$C_9$-heterocyclyl" covers saturated or partly unsaturated heterocyclic residues with 1 to 9 ring carbon atoms, but not aromatic residues and covers also bicyclic saturated or partly unsaturated residues with 1 to 9 ring carbon atoms, but preferably not fully aromatic residues which are aromatic throughout the bicyclic system but may comprise partly aromatic ring systems, wherein one ring of the bicyclic ring system is aromatic. Preferably "$C_1$-$C_9$-heterocyclyl" refers to
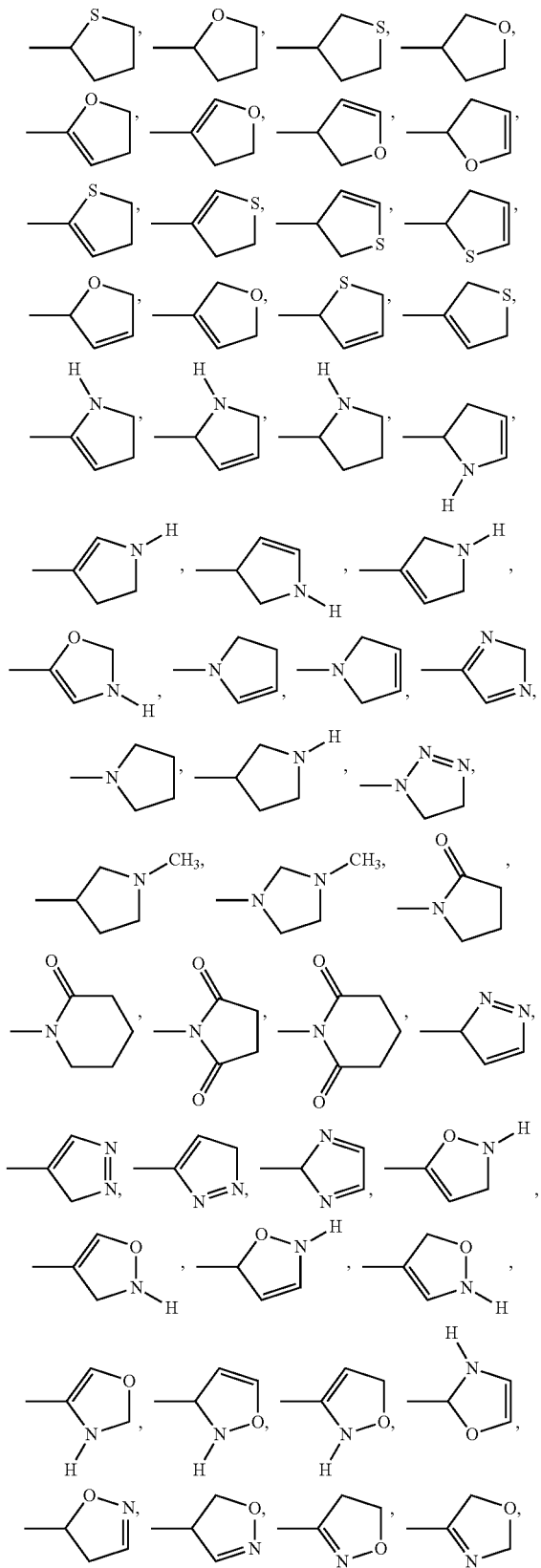
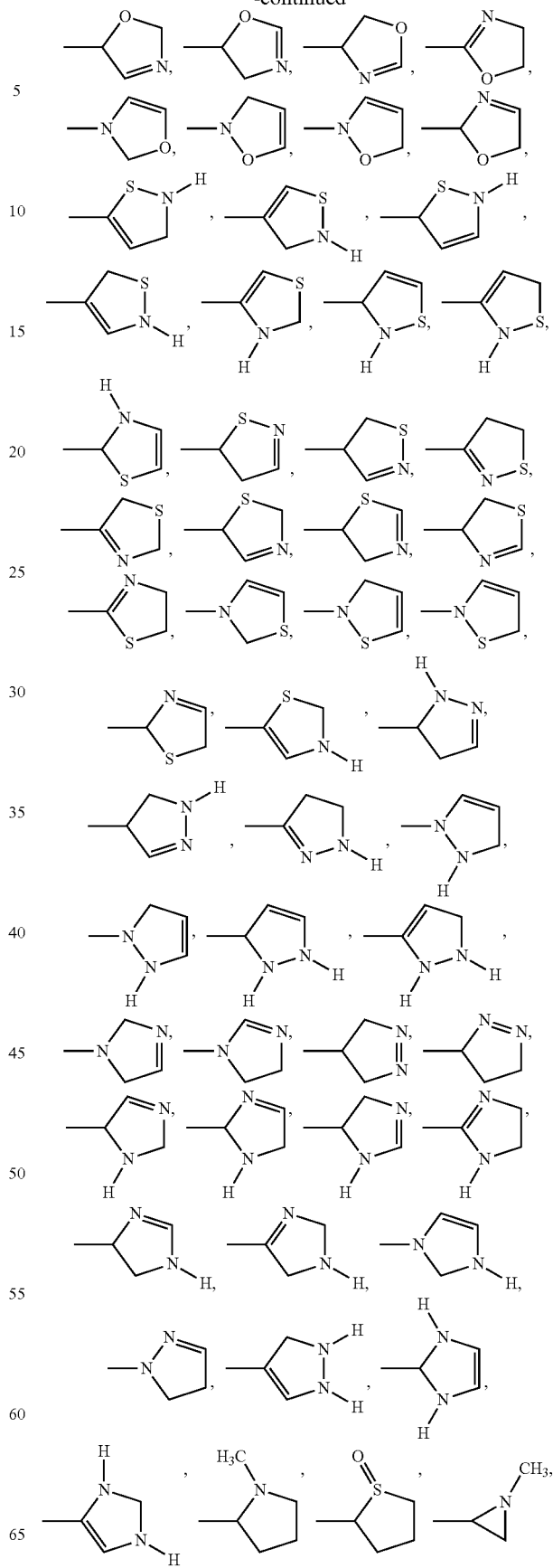

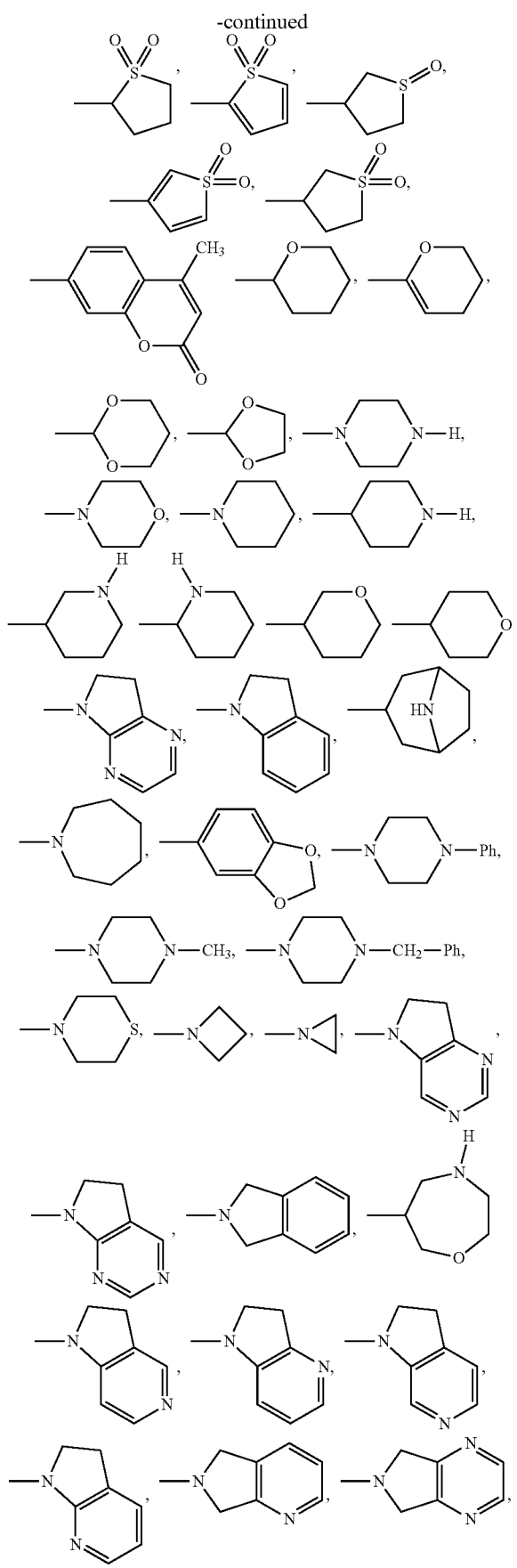
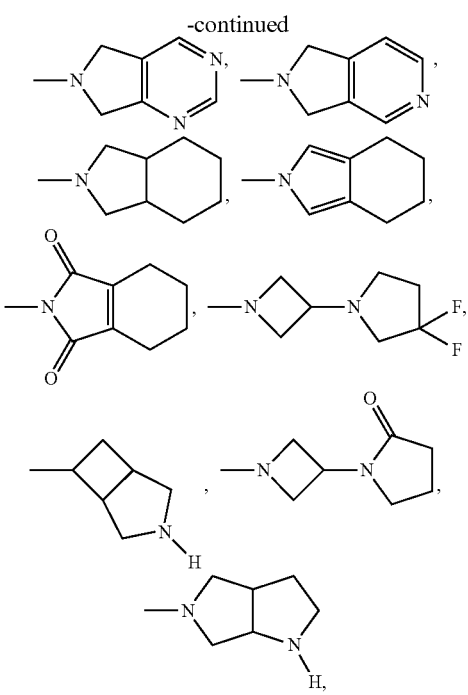

wherein these residues can be substituted with 1 to 5 substituents selected from $Z^8$, $Z^9$, $Z^{10}$, $Z^{11}$ and $Z^{12}$. However it is clear to a skilled person that the term "can be substituted" refers to the replacement of a hydrogen atom by one of the substituents $Z^8$, $Z^9$, $Z^{10}$, $Z^{11}$ or $Z^{12}$. Moreover it is clear to a skilled person that only these hydrogen atoms which are present in the residue can be replaced by the substituents $Z^8$, $Z^9$, $Z^{10}$, $Z^{11}$ and $Z^{12}$. Thus, since the oxirane group (also named as ethylene oxide group) has only three hydrogen atoms, only three hydrogen atoms can be replaced by three substituents selected from $Z^8$, $Z^9$, $Z^{10}$, $Z^{11}$ and $Z^{12}$.

The carbon atom number of $C_1$-$C_9$ refers only to the carbon atoms of the heterocyclic ring system (heterocyclyl) and does not include the carbon atoms of the substituents $Z^8$ to $Z^{12}$.

The term "heterocyclyl" as used herein refers to $C_1$-$C_9$-heterocyclyl, 3-membered heterocyclyl, 4-membered heterocyclyl, 5-membered heterocyclyl, 6-membered heterocyclyl, monounsaturated 4-membered heterocyclyl, monounsaturated 5-membered heterocyclyl, and monounsaturated 6-membered heterocyclyl.

Examples of preferred substituted $C_1$-$C_9$-heterocyclyl residues are

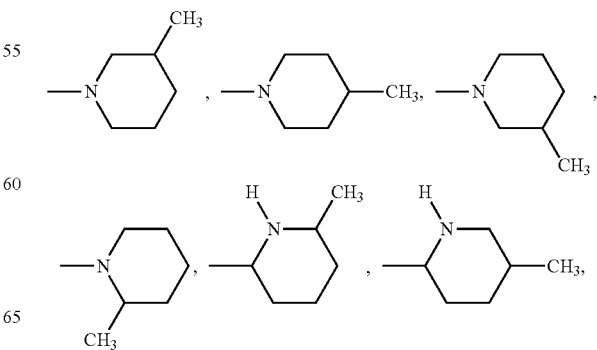

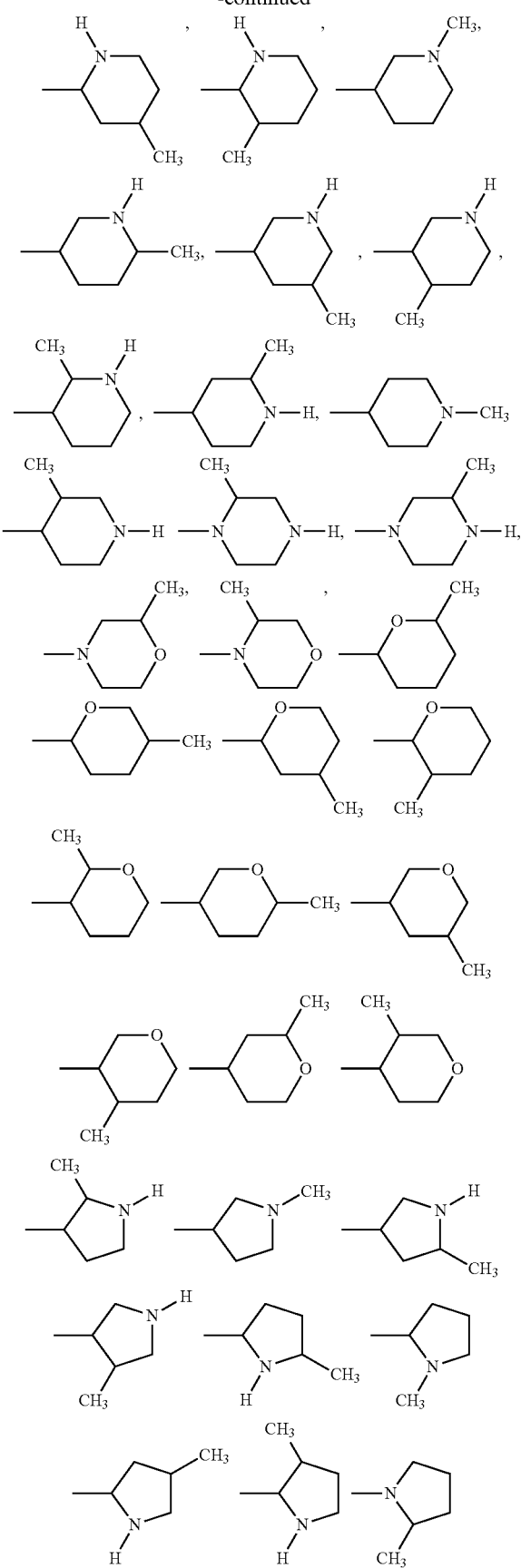
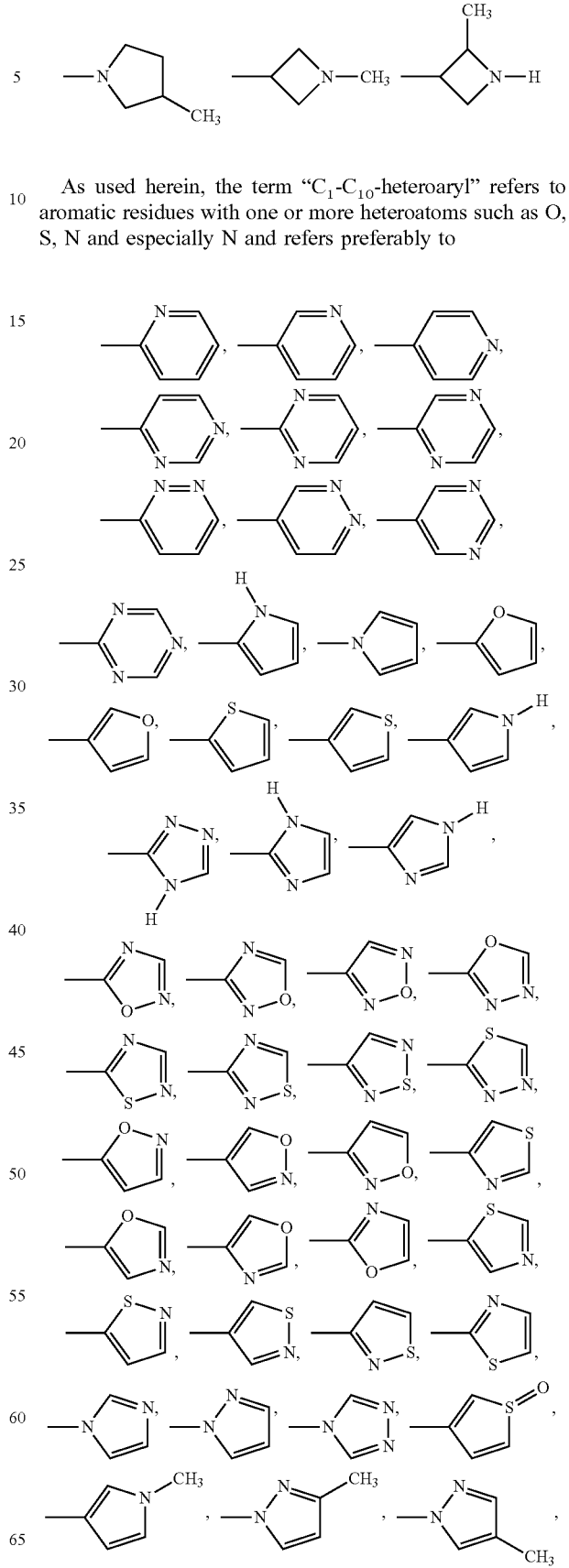
As used herein, the term "$C_1$-$C_{10}$-heteroaryl" refers to aromatic residues with one or more heteroatoms such as O, S, N and especially N and refers preferably to -continued
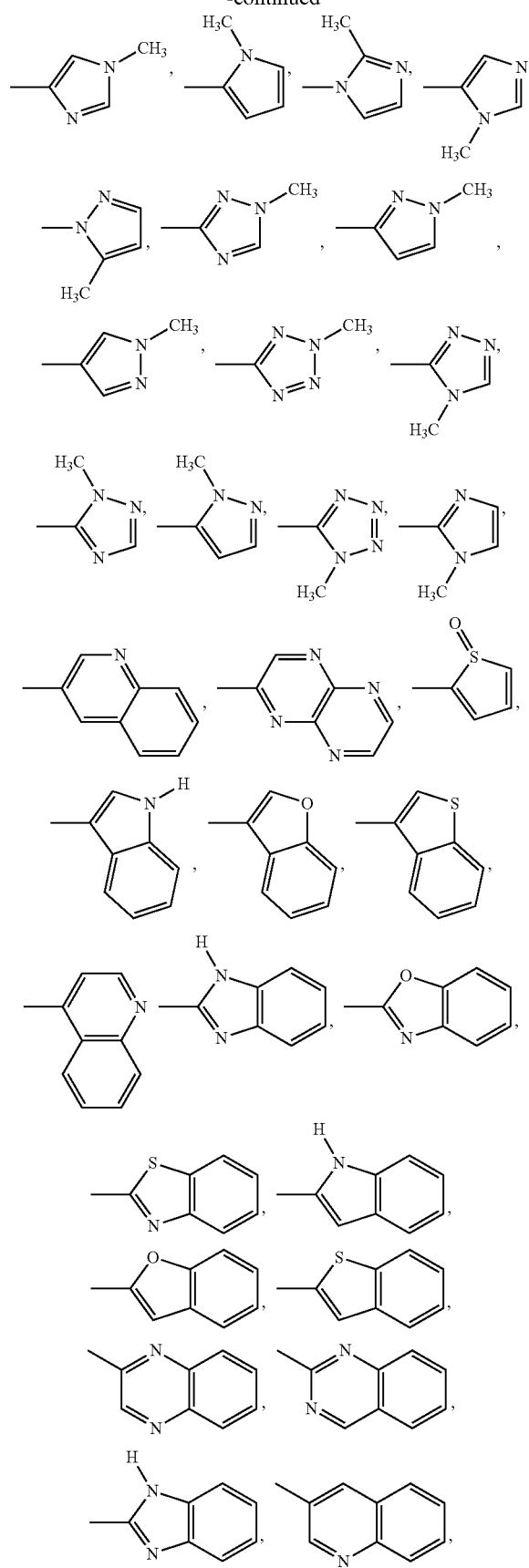
-continued
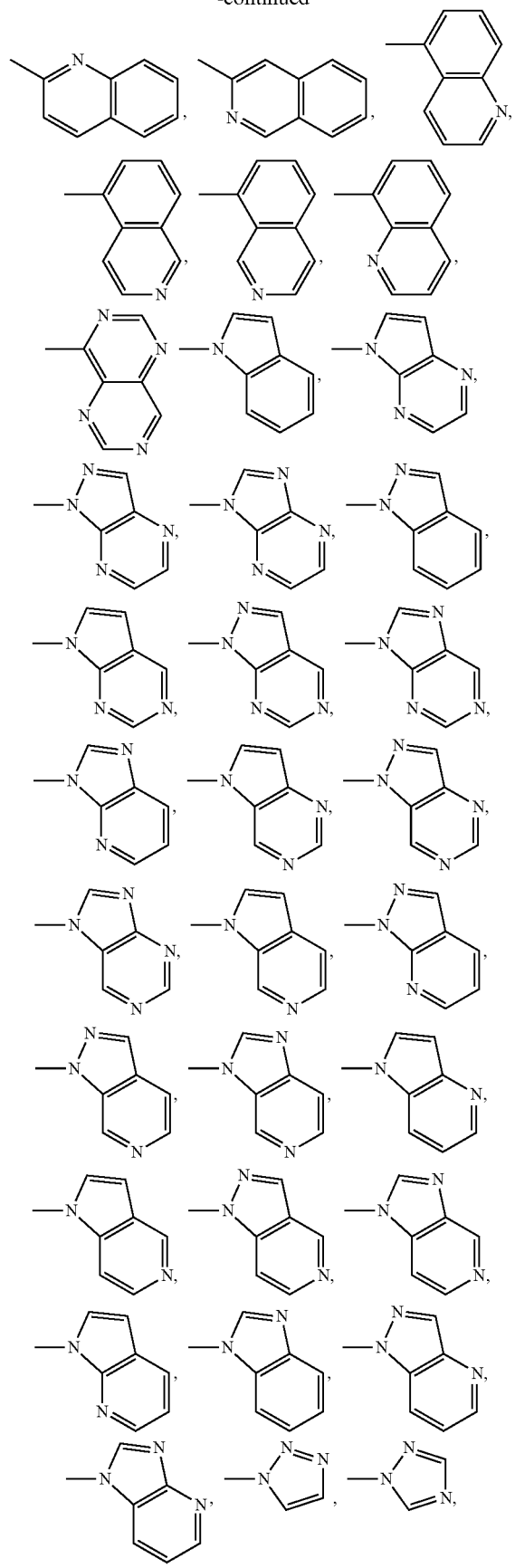

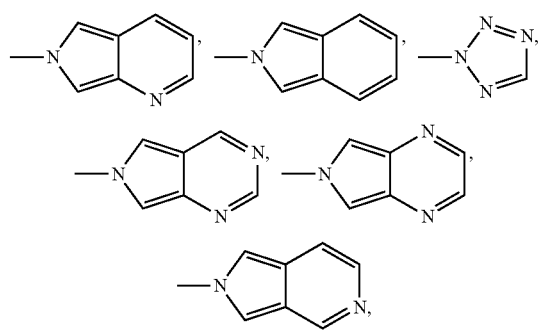

wherein these residues can be substituted with 1 to 5 substituents selected from $Z^8$, $Z^9$, $Z^{10}$, $Z^{11}$ and $Z^{12}$. However it is clear to a skilled person that the term "can be substituted" refers to the replacement of a hydrogen atom by one of the substituents $Z^8$, $Z^9$, $Z^{10}$, $Z^{11}$ or $Z^{12}$. Moreover it is clear to a skilled person that only these hydrogen atoms which are present in the residue can be replaced by the substituents $Z^8$, $Z^9$, $Z^{10}$, $Z^{11}$ and $Z^{12}$. Thus, since the oxadiazole group has only one hydrogen atom, only one hydrogen atom can be replaced by one substituent selected from $Z^8$, $Z^9$, $Z^{10}$, $Z^{11}$ and $Z^{12}$. The carbon atom number of $C_1$-$C_{10}$ refers only to the carbon atoms of the heteroaromatic ring system (heteroaryl) and does not include the carbon atoms of the substituents $Z^8$ to $Z^{12}$.

Examples of preferred substituted $C_1$-$C_{10}$-heteroaryl residues are

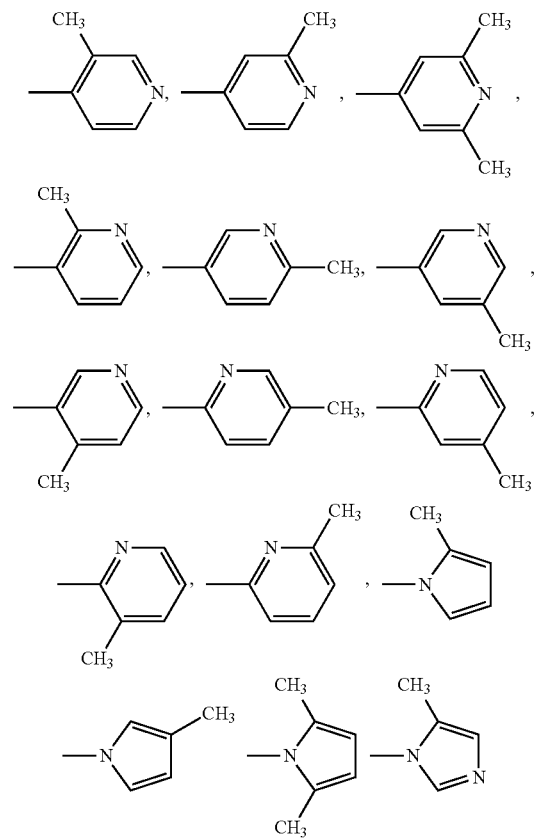

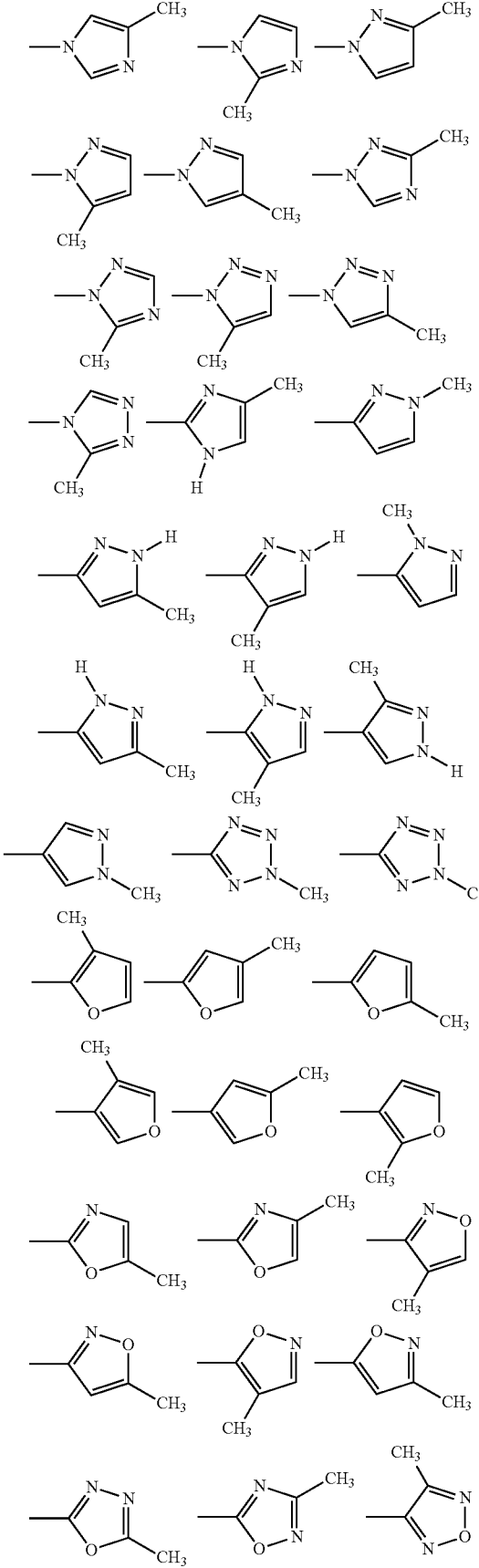

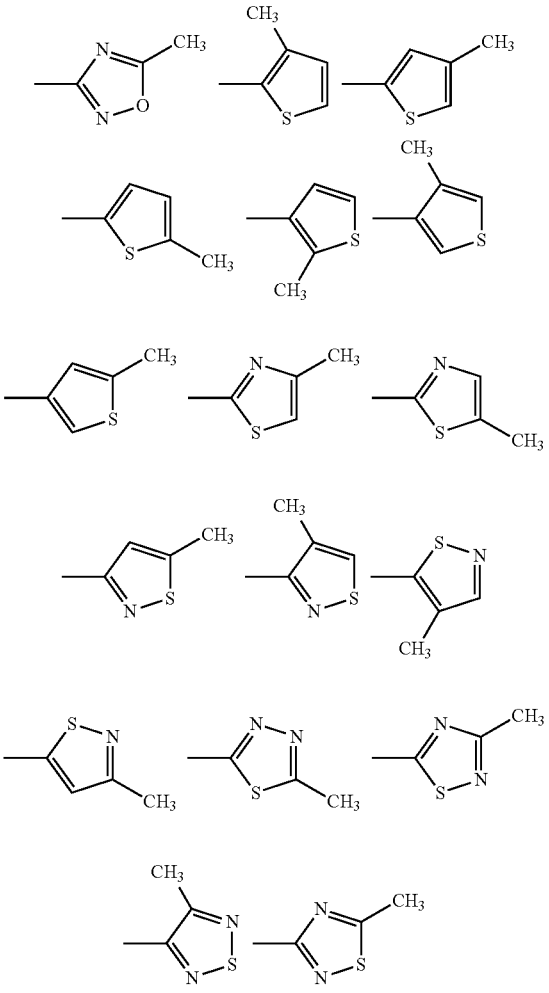

As used herein, the term "$C_6$-$C_{14}$-aryl" refers to aromatic residues or more specific to aromatic carbocyclic residues with one, two or three aromatic rings and refers preferably to phenyl and naphthyl, wherein these phenyl and naphthyl residues can be substituted with 1 to 5 substituents selected from $Z^8$, $Z^9$, $Z^{10}$, $Z^{11}$ and $Z^{12}$. However it is clear to a skilled person that the term "can be substituted" refers to the replacement of a hydrogen atom by one of the substituents $Z^8$, $Z^9$, $Z^{10}$, $Z^{11}$ or $Z^{12}$. The carbon atom number of $C_6$-$C_{14}$ refers only to the carbon atoms of the aromatic ring system (aryl) and does not include the carbon atoms of the substituents $Z^8$ to $Z^{12}$.

Examples of preferred $C_6$-$C_{14}$-aryl groups and substituted $C_6$-$C_{14}$-aryl residues are

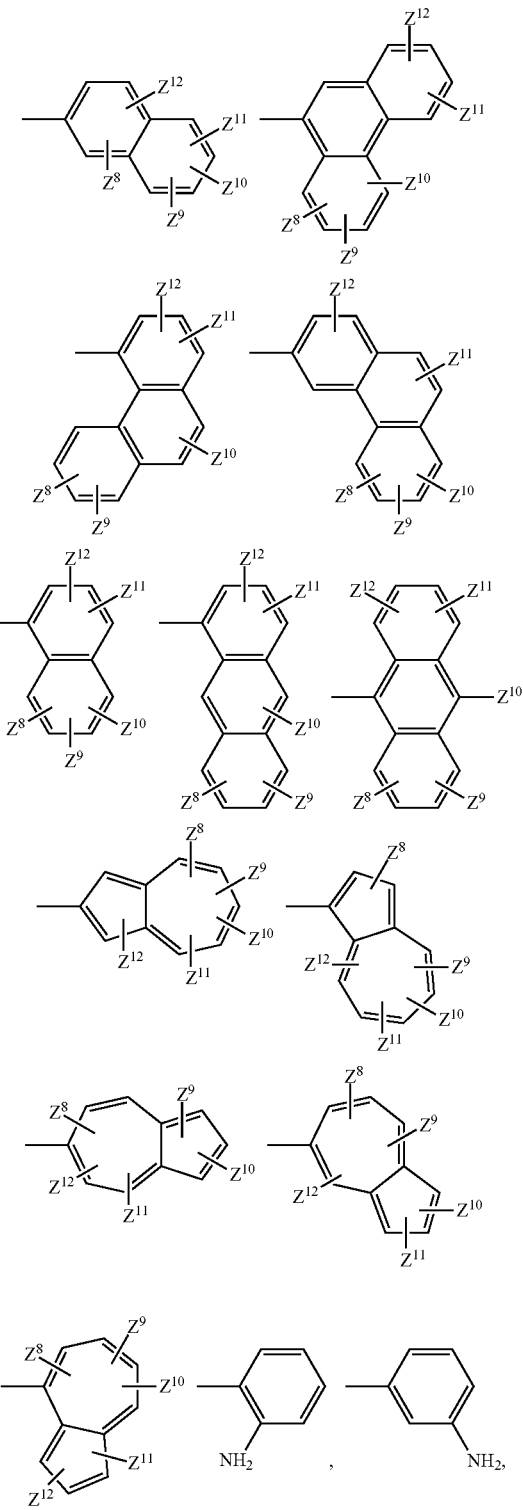

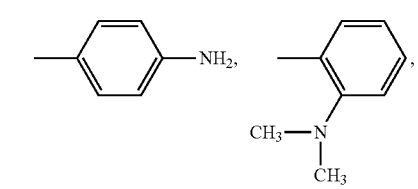

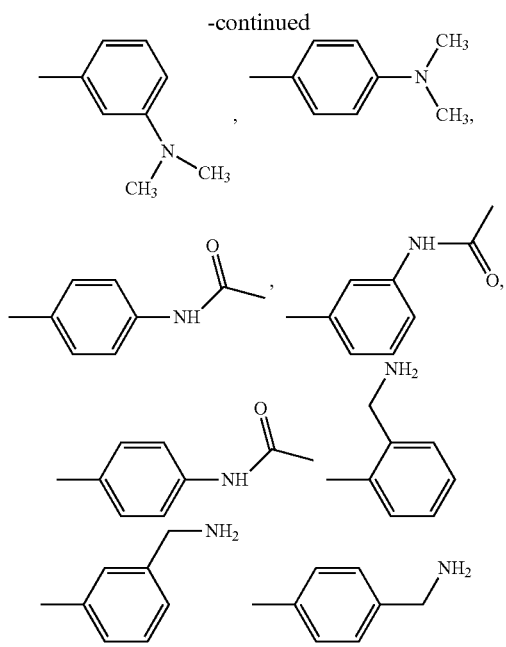

As used herein, the term "$C_7$-$C_{16}$-spiroalkyl" refers to spirocarbocyclic residues, wherein these spirocarbocyclic residues can be substituted with 1 to 3 substituents selected from $Z^5$, $Z^6$ and $Z^7$. However it is clear to a skilled person that the term "can be substituted" refers to the replacement of a hydrogen atom by one of the substituents $Z^5$, $Z^6$ and $Z^7$. It is also possible that two of the substituents $Z^5$, $Z^6$ and $Z^7$ represent together an oxygen atom and form together with the carbon atom of the spiroalkyl residue to which they are both attached a carbonyl moiety. The carbon atom number of $C_7$-$C_{16}$ refers only to the carbon atoms of the spiro ring system and does not include the carbon atoms of the substituents. Thus a spiro[4,5]decyl residue is counted as a $C_{10}$-spiroalkyl regardless if this spiro residue carries five pentyl substituents.

Examples of preferred $C_7$-$C_{16}$-spiroalkyl groups and substituted $C_7$-$C_{16}$-spiroalkyl groups are

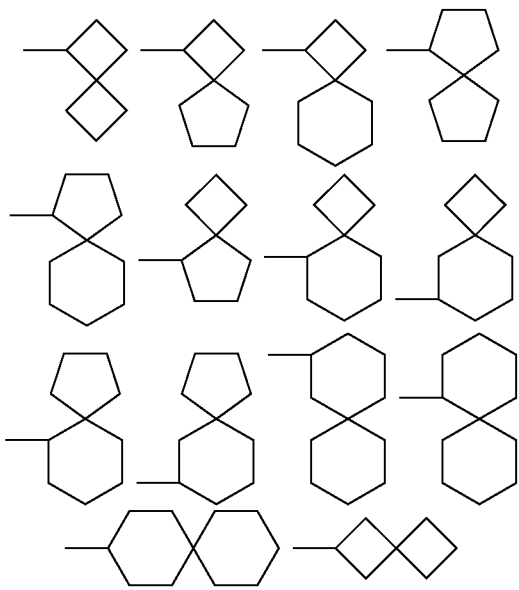

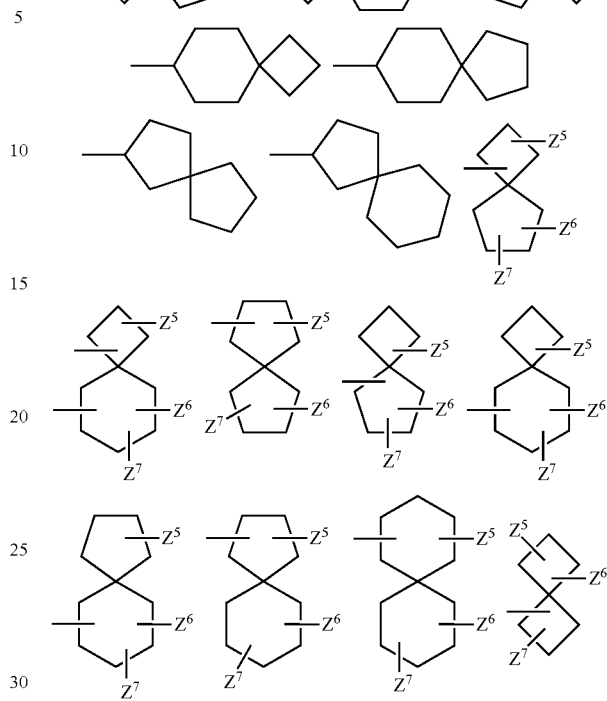

preferred substituents $Z^5$, $Z^6$ and $Z^7$ are —$CH_3$, —$C_2H_5$, —$C_3H_7$, —$CH(CH_3)_2$, —OH, —$OCH_3$, —$OC_2H_5$, —$OC_3H_7$, —$NH_2$, —$N(CH_3)_2$, —F, —Cl, —Br, —I, —CN, —$CH_2F$, —$CHF_2$, —$CF_3$, —$OCHF_2$, —$OCF_3$.

As used herein, the term "$C_5$-$C_{14}$-spiroheterocyclyl" refers to spiro residues with one, two or three heteroatoms such as O, S, N in the spiro ring system, wherein these spiroheterocyclic residues can be substituted with 1 to 3 substituents selected from $Z^5$, $Z^6$ and $Z^7$. However it is clear to a skilled person that the term "can be substituted" refers to the replacement of a hydrogen atom by one of the substituents $Z^5$, $Z^6$ and $Z^7$. The carbon atom number of $C_5$-$C_{14}$ refers only to the carbon atoms of the spiro ring system and does not include the carbon atoms of the substituents. Thus a azaspiro[4,5]decyl residue is counted as a $C_9$-spiroalkyl regardless if this azaspiro[4,5]decyl residue carries five isopropyl substituents.

Examples of preferred $C_5$-$C_{14}$-spiroheterocyclyl groups and substituted $C_5$-$C_{14}$-spiroheterocyclyl groups are

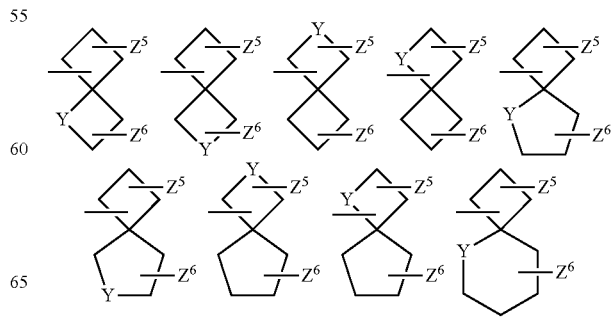

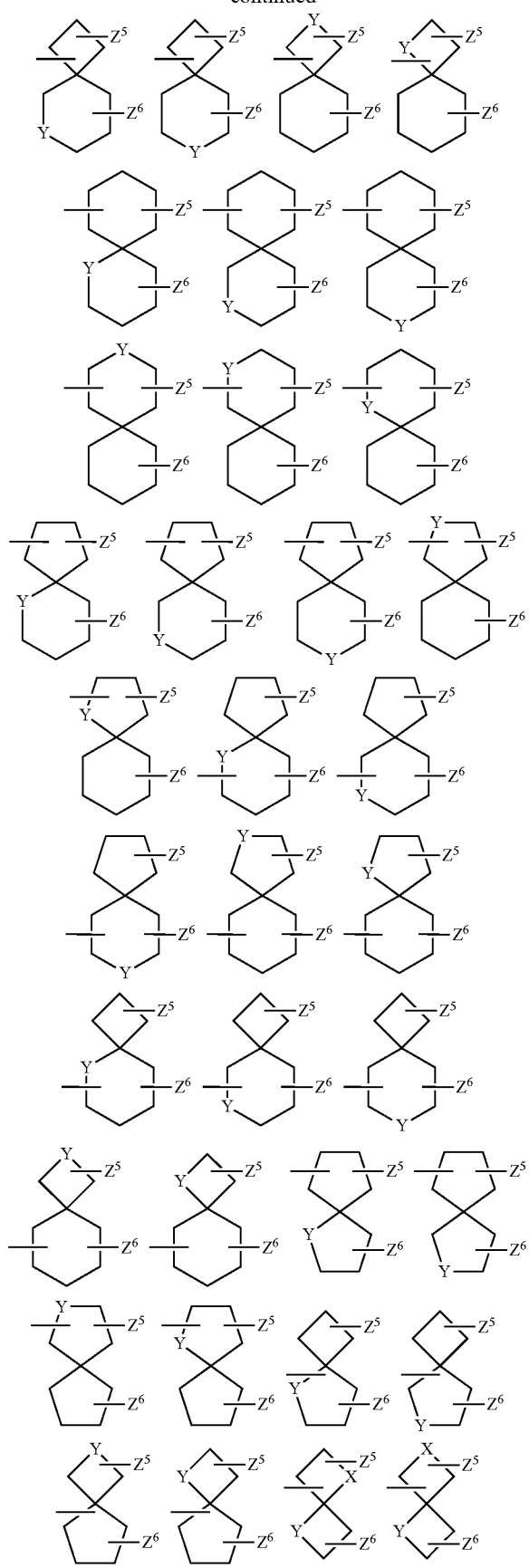
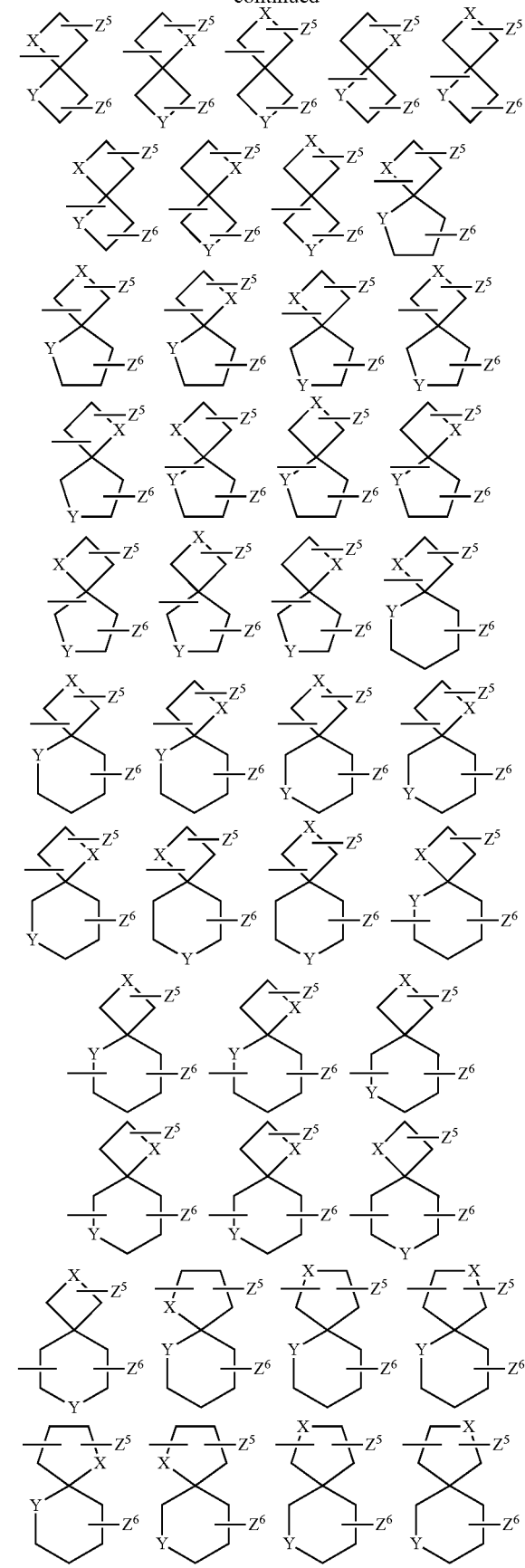

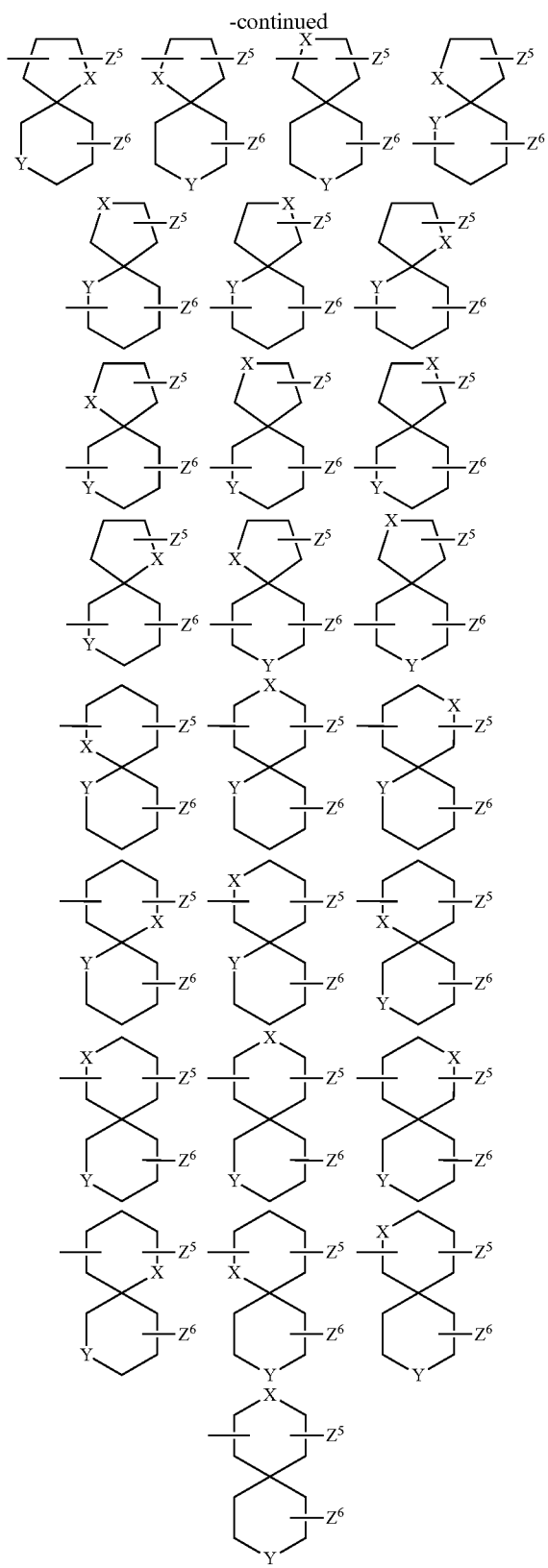

wherein Y and X represent independently of each other —O—, —NH—, —NR$^{11}$—, —SO—, or —SO$_2$—, preferably —NH— and —NR$^{11}$— and Z$^5$ and Z$^6$ represent independently of each other —CH$_3$, —C$_2$H$_5$, —C$_3$H$_7$, —CH(CH$_3$)$_2$, —OH, —OCH$_3$, —OC$_2$H$_5$, —OC$_3$H$_7$, —NH$_2$, —N(CH$_3$)$_2$, —F, —Cl, —Br, —I, —CN, —CH$_2$F, —CHF$_2$, —CF$_3$, —OCHF$_2$, or —OCF$_3$.

As used herein, the term "3-membered heterocyclyl" refers to a substituted or non substituted ring system of three atoms including at least one heteroatom such as O, S, SO, SO$_2$, N, NO, wherein these 3-membered heterocyclic residues can be substituted with 1 to 4 substituents selected from Z$^1$, Z$^2$, Z$^3$ and Z$^4$. However it is clear to a skilled person that the term "can be substituted" refers to the replacement of a hydrogen atom by one of the substituents Z$^1$, Z$^2$, Z$^3$ or Z$^4$. Moreover it is clear to a skilled person that only these hydrogen atoms which are present in the 3-membered heterocyclic group can be replaced by the substituents Z$^1$, Z$^2$, Z$^3$ and Z$^4$. Thus, since the diazirene group has only one hydrogen atom, only one hydrogen atom can be replaced by one substituent selected from Z$^1$, Z$^2$, Z$^3$ and Z$^4$. It is also possible that two of the substituents Z$^1$, Z$^2$, Z$^3$ and Z$^4$ represent together an oxygen atom and form together with the ring carbon atom of the heterocyclic ring to which they are both attached a carbonyl moiety or a sulfoxide moiety together with the ring sulphur atom to which they are attached or both Z substituents represent oxygen and form a sulfone moiety together with the ring sulphur atom to which they are attached. If the 3-membered heterocyclic residue contains a nitrogen atom which is substituted by one of the substituents Z$^1$, Z$^2$, Z$^3$ and Z$^4$, said Z substituent represents R$^{11}$. If the 3-membered heterocyclic residue contains two nitrogen atoms which are both substituted by one of the substituents Z$^1$, Z$^2$, Z$^3$ and Z$^4$, the first Z substituent represents R$^{11}$ and the second Z substituent represents R$^{12}$.

Examples of preferred 3-membered heterocyclic groups and substituted 3-membered heterocyclic groups are

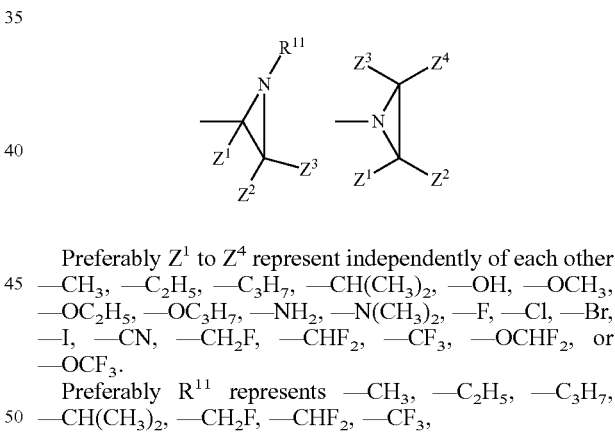

Preferably Z$^1$ to Z$^4$ represent independently of each other —CH$_3$, —C$_2$H$_5$, —C$_3$H$_7$, —CH(CH$_3$)$_2$, —OH, —OCH$_3$, —OC$_2$H$_5$, —OC$_3$H$_7$, —NH$_2$, —N(CH$_3$)$_2$, —F, —Cl, —Br, —I, —CN, —CH$_2$F, —CHF$_2$, —CF$_3$, —OCHF$_2$, or —OCF$_3$.

Preferably R$^{11}$ represents —CH$_3$, —C$_2$H$_5$, —C$_3$H$_7$, —CH(CH$_3$)$_2$, —CH$_2$F, —CHF$_2$, —CF$_3$,

cyclo-C$_3$H$_5$, cyclo-C$_4$H$_7$, cyclo-C$_5$H$_9$, cyclo-C$_6$H$_{11}$, cyclo-C$_7$H$_{13}$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, -Ph, —CH$_2$-Ph, —CH$_2$—CH$_2$-Ph, —CH═CH-Ph, —CH═CH$_2$, —CH$_2$—CH═CH$_2$, —C(CH$_3$)═CH$_2$, —CH═CH—CH$_3$, —C$_2$H$_4$—CH═CH$_2$, —CH$_2$—CH═CH—CH$_3$, —CH═CH—C$_2$H$_5$, —CH$_2$—C(CH$_3$)═CH$_2$, —CH (CH₃)—CH=CH₂, —CH=C(CH₃)₂, —C(CH₃)=CH—CH₃, —C≡CH, —C≡C—CH₃, —CH₂—C≡CH, —C₂H₄—C≡CH, —CH₂—C≡C—CH₃, —C≡C—C₂H₅, —CH₂—OCF₃, —C₂H₄—OCF₃, —C₃H₆—OCF₃, —CH₂—OCH₃, —C₂H₄—OCH₃, —C₃H₆—OCH₃, —CH₂—OC₂H₅, —C₂H₄—OC₂H₅, or —C₃H₆—OC₂H₅;

As used herein for the substituent R³, the term "4-membered heterocyclyl" refers to a substituted or non substituted ring system of four atoms including at least one heteroatom such as O, S, SO, SO₂, N, NO, wherein these 4-membered heterocyclic residues can be substituted with 1 to 4 substituents selected from Z¹, Z², Z³ and Z⁴. It is also possible that two of the substituents Z¹, Z², Z³ and Z⁴ represent together an oxygen atom and form together with the ring carbon atom of the heterocyclic ring to which they are both attached a carbonyl moiety or a sulfoxide moiety together with the ring sulphur atom to which they are attached or both Z substituents represent oxygen and form a sulfone moiety together with the ring sulphur atom to which they are attached. If the 4-membered heterocyclic residue contains a nitrogen atom which is substituted by one of the substituents Z¹, Z², Z³ and Z⁴, said Z substituent represents R¹¹. If the 4-membered heterocyclic residue contains two nitrogen atoms which are both substituted by one of the substituents Z¹, Z², Z³ and Z⁴, the first Z substituent represents R¹¹ and the second Z substituent represents R¹². The same definition applies for the substituent R⁸ with the only difference that the optional substituents of the 4-membered heterocyclyl residue are Z⁵ to Z⁷ instead of Z¹ to Z⁴. Thus for R⁸ the optional substituent Z¹ is replaced by Z⁵, Z² is replaced by Z⁶, Z³ is replaced by Z⁷, and Z⁴ is hydrogen.

Examples of preferred 4-membered heterocyclic groups and substituted 4-membered heterocyclic groups for R³ are

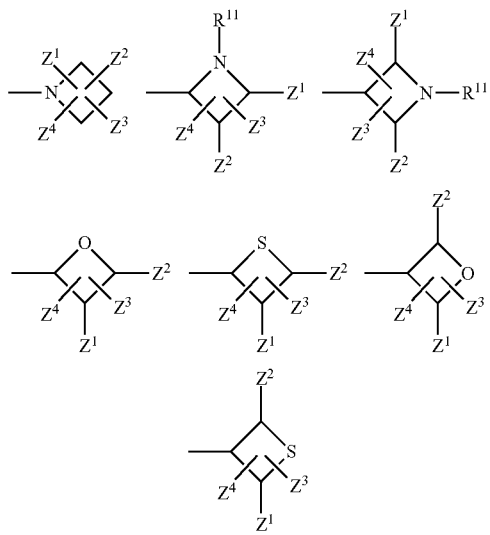

Preferably Z¹ to Z⁴ represent independently of each other —CH₃, —C₂H₅, —C₃H₇, —CH(CH₃)₂, —OH, —OCH₃, —OC₂H₅, —OC₃H₇, —NH₂, —N(CH₃)₂, —F, —Cl, —Br, —I, —CN, —CH₂F, —CHF₂, —CF₃, —OCHF₂, and —OCF₃.

Preferred substituents for R¹¹ are —CH₃, —C₂H₅, —C₃H₇, —CH(CH₃)₂, —CH₂F, —CHF₂, —CF₃,

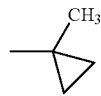

cyclo-C₃H₅, cyclo-C₄H₇, cyclo-C₅H₉, cyclo-C₆H₁₁, cyclo-C₇H₁₃, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, -Ph, —CH₂-Ph, —CH₂—CH₂-Ph, —CH=CH-Ph, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH₂, —CH=C(CH₃)₂, —C(CH₃)=CH—CH₃, —C≡CH, —C≡C—CH₃, —CH₂—C≡CH, —C₂H₄—C≡CH, —CH₂—C≡C—CH₃, —C≡C—C₂H₅, —CH₂—OCF₃, —C₂H₄—OCF₃, —C₃H₆—OCF₃, —CH₂—OCH₃, —C₂H₄—OCH₃, —C₃H₆—OCH₃, —CH₂—OC₂H₅, —C₂H₄—OC₂H₅, and —C₃H₆—OC₂H₅.

Preferred 4-membered heterocyclyl groups are

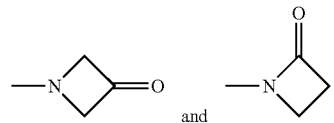

and

As used herein, the term "5-membered heterocyclyl" refers to a substituted or non substituted ring system of five atoms including at least one heteroatom such as O, S, SO, SO₂, N, NO, wherein these 5-membered heterocyclic residues can be substituted with 1 to 4 substituents selected from Z¹, Z², Z³ and Z⁴. It is also possible that two of the substituents Z¹, Z², Z³ and Z⁴ represent together an oxygen atom and form together with the ring carbon atom of the heterocyclic ring to which they are both attached a carbonyl moiety or a sulfoxide moiety together with the ring sulphur atom to which they are attached or both Z substituents represent oxygen and form a sulfone moiety together with the ring sulphur atom to which they are attached. If the 5-membered heterocyclic residue contains a nitrogen atom which is substituted by one of the substituents Z¹, Z², Z³ and Z⁴, said Z substituent represents R¹¹. If the 5-membered heterocyclic residue contains two nitrogen atoms which are both substituted by one of the substituents Z¹, Z², Z³ and Z⁴, the first Z substituent represents R¹¹ and the second Z substituent represents R¹². The same definition applies for the substituent R⁸ with the only difference that the optional substituents of the 5-membered heterocyclyl residue are Z⁵ to Z⁷ instead of Z¹ to Z⁴. Thus for R⁸ the optional substituent Z¹ is replaced by Z⁵, Z² is replaced by Z⁶, Z³ is replaced by Z⁷, and Z⁴ is hydrogen.

Examples of preferred 5-membered heterocyclic groups and substituted 5-membered heterocyclic groups for R³ are

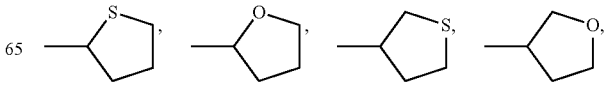

-continued

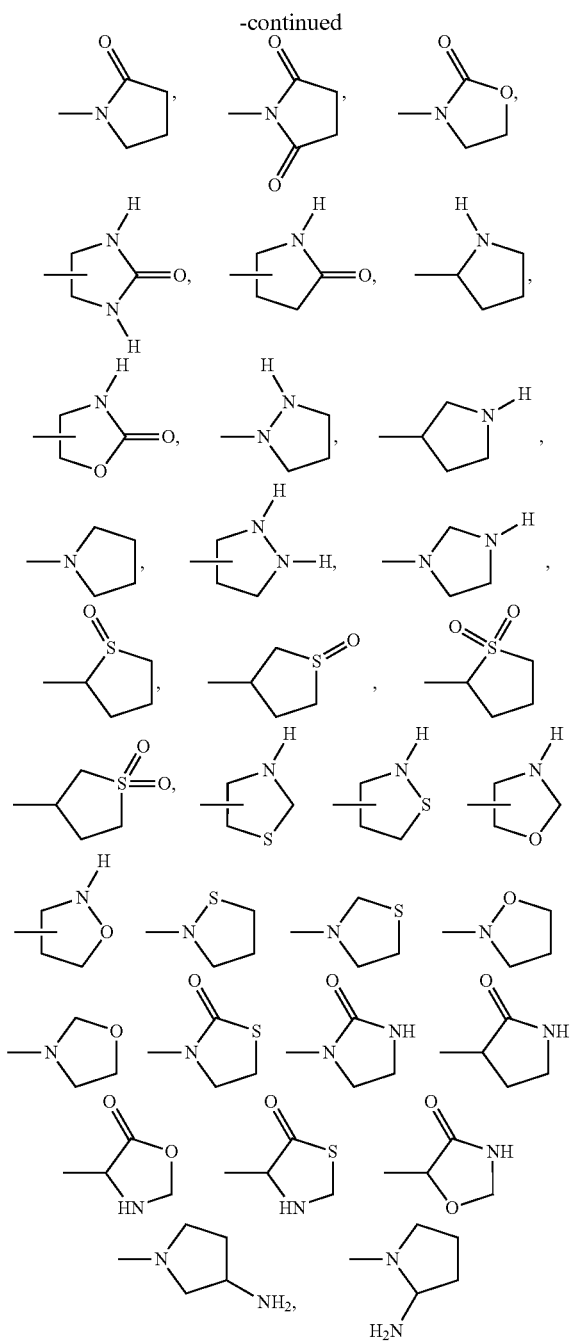

wherein the afore-mentioned 5-membered heterocyclic groups can be substituted with 1 to 4 substituents selected from $Z^1$, $Z^2$, $Z^3$ and $Z^4$.

As used herein, the term "6-membered heterocyclyl" refers to a substituted or non substituted ring system of six atoms including at least one heteroatom such as O, S, SO, $SO_2$, N, NO, wherein these 6-membered heterocyclic residues can be substituted with 1 to 4 substituents selected from $Z^1$, $Z^2$, $Z^3$ and $Z^4$. It is also possible that two of the substituents $Z^1$, $Z^2$, $Z^3$ and $Z^4$ represent together an oxygen atom and form together with the ring carbon atom of the heterocyclic ring to which they are both attached a carbonyl moiety or a sulfoxide moiety together with the ring sulphur atom to which they are attached or both Z substituents represent oxygen and form a sulfone moiety together with the ring sulphur atom to which they are attached. If the 6-membered heterocyclic residue contains a nitrogen atom which is substituted by one of the substituents $Z^1$, $Z^2$, $Z^3$ and $Z^4$, said Z substituent represents $R^{11}$. If the 6-membered heterocyclic residue contains two nitrogen atoms which are both substituted by one of the substituents $Z^1$, $Z^2$, $Z^3$ and $Z^4$, the first Z substituent represents $R^{11}$ and the second Z substituent represents $R^{12}$. The same definition applies for the substituent $R^8$ with the only difference that the optional substituents of the 6-membered heterocyclyl residue are $Z^5$ to $Z^7$ instead of $Z^1$ to $Z^4$. Thus for $R^8$ the optional substituent $Z^1$ is replaced by $Z^5$, $Z^2$ is replaced by $Z^6$, $Z^3$ is replaced by $Z^7$, and $Z^4$ is hydrogen.

Examples of preferred 6-membered heterocyclic groups and substituted 6-membered heterocyclic groups for $R^3$ are

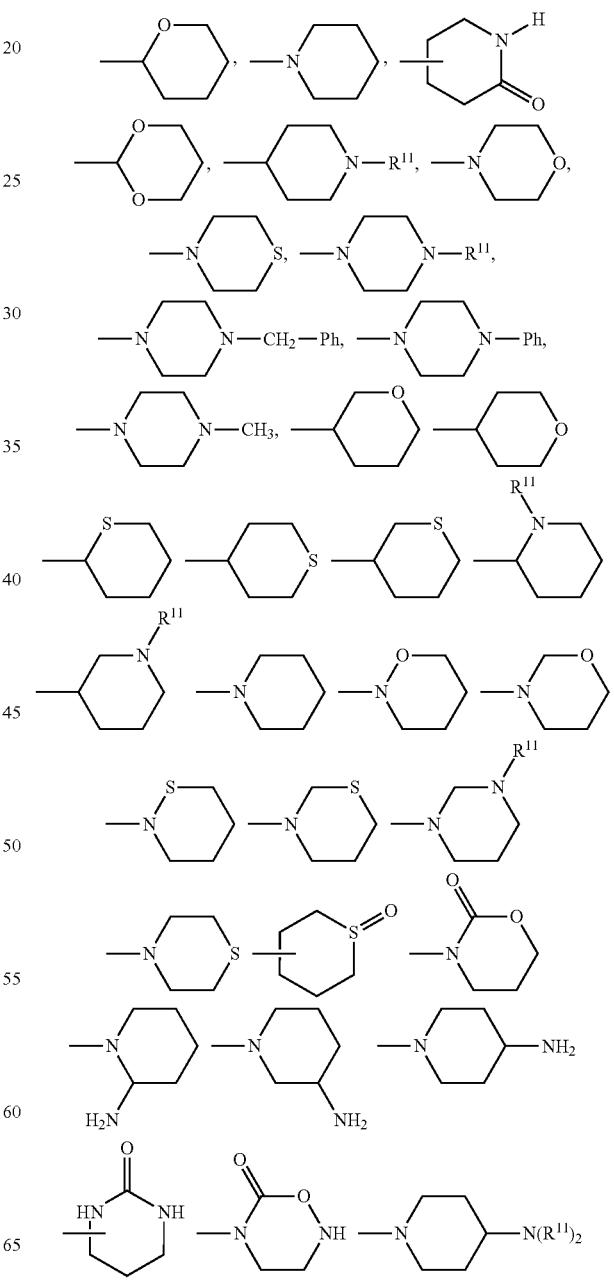

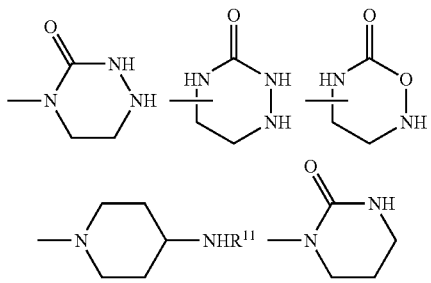

wherein the afore-mentioned 6-membered heterocyclic groups can be substituted with 1 to 4 substituents selected from $Z^1$, $Z^2$, $Z^3$ and $Z^4$. Preferred residues for the substituents $Z^1$ to $Z^4$ are disclosed above.

As used herein, the term "monounsaturated 4-membered heterocyclyl" refers to a substituted or non substituted ring system of four atoms including at least one heteroatom such as O, S, SO, $SO_2$, N, NO, and one double bond, wherein these monounsaturated 4-membered heterocyclic residues can be substituted with 1 to 4 substituents selected from $Z^1$, $Z^2$, $Z^3$ and $Z^4$. However it is clear to a skilled person that the term "can be substituted" refers to the replacement of a hydrogen atom by one of the substituents $Z^1$, $Z^2$, $Z^3$ or $Z^4$. Moreover it is clear to a skilled person that only these hydrogen atoms which are present in the monounsaturated 4-membered heterocyclic residue can be replaced by the substituents $Z^1$, $Z^2$, $Z^3$ and $Z^4$. It is also possible that two of the substituents $Z^1$, $Z^2$, $Z^3$ and $Z^4$ represent together an oxygen atom and form together with the ring carbon atom of the heterocyclic ring to which they are both attached a carbonyl moiety or a sulfoxide moiety together with the ring sulphur atom to which they are attached or both Z substituents represent oxygen and form a sulfone moiety together with the ring sulphur atom to which they are attached. If the monounsaturated 4-membered heterocyclic residue contains a nitrogen atom which is substituted by one of the substituents $Z^1$, $Z^2$, $Z^3$ and $Z^4$, said Z substituent represents $R^{11}$. If the monounsaturated 4-membered heterocyclic residue contains two nitrogen atoms which are both substituted by one of the substituents $Z^1$, $Z^2$, $Z^3$ and $Z^4$, the first Z substituent represents $R^{11}$ and the second Z substituent represents $R^{12}$.

Examples of preferred monounsaturated 4-membered heterocyclic groups and substituted 4-membered heterocyclic groups for $R^3$ are

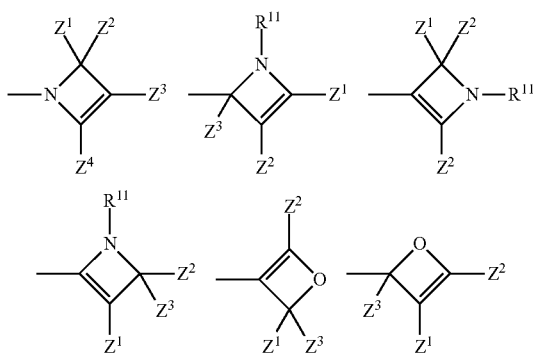

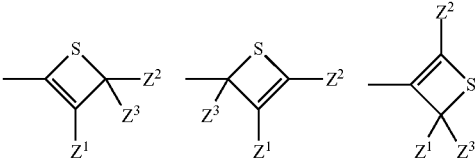

Preferably $Z^1$ to $Z^4$ represent independently of each other —$CH_3$, —$C_2H_5$, —$C_3H_7$, —$CH(CH_3)_2$, —OH, —$OCH_3$, —$OC_2H_5$, —$OC_3H_7$, —$NH_2$, —$N(CH_3)_2$, —F, —Cl, —Br, —I, —CN, —$CH_2F$, —$CHF_2$, —$CF_3$, —$OCHF_2$, and —$OCF_3$.

Preferred substituents for $R^{11}$ are —$CH_3$, —$C_2H_5$, —$C_3H_7$, —$CH(CH_3)_2$, —$CH_2F$, —$CHF_2$,

—$CF_3$, cyclo-$C_3H_5$, cyclo-$C_4H_7$, cyclo-$C_5H_9$, cyclo-$C_6H_{11}$, cyclo-$C_7H_{13}$, —$C_4H_9$, —$CH_2$—$CH(CH_3)_2$, —$CH(CH_3)$—$C_2H_5$, —$C(CH_3)_3$, —$C_5H_{11}$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$CH(C_2H_5)_2$, —$C_2H_4$—$CH(CH_3)_2$, —$C_6H_{13}$, —$C_7H_{15}$, —$C_8H_{17}$, -Ph, —$CH_2$-Ph, —$CH_2$—$CH_2$-Ph, —CH=CH-Ph, —CH=$CH_2$, —$CH_2$—CH=$CH_2$, —C($CH_3$)=$CH_2$, —CH=CH—$CH_3$, —$C_2H_4$—CH=$CH_2$, —$CH_2$—CH=CH—$CH_3$, —CH=CH—$C_2H_5$, —$CH_2$—C($CH_3$)=$CH_2$, —CH($CH_3$)—CH=$CH_2$, —CH=C($CH_3$)$_2$, —C($CH_3$)=CH—$CH_3$, —C≡CH, —C≡C—$CH_3$, —$CH_2$—C≡CH, —$C_2H_4$C≡CH, —$CH_2$—C≡C—$CH_3$, —C≡C—$C_2H_5$, —$CH_2$—$OCF_3$, —$C_2H_4$—$OCF_3$, —$C_3H_6$—$OCF_3$, —$CH_2$—$OCH_3$, —$C_2H_4$—$OCH_3$, —$C_3H_6$—$OCH_3$, —$CH_2$—$OC_2H_5$, —$C_2H_4$—$OC_2H_5$, and —$C_3H_6$—$OC_2H_5$.

As used herein, the term "monounsaturated 5-membered heterocyclyl" refers to a substituted or non substituted ring system of five atoms including at least one heteroatom such as O, S, SO, $SO_2$, N, NO, and one double bond, wherein these monounsaturated 5-membered heterocyclic residues can be substituted with 1 to 4 substituents selected from $Z^1$, $Z^2$, $Z^3$ and $Z^4$. It is also possible that two of the substituents $Z^1$, $Z^2$, $Z^3$ and $Z^4$ represent together an oxygen atom and form together with the ring carbon atom of the heterocyclic ring to which they are both attached a carbonyl moiety or a sulfoxide moiety together with the ring sulphur atom to which they are attached or both Z substituents represent oxygen and form a sulfone moiety together with the ring sulphur atom to which they are attached. If the monounsaturated 5-membered heterocyclic residue contains a nitrogen atom which is substituted by one of the substituents $Z^1$, $Z^2$, $Z^3$ and $Z^4$, said Z substituent represents $R^{11}$. If the monounsaturated 5-membered heterocyclic residue contains two nitrogen atoms which are both substituted by one of the substituents $Z^1$, $Z^2$, $Z^3$ and $Z^4$, the first Z substituent represents $R^{11}$ and the second Z substituent represents $R^{12}$.

Examples of preferred monounsaturated 5-membered heterocyclic groups and substituted 5-membered heterocyclic groups for $R^3$ are

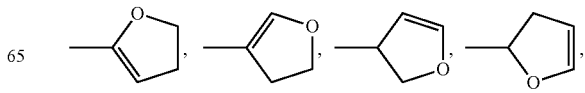

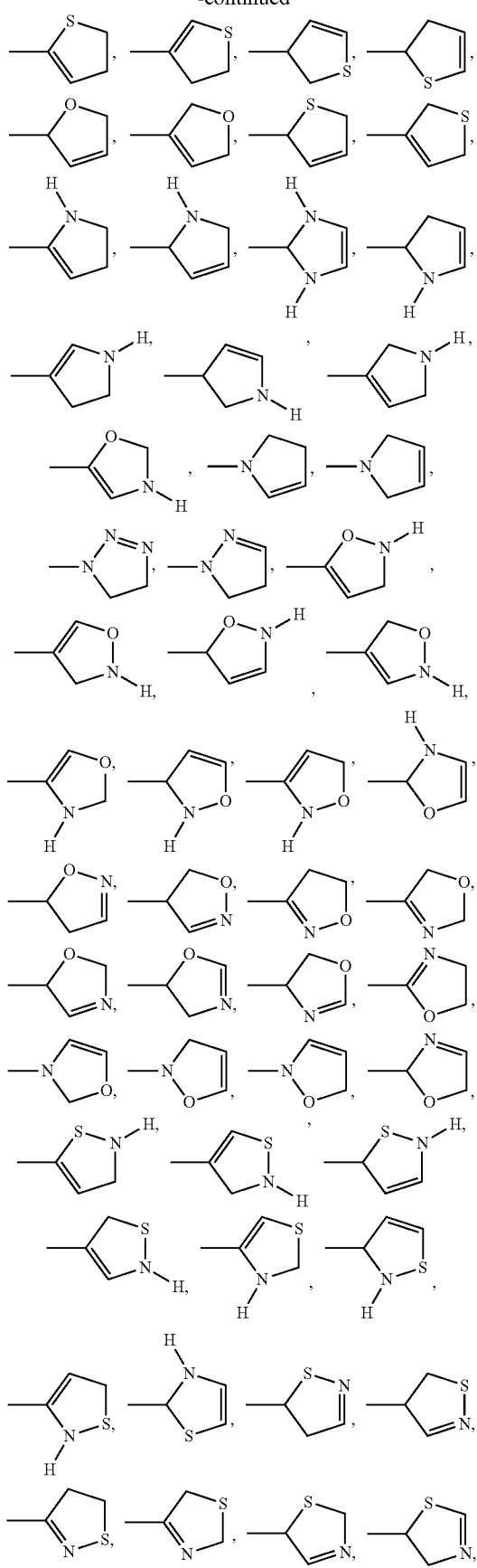
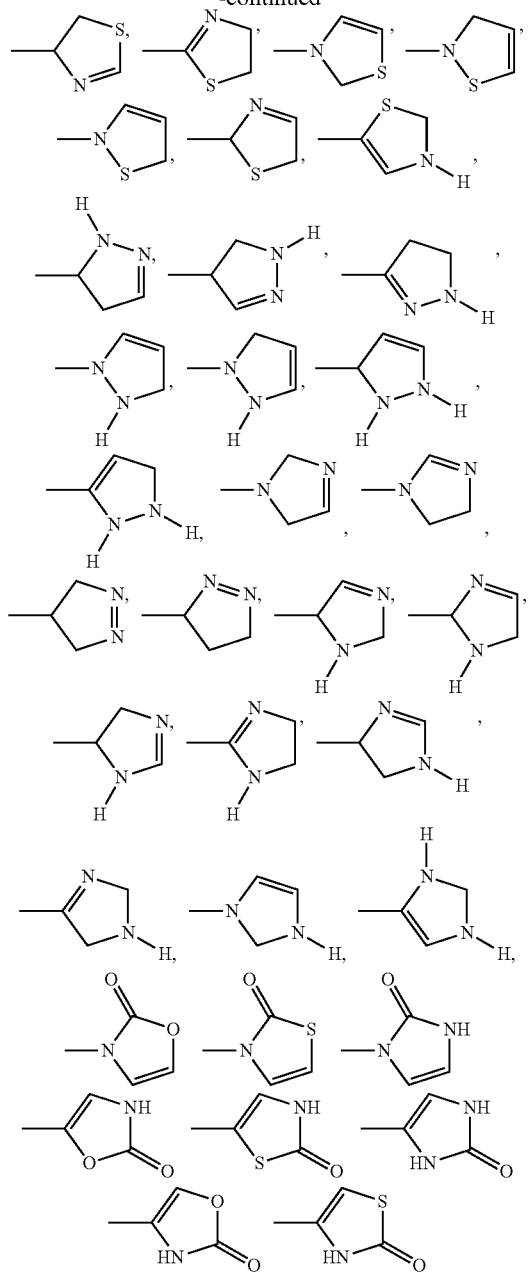

wherein the afore-mentioned monounsaturated 5-membered heterocyclic groups can be substituted with 1 to 4 substituents selected from $Z^1$, $Z^2$, $Z^3$ and $Z^4$.

Preferably $Z^1$ to $Z^4$ represent independently of each other —$CH_3$, —$C_2H_5$, —$C_3H_7$, —$CH(CH_3)_2$, —OH, —$OCH_3$, —$OC_2H_5$, —$OC_3H_7$, —$NH_2$, —$N(CH_3)_2$, —F, —Cl, —Br, —I, —CN, —$CH_2F$, —$CHF_2$, —$CF_3$, —$OCHF_2$, and —$OCF_3$.

As used herein, the term "monounsaturated 6-membered heterocyclyl" refers to a substituted or non substituted ring system of six atoms including at least one heteroatom such as O, S, SO, $SO_2$, N, NO, and one double bond, wherein these monounsaturated 6-membered heterocyclic residues can be substituted with 1 to 4 substituents selected from $Z^1$, $Z^2$, $Z^3$ and $Z^4$. It is also possible that two of the substituents $Z^1$, $Z^2$, $Z^3$ and $Z^4$ represent together an oxygen atom and form together with the ring carbon atom of the heterocyclic ring to which they are both attached a carbonyl moiety or a sulfoxide moiety together with the ring sulphur atom to which they are attached or both Z substituents represent oxygen and form a sulfone moiety together with the ring sulphur atom to which they are attached. If the monounsaturated 6-membered heterocyclic residue contains a nitrogen atom which is substituted by one of the substituents $Z^1$, $Z^2$, $Z^3$ and $Z^4$, said Z substituent represents $R^{11}$. If the monounsaturated 6-membered heterocyclic residue contains two nitrogen atoms which are both substituted by one of the substituents $Z^1$, $Z^2$, $Z^3$ and $Z^4$, the first Z substituent represents $R^{11}$ and the second Z substituent represents $R^{12}$.

Examples of preferred monounsaturated 6-membered heterocyclic groups and substituted 6-membered heterocyclic groups for $R^3$ are

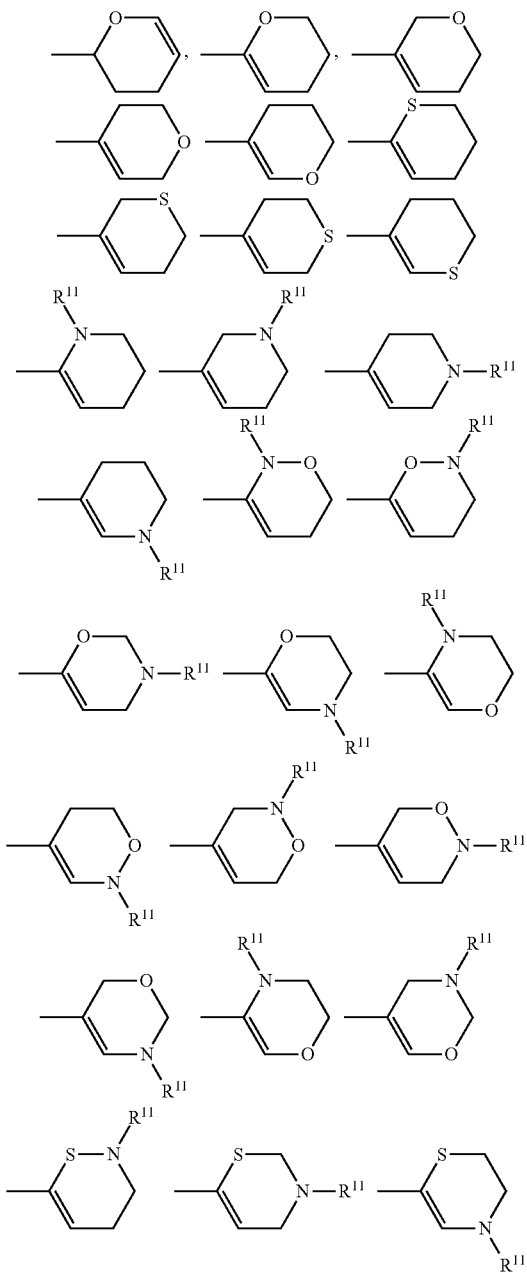

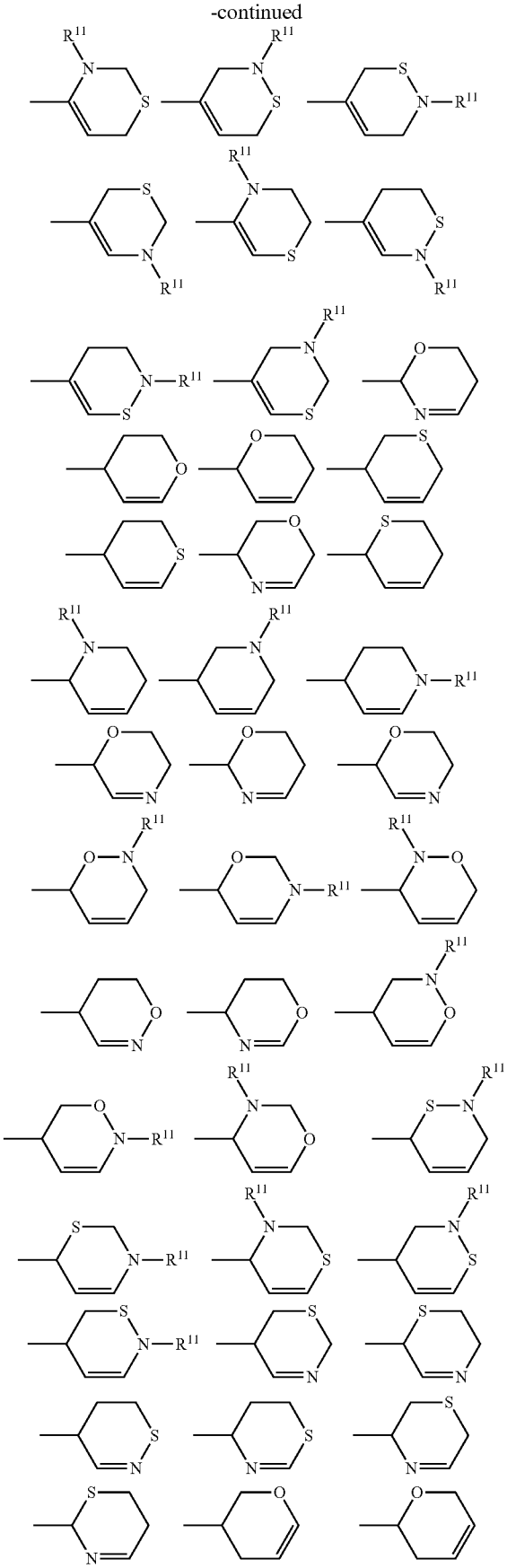

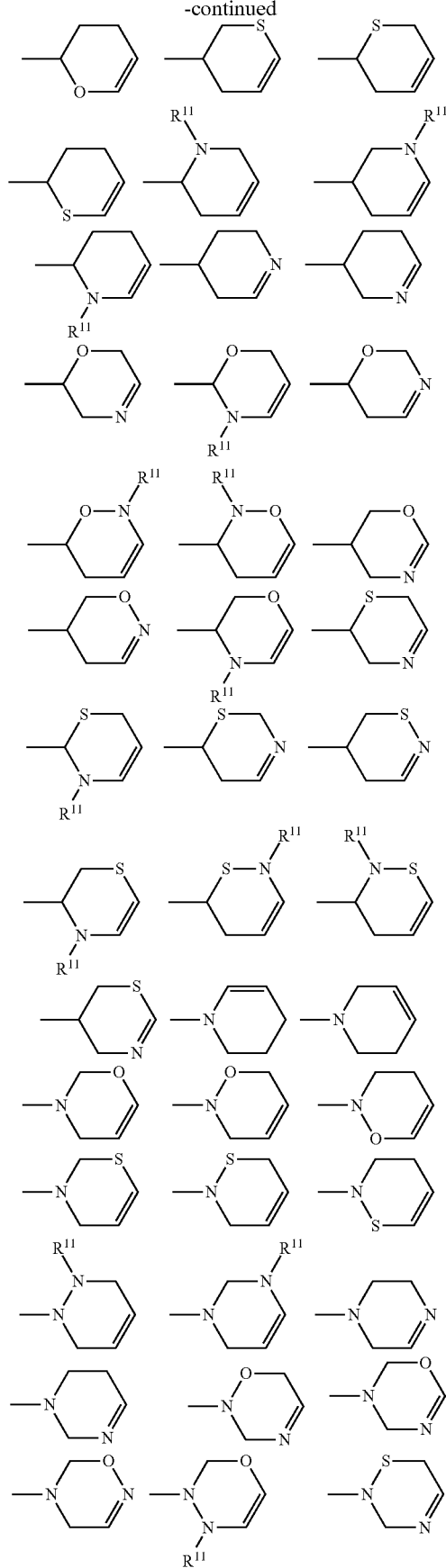
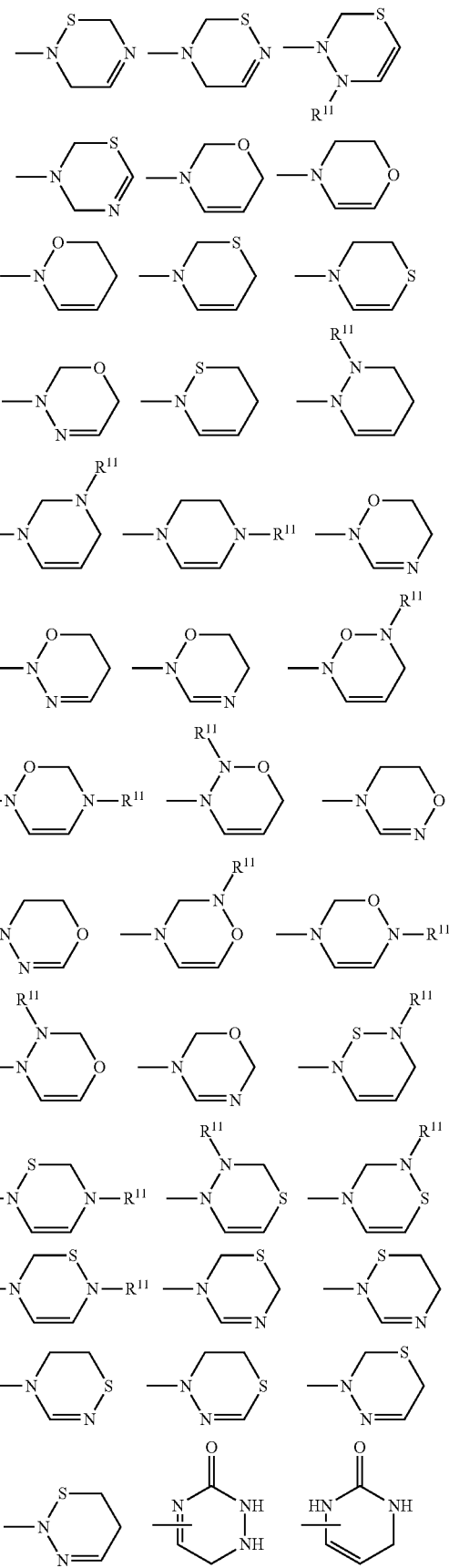

-continued

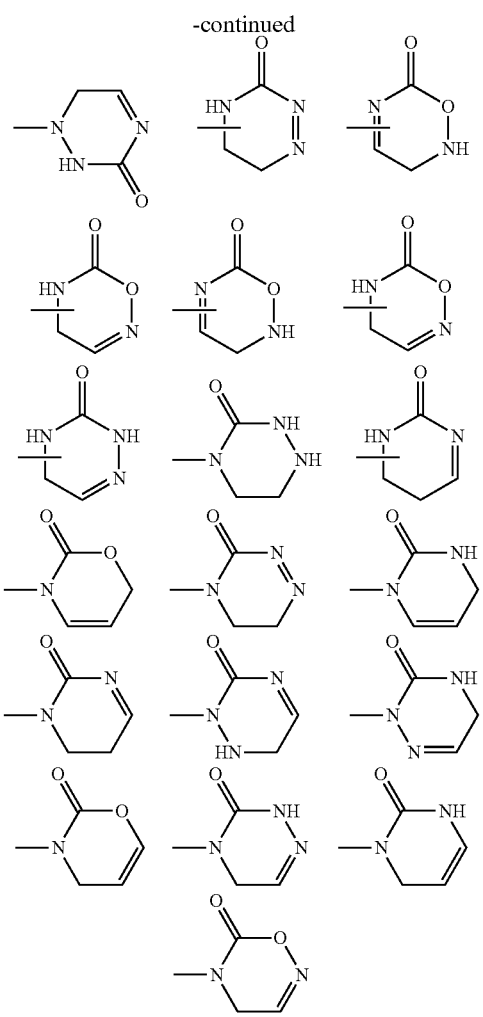

wherein the afore-mentioned monounsaturated 6-membered heterocyclic groups can be substituted with 1 to 4 substituents selected from $Z^1$, $Z^2$, $Z^3$ and $Z^4$.

Preferably $Z^1$ to $Z^4$ represent independently of each other —$CH_3$, —$C_2H_5$, —$C_3H_7$, —$CH(CH_3)_2$, —OH, —$OCH_3$, —$OC_2H_5$, —$OC_3H_7$, —$NH_2$, —$N(CH_3)_2$, —F, —Cl, —Br, —I, —CN, —$CH_2F$, —$CHF_2$, —$CF_3$, —$OCHF_2$, and —$OCF_3$.

Preferred substituents for $R^{11}$ are —$CH_3$, —$C_2H_5$, —$C_3H_7$, —$CH(CH_3)_2$, —$CH_2F$, —$CHF_2$,

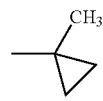

—$CF_3$, cyclo-$C_3H_5$, cyclo-$C_4H_7$, cyclo-$C_5H_9$, cyclo-$C_6H_{11}$, cyclo-$C_7H_{13}$, —$C_4H_9$, —$CH_2$—$CH(CH_3)_2$, —$CH(CH_3)$—$C_2H_5$, —$C(CH_3)_3$, —$C_5H_{11}$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$CH(C_2H_5)_2$, —$C_2H_4$—$CH(CH_3)_2$, —$C_6H_{13}$, —$C_7H_{15}$, —$C_8H_{17}$, -Ph, —$CH_2$-Ph, —$CH_2$—$CH_2$-Ph, —CH═CH-Ph, —CH═$CH_2$, —$CH_2$—CH═$CH_2$, —C($CH_3$)═$CH_2$, —CH═CH—$CH_3$, —$C_2H_4$—CH═$CH_2$, —$CH_2$—CH═CH—$CH_3$, —CH═CH—$C_2H_5$, —$CH_2$—C($CH_3$)═$CH_2$, —CH($CH_3$)—CH═$CH_2$, —CH═C($CH_3$)$_2$, —C($CH_3$)═CH—$CH_3$, —C≡CH, —C≡C—$CH_3$, —$CH_2$—C≡CH, —$C_2H_4$—C≡CH, —$CH_2$—C≡C—$CH_3$, —C≡C—$C_2H_5$, —$CH_2$—$OCF_3$, —$C_2H_4$—$OCF_3$, —$C_3H_6$—$OCF_3$, —$CH_2$—$OCH_3$, —$C_2H_4$—$OCH_3$, —$C_3H_6$—$OCH_3$, —$CH_2$—$OC_2H_5$, —$C_2H_4$—$OC_2H_5$, and —$C_3H_6$—$OC_2H_5$.

The term "carbocyclyl" as used herein refers to $C_3$-$C_8$-cycloalkyl, 3-membered carbocyclyl, 4-membered carbocyclyl, 5-membered carbocyclyl, and 6-membered carbocyclyl.

As used herein for the substituent $R^3$, the term "3-membered carbocyclyl" refers to

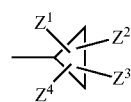

As used herein for the substituent $R^3$, the term "4-membered carbocyclyl" refers to

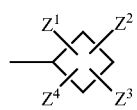

The same definition applies for the substituent $R^8$ with the only difference that the optional substituents of the 4-membered carbocyclyl residue are $Z^5$ to $Z^7$ instead of $Z^1$ to $Z^4$. Thus for $R^8$ the optional substituent $Z^1$ is replaced by $Z^5$, $Z^2$ is replaced by $Z^6$, $Z^3$ is replaced by $Z^7$, and $Z^4$ is hydrogen.

As used herein for the substituent $R^3$, the term "5-membered carbocyclyl" refers to

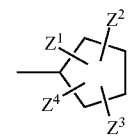

The same definition applies for the substituent $R^8$ with the only difference that the optional substituents of the 5-membered carbocyclyl residue are $Z^5$ to $Z^7$ instead of $Z^1$ to $Z^4$. Thus for $R^8$ the optional substituent $Z^1$ is replaced by $Z^5$, $Z^2$ is replaced by $Z^6$, $Z^3$ is replaced by $Z^7$, and $Z^4$ is hydrogen.

As used herein for the substituent $R^3$, the term "6-membered carbocyclyl" refers to

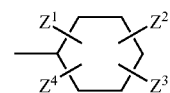

The same definition applies for the substituent $R^8$ with the only difference that the optional substituents of the 6-membered carbocyclyl residue are $Z^5$ to $Z^7$ instead of $Z^1$ to $Z^4$. Thus for $R^8$ the optional substituent $Z^1$ is replaced by $Z^5$, $Z^2$ is replaced by $Z^6$, $Z^3$ is replaced by $Z^7$, and $Z^4$ is hydrogen.

As used herein, the term "6-membered aryl" refers to phenyl, substituted phenyl as well as to benzo residues where a non aromatic ring is condensed to a benzo ring such as a benzodioxol:

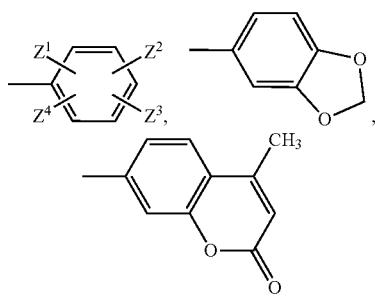

wherein the afore-mentioned 6-membered aryl groups can be substituted with 1 to 4 substituents selected from $Z^1$, $Z^2$, $Z^3$ and $Z^4$.

As used herein, the term "naphthyl" refers to

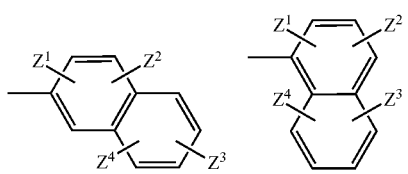

As used herein, the term "5-membered heteroaryl" refers to a substituted or non substituted aromatic ring system of five atoms including at least one heteroatom such as O, S, SO, $SO_2$, N, NO, wherein these aromatic 5-membered heterocyclic residues can be substituted with 1 to 4 substituents selected from $Z^1$, $Z^2$, $Z^3$ and $Z^4$. However it is clear to a skilled person that the term "can be substituted" refers to the replacement of a hydrogen atom by one of the substituents $Z^1$, $Z^2$, $Z^3$ or $Z^4$. Moreover it is clear to a skilled person that only these hydrogen atoms which are present in the aromatic 5-membered heterocyclic group can be replaced by the substituents $Z^1$, $Z^2$, $Z^3$ and $Z^4$. Thus, since the tetrazole group has only one hydrogen atom, only one hydrogen atom can be replaced by one substituent selected from $Z^1$, $Z^2$, $Z^3$ and $Z^4$. If the aromatic 5-membered heterocyclic residue contains a nitrogen atom which is substituted by one of the substituents $Z^1$, $Z^2$, $Z^3$ and $Z^4$, said Z substituent represents $R^{11}$.

Examples of preferred aromatic 5-membered heterocyclic groups and substituted aromatic 5-membered heterocyclic groups are

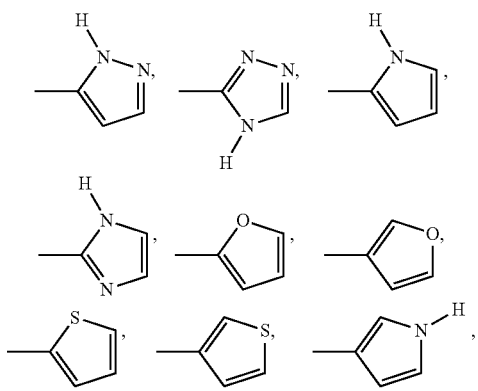

-continued

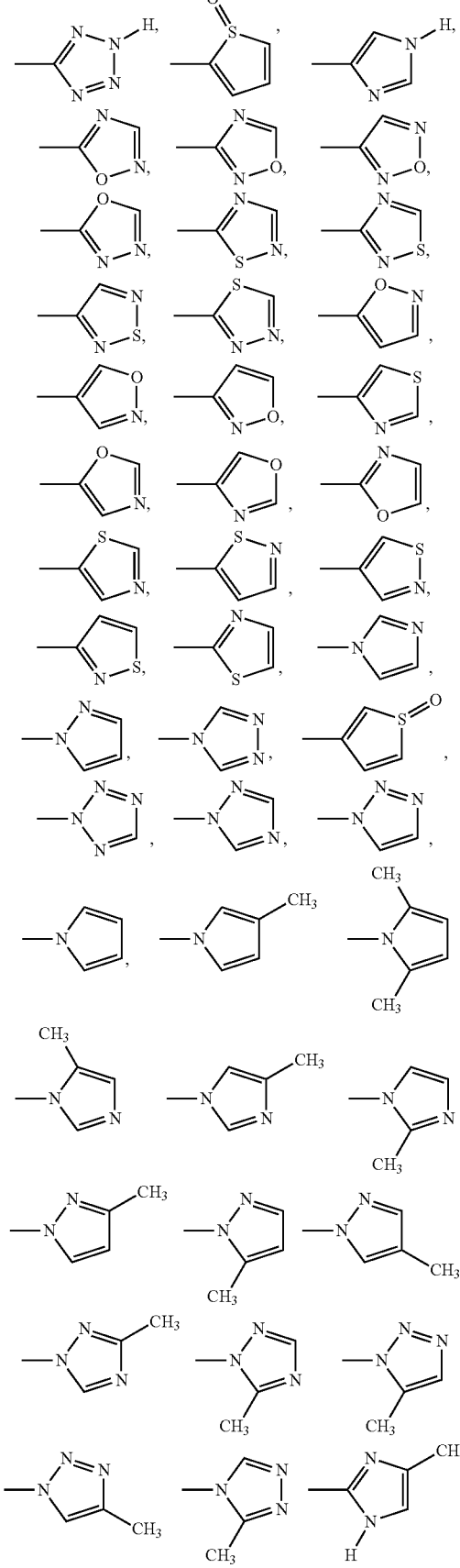

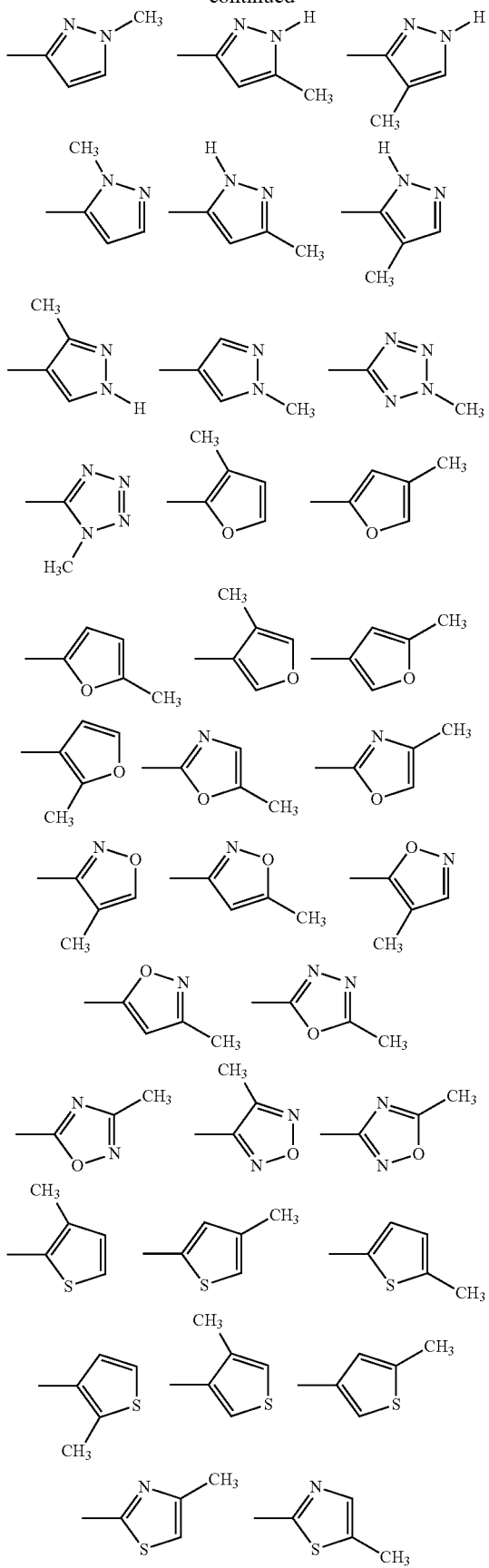

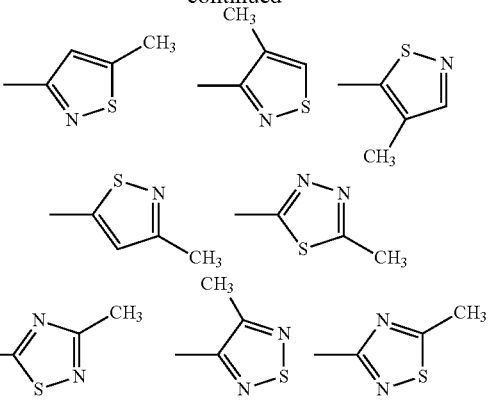

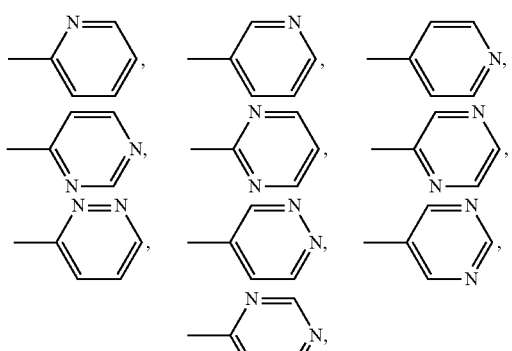

wherein the afore-mentioned 5-membered heteroaryl groups can be substituted with 1 to 4 substituents selected from $Z^1$, $Z^2$, $Z^3$ and $Z^4$.

Preferably $Z^1$ to $Z^4$ represent independently of each other —$CH_3$, —$C_2H_5$, —$C_3H_7$, —$CH(CH_3)_2$, —OH, —$OCH_3$, —$OC_2H_5$, —$OC_3H_7$, —$NH_2$, —$N(CH_3)_2$, —F, —Cl, —Br, —I, —CN, —$CH_2F$, —$CHF_2$, —$CF_3$, —$OCHF_2$, and —$OCF_3$.

As used herein, the term "6-membered heteroaryl" refers to a substituted or non substituted aromatic ring system of six atoms including at least one heteroatom such as O, S, SO, $SO_2$, N, NO, wherein these aromatic 6-membered heterocyclic residues can be substituted with 1 to 4 substituents selected from $Z^1$, $Z^2$, $Z^3$ and $Z^4$. However it is clear to a skilled person that the term "can be substituted" refers to the replacement of a hydrogen atom by one of the substituents $Z^1$, $Z^2$, $Z^3$ or $Z^4$. Moreover it is clear to a skilled person that only these hydrogen atoms which are present in the aromatic 6-membered heterocyclic group can be replaced by the substituents $Z^1$, $Z^2$, $Z^3$ and $Z^4$. Thus, since the triazine group has only two hydrogen atoms, only two hydrogen atoms can be replaced by two substituents selected from $Z^1$, $Z^2$, $Z^3$ and $Z^4$.

Examples of preferred aromatic 6-membered heterocyclic groups and substituted aromatic 6-membered heterocyclic groups are wherein the afore-mentioned 6-membered heteroaryl groups can be substituted with 1 to 4 substituents selected from $Z^1$, $Z^2$, $Z^3$ and $Z^4$.

It is also possible that the substituents $R^3$ and $R^4$ are not single substituent and that $R^3$ together with $R^4$ can form a carbocyclic or heterocyclic 4-, 5-, 6- or 7-membered ring with the two carbon atoms of the benzo ring to which $R^3$ and $R^4$ are attached and that 4-, 5-, 6- or 7-membered ring can be aromatic or non aromatic and can be substituted with 1 to 4 substituents selected from $Z^1$, $Z^2$, $Z^3$ and $Z^4$.

The term "carbocyclic 4-membered ring" is used synonymic for the term "4-membered carbocyclyl". In case $R^{11}$ and $R^{12}$ together with the atoms to which they are attached represent a "carbocyclic 4-membered ring", the optional substituents $Z^1$ to $Z^4$ are replaced by the optional substituents $Z^8$ to $Z^{13}$.

The term "carbocyclic 5-membered ring" is used synonymic for the term "5-membered carbocyclyl". In case $R^{11}$ and $R^{12}$ together with the atoms to which they are attached represent a "carbocyclic 5-membered ring", the optional substituents $Z^1$ to $Z^4$ are replaced by the optional substituents $Z^8$ to $Z^{15}$.

The term "carbocyclic 6-membered ring" is used synonymic for the term "6-membered carbocyclyl". In case $R^{11}$ and $R^{12}$ together with the atoms to which they are attached represent a "carbocyclic 6-membered ring", the optional substituents $Z^1$ to $Z^4$ are replaced by the optional substituents $Z^8$ to $Z^{15}$.

The term "carbocyclic 7-membered ring" is used synonymic for the term "7-membered carbocyclyl".

The term "heterocyclic 4-membered ring" is used synonymic for the term "4-membered heterocyclyl". In case $R^{11}$ and $R^{12}$ together with the atoms to which they are attached represent a "heterocyclic 4-membered ring", the optional substituents $Z^1$ to $Z^4$ are replaced by the optional substituents $Z^8$ to $Z^{13}$.

The term "heterocyclic 5-membered ring" is used synonymic for the term "5-membered heterocyclyl". In case $R^{11}$ and $R^{12}$ together with the atoms to which they are attached represent a "heterocyclic 5-membered ring", the optional substituents $Z^1$ to $Z^4$ are replaced by the optional substituents $Z^8$ to $Z^{15}$.

The term "heterocyclic 6-membered ring" is used synonymic for the term "6-membered heterocyclyl". In case $R^{11}$ and $R^{12}$ together with the atoms to which they are attached represent a "heterocyclic 6-membered ring", the optional substituents $Z^1$ to $Z^4$ are replaced by the optional substituents $Z^8$ to $Z^{15}$.

The term "heterocyclic 7-membered ring" is used synonymic for the term "7-membered heterocyclyl".

Thus if $R^3$ and $R^4$ form together with the two carbon atoms of the phenyl group to which they are attached a fused ring system so that the moiety

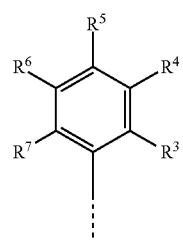

represents a bicyclic moiety, the following ring fragments are preferred:

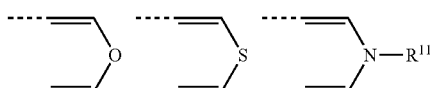

-continued

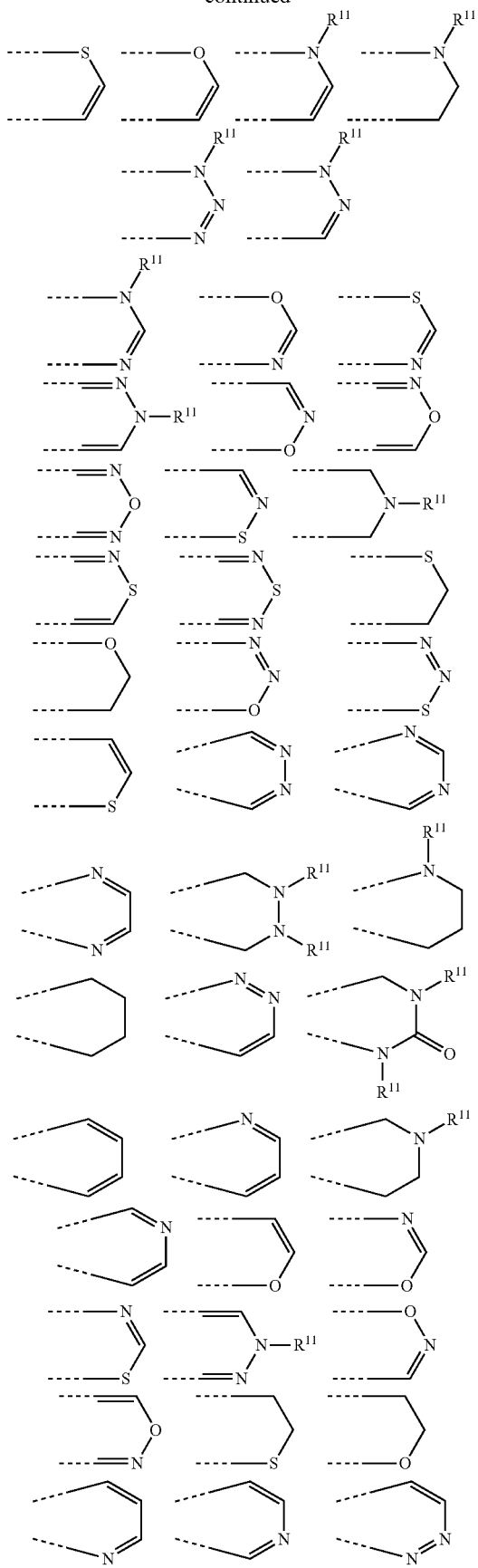

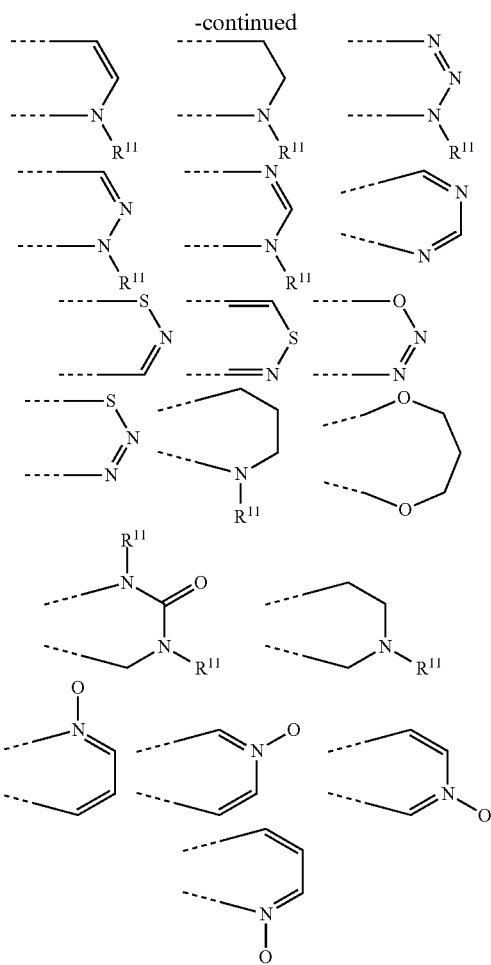

wherein the afore-mentioned 5-membered or 6-membered moieties or the afore-mentioned ring fragments consisting of 3 or 4 ring fragment atoms can be substituted with 1 to 4 substituents selected from $Z^1$, $Z^2$, $Z^3$ and $Z^4$. However it is clear to a skilled person that the term "can be substituted" refers to the replacement of a hydrogen atom by one of the substituents $Z^1$, $Z^2$, $Z^3$ or $Z^4$. Moreover it is clear to a skilled person that only these hydrogen atoms which are present in the afore-mentioned carbocyclic or heterocyclic 4-, 5-, 6- or 7-membered rings or in the afore-mentioned ring fragments can be replaced by the substituents $Z^1$, $Z^2$, $Z^3$ and $Z^4$. Thus, since the ring fragment =N—O—N= does not have any hydrogen atoms, no substitution is possible at this 3 atom ring fragment.

Thus, it is preferred that the phenyl group together with $R^3$ and $R^4$ form the following bicyclic systems which can be further substituted with 1 to 4 substituents selected from $Z^1$, $Z^2$, $Z^3$ and $Z^4$ on the ring formed by $R^3$ and $R^4$ as well as with $R^5$, $R^6$ and $R^7$ on the phenyl group which is the benzo group in the bicyclic ring:

1H-indolyl, 2H-isoindolyl, 1-benzo-thiophenyl, 1-benzofuranyl, 2-benzofuranyl, 2-benzothiophenyl, 1H-indazolyl, 1H-benz-imidazolyl, 1,3-benzoxazolyl, 1,3-benzothiazolyl, 1,2-benzisoxazolyl, 2,1-benzisoxazolyl, 2,1,3-benzoxadiazolyl, 1,2-benzisothiazolyl, 2,1-benzisothiazolyl, 2,1,3-benzothiadiazolyl, 2H-indazolyl, 1H-1,2,3-benzotriazolyl, 1,2,3-benzoxadiazolyl, 1,2,3-benzothiadiazolyl, naphthyl, quinolinyl, isoquinolinyl, cinnolinyl, phthalazinyl, quinazolinyl, quinoxalinyl, indolinyl, isoindolinyl, 2,3-dihydro-1-benzofuranyl, 2,3-dihydro-1-benzothiophenyl, 1,2,3,4-tetrahydronaphthyl, 1,2,3,4-tetrahydroquinolinyl, 1,2,3,4-tetrahydroisoquinolinyl, 1,2,3,4-tetrahydrophthalazinyl, and 3,4-dihydroquinazolin-2(1H)-onyl.

As used herein, the term "carbocyclyl" refers preferably to a $C_3$-$C_8$-cycloalkyl as disclosed above. Moreover the carbocyclyl residues can be substituted with 1 to 3 substituents selected from $Z^5$, $Z^6$ and $Z^7$. Thus, the above-mentioned $C_3$-$C_8$-cycloalkyl residues are examples for carbocyclyl residues which can be substituted with one, two or three substituents selected from $Z^5$, $Z^6$ and $Z^7$. Further, it is clear to a skilled person that the term "can be substituted" refers to the replacement of a hydrogen atom by one of the substituents $Z^5$, $Z^6$ and $Z^7$. Moreover it is clear to a skilled person that only these hydrogen atoms which are present in the carbocyclic group can be replaced by the substituents $Z^5$, $Z^6$ and $Z^7$. Further, as used herein the term "carbocyclyl" refers to carbocyclic residues with 3 to 8 ring carbon atoms which may also be partly unsaturated but not aromatic such as. Thus, the term "carbocyclyl" refers for example to cyclohexdienyl (—$C_6H_7$), but not to phenyl (—$C_6H_5$).

Examples of preferred carbocyclic residues are:

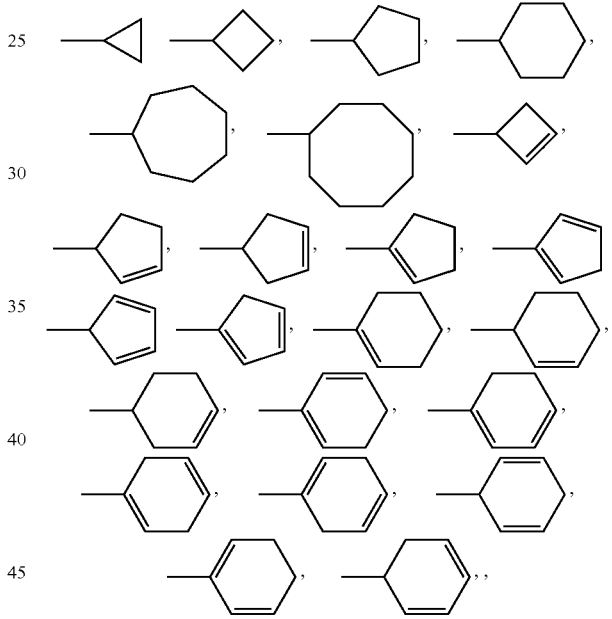

wherein these residues can be substituted with 1 to 3 substituents selected from $Z^5$, $Z^6$, and $Z^7$.

Preferably $Z^5$, $Z^6$ and $Z^7$ represent independently of each other —$CH_3$, —$C_2H_5$, —$C_3H_7$, —$CH(CH_3)_2$, —OH, —$OCH_3$, —$OC_2H_5$, —$OC_3H_7$, —$NH_2$, —$N(CH_3)_2$, —F, —Cl, —Br, —I, —CN, —$CH_2F$, —$CHF_2$, —$CF_3$, —$OCHF_2$, and —$OCF_3$.

Examples of preferred substituted carbocyclic residues are

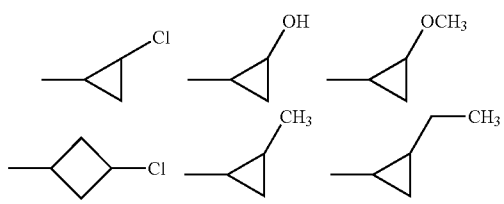

-continued

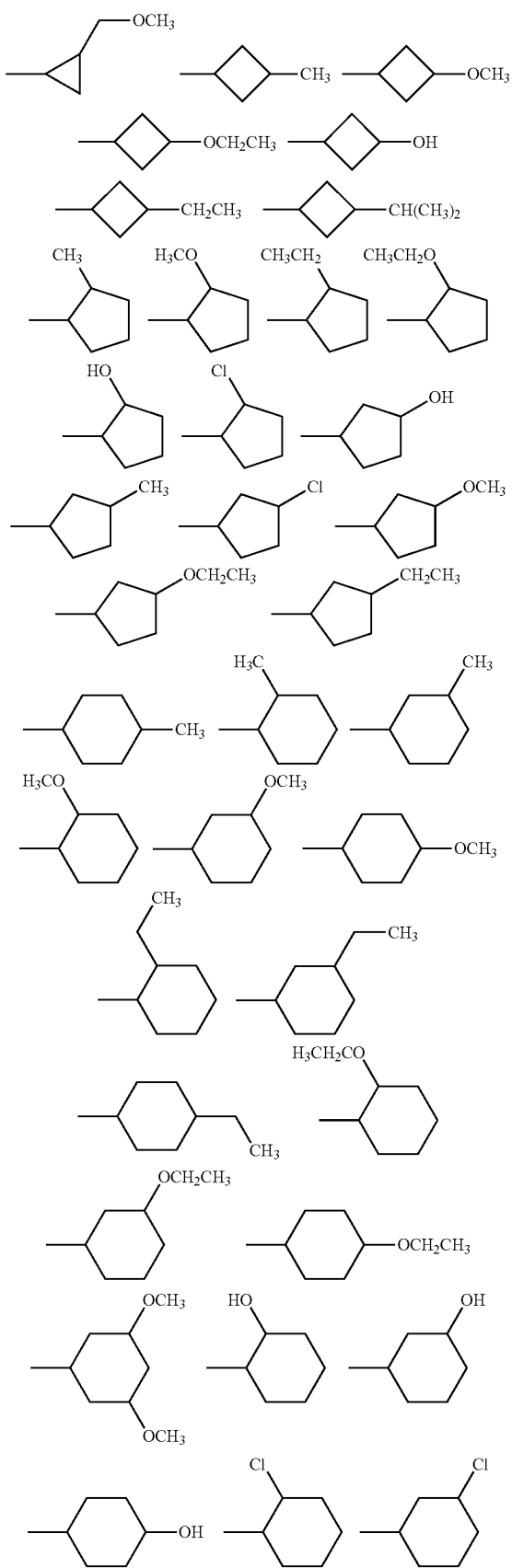
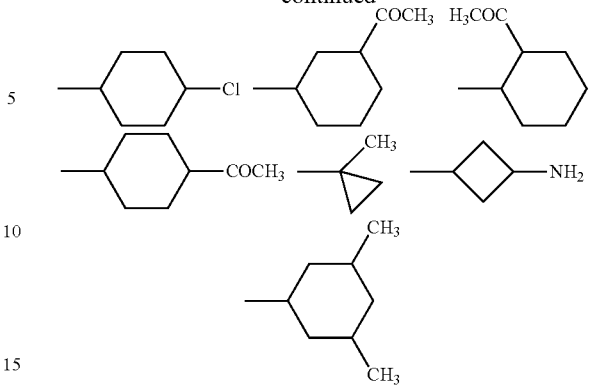

The term "bridging carbocyclyl" refers to a carbocyclyl residue as disclosed herein, which is further bonded to a second substituent independent from any optional substitution with substituents $Z^1$, $Z^2$, $Z^3$ or $Z^4$. Thus, in a "bridging carbocyclyl" two hydrogen atoms are replaced by residues rendering the "bridging carbocyclyl" a di-yl moiety. Further, the "bridging carbocyclyl" binds the two different residues with two different carbon atoms, thereby preventing a substitution pattern wherein the two residues are bonded to the same carbon atom. The "bridging carbocyclyl" can be substituted with 1 to 4 substituents selected from $Z^1$, $Z^2$, $Z^3$ or $Z^4$. It is clear to a skilled person that the term "can be substituted" refers to the replacement of a hydrogen atom by one of the substituents $Z^1$, $Z^2$, $Z^3$ or $Z^4$. Further, it is clear to a skilled person that the term "can be substituted" refers to the replacement of a hydrogen atom by one of the substituents $Z^1$, $Z^2$, $Z^3$ or $Z^4$. Moreover, it is clear to a skilled person that only these hydrogen atoms which are present in the "bridging carbocyclyl" group can be replaced by the substituents $Z^1$, $Z^2$, $Z^3$ and $Z^4$.

The person skilled in the art will understand that when $R^2$ being $-(CH_2)_a$-$(Q)_b$-$(CH_2)_c$-$(G^1)_d$-$(CH_2)_e$-$(G^2)_f$-$(CH_2)_g$—$R^8$ and for example Q represents "a bridging carbocyclyl" (b=1), then this "bridging carbocyclyl" is attached to a first part of $R^2$, for example —$CH_2$— in case a=1 and a second part of $R^2$, for instance —$CH_2$—$R^8$ in case c=1 and d, e, f and g are 0. Thus, "a bridging carbocyclyl" is attached to two different residues redering it a di-yl residue.

As used herein, the term "heterocyclyl" refers preferably to a $C_1$-$C_9$-heterocyclyl as disclosed above. Moreover the heterocyclyl residues can be substituted with 1 to 3 substituents selected from $Z^5$, $Z^6$ and $Z^7$. Thus, the above-mentioned $C_1$-$C_9$-heterocyclyl residues are examples for heterocyclyl residues which can be substituted with one, two or three substituents selected from $Z^5$, $Z^6$ and $Z^7$. The number of 1 to 9 carbon atoms ($C_1$-$C_9$) refers to the number of ring carbon atoms and does not include any carbon atoms probably present in the substituents $Z^5$ to $Z^7$.

As used herein, the term "$C_1$-$C_9$-nitrogenheterocyclyl" refers to cyclic substituents with 1 to 9 carbon atoms and at least one nitrogen atom and optionally further heteroatoms such as N, S, O, S=O, $SO_2$ in the cyclus and refers preferably to the $C_1$-$C_9$-heterocyclyl residues as disclosed above, wherein one heteroatom is nitrogen. The $C_1$-$C_9$-nitrogenheterocyclyl residue is linked through the at least one nitrogen ring atom to the rest of the molecule. Moreover the $C_1$-$C_9$-nitrogenheterocyclyl residue can be substituted with 1 to 3 substituents selected from $Z^5$, $Z^6$ and $Z^7$.

The term "bridging heterocyclyl" refers to a heterocyclyl residue as disclosed above, which is further bonded to a second substituent independent from any optional substitution with substituents $Z^1$, $Z^2$, $Z^3$ or $Z^4$. Thus, in a "bridging heterocyclyl" two hydrogen atoms are replaced by residues rendering the "bridging heterocyclyl" a di-yl moiety. Further, the "bridging heterocyclyl" binds the two different residues with two different atoms of the heterocyclyl skeleton, thereby preventing a substitution pattern wherein the two residues are bonded to the same atom. The "bridging heterocyclyl" can be substituted with 1 to 4 substituents selected from $Z^1$, $Z^2$, $Z^3$ or $Z^4$. It is clear to a skilled person that the term "can be substituted" refers to the replacement of a hydrogen atom by one of the substituents $Z^1$, $Z^2$, $Z^3$ or $Z^4$. Further, it is clear to a skilled person that the term "can be substituted" refers to the replacement of a hydrogen atom by one of the substituents $Z^1$, $Z^2$, $Z^3$ or $Z^4$. Moreover, it is clear to a skilled person that only these hydrogen atoms which are present in the "bridging heterocyclyl" group can be replaced by the substituents $Z^1$, $Z^2$, $Z^3$ and $Z^4$.

The person skilled in the art will understand that when $R^2$ being $-(CH_2)_a$-$(Q)_b$-$(CH_2)_c$-$(G^1)_d$-$(CH_2)_e$-$(G^2)_f$-$(CH_2)_g$-$R^8$ and for example $G^1$ represents "a bridging heterocyclyl" (d=1), then this "bridging heterocyclyl" is attached to a first residue of $R^2$, for example $-C_3H_6-$ in case a=3 and b=c=0 and a second residue of $R^2$, for example $-CH_2-OCH_2-R^8$ in case e=f=g=1 and $G^2=-O-$. Thus, "a bridging heterocyclyl" is attached to two different residues redering it a di-yl residue.

As used herein, the term "spirocarbocyclyl" refers also to the $C_7$-$C_{16}$-spiroalkyl residues as disclosed above but is not limited to these $C_7$-$C_{16}$-spiroalkyl residues. Moreover the spirocarbocyclyl residues can be substituted with 1 to 3 substituents selected from $Z^5$, $Z^6$ and $Z^7$. Thus, the above-mentioned $C_7$-$C_{16}$-spiroalkyl residues are examples for spirocarbocyclyl residues which can be substituted with one, two or three substituents selected from $Z^5$, $Z^6$ and $Z^7$. However it is clear to a skilled person that the term "can be substituted" refers to the replacement of a hydrogen atom by one of the substituents $Z^5$, $Z^6$ or $Z^7$. It is also possible that two of the substituents $Z^5$, $Z^6$ and $Z^7$ represent together an oxygen atom and form together with the carbon atom of the spirocarbocyclyl residue to which they are both attached a carbonyl moiety. The carbon atom number of $C_7$-$C_{16}$ refers only to the carbon atoms of the spiro residue (spiroalkyl) and does not include the carbon atoms of the substituents $Z^5$ to $Z^7$.

$R^8$ represents preferably the following spirocarbocyclyl residues: spiro[2,3]hexyl, spiro[2,4]heptyl, spiro[2,5]octyl, spiro[2,7]nonyl, spiro[3,3]heptyl, spiro[3,4]octyl, spiro[3,5]nonyl, spiro[3,6]decyl, spiro[4,4]nonyl, spiro[4,5]decyl, spiro[4,6]undecyl, spiro[5,5]undecyl, spiro[5,6]dodecyl, spiro[6,6]tridecyl, wherein the afore-mentioned spirocarbocyclyl residues can be substituted with one to three substituents selected from $Z^5$, $Z^6$ and $Z^7$.

The term "bridging spirocarbocyclyl" refers to a spirocarbocyclyl residue as disclosed above, which is further bonded to a second substituent independent from any optional substitution with substituents $Z^1$, $Z^2$, $Z^3$ or $Z^4$. Thus, in a "bridging spirocarbocycly" two hydrogen atoms are replaced by residues rendering the "bridging spirocarbocyclyl" a di-yl moiety. Further, the "bridging spirocarbocyclyl" binds the two different residues with two different atoms of the spirocarbocyclyl skeleton, thereby preventing a substitution pattern wherein the two residues are bonded to the same atom. The "bridging spirocarbocyclyl" can be substituted with 1 to 4 substituents selected from $Z^1$, $Z^2$, $Z^3$ or $Z^4$. It is clear to a skilled person that the term "can be substituted" refers to the replacement of a hydrogen atom by one of the substituents $Z^1$, $Z^2$, $Z^3$ or $Z^4$. Further, it is clear to a skilled person that the term "can be substituted" refers to the replacement of a hydrogen atom by one of the substituents $Z^1$, $Z^2$, $Z^3$ or $Z^4$. Moreover, it is clear to a skilled person that only these hydrogen atoms which are present in the "bridging spirocarbocyclyl" group can be replaced by the substituents $Z^1$, $Z^2$, $Z^3$ and $Z^4$.

The person skilled in the art will understand that when $R^2$ being $-(CH_2)_a$-$(Q)_b$-$(CH_2)_c$-$(G^1)_d$-$(CH_2)_e$-$(G^2)_f$-$(CH_2)_g$-$R^8$ and for example $G^2$ represents "a bridging spirocarbocyclyl" (f=1), then this "bridging spirocarbocyclyl" is attached to a first part of $R^2$, for example $-CH_2-CO-C_2H_4-$ in case a=b=c=e=1, d=0, Q=—CO—, and a second residue of $R^2$, for instance $-C_2H_4-R^8$ in case g=2. Thus, "a bridging spirocarbocyclyl" is attached to two different residues redering it a di-yl residue.

As used herein, the term "spiroheterocyclyl" refers to $C_5$-$C_{14}$/$N_0$-$N_2$/$O_0$-$O_2$/$S_0$-$S_1$-spiroheterocyclyl residues comprising or including the $C_5$-$C_{14}$-spiroheterocyclyl residues as disclosed above. Moreover the $C_5$-$C_{14}$/$N_0$-$N_2$/$O_0$-$O_2$/$S_0$-$S_1$-spiroheterocyclyl residues or the $C_5$-$C_{14}$-spiroheterocyclyl residues can be substituted with 1 to 3 substituents selected from $Z^5$, $Z^6$ and $Z^7$. Thus, the above-mentioned $C_5$-$C_{14}$-spiroheterocyclyl residues are examples for $C_5$-$C_{14}$/$N_0$-$N_2$/$O_0$-$O_2$/$S_0$-$S_1$-spiroheterocyclyl residues which can be substituted with one, two or three substituents selected from $Z^5$, $Z^6$ and $Z^7$. However it is clear to a skilled person that the term "can be substituted" refers to the replacement of a hydrogen atom by one of the substituents $Z^5$, $Z^6$ or $Z^7$. It is also possible that two of the substituents $Z^5$, $Z^6$ and $Z^7$ represent together an oxygen atom and form together with the carbon atom of the spiroheterocyclyl residue to which they are both attached a carbonyl moiety. Moreover, the $C_5$-$C_{14}$/$N_0$-$N_2$/$O_0$-$O_2$/$S_0$-$S_1$-spiroheterocyclyl residues are characterized by that the spiroheterocyclyl residue is linked through a carbon atom of the spiro ring system and not through the hetero atom, i.e. the nitrogen atom of the spiro ring system. If the spiroheterocyclyl residue contains a nitrogen atom which is substituted by one of the substituents $Z^5$, $Z^6$ and $Z^7$, said Z substituent represents $R^{12}$. Thus the indication "$N_1$" refers to the group

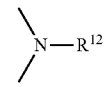

of the spiro ring system. If the spiroheterocyclyl residue contains two nitrogen atoms which are both substituted by one of the substituents $Z^5$, $Z^6$ and $Z^7$, the first Z substituent represents $R^{11}$ and the second Z substituent represents $R^{12}$. Thus the indication "$N_2$" refers to the groups

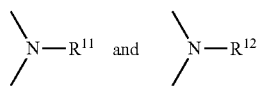

of the spiro ring system. The indication "$S_1$" refers to the group —S— or —SO— or —$SO_2$— of the spiro ring system. The indication "$S_0$" means that no sulfur is present in the spiroheterocyclyl residue. The indication "$O_1$" refers to the group —O— and the indication "$O_2$" to two groups —O— which are not directly linked to each other, while "$O_0$" indicates that no oxygen is present in the spiro ring system. Thus the $C_5$-$C_{14}$/$N_0$-$N_2$/$O_0$-$O_2$/$S_0$-$S_1$-spiroheterocyclyl residues can contain up to two nitrogen atoms and up to two oxygen atoms and one sulfur atom while in total not more than 3 hetero atoms should be present in the spiro ring system. Moreover, it is preferred that the heteroatoms in the spiro ring system are not directly bond to each other. The numbers of atoms "$C_5$-$C_{14}$/$N_0$-$N_2$/$O_0$-$O_2$/$S_0$-$S_1$" do not include C, N, O and/or S atoms from the substituents $Z^5$ to $Z^7$.

Preferred is the presence of one nitrogen atom or two nitrogen atoms or one sulfur atom or one sulfoxide moiety or one sulphone moiety or one oxygen atom or two oxygen atoms or one oxygen and one nitrogen atom in the spiro ring system.

As used herein, the term "$C_5$-$C_{14}$-spironitrogenheterocyclyl" refers to spiro substituents with 5 to 14 carbon atoms and at least one nitrogen atom and optionally further heteroatoms such as N, S, O, S=O, $SO_2$ in the spiro cyclus and refers preferably to the $C_5$-$C_{14}$-spiroheterocyclyl residues as disclosed above, wherein one heteroatom is nitrogen. The $C_5$-$C_{14}$-spironitrogenheterocyclyl residue is linked through the at least one nitrogen spiro cyclus atom to the rest of the molecule. Moreover, the $C_5$-$C_{14}$-spironitrogenheterocyclyl residue can be substituted with 1 to 3 substituents selected from $Z^5$, $Z^6$ and $Z^7$.

The term "bridging spiroheterocyclyl" refers to a spiroheterocyclyl residue as disclosed above, which is further bonded to a second substituent independent from any optional substitution with substituents $Z^1$, $Z^2$, $Z^3$ or $Z^4$. Thus, in a "bridging spiroheterocycly" two hydrogen atoms are replaced by residues rendering the "bridging spiroheterocyclyl" a di-yl moiety. Further, the "bridging spiroheterocyclyl" binds the two different residues with two different atoms of the spiroheterocyclyl skeleton, thereby preventing a substitution pattern wherein the two residues are bonded to the same atom. The "bridging spiroheterocyclyl" can be substituted with 1 to 4 substituents selected from $Z^1$, $Z^2$, $Z^3$ or $Z^4$. It is clear to a skilled person that the term "can be substituted" refers to the replacement of a hydrogen atom by one of the substituents $Z^1$, $Z^2$, $Z^3$ or $Z^4$. Further, it is clear to a skilled person that the term "can be substituted" refers to the replacement of a hydrogen atom by one of the substituents $Z^1$, $Z^2$, $Z^3$ or $Z^4$. Moreover, it is clear to a skilled person that only these hydrogen atoms which are present in the "bridging spiroheterocyclyl" group can be replaced by the substituents $Z^1$, $Z^2$, $Z^3$ and $Z^4$.

The person skilled in the art will understand that when $R^2$ being —$(CH_2)_a$-$(Q)_b$-$(CH_2)_c$-$(G^1)_d$-$(CH_2)_e$-$(G^2)_f$-$CH_2$—$R^9$ and for example $G^1$ represents "a bridging spiroheterocyclyl" (d=1), then this "bridging spiroheterocyclyl" is attached to a first part of $R^2$, for instance —$NR^{15}$—$CH_2$— in case a=0, b=c=1, Q=—$NR^{15}$—, and a second part of $R^2$, for instance —$C_4H_8$—$R^9$ in case f=0 and e=3. Thus, "a bridging spiroheterocyclyl" is attached to two different residues redering it a di-yl residue.

$R^8$ represents preferably the following spiroheterocyclyl or $C_5$-$C_{14}$/$N_0$-$N_2$/$O_0$-$O_2$/$S_0$-$S_1$-spiroheterocyclyl residues: spiro[2,3]heterohexyl, spiro[2,4]heteroheptyl, spiro[2,5]heterooctyl, spiro[2,7]heterononyl, spiro[3,3]heteroheptyl, spiro[3,4]heterooctyl, spiro[3,5]heterononyl, spiro[3,6]heterodecyl, spiro[4,4]heterononyl, spiro[4,5]heterodecyl, spiro[4,6]heteroundecyl, spiro[5,5]heteroundecyl, spiro[5,6]heterododecyl, spiro[6,6]heterotridecyl, wherein the afore-mentioned spiroheterocyclyl or $C_5$-$C_{14}$/$N_0$-$N_2$/$O_0$-$O_2$/$S_0$-$S_1$-spiroheterocyclyl residues are linked through a ring carbon atom to the rest of the molecule and wherein the afore-mentioned spiroheterocyclyl or $C_5$-$C_{14}$/$N_0$-$N_2$/$O_0$-$O_2$/$S_0$-$S_1$-spiroheterocyclyl residues are optionally substituted with one to three substituents selected from $Z^5$, $Z^6$ and $Z^7$. The heteroatom in the afore-mentioned spiroheterocyclyl or $C_5$-$C_{14}$/$N_0$-$N_2$/$O_0$-$O_2$/$S_0$-$S_1$-spiroheterocyclyl residues is preferably selected from —O—, —NH—, —$NR^{11}$—, —SO—, and —$SO_2$—.

More preferably $R^8$ represents preferably the following spiroheterocyclyl or $C_5$-$C_{14}$/$N_0$-$N_2$/$O_0$-$O_2$/$S_0$-$S_1$-spiroheterocyclyl residues: azaspiro[3,3]heptyl, azaspiro[3,4]octyl, azaspiro[3,5]nonyl, azaspiro[3,6]decyl, azaspiro[4,4]nonyl, azaspiro[4,5]decyl, azaspiro[4,6]undecyl, azaspiro[5,5]undecyl, azaspiro[5,6]dodecyl, azaspiro[6,6]tridecyl, diazaspiro[3,3]heptyl, diazaspiro[3,4]octyl, diazaspiro[3,5]nonyl, diazaspiro[3,6]decyl, diazaspiro[4,4]nonyl, diazaspiro[4,5]decyl, diazaspiro[4,6]undecyl, diazaspiro[5,5]undecyl, diazaspiro[5,6]dodecyl, diazaspiro[6,6]tridecyl, triazaspiro[3,5]nonyl, triazaspiro[3,6]decyl, triazaspiro[4,5]decyl, triazaspiro[4,6]undecyl, triazaspiro[5,5]undecyl, triazaspiro[5,6]dodecyl, triazaspiro[6,6]tridecyl, oxazaspiro[3,3]heptyl, oxazaspiro[3,4]octyl, oxazaspiro[3,5]nonyl, oxazaspiro[3,6]decyl, oxazaspiro[4,4]nonyl, oxazaspiro[4,5]decyl, oxazaspiro[4,6]undecyl, oxazaspiro[5,5]undecyl, oxazaspiro[5,6]dodecyl, oxazaspiro[6,6]tridecyl, oxadiazaspiro[3,5]nonyl, oxadiazaspiro[3,6]decyl, oxadiazaspiro[4,5]decyl, oxadiazaspiro[4,6]undecyl, oxadiazaspiro[5,5]undecyl, oxadiazaspiro[5,6]dodecyl, oxadiazaspiro[6,6]tridecyl, wherein the afore-mentioned spiroheterocyclyl or $C_5$-$C_{14}$/$N_0$-$N_2$/$O_0$-$O_2$/$S_0$-$S_1$-spiroheterocyclyl residues are linked through a ring carbon atom to the rest of the molecule and wherein the afore-mentioned spiroheterocyclyl or $C_5$-$C_{14}$/$N_0$-$N_2$/$O_0$-$O_2$/$S_0$-$S_1$-spiroheterocyclyl residues are optionally substituted with one to three substituents selected from $Z^5$, $Z^6$ and $Z^7$.

Also, $R^8$ represents more preferably the following residues: —$(CH_2)_p$—$NH_2$, —$(CH_2)_p$—$NR^{16}R^{17}$, substituted or unsubstituted 4-membered carbocyclyl, substituted or unsubstituted 5-membered carbocyclyl, substituted or unsubstituted 6-membered carbocyclyl, 4-membered heterocyclyl, 5-membered heterocyclyl, 6-membered heterocyclyl, substituted 4-membered heterocyclyl, substituted 5-membered heterocyclyl, substituted 6-membered heterocyclyl, 4-membered nitrogenheterocyclyl, 5-membered nitrogenheterocyclyl, 6-membered nitrogenheterocyclyl, substituted 4-membered nitrogenheterocyclyl, substituted 5-membered nitrogenheterocyclyl, substituted 6-membered nitrogenheterocyclyl, spiro[2,3]heterohexyl, spiro[2,4]heteroheptyl, spiro[2,5]heterooctyl, spiro[2,7]heterononyl, spiro[3,3]heteroheptyl, spiro[3,4]heterooctyl, spiro[3,5]heterononyl, spiro[3,6]heterodecyl, spiro[4,4]heterononyl, spiro[4,5]heterodecyl, spiro[4,6]heteroundecyl, spiro[5,5]heteroundecyl, spiro[5,6]heterododecyl, spiro[6,6]heterotridecyl, substituted spiro[2,3]heterohexyl, substituted spiro[2,4]heteroheptyl, substituted spiro[2,5]heterooctyl, substituted spiro[2,7]heterononyl, substituted spiro[3,3]heteroheptyl, substituted spiro[3,4]heterooctyl, substituted spiro[3,5]heterononyl, substituted spiro[3,6]heterodecyl, substituted spiro[4,4]heterononyl, substituted spiro[4,5]heterodecyl, substituted spiro[4,6]heteroundecyl, substituted spiro[5,5]heteroundecyl, substituted spiro[5,6]heterododecyl, substituted spiro[6,6]heterotridecyl, azaspiro[3,3]heptyl, azaspiro[3,4]octyl, azaspiro[3,5]nonyl, azaspiro[3,6]decyl, azaspiro[4,4]nonyl, azaspiro[4,5]decyl, azaspiro[4,6]undecyl, azaspiro[5,5]undecyl, azaspiro[5,6]dodecyl, azaspiro[6,6]tridecyl, substituted azaspiro[3,3]heptyl, substituted azaspiro[3,4]octyl, substituted azaspiro[3,5]nonyl, substituted azaspiro[3,6]decyl, substituted azaspiro[4,4]nonyl, substituted azaspiro[4,5]decyl, substituted azaspiro[4,6]undecyl, substituted azaspiro[5,5]undecyl, substituted azaspiro

[5,6]dodecyl, substituted azaspiro[6,6]tridecyl, diazaspiro[3,3]heptyl, diazaspiro[3,4]octyl, diazaspiro[3,5]nonyl, diazaspiro[3,6]decyl, diazaspiro[4,4]nonyl, diazaspiro[4,5]decyl, diazaspiro[4,6]undecyl, diazaspiro[5,5]undecyl, diazaspiro[5,6]dodecyl, diazaspiro[6,6]tridecyl, substituted diazaspiro[3,3]heptyl, substituted diazaspiro[3,4]octyl, substituted diazaspiro[3,5]nonyl, substituted diazaspiro[3,6]decyl, substituted diazaspiro[4,4]nonyl, substituted diazaspiro[4,5]decyl, substituted diazaspiro[4,6]undecyl, substituted diazaspiro[5,5]undecyl, substituted diazaspiro[5,6]dodecyl, substituted diazaspiro[6,6]tridecyl, triazaspiro[3,5]nonyl, triazaspiro[3,6]decyl, triazaspiro[4,5]decyl, triazaspiro[4,6]undecyl, triazaspiro[5,5]undecyl, triazaspiro[5,6]dodecyl, triazaspiro[6,6]tridecyl, substituted triazaspiro[3,5]nonyl, substituted triazaspiro[3,6]decyl, substituted triazaspiro[4,5]decyl, substituted triazaspiro[4,6]undecyl, substituted triazaspiro[5,5]undecyl, substituted triazaspiro[5,6]dodecyl, or substituted triazaspiro[6,6]tridecyl, oxazaspiro[3,3]heptyl, oxazaspiro[3,4]octyl, oxazaspiro[3,5]nonyl, oxazaspiro[3,6]decyl, oxazaspiro[4,4]nonyl, oxazaspiro[4,5]decyl, oxazaspiro[4,6]undecyl, oxazaspiro[5,5]undecyl, oxazaspiro[5,6]dodecyl, oxazaspiro[6,6]tridecyl, substituted oxazaspiro[3,3]heptyl, substituted oxazaspiro[3,4]octyl, substituted oxazaspiro[3,5]nonyl, substituted oxazaspiro[3,6]decyl, substituted oxazaspiro[4,4]nonyl, substituted oxazaspiro[4,5]decyl, substituted oxazaspiro[4,6]undecyl, substituted oxazaspiro[5,5]undecyl, substituted oxazaspiro[5,6]dodecyl, substituted oxazaspiro[6,6]tridecyl, oxadiazaspiro[3,5]nonyl, oxadiazaspiro[3,6]decyl, oxadiazaspiro[4,5]decyl, oxadiazaspiro[4,6]undecyl, oxadiazaspiro[5,5]undecyl, oxadiazaspiro[5,6]dodecyl, oxadiazaspiro[6,6]tridecyl, substituted oxadiazaspiro[3,5]nonyl, substituted oxadiazaspiro[3,6]decyl, substituted oxadiazaspiro[4,5]decyl, substituted oxadiazaspiro[4,6]undecyl, substituted oxadiazaspiro[5,5]undecyl, substituted oxadiazaspiro[5,6]dodecyl, or substituted oxadiazaspiro[6,6]tridecyl,
wherein the afore-mentioned substituted or non-substituted spiroheterocyclyl or $C_5$-$C_{14}$/$N_0$-$N_2$/$O_0$-$O_2$/$S_0$-$S_1$-spiroheterocyclyl residues are linked through a ring carbon atom to the rest of the molecule and wherein the afore-mentioned substituted or non-substituted spiroheterocyclyl or $C_5$-$C_{14}$/$N_0$-$N_2$/$O_0$-$O_2$/$S_0$-$S_1$-spiroheterocyclyl residues are optionally substituted with one to three substituents selected from $Z^5$, $Z^6$ and $Z^7$. The heteroatom in the afore-mentioned substituted or non-substituted spiroheterocyclyl or $C_5$-$C_{14}$/$N_0$-$N_2$/$O_0$-$O_2$/$S_0$-$S_1$-spiroheterocyclyl residues is preferably selected from —O—, —NH—, —NR$^{11}$—, —SO—, and —SO$_2$—.

Preferably $Z^5$, $Z^6$ and $Z^7$ represent independently of each other —CH$_3$, —C$_2$H$_5$, —C$_3$H$_7$, —CH(CH$_3$)$_2$, —OH, —OCH$_3$, —OC$_2$H$_5$, —OC$_3$H$_7$, —NH$_2$, —N(CH$_3$)$_2$, —F, —Cl, —Br, —I, —CN, —CH$_2$F, —CHF$_2$, —CF$_3$, —OCHF$_2$, and —OCF$_3$.

Preferred substituents for R$^{11}$ are —CH$_3$, —C$_2$H$_5$, —C$_3$H$_7$, —CH(CH$_3$)$_2$, —CH$_2$F, —CHF$_2$,

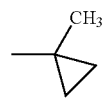

—CF$_3$, cyclo-C$_3$H$_5$, cyclo-C$_4$H$_7$, cyclo-C$_5$H$_9$, cyclo-C$_6$H$_{11}$, cyclo-C$_7$H$_{13}$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH (CH$_3$)$_2$, —C$_6$H$_{13}$, —C$_7$H$_{15}$, —C$_8$H$_{17}$, -Ph, —CH$_2$-Ph, —CH$_2$—CH$_2$-Ph, —CH=CH-Ph, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH$_2$, —CH=C(CH$_3$)$_2$, —C(CH$_3$)=CH—CH$_3$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —CH$_2$—OCF$_3$, —C$_2$H$_4$—OCF$_3$, —C$_3$H$_6$—OCF$_3$, —CH$_2$—OCH$_3$, —C$_2$H$_4$—OCH$_3$, —C$_3$H$_6$—OCH$_3$, —CH$_2$—OC$_2$H$_5$, —C$_2$H$_4$—OC$_2$H$_5$, and —C$_3$H$_6$—OC$_2$H$_5$.

The term "4-membered nitrogenheterocyclyl" refers to the residue "4-membered heterocyclyl" as defined above, wherein at least one heteroatom is a nitrogen atom and the residue is linked through the at least one nitrogen ring atom to the rest of the molecule and wherein $Z^1$ is replaced by $Z^5$, $Z^2$ is replaced by $Z^6$, $Z^3$ is replaced by $Z^7$, and $Z^4$ is hydrogen.

The term "5-membered nitrogenheterocyclyl" refers to the residue "5-membered heterocyclyl" as defined above, wherein at least one heteroatom is a nitrogen atom and the residue is linked through the at least one nitrogen ring atom to the rest of the molecule and wherein $Z^1$ is replaced by $Z^5$, $Z^2$ is replaced by $Z^6$, $Z^3$ is replaced by $Z^7$, and $Z^4$ is hydrogen.

The term "6-membered nitrogenheterocyclyl" refers to the residue "6-membered heterocyclyl" as defined above, wherein at least one heteroatom is a nitrogen atom and the residue is linked through the at least one nitrogen ring atom to the rest of the molecule and wherein $Z^1$ is replaced by $Z^5$, $Z^2$ is replaced by $Z^6$, $Z^3$ is replaced by $Z^7$, and $Z^4$ is hydrogen.

Still more preferably R$^8$ represents the following residues: —(CH$_2$)$_p$—NH$_2$, —(CH$_2$)$_p$—N(R$^{16}$R$^{17}$),

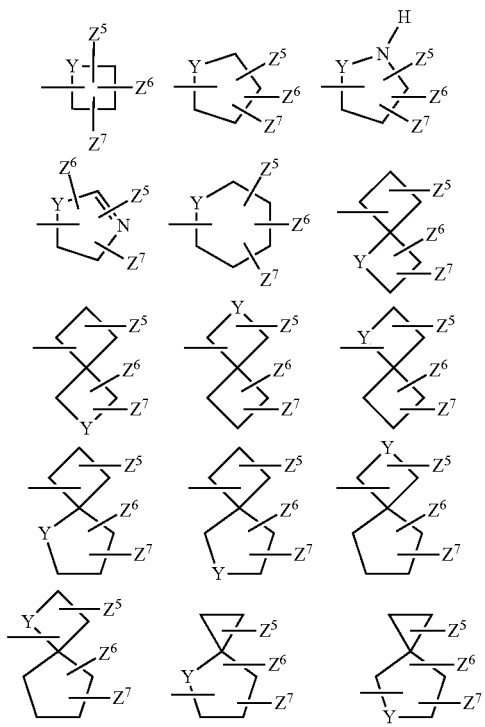

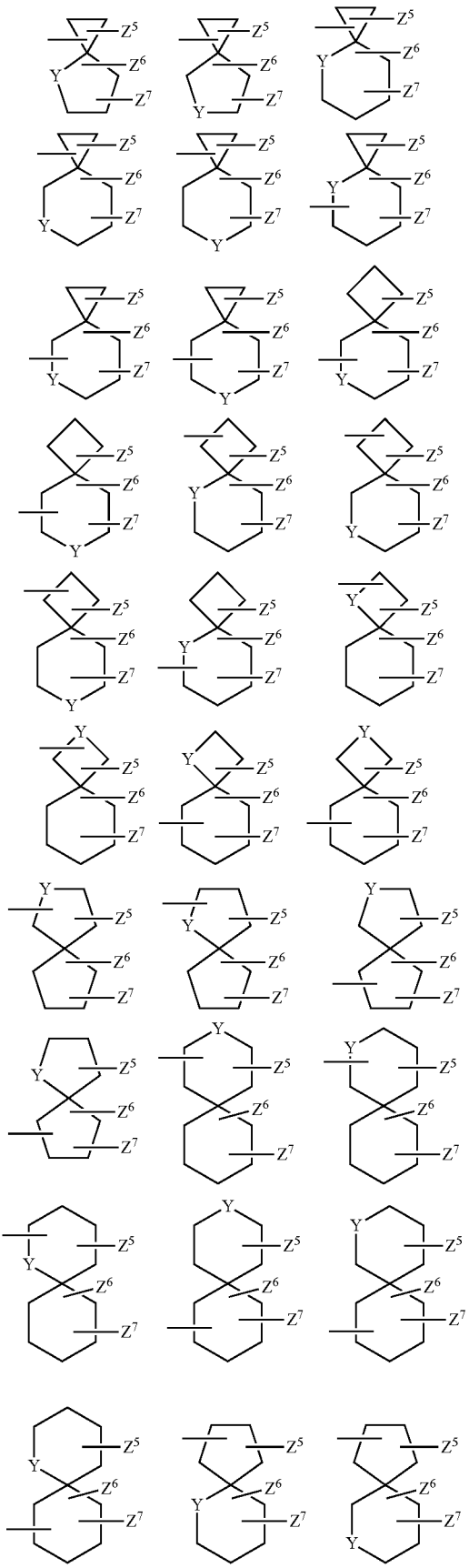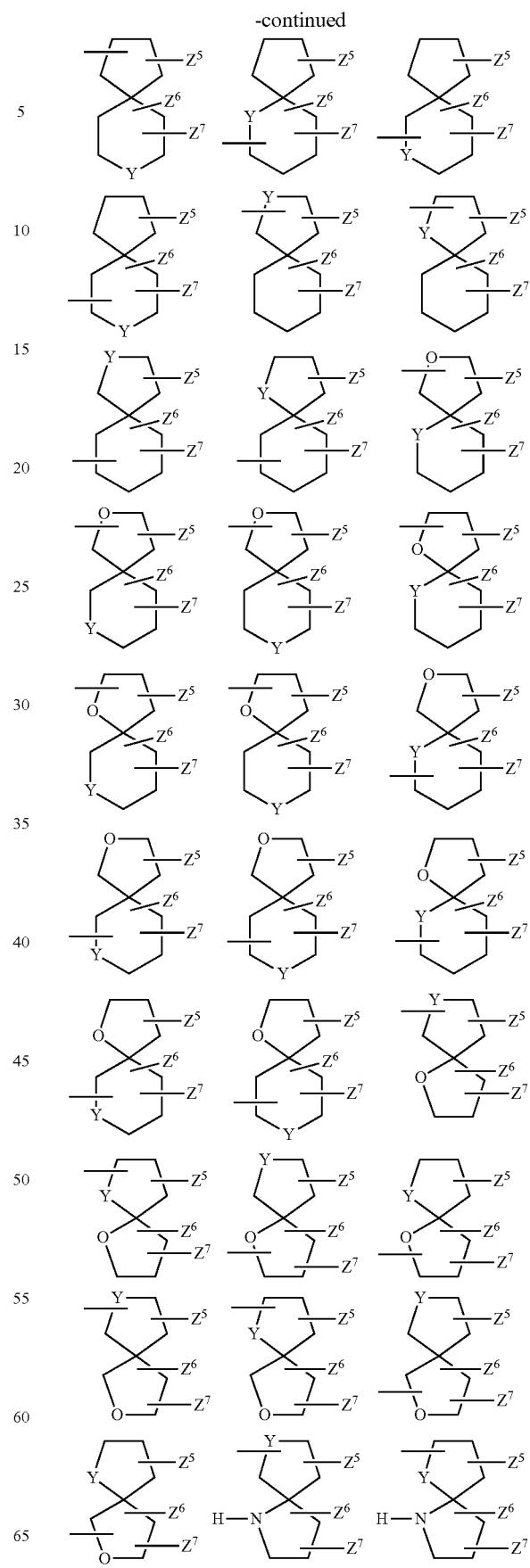

-continued
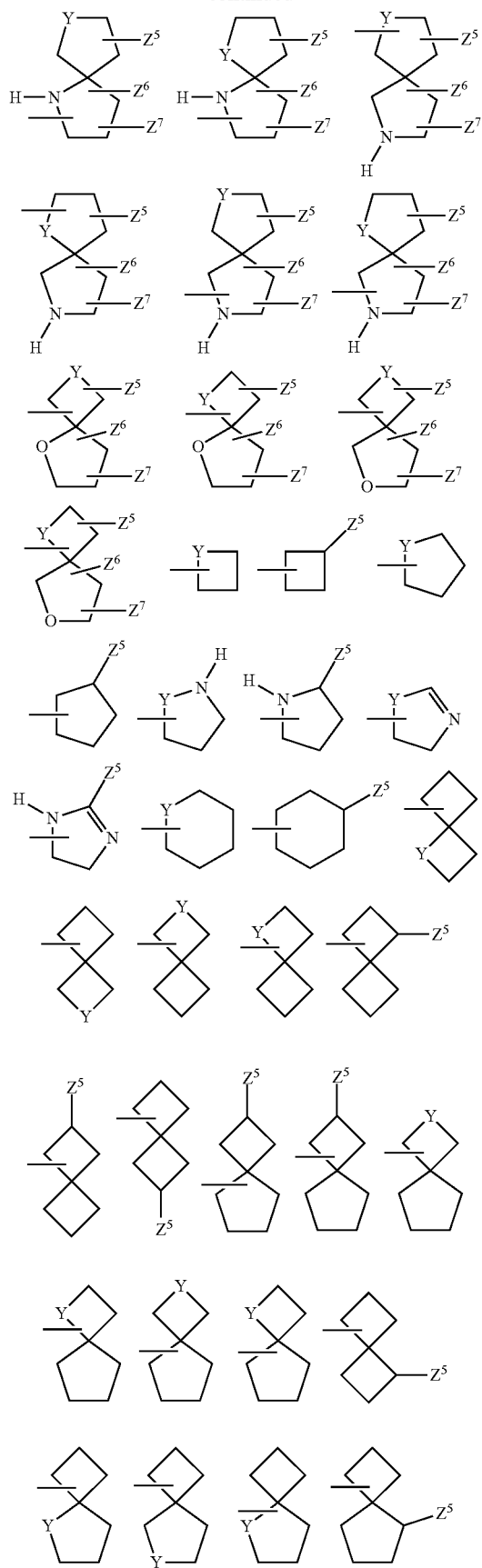
-continued
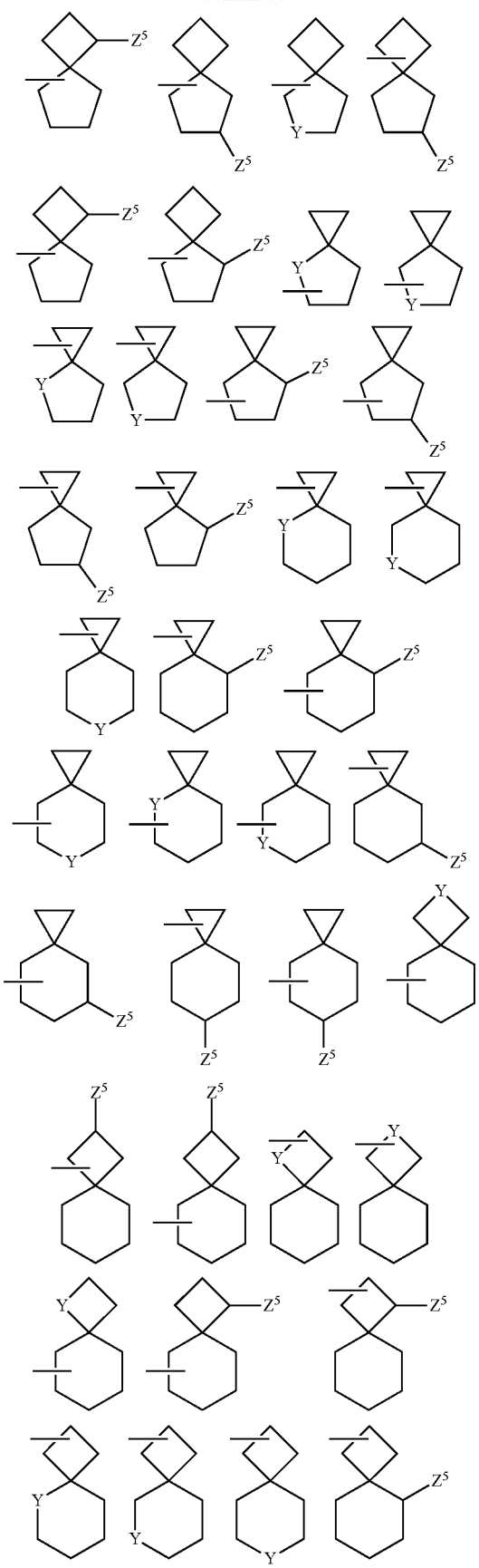

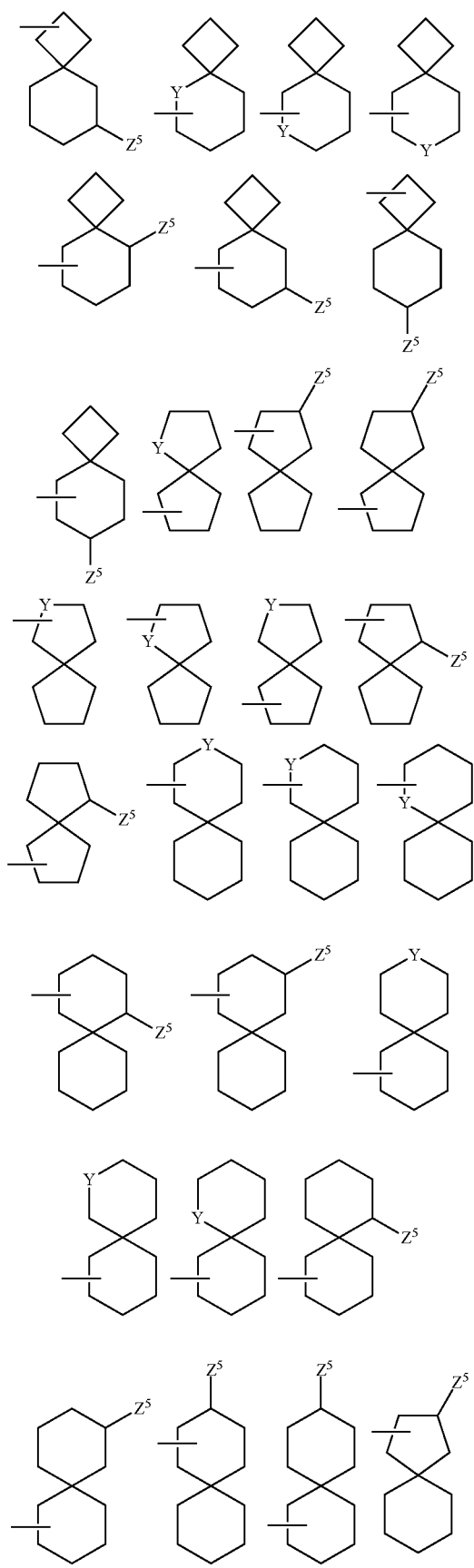
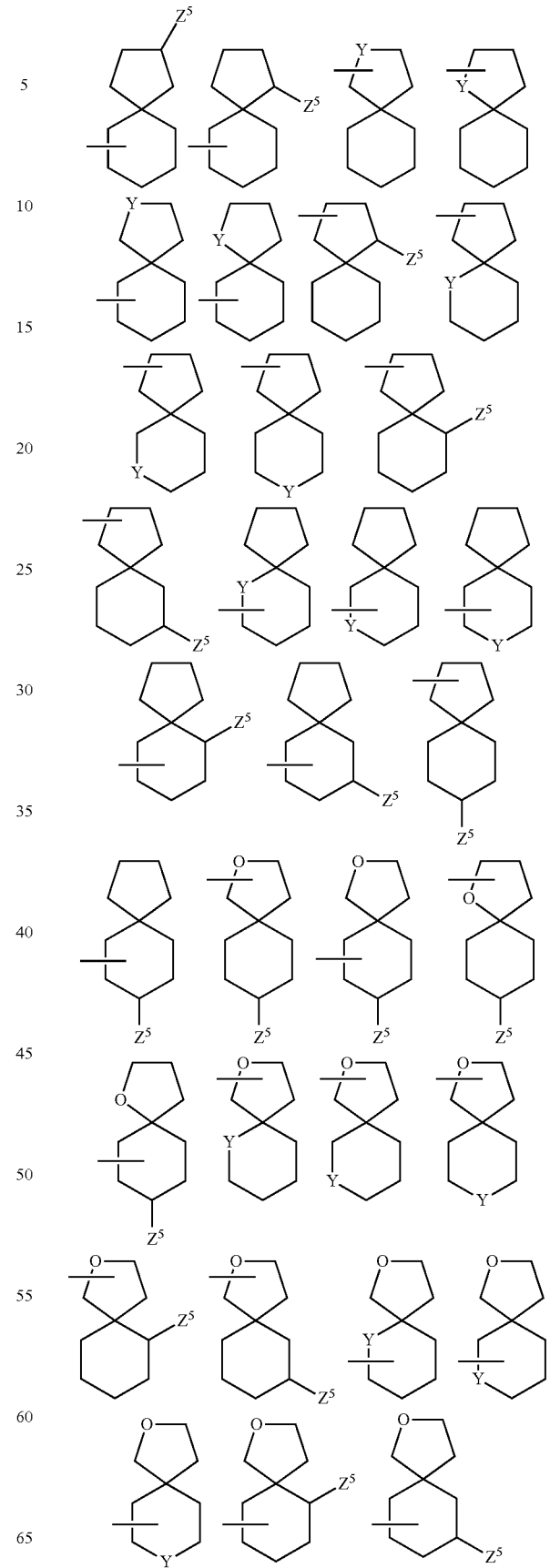

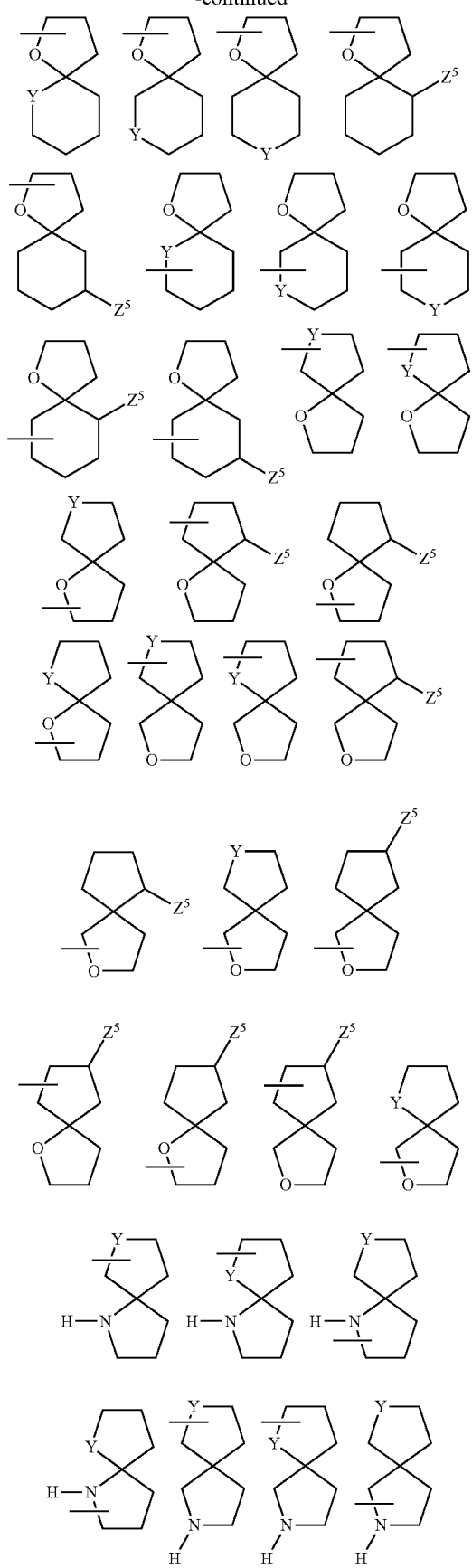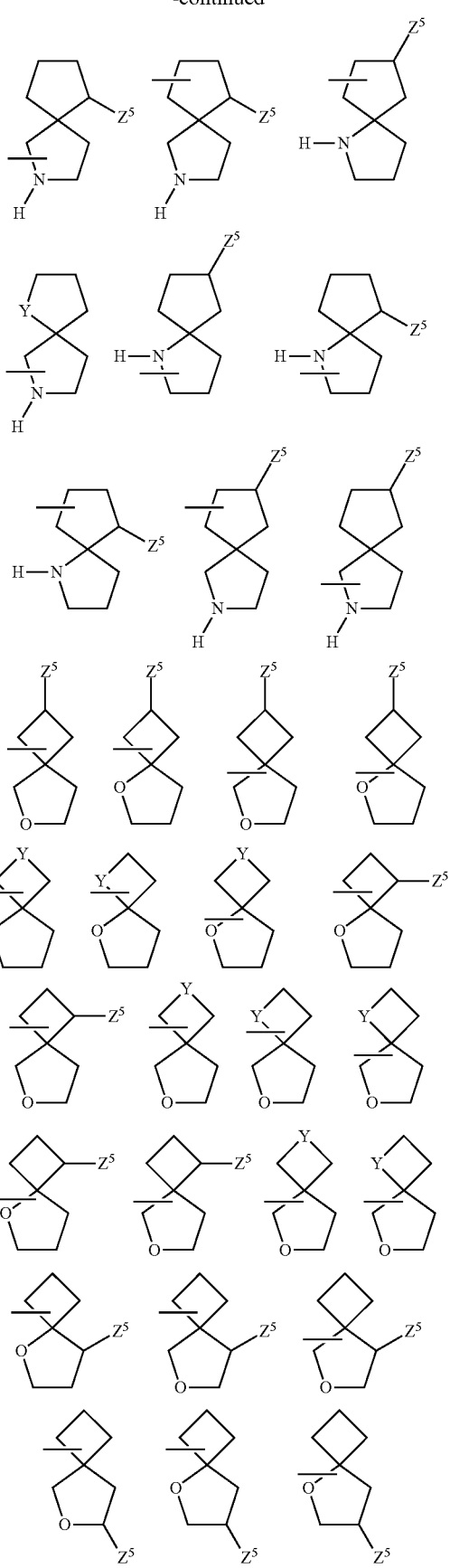

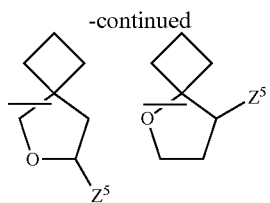

wherein Y represents —O—, —NH—, —NR$^{11}$—, —SO—, or —SO$_2$—, preferably —NH— and —NR$^{11}$— and wherein the substituents Z$^5$, Z$^6$ and Z$^7$ have the meanings as defined herein.

As used herein, the term "spironitrogencyclyl" refers to the C$_5$-C$_{14}$/N$_1$-N$_3$-spironitrogencyclyl residues comprising or including the C$_5$-C$_{14}$-spiroheterocyclyl residues as disclosed above, wherein the heteroatom is nitrogen, i.e. Y is NH or NR$^{11}$. The term "C$_5$-C$_{14}$/N$_1$-N$_3$" means that the spiro ring system consists of 5 to 14 carbon atoms and 1 to 3 nitrogen atoms. Moreover the spironitrogencyclyl residues can be substituted with 1 to 3 substituents selected from Z$^5$, Z$^6$ and Z$^7$. However it is clear to a skilled person that the term "can be substituted" refers to the replacement of a hydrogen atom by one of the substituents Z$^5$, Z$^6$ or Z$^7$. It is also possible that two of the substituents Z$^5$, Z$^6$ and Z$^7$ represent together an oxygen atom and form together with the carbon atom of the spironitrogencyclyl residue to which they are both attached a carbonyl moiety. Moreover the C$_5$-C$_{14}$/N$_1$-N$_3$-spironitrogencyclyl residues are characterized in that the spironitrogencyclyl residue is linked through a nitrogen atom of the spiro ring system and not through a carbon atom of the spiro ring system. This means in regard to the above-mentioned C$_5$-C$_{14}$-spiroheterocycly residue that the heteroatom Y is nitrogen and that this C$_5$-C$_{14}$-spiroheterocycly residue is linked to the rest of the molecule through this nitrogen atom (which is Y). If the C$_5$-C$_{14}$/N$_1$-N$_3$-spironitrogencyclyl residue contains a second nitrogen atom which is substituted by one of the substituents Z$^5$, Z$^6$ and Z$^7$, said Z substituent represents R$^{12}$. Thus the indication "N$_2$" refers to a first nitrogen atom through which the spironitrogencyclyl residue is linked and to the group

of the spiro ring system. If the spironitrogencyclyl residue contains a third nitrogen atom and both nitrogen atoms are substituted by one of the substituents Z$^5$, Z$^6$ and Z$^7$, the first Z substituent on the second nitrogen atom represents R$^{12}$ and the second Z substituent on the third nitrogen atom represents R$^{11}$. Thus the indication "N$_3$" refers to a first nitrogen atom through which the spironitrogencyclyl residue is linked and to the groups

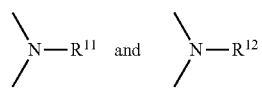

of the spiro ring system. Thus the C$_5$-C$_{14}$/N$_1$-N$_3$-spironitrogencyclyl residue can contain one, two or three nitrogen atoms in the spiro ring system. The numbers of atoms "C$_5$-C$_{14}$/N$_1$-N$_2$" do not include C and N atoms from the substituents Z$^5$ to Z$^7$.

As used herein, the term "nitrogenheterocyclyl" refers to C$_5$-C$_{14}$/N$_1$-N$_3$/O$_0$-O$_2$/S$_0$-S$_1$-nitrogenheterocyclyl residues comprising or including the C$_5$-C$_{14}$-spiroheterocyclyl residues as disclosed above, wherein the heteroatom is nitrogen, i.e. Y is NH or NR$^{11}$. The term "C$_5$-C$_{14}$/N$_1$-N$_3$/O$_0$-O$_2$/S$_0$-S$_1$" means that the spiro ring system consists of 5 to 14 carbon atoms and 1 to 3 nitrogen atoms, 0 to 2 oxygen atoms and 0 or 1 sulfur atom. Moreover the nitrogenheterocyclyl residues can be substituted with 1 to 3 substituents selected from Z$^5$, Z$^6$ and Z$^7$. However it is clear to a skilled person that the term "can be substituted" refers to the replacement of a hydrogen atom by one of the substituents Z$^5$, Z$^6$ or Z$^7$. It is also possible that two of the substituents Z$^5$, Z$^6$ and Z$^7$ represent together an oxygen atom and form together with the carbon atom of the nitrogenheterocyclyl residue to which they are both attached a carbonyl moiety. Moreover the C$_5$-C$_{14}$/N$_1$-N$_3$/O$_0$-O$_2$/S$_0$-S$_1$-nitrogenheterocyclyl residues are characterized by that the nitrogenheterocyclyl residue is linked through a nitrogen atom of the spiro ring system and not through a carbon atom of the spiro ring system. This means in regard to the above-mentioned C$_5$-C$_{14}$-spiroheterocycly residue that the heteroatom Y is nitrogen and that this C$_5$-C$_{14}$-spiroheterocycly residue is linked to the rest of the molecule through this nitrogen atom (which is Y). If the C$_5$-C$_{14}$/N$_1$-N$_3$/O$_0$-O$_2$/S$_0$-S$_1$-nitrogenheterocyclyl residue contains a second nitrogen atom which is substituted by one of the substituents Z$^5$, Z$^6$ and Z$^7$, said Z substituent represents R$^{12}$. Thus, the indication "N$_2$" refers to a first nitrogen atom through which the nitrogenheterocyclyl residue is linked and to the group

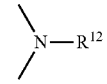

of the spiro ring system. If the nitrogenheterocyclyl residue contains a third nitrogen atom and both nitrogen atoms are substituted by one of the substituents Z$^5$, Z$^6$ and Z$^7$, the first Z substituent on the second nitrogen atom represents R$^{12}$ and the second Z substituent on the third nitrogen atom represents R$^{11}$. Thus, the indication "N$_3$" refers to a first nitrogen atom through which the nitrogenheterocyclyl residue is linked and to the groups

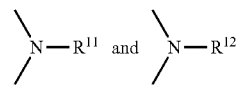

of the spiro ring system. The indication "S$_1$" refers to the group —S— or —SO— or —SO$_2$— of the spiro ring system. The indication "S$_0$" means that no sulfur is present in the nitrogenheterocyclyl residue. The indication "O$_1$" refers to the group —O— and the indication "O$_2$" to two groups —O— which are not directly linked to each other, while "O$_0$" indicates that no oxygen is present in the spiro ring system. Thus, the C$_5$-C$_{14}$/N$_1$-N$_3$/O$_0$-O$_2$/S$_0$-S$_1$-nitrogenheterocyclyl residue can contain in total 6 hetero atoms while in total not more than 3 hetero atoms should be present in the spiro ring system. Moreover it is preferred that the heteroatoms in the spiro ring system are not directly bond to each other. The numbers of atoms "C$_5$-C$_{14}$/N$_1$-N$_3$/O$_0$-O$_2$/S$_0$-S$_1$" do not include C, O, S and N atoms from the substituents Z$^5$ to Z$^7$.

Preferred is the presence of one nitrogen atom or two nitrogen atoms or one nitrogen atom and one sulfur atom or one nitrogen atom and one sulfoxide moiety or one nitrogen atom and one sulphone moiety or one nitrogen atom and one oxygen atom or one nitrogen atom and two oxygen atoms or one oxygen atom and two nitrogen atoms in the spiro ring system.

$R^9$ represents preferably the following spironitrogencyclyl, nitrogenheterocyclyl, $C_5$-$C_{14}$/$N_1$-$N_3$-spironitrogencyclyl or $C_5$-$C_{14}$/$N_1$-$N_3$/$O_0$-$O_2$/$S_0$-$S_1$-residues: 4-membered nitrogenheterocyclyl, 5-membered nitrogenheterocyclyl, 6-membered nitrogenheterocyclyl, 5-membered dinitrogenheterocyclyl, 6-membered dinitrogenheterocyclyl, spiro[2,3]heterohexyl, spiro[2,4]heteroheptyl, spiro[2,5]heterooctyl, spiro[2,7]heterononyl, spiro[3,3]heteroheptyl, spiro[3,4]heterooctyl, spiro[3,5]heterononyl, spiro[3,6]heterodecyl, spiro[4,4]heterononyl, spiro[4,5]heterodecyl, spiro[4,6]heteroundecyl, spiro[5,5]heteroundecyl, spiro[5,6]heterododecyl, spiro[6,6]heterotridecyl, wherein the afore-mentioned spironitrogencyclyl, nitrogenheterocyclyl, $C_5$-$C_{14}$/$N_1$-$N_3$-spironitrogencyclyl or $C_5$-$C_{14}$/$N_1$-$N_3$/$O_0$-$O_2$/$S_0$-$S_1$-nitrogenheterocyclyl residues are linked through a ring nitrogen atom to the rest of the molecule and wherein the afore-mentioned spironitrogencyclyl, nitrogenheterocyclyl, $C_5$-$C_{14}$/$N_1$-$N_3$-spironitrogencyclyl or $C_5$-$C_{14}$/$N_1$-$N_3$/$O_0$-$O_2$/$S_0$-$S_1$-nitrogenheterocyclyl residues are optionally substituted with one to three substituents selected from $Z^5$, $Z^6$ and $Z^7$.

The term "5-membered dinitrogenheterocyclyl" refers to the residue "5-membered heterocyclyl" as defined above, wherein two heteroatoms are nitrogen atoms and the residue is linked through a nitrogen ring atom to the rest of the molecule and wherein $Z^1$ is replaced by $Z^5$, $Z^2$ is replaced by $Z^6$, $Z^3$ is replaced by $Z^7$, and $Z^4$ is hydrogen.

The term "6-membered dinitrogenheterocyclyl" refers to the residue "6-membered heterocyclyl" as defined above, wherein two heteroatoms are nitrogen atoms and the residue is linked through a nitrogen ring atom to the rest of the molecule and wherein $Z^1$ is replaced by $Z^5$, $Z^2$ is replaced by $Z^6$, $Z^3$ is replaced by $Z^7$, and $Z^4$ is hydrogen.

Moreover the afore-mentioned spironitrogencyclyl, nitrogenheterocyclyl, $C_5$-$C_{14}$/$N_1$-$N_3$-spironitrogencyclyl or $C_5$-$C_{14}$/$N_1$-$N_3$/$O_0$-$O_2$/$S_0$-$S_1$-nitrogenheterocyclyl residues contain at least one nitrogen atom through which these residues are linked to the rest of the molecule and may contain one or two further moieties selected from oxygen (—O—), sulfoxide (—SO—), sulfone (—SO$_2$—), carbonyl (—CO—) and nitrogen (—NR$^{11}$—).

Preferable substituents $Z^5$, $Z^6$ and $Z^7$ represent independently of each other —CH$_3$, —C$_2$H$_5$, —C$_3$H$_7$, —CH(CH$_3$)$_2$, —OH, —OCH$_3$, —OC$_2$H$_5$, —OC$_3$H$_7$, —NH$_2$, —NHCH$_3$, —N(CH$_3$)$_2$, —F, —Cl, —Br, —I, —CN, —CH$_2$F, —CHF$_2$, —CF$_3$, —OCHF$_2$, and —OCF$_3$. If present, R$^{11}$ and R$^{12}$ are preferably selected from: —CH$_3$, —C$_2$H$_5$, —C$_3$H$_7$, —CH(CH$_3$)$_2$, —CH$_2$F, —CHF$_2$, —CF$_3$,

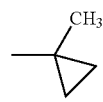

cyclo-C$_3$H$_5$, cyclo-C$_4$H$_7$, cyclo-C$_5$H$_9$, cyclo-C$_6$H$_{11}$, cyclo-C$_7$H$_{13}$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH (CH$_3$)$_2$, —C$_6$H$_{13}$, —C$_7$H$_{15}$, —C$_8$H$_{17}$, -Ph, —CH$_2$-Ph, —CH$_2$—CH$_2$-Ph, —CH=CH-Ph, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH (CH$_3$)—CH=CH$_2$, —CH=C(CH$_3$)$_2$, —C(CH$_3$)=CH—CH$_3$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —CH$_2$—OCF$_3$, —C$_2$H$_4$—OCF$_3$, —C$_3$H$_6$—OCF$_3$, —CH$_2$—OCH$_3$, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$.

More preferably $R^9$ represents the following spironitrogencyclyl, nitrogenheterocyclyl, $C_5$-$C_{14}$/$N_1$-$N_3$-spironitrogencyclyl or $C_5$-$C_{14}$/$N_1$-$N_3$/$O_0$-$O_2$/$S_0$-$S_1$-nitrogenheterocyclyl residues: 4-membered nitrogenheterocyclyl linked through the nitrogen atom to the rest of the molecule, 5-membered nitrogenheterocyclyl linked through the nitrogen atom to the rest of the molecule, 6-membered nitrogenheterocyclyl linked through the nitrogen atom, substituted 4-membered nitrogenheterocyclyl linked through the nitrogen atom, substituted 5-membered nitrogenheterocyclyl linked through the nitrogen atom, substituted 6-membered nitrogenheterocyclyl linked through the nitrogen atom, 5-membered dinitrogenheterocyclyl linked through a nitrogen atom, 6-membered dinitrogenheterocyclyl linked through a nitrogen atom, substituted 5-membered dinitrogenheterocyclyl linked through a nitrogen atom, substituted 6-membered dinitrogenheterocyclyl linked through a nitrogen atom to the rest of the molecule, wherein the afore-mentioned spironitrogencyclyl, nitrogenheterocyclyl, $C_5$-$C_{14}$/$N_1$-$N_3$-spironitrogencyclyl or $C_5$-$C_{14}$/$N_1$-$N_3$/$O_0$-$O_2$/$S_0$-$S_1$-nitrogenheterocyclyl residues are optionally substituted with one to three substituents selected from $Z^5$, $Z^6$ and $Z^7$.

Still more preferably $R^9$ represents the following spironitrogencyclyl, nitrogenheterocyclyl, $C_5$-$C_{14}$/$N_1$-$N_3$-spironitrogencyclyl or $C_5$-$C_{14}$/$N_1$-$N_3$/$O_0$-$O_2$/$S_0$-$S_1$-nitrogenheterocyclyl residues:
azaspiro[3,3]heptyl linked through the nitrogen atom, azaspiro[3,4]octyl linked through the nitrogen atom, azaspiro[3,5]nonyl linked through the nitrogen atom, azaspiro[3,6]decyl linked through the nitrogen atom, azaspiro[4,4]nonyl linked through the nitrogen atom, azaspiro[4,5]decyl linked through the nitrogen atom, azaspiro[4,6]undecyl linked through the nitrogen atom, azaspiro[5,5]undecyl linked through the nitrogen atom, azaspiro[5,6]dodecyl linked through the nitrogen atom, azaspiro[6,6]tridecyl linked through the nitrogen atom,
substituted azaspiro[3,3]heptyl linked through the nitrogen atom, substituted azaspiro[3,4]octyl linked through the nitrogen atom, substituted azaspiro[3,5]nonyl linked through the nitrogen atom, substituted azaspiro[3,6]decyl linked through the nitrogen atom, substituted azaspiro[4,4] nonyl linked through the nitrogen atom, substituted azaspiro [4,5]decyl linked through the nitrogen atom, substituted azaspiro[4,6]undecyl linked through the nitrogen atom, substituted azaspiro[5,5]undecyl linked through the nitrogen atom, substituted azaspiro[5,6]dodecyl linked through the nitrogen atom, substituted azaspiro[6,6]tridecyl linked through the nitrogen atom,
diazaspiro[3,3]heptyl linked through a nitrogen atom, diazaspiro[3,4]octyl linked through a nitrogen atom, diazaspiro [3,5]nonyl linked through a nitrogen atom, diazaspiro[3,6] decyl linked through a nitrogen atom, diazaspiro[4,4]nonyl linked through a nitrogen atom, diazaspiro[4,5]decyl linked through a nitrogen atom, diazaspiro[4,6]undecyl linked through a nitrogen atom, diazaspiro[5,5]undecyl linked through a nitrogen atom, diazaspiro[5,6]dodecyl linked through a nitrogen atom, diazaspiro[6,6]tridecyl linked through a nitrogen atom,
substituted diazaspiro[3,3]heptyl linked through a nitrogen atom, substituted diazaspiro[3,4]octyl linked through a nitrogen atom, substituted diazaspiro[3,5]nonyl linked through a nitrogen atom, substituted diazaspiro[3,6]decyl linked through a nitrogen atom, substituted diazaspiro[4,4]nonyl linked through a nitrogen atom, substituted diazaspiro[4,5]decyl linked through a nitrogen atom, substituted diazaspiro[4,6]undecyl linked through a nitrogen atom, substituted diazaspiro[5,5]undecyl linked through a nitrogen atom, substituted diazaspiro[5,6]dodecyl linked through a nitrogen atom, substituted diazaspiro[6,6]tridecyl linked through a nitrogen atom,
triazaspiro[3,5]nonyl linked through a nitrogen atom, triazaspiro[3,6]decyl linked through a nitrogen atom, triazaspiro[4,5]decyl linked through a nitrogen atom, triazaspiro[4,6]undecyl linked through a nitrogen atom, triazaspiro[5,5]undecyl linked through a nitrogen atom, triazaspiro[5,6]dodecyl linked through a nitrogen atom, triazaspiro[6,6]tridecyl linked through a nitrogen atom,
substituted triazaspiro[3,5]nonyl linked through a nitrogen atom, substituted triazaspiro[3,6]decyl linked through a nitrogen atom, substituted triazaspiro[4,5]decyl linked through a nitrogen atom, substituted triazaspiro[4,6]undecyl linked through a nitrogen atom, substituted triazaspiro[5,5]undecyl linked through a nitrogen atom, substituted triazaspiro[5,6]dodecyl linked through a nitrogen atom, substituted triazaspiro[6,6]tridecyl linked through a nitrogen atom,
oxazaspiro[3,3]heptyl linked through a nitrogen atom, oxazaspiro[3,4]octyl linked through a nitrogen atom, oxazaspiro[3,5]nonyl linked through a nitrogen atom, oxazaspiro[3,6]decyl linked through a nitrogen atom, oxazaspiro[4,4]nonyl linked through a nitrogen atom, oxazaspiro[4,5]decyl linked through a nitrogen atom, oxazaspiro[4,6]undecyl linked through a nitrogen atom, oxazaspiro[5,5]undecyl linked through a nitrogen atom, oxazaspiro[5,6]dodecyl linked through a nitrogen atom, oxazaspiro[6,6]tridecyl linked through a nitrogen atom,
substituted oxazaspiro[3,3]heptyl linked through a nitrogen atom, substituted oxazaspiro[3,4]octyl linked through a nitrogen atom, substituted oxazaspiro[3,5]nonyl linked through a nitrogen atom, substituted oxazaspiro[3,6]decyl linked through a nitrogen atom, substituted oxazaspiro[4,4]nonyl linked through a nitrogen atom, substituted oxazaspiro[4,5]decyl linked through a nitrogen atom, substituted oxazaspiro[4,6]undecyl linked through a nitrogen atom, substituted oxazaspiro[5,5]undecyl linked through a nitrogen atom, substituted oxazaspiro[5,6]dodecyl linked through a nitrogen atom, substituted oxazaspiro[6,6]tridecyl linked through a nitrogen atom,
oxadiazaspiro[3,5]nonyl linked through a nitrogen atom, oxadiazaspiro[3,6]decyl linked through a nitrogen atom, oxadiazaspiro[4,5]decyl linked through a nitrogen atom, oxadiazaspiro[4,6]undecyl linked through a nitrogen atom, oxadiazaspiro[5,5]undecyl linked through a nitrogen atom, oxadiazaspiro[5,6]dodecyl linked through a nitrogen atom, oxadiazaspiro[6,6]tridecyl linked through a nitrogen atom,
substituted oxadiazaspiro[3,5]nonyl linked through a nitrogen atom, substituted oxadiazaspiro[3,6]decyl linked through a nitrogen atom, substituted oxadiazaspiro[4,5]decyl linked through a nitrogen atom, substituted oxadiazaspiro[4,6]undecyl linked through a nitrogen atom, substituted oxadiazaspiro[5,5]undecyl linked through a nitrogen atom, substituted oxadiazaspiro[5,6]dodecyl linked through a nitrogen atom, substituted oxadiazaspiro[6,6]tridecyl linked through a nitrogen atom, wherein the afore-mentioned substituted spironitrogencyclyl, substituted nitrogenheterocyclyl, substituted $C_5$-$C_{14}$/$N_1$-$N_3$-spironitrogencyclyl or substituted $C_5$-$C_{14}$/$N_1$-$N_3$/$O_0$-$O_2$/$S_0$-$S_1$-nitrogenheterocyclyl residues are optionally substituted with one to three substituents selected from $Z^5$, $Z^6$ and $Z^7$. Moreover the afore-mentioned substituted or non-substituted spironitrogencyclyl, substituted or non-substituted nitrogenheterocyclyl, substituted or non-substituted $C_5$-$C_{14}$/$N_1$-$N_3$-spironitrogencyclyl or substituted or non-substituted $C_5$-$C_{14}$/$N_1$-$N_3$/$O_0$-$O_2$/$S_0$-$S_1$-nitrogenheterocyclyl residues contain at least one nitrogen atom through which these residues are linked through the rest of the molecule and may contain one or two further moieties selected from oxygen (—O—), sulfoxide (—SO—), sulfone (—SO$_2$—), carbonyl (—CO—) and nitrogen (—NR$^{12}$—).

Still more preferably $R^9$ represents the following spironitrogencyclyl, nitrogenheterocyclyl, $C_5$-$C_{14}$/$N_1$-$N_3$-spironitrogencyclyl or $C_5$-$C_{14}$/$N_1$-$N_3$/$O_0$-$O_2$/$S_0$-$S_1$-nitrogenheterocyclyl residues:

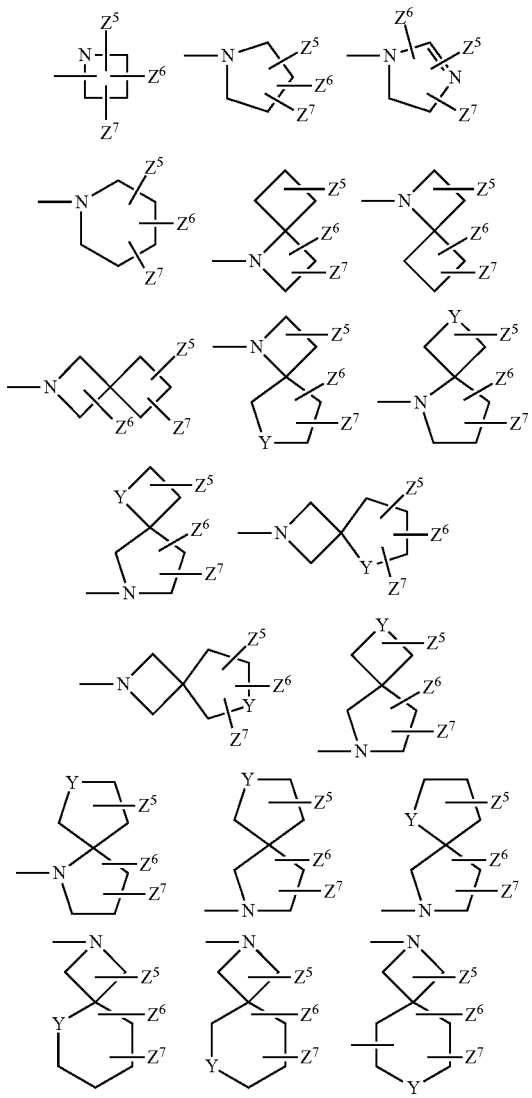

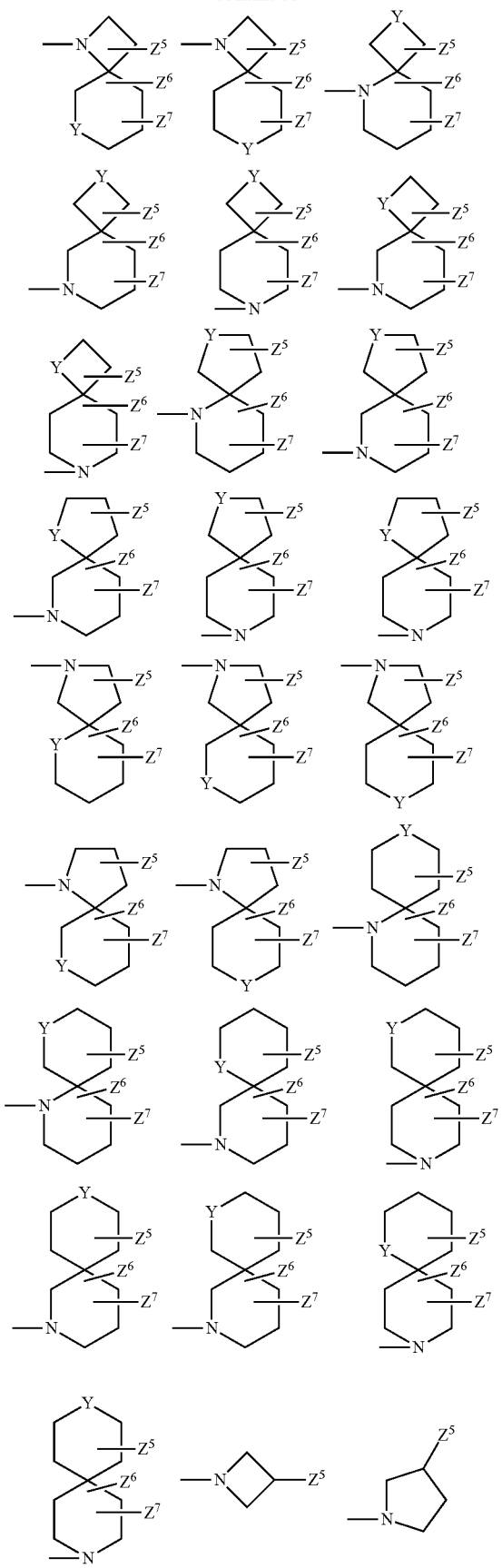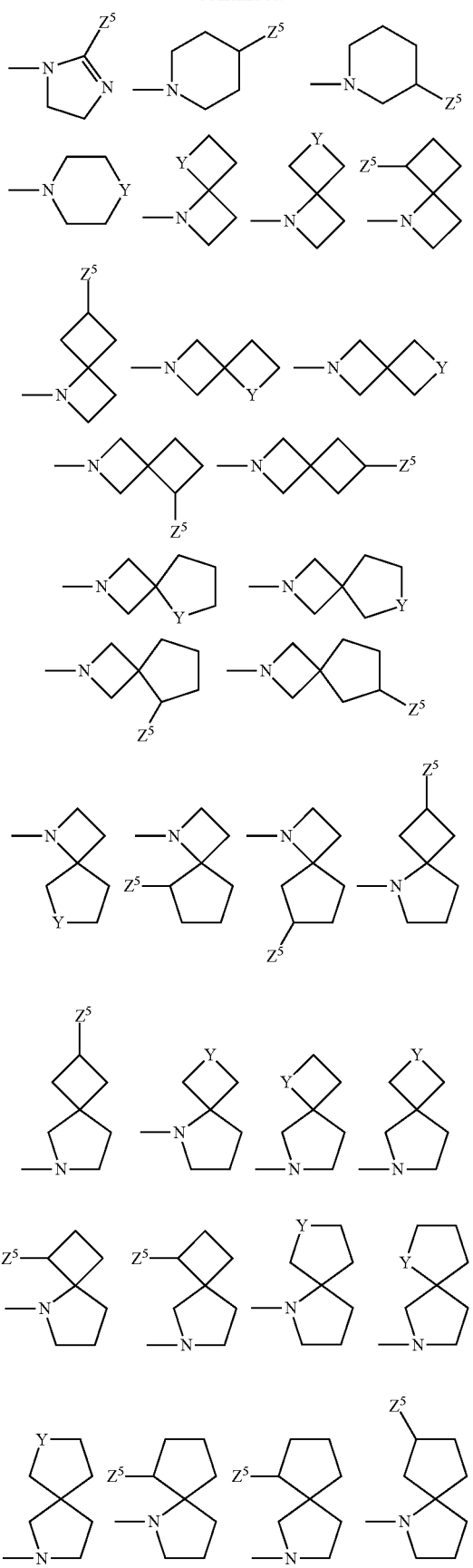

-continued

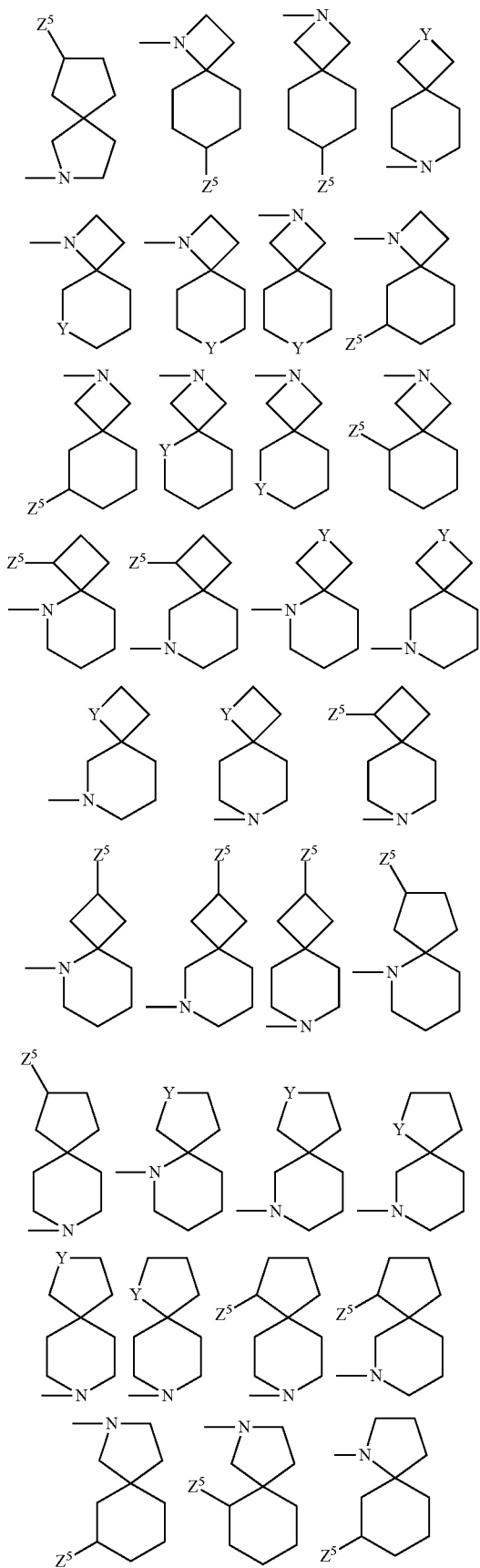

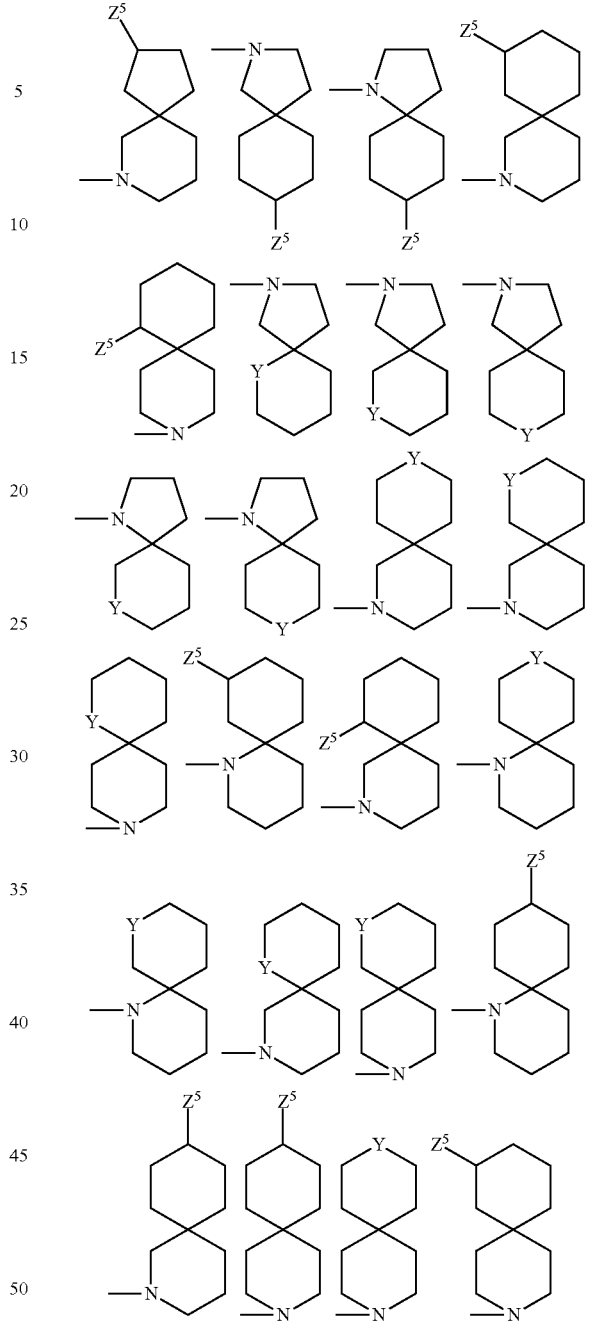

wherein Y represents —O—, —NH—, —NR$^{11}$—, —SO—, or —SO$_2$—, preferably —NH— and —NR$^{11}$— and wherein the substituents Z$^5$, Z$^6$ and Z$^7$ have the meanings as defined herein.

Preferably Z$^5$, Z$^6$ and Z$^7$ represent independently of each other —CH$_3$, —C$_2$H$_5$, —C$_3$H$_7$, —CH(CH$_3$)$_2$, —OH, —OCH$_3$, —OC$_2$H$_5$, —OC$_3$H$_7$, —NH$_2$, —NH(CH$_3$), —N(CH$_3$)$_2$, —F, —Cl, —Br, —I, —CN, —CH$_2$F, —CHF$_2$, —CF$_3$, —OCHF$_2$, and —OCF$_3$, more preferably —NH$_2$, —NH(CH$_3$), —N(CH$_3$)$_2$.

If present, R$^{11}$ and R$^{12}$ is preferably selected from: —CH$_3$, —C$_2$H$_5$, —C$_3$H$_7$, —CH(CH$_3$)$_2$, —CH$_2$F, —CHF$_2$, —CF$_3$,

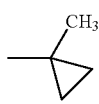

cyclo-C$_3$H$_5$, cyclo-C$_4$H$_7$, cyclo-C$_5$H$_9$, cyclo-C$_6$H$_{11}$, cyclo-C$_7$H$_{13}$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, -Ph, —CH$_2$-Ph, —CH$_2$—CH$_2$-Ph, —CH═CH-Ph, —CH═CH$_2$, —CH$_2$—CH═CH$_2$, —C(CH$_3$)═CH$_2$, —CH═CH—CH$_3$, —C$_2$H$_4$—CH═CH$_2$, —CH$_2$—CH═CH—CH$_3$, —CH═CH—C$_2$H$_5$, —CH$_2$—C(CH$_3$)═CH$_2$, —CH(CH$_3$)—CH═CH$_2$, —CH═C(CH$_3$)$_2$, —C(CH$_3$)═CH—CH$_3$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —CH$_2$—OCF$_3$, —C$_2$H$_4$—OCF$_3$, —C$_3$H$_6$—OCF$_3$, —CH$_2$—OCH$_3$, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$.

In a further aspect of the present invention, the novel compounds according to the general formula (I) represent chiral compounds. The novel compounds according to the general formula (I) represent a racemate, or a S or a R enantiomer or a mixture of isomers.

In yet another preferred embodiment of the present invention, the compound according to the general formula (I) is selected from the group of compounds depicted in the following Table 1.

TABLE 1

| compound | name |
| --- | --- |
| (VII-01) | N-(2-(1H-pyrazol-1-yl)benzyl)-8-isopropyl-2-(piperidin-4-yloxy)pyrazolo[1,5-a][1,3,5]triazin-4-amine |
| (VII-02) | (R)-N-(2-(1H-pyrazol-1-yl)benzyl)-8-isopropyl-2-(pyrrolidin-3-yloxy)pyrazolo[1,5-a][1,3,5]triazin-4-amine |
| (VII-03) | (R)-N-(2-(1H-pyrazol-1-yl)benzyl)-8-isopropyl-2-(piperidin-3-yloxy)pyrazolo[1,5-a][1,3,5]triazin-4-amine |
| (VII-04) | N-(2-(1H-pyrazol-1-yl)benzyl)-2-(2-azaspiro[3.3]heptan-6-yloxy)-8-isopropylpyrazolo[1,5-a][1,3,5]triazin-4-amine |
| (VII-05) | 2-(1-oxa-8-azaspiro[4.5]decan-3-yloxy)-N-(2-(1H-pyrazol-1-yl)benzyl)-8-isopropylpyrazolo[1,5-a][1,3,5]triazin-4-amine |
| (VII-06) | N-(1-(2-(1H-pyrazol-1-yl)phenyl)ethyl)-8-isopropyl-2-((R)-piperidin-3-yloxy)pyrazolo[1,5-a][1,3,5]triazin-4-amine |
| (VII-07) | (R)-N-([1,1'-biphenyl]-2-ylmethyl)-8-isopropyl-2-(piperidin-3-yloxy)pyrazolo[1,5-a][1,3,5]triazin-4-amine |
| (VII-08) | (R)-N-([1,1'-biphenyl]-2-ylmethyl)-8-isopropyl-2-(pyrrolidin-3-yloxy)pyrazolo[1,5-a][1,3,5]triazin-4-amine |
| (VII-09) | N-([1,1'-biphenyl]-2-ylmethyl)-8-isopropyl-2-(piperidin-4-yloxy)pyrazolo[1,5-a][1,3,5]triazin-4-amine |
| (VII-10) | 8-isopropyl-N-((S)-1-(2-methoxyphenyl)ethyl)-2-((R)-piperidin-3-yloxy)pyrazolo[1,5-a][1,3,5]triazin-4-amine |
| (VII-11) | 8-isopropyl-N-((S)-1-(2-methoxyphenyl)ethyl)-2-((R)-pyrrolidin-3-yloxy)pyrazolo[1,5-a][1,3,5]triazin-4-amine |
| (VII-12) | (R)-8-isopropyl-2-(piperidin-3-yloxy)-N-(2-(thiophen-2-yl)benzyl)pyrazolo[1,5-a][1,3,5]triazin-4-amine |
| (VII-13) | (R)-8-isopropyl-2-(pyrrolidin-3-yloxy)-N-(2-(thiophen-2-yl)benzyl)pyrazolo[1,5-a][1,3,5]triazin-4-amine |
| (VII-14) | 8-isopropyl-2-(piperidin-4-yloxy)-N-(2-(thiophen-2-yl)benzyl)pyrazolo[1,5-a][1,3,5]triazin-4-amine |
| (VII-15) | (S)-8-isopropyl-N-(1-(2-methoxyphenyl)ethyl)-2-(piperidin-4-yloxy)pyrazolo[1,5-a][1,3,5]triazin-4-amine |
| (VII-16) | (R)-N-(2-isopropoxybenzyl)-8-isopropyl-2-(pyrrolidin-3-yloxy)pyrazolo[1,5-a][1,3,5]triazin-4-amine |
| (VII-17) | N-(2-isopropoxybenzyl)-8-isopropyl-2-(piperidin-4-yloxy)pyrazolo[1,5-a][1,3,5]triazin-4-amine |
| (VII-18) | (R)-N-(2-isopropoxybenzyl)-8-isopropyl-2-(piperidin-3-yloxy)pyrazolo[1,5-a][1,3,5]triazin-4-amine |
| (VII-19) | N-(2-(1H-imidazol-1-yl)benzyl)-8-isopropyl-2-(piperidin-4-yloxy)pyrazolo[1,5-a][1,3,5]triazin-4-amine |
| (VII-20) | (R)-N-(2-(1H-1,2,4-triazol-1-yl)benzyl)-8-isopropyl-2-(piperidin-3-yloxy)pyrazolo[1,5-a][1,3,5]triazin-4-amine |
| (VII-21) | (R)-N-(2-(1H-1,2,4-triazol-1-yl)benzyl)-8-isopropyl-2-(pyrrolidin-3-yloxy)pyrazolo[1,5-a][1,3,5]triazin-4-amine |
| (VII-22) | N-(2-(1H-1,2,4-triazol-1-yl)benzyl)-8-isopropyl-2-(piperidin-4-yloxy)pyrazolo[1,5-a][1,3,5]triazin-4-amine |
| (VII-23) | (R)-8-isopropyl-N-(2-(2-methyl-1H-imidazol-1-yl)benzyl)-2-(piperidin-3-yloxy)pyrazolo[1,5-a][1,3,5]triazin-4-amine |
| (VII-24) | 8-isopropyl-N-(2-(2-methyl-1H-imidazol-1-yl)benzyl)-2-(piperidin-4-yloxy)pyrazolo[1,5-a][1,3,5]triazin-4-amine |
| (VII-25) | (R)-8-isopropyl-N-(2-(2-methyl-1H-imidazol-1-yl)benzyl)-2-(pyrrolidin-3-yloxy)pyrazolo[1,5-a][1,3,5]triazin-4-amine |
| (VII-26) | (R)-N-(2-(1H-imidazol-1-yl)benzyl)-8-isopropyl-2-(piperidin-3-yloxy)pyrazolo[1,5-a][1,3,5]triazin-4-amine |
| (VII-27) | (R)-N-(2-(1H-imidazol-1-yl)benzyl)-8-isopropyl-2-(pyrrolidin-3-yloxy)pyrazolo[1,5-a][1,3,5]triazin-4-amine |
| (VII-28) | N-((S)-1-(2-chlorophenyl)ethyl)-8-isopropyl-2-((R)-piperidin-3-yloxy)pyrazolo[1,5-a][1,3,5]triazin-4-amine |

TABLE 1-continued

| compound | name |
|---|---|
| (VII-29) | (R)-8-isopropyl-N-(2-(1-methyl-1H-tetrazol-5-yl)benzyl)-2-(piperidin-3-yloxy)pyrazolo[1,5-a][1,3,5]triazin-4-amine |
| (VII-30) | (R)-5-(((8-isopropyl-2-(piperidin-3-yloxy)pyrazolo[1,5-a][1,3,5]triazin-4-yl)amino)methyl)quinoline 1-oxide |
| (VII-31) | (R)-8-isopropyl-N-(isoquinolin-8-ylmethyl)-2-(piperidin-3-yloxy)pyrazolo[1,5-a][1,3,5]triazin-4-amine |
| (VII-32) | (R)-8-(((8-isopropyl-2-(piperidin-3-yloxy)pyrazolo[1,5-a][1,3,5]triazin-4-yl)amino)methyl)isoquinoline 2-oxide |
| (VII-33) | (R)-8-isopropyl-N-((1-methyl-1H-indazol-4-yl)methyl)-2-(piperidin-3-yloxy)pyrazolo[1,5-a][1,3,5]triazin-4-amine |
| (VII-34) | (R)-8-isopropyl-2-(piperidin-3-yloxy)-N-(2-(pyridin-2-yl)benzyl)pyrazolo[1,5-a][1,3,5]triazin-4-amine |
| (VII-35) | (R)-8-isopropyl-2-(piperidin-3-yloxy)-N-(quinolin-8-ylmethyl)pyrazolo[1,5-a][1,3,5]triazin-4-amine |
| (VII-36) | (R)-N-((1H-indazol-4-yl)methyl)-8-isopropyl-2-(piperidin-3-yloxy)pyrazolo[1,5-a][1,3,5]triazin-4-amine |
| (VII-37) | (R)-8-isopropyl-N-(2-(2-methyl-2H-tetrazol-5-yl)benzyl)-2-(piperidin-3-yloxy)pyrazolo[1,5-a][1,3,5]triazin-4-amine |
| (VII-38) | (R)-2-(((8-isopropyl-2-(piperidin-3-yloxy)pyrazolo[1,5-a][1,3,5]triazin-4-yl)amino)methyl)-N,N-dimethylbenzenesulfonamide |
| (VII-39) | (R)-1-(2-(((8-isopropyl-2-(piperidin-3-yloxy)pyrazolo[1,5-a][1,3,5]triazin-4-yl)amino)methyl)phenyl)pyrrolidin-2-one |
| (VII-40) | (R)-1-(2-(((8-isopropyl-2-(piperidin-3-yloxy)pyrazolo[1,5-a][1,3,5]triazin-4-yl)amino)methyl)phenyl)azetidin-2-one |
| (VII-41) | (R)-N-(5-fluoro-2-(1H-pyrazol-1-yl)benzyl)-8-isopropyl-2-(piperidin-3-yloxy)pyrazolo[1,5-a][1,3,5]triazin-4-amine |
| (VII-42) | (R)-N-(3-fluoro-2-(1H-pyrazol-1-yl)benzyl)-8-isopropyl-2-(piperidin-3-yloxy)pyrazolo[1,5-a][1,3,5]triazin-4-amine |
| (VII-43) | (R)-N-(4-fluoro-2-(1H-pyrazol-1-yl)benzyl)-8-isopropyl-2-(piperidin-3-yloxy)pyrazolo[1,5-a][1,3,5]triazin-4-amine |
| (VII-44) | (R)-N-(2-fluoro-6-(1H-pyrazol-1-yl)benzyl)-8-isopropyl-2-(piperidin-3-yloxy)pyrazolo[1,5-a][1,3,5]triazin-4-amine |
| (VII-45) | 8-isopropyl-2-((1-methylpiperidin-4-yl)oxy)-N-(2-(pyridin-3-yl)benzyl)pyrazolo[1,5-a][1,3,5]triazin-4-amine |
| (VII-46) | (R)-8-isopropyl-2-(piperidin-3-yloxy)-N-(2-(pyridin-3-yl)benzyl)pyrazolo[1,5-a][1,3,5]triazin-4-amine |
| (VII-47) | 8-isopropyl-2-((1-methylpiperidin-4-yl)oxy)-N-(2-phenoxybenzyl)pyrazolo[1,5-a][1,3,5]triazin-4-amine |
| (VII-48) | (R)-8-isopropyl-N-(2-phenoxybenzyl)-2-(piperidin-3-yloxy)pyrazolo[1,5-a][1,3,5]triazin-4-amine |
| (VII-49) | (R)-8-isopropyl-N-(2-(oxazol-2-yl)benzyl)-2-(piperidin-3-yloxy)pyrazolo[1,5-a][1,3,5]triazin-4-amine |
| (VII-50) | (R)-N-(2-(furan-2-yl)benzyl)-8-isopropyl-2-(piperidin-3-yloxy)pyrazolo[1,5-a][1,3,5]triazin-4-amine |
| (VII-51) | (R)-N-(2-(((8-isopropyl-2-(piperidin-3-yloxy)pyrazolo[1,5-a][1,3,5]triazin-4-yl)amino)methyl)phenyl)acetamide |
| (VII-52) | (R)-N-(2-(4-chloro-1H-pyrazol-1-yl)benzyl)-8-isopropyl-2-(piperidin-3-yloxy)pyrazolo[1,5-a][1,3,5]triazin-4-amine |
| (VII-53) | 8-isopropyl-N-(2-methylbenzyl)-2-((1-methylpiperidin-4-yl)oxy)pyrazolo[1,5-a][1,3,5]triazin-4-amine |
| (VII-54) | N-(2-(dimethylamino)benzyl)-8-isopropyl-2-((1-methylpiperidin-4-yl)oxy)pyrazolo[1,5-a][1,3,5]triazin-4-amine |
| (VII-55) | 2-(((8-isopropyl-2-((1-methylpiperidin-4-yl)oxy)pyrazolo[1,5-a][1,3,5]triazin-4-yl)amino)methyl)benzonitrile |
| (VII-56) | N-(2-fluorobenzyl)-8-isopropyl-2-((1-methylpiperidin-4-yl)oxy)pyrazolo[1,5-a][1,3,5]triazin-4-amine |
| (VII-57) | N-([1,1'-biphenyl]-2-ylmethyl)-8-isopropyl-2-((1-methylpiperidin-4-yl)oxy)pyrazolo[1,5-a][1,3,5]triazin-4-amine |
| (VII-58) | 8-isopropyl-2-((1-methylpiperidin-4-yl)oxy)-N-(2-(trifluoromethyl)benzyl)pyrazolo[1,5-a][1,3,5]triazin-4-amine |
| (VII-59) | N-(2-(1H-imidazol-1-yl)benzyl)-8-isopropyl-2-((1-methylpiperidin-4-yl)oxy)pyrazolo[1,5-a][1,3,5]triazin-4-amine |
| (VII-60) | 8-isopropyl-2-((1-methylpiperidin-4-yl)oxy)-N-(2-morpholinobenzyl)pyrazolo[1,5-a][1,3,5]triazin-4-amine |
| (VII-61) | 8-isopropyl-2-((1-methylpiperidin-4-yl)oxy)-N-(naphthalen-1-ylmethyl)pyrazolo[1,5-a][1,3,5]triazin-4-amine |
| (VII-62) | N-(2-chloro-6-methylbenzyl)-8-isopropyl-2-((1-methylpiperidin-4-yl)oxy)pyrazolo[1,5-a][1,3,5]triazin-4-amine |
| (VII-63) | N-(2,6-dichlorobenzyl)-8-isopropyl-2-((1-methylpiperidin-4-yl)oxy)pyrazolo[1,5-a][1,3,5]triazin-4-amine |
| (VII-64) | N-(2,6-difluorobenzyl)-8-isopropyl-2-((1-methylpiperidin-4-yl)oxy)pyrazolo[1,5-a][1,3,5]triazin-4-amine |
| (VII-65) | 8-isopropyl-2-((1-methylpiperidin-4-yl)oxy)-N-(2-(thiophen-2-yl)benzyl)pyrazolo[1,5-a][1,3,5]triazin-4-amine |
| (VII-66) | N-(2-isopropoxybenzyl)-8-isopropyl-2-((1-methylpiperidin-4-yl)oxy)pyrazolo[1,5-a][1,3,5]triazin-4-amine |
| (VII-67) | (S)-8-isopropyl-N-(1-(2-methoxyphenyl)ethyl)-2-((1-methylpiperidin-4-yl)oxy)pyrazolo[1,5-a][1,3,5]triazin-4-amine |

TABLE 1-continued

| compound | name |
| --- | --- |
| (VII-68) | N-(2-chlorobenzyl)-8-isopropyl-2-((1-methylpiperidin-4-yl)oxy)pyrazolo[1,5-a][1,3,5]triazin-4-amine |
| (VII-69) | (S)-8-isopropyl-2-((1-methylpiperidin-4-yl)oxy)-N-(1-(naphthalen-1-yl)ethyl)pyrazolo[1,5-a][1,3,5]triazin-4-amine |
| (VII-70) | N-(2-ethoxybenzyl)-8-isopropyl-2-((1-methylpiperidin-4-yl)oxy)pyrazolo[1,5-a][1,3,5]triazin-4-amine |
| (VII-71) | 8-isopropyl-N-(2-methoxybenzyl)-2-((1-methylpiperidin-4-yl)oxy)pyrazolo[1,5-a][1,3,5]triazin-4-amine |
| (VII-72) | N-(2-(difluoromethoxy)benzyl)-8-isopropyl-2-((1-methylpiperidin-4-yl)oxy)pyrazolo[1,5-a][1,3,5]triazin-4-amine |
| (VII-73) | N-(2-(1H-pyrazol-1-yl)benzyl)-8-isopropyl-2-((1-methylpiperidin-4-yl)oxy)pyrazolo[1,5-a][1,3,5]triazin-4-amine |
| (VII-74) | N-(2-(1H-1,2,4-triazol-1-yl)benzyl)-8-isopropyl-2-((1-methylpiperidin-4-yl)oxy)pyrazolo[1,5-a][1,3,5]triazin-4-amine |
| (VII-75) | 8-isopropyl-N-(2-(2-methyl-1H-imidazol-1-yl)benzyl)-2-((1-methylpiperidin-4-yl)oxy)pyrazolo[1,5-a][1,3,5]triazin-4-amine |
| (VII-76) | N-(2-(difluoromethoxy)benzyl)-8-isopropyl-2-((1-methylpiperidin-4-yl)oxy)pyrazolo[1,5-a][1,3,5]triazin-4-amine |
| (VII-77) | methyl 2-(((2-(2-(dimethylamino)ethoxy)-8-isopropylpyrazolo[1,5-a][1,3,5]triazin-4-yl)amino)methyl)benzoate |
| (VII-78) | 2-((6-aminospiro[3.3]heptan-2-yl)oxy)-8-isopropyl-N-(quinolin-5-ylmethyl)pyrazolo[1,5-a][1,3,5]triazin-4-amine |
| (VII-79) | 8-isopropyl-2-(2-(piperidin-4-yl)ethoxy)-N-(quinolin-5-ylmethyl)pyrazolo[1,5-a][1,3,5]triazin-4-amine |
| (VII-80) | N-(2-aminobenzyl)-2-(azetidin-3-ylmethoxy)-8-isopropylpyrazolo[1,5-a][1,3,5]triazin-4-amine |
| (VII-89) | tert-butyl (2-(((8-isopropyl-2-(2-(piperidin-1-yl)ethoxy)pyrazolo[1,5-a][1,3,5]triazin-4-yl)amino)methyl)phenyl)carbamate |
| (VII-90) | N-(2-(((2-(2-(2-(dimethylamino)ethoxy)ethoxy)-8-isopropylpyrazolo[1,5-a][1,3,5]triazin-4-yl)amino)methyl)phenyl)methanesulfonamide |
| (VII-91) | N-(2-(((2-(2-((2-(dimethylamino)ethyl)(methyl)amino)ethoxy)-8-isopropylpyrazolo[1,5-a][1,3,5]triazin-4-yl)amino)methyl)phenyl)methanesulfonamide |
| (VIII-01) | N4-(2-(1H-pyrazol-1-yl)benzyl)-8-isopropyl-N2-(piperidin-3-yl)pyrazolo[1,5-a][1,3,5]triazine-2,4-diamine |
| (VIII-02) | N-(2-(1H-pyrazol-1-yl)benzyl)-8-isopropyl-2-(2,6-diazaspiro[3.4]octan-2-yl)pyrazolo[1,5-a][1,3,5]triazin-4-amine |
| (VIII-03) | N-(2-(1H-pyrazol-1-yl)benzyl)-8-isopropyl-2-(2,7-diazaspiro[4.4]nonan-2-yl)pyrazolo[1,5-a][1,3,5]triazin-4-amine |
| (VIII-04) | N-(2-(1H-pyrazol-1-yl)benzyl)-8-isopropyl-2-(1,6-diazaspiro[3.5]nonan-1-yl)pyrazolo[1,5-a][1,3,5]triazin-4-amine |
| (VIII-05) | N-(2-(1H-pyrazol-1-yl)benzyl)-8-isopropyl-2-(2,6-diazaspiro[3.5]nonan-2-yl)pyrazolo[1,5-a][1,3,5]triazin-4-amine |
| (VIII-06) | N-(2-(1H-pyrazol-1-yl)benzyl)-8-isopropyl-2-(2,6-diazaspiro[4.5]decan-2-yl)pyrazolo[1,5-a][1,3,5]triazin-4-amine |
| (VIII-07) | N-(2-(1H-pyrazol-1-yl)benzyl)-8-isopropyl-2-(2,6-diazaspiro[3.4]octan-6-yl)pyrazolo[1,5-a][1,3,5]triazin-4-amine |
| (VIII-08) | N-(2-(1H-pyrazol-1-yl)benzyl)-8-isopropyl-2-(1,6-diazaspiro[3.3]heptan-1-yl)pyrazolo[1,5-a][1,3,5]triazin-4-amine |
| (VIII-09) | N-(2-(1H-pyrazol-1-yl)benzyl)-8-isopropyl-2-(2,8-diazaspiro[4.5]decan-8-yl)pyrazolo[1,5-a][1,3,5]triazin-4-amine |
| (VIII-10) | N-(2-(1H-pyrazol-1-yl)benzyl)-8-isopropyl-2-(2,6-diazaspiro[3.3]heptan-2-yl)pyrazolo[1,5-a][1,3,5]triazin-4-amine |
| (VIII-11) | N-(2-(1H-pyrazol-1-yl)benzyl)-8-isopropyl-2-(1,8-diazaspiro[4.5]decan-8-yl)pyrazolo[1,5-a][1,3,5]triazin-4-amine |
| (VIII-12) | N-(2-(1H-pyrazol-1-yl)benzyl)-8-isopropyl-2-(2,7-diazaspiro[3.5]nonan-2-yl)pyrazolo[1,5-a][1,3,5]triazin-4-amine |
| (VIII-13) | N-(2-(1H-pyrazol-1-yl)benzyl)-8-isopropyl-2-(1,7-diazaspiro[4.4]nonan-1-yl)pyrazolo[1,5-a][1,3,5]triazin-4-amine |
| (VIII-14) | N-(2-(1H-pyrazol-1-yl)benzyl)-8-isopropyl-2-(2,8-diazaspiro[5.5]undecan-2-yl)pyrazolo[1,5-a][1,3,5]triazin-4-amine |
| (VIII-15) | N-(2-(1H-pyrazol-1-yl)benzyl)-8-isopropyl-2-(1,8-diazaspiro[5.5]undecan-8-yl)pyrazolo[1,5-a][1,3,5]triazin-4-amine |
| (VIII-16) | N-(2-(1H-pyrazol-1-yl)benzyl)-8-isopropyl-2-(2,7-diazaspiro[3.5]nonan-7-yl)pyrazolo[1,5-a][1,3,5]triazin-4-amine |
| (VIII-17) | N-(2-(1H-pyrazol-1-yl)benzyl)-8-isopropyl-2-(1,7-diazaspiro[4.4]nonan-7-yl)pyrazolo[1,5-a][1,3,5]triazin-4-amine |
| (VIII-18) | 8-isopropyl-N-(2-(1-methyl-1H-tetrazol-5-yl)benzyl)-2-(1,8-diazaspiro[4.5]decan-8-yl)pyrazolo[1,5-a][1,3,5]triazin-4-amine |
| (VIII-19) | 8-isopropyl-N-(2-(2-methyl-2H-tetrazol-5-yl)benzyl)-2-(1,8-diazaspiro[4.5]decan-8-yl)pyrazolo[1,5-a][1,3,5]triazin-4-amine |
| (VIII-20) | N-(2-(1H-pyrazol-1-yl)benzyl)-8-isopropyl-2-(1,7-diazaspiro[3.5]nonan-7-yl)pyrazolo[1,5-a][1,3,5]triazin-4-amine |
| (VIII-21) | N-(2-(1H-pyrazol-1-yl)benzyl)-8-isopropyl-2-(2,9-diazaspiro[5.5]undecan-2-yl)pyrazolo[1,5-a][1,3,5]triazin-4-amine |
| (VIII-22) | N-(2-(1H-pyrazol-1-yl)benzyl)-8-isopropyl-2-(1,8-diazaspiro[4.5]decan-1-yl)pyrazolo[1,5-a][1,3,5]triazin-4-amine |

TABLE 1-continued

| compound | name |
| --- | --- |
| (VIII-23) | N-(2-(1H-pyrazol-1-yl)benzyl)-8-isopropyl-2-(1,9-diazaspiro[5.5]undecan-9-yl)pyrazolo[1,5-a][1,3,5]triazin-4-amine |
| (VIII-24) | N-(2-(1H-pyrazol-1-yl)benzyl)-2-(4-(dimethylamino)piperidin-1-yl)-8-isopropylpyrazolo[1,5-a][1,3,5]triazin-4-amine |
| (VIII-25) | N-(2-(1H-pyrazol-1-yl)benzyl)-8-isopropyl-2-(4-(methylamino)piperidin-1-yl)pyrazolo[1,5-a][1,3,5]triazin-4-amine |
| (VIII-26) | N-(2-(1H-pyrazol-1-yl)benzyl)-8-isopropyl-2-(3,9-diazaspiro[5.5]undecan-3-yl)pyrazolo[1,5-a][1,3,5]triazin-4-amine |
| (VIII-27) | N-(2-(1H-pyrazol-1-yl)benzyl)-8-isopropyl-2-(2,7-diazaspiro[4.5]decan-2-yl)pyrazolo[1,5-a][1,3,5]triazin-4-amine |
| (VIII-28) | N-(2-(1H-pyrazol-1-yl)benzyl)-8-isopropyl-2-(1,6-diazaspiro[3.4]octan-1-yl)pyrazolo[1,5-a][1,3,5]triazin-4-amine |
| (VIII-31) | 8-isopropyl-N4-((S)-1-(2-methoxyphenyl)ethyl)-N2-((R)-piperidin-3-yl)pyrazolo[1,5-a][1,3,5]triazine-2,4-diamine |
| (VIII-32) | (R)-N4-(2-isopropoxybenzyl)-8-isopropyl-N2-(piperidin-3-yl)pyrazolo[1,5-a][1,3,5]triazine-2,4-diamine |
| (VIII-33) | (R)-N4-(2-(1H-1,2,4-triazol-1-yl)benzyl)-8-isopropyl-N2-(piperidin-3-yl)pyrazolo[1,5-a][1,3,5]triazine-2,4-diamine |
| (VIII-34) | N-(2-(1H-pyrazol-1-yl)benzyl)-8-isopropyl-2-(1,7-diazaspiro[3.5]nonan-1-yl)pyrazolo[1,5-a][1,3,5]triazin-4-amine |
| (VIII-35) | 2-(((8-isopropyl-2-(1,8-diazaspiro[4.5]decan-8-yl)pyrazolo[1,5-a][1,3,5]triazin-4-yl)amino)methyl)-N,N-dimethylbenzenesulfonamide |
| (VIII-36) | N-(benzo[c][1,2,5]oxadiazol-4-ylmethyl)-8-isopropyl-2-(1,8-diazaspiro[4.5]decan-8-yl)pyrazolo[1,5-a][1,3,5]triazin-4-amine |
| (VIII-37) | N-(2-(1H-pyrazol-1-yl)benzyl)-8-isopropyl-2-(2,8-diazaspiro[4.5]decan-2-yl)pyrazolo[1,5-a][1,3,5]triazin-4-amine |
| (VIII-38) | 1-(2-(((8-isopropyl-2-(1,8-diazaspiro[4.5]decan-8-yl)pyrazolo[1,5-a][1,3,5]triazin-4-yl)amino)methyl)phenyl)pyrrolidin-2-one |
| (X-1) | N-(2-(1H-pyrazol-1-yl)benzyl)-8-isopropyl-2-(piperidin-4-ylsulfinyl)pyrazolo[1,5-a][1,3,5]triazin-4-amine |
| (X-2) | 8-isopropyl-2-(piperidin-4-ylsulfinyl)-N-(2-(thiophen-2-yl)benzyl)pyrazolo[1,5-a][1,3,5]triazin-4-amine |
| (X-3) | N-([1,1'-biphenyl]-2-ylmethyl)-8-isopropyl-2-(piperidin-4-ylsulfinyl)pyrazolo[1,5-a][1,3,5]triazin-4-amine |
| (X-4) | N-(2-(1H-1,2,4-triazol-1-yl)benzyl)-8-isopropyl-2-(piperidin-4-ylsulfinyl)pyrazolo[1,5-a][1,3,5]triazin-4-amine |
| (X-5) | 8-isopropyl-N-(2-(2-methyl-1H-imidazol-1-yl)benzyl)-2-(piperidin-4-ylsulfinyl)pyrazolo[1,5-a][1,3,5]triazin-4-amine |
| (XII-1) | 4-((2-(1H-pyrazol-1-yl)benzyl)amino)-8-isopropyl-N-(piperidin-4-ylmethyl)pyrazolo[1,5-a][1,3,5]triazine-2-carboxamide |
| (XII-2) | 4-((2-(1H-pyrazol-1-yl)benzyl)amino)-N-(azetidin-3-ylmethyl)-8-isopropylpyrazolo[1,5-a][1,3,5]triazine-2-carboxamide |
| (XII-3) | 4-((2-(1H-pyrazol-1-yl)benzyl)amino)-8-isopropyl-N-(pyrrolidin-3-ylmethyl)pyrazolo[1,5-a][1,3,5]triazine-2-carboxamide |
| (XII-4) | 4-((2-(1H-pyrazol-1-yl)benzyl)amino)-8-isopropyl-N-(piperidin-3-ylmethyl)pyrazolo[1,5-a][1,3,5]triazine-2-carboxamide |
| (XII-5) | 4-((2-(1H-pyrazol-1-yl)benzyl)amino)-N-(4-aminobutyl)-8-isopropylpyrazolo[1,5-a][1,3,5]triazine-2-carboxamide |
| | (R)-N-(4-chloro-2-methylbenzyl)-8-isopropyl-2-(piperidin-3-yloxy)pyrazolo[1,5-a][1,3,5]triazin-4-amine |
| | (R)-N-(2-bromobenzyl)-8-isopropyl-2-(piperidin-3-yloxy)pyrazolo[1,5-a][1,3,5]triazin-4-amine |
| | (R)-8-isopropyl-N-(2-(morpholinosulfonyl)benzyl)-2-(piperidin-3-yloxy)pyrazolo[1,5-a][1,3,5]triazin-4-amine |
| | (R)-8-isopropyl-2-(piperidin-3-yloxy)-N-(2-(pyridin-2-yloxy)benzyl)pyrazolo[1,5-a][1,3,5]triazin-4-amine |
| | (R)-N-(2-cyclobutoxybenzyl)-8-isopropyl-2-(piperidin-3-yloxy)pyrazolo[1,5-a][1,3,5]triazin-4-amine |
| | (R)-2-(((8-isopropyl-2-(piperidin-3-yloxy)pyrazolo[1,5-a][1,3,5]triazin-4-yl)amino)methyl)benzamide |
| | (R)-N-(2-(cyclopentyloxy)benzyl)-8-isopropyl-2-(piperidin-3-yloxy)pyrazolo[1,5-a][1,3,5]triazin-4-amine |
| | (R)-N-(2,4-dichlorobenzyl)-8-isopropyl-2-(piperidin-3-yloxy)pyrazolo[1,5-a][1,3,5]triazin-4-amine |
| | 8-isopropyl-N-(4-methyl-2-((tetrahydrofuran-3-yl)oxy)benzyl)-2-((R)-piperidin-3-yloxy)pyrazolo[1,5-a][1,3,5]triazin-4-amine |
| | (R)-1-(2-(((8-isopropyl-2-(piperidin-3-yloxy)pyrazolo[1,5-a][1,3,5]triazin-4-yl)amino)methyl)benzyl)pyrrolidin-2-one |
| | N-(2-(((8-isopropyl-2-(methylsulfonyl)pyrazolo[1,5-a][1,3,5]triazin-4-yl)amino)methyl)phenyl)methanesulfonamide |
| | 4-(benzyloxy)-8-isopropyl-2-(methylsulfonyl)pyrazolo[1,5-a][1,3,5]triazine |
| | N-(2-(1H-pyrazol-1-yl)benzyl)-8-isopropyl-2-(2-(piperazin-1-yl)ethoxy)pyrazolo[1,5-a][1,3,5]triazin-4-amine |
| | N-(2-(1H-pyrazol-1-yl)benzyl)-2-((1R,5S)-3-azabicyclo[3.2.0]heptan-6-yloxy)-8-isopropylpyrazolo[1,5-a][1,3,5]triazin-4-amine |
| | 2-((1,4-oxazepan-6-yl)oxy)-N-(2-(1H-pyrazol-1-yl)benzyl)-8-isopropylpyrazolo[1,5-a][1,3,5]triazin-4-amine |
| | 2-(1-oxa-8-azaspiro[4.5]decan-3-yloxy)-N-(2-(1H-pyrazol-1-yl)benzyl)-8- |

TABLE 1-continued

| compound name |
|---|
| isopropylpyrazolo[1,5-a][1,3,5]triazin-4-amine |
| N-(2-(1H-pyrazol-1-yl)benzyl)-8-isopropyl-2-((1,2,3,6-tetrahydropyridin-3-yl)oxy)pyrazolo[1,5-a][1,3,5]triazin-4-amine |
| (R)-N-(2-(cyclopentylthio)benzyl)-8-isopropyl-2-(piperidin-3-yloxy)pyrazolo[1,5-a][1,3,5]triazin-4-amine |
| (R)-8-isopropyl-N-(2-(methylthio)benzyl)-2-(piperidin-3-yloxy)pyrazolo[1,5-a][1,3,5]triazin-4-amine |
| (R)-8-isopropyl-2-(piperidin-3-yloxy)-N-((2',3',4',5'-tetrahydro-[1,1'-biphenyl]-2-yl)methyl)pyrazolo[1,5-a][1,3,5]triazin-4-amine |
| (R)-N-((3,4-dihydro-2H-benzo[b][1,4]dioxepin-6-yl)methyl)-8-isopropyl-2-(piperidin-3-yloxy)pyrazolo[1,5-a][1,3,5]triazin-4-amine |
| (R)-N-(2-isobutoxy-4-methylbenzyl)-8-isopropyl-2-(piperidin-3-yloxy)pyrazolo[1,5-a][1,3,5]triazin-4-amine |
| (R)-1-ethyl-3-(2-(((8-isopropyl-2-(piperidin-3-yloxy)pyrazolo[1,5-a][1,3,5]triazin-4-yl)amino)methyl)phenyl)urea |
| (R)-1-benzyl-3-(2-(((8-isopropyl-2-(piperidin-3-yloxy)pyrazolo[1,5-a][1,3,5]triazin-4-yl)amino)methyl)phenyl)urea |
| (R)-1-cyclohexyl-3-(2-(((8-isopropyl-2-(piperidin-3-yloxy)pyrazolo[1,5-a][1,3,5]triazin-4-yl)amino)methyl)phenyl)urea |
| (R)-1-(2-(((8-isopropyl-2-(piperidin-3-yloxy)pyrazolo[1,5-a][1,3,5]triazin-4-yl)amino)methyl)phenyl)-3-phenylurea |
| (R)-1-(2-(((8-isopropyl-2-(piperidin-3-yloxy)pyrazolo[1,5-a][1,3,5]triazin-4-yl)amino)methyl)phenyl)-3-propylurea |
| N-(but-3-yn-2-yl)-2-(((8-isopropyl-2-((R)-piperidin-3-yloxy)pyrazolo[1,5-a][1,3,5]triazin-4-yl)amino)methyl)benzamide |
| (R)-2-(((8-isopropyl-2-(piperidin-3-yloxy)pyrazolo[1,5-a][1,3,5]triazin-4-yl)amino)methyl)-N-methylbenzamide |
| (R)-8-isopropyl-N-(2-((4-methylpiperazin-1-yl)sulfonyl)benzyl)-2-(piperidin-3-yloxy)pyrazolo[1,5-a][1,3,5]triazin-4-amine |
| (R)-8-isopropyl-2-(piperidin-3-yloxy)-N-(2-(pyrrolidin-1-ylsulfonyl)benzyl)pyrazolo[1,5-a][1,3,5]triazin-4-amine |
| (R)-N-isopropyl-2-(((8-isopropyl-2-(piperidin-3-yloxy)pyrazolo[1,5-a][1,3,5]triazin-4-yl)amino)methyl)benzenesulfonamide |
| (R)-2-(((8-isopropyl-2-(piperidin-3-yloxy)pyrazolo[1,5-a][1,3,5]triazin-4-yl)amino)methyl)-N-methylbenzenesulfonamide |
| (R)-N-(2,3-dichlorobenzyl)-8-isopropyl-2-(piperidin-3-yloxy)pyrazolo[1,5-a][1,3,5]triazin-4-amine |
| (R)-N-(4-chloro-2-(trifluoromethyl)benzyl)-8-isopropyl-2-(piperidin-3-yloxy)pyrazolo[1,5-a][1,3,5]triazin-4-amine |
| N-(2-(1H-pyrazol-1-yl)benzyl)-2-(2-azabicyclo[2.2.1]heptan-5-yloxy)-8-isopropylpyrazolo[1,5-a][1,3,5]triazin-4-amine |
| N-(2-iodobenzyl)-8-isopropyl-2-(piperidin-3-yloxy)pyrazolo[1,5-a][1,3,5]triazin-4-amine |
| N-(2-(((8-isopropyl-2-((R)-piperidin-3-yloxy)pyrazolo[1,5-a][1,3,5]triazin-4-yl)amino)methyl)phenyl)-2-methylpropane-2-sulfinamide |
| (R)-isobutyl (2-(((8-isopropyl-2-(piperidin-3-yloxy)pyrazolo[1,5-a][1,3,5]triazin-4-yl)amino)methyl)phenyl)carbamate |
| (R)-N-(2-((1H-pyrazol-1-yl)methyl)benzyl)-8-isopropyl-2-(piperidin-3-yloxy)pyrazolo[1,5-a][1,3,5]triazin-4-amine |
| (R)-N-(2,5-dichlorobenzyl)-8-isopropyl-2-(piperidin-3-yloxy)pyrazolo[1,5-a][1,3,5]triazin-4-amine |
| (R)-8-isopropyl-2-(piperidin-3-yloxy)-N-(2-(pyrrolidin-1-yl)benzyl)pyrazolo[1,5-a][1,3,5]triazin-4-amine |
| (R)-8-isopropyl-N-(2-(piperidin-1-yl)benzyl)-2-(piperidin-3-yloxy)pyrazolo[1,5-a][1,3,5]triazin-4-amine |
| azetidin-3-yl (2-((4-((2-(1H-pyrazol-1-yl)benzyl)amino)-8-isopropylpyrazolo[1,5-a][1,3,5]triazin-2-yl)oxy)ethyl)(methyl)carbamate |
| N-(2-((4-((2-(1H-pyrazol-1-yl)benzyl)amino)-8-isopropylpyrazolo[1,5-a][1,3,5]triazin-2-yl)oxy)ethyl)-3-(dimethylamino)-N-methylpropane-1-sulfonamide |
| N-(2-((4-((2-(1H-pyrazol-1-yl)benzyl)amino)-8-isopropylpyrazolo[1,5-a][1,3,5]triazin-2-yl)oxy)ethyl)-N-methylpiperidine-4-sulfonamide |
| 2-((4-((2-(1H-pyrazol-1-yl)benzyl)amino)-8-isopropylpyrazolo[1,5-a][1,3,5]triazin-2-yl)oxy)ethyl azetidin-3-ylcarbamate |
| 2-((4-((2-(1H-pyrazol-1-yl)benzyl)amino)-8-isopropylpyrazolo[1,5-a][1,3,5]triazin-2-yl)oxy)-N-(pyrrolidin-3-yl)ethanesulfonamide |
| N-(2-(1H-pyrazol-1-yl)benzyl)-2-(8-azabicyclo[3.2.1]octan-3-yloxy)-8-isopropylpyrazolo[1,5-a][1,3,5]triazin-4-amine |
| N-(2-(1H-pyrazol-1-yl)benzyl)-2-(2-azaspiro[3.3]heptan-5-yloxy)-8-isopropylpyrazolo[1,5-a][1,3,5]triazin-4-amine |
| N-(2-(1H-pyrazol-1-yl)benzyl)-2-((4-aminocyclohexyl)oxy)-8-isopropylpyrazolo[1,5-a][1,3,5]triazin-4-amine |
| (R)-N-(2-cyclobutylbenzyl)-8-isopropyl-2-(piperidin-3-yloxy)pyrazolo[1,5-a][1,3,5]triazin-4-amine |
| (R)-N-(2-cyclopentylbenzyl)-8-isopropyl-2-(piperidin-3-yloxy)pyrazolo[1,5-a][1,3,5]triazin-4-amine |
| N-(2-cyclopropylbenzyl)-8-isopropyl-2-(piperidin-3-yloxy)pyrazolo[1,5-a][1,3,5]triazin-4-amine |

TABLE 1-continued

| compound name |
|---|
| (R)-N-(2-cyclohexylbenzyl)-8-isopropyl-2-(piperidin-3-yloxy)pyrazolo[1,5-a][1,3,5]triazin-4-amine |
| (R)-2-(((8-isopropyl-2-(piperidin-3-yloxy)pyrazolo[1,5-a][1,3,5]triazin-4-yl)amino)methyl)phenyl acetate |
| (R)-2-(((8-isopropyl-2-(piperidin-3-yloxy)pyrazolo[1,5-a][1,3,5]triazin-4-yl)amino)methyl)phenyl ethylcarbamate |
| (R)-2-(((8-isopropyl-2-(piperidin-3-yloxy)pyrazolo[1,5-a][1,3,5]triazin-4-yl)amino)methyl)phenyl methanesulfonate |
| 2-(((8-isopropyl-2-((R)-piperidin-3-yloxy)pyrazolo[1,5-a][1,3,5]triazin-4-yl)amino)methyl)phenyl 2-methylpropane-2-sulfinate |
| (R)-isobutyl (2-(((8-isopropyl-2-(piperidin-3-yloxy)pyrazolo[1,5-a][1,3,5]triazin-4-yl)amino)methyl)phenyl) carbonate |
| (R)-2-(((8-isopropyl-2-(piperidin-3-yloxy)pyrazolo[1,5-a][1,3,5]triazin-4-yl)amino)methyl)phenol |
| (R)-8-isopropyl-N-(2-(methylsulfonyl)benzyl)-2-(piperidin-3-yloxy)pyrazolo[1,5-a][1,3,5]triazin-4-amine |
| 8-isopropyl-N-(2-(methylsulfinyl)benzyl)-2-((R)-piperidin-3-yloxy)pyrazolo[1,5-a][1,3,5]triazin-4-amine |
| N-(2-(cyclopentylsulfinyl)benzyl)-8-isopropyl-2-((R)-piperidin-3-yloxy)pyrazolo[1,5-a][1,3,5]triazin-4-amine |
| N4-(2-(1H-pyrazol-1-yl)benzyl)-N2-(3-aminopropyl)-8-isopropylpyrazolo[1,5-a][1,3,5]triazine-2,4-diamine |
| N4-(2-(1H-pyrazol-1-yl)benzyl)-8-isopropyl-N2-(2-(pyrrolidin-1-yl)ethyl)pyrazolo[1,5-a][1,3,5]triazine-2,4-diamine |
| N-(2-(1H-pyrazol-1-yl)benzyl)-2-(3-(3,3-difluoropyrrolidin-1-yl)azetidin-1-yl)-8-isopropylpyrazolo[1,5-a][1,3,5]triazin-4-amine |
| N4-(2-(1H-pyrazol-1-yl)benzyl)-8-isopropyl-N2-methyl-N2-(2-morpholinoethyl)pyrazolo[1,5-a][1,3,5]triazine-2,4-diamine |
| N4-(2-(1H-pyrazol-1-yl)benzyl)-8-isopropyl-N2-(pyrrolidin-3-yl)pyrazolo[1,5-a][1,3,5]triazine-2,4-diamine |
| N4-(2-(1H-pyrazol-1-yl)benzyl)-8-isopropyl-N2-(3-morpholinopropyl)pyrazolo[1,5-a][1,3,5]triazine-2,4-diamine |
| N4-(2-(1H-pyrazol-1-yl)benzyl)-8-isopropyl-N2-methyl-N2-(2-(pyrrolidin-1-yl)ethyl)pyrazolo[1,5-a][1,3,5]triazine-2,4-diamine |
| N4-(2-(1H-pyrazol-1-yl)benzyl)-8-isopropyl-N2-(2-morpholinoethyl)pyrazolo[1,5-a][1,3,5]triazine-2,4-diamine |
| 1-(1-(4-((2-(1H-pyrazol-1-yl)benzyl)amino)-8-isopropylpyrazolo[1,5-a][1,3,5]triazin-2-yl)azetidin-3-yl)pyrrolidin-2-one |
| N4-(2-(1H-pyrazol-1-yl)benzyl)-N2-(2-(2-aminoethoxy)ethyl)-8-isopropylpyrazolo[1,5-a][1,3,5]triazine-2,4-diamine |
| N4-(2-(1H-pyrazol-1-yl)benzyl)-8-isopropyl-N2-methyl-N2-(3-(piperidin-1-yl)propyl)pyrazolo[1,5-a][1,3,5]triazine-2,4-diamine |
| N-(2-(1H-pyrazol-1-yl)benzyl)-2-(hexahydropyrrolo[3,4-b]pyrrol-5(1H)-yl)-8-isopropylpyrazolo[1,5-a][1,3,5]triazin-4-amine |
| N4-(2-(1H-pyrazol-1-yl)benzyl)-N2-(2-aminoethyl)-8-isopropylpyrazolo[1,5-a][1,3,5]triazine-2,4-diamine |
| N4-(2-(1H-pyrazol-1-yl)benzyl)-8-isopropyl-N2-(pyrrolidin-3-ylmethyl)pyrazolo[1,5-a][1,3,5]triazine-2,4-diamine |
| N-(2-(1H-pyrazol-1-yl)benzyl)-2-(3-aminopiperidin-1-yl)-8-isopropylpyrazolo[1,5-a][1,3,5]triazin-4-amine |
| N-(2-(1H-pyrazol-1-yl)benzyl)-2-(3-aminopyrrolidin-1-yl)-8-isopropylpyrazolo[1,5-a][1,3,5]triazin-4-amine |
| methyl 2-((4-((2-(1H-pyrazol-1-yl)benzyl)amino)-8-isopropylpyrazolo[1,5-a][1,3,5]triazin-2-yl)amino)-3-aminopropanoate |
| N4-(2-(1H-pyrazol-1-yl)benzyl)-N2-(2-amino-1-phenylethyl)-8-isopropylpyrazolo[1,5-a][1,3,5]triazine-2,4-diamine |
| N4-(2-(1H-pyrazol-1-yl)benzyl)-N2-(azetidin-3-ylmethyl)-8-isopropyl-N2-methylpyrazolo[1,5-a][1,3,5]triazine-2,4-diamine |
| N4-(2-(1H-pyrazol-1-yl)benzyl)-8-isopropyl-N2-methyl-N2-(2-morpholinoethyl)pyrazolo[1,5-a][1,3,5]triazine-2,4-diamine |
| N-(2-(1H-pyrazol-1-yl)benzyl)-2-(4-aminopiperidin-1-yl)-8-isopropylpyrazolo[1,5-a][1,3,5]triazin-4-amine |
| N4-(2-(1H-pyrazol-1-yl)benzyl)-N2-(4-aminocyclohexyl)-8-isopropylpyrazolo[1,5-a][1,3,5]triazine-2,4-diamine |
| N-(2-(1H-pyrazol-1-yl)benzyl)-8-isopropyl-2-((R)-((R)-piperidin-3-yl)sulfinyl)pyrazolo[1,5-a][1,3,5]triazin-4-amine |
| N-(2-(1H-pyrazol-1-yl)benzyl)-8-isopropyl-2-(piperidin-4-ylsulfonyl)pyrazolo[1,5-a][1,3,5]triazin-4-amine |
| (R)-N-(2-(1H-pyrazol-1-yl)benzyl)-8-isopropyl-2-(piperidin-3-ylthio)pyrazolo[1,5-a][1,3,5]triazin-4-amine |
| N-(2-(1H-pyrazol-1-yl)benzyl)-8-isopropyl-2-(piperidin-4-ylthio)pyrazolo[1,5-a][1,3,5]triazin-4-amine |
| (4-((2-(1H-pyrazol-1-yl)benzyl)amino)-8-isopropylpyrazolo[1,5-a][1,3,5]triazin-2-yl)(2,6-diazaspiro[3.3]heptan-2-yl)methanone |
| 4-((2-(1H-pyrazol-1-yl)benzyl)amino)-8-isopropyl-N-methyl-N-(2-morpholinoethyl)pyrazolo[1,5-a][1,3,5]triazine-2-carboxamide |
| 4-((2-(1H-pyrazol-1-yl)benzyl)amino)-8-isopropyl-N-methyl-N-(2-(pyrrolidin-1-yl)ethyl)pyrazolo[1,5-a][1,3,5]triazine-2-carboxamide |

TABLE 1-continued

| compound name |
|---|
| (4-((2-(1H-pyrazol-1-yl)benzyl)amino)-8-isopropylpyrazolo[1,5-a][1,3,5]triazin-2-yl)(piperazin-1-yl)methanone |
| 4-((2-(1H-pyrazol-1-yl)benzyl)amino)-N-(3-aminopropyl)-8-isopropylpyrazolo[1,5-a][1,3,5]triazine-2-carboxamide |
| (4-((2-(1H-pyrazol-1-yl)benzyl)amino)-8-isopropylpyrazolo[1,5-a][1,3,5]triazin-2-yl)(4-aminopiperidin-1-yl)methanone |
| N1-((4-((2-(1H-pyrazol-1-yl)benzyl)amino)-8-isopropylpyrazolo[1,5-a][1,3,5]triazin-2-yl)methyl)ethane-1,2-diamine |
| N-(2-(1H-pyrazol-1-yl)benzyl)-8-isopropyl-2-(((3-morpholinopropyl)amino)methyl)pyrazolo[1,5-a][1,3,5]triazin-4-amine |
| N-(2-(1H-pyrazol-1-yl)benzyl)-8-isopropyl-2-((methyl(2-(pyrrolidin-1-yl)ethyl)amino)methyl)pyrazolo[1,5-a][1,3,5]triazin-4-amine |
| N-(2-(1H-pyrazol-1-yl)benzyl)-8-isopropyl-2-(((2-(pyrrolidin-1-yl)ethyl)amino)methyl)pyrazolo[1,5-a][1,3,5]triazin-4-amine |
| N-(2-(1H-pyrazol-1-yl)benzyl)-8-isopropyl-2-(((2-morpholinoethyl)amino)methyl)pyrazolo[1,5-a][1,3,5]triazin-4-amine |
| N-(2-(1H-pyrazol-1-yl)benzyl)-8-isopropyl-2-((methyl(3-(piperidin-1-yl)propyl)amino)methyl)pyrazolo[1,5-a][1,3,5]triazin-4-amine |
| N-(2-(1H-pyrazol-1-yl)benzyl)-2-((3-(3,3-difluoropyrrolidin-1-yl)azetidin-1-yl)methyl)-8-isopropylpyrazolo[1,5-a][1,3,5]triazin-4-amine |
| 1-(1-((4-((2-(1H-pyrazol-1-yl)benzyl)amino)-8-isopropylpyrazolo[1,5-a][1,3,5]triazin-2-yl)methyl)azetidin-3-yl)pyrrolidin-2-one |
| N-(2-(1H-pyrazol-1-yl)benzyl)-8-isopropyl-2-((4-(2-methoxyethyl)piperazin-1-yl)methyl)pyrazolo[1,5-a][1,3,5]triazin-4-amine |
| N-(2-(1H-pyrazol-1-yl)benzyl)-8-isopropyl-2-((pyrrolidin-3-ylamino)methyl)pyrazolo[1,5-a][1,3,5]triazin-4-amine |
| N-(2-(1H-pyrazol-1-yl)benzyl)-8-isopropyl-2-(piperazin-1-ylmethyl)pyrazolo[1,5-a][1,3,5]triazin-4-amine |
| N-(2-(1H-pyrazol-1-yl)benzyl)-2-(((azetidin-3-ylmethyl)(methyl)amino)methyl)-8-isopropylpyrazolo[1,5-a][1,3,5]triazin-4-amine |
| N-(2-(2-(((4-((2-(1H-pyrazol-1-yl)benzyl)amino)-8-isopropylpyrazolo[1,5-a][1,3,5]triazin-2-yl)methyl)amino)ethoxy)ethyl)-2-(pyrrolidin-1-yl)acetamide |
| N-(2-(1H-pyrazol-1-yl)benzyl)-2-((4-aminopiperidin-1-yl)methyl)-8-isopropylpyrazolo[1,5-a][1,3,5]triazin-4-amine |
| 1-methylpyrrolidin-3-yl 4-((2-(1H-pyrazol-1-yl)benzyl) amino)-8-isopropylpyrazolo[1,5-a][1,3,5]triazine-2-carboxylate |
| 8-isopropyl-N-(2-(S-methylsulfonimidoyl)benzyl)-2-((R)-piperidin-3-yloxy)pyrazolo[1,5-a][1,3,5]triazin-4-amine |
| 4-((2-(1H-pyrazol-1-yl)benzyl)amino)-8-isopropylpyrazolo [1,5-a][1,3,5]triazin-2-ol |
| N-(2-(1H-pyrazol-1-yl)benzyl)-2-bromo-8-isopropylpyrazolo [1,5-a][1,3,5]triazin-4-amine |
| tert-butyl 2-(1H-pyrazol-1-yl)benzyl(2-bromo-8-isopropyl pyrazolo[1,5-a][1,3,5]triazin-4-yl)carbamate |
| N-(2-(1H-pyrazol-1-yl)benzyl)-8-isopropyl-2-(piperidin-3-ylmethyl)pyrazolo[1,5-a][1,3,5]triazin-4-amine |
| N4-(2-(1H-pyrazol-1-yl)benzyl)-8-isopropyl-N2-methyl-N2-(2-morpholinoethyl)pyrazolo[1,5-a][1,3,5]triazine-2,4-diamine |
| N-(2-(1H-pyrazol-1-yl)benzyl)-2-(4-aminopiperidin-1-yl)-8-isopropylpyrazolo[1,5-a][1,3,5]triazin-4-amine |
| N4-(2-(1H-pyrazol-1-yl)benzyl)-N2-(4-aminocyclohexyl)-8-isopropylpyrazolo[1,5-a][1,3,5]triazine-2,4-diamine |
| N-(2-(2-((4-((2-(1H-pyrazol-1-yl)benzyl)amino)-8-isopropylpyrazolo[1,5-a][1,3,5]triazin-2-yl)amino)ethoxy)ethyl)-2-(pyrrolidin-1-yl)acetamide |
| N4-(2-(1H-pyrazol-1-yl)benzyl)-8-isopropyl-N2-(2-(piperazin-1-yl)ethyl)pyrazolo[1,5-a][1,3,5]triazine-2,4-diamine |
| N-(2-(1H-pyrazol-1-yl)benzyl)-2-(azetidin-3-yloxy)-8-isopropylpyrazolo[1,5-a][1,3,5]triazin-4-amine |

The compounds of the present invention may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, trifluoroacetic acid, and other mineral or carboxylic acids well known to those skilled in the art. The salts are prepared by contacting the free base form with a sufficient amount of the desired acid to produce a salt in the conventional manner.

In the case the inventive compounds bear acidic groups, salts could also be formed with inorganic or organic bases. Examples for suitable inorganic or organic bases are, for example, NaOH, KOH, NH$_4$OH, tetraalkylammonium hydroxide, lysine or arginine and the like. Salts may be prepared in a conventional manner using methods well known in the art, for example by treatment of a solution of the compound of the general formula (I) with a solution of an acid, selected out of the group mentioned above.

Synthesis of Compounds

The inventive pyrazolo[1,5-a][1,3,5]triazines according to the present invention can be prepared by methods known to one skilled in the art. The synthesis is preferably carried out according to the general synthetic sequences, shown in schemes 3 and 4. This enables those skilled in the art to introduce to intermediate (IV) any suitable amine $R^2$—$NH_2$ that is commercially available or can be synthesized according to or in analogy to literature procedures. Further, after introduction of a methylsulfoxide leaving group by oxidation of the thioatom in (V) compounds with this formed

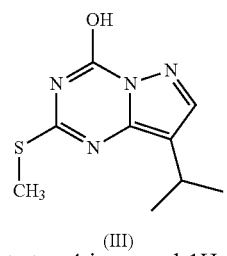

(III)

As depicted in scheme 1 in a first step 4-isopropyl-1H-pyrazol-5-amine was reacted with ethoxycarbonyl isothiocyanate to give a thiourea derivative that was cyclized to 2-mercaptopyrazolo[1,5-a][1,3,5]triazin-4-ol (II). The thiol (II) is then methylated by standard procedure to yield intermediate methylthioether (III).

scheme 2

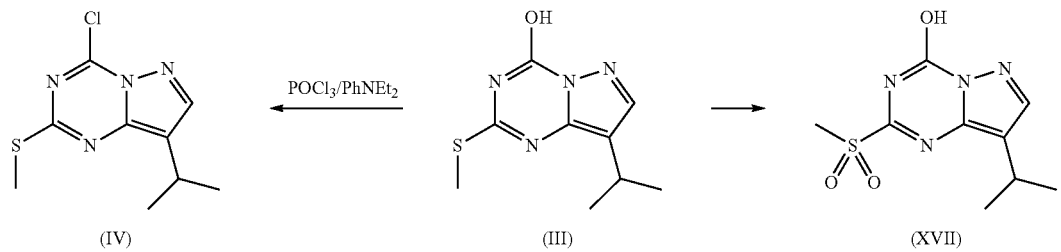

(IV)　(III)　(XVII)

methylsulfoxide group provide the basis to react with many classes of C-, S-, N- or O-nucleophiles that are available either commercially or by synthetic means. Therefore, the synthetic approach according to schemes 3 and 4 enables the synthesis of any of the pyrazolo[1,5-a][1,3,5]triazines disclosed in the present invention. However a person skilled in the art can also prepare these compounds following to other synthetic sequences.

In the following schemes occurring abbreviations mean DCM (dichloromethane); DIPEA (N-ethyl-N,N-diisopropylamine); DMF (dimethylformamide); DMSO (dimethyl sulfoxide); EtOAc (ethyl acetate); EtOH (ethanol); mCPBA (3-chlorobenzoperoxoic acid); MeOH (methanol); MeCN (acetonitrile); TFA (trifluoroacetic acid), PhNEt$_2$ (dimethyl phenyl amine), Boc (tert-butyloxycarbonyl), Ph (phenyl), Ts (tosylate, p-toluenesulfonyl group), Mes (mesylate, methanesulfonyl group).

Starting from (III) two further intermediate compounds can be derived as depicted in scheme 2. Firstly, after said methylation of the mercapto group in (II) 4-chloro-2-(methylthio)pyrazolo[1,5-a][1,3,5]triazine (IV) was obtained by chlorination of (III) with phosphoryl trichloride in the presence of N,N-diethylaniline. Secondly, by oxidation of (III) the sulfone derivative (XVII) can be synthesized. Both, intermediate (IV) and (XVII) can be used for synthesis of the compounds of the present invention of the general formula (I) via various synthetic routes.

scheme 3

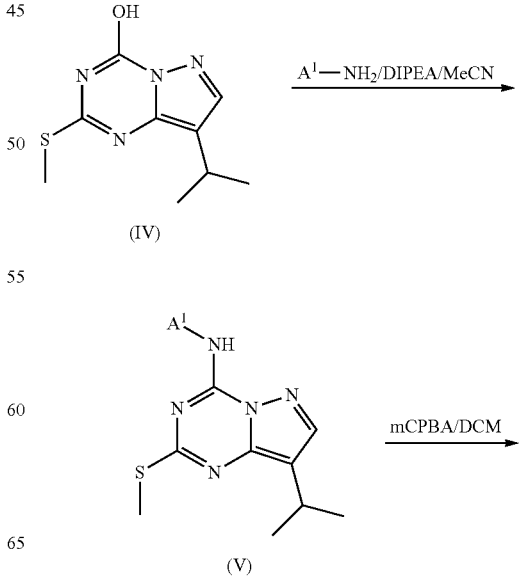

scheme 1

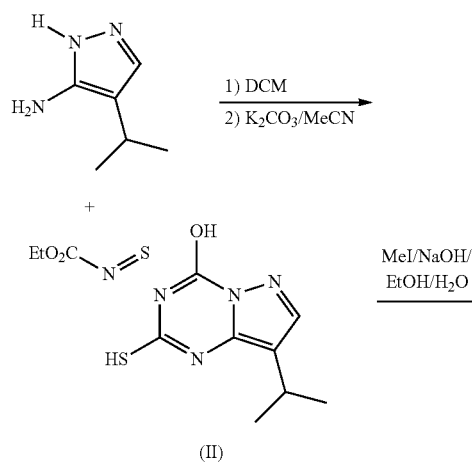

-continued

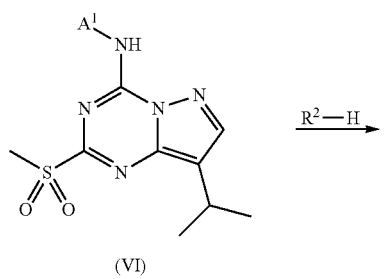

(VI)

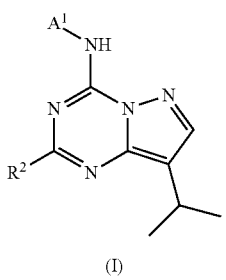

(I)

The residue $A^1$ can be introduced by nuclephilic substitution reaction of (IV) with amines of the formula $A^1NH_2$, and DIPEA as a base yielding 4-amino-2-(methylthio)pyrazolo[1,5-a][1,3,5]triazines (V) as shown in scheme 3, wherein $A^1$ represents the upper benzyl building block of the compounds of the general formula (I)

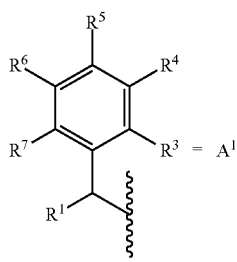

wherein the $R^1$, $R^3$ to $R^7$ represent the residues as defined herein.

Compounds (V) were then oxidized with 3-chlorobenzoperoxoic acid to 4-amino-2-(methylsulfonyl)pyrazolo[1,5-a][1,3,5]triazines (VI) that could be substituted by reaction with compounds of the general formula $R^2$—H yielding the compounds of the present invention of the general formula (I), wherein $R^2$ and $A^1$ represent residues as defined herein.

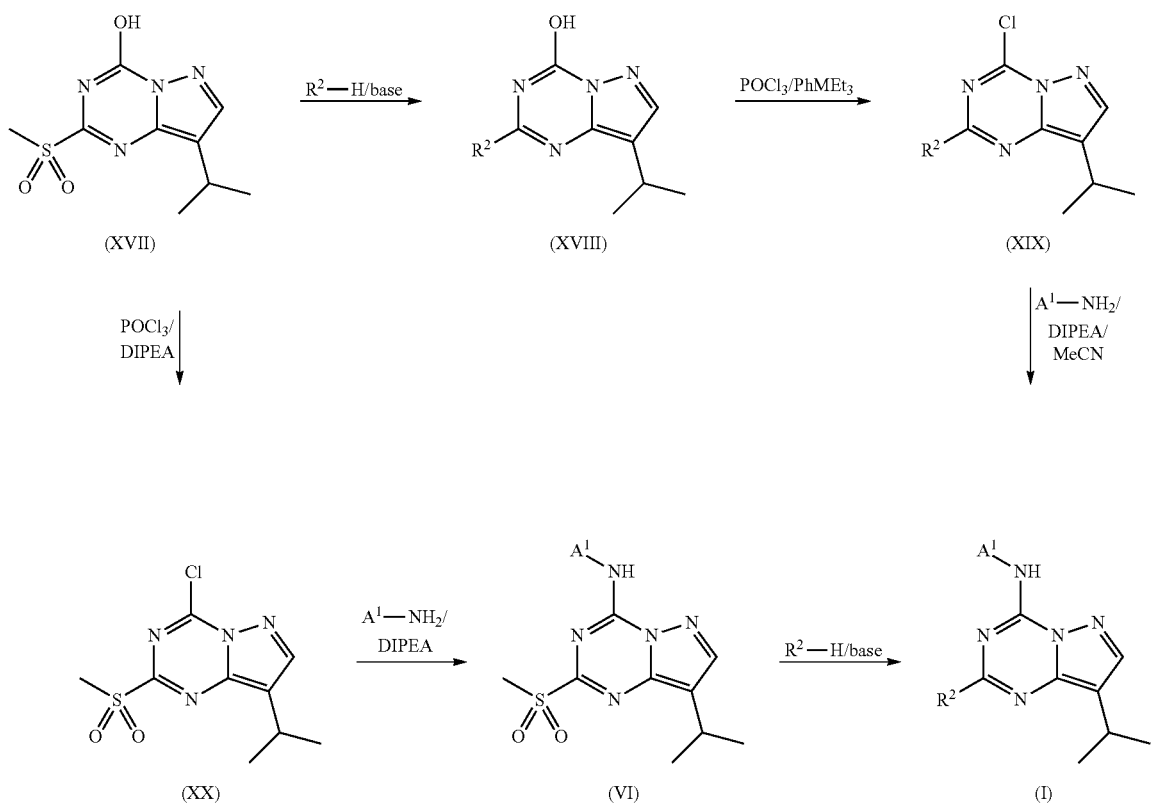

scheme 4

An alternative synthesis to the route outlined in scheme 3 is depicted in scheme 4 starting from intermediate (XVII). As one synthetic option the reaction of a nucleophile ($R^2$—H) for introduction of the residue $R^2$ takes place before the incorporation of the amine $A^1NH_2$ (upper pathway). In addition as a second synthetic option it is possible to obtain chloride (XX) and subsequently substitute said chloride before the sulfone is replaced by $R^2$. The synthetic approach for the compounds of the general formula (I) according to scheme 4 has the advantage that the oxidation step for generating a sulfone from a thioether (here (III) converts to (XVII)) takes place before the introduction of the upper building block $A^1$ by reaction with the amine $A^1NH_2$. Accordingly, moieties $A^1$ being sensitive to oxidative reaction conditions can also be introduced, thereby broadening the scope of the compounds of the present invention significantly.

Conveniently, many ortho-substituted benzylamines $A^1NH_2$ as these are useful starting materials for the synthesis of the compounds of the general formula (I) are commercially available. Additional derivatives can be prepared by a person skilled in the art following known synthetic procedures that are disclosed in patent or non-patent literature.

In principle, following any approach for the preparation of the compounds with the general formula $A^1$-$NH_2$ and thereby for the compounds of the present invention with the general formula (I) two aspects have to be considered. Firstly, the generation of the benzylic amino group in $A^1NH_2$ and secondly, the introduction of the desired substitution pattern as represented by $R^3$-$R^7$.

Commonly used syntheses for said aminomethylphenyl derivatives are shown in scheme 5. Suitable starting materials include aryl halogenides, sulfonates, nitriles, oximes, halogenomethans and related precursors.

Depending on the target molecule with its specific substitution pattern (as represented by $R^3$-$R^7$) a person skilled in the art of organic chemistry will plan the synthetic approach for each benzylamine (XIII) individually and decide at which point the aminomethyl group and their related precursors will be synthesized. Also, scheme 5 shows merely exemplary synthetic methods for the preparation of compounds (XIII) which is only a specific embodiment of the moiety $A^1$, wherein $R^1$ is hydrogen. However, the person skilled in the art will understand that the below synthetic routes are also suitable for the preparation of amines $A^1$-$NH_2$ with any residue $R^1$ as defined herein.

scheme 5

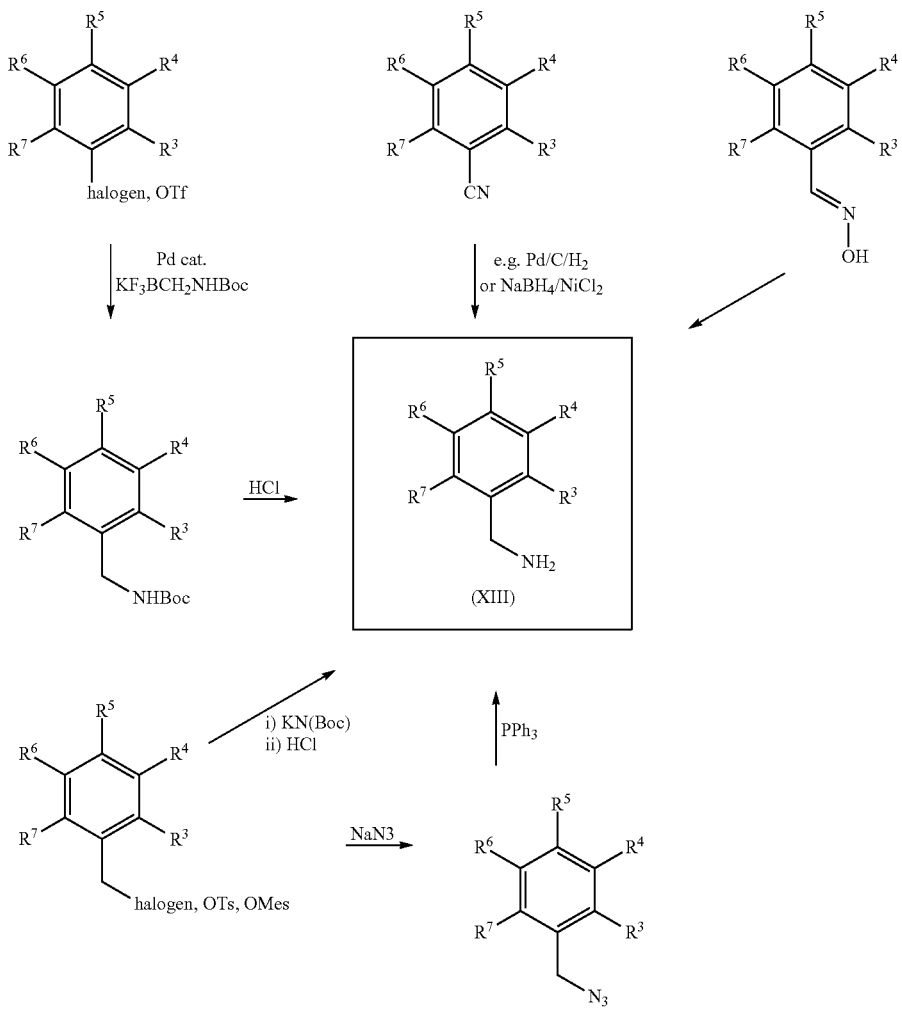

According to the present invention ortho-substituent $R^3$ in compounds of the general formula (I) is different from hydrogen. Starting from a wide range of commercially available materials many synthetic approaches can be applied to introduce the moieties at the respective position to yield compounds as defined in claim 1 and are well known to a person skilled in the art of synthesis.

For example, $R^3$ in formula (I) can derive from a nucleophile. In such a case it can be introduced for example via reaction with a 2-fluorobenzonitrile derivative (XIV, scheme 6). Subsequently, ortho-substituted benzylamines (XVI) can be obtained by reduction of the corresponding nitrile (XV). Examples for nucleophiles represented by NuH are alcohols, amines, thiols or 5-membered heteroaromates such as pyrazole or triazole derivatives. If necessary, compounds of formula (XV) or (XVI) can be further modified in various positions before or after being used as building block ($A^1$-$NH_2$) according to schemes 3 and 4.

scheme 6

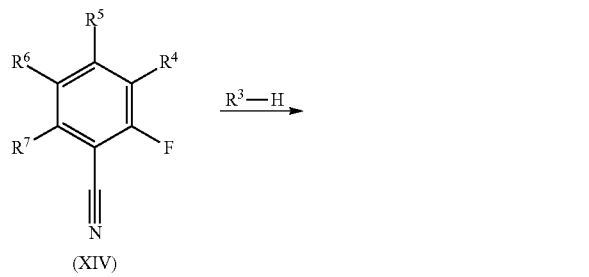

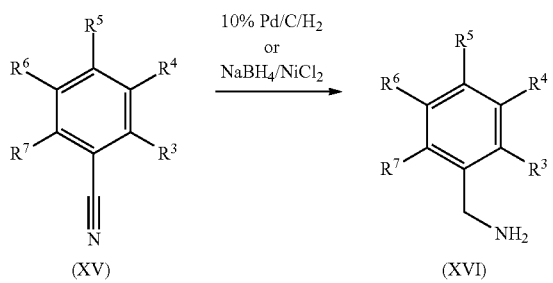

Other examples for aromatic substitutions of aryl halides, triflates or boronates are copper mediated Ullman-type or palladium catalyzed Buchwald-Hartwig reactions with N-, O- or S-nucleophiles.

Further, there is also a huge number of reactions that enable a person skilled in the art of organic chemistry attaching $R^3$ in compounds of the general formula (I) via a carbon-carbon bond. These reactions include but are not limited to catalyzed (e.g. by palladium, nickel, copper or iron species) cross-coupling reactions of an appropriate aryl halides or sulfonate with an alkyl, aryl or heteroaryl boron-, zinc-, magnesium-, tin- or silicon-reagent. Alternatively, for introduction of the substituent $R^3$ it is possible to transform an aryl halide or sulfonate (e.g. triflate) into one of the above mentioned metal species that can be used in a cross-coupling reaction with for example alkyl, aryl or heteroaryl halide $R^3$—X. Further on scheme 3, synthetic options are presented for the rather general introduction of the residue $R^2$ in the following schemes 7-9:

scheme 7

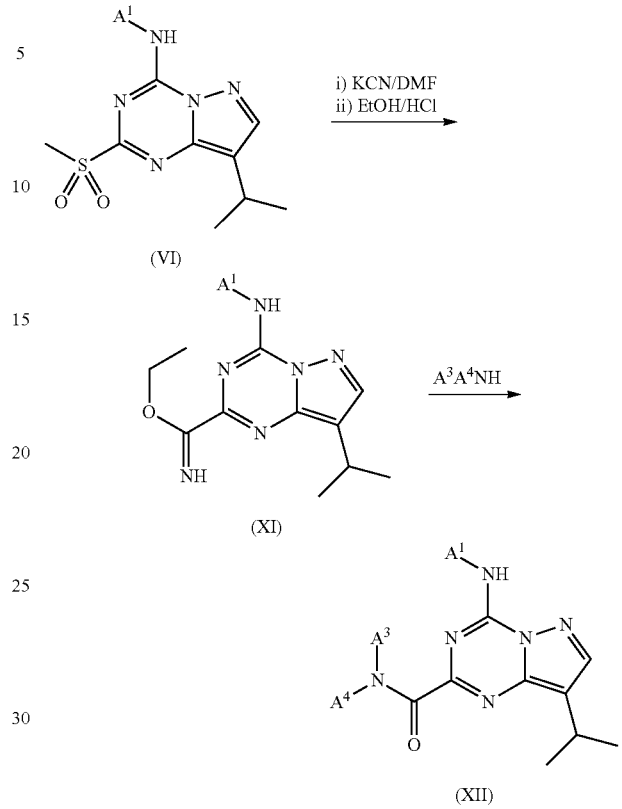

For example intermediate (VI) can be reacted with different nucleophiles to give derivatives (VII)-(IX) that all bear different residues $A^2$ to $A^7$ at the afore-mentioned $R^2$ position in (I) in scheme 3.

In one embodiment in the synthesis of the compounds of the present invention amides of formula (XII) were synthesized via introduction of a cyanide group, transforming the resulting nitriles into imidoesters (XI) which underwent a subsequent nucleophilic attack with primary or secondary amines $A^3A^4$NH and hydrolysis to yield said related amides (scheme 7). In such embodiment the residue $R^2$ is represented by the amide group —CO-$NA^3A^4$. For example, for $A^3$ being $R^{15}$ and $A^4$ being $R^8$ the case $R^2$ being Q-$R^8$ with Q=—CO—$NR^{15}$ is realized. Examples of the residue —CO-$NA^3A^4$ as represented by $R^2$ are -Q-$R^8$ with Q=—CO—, —CO—NH—$(CH_2)_n$—$NH_2$, —CO—NH—$(CH_2)_n$—$R^9$, —CO—$NR^{10}$—$(CH_2)_n$—$R^9$, —$(CH_2)_a$-$(Q)_b$-$(CH_2)_c$-$(G^1)_d$-$(CH_2)_e$-$(G^2)_f$-$(CH_2)_g$-$R^8$, —$(CH_2)_a$-$(Q)_b$-$(CH_2)_c$-$(G^1)_d$-$(CH_2)_e$-$(G^2)_f$-$CH_2$—$R^9$ which can be synthesized according to the synthetic pathway as depicted in scheme 7.

Specifically, for $R^2$=-Q-$R^8$ and Q=—CO—$NR^{15}$—, then $A^3$=$R^{15}$ and $A^4$ represents $R^8$. For $R^2$=—CO—NH—$(CH_2)_n$—$NH_2$, —CO—NH—$(CH_2)_n$—$R^9$, $A^3$=H and $A^4$ represents $(CH_2)_n$—$NH_2$, or $(CH_2)_n$—$R^9$. For $R^2$=—CO—$NR^{10}$—$(CH_2)_n$—$R^9$, $A^3$=$R^{10}$ and $A^4$ represents $(CH_2)_n$—$R^9$. For $R^2$=—$(CH_2)_a$-$(Q)_b$-$(CH_2)_c$-$(G^1)_d$-$(CH_2)_e$-$(G^2)_f$-$(CH_2)_g$—$R^8$, a=0, b=1, and Q=—CO—$NR^{15}$—, then $A^3$=$R^{15}$ and $A^4$ represents $(CH_2)_c$-$(G^1)_d$-$(CH_2)_e$-$(G^2)_f$-$(CH_2)_g$—$R^8$, wherein $G^1$, $G^2$, c, d, e, f, g, n, $R^8$ and $R^9$ are as defined herein.

For $R^2$=—$(CH_2)_a$-$(Q)_b$-$(CH_2)_c$-$(G^1)_d$-$(CH_2)_e$-$(G^2)_f$-$CH_2$—$R^9$, a=0, b=1, and Q=—CO—$NR^{15}$—, then $A^3$=$R^{15}$ and $A^4$ represents $(CH_2)_c$-$(G^1)_d$-$(CH_2)_e$-$(G^2)_f$-$CH_2$—$R^9$, wherein $G^1$, $G^2$, c, d, e, f, g, n, $R^8$ and $R^9$ are as defined herein.

scheme 8

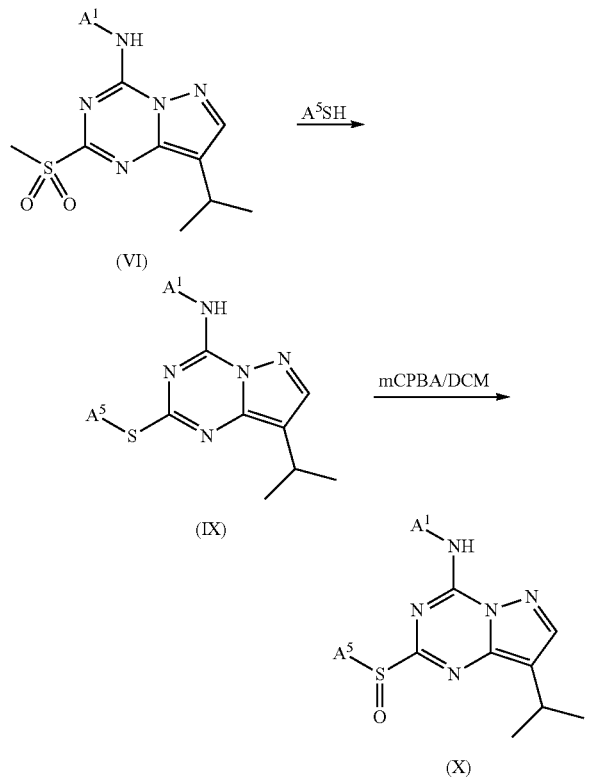

(IX)

(X)

In another embodiment it is possible to introduce the moiety $A^5$ by conversion of a sulfone (e.g. (VI)) with the mercaptan $A^5SH$ furnishing the thioether (IX) which can optionally be oxidized to the sulfoxide (X) as shown in scheme 8. By introduction of $A^5$ via reaction with $A^5SH$ examples for —S-$A^5$ or —SO-$A^5$ as represented by $R^2$ are -Q-$R^8$ with Q=—S— or —SO—, -Q-$(CH_2)_n$—$R^8$ with Q=—S— or —SO—, -Q-$(CH_2)_n$—$R^9$ with Q=—S— or —SO—, —SO—$R^9$, —$(CH_2)_a$-$(Q)_b$-$(CH_2)_c$-$(G^1)_d$-$(CH_2)_e$-$(G^2)_f$-$(CH_2)_g$—$R^8$, —$(CH_2)_a$-$(Q)_b$-$(CH_2)_c$-$(G^1)_d$-$(CH_2)_e$-$(G^2)_f$-$CH_2$—$R^9$ are obtainable, wherein Q can be —S— or —SO—, a=0, b=1 and G, c, d, e, f, g, n, $R^8$ and $R^9$ are as defined herein. Therefore, $A^5$ can be selected from the group consisting of —$R^8$, —$(CH_2)_n$—$R^8$, —$(CH_2)_n$—$R^9$, —$R^9$, —$(CH_2)_c$-$(G^1)_d$-$(CH_2)_e$-$(G^2)_f$-$(CH_2)_g$—$R^8$ and —$(CH_2)_c$-$(G^1)_d$-$(CH_2)_e$-$(G^2)_f$-$CH_2$—$R^9$, wherein G, c, d, e, f, g, n, $R^8$ and $R^9$ are as defined herein for the respective examples of $R^2$ as specified above for scheme 8.

scheme 9

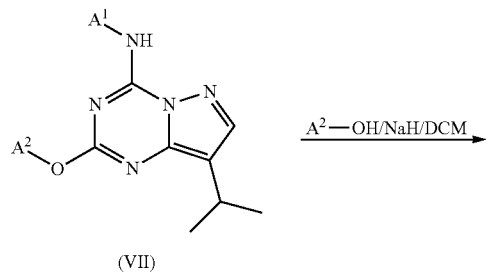

(VII)

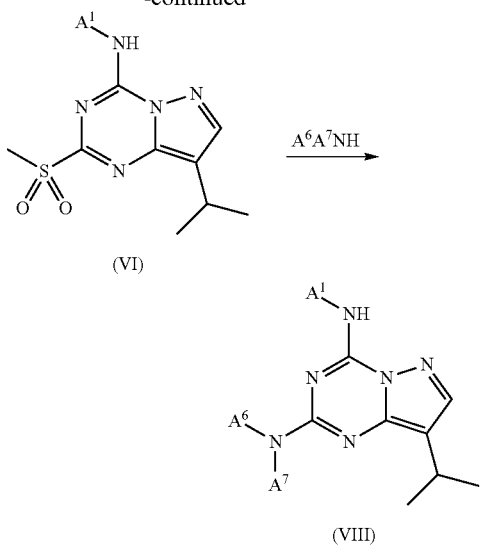

(VI)

(VIII)

In another embodiment it is possible to introduce the moiety $A^2$ by conversion of a sulfone (e.g. (VI)) with the alcohol $A^2OH$ furnishing the ether (VII). By introduction of $A^2$ via reaction with $A^2OH$ examples for —O-$A^2$ as represented by $R^2$ are -Q-$R^8$ with Q=—O—, -Q-$(CH_2)_n$—$R^8$ with Q=—O—, -Q-$(CH_2)_n$—$R^9$ with Q=—O—, —$(CH_2)_a$-$(Q)_b$-$(CH_2)_c$-$(G^1)_d$-$(CH_2)_e$-$(G^2)_f$-$(CH_2)_g$—$R^8$, —$(CH_2)_a$-$(Q)_b$-$(CH_2)_c$-$(G^1)_d$-$(CH_2)_e$-$(G^2)_f$-$CH_2$—$R^9$ are obtainable, wherein Q can be —O—, a=0, b=1 and G, c, d, e, f, g, n, $R^8$ and $R^9$ are as defined herein. Therefore, $A^2$ can be selected from the group consisting of —$R^8$, —$(CH_2)_n$—$R^8$, —$(CH_2)_n$—$R^9$, —$(CH_2)_c$-$(G^1)_d$-$(CH_2)_e$-$(G^2)_f$-$(CH_2)_g$—$R^8$ and —$(CH_2)_c$-$(G^1)_d$-$(CH_2)_e$-$(G^2)_f$-$CH_2$—$R^9$, wherein G, c, d, e, f, g, n, $R^8$ and $R^9$ are as defined herein for the respective examples of $R^2$ as specified above for scheme 9.

Yet in another embodiment it is possible to introduce the moiety —$NA^6A^7$ by conversion of a sulfone (e.g. (VI)) with the amine of the formula $HNA^6A^7$ furnishing compound (VIII). By introduction of —$NA^6A^7$ via reaction with $HNA^6A^7$. Examples for —$NA^6A^7$ as represented by $R^2$ are -Q-$R^8$ with Q=—$NR^{15}$—, —$NR^{15}$—SO—, —$NR^{15}$—$SO_2$—, —$NR^{15}$—CO—, —$NR^{15}$—CO—$NR^{15}$—, —$NR^{15}$—CO—O—, -Q-$(CH_2)_n$—$R^8$ with Q=—$NR^{15}$—, —$NR^{15}$—SO—, —$NR^{15}$—$SO_2$—, —$NR^{15}$—CO—, —$NR^{15}$—CO—$NR^{15}$—, —$NR^{15}$—CO—O—, -Q-$(CH_2)_n$—$R^9$ with Q=—$NR^{15}$—, —$NR^{15}$—SO—, —$NR^{15}$—$SO_2$—, —$NR^{15}$—CO—, —$NR^{15}$—CO—$NR^{15}$—, —$NR^{15}$—CO—O—, —$(CH_2)_m$—NH—$(CH_2)_n$—$R^9$, —$(CH_2)_m$—$NR^{10}$—$(CH_2)_n$—$R^9$, —$(CH_2)_a$-$(Q)_b$-$(CH_2)_c$-$(G^1)_d$-$(CH_2)_e$-$(G^2)_f$-$(CH_2)_g$—$R^8$, —$(CH_2)_a$-$(Q)_b$-$(CH_2)_c$-$(G^1)_d$-$(CH_2)_e$-$(G^2)_f$-$CH_2$—$R^9$ are obtainable.

Specifically, for $R^2$ being -Q-$R^8$, then Q can be selected from the group consisting of —$NR^{15}$—, —$NR^{15}$—SO—, —$NR^{15}$—$SO_2$—, —$NR^{15}$—CO—, —$NR^{15}$—CO—$NR^{15}$—, —$NR^{15}$—CO—O— and —$(CH_2)_m$—$NR^{15}$— with m=0, and then $A^6$ represents $R^{15}$ and $A^7$ is selected from the group consisting of —$R^8$, —$SO_2$—$R^8$, —CO—$R^8$, —CO—$NR^{15}$—$R^8$ and —CO—O—$R^8$, wherein $R^8$ is as defined herein.

For $R^2$ being -Q-$(CH_2)_n$—$R^8$, then Q can be selected from the group consisting of —$NR^{15}$—, —$NR^{15}$—SO—, —$NR^{15}$—$SO_2$—, —$NR^{15}$—CO—, —$NR^{15}$—CO—$NR^{15}$—, —$NR^{15}$—CO—O— and —$(CH_2)_m$—$NR^{15}$— with m=0, and then $A^6$ represents $R^{15}$ and $A^7$ is selected from the group consisting of —$(CH_2)_n$—$R^8$, —$SO_2$—$(CH_2)_n$—$R^8$, —CO—$(CH_2)_n$—$R^8$, —CO—$NR^{15}$—$(CH_2)_n$—$R^8$ and —CO—O—$(CH_2)_n$—$R^8$, wherein $R^8$ is as defined herein.

For $R^2$ being -Q-$(CH_2)_n$—$R^9$, then Q can be selected from the group consisting of —$NR^{15}$—, —$NR^{15}$—SO—, —$NR^{15}$—$SO_2$—, —$NR^{15}$—CO—, —$NR^{15}$—CO—$NR^{15}$—, —$NR^{15}$—CO—O— and —$(CH_2)_m$—$NR^{15}$— with m=0, and then $A^6$ represents $R^{15}$ and $A^7$ is selected from the group consisting of —$(CH_2)_n$—$R^9$, —$SO_2$—$(CH_2)_n$—$R^9$, —CO—$(CH_2)_n$—$R^9$, —CO—$NR^{15}$—$(CH_2)_n$—$R^9$ and —CO—O—$(CH_2)_n$—$R^9$, wherein $R^9$ is as defined herein.

For $R^2$ being —$(CH_2)_m$—NH—$(CH_2)_n$—$R^9$, then m=0 and then $A^6$ represents H and $A^7$ is selected from the group consisting of —$(CH_2)_n$—$R^9$, wherein $R^9$ is as defined herein. For $R^2$ being —$(CH_2)_m$—$NR^{10}$—$(CH_2)_n$—$R^9$, then m=0 and then $A^6$ represents $R^{10}$ and $A^7$ is selected from the group consisting of —$(CH_2)_n$—$R^9$, wherein $R^9$ and $R^{10}$ are as defined herein.

For $R^2$ being —$(CH_2)_a$-$(Q)_b$-$(CH_2)_c$-$(G^1)_d$-$(CH_2)_e$-$(G^2)_f$-$(CH_2)_g$—$R^8$, then a=0 and b=1 and Q can be selected from the group consisting of —$NR^{15}$—, —$NR^{15}$—SO—, —$NR^{15}$—$SO_2$—, —$NR^{15}$—CO—, —$NR^{15}$—CO—$NR^{15}$—, —$NR^{15}$—CO—O— and —$(CH_2)_m$—$NR^{15}$— with m=0, and then $A^6$ represents $R^{15}$ and $A^7$ is selected from the group consisting of —$(CH_2)_c$-$(G^1)_d$-$(CH_2)_e$-$(G^2)_f$-$(CH_2)_g$—$R^8$, —$SO_2$—$(CH_2)_c$-$(G^1)_d$-$(CH_2)_e$-$(G^2)_f$-$(CH_2)_g$—$R^8$, —CO—$(CH_2)_c$-$(G^1)_d$-(CH 2)$_e$-$(G^2)_f$-$(CH_2)_g$—$R^8$, —CO—$NR^{15}$—$(CH_2)_c$-$(G^1)_d$-$(CH_2)_e$-$(G^2)_f$-$(CH_2)_g$—$R^8$ and —CO—O—$(CH_2)_c$-$(G^1)_d$-$(CH_2)_e$-$(G^2)_f$-$(CH_2)_g$—$R^8$, wherein c, d, e, f, g, $G^1$, $G^2$ and $R^8$ is as defined herein.

For $R^2$ being $(CH_2)_a(Q)_b(CH_2)_c(G^1)_d(CH_2)_e(G^2)_f$-$CH_2R^9$, then a=0 and b=1 and Q can be selected from the group consisting of —$NR^{15}$—, —$NR^{15}$—SO—, —$NR^{15}$—$SO_2$—, —$NR^{15}$—CO—, —$NR^{15}$—CO—$NR^{15}$—, —$NR^{15}$—CO—O— and $(CH_2)_m$—$NR^{15}$— with m=0, and then $A^6$ represents $R^{15}$ and $A^7$ is selected from the group consisting of —$(CH_2)_c$-$(G^1)_d$-$(CH_2)_e$-$(G^2)_f$-$CH_2R^9$, —$SO_2$—$(CH_2)_c$-$(G^1)_d$-$(CH_2)_e$-$(G^2)_f$-$CH_2$—$R^9$, —CO—$(CH_2)_c$-$(G^1)_d$-$(CH_2)_e$-$(G^2)_f$-$CH_2$—$R^9$, —CO—$NR^{15}$—$(CH_2)_c$-$(G^1)_d$-$(CH_2)_e$-$(G^2)_f$-$CH_2$—$R^9$ and —CO—O—$(CH_2)_c$-$(G^1)_d$-$(CH_2)_e$-$(G^2)_f$-$CH_2$—$R^9$, wherein c, d, e, f, g, $G^1$, $G^2$ and $R^8$ is as defined herein.

Several compounds of formula (I) may be derivatized by converting substituents which are attached to any position using standard reactions which are known to the person skilled in the art. For example, a nitro group can be reduced to an amino group, such an amino group can be converted to a sulfonamide by reaction with a sulfonyl chloride, to a carboxamide by reaction with a carbonyl chloride or another activated derivative of a carboxylic acid, to an urea by reaction with an isocyanate. Carbamate substituents may be cleaved to amino groups, in particular tert-butyl carbamates by reaction with acids like trifluoroacetic acid or hydrochloric acid. Formyl groups may be converted to aminomethyl groups by reaction with primary amines under conditions of a reductive amination.

Indications

In a further aspect of the present invention, the novel compounds according to the general formula (I) are used as pharmaceutically active agent.

Further aspects of the present invention relate to the use of the compounds of general formula (I) for the preparation of a pharmaceutical composition useful for prophylaxis and/or treatment of infectious diseases including opportunistic diseases, immunological diseases, autoimmune diseases, cardiovascular diseases, cell proliferative diseases, inflammation, erectile dysfunction and stroke.

Infectious Diseases Including Opportunistic Infections

In yet another aspect of the present invention, the compounds according to the general formula (I) are for the preparation of a pharmaceutical composition for the prophylaxis and/or treatment of infectious diseases, including opportunistic diseases and opportunistic infections. The term "infectious diseases" comprises infections caused by viruses, bacteria, prions, fungi, and/or parasites.

Especially, virally induced infectious diseases, including opportunistic diseases are addressed. In a preferred embodiment of this aspect, the virally induced infectious diseases, including opportunistic diseases, are caused by retroviruses, human endogenous retroviruses (HERVs), hepadnaviruses, herpesviruses, flaviviridae, and/or adenoviruses. Preferably, the retroviruses are selected from lentiviruses or oncoretroviruses, wherein the lentivirus is preferably selected from the group comprising: HIV-1, HIV-2, feline immunodeficiency virus (FIV), bovine immunodeficiency virus (BIV), sivian immunodeficiency viruses (SIVs), chimeras of HIV and SIV (SHIV), caprine arthritis encephalitis virus (CAEV), visnamaedi virus (VMV) or equine infectious anemia virus (EIAV), preferably HIV-1 and HIV-2, and the oncoretrovirus is preferably selected from HTLV-I, HTLV-II or bovine leukemia virus (BLV), preferably HTLV-I and HTLV-II.

The hepadnavirus is preferably selected from HBV, ground squirrel hepatitis virus (GSHV) or woodchuck hepatitis virus (WHV), preferably HBV, the herpesvirus is selected from the group comprising: Herpes simplex virus I (HSV I), herpes simplex virus II (HSV II), Epstein-Barr virus (EBV), varicella zoster virus (VZV), human cytomegalovirus (HCMV) or human herpesvirus 8 (HHV-8), preferably HCMV, and the flaviviridae is selected from HCV, West nile or Yellow Fever.

It is to be understood, that all the viruses mentioned above, also comprise drug resistant virus strains.

Examples of infectious diseases are AIDS, Alveolar Hydatid Disease (AHD, Echinococcosis), Amebiasis (Entamoeba histolytica Infection), Angiostrongylus Infection, Anisakiasis, Anthrax, Babesiosis (Babesia Infection), Balantidium Infection (Balantidiasis), Baylisascaris Infection (Raccoon Roundworm), Bilharzia (Schistosomiasis), Blastocystis hominis Infection (Blastomycosis), Boreliosis, Botulism, Brainerd Diarrhea, Brucellosis, BSE (Bovine Spongiform Encephalopathy), Candidiasis, Capillariasis (Capillaria Infection), CFS (Chronic Fatigue Syndrome), Chagas Disease (American Trypanosomiasis), Chickenpox (Varicella-Zoster virus), Chlamydia pneumoniae Infection, Cholera, Chronic Fatigue Syndrome, CJD (Creutzfeldt-Jakob Disease), Clonorchiasis (Clonorchis Infection), CLM (Cutaneous Larva Migrans, Hookworm Infection), Coccidioidomycosis, Conjunctivitis, Coxsackievirus A16 (Hand, Foot and Mouth Disease), Cryptococcosis, Cryptosporidium Infection (Cryptosporidiosis), Culex mosquito (Vector of West Nile Virus), Cutaneous Larva Migrans (CLM), Cyclosporiasis (Cyclospora Infection), Cysticercosis (Neurocysticercosis), Cytomegalovirus Infection, Dengue/Dengue Fever, Dipylidium Infection (Dog and Cat Flea Tapeworm), Ebola Virus Hemorrhagic Fever, Echinococcosis (Alveolar Hydatid Disease), Encephalitis, Entomoeba coli Infection, Entomoeba dispar Infection, Entomoeba hartmanni Infection, Entomoeba histolytica Infection (Amebiasis), Entomoeba polecki Infection, Enterobiasis (Pinworm Infection), Enterovirus Infection (Non-Polio), Epstein-Barr Virus Infection, Escherichia coli Infection, Foodborne Infection, Foot and mouth Disease, Fungal Dermatitis, Gastroenteritis, Group A streptococcal Disease, Group B streptococcal Disease, Hansen's Disease (Leprosy), Hantavirus Pulmonary Syndrome, Head Lice Infestation (Pediculosis), *Helicobacter pylori* Infection, Hematologic Disease, Hendra Virus Infection, Hepatitis (HCV, HBV), Herpes Zoster (Shingles), HIV Infection, Human Ehrlichiosis, Human Parainfluenza Virus Infection, Influenza, Isosporiasis (Isospora Infection), Lassa Fever, Leishmaniasis, Kala-azar (Kala-azar, Leishmania Infection), Leprosy, Lice (Body lice, Head lice, Pubic lice), Lyme Disease, Malaria, Marburg Hemorrhagic Fever, Measles, Meningitis, mycobacteria-induced meningitis, Mosquito-borne Diseases, Mycobacterium avium Complex (MAC) Infection, Naegleria Infection, Nosocomial Infections, Nonpathogenic Intestinal Amebae Infection, Onchocerciasis (River Blindness), Opisthorciasis (Opisthorcis Infection), Parvovirus Infection, Plague, PCP (Pneumocystis carinii Pneumonia), Polio, Q Fever, Rabies, Respiratory Syncytial Virus (RSV) Infection, Rheumatic Fever, Rift Valley Fever, River Blindness (Onchocerciasis), Rotavirus Infection, Roundworms Infection, Salmonellosis, Salmonella Enteritidis, Scabies, Shigellosis, Shingles, Sleeping Sickness, Smallpox, Streptococcal Infection, Tapeworm Infection (Taenia Infection), Tetanus, Toxic Shock Syndrome, Tuberculosis, Ulcers (Peptic Ulcer Disease), Valley Fever, Vibrio parahaemolyticus Infection, Vibrio vulnificus Infection, Viral Hemorrhagic Fever, Warts, Waterborne infectious Diseases, West Nile Virus Infection (West Nile Encephalitis), Whooping Cough, Yellow Fever.

Immunological Diseases

Another aspect of the present invention is directed to the use of at least one compound of the general formula (I) and/or pharmaceutically acceptable salts thereof for prophylaxis and/or treatment of immunological diseases, neuroimmunological diseases, and autoimmune diseases.

Immunological diseases are, for instance, asthma and diabetes, rheumatic and autoimmune diseases, AIDS, rejection of transplanted organs and tissues (cf. below), rhinitis, chronic obstructive pulmonary diseases, osteoporosis, ulcerative colitis, sinusitis, lupus erythematosus, recurrent infections, atopic dermatitis eczema and occupational allergies, food allergies, drug allergies, severe anaphylactic reactions, anaphylaxis, and other manifestations of allergic disease, as well as uncommon problems such as primary immunodeficiencies, including antibody deficiency states, cell mediated immunodeficiencies (e.g., severe combined immunodeficiency, DiGeorge syndrome, Hyper-IgE syndrome, Wiskott-Aldrich syndrome, ataxia-telangiectasia), immune mediated cancers, and white cell defects.

In autoimmune diseases, such as systemic lupus erythematosus, rheumatoid arthritis (RA), multiple sclerosis (MS), immune-mediated or type 1 diabetes mellitus, immune mediated glomerulonephritis, scleroderma, pernicious anemia, alopecia, pemphigus, pemphigus vulgaris, myasthenia gravis, inflammatory bowel diseases, Crohn's disease, psoriasis, autoimmune thyroid diseases, and Hashimoto's disease, dermatomyositis, goodpastture syndrome, myasthenia gravis pseudoparalytica, ophtalmia sympatica, phakogene uveitis, chronical aggressive hepatitis, primary billiary cirrhosis, autoimmunehemolytic anemy, Werlof disease, specific cells uncontrollably attack the body's own tissues and organs (autoimmunity), producing inflammatory reactions and other serious symptoms and diseases.

Hashimoto's thyroiditis is one of the most common autoimmune diseases. "Autoimmune disease" refers to a category of more than 80 chronic illnesses, that can affect everything from the endocrine glands (like the thyroid) to organs like the kidneys, as well as to the digestive system.

There are many different autoimmune diseases, and they can each affect the body in different ways. For example, the autoimmune reaction is directed against the brain in multiple sclerosis and the gut in Crohn's disease. In other autoimmune diseases such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in type 1 diabetes mellitus.

Cardiovascular Diseases

The inventive compounds are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

Proliferative Disease

The term "proliferative diseases" as used herein refers also to tumors, cancer, malignancies and their metastases. Additionally it refers also to benign proliferative diseases, which may be harmful producing a "mass effect" (compression of vital organs or closure of hollow organs such as blood vessels), or benign tumors of endocrine tissues, which may overproduce certain hormones.

The proliferation disorders and cancers are preferably selected from the group comprising or consisting of adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, estrogen dependent and independent breast cancer, Burkitt's lymphoma, corpus cancer, CUP-syndrome (carcinoma of unknown primary), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic neoplasias, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's lymphomas), lymphomas, stomach cancer, malignant melanoma, malignant neoplasia, malignant tumors gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, prostate cancer, pharyngeal cancer, rectal carcinoma, retinoblastoma, vaginal cancer, thyroid carcinoma, Schneeberger disease, esophageal cancer, spinalioms, T-cell lymphoma (mycosis fungoides), thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma, tongue cancer, invasive ductal carcinoma, invasive lobular carcinoma, ductal carcinoma in situ, lobular carcinoma in situ, small-cell lung carcinoma, non-small-cell lung carcinoma, bronchial adenoma, pleuropulmonary blastoma, mesothelioma, brain stem glioma, hypophtalmic glioma, cerebellar astrocytoma, cerebral astrocytoma, neuroectodermal tumours, pineal tumors, sarcoma of the uterus, salivary gland cancers, anal gland adenocarcinomas, mast cell tumors, pelvis tumours, ureter tumours, hereditary papillary renal cancers, sporadic papillary renal cancers, intraocular melanoma, hepatocellular carcinoma (liver cell carcinomas with or without fibrolamellar variant), cholangiocarcinoma (intrahepatic bile duct carcinoma), mixed hepatocellular cholangiocarcinoma, squamous cell carcinoma, malignant melanoma, Merkel cell skin cancer, non-melanoma skin cancer, hypopharyngeal cancer, nasopharyngeal cancer, oropharyngeal cancer, oral cavity cancer, squamous cell cancer, oral melanoma, AIDS-related lymphoma, cutaneous T-cell lymphoma, lymphoma of the central nervous system, malignant fibrous histiocytoma, lymphosarcoma, rhabdomyosarcoma, malignant histiocytosis, fibrosarcoma, hemangiosarcoma, hemangiopericytoma, leiomyosarcoma, canine mammary carcinoma, and feline mammary carcinoma.

In yet another preferred embodiment, the cell proliferative disease is cancer. Preferred are the following cancer types: Leukemias including but not limited to chronic lymphocytic leukemia, chronic myelogenous leukemia, acute lymphoblastic leukemia, acute myeloid leukemia, mixed lineage leukemia, bladder cancer, breast cancer, breast carcinoma, cancer of the central nervous system, colon carcinoma, gastric cancer, lung cancer, kidney cancer, melanoma, head and neck tumors (tumors of the ear, nose and throat area), ovarian cancer, ovarial carcinoma, cervical cancer, cervix, cervical carcinoma, glioblastomas, pancreatic cancer, pancreatic carcinoma, prostate cancer, stomach cancer, skin cancer, skin testis cancer, Hodgkin's lymphoma, liver cancer, liver metastases and renal cell carcinomas.

Inflammation

In yet another preferred embodiment, said inflammation is mediated preferably by the cytokines TNF-α, IL-1β, GM-CSF, IL-6 and/or IL-8.

As described above, the compounds according to general formula (I) are pharmaceutically active agents for prophylaxis and/or treatment of inflammatory diseases. Thus, these compounds are used for the manufacture of a pharmaceutical formulation for prophylaxis and/or treatment of inflammations and inflammatory diseases in mammals, including humans.

Inflammatory diseases can emanate from infectious and non-infectious inflammatory conditions which may result from infection by an invading organism or from irritative, traumatic, metabolic, allergic, autoimmune, or idiopathic causes as shown in the following list.

| I. | Acute infections | |
| --- | --- | --- |
| | A. Viral | B. Bacterial |
| II. | Noninfectious causes | |
| III. | Chronic (granulomatous) diseases | |
| | A. Bacterial | B. Spirochetal |
| | C. Mycotic (Fungal) | D. Idiopathic |
| IV. | Allergic, immune, and idiopathic disorders | |
| | A. Hypersensitivity reactions | |
| | B. Immune and idiopathic disorders | |
| V. | Miscellaneous inflammatory conditions | |
| | A. Parasitic infections | |
| | B. Inhalation causes: | Acute (thermal) injury |
| | | Pollution and inhalant allergy |
| | | Carcinogens |
| | C. Radiation injury: | Radionecrosis |

Thus, the compounds disclosed herein can be used for prophylaxis and/or treatment of inflammations caused by invading organisms such as viruses, bacteria, prions, and parasites as well as for prophylaxis and/or treatment of inflammations caused by irritative, traumatic, metabolic, allergic, autoimmune, or idiopathic reasons.

Consequently, the disclosed compounds are useful for prophylaxis and/or treatment of inflammatory diseases which are initiated or caused by viruses, parasites, and bacteria which are connected to or involved in inflammations.

The following bacteria are known to cause inflammatory diseases: mycoplasma pulmonis (causes e.g. chronic lung diseases (CLD), murine chronic respiratory disease), ureaplasma urealyticum (causes pneumonia in newborns), mycoplasma pneumoniae and chlamydia pneumoniae (cause chronic asthma), C. pneumoniae (causes atherosclerosis, pharyngitis to pneumonia with empyema, human coronary heart disease), *Helicobacter pylori* (human coronary heart disease, stomach ulcers). The following viruses are known to cause inflammatory diseases: herpesviruses especially cytomegalovirus (causes human coronary heart disease).

The compounds disclosed herein are useful for prophylaxis and/or treatment of inflammatory diseases caused and/or induced and/or initiated and/or enhanced by the afore-mentioned bacteria or viruses.

Furthermore, the compounds of formula (I) are useful for prophylaxis and/or treatment of inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, inflammatory diseases of the larynx.

Examples for inflammatory diseases of the central nervous system (CNS) are algal disorders, protothecosis, bacterial disorders, abscessation, bacterial meningitis, idiopathic inflammatory disorders, eosinophilic meningoencephalitis, feline polioencephalomyelitis, granulomatous meningoencephalomyelitis, meningitis, steroid responsive meningitis-arteritis, miscellaneous meningitis meningoencephalitis, meningoencephalitis in greyhounds, necrotizing encephalitis, pyogranulomatous meningoencephalomyelitis, shaker dog disease, mycotic diseases of the CNS, parasitic encephalomyelitis, prion protein induced diseases, feline spongiform encephalopathy, protozoal encephalitis-encephalomyelitis, toxoplasmosis, neosporosis, sarcocystosis, encephalitozoonosis, trypanosomiasis, acanthamebiasis, babesiosis, leishmaniasis, rickettsial disorders, rocky mountain spotted fever, canine ehrlichiosis, salmon poisoning, viral disorders, aujeszky's disease, borna disease, canine herpes virus encephalomyelitis, canine distemper encephalomyelitis, canine distemper encephalomyelitis in immature animals, chronic relapsing encephalomyelitis, post-vaccinal canine distemper encephalitis, feline immunodeficiency virus, feline infectious peritonitis, feline leukemia virus, infectious canine hepatitis, La Crosse virus encephalitis, parvovirus encephalitis, rabies, post-vaccinal rabies.

Examples for inflammatory rheumatic diseases are rheumatoid arthritis, scleroderma, lupus, polymyositis, dermatomyositis, psoriatic arthritis, ankylosing spondylitis, Reiters's syndrome, juvenile rheumatoid arthritis, bursitis, tendinitis (tendonitis), and fibromyositis.

Examples for inflammatory diseases of blood vessels are vasculitis, autoantibodies in vasculitis, microscopic polyangiitis, giant cell arteritis, Takayasu's arteritis, vasculitis of the central nervous system, thromboangiitis obliterans (Buerger's Disease), vasculitis secondary to bacterial, fungal, and parasitic infection, vasculitis and rheumatoid arthritis, vasculitis in systemic lupus erythematosus, vasculitis in the idiopathic inflammatory myopathies, relapsing polychondritis, systemic vasculitis in sarcoidosis, vasculitis and malignancy, and drug-induced vasculitis.

Examples for inflammatory diseases of the middle ear are acute suppurative otitis media, bullous myringitis, granular myringitis, and chronic suppurative otitis media, which can manifest as mucosal disease, cholesteatoma, or both.

Examples for inflammatory bowel diseases are ulcerative colitis, Crohn's disease.

Examples for inflammatory diseases of the skin are acute inflammatory dermatoses, urticaria (hives), spongiotic dermatitis, allergic contact dermatitis, irritant contact dermatitis, atopic dermatitis, erythemal multiforme (EM minor), Stevens-Johnson syndrome (SJS, EM major), toxic epidermal necrolysis (TEN), chronic inflammatory dermatoses, psoriasis, lichen planus, discoid lupus erythematosus, and acne vulgaris.

Uveitis are inflammations located in and/or on the eye and may be associated with inflammation elsewhere in the body. In most circumstances, patients who have uveitis as part of a disease elsewhere in the body are aware of that illness. The majority of patients with uveitis do not have an apparent associated systemic illness. Causes of uveitis can be infectious causes, masquerade syndromes, suspected immune-mediated diseases, and/or syndromes confined primarily to the eye.

The following viruses are associated with inflammations: human immunodeficiency virus-I, herpes simplex virus, herpes zoster virus, and cytomegalovirus.

Bacterial or spirochetal caused, induced, initiated and/or enhanced inflammations are tuberculosis, leprosy, proprionobacterium, syphilis, Whipple's disease, leptospirosis, brucellosis, and lyme disease.

Parasitic (protozoan or helminthic) caused, induced, initiated and/or enhanced inflammations are toxoplasmosis, acanthameba, toxocariasis, cysticercosis, onchocerciasis.

Examples of inflammatory diseases caused, induced, initiated and/or enhanced by fungi are histoplasmosis, coccidioidomycosis, candidiasis, aspergillosis, sporotrichosis, blastomycosis, and cryptococcosis.

Masquerade syndromes are, for instance, leukemia, lymphoma, retinitis pigmentosa, and retinoblastoma.

Suspected immune-mediated diseases can be selected from the group comprising ankylosing spondylitis, Behcet's disease, Crohn's disease, drug or hypersensitivity reaction, interstitial nephritis, juvenile rheumatoid arthritis, Kawasaki's disease, multiple sclerosis, psoriatic arthritis, Reiter's syndrome, relapsing polychondritis, sarcoidosis, Sjogren's syndrome, systemic lupus erythematosus, ulcerative colitis, vasculitis, vitiligo, Vogt Koyanagi Harada syndrome.

Syndromes confined primarily to the eye are, for instance, acute multifocal placoid pigmentary epitheliopathy, acute retinal necrosis, birdshot choroidopathy, Fuch's heterochromic cyclitis, glaucomatocyclitic crisis, lens-induced uveitis, multifocal choroiditis, pars planitis, serpiginous choroiditis, sympathetic ophthalmia, and trauma.

Examples for inflammatory diseases of the larynx are gastroesophageal (laryngopharyngeal) reflux disease, pediatric laryngitis, acute laryngeal infections of adults, chronic (granulomatous) diseases, allergic, immune, and idiopathic disorders and miscellaneous inflammatory conditions.

Pediatric laryngitis is known as acute (viral or bacterial) infection such as laryngotracheitis (croup), supraglottitis (epiglottitis), diphtheria, and noninfectious causes are for example spasmodic croup and traumatic laryngitis.

Acute laryngeal infections of adults are, for instance, viral laryngitis, common upper respiratory infection, laryngotracheitis, herpes simplex, bacterial laryngitis, supraglottitis, laryngeal abscess, and gonorrhea.

Chronic (granulomatous) diseases can be selected from the group comprising bacterial diseases, tuberculosis, leprosy, scleroma, actinomycosis, tularemia, glanders, spirochetal (syphilis) diseases, mycotic (fungal) diseases, candidiasis, blastomycosis, histoplasmosis, coccidiomycosis, aspergillosis, idiopathic diseases, sarcoidosis, and Wegener's granulomatosis.

Allergic, immune, and idiopathic disorders are, for example, hypersensitivity reactions, angioedema, Stevens-Johnson syndrome, immune and idiopathic disorders, infections of the immunocompromised host, rheumatoid arthritis, systemic lupus erythematosus, cicatricial pemphigoid, relapsing polychondritis, Sjogren's syndrome, and amyloidosis.

Miscellaneous inflammatory conditions are, for instance, parasitic infections, trichinosis, leishmaniasis, schistosomiasis, syngamus laryngeus, inhalation laryngitis, acute (thermal) injury, pollution and inhalant allergy, carcinogens, radiation injury, radiation laryngitis, radionecrosis, vocal abuse, vocal-cord hemorrhage, muscle tension dysphonias, and contact ulcer and granuloma.

Stroke

The inventive compounds according to the general formula (I) as well as pharmaceutically acceptable salts thereof are also useful for treatment of stroke.

In another aspect of the present invention, the compounds according to the general formula (I) as well as pharmaceutically acceptable salts thereof are used as an inhibitor for a protein kinase, preferably as an inhibitor for a cellular protein kinase.

In a preferred embodiment of this aspect said cellular protein kinase consists of Cyclin-dependent protein kinases (CDKs).

The cyclin-dependent protein kinase can be selected from the group comprising: CDK1, CDK2, CDK3, CDK4, CDK5, CDK6, CDK7, CDK8, CDK9, CDK10, CDK11, CrkRS (Crk7, CDC2-related protein kinase 7), CDKL1 (cyclin-dependent kinase-like 1); KKIALRE, CDKL2 (cyclin-dependent kinase-like 2), KKIAMRE, CDKL3 (cyclin-dependent kinase-like 3), NKIAMRE, CDKL4, similar to cyclin-dependent kinase-like 1, CDC2L1 (cell division cycle 2-like 1), PITSLRE B, CDC2L1 (cell division cycle 2-like 1), PITSLRE A, CDC2L5 (cell division cycle 2-like 5), PCTK1 (PCTAIRE protein kinase 1), PCTK2 (PCTAIRE protein kinase 2), PCTK3 (PCTAIRE protein kinase 3) or PFTK1 (PFTAIRE protein kinase 1).

In a further preferred embodiment said cyclin-dependent protein kinase is CDK7. Thus, the compounds according to the general formula (I) as well as pharmaceutically acceptable salts thereof are used as an inhibitor for CDK7.

Surprisingly it turned out that the compounds according to the general formula (I) as well as pharmaceutically acceptable salts thereof selectively inhibit CDK7 in comparison to other protein kinases and in comparison to other cyclin-dependent protein kinases. Thus, the compounds according to the general formula (I) as well as pharmaceutically acceptable salts thereof are used as selective inhibitors for CDK7.

As used herein, a kinase "inhibitor" refers to any compound capable of downregulating, decreasing, suppressing or otherwise regulating the amount and/or activity of a kinase. Inhibition of these kinases can be achieved by any of a variety of mechanisms known in the art, including, but not limited to binding directly to the kinase polypeptide, denaturing or otherwise inactivating the kinase, or inhibiting the expression of the gene (e.g., transcription to mRNA, translation to a nascent polypeptide, and/or final polypeptide modifications to a mature protein), which encodes the kinase. Generally, kinase inhibitors may be proteins, polypeptides, nucleic acids, small molecules, or other chemical moieties.

As used herein the term "inhibiting" or "inhibition" refers to the ability of a compound to down regulate, decrease, reduce, suppress, inactivate, or inhibit at least partially the activity of an enzyme, or the expression of an enzyme or protein and/or the virus replication.

In a further aspect of the present invention, a method for preventing and/or treating infectious diseases, including opportunistic diseases, in a mammal, especially in a human, is provided, which method comprises administering to the mammal an amount of at least one compound according to the general formula (I), effective to prevent and/or treat said infectious diseases, including opportunistic diseases. In a preferred embodiment of this method, the infectious diseases, including opportunistic diseases, are virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group consisting of: HTLV-I, HTLV-II or BLV. In a further preferred embodiment of this method, the hepadnavirus is selected from HBV, GSHV or WHV, preferably HBV, the herpesvirus is selected from the group comprising: HSV I, HSV II, EBV, VZV, HCMV or HHV 8, preferably HCMV and the flaviviridae is selected from HCV, West nile or Yellow Fever.

In a further aspect of the present invention, methods for preventing and/or treating infectious diseases including opportunistic diseases, prion diseases, immunological diseases, autoimmune diseases, cardiovascular diseases, cell proliferative diseases, inflammation, erectile dysfunction and stroke in a mammal, especially in a human, are provided, which methods comprise administering to the mammal an amount of at least one compound according to the general formula (I) and/or pharmaceutically acceptable salts thereof, effective to prevent and/or treat said infectious diseases including opportunistic diseases, prion diseases, immunological diseases, autoimmune diseases, cardiovascular diseases, cell proliferative diseases, inflammation, erectile dysfunction and stroke.

In further preferred embodiments, the specific diseases addressed as infectious diseases including opportunistic diseases, prion diseases, immunological diseases, autoimmune diseases, cardiovascular diseases, cell proliferative diseases, inflammation, erectile dysfunction and stroke are selected from the groups disclosed above.

The compounds enlisted explicitly in Table 1 are preferred to be used within the methods or indications disclosed herein. Another aspect of the present invention is that at least one compound according to the general formula (I) used as a pharmaceutically active agent may be administered in combination with further therapeutic compounds.

For the indication HIV compounds according to the general formula (I) may be administered in combination with anti-retroviral drugs, selected from the following five classes:

1) Nucleoside reverse transcriptase inhibitors (NRTIs),
2) Non-nucleoside reverse transcriptase inhibitors (NNRTIs),
3) Protease inhibitors (PIs),
4) Fusion inhibitors or
5) Immune stimuli.

Thus, another aspect of the present invention relates to drug combinations comprising at least one inventive compound according to general formula (I) and/or pharmaceutically acceptable salts thereof together with at least one anti-retroviral drug, especially at least one of the drugs mentioned above.

Thus, the compounds of the present invention are used for the manufacture of a pharmaceutical formulation for prophylaxis and/or treatment of infectious diseases, including opportunistic diseases, immunological diseases, autoimmune diseases, cardiovascular diseases, cell proliferative diseases, inflammation, erectile dysfunction and stroke.

The pharmaceutical compositions or formulations according to the present invention comprise at least one compound according to the present invention as an active ingredient together with at least one pharmaceutically acceptable (i.e. non-toxic) carrier, excipient and/or diluent. The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one compound according to the present invention and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95-weight % of the pyrazolo[1,5-a][1,3,5]triazine derivatives according to the general formula (I) or analogues compound thereof or the respective pharmaceutically active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimise the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration.

Aerosol preparations suitable for inhalation may include solutions and solids in powder form, which may be present in combination with a pharmaceutically acceptable carrier such as an inert, compressed gas, e.g. nitrogen.

For preparing suppositories, a low melting wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methylcellulose, polyvinyl alcohols, or denatured gelatins or starch for holding or containing compositions comprising the active ingredient(s). Capsules with hard shells are typically made of blended of relatively high gel strength gelatins from bones or pork skin. The capsule itself may contain small amounts of dyes, opaquing agents, plasticisers and/or preservatives.

Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix.

Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to ca. 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

EXAMPLES

Preparation of Compounds

Abbreviations Used in the Present Description have the Following Meanings

CDCl$_3$ (deuterated chloroform); cHex (cyclohexane); DCM (dichloromethane); DIPEA (N-ethyl-N,N-diisopropylamine); DMF (dimethylformamide); DMSO (dimethyl sulfoxide); eq (equivalent); ES (electrospray); EtOAc (ethyl acetate); EtOH (ethanol); mCPBA (3-chlorobenzoperoxoic acid); MeOH (methanol); MeCN (acetonitrile); MS (mass spectrometry); NMR (nuclear magnetic resonance); Pd(dppf)Cl$_2$ ([1,1'-bis(diphenylphosphino)ferrocene]dichloro palladium(II) complex with dichloromethane); iPrOH (isopropanol); RT (room temperature); sat. aq. (saturated aqueous); SiO$_2$ (silica gel); TFA (trifluoroacetic acid); THF (tetrahydrofuran), KHMDS (potassium hexamethyldisilazide), FRET-signal (fluorescence resonance energy transfer), MBP substrat (myelin basic protein), ATP (adenosine triphosphate), HEPES (4-(2-hydroxyethyl)-1-piperazineethanesulfonic acid), EGTA (ethylene glycol tetraacetic acid), EDTA (ethylenediaminetetraacetic acid), (DTT (dithiothreitol), CycH (cyclin-H). CycA (cyclin-A), MAT1 (mating type gene 1), PYBOP (benzotriazole-1-yl-oxytripyrrolidinophosphonium hexafluorophosphate), NMP (N-Methyl-2-pyrrolidone), Pd-PEPPSI-IPent (dichloro[1,3-bis(2,6-di-3-pentylphenyl)imidazol-2-ylidene](3-chloropyridyl) palladium(II)).

Preparative Examples

Intermediate (II): 8-isopropyl-2-thioxo-2,3-dihydropyrazolo[1,5-a][1,3,5]triazin-4(1H)-one

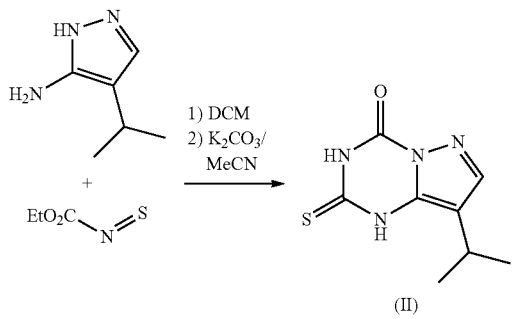

To a chilled solution of 4-isopropyl-1H-pyrazol-5-amine (2.5 g, 20 mmol) in 20 ml DCM ethoxycarbonyl isothiocyanate (2.6 g, 20 mmol) dissolved in 10 ml DCM were added dropwise. The resulting suspension was further diluted with 30 ml DCM and stirred for 2 h. The product was collected, washed with DCM and dried. 2.0 g (7.8 mmol) of this raw material together with 3.2 g (23.4 mmol) were then refluxed in 15 ml MeCN for 2 h. After careful neutralization with acetic acid the solvent was removed in vacuo. The remaining solid was suspended in water. The product was collected, washed with water and dried to yield title compound (II) as colorless powder.

$^1$H-NMR (400 MHz, d$_6$-DMSO, 300K) δ 1.14 (d, J=6.8 Hz, 6H), 3.12 (h, J=6.8 Hz, 1H), 7.88 (s, 1H), 12.60 (s, broad, 1H), 13.34 (s, broad, 1H); MS (ES) C8H10N4OS, requires 210.06. found 211.3 (M+H)$^+$.

Intermediate (III): 8-isopropyl-2-(methylthio)pyrazolo[1,5-a][1,3,5]triazin-4(3H)-one

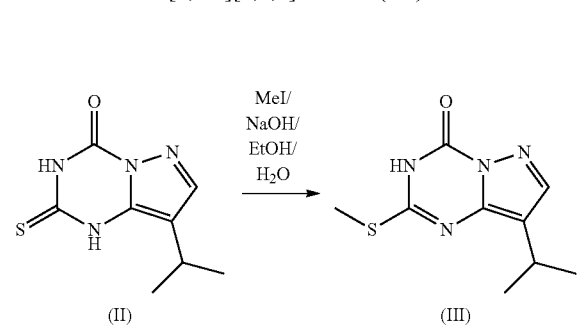

4.0 g (19.1 mmol) starting material (II) were dissolved in 60 ml ethanol and 19.1 ml 2 M NaOH. The solution was cooled in an ice bath and MeI (0.67 g, 4.76 mmol) was added dropwise within 20 minutes. After stirring over night the solution was acidified with 6 M HCl and the solvent was removed under reduced pressure. The remaining solid was suspended in water. The product was collected, washed with water and dried to yield title compound (III) as colorless powder.

¹H-NMR (400 MHz, d₆-DMSO, 300K) δ 1.27 (d, J=7.0 Hz, 6H), 2.55 (s, 3H), 3.02 (h, J=7.0 Hz, 1H), 7.92 (s, 1H), 12.73 (s, broad, 1H); MS (ES) C9H12N4OS requires 224.07. found 225.1 (M+H)⁺.

Intermediate (IV): 4-chloro-8-isopropyl-2-(methylthio)pyrazolo[1,5-a][1,3,5]-triazine

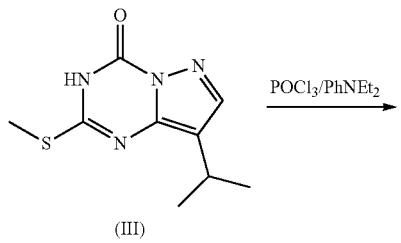

25.0 g (0.111 mol) intermediate (111) and 53 ml (0.334 mol) N,N-diethylaniline in 300 ml POCl₃ were stirred at 90° C. for 3 h. The volatiles were removed under reduced pressure and the remaining oil was used without any further purification.

MS (ES) C9H11ClN4S requires 242.04. found 243.0 (M+H)⁺.

Intermediate (XXI): 4-(benzyloxy)-8-isopropyl-2-(methylthio)pyrazolo[1,5-a][1,3,5]triazine

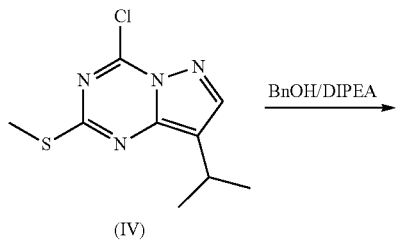

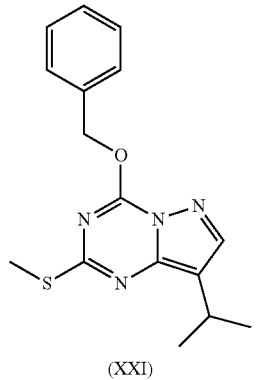

To a solution of intermediate (IV) (raw, prepared from 15 g intermediate (III)) in 10.5 ml (0.101 mol) benzyl alcohol and 20 ml MeCN 46.7 ml of DIPEA (0.268 mmol) were added and the reaction mixture was stirred over night. Additional 7.0 ml of the alcohol and 23.4 ml of DIPEA were added as the reaction was not completed. The reaction mixture was stirred for another 4 h, diluted with ethyl acetate and washed with 2M NaOH. The aqueous phase was extracted twice with ethyl acetate. The combined organic phases were washed with brine, dried over MgSO4, filtered and evaporated. The product was purified by column chromatography using 330 g silica gel and a cyclohexane/ethyl acetate gradient to give the desired product as reddish oil.

¹H-NMR (400 MHz, d₆-DMSO, 300K) δ 1.25 (d, J=6.92 Hz, 6H), 2.52 (s, 3H), 3.05 (h, J=6.92 Hz, 1H), 5.63 (s, 2H), 7.37-7.42 (m, 3H), 7.50-7.53 (m, 2H), 8.01 (s, 1H); MS (ES) C16H18N4OS requires 314.12. found 314.9 (M+H)⁺.

Intermediate (XXII): 4-(benzyloxy)-8-isopropyl-2-(methylsulfonyl)pyrazolo[1,5-a][1,3,5]triazine

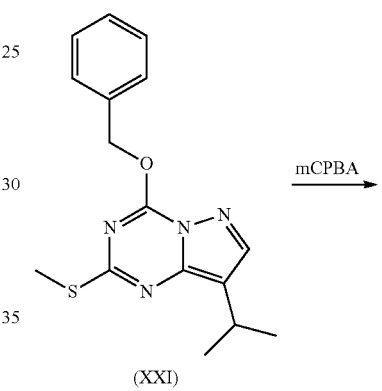

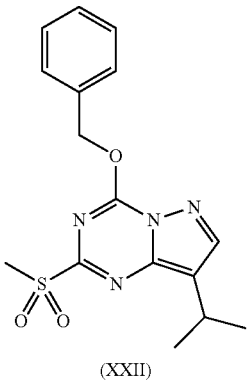

8.9 g (28.3 mmol) thioether (XXI) were dissolved in 200 ml DCM and 8.9 g of mCPBA (51 mmol) were added. After 1 h 4.5 g mCPBA were added. The reaction mixture was stirred for another hour, diluted with ethyl acetate and washed with 2M NaOH. The aqueous phase was extracted twice with ethyl acetate. The combined organic phases were washed with brine, dried over MgSO4, filtered and evaporated. The product was purified by column chromatography using 330 g silica gel and a cyclohexane/ethyl acetate gradient to give the desired product as reddish oil.

¹H-NMR (400 MHz, d₆-DMSO, 300K) δ 1.29 (d, J=6.92 Hz, 6H), 3.18 (h, J=6.92 Hz, 1H), 3.41 (s, 3H), 5.79 (s, 2H), 7.41-7.46 (m, 3H), 7.57-7.59 (m, 2H), 8.35 (s, 1H); MS (ES) C16H18N4O3S requires 346.11. found 347.3 (M+H)⁺.

Method A: Nucleophilic Aromatic Substitution of Chloride (IV) with Amines A¹-NH₂

Intermediate (V-a): N-(2-(1H-pyrazol-1-yl)benzyl)-8-isopropyl-2-(methylthio)-pyrazolo[1,5-a][1.3.5]triazin-4-amine

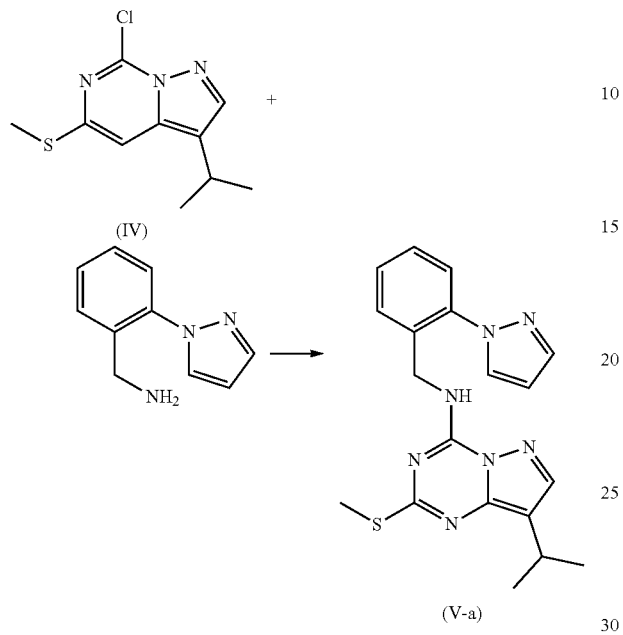

A solution of 13.4 g (60 mmol) intermediate (III) in 47 ml (520 mmol) POCl₃ and 27.1 ml (179 mmol) PhNEt₂ was stirred at 90° C. for 1.5 h. Volatiles were removed under reduced pressure and heating. The remaining oil (crude intermediate (IV)) was added to a solution of 25 g (120 mmol) (2-(1H-pyrazol-1-yl)phenyl)methanamine and 52 ml DIPEA in acetonitrile and stirred at 50° C. over night. The solution was concentrated, diluted with ethyl acetate and washed with 2 N NaOH and brine. The organic phase was dried over MgSat, filtered and evaporated. The crude product was purified by column chromatography (silica, elution with cyclohexaneethyl acetate).

¹H-NMR (400 MHz, d₆-DMSO, 300K) δ 1.27 (d, J=7.2 Hz, 6H), 2.40 (s, 3H), 3.04 (h, J=7.2 Hz, 1H), 4.66 (d, J=4.8 Hz, 2H), 6.56 (m, 1H), 7.37-7.46 (m, 4H), 7.81 (m, 1H), 7.96 (s, 1H), 8.18 (m, 1H), 9.09 (broad, 1H); MS (ES) C19H21N7S requires 379.48. found 379.9 (M+H)⁺.

Intermediates (V-b)-(V-ae)

Title compounds (V-b)-(V-ae) were prepared similar to method A typically on a 1 mmol scale.

| intermediate | A¹—NH₂ | formula | exact mass | MS(ES) [M + H]⁺ | structure |
|---|---|---|---|---|---|
| (V-b) | | C22H23N5S | 389.17 | 390.3 | 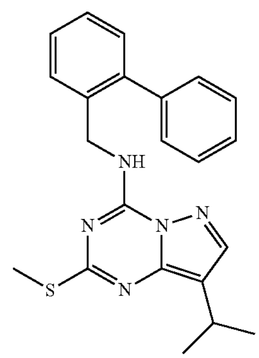 [SMILES: CSc1nc(NCc2ccccc2-c2ccccc2)n2ncc(C(C)C)c2n1] |
| (V-c) | | C18H23N5OS | 357.16 | 358.3 | 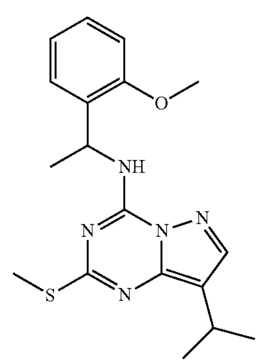 [SMILES: COc1ccccc1C(C)Nc1nc(SC)nc2c(C(C)C)cnn12] |

-continued
| intermediate | A¹—NH₂ | formula | exact mass | MS(ES) [M + H]⁺ | structure |
|---|---|---|---|---|---|
| (V-d) |  | C20H21N5S2 | 395.12 | 396.1 | 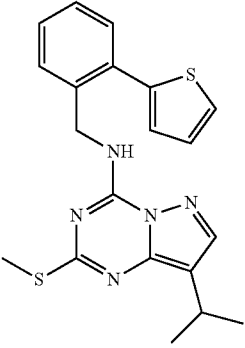 [SMILES: CSc1nc(NCc2ccccc2-c2cccs2)n2ncc(C(C)C)c2n1] |
| (V-e) | 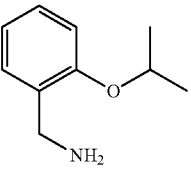 | C19H25N5OS | 371.18 | 372.3 | 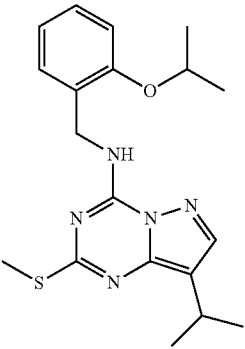 [SMILES: CSc1nc(NCc2ccccc2OC(C)C)n2ncc(C(C)C)c2n1] |
| (V-f) | 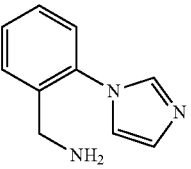 | C19H21N7S | 379.16 | 380.3 | 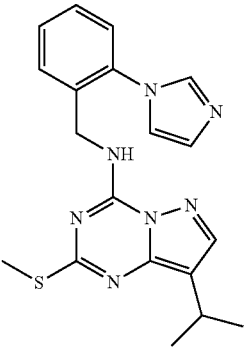 [SMILES: CSc1nc(NCc2ccccc2-n2ccnc2)n2ncc(C(C)C)c2n1] |
| (V-g) | 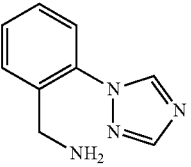 | C18H20N8S | 380.15 | 380.9 | 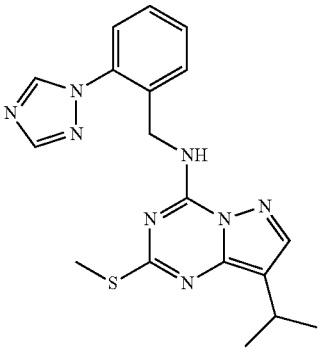 [SMILES: CSc1nc(NCc2ccccc2-n2cncn2)n2ncc(C(C)C)c2n1] |

-continued

| intermediate | A¹—NH₂ | formula | exact mass | MS(ES) [M + H]⁺ | structure |
|---|---|---|---|---|---|
| (V-h) | | C20H23N7S | 393.17 | 394.2 | 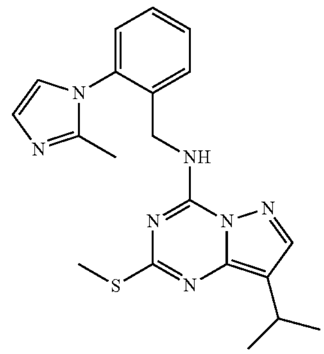 [SMILES: CSc1nc(NCc2ccccc2-n2ccnc2C)n2ncc(C(C)C)c2n1] |
| (V-i) | | C17H20ClN5S | 361.11 | 362.2 | 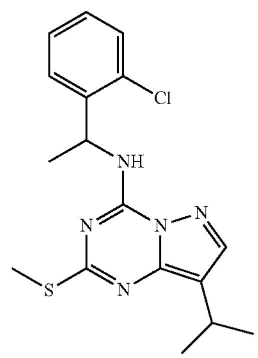 [SMILES: CSc1nc(NC(C)c2ccccc2Cl)n2ncc(C(C)C)c2n1] |
| (V-j) | | C18H21N9S | 395.16 | 396.4 | 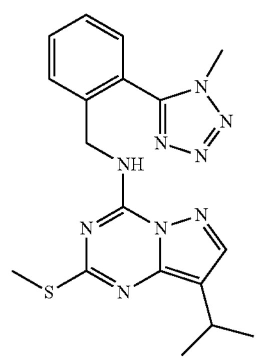 [SMILES: CSc1nc(NCc2ccccc2-c2nnnn2C)n2ncc(C(C)C)c2n1] |
| (V-k) | | C19H20N6S | 364.15 | 364.9 | 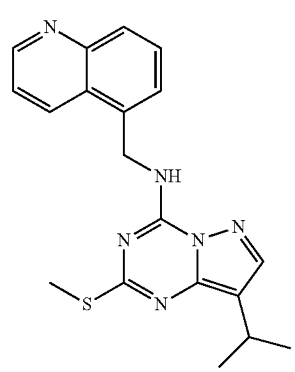 [SMILES: CSc1nc(NCc2cccc3ncccc23)n2ncc(C(C)C)c2n1] |

-continued
| intermediate | A¹—NH₂ | formula | exact mass | MS(ES) [M + H]⁺ | structure |
|---|---|---|---|---|---|
| (V-l) | 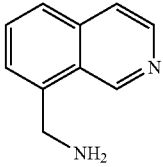 | C19H20N6S | 364.15 | 364.9 | 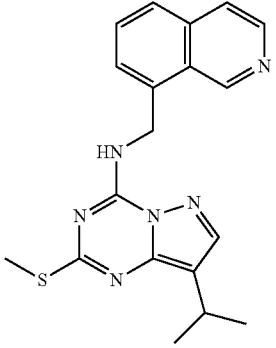 [SMILES: CSc1nc(NCc2cccc3ccncc23)n2ncc(C(C)C)c2n1] |
| (V-m) | 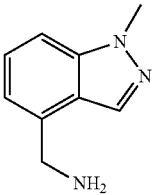 | C18H21N7S | 367.16 | 368.0 | 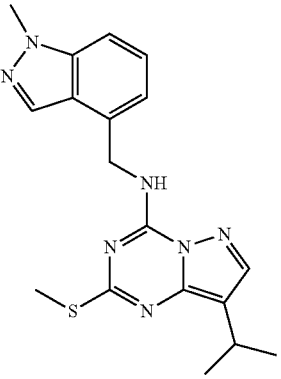 [SMILES: CSc1nc(NCc2cccc3c2cnn3C)n2ncc(C(C)C)c2n1] |
| (V-n) | 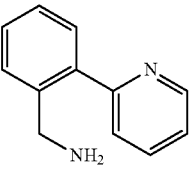 | C21H22N6S | 390.16 | 391.1 | 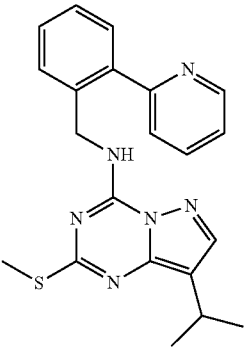 [SMILES: CSc1nc(NCc2ccccc2-c2ccccn2)n2ncc(C(C)C)c2n1] |
| (V-o) | 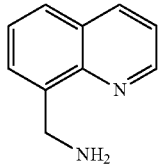 | C19H20N6S | 364.15 | 365.0 | 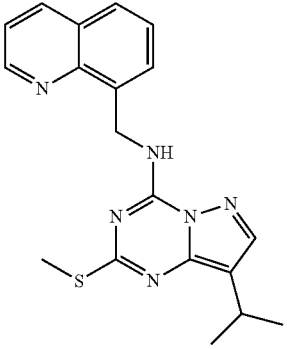 [SMILES: CSc1nc(NCc2cccc3cccnc23)n2ncc(C(C)C)c2n1] |

-continued

| intermediate | A¹—NH₂ | formula | exact mass | MS(ES) [M + H]⁺ | structure |
|---|---|---|---|---|---|
| (V-p) | | C16H17N7OS | 355.12 | 356.2 | 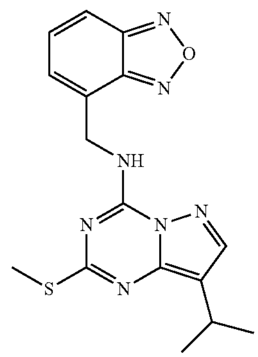 [SMILES: CSc1nc(NCc2cccc3nonc23)n2ncc(C(C)C)c2n1] |
| (V-q) | | C17H19N7S | 353.14 | 354.2 | 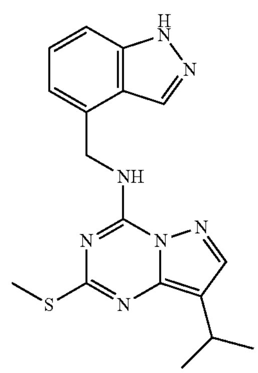 [SMILES: CSc1nc(NCc2cccc3[nH]ncc23)n2ncc(C(C)C)c2n1] |
| (V-r) | | C20H24N6OS | 396.17 | 397.0 | 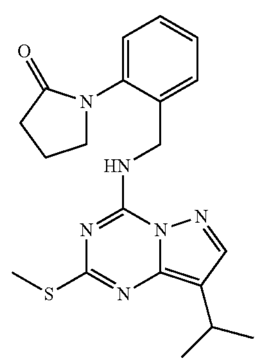 [SMILES: CSc1nc(NCc2ccccc2N2CCCC2=O)n2ncc(C(C)C)c2n1] |
| (V-s) | | C20H23N7S | 393.17 | 395.0 | 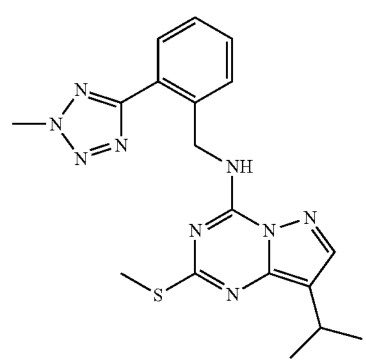 [SMILES: CSc1nc(NCc2ccccc2-c2nnn(C)n2)n2ncc(C(C)C)c2n1] |

-continued
| intermediate | A¹—NH₂ | formula | exact mass | MS(ES) [M + H]⁺ | structure |
|---|---|---|---|---|---|
| (V-t) | 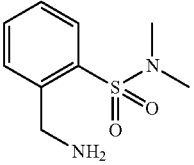 | C18H24N6O2S2 | 420.14 | 421.1 | 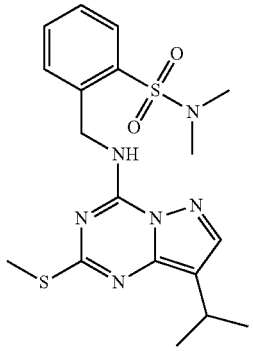 [SMILES: CSc1nc(NCc2ccccc2S(=O)(=O)N(C)C)n2ncc(C(C)C)c2n1] |
| (V-u) |  | C19H22N6OS | 382.16 | 383.2 | 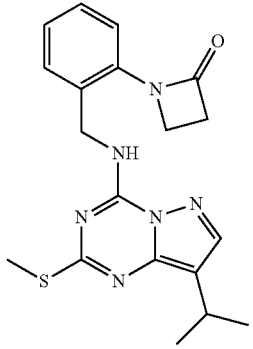 [SMILES: CSc1nc(NCc2ccccc2N2CCC2=O)n2ncc(C(C)C)c2n1] |
| (V-v) |  | C19H20FN7S | 397.15 | 398.3 | 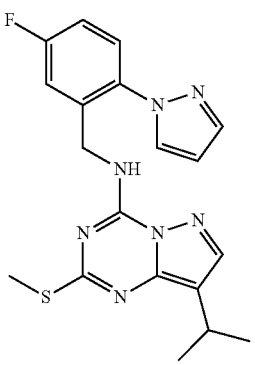 [SMILES: CSc1nc(NCc2cc(F)ccc2-n2cccn2)n2ncc(C(C)C)c2n1] |
| (V-w) |  | C19H20FN7S | 397.15 | 398.3 | 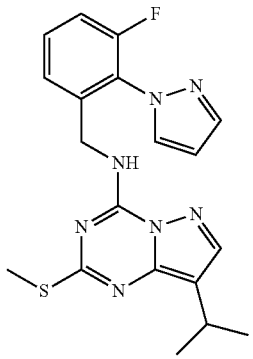 [SMILES: CSc1nc(NCc2cccc(F)c2-n2cccn2)n2ncc(C(C)C)c2n1] |

-continued
| intermediate | A¹—NH₂ | formula | exact mass | MS(ES) [M + H]⁺ | structure |
|---|---|---|---|---|---|
| (V-x) | 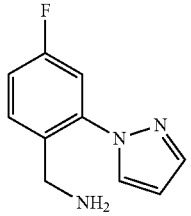 | C19H20FN7S | 397.15 | 398.2 | 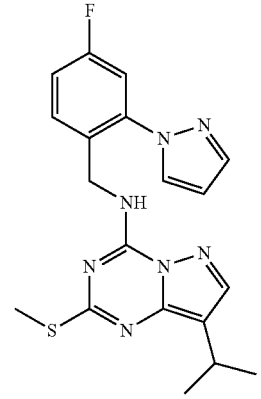 [SMILES: CSc1nc(NCc2ccc(F)cc2-n2cccn2)n2ncc(C(C)C)c2n1] |
| (V-y) |  | C19H20FN7S | 397.15 | 398.1 | 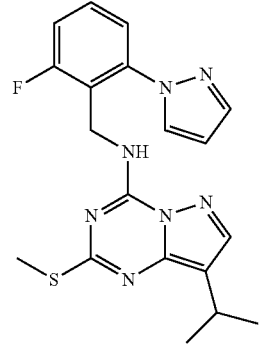 [SMILES: CSc1nc(NCc2c(F)cccc2-n2cccn2)n2ncc(C(C)C)c2n1] |
| (V-z) | 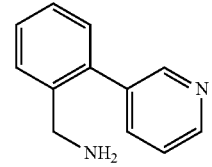 | C21H22N6S | 390.16 | 391.2 | 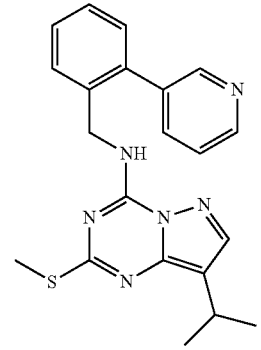 [SMILES: CSc1nc(NCc2ccccc2-c2cccnc2)n2ncc(C(C)C)c2n1] |
| (V-aa) | 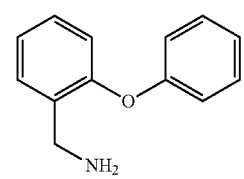 | C22H23N5OS | 405.16 | 406.0 | 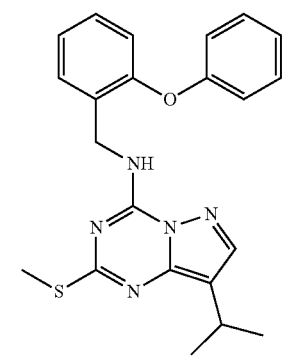 [SMILES: CSc1nc(NCc2ccccc2Oc2ccccc2)n2ncc(C(C)C)c2n1] |

-continued

| intermediate | A¹—NH₂ | formula | exact mass | MS(ES) [M + H]⁺ | structure |
|---|---|---|---|---|---|
| (V-ab) | | C19H20N6OS | 380.14 | 380.8 | 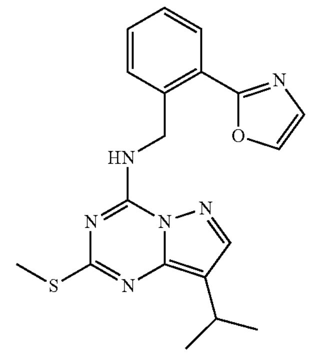 [SMILES: CSc1nc(NCc2ccccc2-c2ncco2)n2ncc(C(C)C)c2n1] |
| (V-ac) | | C20H21N5OS | 379.15 | 379.9 | 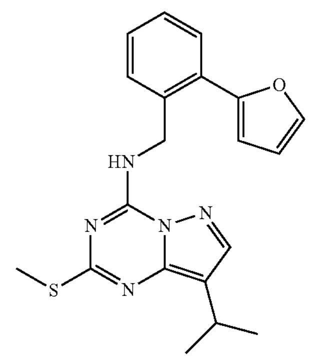 [SMILES: CSc1nc(NCc2ccccc2-c2ccco2)n2ncc(C(C)C)c2n1] |
| (V-ad) | | C18H22N6OS | 370.16 | 371.1 | 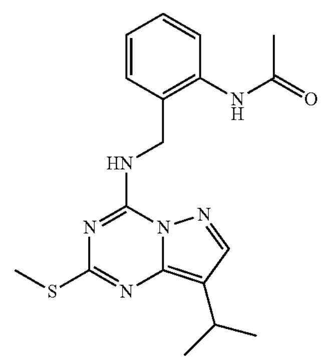 [SMILES: CSc1nc(NCc2ccccc2NC(C)=O)n2ncc(C(C)C)c2n1] |
| (V-ae) | | C19H20ClN7S | 413.12 | 414.2 | 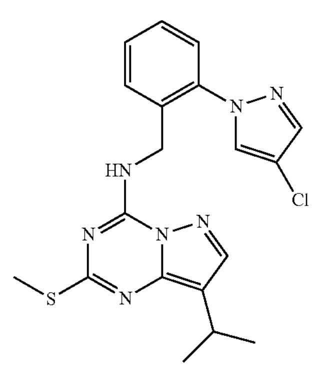 [SMILES: CSc1nc(NCc2ccccc2-n2cc(Cl)cn2)n2ncc(C(C)C)c2n1] |

Method B: Oxidation of Thioethers (V)

Intermediate (VI-a): N-(2-(1H-pyrazol-1-yl)benzyl)-8-isopropyl-2-(methylsulfonyl) pyrazolo[1,5-a][1,3,5]triazin-4-amine

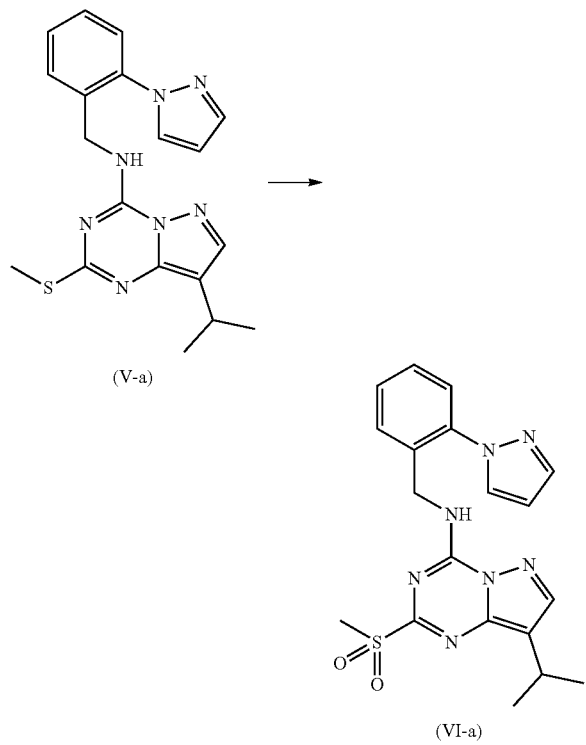

(V-a)

(VI-a)

Thioether (V-a) (17.4 g; 45.9 mmol) was dissolved in 300 ml DCM and 23.9 g (138 mmol) mCPBA were added in small portions to keep the temperature below 30° C. After 4 h the reaction mixture was washed with 2 N NaOH and brine, dried (MgSO₄) and evaporated to dryness. The crude product was chromatographed on silica using ethyl acetate and cyclohexane.

¹H-NMR (400 MHz, d₆-DMSO, 300K) δ 1.30 (d, J=7.2 Hz, 6H), 3.15 (h, J=7.2 Hz, 1H), 3.24 (s, 3H), 4.75 (s, 2H), 6.55 (m, 1H), 7.41-7.56 (m, 4H), 7.80 (m, 1H), 8.21 (m, 1H), 8.28 (s, borad, 1H), 9.73 (broad, 1H); MS (ES) C19H21N7O2S requires 411.2. found 412.3 (M+H)⁺.

Method H: Substitution of Chloride (XX) with Amines A¹NH₂

Intermediate (VI-ad): N-(2-(((8-isopropyl-2-(methylsulfonyl)pyrazolo[1,5-a][1,3,5]triazin-4-yl)amino)methyl)phenyl)methanesulfonamide

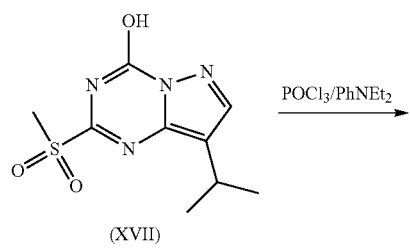

(XVII)

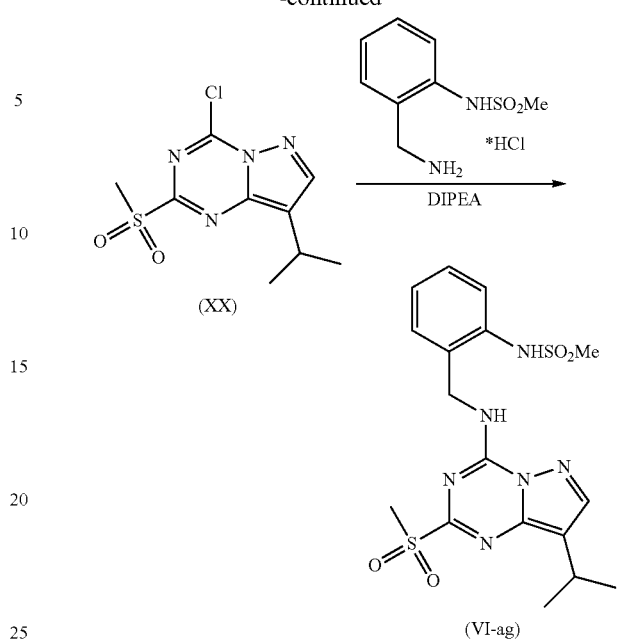

(XX)

(VI-ag)

1.2 g (4.69 mmol) intermediate (XVII) were stirred in 12.8 ml (141 mmol) POCl₃ and 2.1 ml (14.1 mmol) N,N-diethylaniline at 100° C. for 1.5 h. Volatiles were removed under reduced pressure. The remaining oil was dissolved in acetonitrile and evaporated three times. Crude chloride (XX) was the diluted to 9 ml with acetonitrile and used in 1.5 ml (0.782 mmol) aliquots. One aliquot of this stock solution was added to 233 mg (0.938 mmol) N-(2-(aminomethyl)phenyl)methanesulfonamide hydrochloride and 409 µl (2.35 mmol) DIPEA in 2 ml acetonitrile. The reaction mixture was stirred at room temperature over night, diluted with ethyl acetate and washed with saturated aqueous NaHCO₃ solution. The organic phase was dried over MgSO₄ and concentrated in vacuo. Title compound (VI-ag) was obtained after chromatography on silica using ethyl acetate and cyclohexane gradient.

¹H-NMR (400 MHz, d₆-DMSO, 300K) δ 1.31 (d, J=6.9 Hz, 6H), 3.06 (s, 3H), 3.15 (h, J=6.9 Hz, 1H), 3.28 (s, 3H), 4.89 (d, J=6.2 Hz, 2H), 7.21-7.45 (m, 4H), 8.29 (s, 1H), 9.3 (s, 1H), 9.73 (t, J=6.2 Hz, 1H); MS (ES) C17H22N6O4S2 requires 438.11. found 439.4 (M+H)⁺.

Method I: Substitution of Ether (XXII) with Amines A¹NH₂

Intermediate (VI-ak): N-(2-(((8-isopropyl-2-(methylsulfonyl)pyrazolo[1,5-a][1,3,5]triazin-4-yl)amino)methyl)phenyl)methanesulfonamide

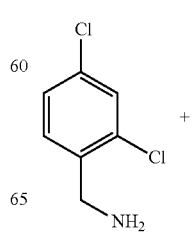

+

-continued

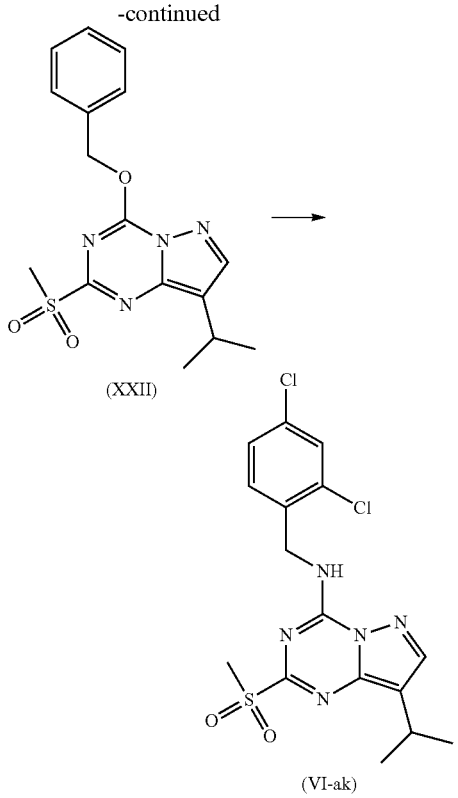

(XXII)

(VI-ak)

30.0 mg (0.087 mmol) intermediate (XXII) and 15.3 mg (0.087 mmol) (2,4-dichlorophenyl)methanamine were heated in 0.5 ml NMP at 120° C. for 40 min. Ethyl acetate was added and the mixture was washed with 2 M aqueous NaOH solution and brine. The organic phase was dried over MgSat and concentrated under reduced pressure. Title compound (VI-ak) was obtained after chromatography on 12 g silica gel using ethyl acetate and cyclohexane gradient.

MS (ES) C16H17Cl2N5O2S requires 413.05. found 414.2 (M+H)+.

Intermediates (VI-b-VI-bs)

Title compounds (VI-b)-(VI-af) were prepared from the related thioethers similar to method B in about 0.1-1 mmol scale. Compounds (VI-ag)-(VI-aj) were synthesized similar to method H. Compounds (VI-al)-(VI-bs) were synthesized similar to method I (if A¹NH₂ were used as hydrochlorides, DIEPA was added).

| intermediate | formula | exact mass | MS(ES) [M + H]+ | from intermediate | structure |
|---|---|---|---|---|---|
| (VI-b) | C22H23N5O2S | 421.16 | 422.3 | (V-b) | 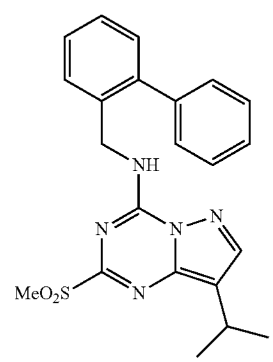 [SMILES: CC(C)c1cnn2c(NCc3ccccc3-c3ccccc3)nc(S(C)(=O)=O)nc12] |
| (VI-c) | C18H23N5O3S | 389.15 | 390.3 | (V-c) | 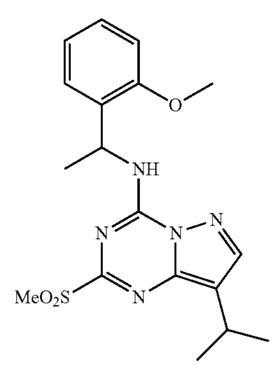 [SMILES: COc1ccccc1C(C)Nc1nc(S(C)(=O)=O)nc2c(C(C)C)cnn12] |

-continued
| intermediate | formula | exact mass | MS(ES) [M + H]+ | from intermediate | structure |
|---|---|---|---|---|---|
| (VI-d) | C20H21N5O2S2 | 427.11 | 428.2 | (V-d) | 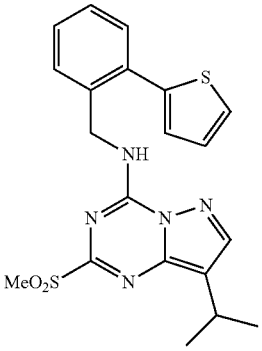 [SMILES: CC(C)c1cnn2c(NCc3ccccc3-c3cccs3)nc(S(C)(=O)=O)nc12] |
| (VI-e) | C19H25N5O3S | 403.17 | 404.3 | (V-e) | 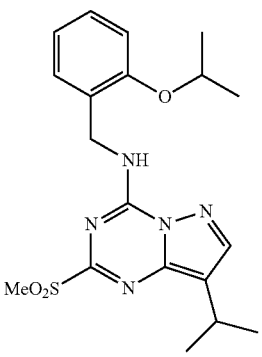 [SMILES: CC(C)Oc1ccccc1CNc1nc(S(C)(=O)=O)nc2c(C(C)C)cnn12] |
| (VI-f) | C19H21N7O2S | 411.15 | 412.3 | (V-f) | 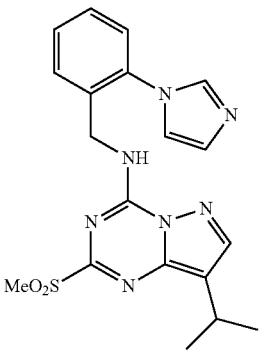 [SMILES: CC(C)c1cnn2c(NCc3ccccc3-n3ccnc3)nc(S(C)(=O)=O)nc12] |
| (VI-g) | C18H20N8O2S | 412.14 | 413.1 | (V-g) | 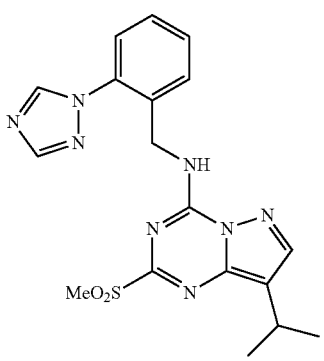 [SMILES: CC(C)c1cnn2c(NCc3ccccc3-n3cncn3)nc(S(C)(=O)=O)nc12] |

-continued

| intermediate | formula | exact mass | MS(ES) [M + H]+ | from intermediate | structure |
|---|---|---|---|---|---|
| (VI-h) | C20H23N7O2S | 425.16 | 426.3 | (V-h) | 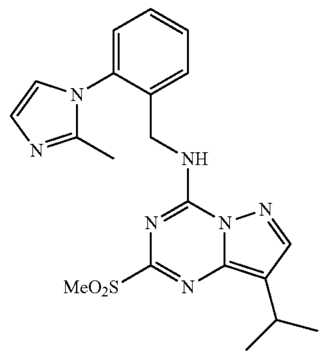 [SMILES: Cc1nccn1-c1ccccc1CNc1nc(S(C)(=O)=O)nc2c(C(C)C)cnn12] |
| (VI-i) | C17H20ClN5O2S | 393.10 | 394.2 | (V-i) | 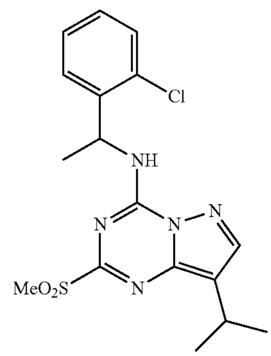 [SMILES: CC(C)c1cnn2c(NC(C)c3ccccc3Cl)nc(S(C)(=O)=O)nc12] |
| (VI-j) | C18H21N9O2S | 427.15 | 428.3 | (V-j) | 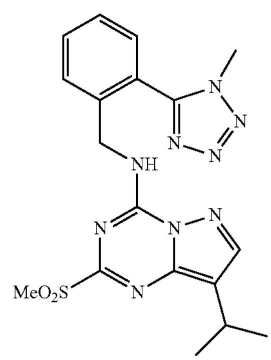 [SMILES: CC(C)c1cnn2c(NCc3ccccc3-c3nnnn3C)nc(S(C)(=O)=O)nc12] |
| (VI-k) | C19H20N6O3S | 412.13 | 413.3 | (V-k) | 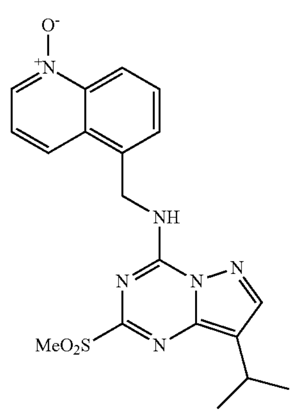 [SMILES: CC(C)c1cnn2c(NCc3cccc4c3ccc[n+]4[O-])nc(S(C)(=O)=O)nc12] |

-continued

| intermediate | formula | exact mass | MS(ES) [M + H]+ | from intermediate | structure |
|---|---|---|---|---|---|
| (VI-l) | C19H20N6O2S | 396.14 | 397.2 | (V-l) | 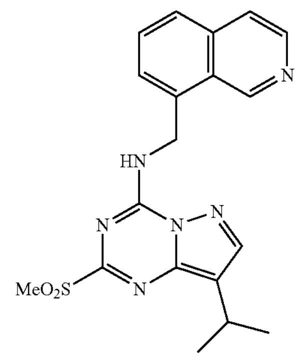 [SMILES: CC(C)c1cnn2c(NCc3cccc4ccncc34)nc(S(C)(=O)=O)nc12] |
| (VI-m) | C19H20N6O3S | 412.13 | 413.2 | (V-l) | 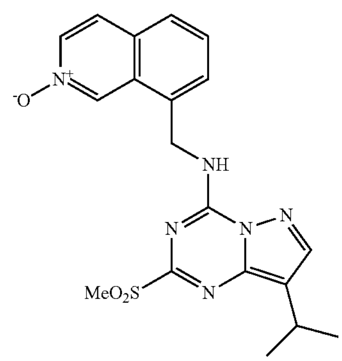 |
| (VI-n) | C19H20N6O3S | 399.15 | 400.3 | (V-m) | 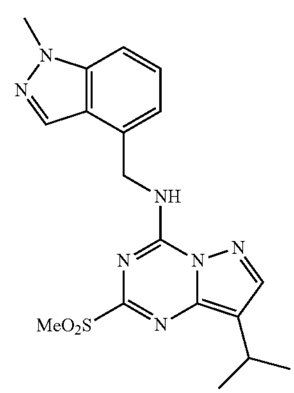 [SMILES: CC(C)c1cnn2c(NCc3cccc4c3cnn4C)nc(S(C)(=O)=O)nc12] |
| (VI-o) | C18H21N7O2S | 422.15 | 423.0 | (V-n) | 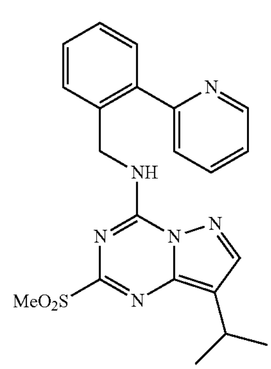 [SMILES: CC(C)c1cnn2c(NCc3ccccc3-c3ccccn3)nc(S(C)(=O)=O)nc12] |

-continued

| intermediate | formula | exact mass | MS(ES) [M + H]+ | from intermediate | structure |
|---|---|---|---|---|---|
| (VI-p) | C21H22N6O2S | 396.14 | 397.1 | (V-o) | 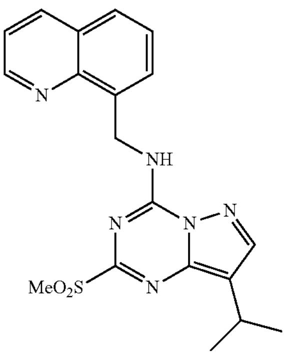 [SMILES: CC(C)c1cnn2c(NCc3cccc4cccnc34)nc(S(C)(=O)=O)nc12] |
| (VI-q) | C19H20N6O2S | 387.11 | 388.3 | (V-p) | 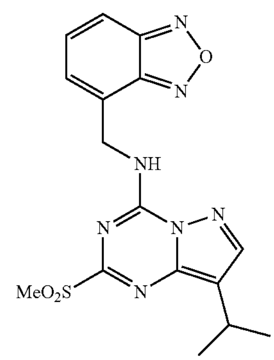 [SMILES: CC(C)c1cnn2c(NCc3cccc4nonc34)nc(S(C)(=O)=O)nc12] |
| (VI-r) | C16H17N7O3S | 385.13 | 386.2 | (V-q) | 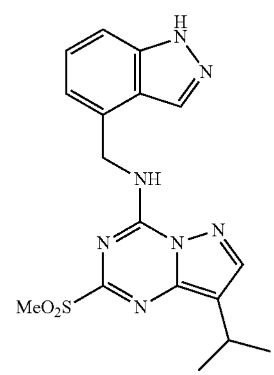 [SMILES: CC(C)c1cnn2c(NCc3cccc4[nH]ncc34)nc(S(C)(=O)=O)nc12] |
| (VI-s) | C20H24N6O3S | 428.16 | 429.3 | (V-r) | 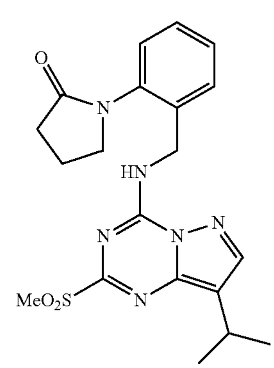 [SMILES: CC(C)c1cnn2c(NCc3ccccc3N3CCCC3=O)nc(S(C)(=O)=O)nc12] |

-continued

| intermediate | formula | exact mass | MS(ES) [M + H]+ | from intermediate | structure |
|---|---|---|---|---|---|
| (VI-t) | C18H21N9O2S | 427.15 | 428.3 | (V-s) | 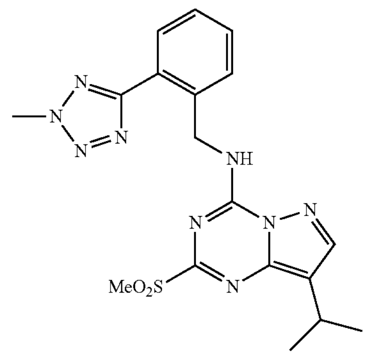 [SMILES: CC(C)c1cnn2c(NCc3ccccc3-c3nnn(C)n3)nc(S(C)(=O)=O)nc12] |
| (VI-u) | C18H24N6O4S2 | 452.13 | 453.3 | (V-t) | 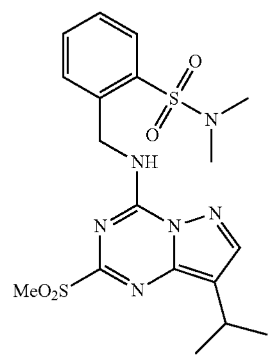 [SMILES: CC(C)c1cnn2c(NCc3ccccc3S(=O)(=O)N(C)C)nc(S(C)(=O)=O)nc12] |
| (VI-v) | C19H22N6O3S | 414.15 | 415.2 | (V-u) | 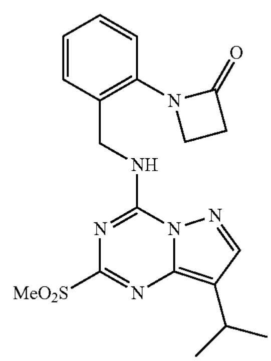 [SMILES: CC(C)c1cnn2c(NCc3ccccc3N3CCC3=O)nc(S(C)(=O)=O)nc12] |
| (VI-w) | C19H20FN7O2S | 429.14 | 430.3 | (V-v) | 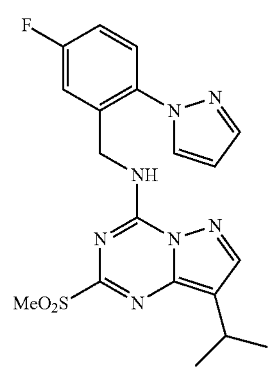 [SMILES: CC(C)c1cnn2c(NCc3cc(F)ccc3-n3cccn3)nc(S(C)(=O)=O)nc12] |

-continued
| intermediate | formula | exact mass | MS(ES) [M + H]+ | from intermediate | structure |
|---|---|---|---|---|---|
| (VI-x) | C19H20FN7O2S | 429.14 | 430.2 | (V-w) | 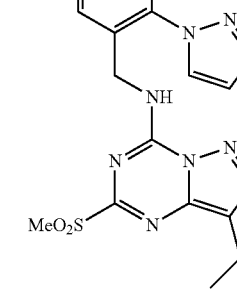 |
| (VI-y) | C19H20FN7O2S | 429.14 | 430.3 | (V-x) | 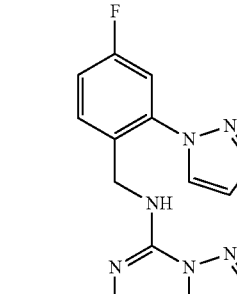 |
| (VI-z) | C19H20FN7O2S | 429.14 | 430.3 | (V-y) | 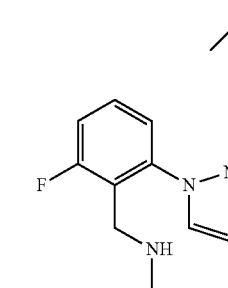 |
| (VI-aa) | C21H22N6O2S | 422.15 | 423.3 | (V-z) | 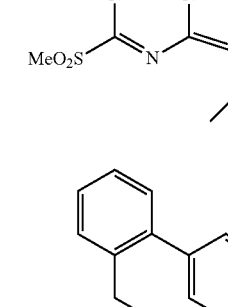 |

-continued

| intermediate | formula | exact mass | MS(ES) [M + H]+ | from intermediate | structure |
|---|---|---|---|---|---|
| (VI-ab) | C22H23N5O3S | 437.15 | 438.0 | (V-aa) | 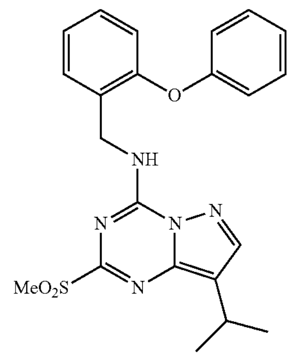 [SMILES: CC(C)c1cnn2c(NCc3ccccc3Oc3ccccc3)nc(S(C)(=O)=O)nc12] |
| (VI-ac) | C19H20N6O3S | 412.13 | 413.6 | (V-ab) | 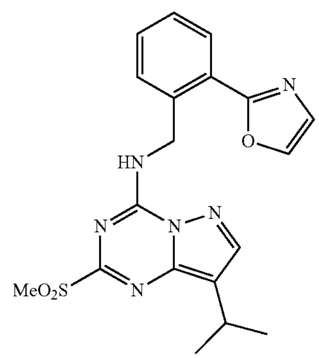 [SMILES: CC(C)c1cnn2c(NCc3ccccc3-c3ncco3)nc(S(C)(=O)=O)nc12] |
| (VI-ad) | C20H21N5O3S | 411.14 | 412.6 | (V-ac) | 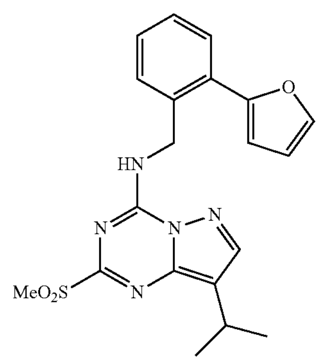 [SMILES: CC(C)c1cnn2c(NCc3ccccc3-c3ccco3)nc(S(C)(=O)=O)nc12] |
| (VI-ae) | C18H22N6O3S | 402.15 | 403.2 | (V-ad) | 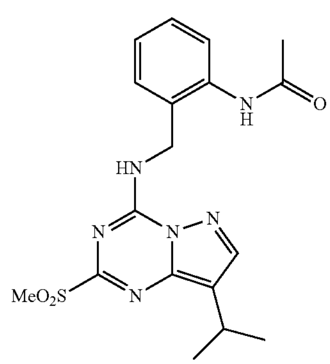 [SMILES: CC(=O)Nc1ccccc1CNc1nc(S(C)(=O)=O)nc2c(C(C)C)cnn12] |

-continued

| intermediate | formula | exact mass | MS(ES) [M + H]+ | from intermediate | structure |
|---|---|---|---|---|---|
| (VI-af) | C19H20ClN7O2S | 445.11 | 446.1 | (V-ae) | 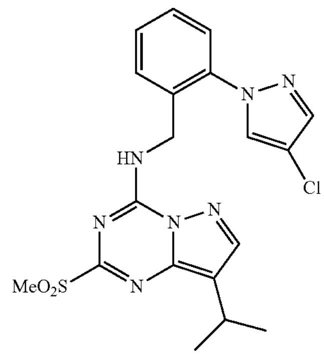 [SMILES: CC(C)c1cnn2c(NCc3ccccc3-n3cc(Cl)cn3)nc(S(C)(=O)=O)nc12] |
| (VI-ag) | C17H22N6O4S2 | 438.11 | 439.4 | (XX) | 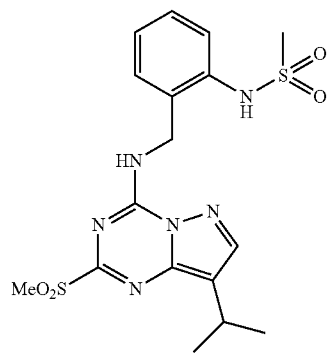 [SMILES: CC(C)c1cnn2c(NCc3ccccc3NS(C)(=O)=O)nc(S(C)(=O)=O)nc12] |
| (VI-ah) | C18H21N5O4S | 403.13 | 404.3 | (XX) | 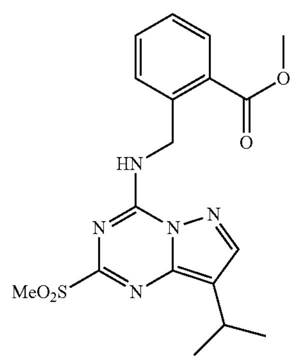 [SMILES: COC(=O)c1ccccc1CNc1nc(S(C)(=O)=O)nc2c(C(C)C)cnn12] |
| (VI-ai) | C21H28N6O4S | 460.19 | 461.6 | (XX) | 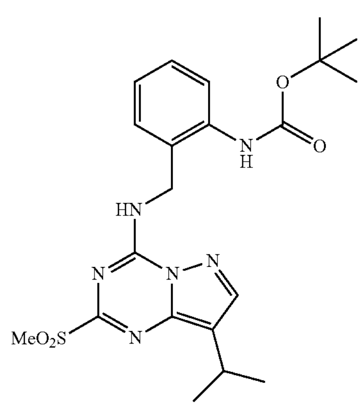 [SMILES: CC(C)c1cnn2c(NCc3ccccc3NC(=O)OC(C)(C)C)nc(S(C)(=O)=O)nc12] |

-continued

| intermediate | formula | exact mass | MS(ES) [M + H]+ | from intermediate | structure |
|---|---|---|---|---|---|
| (VI-aj) | C19H20N6O2S | 396.14 | 397.4 | (XX) | 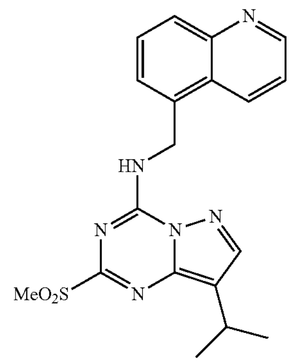 [SMILES: CC(C)c1cnn2c(NCc3cccc4ncccc34)nc(S(C)(=O)=O)nc12] |
| (VI-al) | C21H26N6O3S | 442.18 | 443.4 | (XXII) | 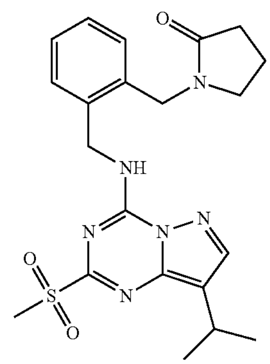 [SMILES: CC(C)c1cnn2c(NCc3ccccc3CN3CCCC3=O)nc(S(C)(=O)=O)nc12] |
| (VI-am) | C21H27N5O4S | 445.18 | 446.4 | (XXII) | 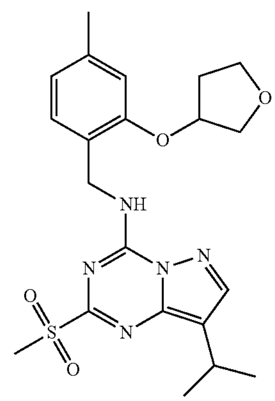 [SMILES: Cc1ccc(CNc2nc(S(C)(=O)=O)nc3c(C(C)C)cnn23)c(OC2CCOC2)c1] |
| (VI-an) | C21H27N5O3S | 429.18 | 430.3 | (XXII) | 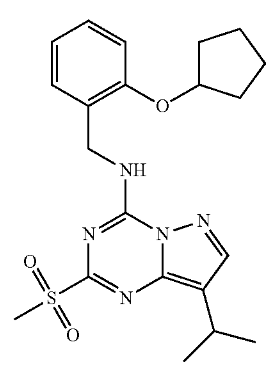 [SMILES: CC(C)c1cnn2c(NCc3ccccc3OC3CCCC3)nc(S(C)(=O)=O)nc12] |

-continued

| intermediate | formula | exact mass | MS(ES) [M + H]+ | from intermediate | structure |
| --- | --- | --- | --- | --- | --- |
| (VI-ao) | C17H20N6O3S | 388.13 | 389.2 | (XXII) | 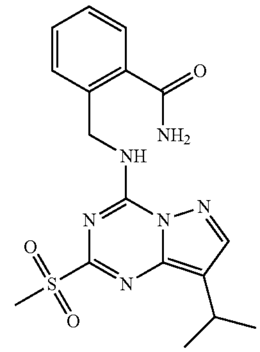 [SMILES: CC(C)c1cnn2c(NCc3ccccc3C(N)=O)nc(S(C)(=O)=O)nc12] |
| (VI-ap) | C20H25N5O3S | 415.17 | 416.4 | (XXII) | 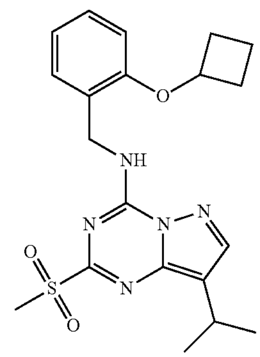 [SMILES: CC(C)c1cnn2c(NCc3ccccc3OC3CCC3)nc(S(C)(=O)=O)nc12] |
| (VI-aq) | C21H22N6O3S | 438.15 | 439.3 | (XXII) | 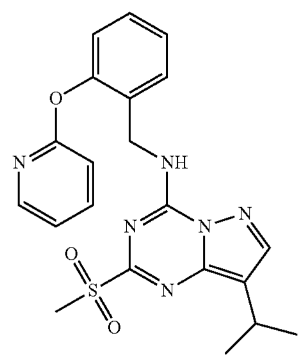 [SMILES: CC(C)c1cnn2c(NCc3ccccc3Oc3ccccn3)nc(S(C)(=O)=O)nc12] |
| (VI-ar) | C20H26N6O5S2 | 494.14 | 495.3 | (XXII) | 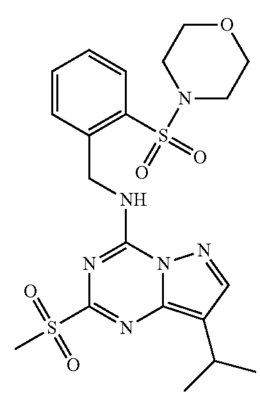 [SMILES: CC(C)c1cnn2c(NCc3ccccc3S(=O)(=O)N3CCOCC3)nc(S(C)(=O)=O)nc12] |

-continued

| intermediate | formula | exact mass | MS(ES) [M + H]⁺ | from intermediate | structure |
|---|---|---|---|---|---|
| (VI-as) | C16H18BrN5O2S | 423.04 | 424.2 | (XXII) | 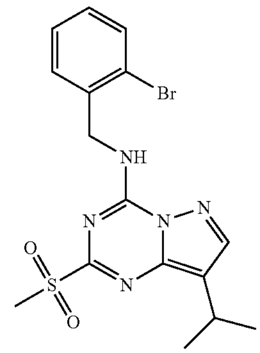 |
| (VI-at) | C17H20ClN5O2S | 393.10 | 394.2 | (XXII) | 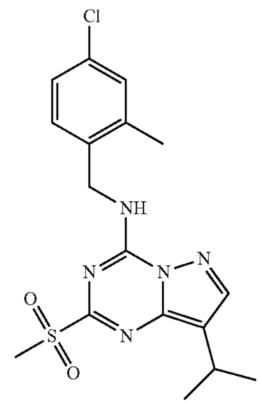 [SMILES: Cc1cc(Cl)ccc1CNc1nc(S(C)(=O)=O)nc2c(C(C)C)cnn12] |
| (VI-au) | C17H17ClF3N5O2S | 447.07 | 448.2 | (XXII) | 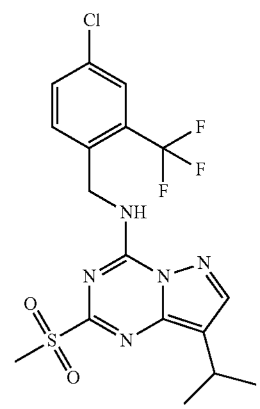 [SMILES: CC(C)c1cnn2c(NCc3ccc(Cl)cc3C(F)(F)F)nc(S(C)(=O)=O)nc12] |
| (VI-av) | C16H17Cl2N5O2S | 413.05 | 414.1 | (XXII) | 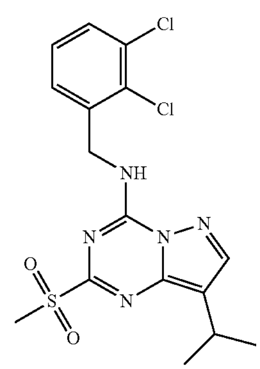 [SMILES: CC(C)c1cnn2c(NCc3cccc(Cl)c3Cl)nc(S(C)(=O)=O)nc12] |

-continued
| intermediate | formula | exact mass | MS(ES) [M + H]+ | from intermediate | structure |
|---|---|---|---|---|---|
| (VI-aw) | C17H22N6O4S2 | 438.11 | 439.3 | (XXII) | 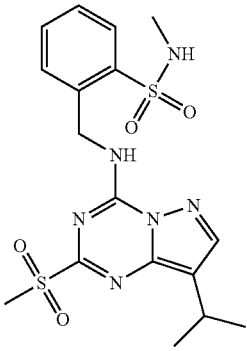 [SMILES: CNS(=O)(=O)c1ccccc1CNc1nc(S(C)(=O)=O)nc2c(C(C)C)cnn12] |
| (VI-ax) | C19H26N6O4S2 | 466.15 | 467.3 | (XXII) | 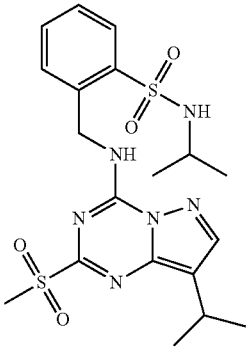 [SMILES: CC(C)NS(=O)(=O)c1ccccc1CNc1nc(S(C)(=O)=O)nc2c(C(C)C)cnn12] |
| (VI-ay) | C20H26N6O4S2 | 478.15 | 479.3 | (XXII) | 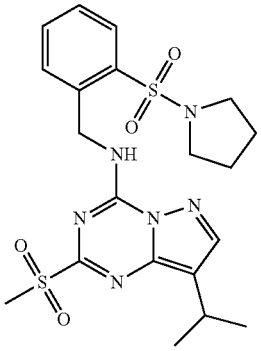 [SMILES: CC(C)c1cnn2c(NCc3ccccc3S(=O)(=O)N3CCCC3)nc(S(C)(=O)=O)nc12] |
| (VI-az) | C21H29N7O4S2 | 507.17 | 508.0 | (XXII) | 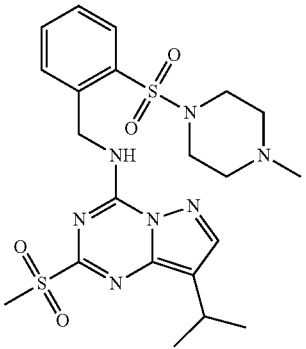 |

-continued

| intermediate | formula | exact mass | MS(ES) [M + H]+ | from intermediate | structure |
|---|---|---|---|---|---|
| (VI-ba) | C17H21N5O2S2 | 391.11 | 392.3 | (XXII) | 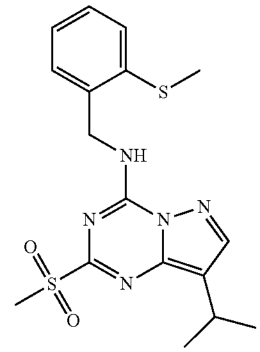 [SMILES: CSc1ccccc1CNc1nc(S(C)(=O)=O)nc2c(C(C)C)cnn12] |
| (VI-bb) | C18H22N6O3S | 402.15 | 403.3 | (XXII) | 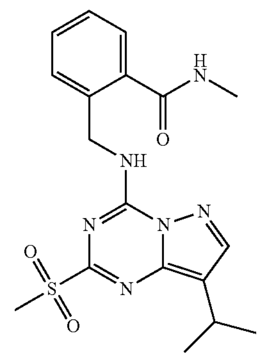 [SMILES: CNC(=O)c1ccccc1CNc1nc(S(C)(=O)=O)nc2c(C(C)C)cnn12] |
| (VI-bc) | C21H24N6O3S | 440.16 | 441.3 | (XXII) | 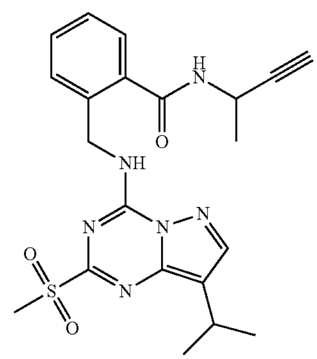 [SMILES: C#CC(C)NC(=O)c1ccccc1CNc1nc(S(C)(=O)=O)nc2c(C(C)C)cnn12] |
| (VI-bd) | C20H27N7O3S | 445.19 | 446.4 | (XXII) | 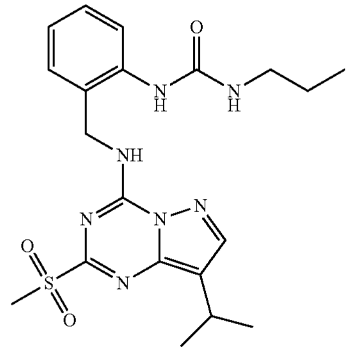 [SMILES: CCCNC(=O)Nc1ccccc1CNc1nc(S(C)(=O)=O)nc2c(C(C)C)cnn12] |

-continued

| intermediate | formula | exact mass | MS(ES) [M + H]+ | from intermediate | structure |
| --- | --- | --- | --- | --- | --- |
| (VI-be) | C23H25N7O3S | 479.17 | 480.2 | (XXII) | 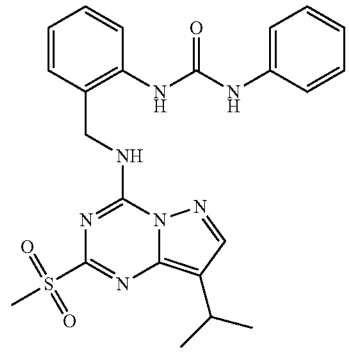 [SMILES: CC(C)c1cnn2c(NCc3ccccc3NC(=O)Nc3ccccc3)nc(S(C)(=O)=O)nc12] |
| (VI-bf) | C23H31N7O3S | 485.22 | 490.4 | (XXII) | 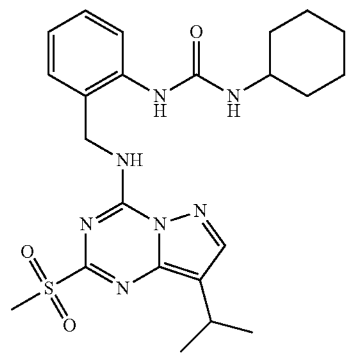 [SMILES: CC(C)c1cnn2c(NCc3ccccc3NC(=O)NC3CCCCC3)nc(S(C)(=O)=O)nc12] |
| (VI-bg) | C24H27N7O3S | 493.19 | 494.4 | (XXII) | 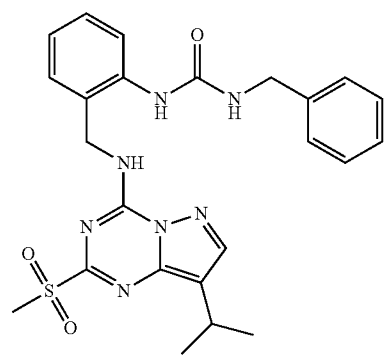 [SMILES: CC(C)c1cnn2c(NCc3ccccc3NC(=O)NCc3ccccc3)nc(S(C)(=O)=O)nc12] |
| (VI-bh) | C19H25N7O3S | 431.17 | 432.3 | (XXII) | 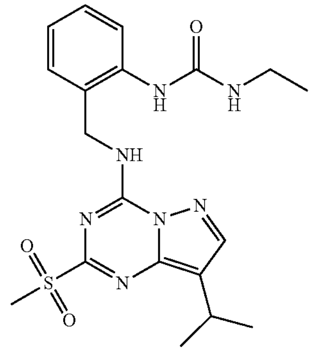 [SMILES: CCNC(=O)Nc1ccccc1CNc1nc(S(C)(=O)=O)nc2c(C(C)C)cnn12] |

-continued

| intermediate | formula | exact mass | MS(ES) [M + H]+ | from intermediate | structure |
|---|---|---|---|---|---|
| (VI-bi) | C21H27N5O2S2 | 445.16 | 446.0 | (XXII) | 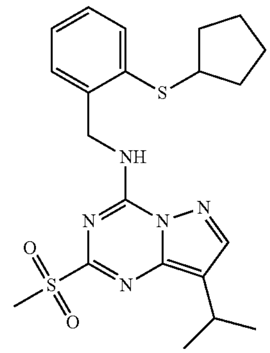 [SMILES: CC(C)c1cnn2c(NCc3ccccc3SC3CCCC3)nc(S(C)(=O)=O)nc12] |
| (VI-bj) | C21H29N5O3S | 431.20 | 431.9 | (XXII) | 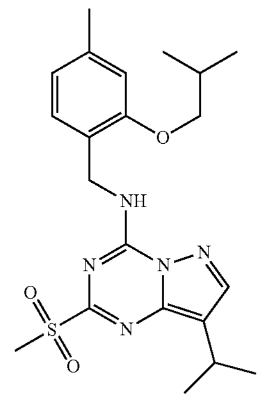 [SMILES: Cc1ccc(CNc2nc(S(C)(=O)=O)nc3c(C(C)C)cnn23)c(OCC(C)C)c1] |
| (VI-bk) | C19H23N5O4S | 417.15 | 417.9 | (XXII) | 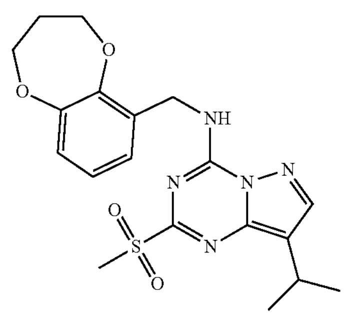 [SMILES: CC(C)c1cnn2c(NCc3cccc4c3OCCCO4)nc(S(C)(=O)=O)nc12] |
| (VI-bl) | C22H27N5O2S | 425.19 | 426.3 | (XXII) | 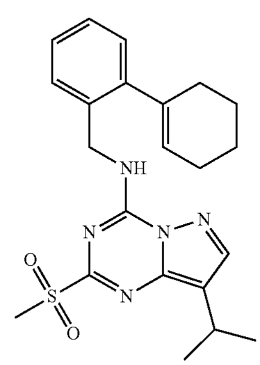 [SMILES: CC(C)c1cnn2c(NCc3ccccc3C3=CCCCC3)nc(S(C)(=O)=O)nc12] |

-continued

| intermediate | formula | exact mass | MS(ES) [M + H]+ | from intermediate | structure |
| --- | --- | --- | --- | --- | --- |
| (VI-bm) | C17H21N5O2S2 | 391.11 | 392.3 | (XXII) | 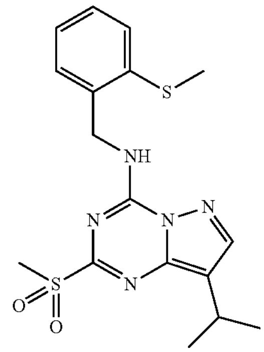 [SMILES: CSc1ccccc1CNc1nc(S(C)(=O)=O)nc2c(C(C)C)cnn12] |
| (VI-bn) | C23H25N5O3S | 451.17 | 452.4 | (XXII) | 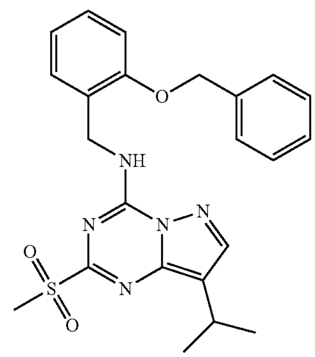 [SMILES: CC(C)c1cnn2c(NCc3ccccc3OCc3ccccc3)nc(S(C)(=O)=O)nc12] |
| (VI-bo) | C16H18IN5O2S | 471.02 | 472.2 | (XXII) | 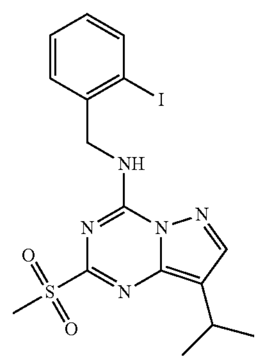 [SMILES: CC(C)c1cnn2c(NCc3ccccc3I)nc(S(C)(=O)=O)nc12] |
| (VI-bp) | C20H23N7O2S | 425.16 | 426.2 | (XXII) | 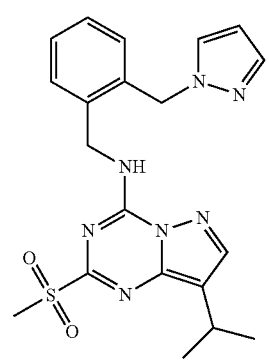 [SMILES: CC(C)c1cnn2c(NCc3ccccc3Cn3cccn3)nc(S(C)(=O)=O)nc12] |

-continued
| intermediate | formula | exact mass | MS(ES) [M + H]+ | from intermediate | structure |
|---|---|---|---|---|---|
| (VI-bq) | C16H17Cl2N5O2S | 413.05 | 414.2 | (XXII) | 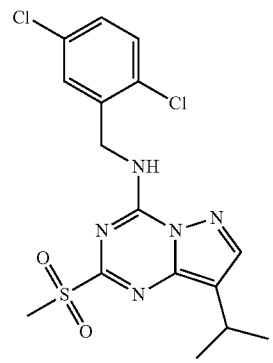 [SMILES: CC(C)c1cnn2c(NCc3cc(Cl)ccc3Cl)nc(S(C)(=O)=O)nc12] |
| (VI-br) | C20H26N6O2S | 414.18 | 415.3 | (XXII) | 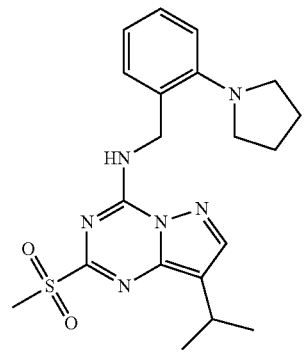 [SMILES: CC(C)c1cnn2c(NCc3ccccc3N3CCCC3)nc(S(C)(=O)=O)nc12] |
| (VI-bs) | C21H28N6O2S | 428.20 | 429.2 | (XXII) | 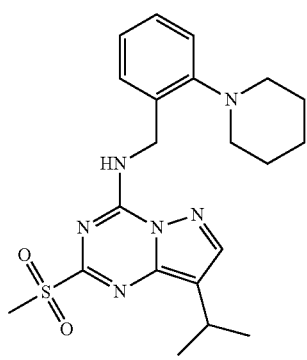 [SMILES: CC(C)c1cnn2c(NCc3ccccc3N3CCCCC3)nc(S(C)(=O)=O)nc12] |

Method C: Nucleophilic Substitution of Sulfones (VI) with O-Nucleophiles

Compound (VII-1): N-(2-(1H-pyrazol-1-yl)benzyl)-8-isopropyl-2-(piperidin-4-yloxy) pyrazolo[1,5-a][1,3,5]triazin-4-amine

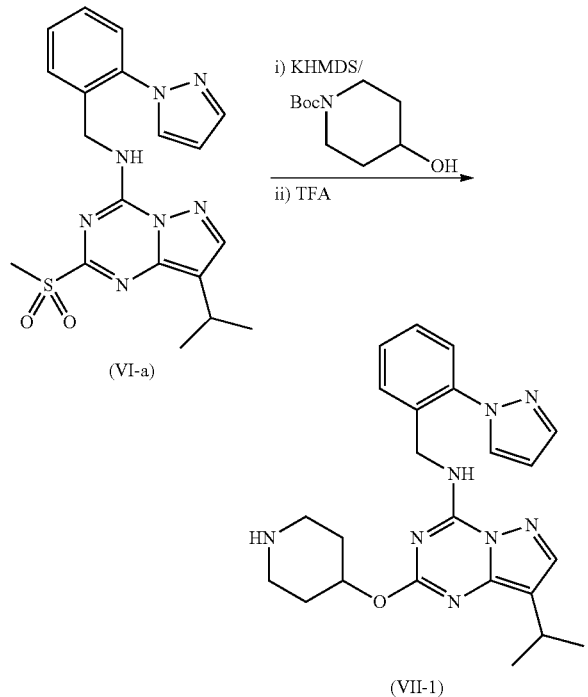

25 mg (0.061 mmol) methylsulfone (VI-a) were added to a solution of tert-butyl 4-hydroxypiperidine-1-carboxylate (37 mg, 0.183 mmol) and KHMDS (0.183 mmol) in DMF and stirred over night at 70° C. The reaction mixture was diluted with ethyl acetate, washed with 10% aqueous NaHCO₃ and brine, dried with MgSO₄, filtered and concentrated in vacuo. The Boc-protecting group was removed in TFA and the pure compound (VII-1) was obtained after RP-HPLC using a water/acetonitrile (0.1% TFA) gradient.

$^1$H-NMR (400 MHz, d$_6$-DMSO, 300K) δ 1.26 (d, J=6.8 Hz, 6H), 1.84 (m, broad, 2H), 2.07 (m, broad, 2H), 2.98 (h, J=6.8 Hz, 1H), 3.10 (m, broad, 2H), 3.20 (m, broad, 2H), 4.66 (d, J=6.4 Hz, 2H), 5.06 (m, 1H), 6.57 (dd, J$^1$=J$^2$=2.4 Hz, 1H), 7.43 (m, 4H), 7.81 (d, J=2.4 Hz, 1H), 7.96 (s, 1H), 8.20 (d, J=2.4 Hz, 1H), 9.15 (t, J=6.4 Hz, 1H); MS (ES) C23H28N8O requires 432.24. found 433.2 (M+H)$^+$.

Intermediate (XVII): 8-isopropyl-2-(methylsulfonyl) pyrazolo[1,5-a][1,3,5]triazin-4-ol

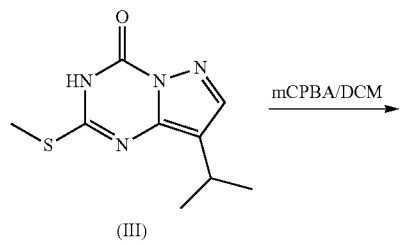

7.3 g (42.7 mmol) mCPBA were added in portions to 3.0 g (13.4 mmol) thioether (III) in 300 ml DCM. After the conversion to the sulfone was complete the reaction mixture was extracted with 2 M aqueous NaOH/brine (1:1). The aqueous phase was brought to pH=1 and extracted with ethyl acetate. The combined organic phases were dried (MgSO₄), filtered and concentrated under reduced pressure. The crude product was purified by silica column chromatography (gradient elution using cyclohexane/ethyl acetate).

$^1$H-NMR (400 MHz, d$_6$-DMSO, 300K) δ 1.25 (d, J=6.9 Hz, 6H), 3.02 (h, J=6.9 Hz, 1H), 3.19 (s, 3H), 7.73 (s, 1H); MS (ES) C9H12N4O3S requires 256.06. found 257.1 (M+H)$^+$.

Intermediate (XVII): 8-isopropyl-2-((1-methylpiperidin-4-yl)oxy)pyrazolo[1,5-a][1,3,5]triazin-4-ol

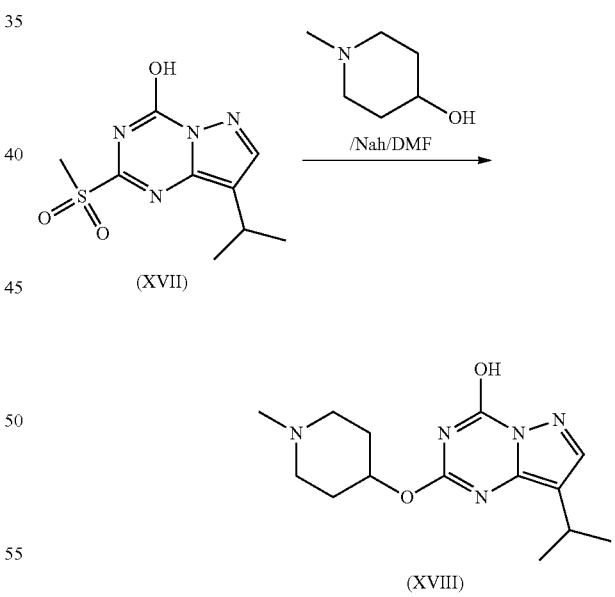

2.7 g (10.6 mmol) methylsulfone (XVII) in 10 ml DMF were added to a solution of 3.6 g (31.6 mmol) 1-methylpiperidin-4-ol and 0.76 g (31.6 mmol) NaH in 5 ml DMF. The reaction mixture was heated to 60° C. for 30 minutes, diluted with methanol, neutralized with 2 M aqueous HCl and absorbed on silica gel. Title compound (XVIII) was obtained after purification by column chromatography (silica gel, gradient elution with cyclohexane/ethyl acetate).

$^1$H-NMR (400 MHz, d$_6$-DMSO, 300K) δ 1.23 (d, J=6.9 Hz, 6H), 2.00-2.10 (m, broad, 2H), 2.17-2.27 (m, broad, 2H), 2.67 (s, 3H), 2.89 (h, J=6.9 Hz, 1H), 3.10-3.26 (m, broad, 4H), 5.13 (m, broad, 1H), 7.75 (s, 1H); MS (ES) C14H21N5O2 requires 291.17. found 292.1 (M+H)$^+$.

Intermediate (XIX): 4-chloro-8-isopropyl-2-((1-methylpiperidin-4-yl)oxy)pyrazolo[1,5-a][1,3,5]triazine

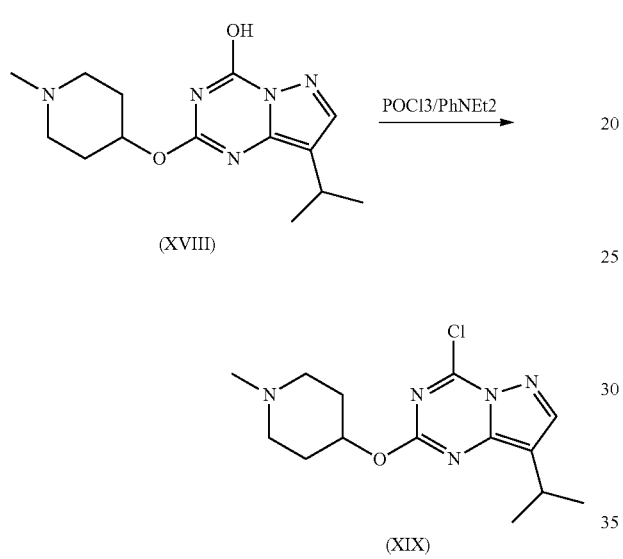

0.30 g (1.03 mmol) intermediate (XVIII), 4.7 g (30.9 mmol) POCl$_3$ and 0.46 g (3.09 mmol) N,N-diethylaniline were mixed and stirred at 80° C. for 2 h. Volatiles were removed under reduced pressure and the crude product was used in aliquots.

MS (ES) C14H20ClN5O requires 309.14. found 310.3 (M+H)$^+$.

Method G: Nucleophilic Substitution of Chloride (XIX) with Amines A$^1$NH$_2$

Compound (VII-56): N-(2-fluorobenzyl)-8-isopropyl-2-((1-methylpiperidin-4-yl)oxy)pyrazolo[1,5-a][1,3,5]triazin-4-amine

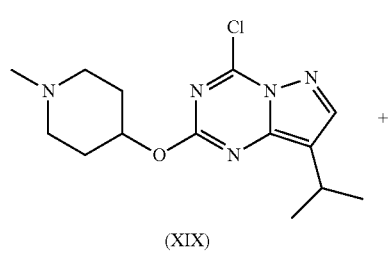

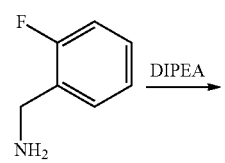

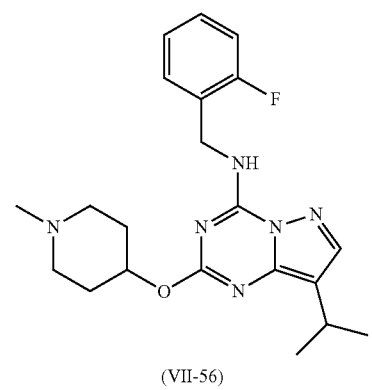

To 0.103 mmol intermediate (XIX) in 0.5 ml acetonitrile at 0° C. were added 66 µl DIPEA and 24 mg (0.19 mmol) (2-fluorophenyl)methanamine. The mixture was stirred at 40° C. for 1 h. compound (VII-56) was obtained after purification by RP-HPLC (gradient using water/acetonitrile containing 0.1% TFA).

$^1$H-NMR (400 MHz, d$_6$-DMSO, 300K) δ 1.25 (d, J=6.8 Hz, 6H), 1.71-2.2 (m, 4H), 2.79 (m, 3H), 2.97 (h, J=6.8 Hz, 1H), 3.11 (m, broad, 2H), 3.29-3.48 (m, broad, 2H), 4.70 (m, 2H), 5.00 (m, 1H), 7.12-7.20 (m, 4H), 7.96 (s, 1H), 9.29 (m, 1H); MS (ES) C21H27FN6O requires 398.22. found 399.5 (M+H)$^+$.

Compounds (VII-01)-(VII-141)

Title compounds (VII-2)-(VII-52), (VII-77)-(VII-126) and (VII-129)-(VII-141) were prepared from related methylsulfones (VI) similar to method C (in some cases NaH was used as base instead of KHMDS). Compounds (VII-53)-(VII-76) and (VII-127)-(VII-128) were synthesized similar to method G.

| Compound | formula | calculated | MS(ES) [M + H]+ | Starting material | name | structure |
|---|---|---|---|---|---|---|
| (VII-01) | C23H28N8O | 432.24 | 433.2 | (VI-a) | N-(2-(1H-pyrazol-1-yl)benzyl)-8-isopropyl-2-(piperidin-4-yloxy)pyrazolo[1,5-a][1,3,5]triazin-4-amine | 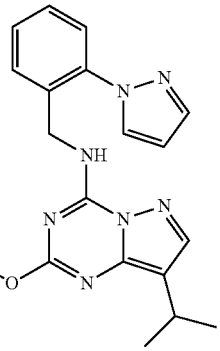 |
| (VII-02) | C22H26N8O | 418.22 | 418.9 | (VI-a) | (R)-N-(2-(1H-pyrazol-1-yl)benzyl)-8-isopropyl-2-(pyrrolidin-3-yloxy)pyrazolo[1,5-a][1,3,5]triazin-4-amine | 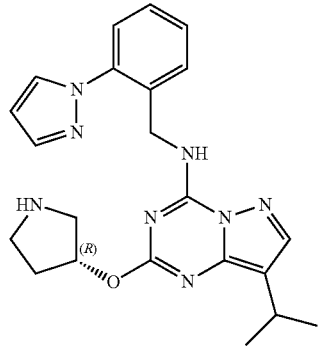 |
| (VII-03) | C23H28N8O | 432.24 | 433.3 | (VI-a) | (R)-N-(2-(1H-pyrazol-1-yl)benzyl)-8-isopropyl-2-(piperidin-3-yloxy)pyrazolo[1,5-a][1,3,5]triazin-4-amine | 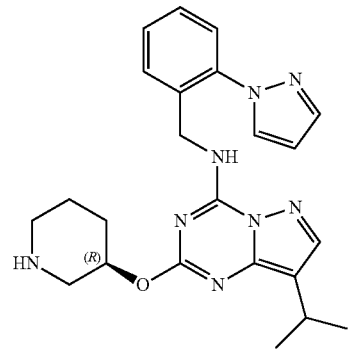 |
| VII-04) | C24H28N8O | 444.24 | 445.7 | (VI-a) | N-(2-(1H-pyrazol-1-yl)benzyl)-2-(2-azaspiro[3.3]heptan-6-yloxy)-8-isopropylpyrazolo[1,5-a][1,3,5]triazin-4-amine | 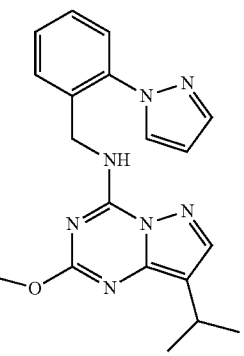 |

-continued

| Compound | formula | calculated | MS(ES) [M + H]+ | Starting material | name |
|---|---|---|---|---|---|
| (VII-05) | C26H32N8O2 | 488.26 | 489.4 | (VI-a) | 2-(1-oxa-8-azaspiro[4.5]decan-3-yloxy)-N-(2-(1H-pyrazol-1-yl)benzyl)-8-isopropylpyrazolo[1,5-a][1,3,5]triazin-4-amine |
| (VII-06) | C24H30N8O | 446.25 | 447.4 | (VI-a) | N-(1-(2-(1H-pyrazol-1-yl)phenyl)ethyl)-8-isopropyl-2-((R)-piperidin-3-yloxy)pyrazolo[1,5-a][1,3,5]triazin-4-amine |
| (VII-07) | C26H30N6O | 442.25 | 443.5 | (VI-b) | (R)-N-([1,1'-biphenyl]-2-ylmethyl)-8-isopropyl-2-(piperidin-3-yloxy)pyrazolo[1,5-a][1,3,5]triazin-4-amine |
| (VII-08) | C25H28N6O | 428.23 | 429.2 | (VI-b) | (R)-N-([1,1'-biphenyl]-2-ylmethyl)-8-isopropyl-2-(pyrrolidin-3-yloxy)pyrazolo[1,5-a][1,3,5]triazin-4-amine |

-continued

| Compound | formula | calculated | MS(ES) [M + H]+ | Starting material | name | structure |
| --- | --- | --- | --- | --- | --- | --- |
| (VII-09) | C26H30N6O | 442.25 | 443.3 | (VI-b) | N-([1,1'-biphenyl]-2-ylmethyl)-8-isopropyl-2-(piperidin-4-yloxy)pyrazolo[1,5-a][1,3,5]triazin-4-amine | 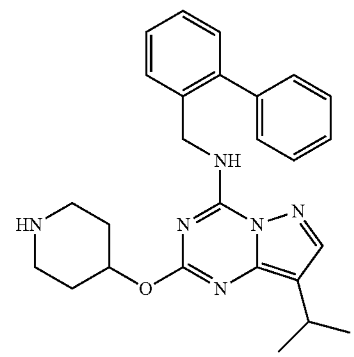 [SMILES: CC(C)c1cnn2c(NCc3ccccc3-c3ccccc3)nc(OC3CCNCC3)nc12] |
| (VII-10) | C22H30N6O2 | 410.24 | 411.4 | (VI-c) | 8-isopropyl-N-((S)-1-(2-methoxyphenyl)ethyl)-2-((R)-piperidin-3-yloxy)pyrazolo[1,5-a][1,3,5]triazin-4-amine | 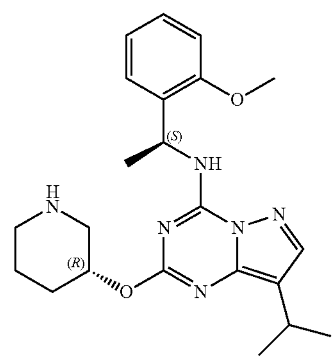 |
| (VII-11) | C21H28N6O2 | 396.23 | 397.4 | (VI-c) | 8-isopropyl-N-((S)-1-(2-methoxyphenyl)ethyl)-2-((R)-pyrrolidin-3-yloxy)pyrazolo[1,5-a][1,3,5]triazin-4-amine | 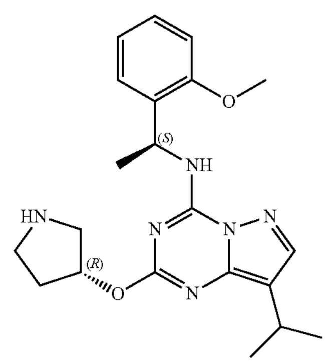 |
| (VII-12) | C24H28N6OS | 448.20 | 449.3 | (VI-d) | (R)-8-isopropyl-2-(piperidin-3-yloxy)-N-(2-(thiophen-2-yl)benzyl)pyrazolo[1,5-a][1,3,5]triazin-4-amine | 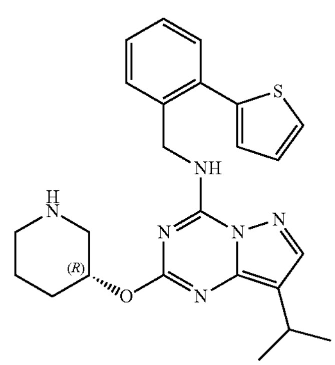 |

-continued

| Compound | formula | calculated | MS(ES) [M + H]+ | Starting material | name | structure |
|---|---|---|---|---|---|---|
| (VII-13) | C23H26N6OS | 434.19 | 435.3 | (VI-d) | (R)-8-isopropyl-2-(pyrrolidin-3-yloxy)-N-(2-(thiophen-2-yl)benzyl)pyrazolo[1,5-a][1,3,5]triazin-4-amine | 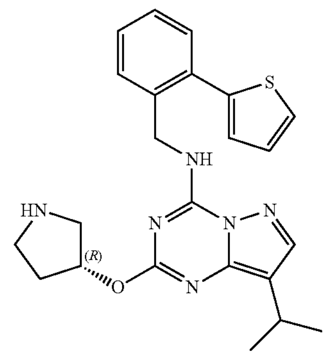 |
| (VII-14) | C24H28N6OS | 448.20 | 449.1 | (VI-d) | 8-isopropyl-2-(piperidin-4-yloxy)-N-(2-(thiophen-2-yl)benzyl)pyrazolo[1,5-a][1,3,5]triazin-4-amine | 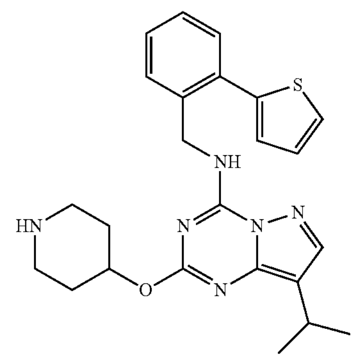 [SMILES: CC(C)c1cnn2c(NCc3ccccc3-c3cccs3)nc(OC3CCNCC3)nc12] |
| (VII-15) | C22H30N6O2 | 410.24 | 411.3 | (VI-c) | (S)-8-isopropyl-N-(1-(2-methoxyphenyl)ethyl)-2-(piperidin-4-yloxy)pyrazolo[1,5-a][1,3,5]triazin-4-amine | 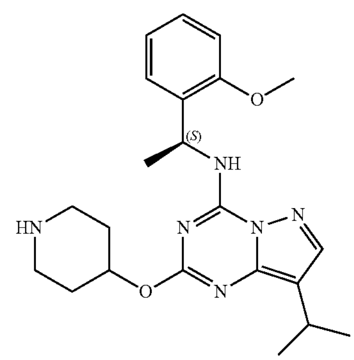 |
| (VII-16) | C22H30N6O2 | 410.24 | 411.1 | (VI-e) | (R)-N-(2-isopropoxybenzyl)-8-isopropyl-2-(pyrrolidin-3-yloxy)pyrazolo[1,5-a][1,3,5]triazin-4-amine | 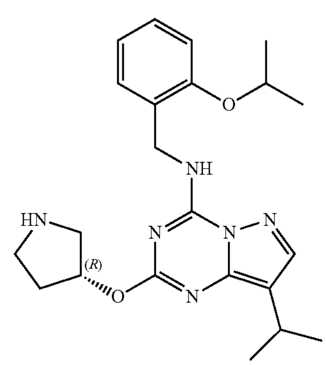 |

-continued

| Compound | formula | calculated | MS(ES) [M + H]+ | Starting material | name | structure |
| --- | --- | --- | --- | --- | --- | --- |
| (VII-17) | C23H32N6O2 | 424.26 | 425.4 | (VI-e) | N-(2-isopropoxybenzyl)-8-isopropyl-2-(piperidin-4-yloxy)pyrazolo[1,5-a][1,3,5]triazin-4-amine | 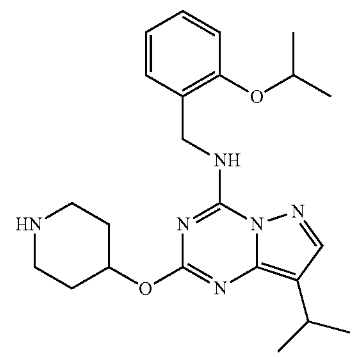 [SMILES: CC(C)Oc1ccccc1CNc1nc(OC2CCNCC2)nc2c(C(C)C)cnn12] |
| (VII-18) | C23H32N6O2 | 424.26 | 425.3 | (VI-e) | (R)-N-(2-isopropoxybenzyl)-8-isopropyl-2-(piperidin-3-yloxy)pyrazolo[1,5-a][1,3,5]triazin-4-amine | 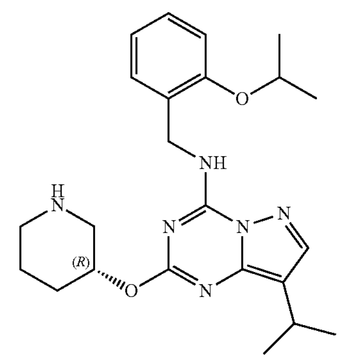 |
| (VII-19) | C23H28N8O | 432.24 | 433.4 | (VI-f) | N-(2-(1H-imidazol-1-yl)benzyl)-8-isopropyl-2-(piperidin-4-yloxy)pyrazolo[1,5-a][1,3,5]triazin-4-amine | 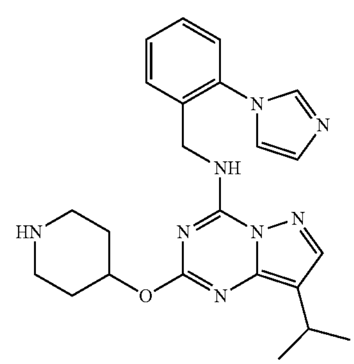 [SMILES: CC(C)c1cnn2c(NCc3ccccc3-n3ccnc3)nc(OC3CCNCC3)nc12] |
| (VII-20) | C22H27N9O | 433.23 | 434.3 | (VI-g) | (R)-N-(2-(1H-1,2,4-triazol-1-yl)benzyl)-8-isopropyl-2-(piperidin-3-yloxy)pyrazolo[1,5-a][1,3,5]triazin-4-amine | 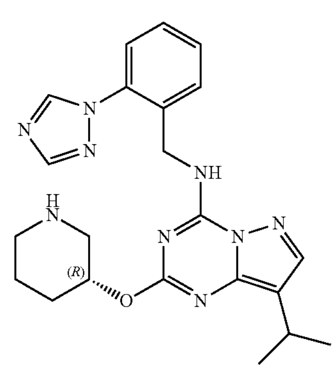 |

-continued

| Compound | formula | calculated | MS(ES) [M + H]+ | Starting material | name | structure |
|---|---|---|---|---|---|---|
| (VII-21) | C21H25N9O | 419.22 | 419.8 | (VI-g) | (R)-N-(2-(1H-1,2,4-triazol-1-yl)benzyl)-8-isopropyl-2-(pyrrolidin-3-yloxy)pyrazolo[1,5-a][1,3,5]triazin-4-amine | 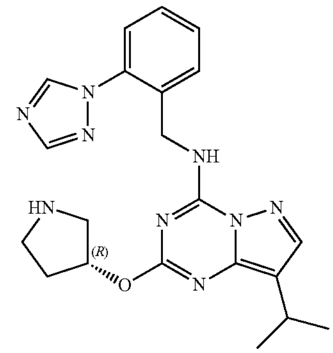 |
| (VII-22) | C22H27N9O | 433.23 | 434.0 | (VI-g) | N-(2-(1H-1,2,4-triazol-1-yl)benzyl)-8-isopropyl-2-(piperidin-4-yloxy)pyrazolo[1,5-a][1,3,5]triazin-4-amine | 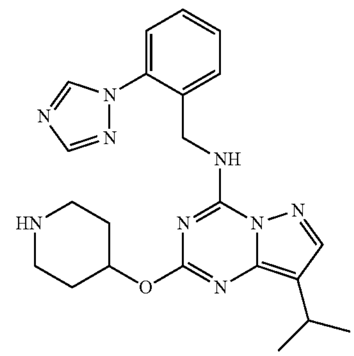 [SMILES: CC(C)c1cnn2c(NCc3ccccc3-n3cncn3)nc(OC3CCNCC3)nc12] |
| (VII-23) | C24H30N8O | 446.25 | 447.2 | (VI-h) | (R)-8-isopropyl-N-(2-(2-methyl-1H-imidazol-1-yl)benzyl)-2-(piperidin-3-yloxy)pyrazolo[1,5-a][1,3,5]triazin-4-amine | 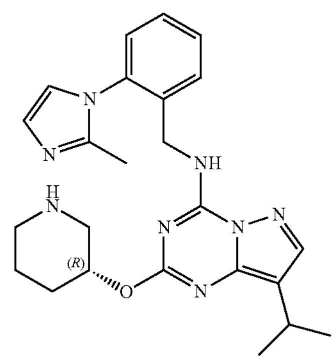 |
| (VII-24) | C24H30N8O | 446.25 | 447.3 | (VI-h) | 8-isopropyl-N-(2-(2-methyl-1H-imidazol-1-yl)benzyl)-2-(piperidin-4-yloxy)pyrazolo[1,5-a][1,3,5]triazin-4-amine | 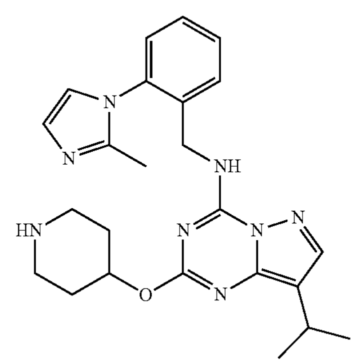 [SMILES: Cc1nccn1-c1ccccc1CNc1nc(OC2CCNCC2)nc2c(C(C)C)cnn12] |

-continued

| Compound | formula | calculated | MS(ES) [M + H]+ | Starting material | name | structure |
|---|---|---|---|---|---|---|
| (VII-25) | C23H28N8O*2C2HF3O2 | 432.24 | 433.3 | (VI-h) | (R)-8-isopropyl-N-(2-(2-methyl-1H-imidazol-1-yl)benzyl)-2-(pyrrolidin-3-yloxy)pyrazolo[1,5-a][1,3,5]triazin-4-amine | 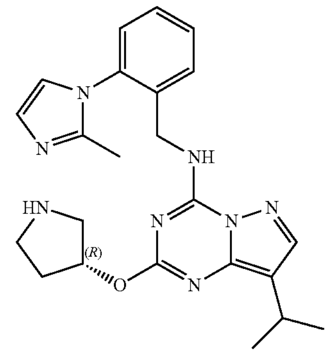 |
| (VII-26) | C23H28N8O | 432.24 | 433.2 | (VI-f) | (R)-N-(2-(1H-imidazol-1-yl)benzyl)-8-isopropyl-2-(piperidin-3-yloxy)pyrazolo[1,5-a][1,3,5]triazin-4-amine | 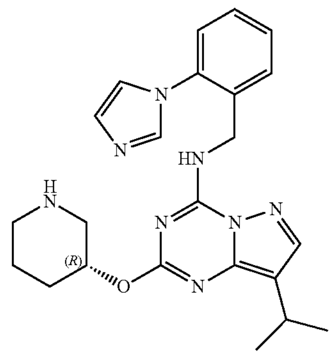 |
| (VII-27) | C22H26N8O*2C2HF3O2 | 418.22 | 419.3 | (VI-f) | (R)-N-(2-(1H-imidazol-1-yl)benzyl)-8-isopropyl-2-(pyrrolidin-3-yloxy)pyrazolo[1,5-a][1,3,5]triazin-4-amine | 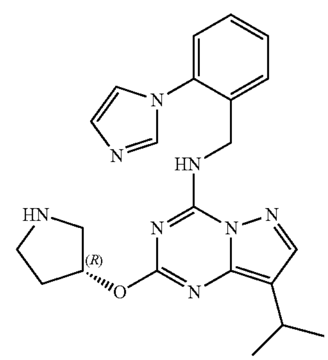 |
| (VII-28) | C21H27ClN6O | 414.19 | 415.4 | (VI-i) | N-((S)-1-(2-chlorophenyl)ethyl)-8-isopropyl-2-((R)-piperidin-3-yloxy)pyrazolo[1,5-a][1,3,5]triazin-4-amine | 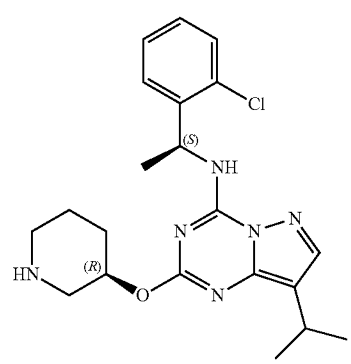 |

-continued

| Compound | formula | calculated | MS(ES) [M + H]+ | Starting material | name | structure |
|---|---|---|---|---|---|---|
| (VII-29) | C22H28N10O | 448.24 | 449.3 | (VI-j) | (R)-8-isopropyl-N-(2-(1-methyl-1H-tetrazol-5-yl)benzyl)-2-(piperidin-3-yloxy)pyrazolo[1,5-a][1,3,5]triazin-4-amine | 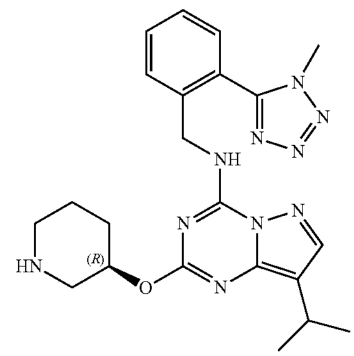 |
| (VII-30) | C23H27N7O2 | 433.22 | 434.1 | (VI-k) | (R)-5-(((8-isopropyl-2-(piperidin-3-yloxy)pyrazolo[1,5-a][1,3,5]triazin-4-yl)amino)methyl)quinoline 1-oxide | 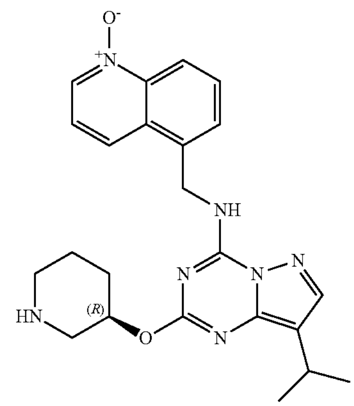 |
| (VII-31) | C23H27N7O | 417.23 | 418.3 | (VI-l) | (R)-8-isopropyl-N-(isoquinolin-8-ylmethyl)-2-(piperidin-3-yloxy)pyrazolo[1,5-a][1,3,5]triazin-4-amine | 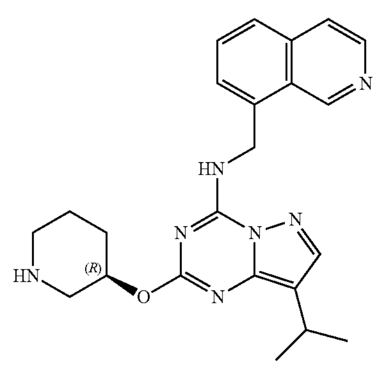 |
| (VII-32) | C23H27N7O2 | 433.22 | 434.0 | (VI-m) | (R)-8-(((8-isopropyl-2-(piperidin-3-yloxy)pyrazolo[1,5-a][1,3,5]triazin-4-yl)amino)methyl)isoquinoline 2-oxide | 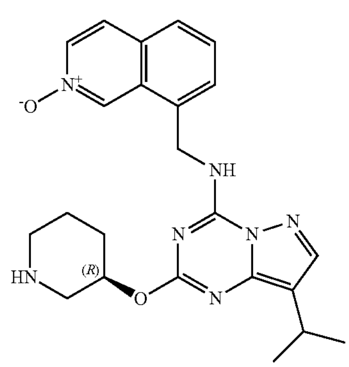 |

-continued

| Compound | formula | calculated | MS(ES) [M + H]⁺ | Starting material | name | structure |
|---|---|---|---|---|---|---|
| (VII-33) | C22H28N8O | 420.24 | 421.4 | (VI-n) | (R)-8-isopropyl-N-((1-methyl-1H-indazol-4-yl)methyl)-2-(piperidin-3-yloxy)pyrazolo[1,5-a][1,3,5]triazin-4-amine | 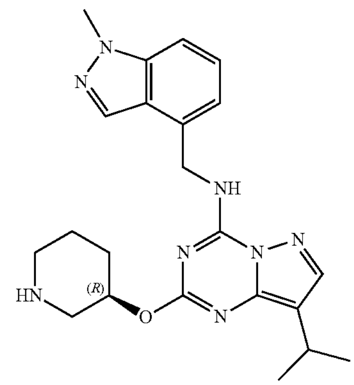 |
| (VII-34) | C25H29N7O | 443.24 | 444.4 | (VI-o) | (R)-8-isopropyl-2-(piperidin-3-yloxy)-N-(2-(pyridin-2-yl)benzyl)pyrazolo[1,5-a][1,3,5]triazin-4-amine | 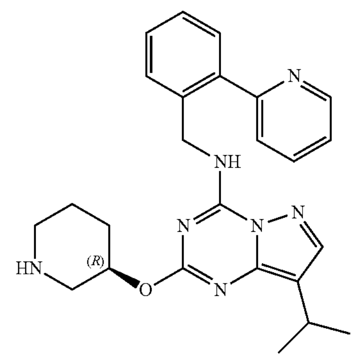 |
| (VII-35) | C23H27N7O | 417.23 | 418.3 | (VI-p) | (R)-8-isopropyl-2-(piperidin-3-yloxy)-N-(quinolin-8-ylmethyl)pyrazolo[1,5-a][1,3,5]triazin-4-amine | 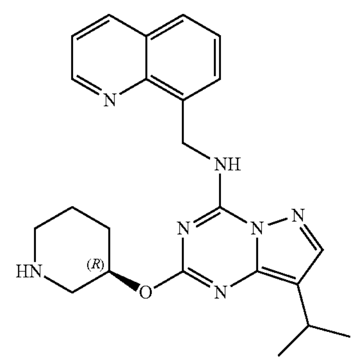 |
| (VII-36) | C21H26N8O | 406.22 | 407.3 | (VI-r) | (R)-N-((1H-indazol-4-yl)methyl)-8-isopropyl-2-(piperidin-3-yloxy)pyrazolo[1,5-a][1,3,5]triazin-4-amine | 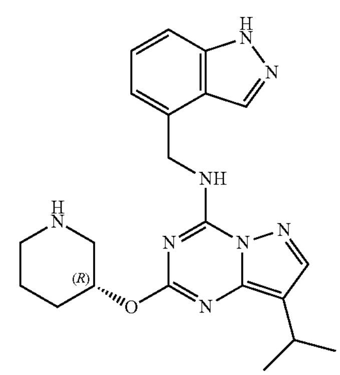 |

-continued

| Compound | formula | calculated | MS(ES) [M + H]+ | Starting material | name | structure |
|---|---|---|---|---|---|---|
| (VII-37) | C22H28N10O | 448.24 | 449.5 | (VI-t) | (R)-8-isopropyl-N-(2-(2-methyl-2H-tetrazol-5-yl)benzyl)-2-(piperidin-3-yloxy)pyrazolo[1,5-a][1,3,5]triazin-4-amine | 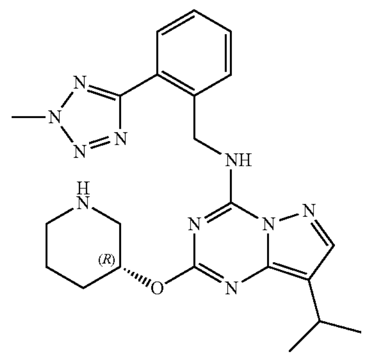 |
| (VII-38) | C22H31N7O3S | 473.22 | 474.4 | (VI-u) | (R)-2-(((8-isopropyl-2-(piperidin-3-yloxy)pyrazolo[1,5-a][1,3,5]triazin-4-yl)amino)methyl)-N,N-dimethylbenzene-sulfonamide | 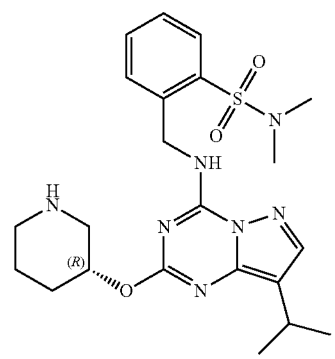 |
| (VII-39) | C24H31N7O2 | 449.25 | 450.5 | (VI-s) | (R)-1-(2-(((8-isopropyl-2-(piperidin-3-yloxy)pyrazolo[1,5-a][1,3,5]triazin-4-yl)amino)methyl)phenyl)pyrrolidin-2-one | 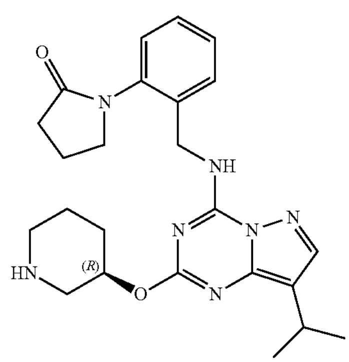 |
| (VII-40) | C23H29N7O2 | 435.238273 | 436.4 | (VI-v) | (R)-1-(2-(((8-isopropyl-2-(piperidin-3-yloxy)pyrazolo[1,5-a][1,3,5]triazin-4-yl)amino)methyl)phenyl)azetidin-2-one | 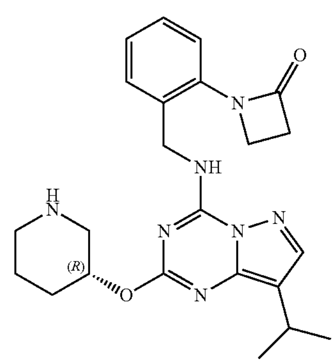 |

-continued

| Compound | formula | calculated | MS(ES) [M + H]+ | Starting material | name | structure |
| --- | --- | --- | --- | --- | --- | --- |
| (VII-41) | C23H27FN8O | 450.23 | 451.5 | (VI-w) | (R)-N-(5-fluoro-2-(1H-pyrazol-1-yl)benzyl)-8-isopropyl-2-(piperidin-3-yloxy)pyrazolo[1,5-a][1,3,5]triazin-4-amine | 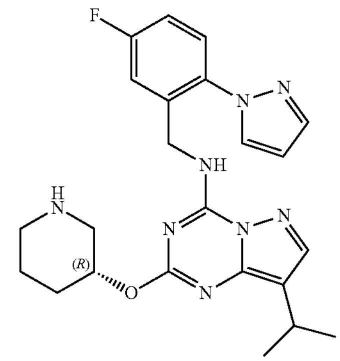 |
| (VII-42) | C23H27FN8O | 450.23 | 451.4 | (VI-x) | (R)-N-(3-fluoro-2-(1H-pyrazol-1-yl)benzyl)-8-isopropyl-2-(piperidin-3-yloxy)pyrazolo[1,5-a][1,3,5]triazin-4-amine | 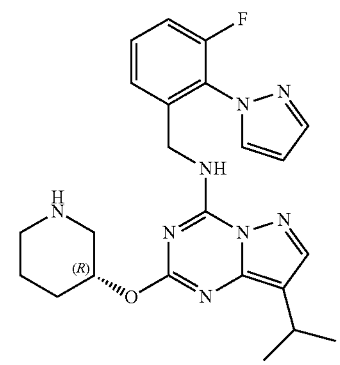 |
| (VII-43) | C23H27FN8O | 450.23 | 451.4 | (VI-y) | (R)-N-(4-fluoro-2-(1H-pyrazol-1-yl)benzyl)-8-isopropyl-2-(piperidin-3-yloxy)pyrazolo[1,5-a][1,3,5]triazin-4-amine | 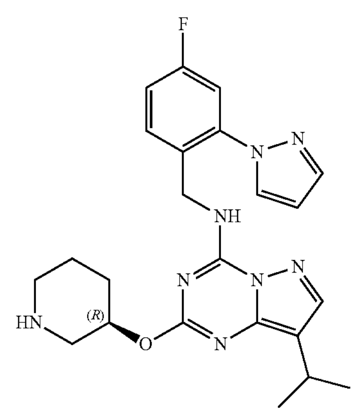 |
| (VII-44) | C23H27FN8O | 450.23 | 451.5 | (VI-z) | (R)-N-(2-fluoro-6-(1H-pyrazol-1-yl)benzyl)-8-isopropyl-2-(piperidin-3-yloxy)pyrazolo[1,5-a][1,3,5]triazin-4-amine | 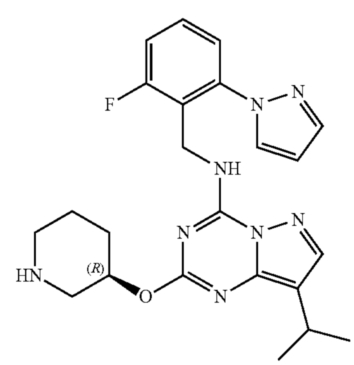 |

-continued

| Compound | formula | calculated | MS(ES) [M + H]+ | Starting material | name | structure |
|---|---|---|---|---|---|---|
| (VII-45) | C26H31N7O | 457.26 | 458.3 | (VI-aa) | 8-isopropyl-2-((1-methylpiperidin-4-yl)oxy)-N-(2-(pyridin-3-yl)benzyl)pyrazolo[1,5-a][1,3,5]triazin-4-amine | 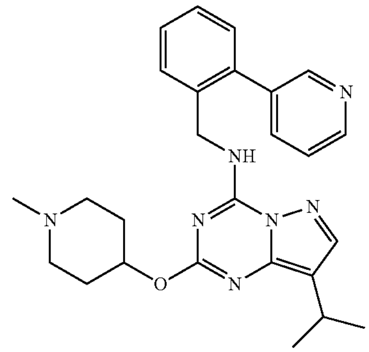 [SMILES: CC(C)c1cnn2c(NCc3ccccc3-c3cccnc3)nc(OC3CCN(C)CC3)nc12] |
| (VII-46) | C25H29N7O | 443.24 | 444.3 | (VI-aa) | (R)-8-isopropyl-2-(piperidin-3-yloxy)-N-(2-(pyridin-3-yl)benzyl)pyrazolo[1,5-a][1,3,5]triazin-4-amine | 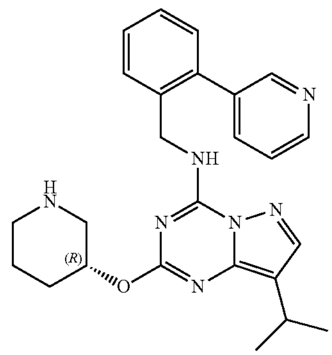 |
| (VII-47) | C27H32N6O2 | 472.26 | 472.9 | (VI-ab) | 8-isopropyl-2-((1-methylpiperidin-4-yl)oxy)-N-(2-phenoxybenzyl)pyrazolo[1,5-a][1,3,5]triazin-4-amine | 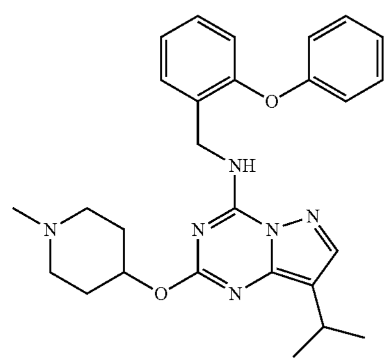 [SMILES: CC(C)c1cnn2c(NCc3ccccc3Oc3ccccc3)nc(OC3CCN(C)CC3)nc12] |
| (VII-48) | C26H30N6O2 | 458.24 | 459.0 | (VI-ab) | (R)-8-isopropyl-N-(2-phenoxybenzyl)-2-(piperidin-3-yloxy)pyrazolo[1,5-a][1,3,5]triazin-4-amine | 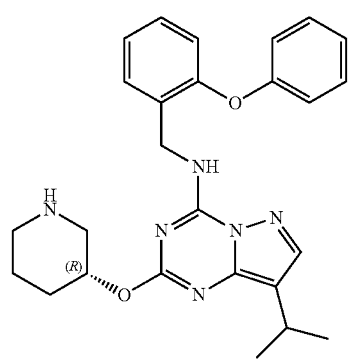 |

-continued

| Compound | formula | calculated | MS(ES) [M + H]+ | Starting material | name | structure |
| --- | --- | --- | --- | --- | --- | --- |
| (VII-49) | C23H27N7O2 | 433.22 | 434.7 | (VI-ac) | (R)-8-isopropyl-N-(2-(oxazol-2-yl)benzyl)-2-(piperidin-3-yloxy)pyrazolo[1,5-a][1,3,5]triazin-4-amine | 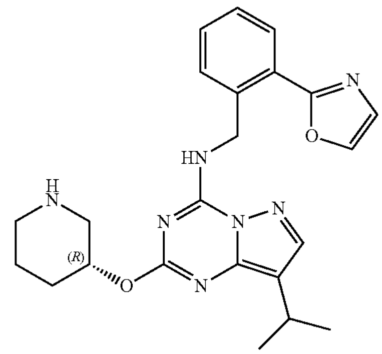 |
| (VII-50) | C24H28N6O2 | 432.23 | 433.6 | (VI-ad) | (R)-N-(2-(furan-2-yl)benzyl)-8-isopropyl-2-(piperidin-3-yloxy)pyrazolo[1,5-a][1,3,5]triazin-4-amine | 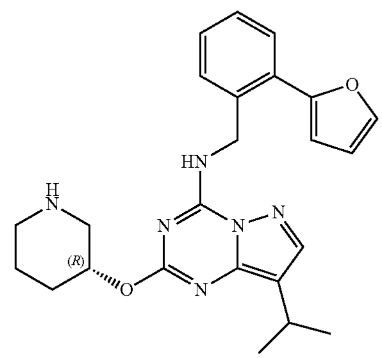 |
| (VII-51) | C22H29N7O2 | 423.24 | 424.3 | (VI-ae) | (R)-N-(2-(((8-isopropyl-2-(piperidin-3-yloxy)pyrazolo[1,5-a][1,3,5]triazin-4-yl)amino)methyl)phenyl)acetamide | 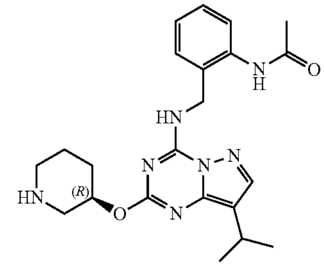 |
| (VII-52) | C23H27ClN8O | 466.20 | 467.3 | (VI-af) | (R)-N-(2-(4-chloro-1H-pyrazol-1-yl)benzyl)-8-isopropyl-2-(piperidin-3-yloxy)pyrazolo[1,5-a][1,3,5]triazin-4-amine | 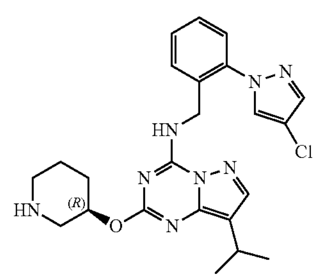 |

-continued

| Compound | formula | calculated | MS(ES) [M + H]+ | Starting material | name | structure |
|---|---|---|---|---|---|---|
| (VII-53) | C22H30N6O | 394.25 | 395.47 | (XIX) | 8-isopropyl-N-(2-methylbenzyl)-2-((1-methylpiperidin-4-yl)oxy)pyrazolo[1,5-a][1,3,5]triazin-4-amine | 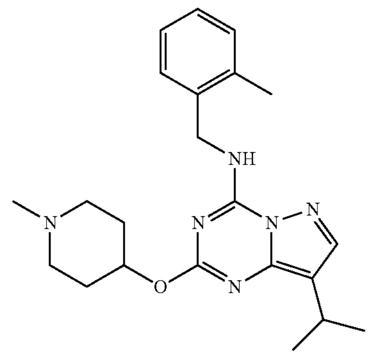 [SMILES: Cc1ccccc1CNc1nc(OC2CCN(C)CC2)nc2c(C(C)C)cnn12] |
| (VII-54) | C23H33N7O | 423.27 | 424.46 | (XIX) | N-(2-(dimethylamino)benzyl)-8-isopropyl-2-((1-methylpiperidin-4-yl)oxy)pyrazolo[1,5-a][1,3,5]triazin-4-amine | 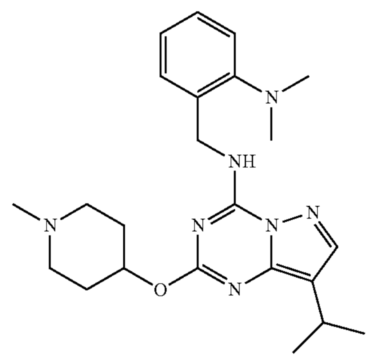 [SMILES: CC(C)c1cnn2c(NCc3ccccc3N(C)C)nc(OC3CCN(C)CC3)nc12] |
| (VII-55) | C22H27N7O | 405.23 | 406.3 | (XIX) | 2-(((8-isopropyl-2-((1-methylpiperidin-4-yl)oxy)pyrazolo[1,5-a][1,3,5]triazin-4-yl)amino)methyl)benzonitrile | 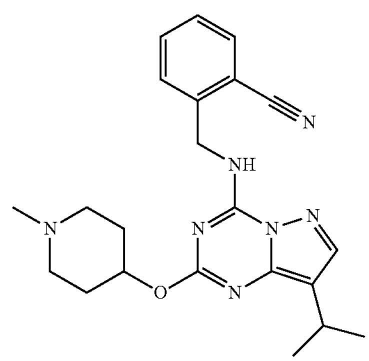 [SMILES: CC(C)c1cnn2c(NCc3ccccc3C#N)nc(OC3CCN(C)CC3)nc12] |
| (VII-56) | C21H27FN6O | 398.22 | 399.4 | (XIX) | N-(2-fluorobenzyl)-8-isopropyl-2-((1-methylpiperidin-4-yl)oxy)pyrazolo[1,5-a][1,3,5]triazin-4-amine | 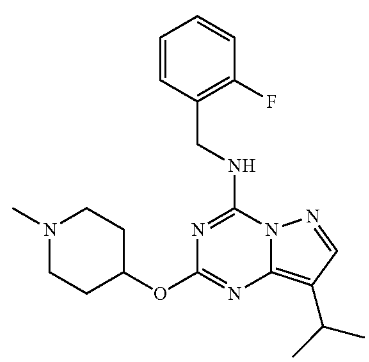 |

-continued

| Compound | formula | calculated | MS(ES) [M + H]+ | Starting material | name | structure |
|---|---|---|---|---|---|---|
| (VII-57) | C27H32N6O | 456.26 | 457.09 | (XIX) | N-([1,1'-biphenyl]-2-ylmethyl)-8-isopropyl-2-((1-methylpiperidin-4-yl)oxy)pyrazolo[1,5-a][1,3,5]triazin-4-amine | 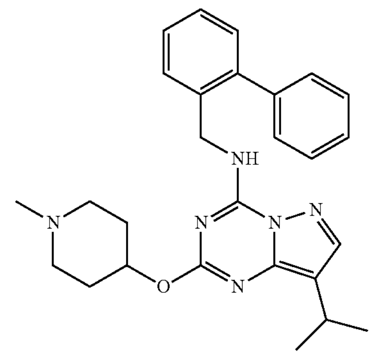 [SMILES: CC(C)c1cnn2c(NCc3ccccc3-c3ccccc3)nc(OC3CCN(C)CC3)nc12] |
| (VII-58) | C22H27F3N6O | 448.22 | 449.18 | (XIX) | 8-isopropyl-2-((1-methylpiperidin-4-yl)oxy)-N-(2-(trifluoromethyl)benzyl)pyrazolo[1,5-a][1,3,5]triazin-4-amine | 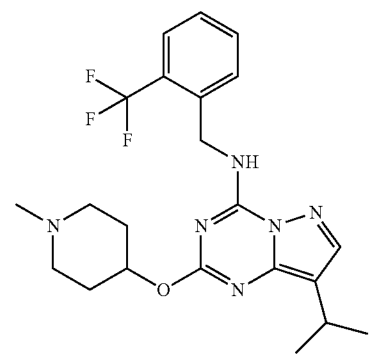 [SMILES: CC(C)c1cnn2c(NCc3ccccc3C(F)(F)F)nc(OC3CCN(C)CC3)nc12] |
| (VII-59) | C24H30N8O | 446.25 | 447.49 | (XIX) | N-(2-(1H-imidazol-1-yl)benzyl)-8-isopropyl-2-((1-methylpiperidin-4-yl)oxy)pyrazolo[1,5-a][1,3,5]triazin-4-amine | 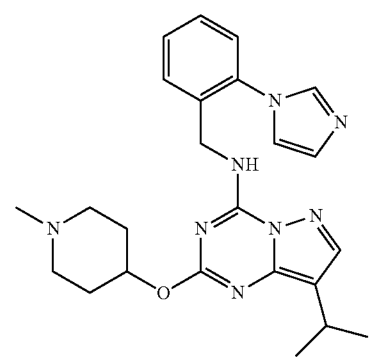 [SMILES: CC(C)c1cnn2c(NCc3ccccc3-n3ccnc3)nc(OC3CCN(C)CC3)nc12] |
| (VII-60) | C25H35N7O2 | 465.29 | 466.36 | (XIX) | 8-isopropyl-2-((1-methylpiperidin-4-yl)oxy)-N-(2-morpholinobenzyl)pyrazolo[1,5-a][1,3,5]triazin-4-amine | 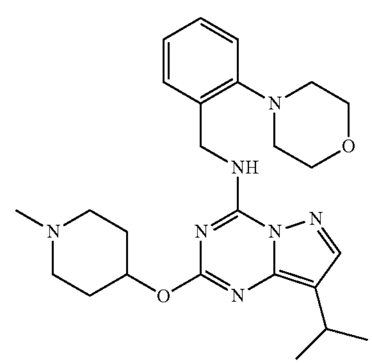 [SMILES: CC(C)c1cnn2c(NCc3ccccc3N3CCOCC3)nc(OC3CCN(C)CC3)nc12] |

-continued

| Compound | formula | calculated | MS(ES) [M + H]+ | Starting material | name | structure |
|---|---|---|---|---|---|---|
| (VII-61) | C25H30N6O | 430.25 | 431.21 | (XIX) | 8-isopropyl-2-((1-methylpiperidin-4-yl)oxy)-N-(naphthalen-1-ylmethyl)pyrazolo[1,5-a][1,3,5]triazin-4-amine | 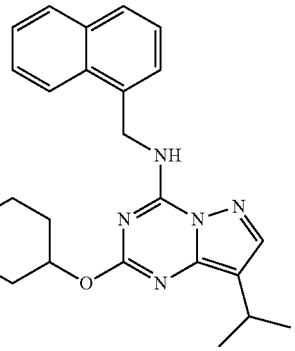 |
| (VII-62) | C22H29ClN6O | 428.21 | 429.19 | (XIX) | N-(2-chloro-6-methylbenzyl)-8-isopropyl-2-((1-methylpiperidin-4-yl)oxy)pyrazolo[1,5-a][1,3,5]triazin-4-amine | 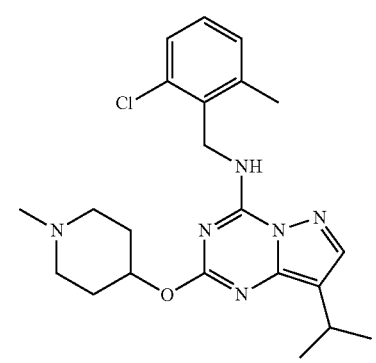 [SMILES: Cc1cccc(Cl)c1CNc1nc(OC2CCN(C)CC2)nc2c(C(C)C)cnn12] |
| (VII-63) | C21H26Cl2N6O | 448.15 | 449.14 | (XIX) | N-(2,6-dichlorobenzyl)-8-isopropyl-2-((1-methylpiperidin-4-yl)oxy)pyrazolo[1,5-a][1,3,5]triazin-4-amine | 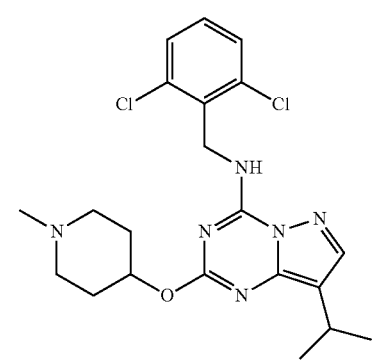 [SMILES: CC(C)c1cnn2c(NCc3c(Cl)cccc3Cl)nc(OC3CCN(C)CC3)nc12] |
| (VII-64) | C21H26F2N6O | 416.21 | 417.19 | (XIX) | N-(2,6-difluorobenzyl)-8-isopropyl-2-((1-methylpiperidin-4-yl)oxy)pyrazolo[1,5-a][1,3,5]triazin-4-amine | 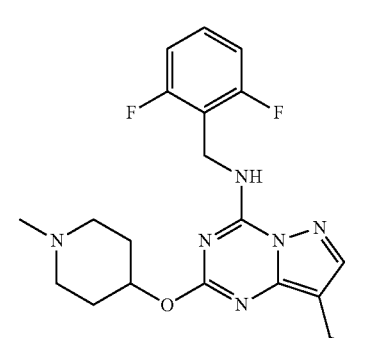 |

-continued

| Compound | formula | calculated | MS(ES) [M + H]+ | Starting material | name | structure |
| --- | --- | --- | --- | --- | --- | --- |
| (VII-65) | C25H30N6OS | 462.22 | 463.43 | (XIX) | 8-isopropyl-2-((1-methylpiperidin-4-yl)oxy)-N-(2-(thiophen-2-yl)benzyl)pyrazolo[1,5-a][1,3,5]triazin-4-amine | 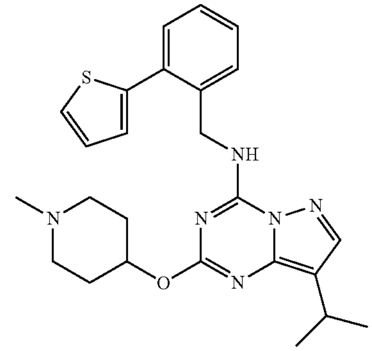 [SMILES: CC(C)c1cnn2c(NCc3ccccc3-c3cccs3)nc(OC3CCN(C)CC3)nc12] |
| (VII-66) | C24H34N6O2 | 438.27 | 439.09 | (XIX) | N-(2-isopropoxybenzyl)-8-isopropyl-2-((1-methylpiperidin-4-yl)oxy)pyrazolo[1,5-a][1,3,5]triazin-4-amine | 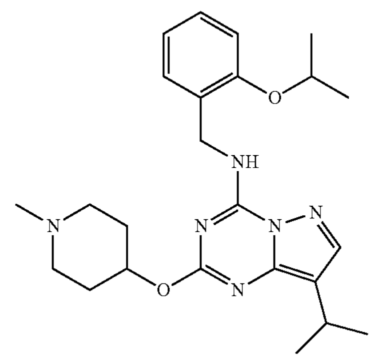 [SMILES: CC(C)Oc1ccccc1CNc1nc(OC2CCN(C)CC2)nc2c(C(C)C)cnn12] |
| (VII-67) | C23H32N6O2 | 424.26 | 425.25 | (XIX) | (S)-8-isopropyl-N-(1-(2-methoxyphenyl)ethyl)-2-((1-methylpiperidin-4-yl)oxy)pyrazolo[1,5-a][1,3,5]triazin-4-amine | 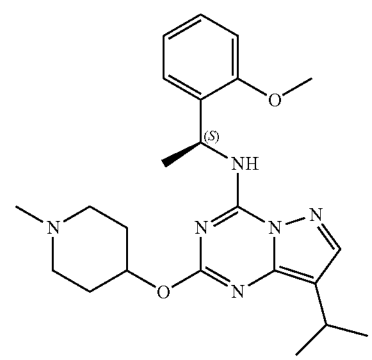 |
| (VII-68) | C21H27ClN6O | 414.19 | 415.35 | (XIX) | N-(2-chlorobenzyl)-8-isopropyl-2-((1-methylpiperidin-4-yl)oxy)pyrazolo[1,5-a][1,3,5]triazin-4-amine | 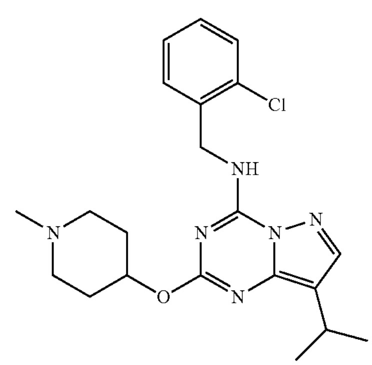 [SMILES: CC(C)c1cnn2c(NCc3ccccc3Cl)nc(OC3CCN(C)CC3)nc12] |

-continued

| Compound | formula | calculated | MS(ES) [M + H]+ | Starting material | name | structure |
|---|---|---|---|---|---|---|
| (VII-69) | C26H32N6O | 444.26 | 445.39 | (XIX) | (S)-8-isopropyl-2-((1-methylpiperidin-4-yl)oxy)-N-(1-(naphthalen-1-yl)ethyl)pyrazolo[1,5-a][1,3,5]triazin-4-amine | 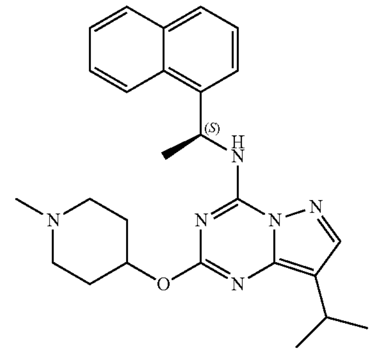 |
| (VII-70) | C23H32N6O2 | 424.26 | 425.17 | (XIX) | N-(2-ethoxybenzyl)-8-isopropyl-2-((1-methylpiperidin-4-yl)oxy)pyrazolo[1,5-a][1,3,5]triazin-4-amine | 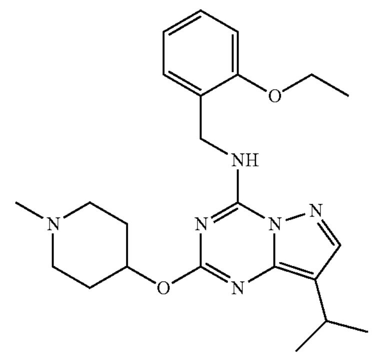 [SMILES: CCOc1ccccc1CNc1nc(OC2CCN(C)CC2)nc2c(C(C)C)cnn12] |
| (VII-71) | C22H30N6O2 | 410.24 | 411.07 | (XIX) | 8-isopropyl-N-(2-methoxybenzyl)-2-((1-methylpiperidin-4-yl)oxy)pyrazolo[1,5-a][1,3,5]triazin-4-amine | 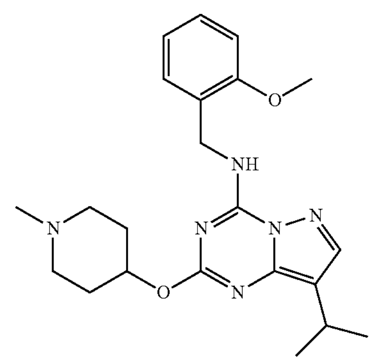 [SMILES: COc1ccccc1CNc1nc(OC2CCN(C)CC2)nc2c(C(C)C)cnn12] |
| (VII-72) | C22H28F2N6O2 | 446.22 | 447.08 | (XIX) | N-(2-(difluoromethoxy)benzyl)-8-isopropyl-2-((1-methylpiperidin-4-yl)oxy)pyrazolo[1,5-a][1,3,5]triazin-4-amine | 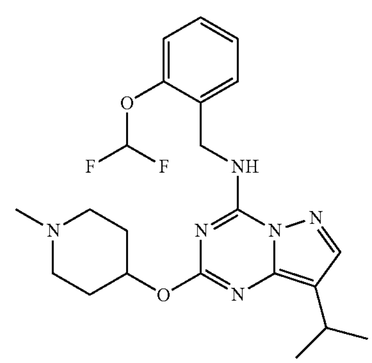 [SMILES: CC(C)c1cnn2c(NCc3ccccc3OC(F)F)nc(OC3CCN(C)CC3)nc12] |

-continued

| Compound | formula | calculated | MS(ES) [M + H]+ | Starting material | name | structure |
|---|---|---|---|---|---|---|
| (VII-73) | C24H30N8O | 446.25 | 447.00 | (XIX) | N-(2-(1H-pyrazol-1-yl)benzyl)-8-isopropyl-2-((1-methylpiperidin-4-yl)oxy)pyrazolo[1,5-a][1,3,5]triazin-4-amine | 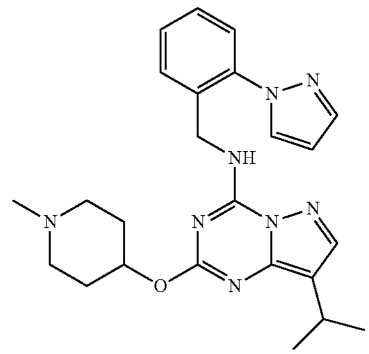 [SMILES: CC(C)c1cnn2c(NCc3ccccc3-n3cccn3)nc(OC3CCN(C)CC3)nc12] |
| (VII-74) | C23H29N9O | 447.25 | 447.94 | (XIX) | N-(2-(1H-1,2,4-triazol-1-yl)benzyl)-8-isopropyl-2-((1-methylpiperidin-4-yl)oxy)pyrazolo[1,5-a][1,3,5]triazin-4-amine | 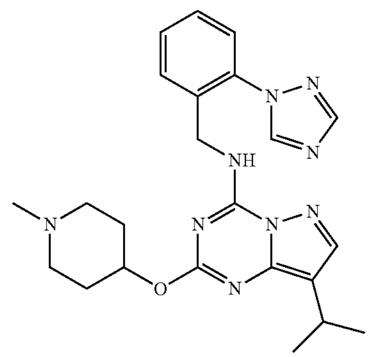 [SMILES: CC(C)c1cnn2c(NCc3ccccc3-n3cncn3)nc(OC3CCN(C)CC3)nc12] |
| (VII-75) | C25H32N8O*2C2HF3O2 | 460.27 | 461.35 | (XIX) | 8-isopropyl-N-(2-(2-methyl-1H-imidazol-1-yl)benzyl)-2-((1-methylpiperidin-4-yl)oxy)pyrazolo[1,5-a][1,3,5]triazin-4-amine | 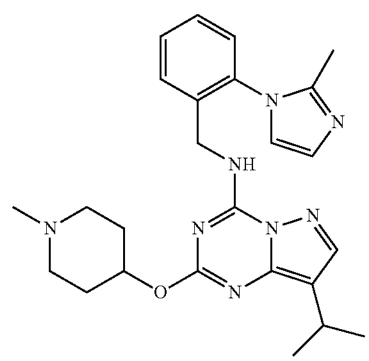 [SMILES: Cc1nccn1-c1ccccc1CNc1nc(OC2CCN(C)CC2)nc2c(C(C)C)cnn12] |
| (VII-76) | C22H27F3N6O2 | 464.21 | 464.97 | (XIX) | N-(2-(difluoromethoxy)benzyl)-8-isopropyl-2-((1-methylpiperidin-4-yl)oxy)pyrazolo[1,5-a][1,3,5]triazin-4-amine | 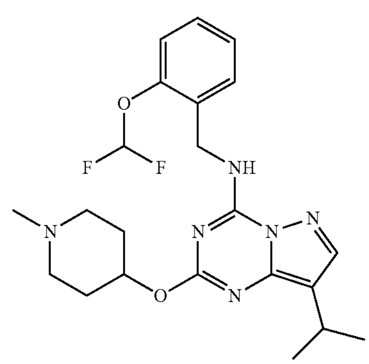 [SMILES: CC(C)c1cnn2c(NCc3ccccc3OC(F)F)nc(OC3CCN(C)CC3)nc12] |

-continued

| Compound | formula | calculated | MS(ES) [M + H]+ | Starting material | name | structure |
|---|---|---|---|---|---|---|
| (VII-77) | C21H28N6O3 | 412.22 | 413.6 | (VI-ah) | methyl 2-(((2-(2-(dimethylamino)ethoxy)-8-isopropylpyrazolo[1,5-a][1,3,5]triazin-4-yl)amino)methyl)benzoate | 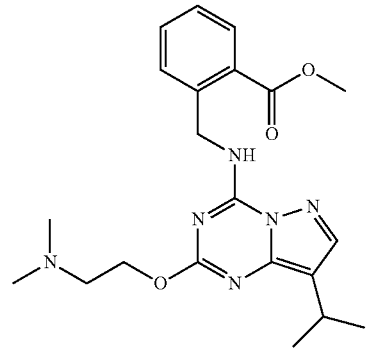 [SMILES: COC(=O)c1ccccc1CNc1nc(OCCN(C)C)nc2c(C(C)C)cnn12] |
| (VII-78) | C25H29N7O | 443.24 | 444.7 | (VI-aj) | 2-((6-aminospiro[3.3]heptan-2-yl)oxy)-8-isopropyl-N-(quinolin-5-ylmethyl)pyrazolo[1,5-a][1,3,5]triazin-4-amine | 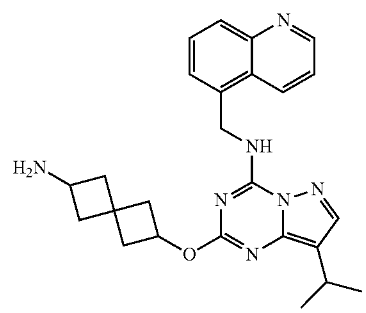 [SMILES: CC(C)c1cnn2c(NCc3cccc4ncccc34)nc(OC3CC4(CC(N)C4)C3)nc12] |
| (VII-79) | C25H31N7O | 445.26 | 446.6 | (VI-aj) | 8-isopropyl-2-(2-(piperidin-4-yl)ethoxy)-N-(quinolin-5-ylmethyl)pyrazolo[1,5-a][1,3,5]triazin-4-amine | 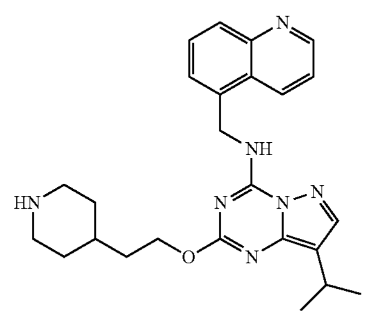 [SMILES: CC(C)c1cnn2c(NCc3cccc4ncccc34)nc(OCCC3CCNCC3)nc12] |
| (VII-80) | C19H25N7O | 367.21 | 368.5 | (VI-ai) | N-(2-aminobenzyl)-2-(azetidin-3-ylmethoxy)-8-isopropylpyrazolo[1,5-a][1,3,5]triazin-4-amine | 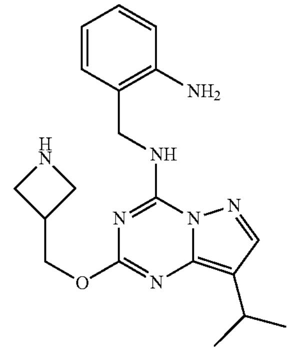 [SMILES: CC(C)c1cnn2c(NCc3ccccc3N)nc(OCC3CNC3)nc12] |

-continued

| Compound | formula | calculated | MS(ES) [M + H]+ | Starting material | name | structure |
|---|---|---|---|---|---|---|
| (VII-89) | C27H39N7O3 | 509.31 | 510.7 | (VI-ai) | tert-butyl (2-(((8-isopropyl-2-(2-(piperidin-1-yl)ethoxy)pyrazolo[1,5-a][1,3,5]triazin-4-yl)amino)methyl)phenyl)carbamate | 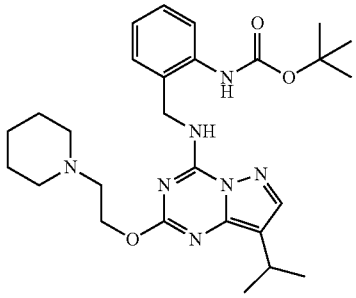 [SMILES: CC(C)c1cnn2c(NCc3ccccc3NC(=O)OC(C)(C)C)nc(OCCN3CCCCC3)nc12] |
| (VII-90) | C22H33N7O4S | 491.23 | 492.6 | (VI-ag) | N-(2-(((2-(2-(2-(dimethylamino)ethoxy)ethoxy)-8-isopropylpyrazolo[1,5-a][1,3,5]triazin-4-yl)amino)methyl)phenyl)methanesulfonamide | 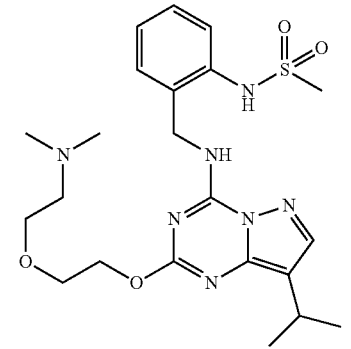 [SMILES: CC(C)c1cnn2c(NCc3ccccc3NS(C)(=O)=O)nc(OCCOCCN(C)C)nc12] |
| (VII-91) | C23H36N8O3S | 504.26 | 505.5 | (VI-ag) | N-(2-(((2-(2-((2-(dimethylamino)ethyl)(methyl)amino)ethoxy)-8-isopropylpyrazolo[1,5-a][1,3,5]triazin-4-yl)amino)methyl)phenyl)methanesulfonamide | 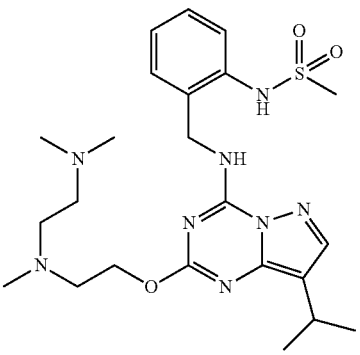 [SMILES: CC(C)c1cnn2c(NCc3ccccc3NS(C)(=O)=O)nc(OCCN(C)CCN(C)C)nc12] |
| (VII-92) | C25H33N7O2 | 463.27 | 464.4 | (VI-al) | (R)-1-(2-(((8-isopropyl-2-(piperidin-3-yloxy)pyrazolo[1,5-a][1,3,5]triazin-4-yl)amino)methyl)benzyl)pyrrolidin-2-one | 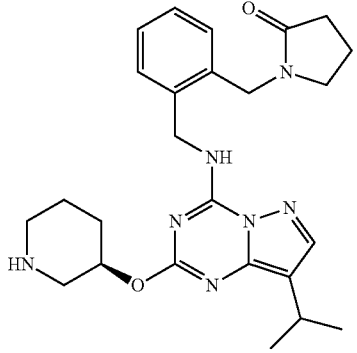 [SMILES: CC(C)c1cnn2c(NCc3ccccc3CN3CCCC3=O)nc(O[C@@H]3CCCNC3)nc12] |

-continued

| Compound | formula | calculated | MS(ES) [M + H]+ | Starting material | name | structure |
|---|---|---|---|---|---|---|
| (VII-93) | C25H34N6O3 | 466.27 | 467.4 | (VI-am) | 8-isopropyl-N-(4-methyl-2-((tetrahydrofuran-3-yl)oxy)benzyl)-2-((R)-piperidin-3-yloxy)pyrazolo[1,5-a][1,3,5]triazin-4-amine | 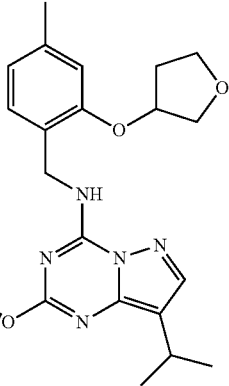 |
| (VII-94) | C20H24Cl2N6O | 434.14 | 435.3 | (VI-ak) | (R)-N-(2,4-dichlorobenzyl)-8-isopropyl-2-(piperidin-3-yloxy)pyrazolo[1,5-a][1,3,5]triazin-4-amine | 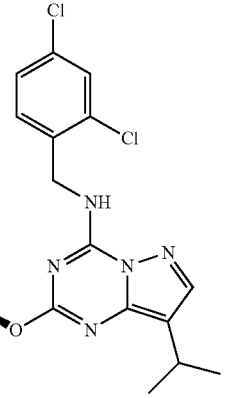 |
| (VII-95) | C25H34N6O2 | 450.27 | 451.4 | (VI-an) | (R)-N-(2-(cyclopentyloxy)benzyl)-8-isopropyl-2-(piperidin-3-yloxy)pyrazolo[1,5-a][1,3,5]triazin-4-amine | 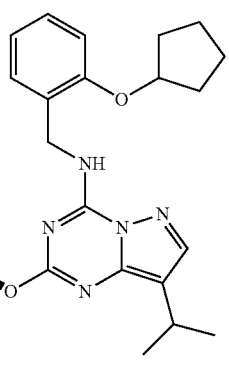 |
| (VII-96) | C21H27N7O2 | 409.22 | 410.4 | (VI-ao) | (R)-2-(((8-isopropyl-2-(piperidin-3-yloxy)pyrazolo[1,5-a][1,3,5]triazin-4-yl)amino)methyl)benzamide | 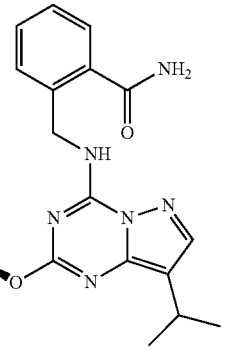 |

-continued

| Compound | formula | calculated | MS(ES) [M + H]+ | Starting material | name | structure |
|---|---|---|---|---|---|---|
| (VII-97) | C24H32N6O2 | 436.26 | 437.4 | (VI-ap) | (R)-N-(2-cyclobutoxybenzyl)-8-isopropyl-2-(piperidin-3-yloxy)pyrazolo[1,5-a][1,3,5]triazin-4-amine | 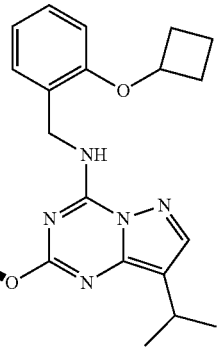 |
| (VII-98) | C25H29N7O2 | 459.24 | 460.4 | (VI-aq) | (R)-8-isopropyl-2-(piperidin-3-yloxy)-N-(2-(pyridin-2-yloxy)benzyl)pyrazolo[1,5-a][1,3,5]triazin-4-amine | 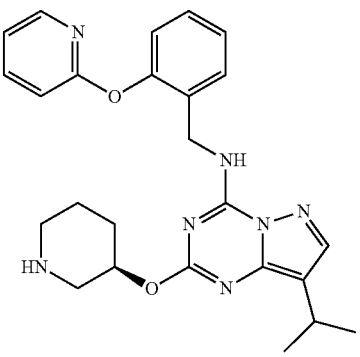 [SMILES: CC(C)c1cnn2c(NCc3ccccc3Oc3ccccn3)nc(O[C@@H]3CCCNC3)nc12] |
| (VII-99) | C24H33N7O4S | 515.23 | 516.4 | (VI-ar) | (R)-8-isopropyl-N-(2-(morpholinosulfonyl)benzyl)-2-(piperidin-3-yloxy)pyrazolo[1,5-a][1,3,5]triazin-4-amine | 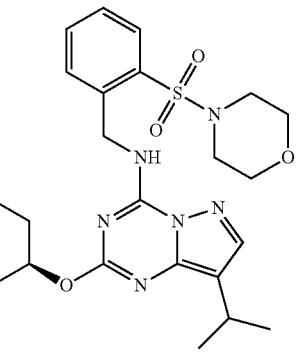 |
| (VII-100) | C20H25BrN6O | 444.13 | 445.3 | (VI-as) | (R)-N-(2-bromobenzyl)-8-isopropyl-2-(piperidin-3-yloxy)pyrazolo[1,5-a][1,3,5]triazin-4-amine | 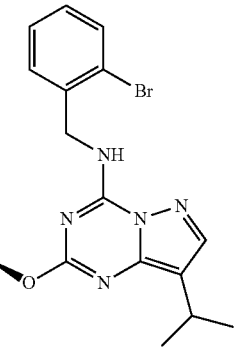 |

-continued

| Compound | formula | calculated | MS(ES) [M + H]+ | Starting material | name | structure |
|---|---|---|---|---|---|---|
| (VII-101) | C21H27ClN6O | 414.19 | 415.3 | (VI-at) | (R)-N-(4-chloro-2-methylbenzyl)-8-isopropyl-2-(piperidin-3-yloxy)pyrazolo[1,5-a][1,3,5]triazin-4-amine | 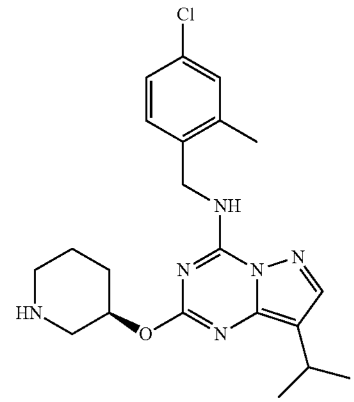 [SMILES: Cc1cc(Cl)ccc1CNc1nc(O[C@@H]2CCCNC2)nc2c(C(C)C)cnn12] |
| (VII-102) | C21H24ClF3N6O | 468.17 | 469.3 | (VI-au) | (R)-N-(4-chloro-2-(trifluoromethyl)benzyl)-8-isopropyl-2-(piperidin-3-yloxy)pyrazolo[1,5-a][1,3,5]triazin-4-amine | 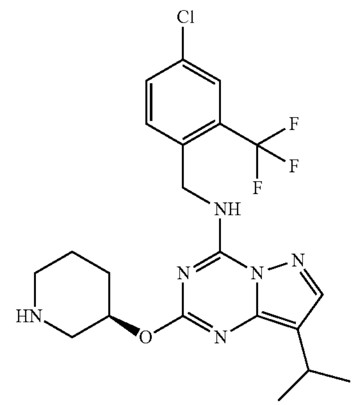 [SMILES: CC(C)c1cnn2c(NCc3ccc(Cl)cc3C(F)(F)F)nc(O[C@@H]3CCCNC3)nc12] |
| (VII-103) | C20H24Cl2N6O | 434.14 | 435.3 | (VI-av) | (R)-N-(2,3-dichlorobenzyl)-8-isopropyl-2-(piperidin-3-yloxy)pyrazolo[1,5-a][1,3,5]triazin-4-amine | 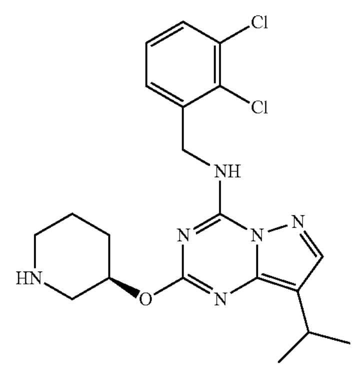 [SMILES: CC(C)c1cnn2c(NCc3cccc(Cl)c3Cl)nc(O[C@@H]3CCCNC3)nc12] |
| (VII-104) | C21H29N7O3S | 459.21 | 460.4 | (VI-aw) | (R)-2-(((8-isopropyl-2-(piperidin-3-yloxy)pyrazolo[1,5-a][1,3,5]triazin-4-yl)amino)methyl)-N-methylbenzenesulfonamide | 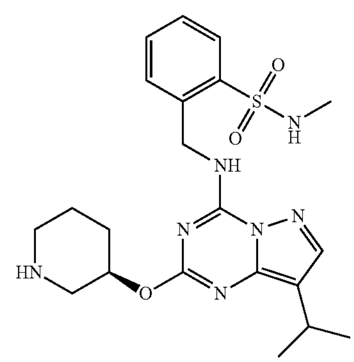 [SMILES: CNS(=O)(=O)c1ccccc1CNc1nc(O[C@@H]2CCCNC2)nc2c(C(C)C)cnn12] |

-continued

| Compound | formula | calculated | MS(ES) [M + H]+ | Starting material | name | structure |
|---|---|---|---|---|---|---|
| (VII-105) | C23H33N7O3S | 487.24 | 488.4 | (VI-ax) | (R)-N-isopropyl-2-(((8-isopropyl-2-(piperidin-3-yloxy)pyrazolo[1,5-a][1,3,5]triazin-4-yl)amino)methyl)benzenesulfonamide | 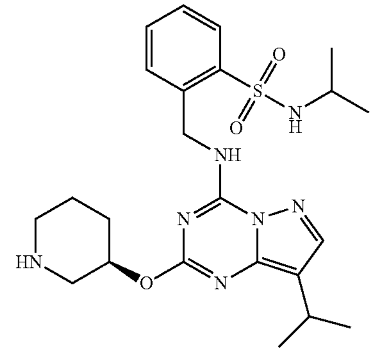 [SMILES: CC(C)NS(=O)(=O)c1ccccc1CNc1nc(O[C@@H]2CCCNC2)nc2c(C(C)C)cnn12] |
| (VII-106) | C24H33N7O3S | 499.24 | 500.4 | (VI-ay) | (R)-8-isopropyl-2-(piperidin-3-yloxy)-N-(2-(pyrrolidin-1-ylsulfonyl)benzyl)pyrazolo[1,5-a][1,3,5]triazin-4-amine | 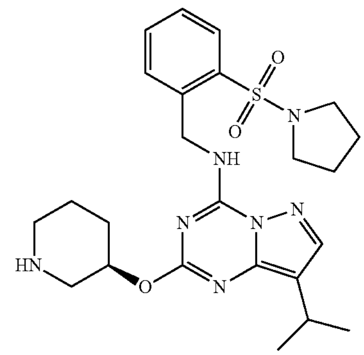 [SMILES: CC(C)c1cnn2c(NCc3ccccc3S(=O)(=O)N3CCCC3)nc(O[C@@H]3CCCNC3)nc12] |
| (VII-107) | C25H36N8O3S | 528.26 | 529.4 | (VI-az) | (R)-8-isopropyl-N-(2-((4-methylpiperazin-1-yl)sulfonyl)benzyl)-2-(piperidin-3-yloxy)pyrazolo[1,5-a][1,3,5]triazin-4-amine | 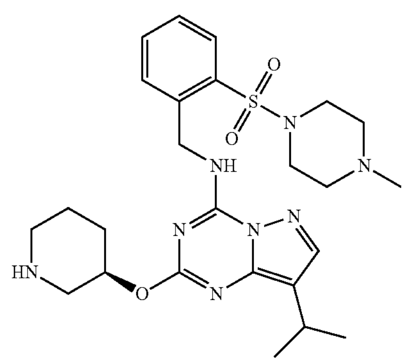 [SMILES: CC(C)c1cnn2c(NCc3ccccc3S(=O)(=O)N3CCN(C)CC3)nc(O[C@@H]3CCCNC3)nc12] |
| (VII-108) | C22H29N7O2 | 423.24 | 424.5 | (VI-ba) | (R)-2-(((8-isopropyl-2-(piperidin-3-yloxy)pyrazolo[1,5-a][1,3,5]triazin-4-yl)amino)methyl)-N-methylbenzamide | 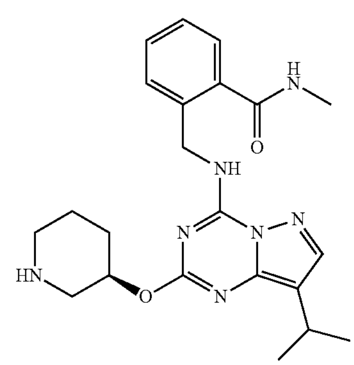 [SMILES: CNC(=O)c1ccccc1CNc1nc(O[C@@H]2CCCNC2)nc2c(C(C)C)cnn12] |

-continued

| Compound | formula | calculated | MS(ES) [M + H]+ | Starting material | name | structure |
|---|---|---|---|---|---|---|
| (VII-109) | C25H31N7O2 | 461.25 | 462.5 | (VI-bc) | N-(but-3-yn-2-yl)-2-(((8-isopropyl-2-((R)-piperidin-3-yloxy)pyrazolo[1,5-a][1,3,5]triazin-4-yl)amino)methyl)benzamide | 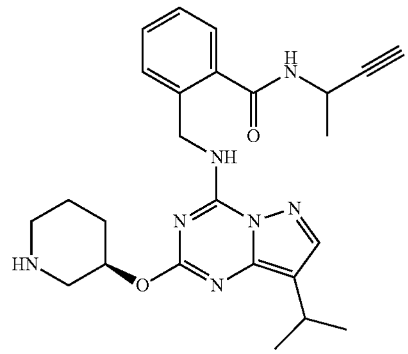 [SMILES: C#CC(C)NC(=O)c1ccccc1CNc1nc(O[C@@H]2CCCNC2)nc2c(C(C)C)cnn12] |
| (VII-110) | C24H34N8O2 | 466.28 | 467.5 | (VI-bd) | (R)-1-(2-(((8-isopropyl-2-(piperidin-3-yloxy)pyrazolo[1,5-a][1,3,5]triazin-4-yl)amino)methyl)phenyl)-3-propylurea | 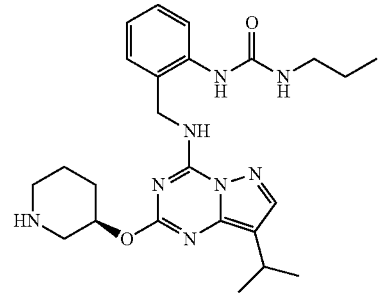 [SMILES: CCCNC(=O)Nc1ccccc1CNc1nc(O[C@@H]2CCCNC2)nc2c(C(C)C)cnn12] |
| (VII-111) | C27H32N8O2 | 500.26 | 501.4 | (VI-be) | (R)-1-(2-(((8-isopropyl-2-(piperidin-3-yloxy)pyrazolo[1,5-a][1,3,5]triazin-4-yl)amino)methyl)phenyl)-3-phenylurea | 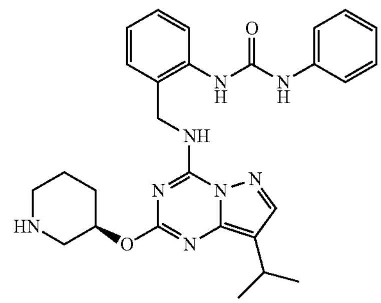 [SMILES: CC(C)c1cnn2c(NCc3ccccc3NC(=O)Nc3ccccc3)nc(O[C@@H]3CCCNC3)nc12] |
| (VII-112) | C27H38N8O2 | 506.31 | 507.5 | (VI-bf) | (R)-1-cyclohexyl-3-(2-(((8-isopropyl-2-(piperidin-3-yloxy)pyrazolo[1,5-a][1,3,5]triazin-4-yl)amino)methyl)phenyl)urea | 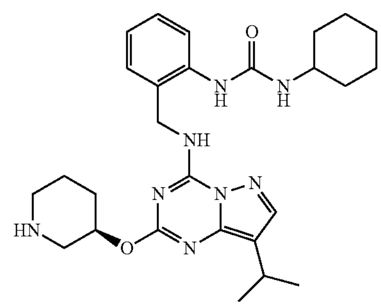 [SMILES: CC(C)c1cnn2c(NCc3ccccc3NC(=O)NC3CCCCC3)nc(O[C@@H]3CCCNC3)nc12] |
| (VII-113) | C28H34N8O2 | 514.28 | 515.4 | (VI-bg) | (R)-1-benzyl-3-(2-(((8-isopropyl-2-(piperidin-3-yloxy)pyrazolo[1,5-a][1,3,5]triazin-4-yl)amino)methyl)phenyl)urea | 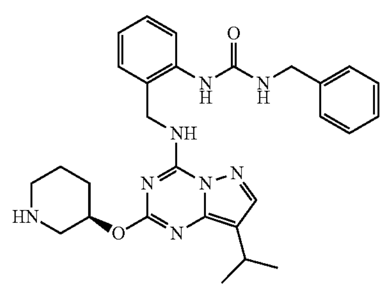 [SMILES: CC(C)c1cnn2c(NCc3ccccc3NC(=O)NCc3ccccc3)nc(O[C@@H]3CCCNC3)nc12] |

-continued

| Compound | formula | calculated | MS(ES) [M + H]+ | Starting material | name | structure |
|---|---|---|---|---|---|---|
| (VII-114) | C23H32N8O2 | 452.26 | 453.5 | (VI-bh) | (R)-1-ethyl-3-(2-(((8-isopropyl-2-(piperidin-3-yloxy)pyrazolo[1,5-a][1,3,5]triazin-4-yl)amino)methyl)phenyl)urea | 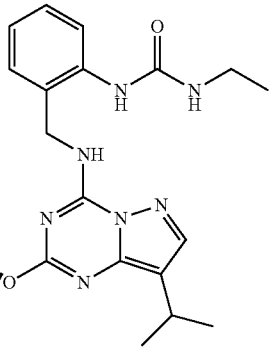 |
| (VII-115) | C25H36N6O2 | 452.29 | 453.4 | (VI-bj) | (R)-N-(2-isobutoxy-4-methylbenzyl)-8-isopropyl-2-(piperidin-3-yloxy)pyrazolo[1,5-a][1,3,5]triazin-4-amine | 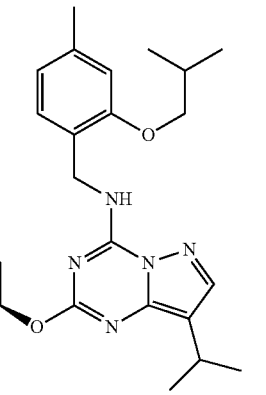 |
| (VII-116) | C23H30N6O3 | 438.24 | 439.4 | (VI-bk) | (R)-N-((3,4-dihydro-2H-benzo[b][1,4]dioxepin-6-yl)methyl)-8-isopropyl-2-(piperidin-3-yloxy)pyrazolo[1,5-a][1,3,5]triazin-4-amine | 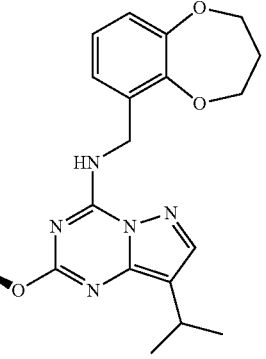 |
| (VII-117) | C26H34N6O | 446.28 | 447.4 | (VI-bl) | (R)-8-isopropyl-2-(piperidin-3-yloxy)-N-((2',3',4',5'-tetrahydro-[1,1'-biphenyl]-2-yl)methyl)pyrazolo[1,5-a][1,3,5]triazin-4-amine | 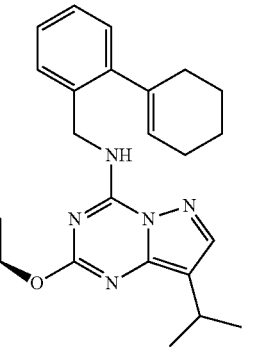 |

-continued

| Compound | formula | calculated | MS(ES) [M + H]+ | Starting material | name | structure |
|---|---|---|---|---|---|---|
| (VII-118) | C21H28N6OS | 412.20 | 413.3 | (VI-bm) | (R)-8-isopropyl-N-(2-(methylthio)benzyl)-2-(piperidin-3-yloxy)pyrazolo[1,5-a][1,3,5]triazin-4-amine | 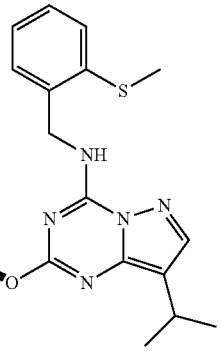 |
| (VII-119) | C25H34N6OS | 466.25 | 467.4 | (VI-bi) | (R)-N-(2-(cyclopentylthio)benzyl)-8-isopropyl-2-(piperidin-3-yloxy)pyrazolo[1,5-a][1,3,5]triazin-4-amine | 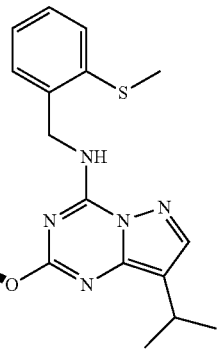 |
| (VII-120) | C23H26N8O | 430.22 | 453.1 [M + Na]+ | (VI-a) | N-(2-(1H-pyrazol-1-yl)benzyl)-8-isopropyl-2-((1,2,3,6-tetrahydropyridin-3-yl)oxy)pyrazolo[1,5-a][1,3,5]triazin-4-amine | 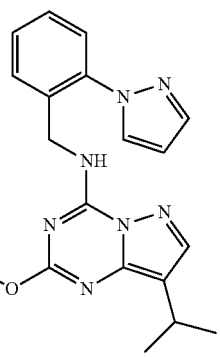 |
| (VII-121) | C26H32N8O2 | 488.26 | 489.2 | (VI-a) | 2-(1-oxa-8-azaspiro[4.5]decan-3-yloxy)-N-(2-(1H-pyrazol-1-yl)benzyl)-8-isopropylpyrazolo[1,5-a][1,3,5]triazin-4-amine | 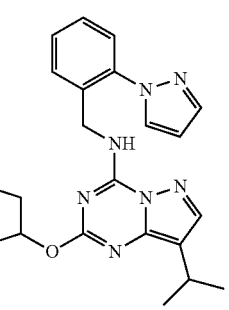 |

-continued

| Compound | formula | calculated | MS(ES) [M + H]+ | Starting material | name | structure |
|---|---|---|---|---|---|---|
| (VII-122) | C23H28N8O2 | 448.23 | 449.2 | (VI-a) | 2-((1,4-oxazepan-6-yl)oxy)-N-(2-(1H-pyrazol-1-yl)benzyl)-8-isopropylpyrazolo[1,5-a][1,3,5]triazin-4-amine | 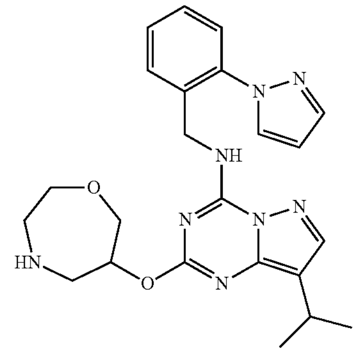 [SMILES: CC(C)c1cnn2c(NCc3ccccc3-n3cccn3)nc(OC3CNCCOC3)nc12] |
| (VII-123) | C24H28N8O | 444.24 | 445.2 | (VI-a) | N-(2-(1H-pyrazol-1-yl)benzyl)-2-(((1R,5S)-3-azabicyclo[3.2.0]heptan-6-yloxy)-8-isopropylpyrazolo[1,5-a][1,3,5]triazin-4-amine | 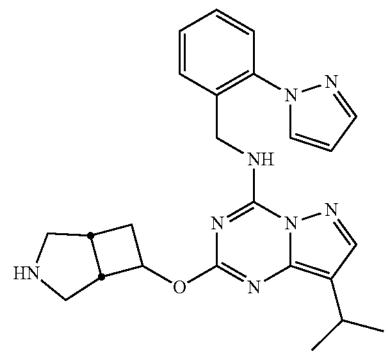 [SMILES: CC(C)c1cnn2c(NCc3ccccc3-n3cccn3)nc(OC3C[C@H]4CNC[C@@H]34)nc12] |
| (VII-124) | C24H31N9O | 461.27 | 462.2 | (VI-a) | N-(2-(1H-pyrazol-1-yl)benzyl)-8-isopropyl-2-(2-(piperazin-1-yl)ethoxy)pyrazolo[1,5-a][1,3,5]triazin-4-amine | 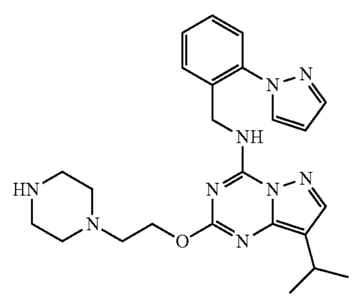 [SMILES: CC(C)c1cnn2c(NCc3ccccc3-n3cccn3)nc(OCCN3CCNCC3)nc12] |
| (VII-125) | C24H28N8O | 444.24 | 445.3 | (VI-a) | N-(2-(1H-pyrazol-1-yl)benzyl)-2-(2-azabicyclo[2.2.1]heptan-5-yloxy)-8-isopropylpyrazolo[1,5-a][1,3,5]triazin-4-amine | 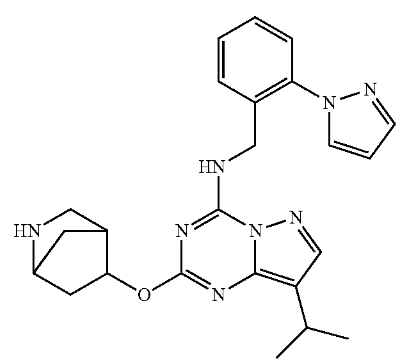 [SMILES: CC(C)c1cnn2c(NCc3ccccc3-n3cccn3)nc(OC3CC4CC3CN4)nc12] |

-continued

| Compound | formula | calculated | MS(ES) [M + H]+ | Starting material | name | structure |
|---|---|---|---|---|---|---|
| (VII-126) | C20H25IN6O | 492.11 | 493.2 | (VI-bo) | N-(2-iodobenzyl)-8-isopropyl-2-(piperidin-3-yloxy)pyrazolo[1,5-a][1,3,5]triazin-4-amine | 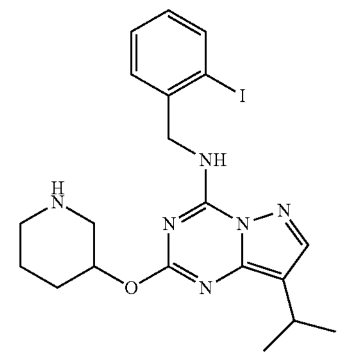 [SMILES: CC(C)c1cnn2c(NCc3ccccc3I)nc(OC3CCCNC3)nc12] |
| (VII-127) | C25H37N7O2S | 499.27 | 500.3 | (XIX) | N-(2-(((8-isopropyl-2-((1-methylpiperidin-4-yl)oxy)pyrazolo[1,5-a][1,3,5]triazin-4-yl)amino)methyl)phenyl)-2-methylpropane-2-sulfinamide | 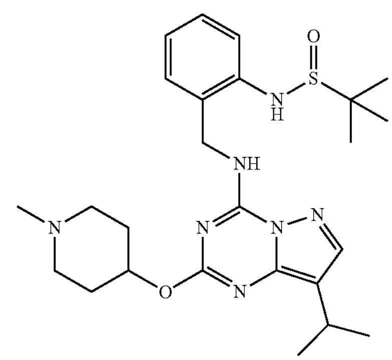 [SMILES: CC(C)c1cnn2c(NCc3ccccc3NS(=O)C(C)(C)C)nc(OC3CCN(C)CC3)nc12] |
| (VII-128) | C26H37N7O3 | 495.30 | 496.4 | (XIX) | isobutyl (2-(((8-isopropyl-2-((1-methylpiperidin-4-yl)oxy)pyrazolo[1,5-a][1,3,5]triazin-4-yl)amino)methyl)phenyl)carbamate | 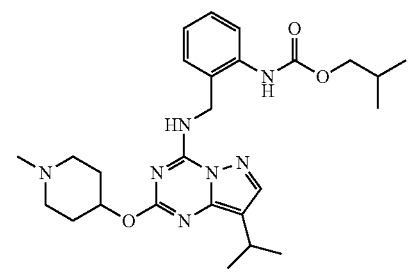 [SMILES: CC(C)COC(=O)Nc1ccccc1CNc1nc(OC2CCN(C)CC2)nc2c(C(C)C)cnn12] |
| (VII-129) | C24H30N8O | 446.25 | 447.2 | (VI-bp) | (R)-N-(2-((1H-pyrazol-1-yl)methyl)benzyl)-8-isopropyl-2-(piperidin-3-yloxy)pyrazolo[1,5-a][1,3,5]triazin-4-amine | 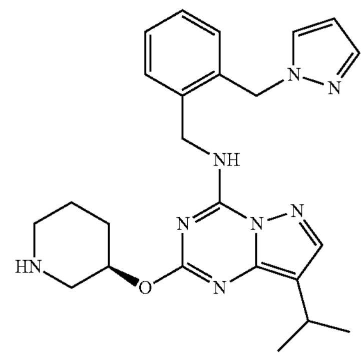 [SMILES: CC(C)c1cnn2c(NCc3ccccc3Cn3cccn3)nc(O[C@@H]3CCCNC3)nc12] |

-continued

| Compound | formula | calculated | MS(ES) [M + H]+ | Starting material | name | structure |
|---|---|---|---|---|---|---|
| (VII-130) | C20H24Cl2N6O | 434.1 | 435.2 | (VI-bq) | (R)-N-(2,5-dichlorobenzyl)-8-isopropyl-2-(piperidin-3-yloxy)pyrazolo[1,5-a][1,3,5]triazin-4-amine | 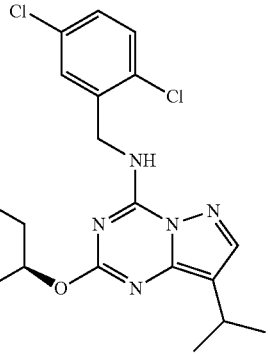 |
| (VII-131) | C24H33N7O | 435.27 | 436.3 | (VI-br) | (R)-8-isopropyl-2-(piperidin-3-yloxy)-N-(2-(pyrrolidin-1-yl)benzyl)pyrazolo[1,5-a][1,3,5]triazin-4-amine | 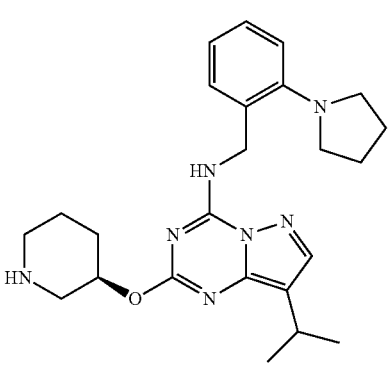 [SMILES: CC(C)c1cnn2c(NCc3ccccc3N3CCCC3)nc(O[C@@H]3CCCNC3)nc12] |
| (VII-132) | C25H35N7O | 449.29 | 450.4 | (VI-bs) | (R)-8-isopropyl-N-(2-(piperidin-1-yl)benzyl)-2-(piperidin-3-yloxy)pyrazolo[1,5-a][1,3,5]triazin-4-amine | 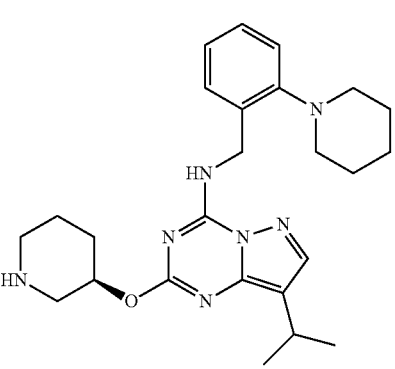 [SMILES: CC(C)c1cnn2c(NCc3ccccc3N3CCCCC3)nc(O[C@@H]3CCCNC3)nc12] |
| (VII-133) | C25H31N9O3 | 505.25 | 506.2 | (VI-a) | azetidin-3-yl (2-((4-((2-(1H-pyrazol-1-yl)benzyl)amino)-8-isopropylpyrazolo[1,5-a][1,3,5]triazin-2-yl)oxy)ethyl)(methyl)carbamate | 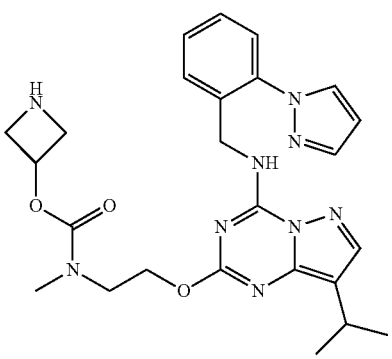 [SMILES: CC(C)c1cnn2c(NCc3ccccc3-n3cccn3)nc(OCCN(C)C(=O)OC3CNC3)nc12] |

-continued

| Compound | formula | calculated | MS(ES) [M + H]+ | Starting material | name | structure |
|---|---|---|---|---|---|---|
| (VII-134) | C26H37N9O3S | 555.27 | 556.1 | (VI-a) | N-(2-((4-((2-(1H-pyrazol-1-yl)benzyl)amino)-8-isopropylpyrazolo[1,5-a][1,3,5]triazin-2-yl)oxy)ethyl)-3-(dimethylamino)-N-methylpropane-1-sulfonamide | 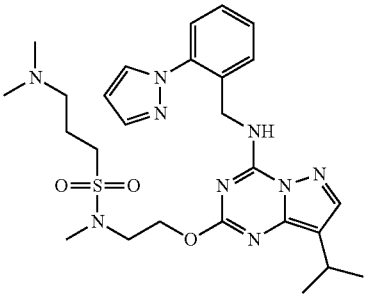 [SMILES: CC(C)c1cnn2c(NCc3ccccc3-n3cccn3)nc(OCCN(C)S(=O)(=O)CCCN(C)C)nc12] |
| (VII-135) | C26H35N9O3S | 553.26 | 554.0 | (VI-a) | N-(2-((4-((2-(1H-pyrazol-1-yl)benzyl)amino)-8-isopropylpyrazolo[1,5-a][1,3,5]triazin-2-yl)oxy)ethyl)-N-methylpiperidine-4-sulfonamide | 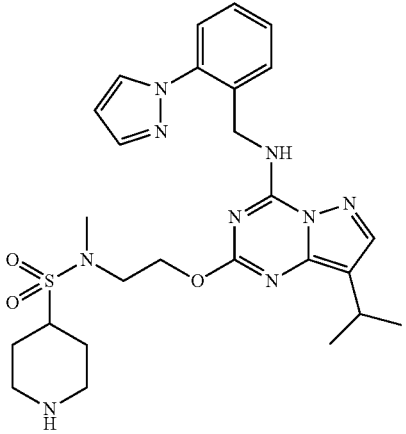 [SMILES: CC(C)c1cnn2c(NCc3ccccc3-n3cccn3)nc(OCCN(C)S(=O)(=O)C3CCNCC3)nc12] |
| (VII-136) | C24H29N9O3 | 491.24 | 492.4 | (VI-a) | 2-((4-((2-(1H-pyrazol-1-yl)benzyl)amino)-8-isopropylpyrazolo[1,5-a][1,3,5]triazin-2-yl)oxy)ethyl azetidin-3-ylcarbamate | 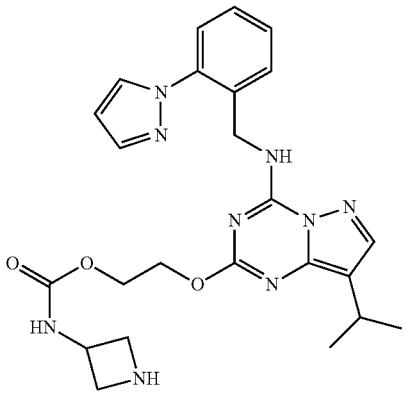 [SMILES: CC(C)c1cnn2c(NCc3ccccc3-n3cccn3)nc(OCCOC(=O)NC3CNC3)nc12] |
| (VII-137) | C24H31N9O3S | 525.23 | 526.3 | (VI-a) | 2-((4-((2-(1H-pyrazol-1-yl)benzyl)amino)-8-isopropylpyrazolo[1,5-a][1,3,5]triazin-2-yl)oxy)-N-(pyrrolidin-3-yl)ethanesulfonamide | 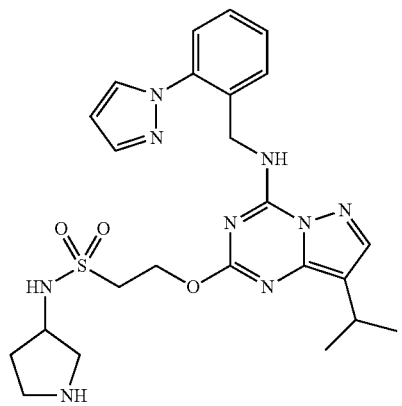 [SMILES: CC(C)c1cnn2c(NCc3ccccc3-n3cccn3)nc(OCCS(=O)(=O)NC3CCNC3)nc12] |

-continued

| Compound | formula | calculated | MS(ES) [M + H]+ | Starting material | name | structure |
| --- | --- | --- | --- | --- | --- | --- |
| (VII-138) | C25H30N8O | 458.25 | 459.2 | (VI-a) | N-(2-(1H-pyrazol-1-yl)benzyl)-2-(8-azabicyclo[3.2.1]octan-3-yloxy)-8-isopropylpyrazolo[1,5-a][1,3,5]triazin-4-amine | 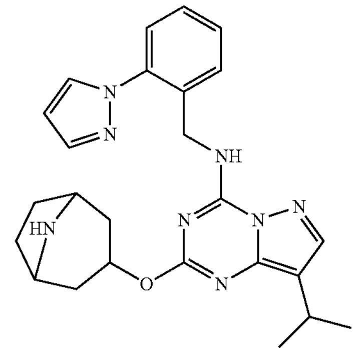 [SMILES: CC(C)c1cnn2c(NCc3ccccc3-n3cccn3)nc(OC3CC4CCC(C3)N4)nc12] |
| (VII-139) | C24H28N8O | 444.24 | 445.2 | (VI-a) | N-(2-(1H-pyrazol-1-yl)benzyl)-2-(2-azaspiro[3.3]heptan-5-yloxy)-8-isopropylpyrazolo[1,5-a][1,3,5]triazin-4-amine | 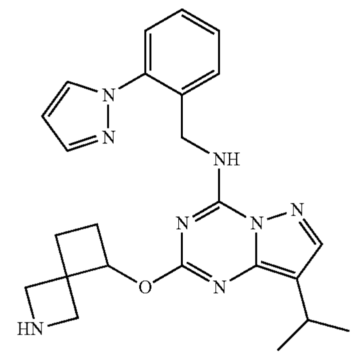 [SMILES: CC(C)c1cnn2c(NCc3ccccc3-n3cccn3)nc(OC3CCC34CNC4)nc12] |
| (VII-140) | C24H30N8O | 446.25 | 447.2 | (VI-a) | N-(2-(1H-pyrazol-1-yl)benzyl)-2-((4-aminocyclohexyl)oxy)-8-isopropylpyrazolo[1,5-a][1,3,5]triazin-4-amine | 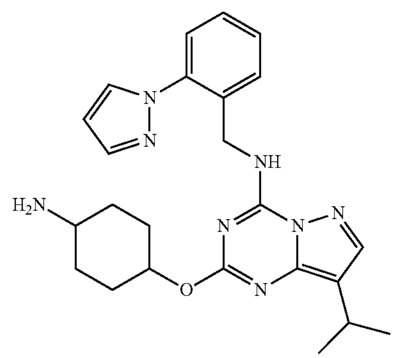 |
| (VII-141) | C21H24N8O | 404.21 | 405.2 | (VI-a) | N-(2-(1H-pyrazol-1-yl)benzyl)-2-(azetidin-3-yloxy)-8-isopropylpyrazolo[1,5-a][1,3,5]triazin-4-amine | 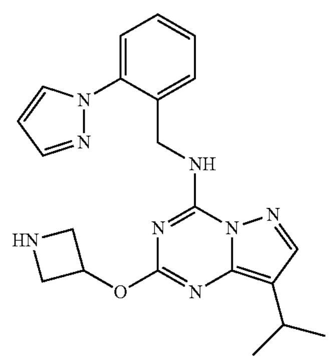 [SMILES: CC(C)c1cnn2c(NCc3ccccc3-n3cccn3)nc(OC3CNC3)nc12] |

Method J: C-C Cross Couplings with Intermediate (XXIII)

Compound (VII-141): N-(2-cyclobutylbenzyl)-8-isopropyl-2-(piperidin-3-yloxy)pyrazolo[1,5-a][1,3,5]triazin-4-amine

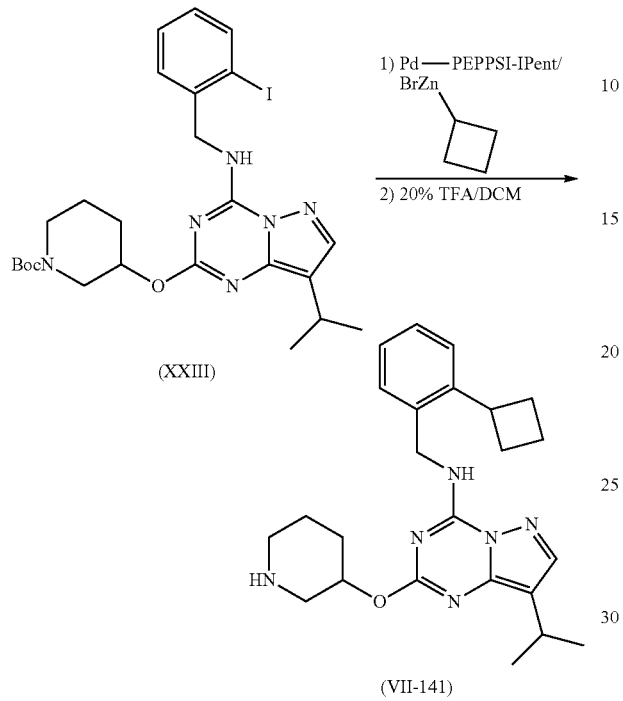

To a solution of 40 mg (0.068 mmol) iodine (XXIII) (prepared from intermediate (VI-bo) similar to method C without the final Boc-deprotection step) in 0.5 ml toluene 5.4 mg (0.0068 mmol) dichloro[1,3-bis(2,6-di-3-pentylphenyl)imidazol-2-ylidene](3-chloro-pyridyl)-palladium(11) were added. The reaction mixture was degassed with nitrogen and 0.544 ml (0.272 mmol) of a cyclobutylzinc bromide solution (0.5 M in THF) were added dropwise at 0° C. The ice bath was removed and the reaction mixture stirred for 90 min at room temperature. The intermediate product was purified by column chromatography (12 g silica gel, cyclohexane/ethyl acetate). The Boc-protecting group was removed with 20% TFA/DCM and the pure compound was obtained after RP-HPLC using a water/acetonitril (0.1% TFA) gradient.

MS (ES) C24H32N6O requires 420.26. found 421.2 (M+H)$^+$.

Compounds (VII-141)-(VII-144)

Compounds (VII-142)-(VII-144) were synthesized similar to method J.

| Compound | formula | calculated | MS(ES) [M + H]+ | starting material | name | structure |
|---|---|---|---|---|---|---|
| (VII-141) | C24H32N6O | 420.26 | 421.2 | (XXIII) | (R)-N-(2-cyclobutylbenzyl)-8-isopropyl-2-(piperidin-3-yloxy)pyrazolo[1,5-a][1,3,5]triazin-4-amine | 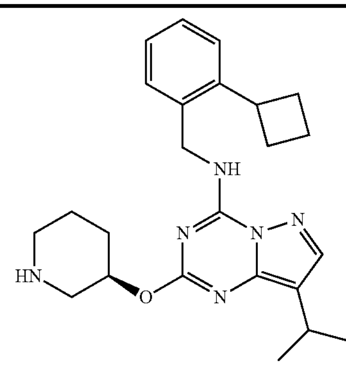 |
| (VII-142) | C25H34N6O | 434.28 | 435.2 | (XXIII) | (R)-N-(2-cyclopentylbenzyl)-8-isopropyl-2-(piperidin-3-yloxy)pyrazolo[1,5-a][1,3,5]triazin-4-amine | 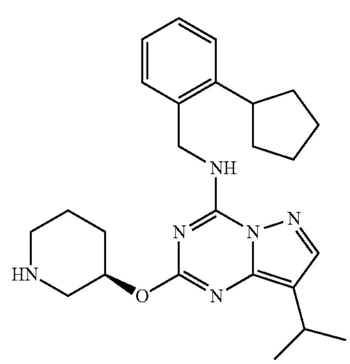 [SMILES: CC(C)c1cnn2c(NCc3ccccc3C3CCCC3)nc(O[C@@H]3CCCNC3)nc12] |

-continued

| Compound | formula | calculated | MS(ES) [M + H]+ | starting material | name | structure |
|---|---|---|---|---|---|---|
| (VII-143) | C23H30N6O | 406.52 | 407.4 | (XXIII) | N-(2-cyclopropylbenzyl)-8-isopropyl-2-(piperidin-3-yloxy)pyrazolo[1,5-a][1,3,5]triazin-4-amine | 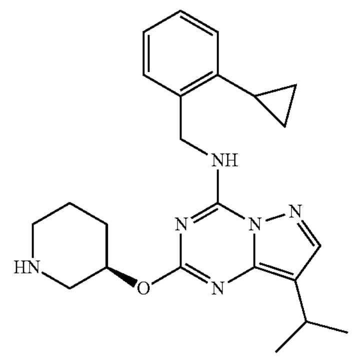 [SMILES: CC(C)c1cnn2c(NCc3ccccc3C3CC3)nc(O[C@@H]3CCCNC3)nc12] |
| (VII-144) | C26H36N6O | 448.30 | 449.4 | (XXIII) | (R)-N-(2-cyclohexylbenzyl)-8-isopropyl-2-(piperidin-3-yloxy)pyrazolo[1,5-a][1,3,5]triazin-4-amine | 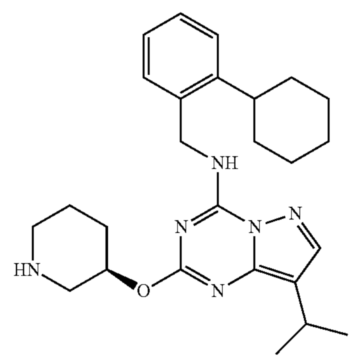 [SMILES: CC(C)c1cnn2c(NCc3ccccc3C3CCCCC3)nc(O[C@@H]3CCCNC3)nc12] |

Intermediate (XXV): (R)-tert-butyl 3-((4-((tert-butoxycarbonyl)(2-hydroxy-benzyl)amino)-8-isopropylpyrazolo[1,5-a][1,3,5]triazin-2-yl)oxy)piperidine-1-carboxylate

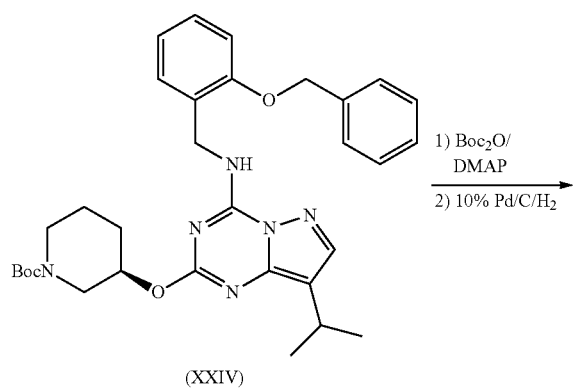

(XXIV)

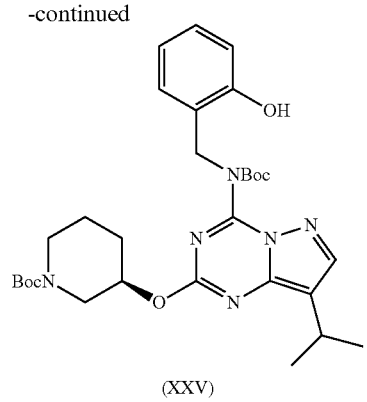

(XXV)

To a solution of 483 mg (0.83 mmol) intermediate (XXIV) (prepared from intermediate (VI-bn) similar to method C without the final Boc-deprotection step) in 10 ml DCM were added 543 mg (2.49 mmol) Boc₂O and 20.3 mg (0.083 mmol) DMAP. After the mixture was stirred at room temperature for 2 h, the same amount of Boc₂O and DMAP was added. After 1 h the solvent was removed under reduced pressure and the crude product was purified by column chromatography (12 g silica gel, cyclohexane/ethyl acetate).

MS (ES) C37H48N6O6 requires 672.36. found 673.6 (M+H)+.

577 mg (0.86 mmol) of the intermediate benzyl ether were hydrogenated in 25 ml ethanol ethyl acetate (1:1) (H-Cube: flow 1 m/min; 10% Pd/C; 60° C.). The crude product was purified by column chromatography (12 g silica gel, cyclohexane/ethyl acetate).

MS (ES) C25H34N6O4 requires 582.32. found 583.6 (M+H)+.

Method K: Derivatives of Intermediate (XXV)

Compound (VII-145): (R)-2-(((8-isopropyl-2-(piperidin-3-yloxy)pyrazolo[1,5-a][1,3,5]triazin-4-yl)amino)methyl)phenyl acetate

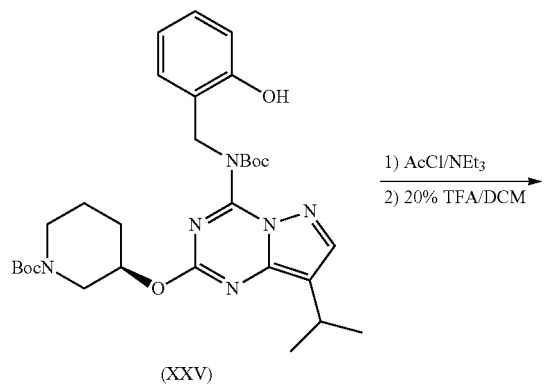

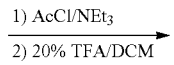

(XXV)

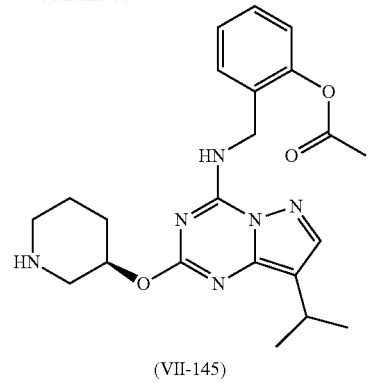

(VII-145)

3 µL acetyl chloride were added at 0° C. to a solution of 20 mg of intermediate (XXV) and 14.2 µL of triethylamine in 0.4 ml DCM. The mixture was stirred at 0° C. until the reaction was complete. The reaction mixture was purified by column chromatography (12 g silica gel, cyclohexane/ethyl acetate). The Boc-protecting group was removed with 20% TFA/DCM and the pure compound was obtained after RP-HPLC using a water/acetonitril (0.1% TFA) gradient.

MS (ES) C22H28N6O3 requires 424.22. found 425.4 (M+H)+.

Compounds (VII-145)-(VII-150)

Compounds (VII-146)-(VII-150) were synthesized from intermediate (XXV) similar to method K. Depending on the nature of the related electrophile the reaction was also carried out at room temperature.

| Compound | formula | calculated | MS(ES) [M + H]+ | starting materials | name | structure |
| --- | --- | --- | --- | --- | --- | --- |
| (VII-145) | C22H28N6O3 | 424.22 | 425.4 | (XXV) and acetyl chloride | (R)-2-(((8-isopropyl-2-(piperidin-3-yloxy)pyrazolo[1,5-a][1,3,5]triazin-4-yl)amino)methyl)phenyl acetate | 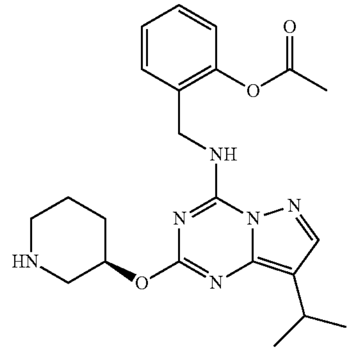 [SMILES: CC(=O)Oc1ccccc1CNc1nc(O[C@@H]2CCCNC2)nc2c(C(C)C)cnn12] |
| (VII-146) | C23H31N7O3 | 453.25 | 454.4 | (XXV) and ethyl isocyanate | (R)-2-(((8-isopropyl-2-(piperidin-3-yloxy)pyrazolo[1,5-a][1,3,5]triazin-4-yl)amino)methyl)phenyl ethylcarbamate | 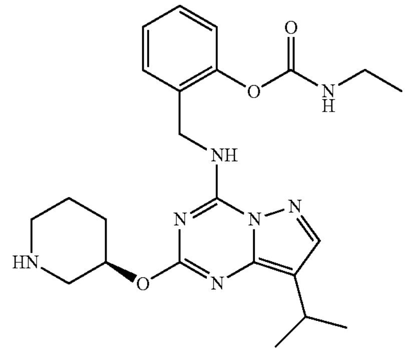 [SMILES: CCNC(=O)Oc1ccccc1CNc1nc(O[C@@H]2CCCNC2)nc2c(C(C)C)cnn12] |

-continued

| Compound | formula | calculated | MS(ES) [M + H]+ | starting materials | name | structure |
| --- | --- | --- | --- | --- | --- | --- |
| (VII-147) | C21H28N6O4S | 460.19 | 461.3 | (XXV) and Methane sulfonyl chloride | (R)-2-(((8-isopropyl-2-(piperidin-3-yloxy)pyrazolo[1,5-a][1,3,5]triazin-4-yl)amino)methyl) phenyl methanesulfonate | 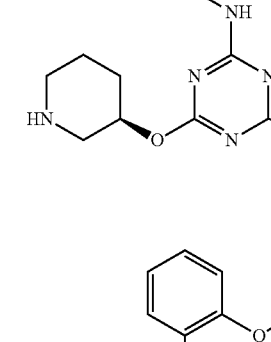 |
| (VII-148) | C24H34N6O3S | 486.24 | 487.4 | (XXV) and tert-butyl-sulfinyl chloride | 2-(((8-isopropyl-2-((R)-piperidin-3-yloxy)pyrazolo[1,5-a][1,3,5]triazin-4-yl)amino)methyl) phenyl 2-methylpropane-2-sulfinate | 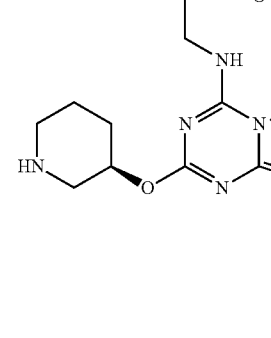 |
| (VII-149) | C25H34N6O4 | 482.26 | 483.4 | (XXV) and iso-butyl chloroformate | (R)-isobutyl (2-(((8-isopropyl-2-(piperidin-3-yloxy)pyrazolo[1,5-a][1,3,5]triazin-4-yl)amino)methyl) phenyl) carbonate | 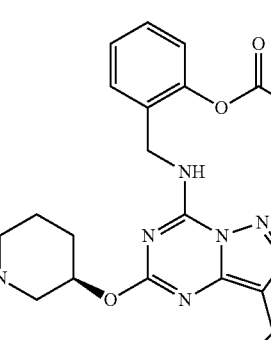 |
| (VII-150) | LDC191336 | 382.21 | 383.3 | (XXV) | (R)-2-(((8-isopropyl-2-(piperidin-3-yloxy)pyrazolo[1,5-a][1,3,5]triazin-4-yl)amino)methyl) phenol | 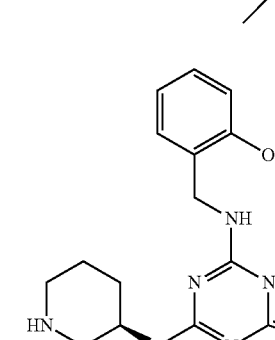 |

Method N: Sulfoximines from Intermediate (XXIII)

Compound (VII-151): N-(2-(((8-isopropyl-2-((R)-piperidin-3-yloxy)pyrazolo[1,5-a][1,3,5]triazin-4-yl)amino)methyl)phenyl)-S,S-dimethylsulfoximine

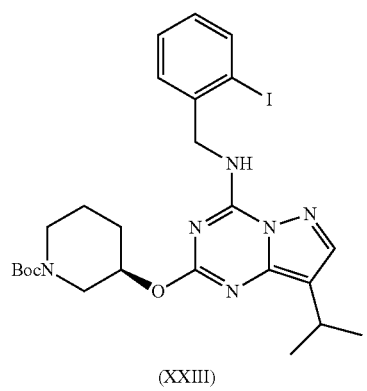

(XXIII)

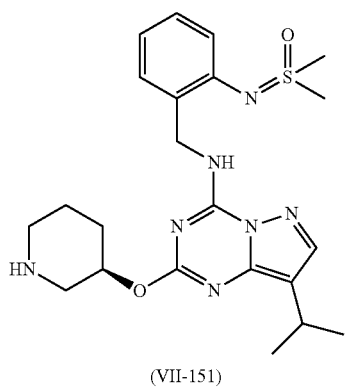

(VII-151)

20 mg (0.034 mmol) iodine (XXIII) (prepared from intermediate (VII-bo) similar to method C without the final Boc-deprotection step), 3.7 µl (dimethylsulfinylidene)amine, 1.6 mg CuI and 27.7 mg Cs2CO3 were stirred in 0.5 ml toluene at 110° C. over night. The reaction mixture was diluted with ethyl acetate, washed with brine, dried with MgSO4, filtered and concentrated in vacuo. The crude product was purified on silica gel using an ethyl acetate/cyclohexane gradient.

The resulting intermediate was dissolved in 20% TFA/DCM. After the Boc-group was cleaved the title compound was obtained after RP-HPLC using a water/acetonitrile (0.1% TFA) gradient.

MS (ES) C22H31N7O2S requires 457.23. found 458.1 (M+H)$^+$.

Method O: Oxidation of Thioethers

Compound (VII-152): 8-isopropyl-N-(2-(methylsulfinyl)benzyl)-2-((R)-piperidin-3-yloxy)pyrazolo[1,5-a][1,3,5]triazin-4-amine

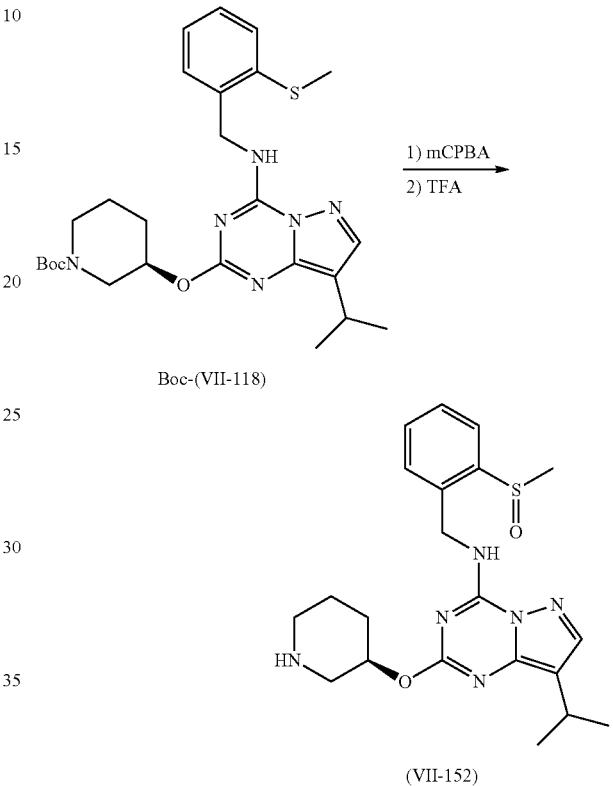

Boc-protected (VII-118) was obtained as described for (VII-118) but without the deprotection step. The 223 mg (0.436 mmol) thioether were then oxidized in 10 ml DCM at 0° C. using 83 mg (0.48 mmol) mCPBA. After 1 h the reaction mixture was diluted with ethylk acetate and washed with 2 M NaOH solution and brine. The organic phase was dried over MgSO4, concentrated under reduced pressure and purified on silica gel using an ethyl acetate/cyclohexane gradient. The resulting intermediate was dissolved in 20% TFA/DCM. After the Boc-group was cleaved the title compound was obtained after RP-HPLC using a water/acetonitrile (0.1% TFA) gradient.

MS (ES) C21H28N6O2S requires 428.20. found 429.2 (M+H)$^+$.

Compounds (VII-152)-(VII-154)

Compounds (VII-152)-(VII-154) were synthesized similar to method O. In case the related sulfonyl instead of the sulfinyl was desired, additional equivalents of mCPBA were used at elevated temperatures.

| Compound | formula | calculated | MS(ES) [M + H]+ | name |
| --- | --- | --- | --- | --- |
| (VII-154) | C21H28N6O3S | 444.19 | 445.4 | (R)-8-isopropyl-N-(2-(methylsulfonyl)benzyl)-2-(piperidin-3-yloxy)pyrazolo[1,5-a][1,3,5]triazin-4-amine |
| (VII-152) | C21H28N6O2S | 428.20 | 429.2 | 8-isopropyl-N-(2-(methylsulfinyl)benzyl)-2-((R)-piperidin-3-yloxy)pyrazolo[1,5-a][1,3,5]triazin-4-amine |
| (VII-153) | C25H34N6O2S | 482.25 | 483.3 | N-(2-(cyclopentylsulfinyl)benzyl)-8-isopropyl-2-((R)-piperidin-3-yloxy)pyrazolo[1,5-a][1,3,5]triazin-4-amine |

Method D: Substitution of Methylsulfones (VI) with N-Nucleophiles

Compound (VIII-16):

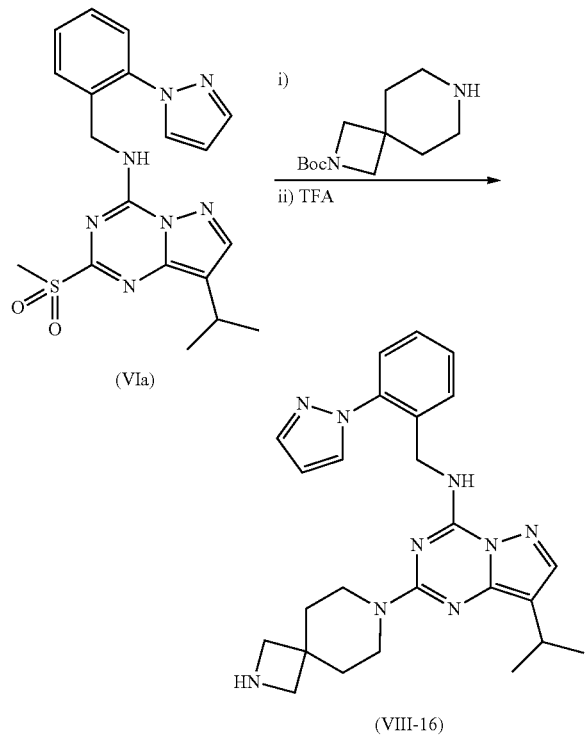

25 mg (0.061 mmol) methylsulfone (VI-a) were added to a solution of tert-butyl 2,7-diazaspiro[3.5]nonane-2-carboxylate (28 mg, 0.122 mmol) in NMP and stirred 18 h at 120° C. The reaction mixture was diluted with ethyl acetate, washed with 10% aqueous NaHCO3 and brine, dried with MgSO4, filtered and concentrated in vacuo. The remaining Boc-protecting group was removed in TFA and the pure compound (VIII-16) was obtained after RP-HPLC using a water/acetonitrile (0.1% TFA) gradient.

$^1$H-NMR (400 MHz, CDCl$_3$, 300K) δ 1.18 (d, J=6.8 Hz, 6H), 2.09 (m, broad, 4H), 3.23 (h, J=6.8 Hz, 1H), 3.95-4.05 (m, broad, 8H), 4.72 (d, J=6.0 Hz, 2H), 6.55 (m, 1H), 7.26-7.42 (m, 4H), 7.54 (s, 1H), 7.81 (m, 1H), 7.87 (m, 1H), 9.26 (t, J=6.0 Hz, 1H), 9.85 (s, broad, 2H); MS (ES) C25H31N9 requires 457.27. found 458.4 (M+H)$^+$.

Compounds (VIII-1)-(VIII-62)

Compounds (VIII-1)-(VIII-62) were prepared from the related methylsulfones (VI) according to method D and as exemplified for compound (VIII-16). In some cases DMF was used as solvent and 4 equivalents NEt$_3$ were used as additional base.

| Compound | formula | calculated | MS(ES) [M + H]+ | starting material | name | structure |
|---|---|---|---|---|---|---|
| (VIII-01) | C23H29N9 | 431.25 | 432.4 | (VI-a) | N4-(2-(1H-pyrazol-1-yl)benzyl)-8-isopropyl-N2-(piperidin-3-yl)pyrazolo[1,5-a][1,3,5]triazine-2,4-diamine | 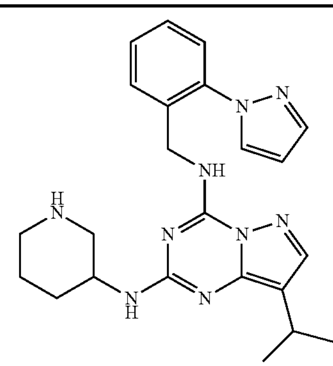 |
| (VIII-02) | C24H29N9 | 443.25 | 444.1 | (VI-a) | N-(2-(1H-pyrazol-1-yl)benzyl)-8-isopropyl-2-(2,6-diazaspiro[3,4]octan-2-yl)pyrazolo[1,5-a][1,3,5]triazin-4-amine | 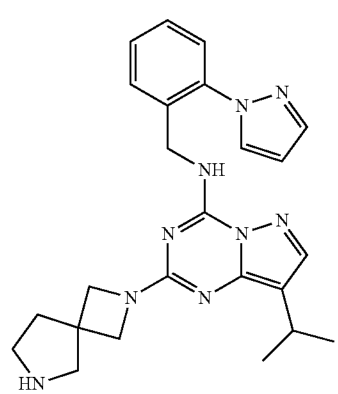 [SMILES: CC(C)c1cnn2c(NCc3ccccc3-n3cccn3)nc(N3CC4(CCNC4)C3)nc12] |

-continued

| Compound | formula | calculated | MS(ES) [M + H]+ | starting material | name | structure |
| --- | --- | --- | --- | --- | --- | --- |
| (VIII-03) | C25H31N9 | 457.27 | 458.2 | (VI-a) | N-(2-(1H-pyrazol-1-yl)benzyl)-8-isopropyl-2-(2,7-diazaspiro[4.4]nonan-2-yl)pyrazolo[1,5-a][1,3,5]triazin-4-amine | 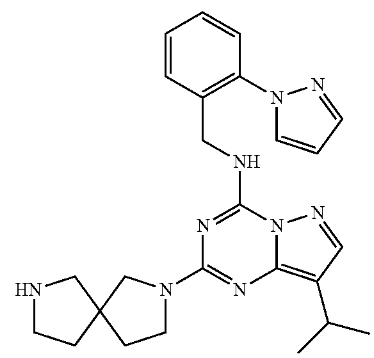 [SMILES: CC(C)c1cnn2c(NCc3ccccc3-n3cccn3)nc(N3CCC4(CCNC4)C3)nc12] |
| (VIII-04) | C25H31N9 | 457.27 | 458.3 | (VI-a) | N-(2-(1H-pyrazol-1-yl)benzyl)-8-isopropyl-2-(1,6-diazaspiro[3.5]nonan-1-yl)pyrazolo[1,5-a][1,3,5]triazin-4-amine | 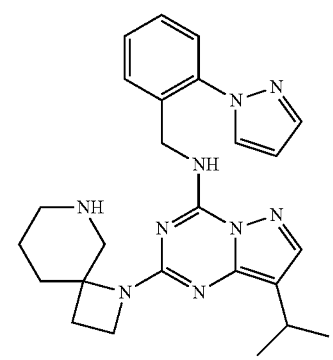 [SMILES: CC(C)c1cnn2c(NCc3ccccc3-n3cccn3)nc(N3CCC34CCCNC4)nc12] |
| (VIII-05) | C25H31N9 | 457.27 | 458.2 | (VI-a) | N-(2-(1H-pyrazol-1-yl)benzyl)-8-isopropyl-2-(2,6-diazaspiro[3.5]nonan-2-yl)pyrazolo[1,5-a][1,3,5]triazin-4-amine | 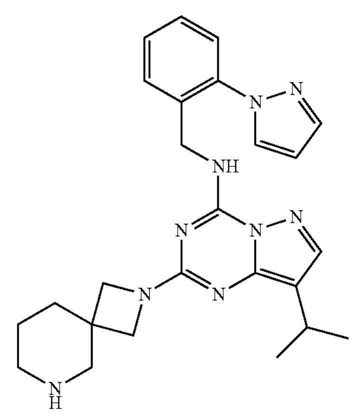 [SMILES: CC(C)c1cnn2c(NCc3ccccc3-n3cccn3)nc(N3CC4(CCCNC4)C3)nc12] |
| (VIII-06) | C26H33N9 | 471.29 | 472.2 | (VI-a) | N-(2-(1H-pyrazol-1-yl)benzyl)-8-isopropyl-2-(2,6-diazaspiro[4.5]decan-2-yl)pyrazolo[1,5-a][1,3,5]triazin-4-amine | 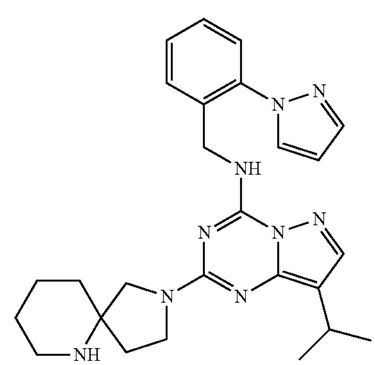 [SMILES: CC(C)c1cnn2c(NCc3ccccc3-n3cccn3)nc(N3CCC4(CCCCN4)C3)nc12] |

-continued

| Compound | formula | calculated | MS(ES) [M + H]+ | starting material | name | structure |
|---|---|---|---|---|---|---|
| (VIII-07) | C24H29N9 | 443.25 | 444.2 | (VI-a) | N-(2-(1H-pyrazol-1-yl)benzyl)-8-isopropyl-2-(2,6-diazaspiro[3.4]octan-6-yl)pyrazolo[1,5-a][1,3,5]triazin-4-amine | 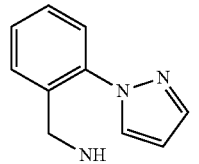 |
| (VIII-08) | C23H27N9 | 429.24 | 530.1 | (VI-a) | N-(2-(1H-pyrazol-1-yl)benzyl)-8-isopropyl-2-(1,6-diazaspiro[3.3]heptan-1-yl)pyrazolo[1,5-a][1,3,5]triazin-4-amine | 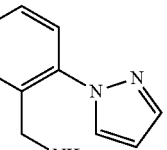 |
| (VIII-09) | C26H33N9 | 471.29 | 572.1 | (VI-a) | N-(2-(1H-pyrazol-1-yl)benzyl)-8-isopropyl-2-(2,8-diazaspiro[4.5]decan-8-yl)pyrazolo[1,5-a][1,3,5]triazin-4-amine | 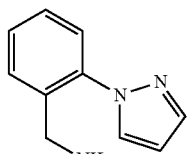 |
| (VIII-10) | C23H27N9 | 429.24 | 530.0 | (VI-a) | N-(2-(1H-pyrazol-1-yl)benzyl)-8-isopropyl-2-(2,6-diazaspiro[3.3]heptan-2-yl)pyrazolo[1,5-a][1,3,5]triazin-4-amine | 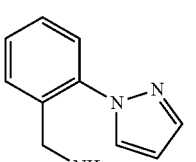 |

-continued

| Compound | formula | calculated | MS(ES) [M + H]+ | starting material | name | structure |
|---|---|---|---|---|---|---|
| (VIII-11) | C26H33N9 | 471.29 | 472.4 | (VI-a) | N-(2-(1H-pyrazol-1-yl)benzyl)-8-isopropyl-2-(1,8-diazaspiro[4.5]decan-8-yl)pyrazolo[1,5-a][1,3,5]triazin-4-amine | 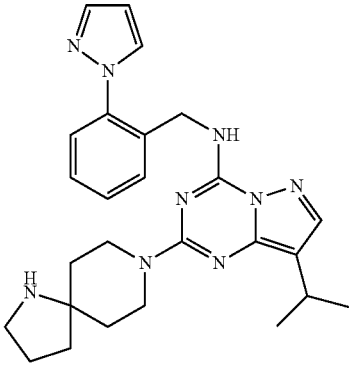 [SMILES: CC(C)c1cnn2c(NCc3ccccc3-n3cccn3)nc(N3CCC4(CCCN4)CC3)nc12] |
| (VIII-12) | C25H31N9 | 457.27 | 458.4 | (VI-a) | N-(2-(1H-pyrazol-1-yl)benzyl)-8-isopropyl-2-(2,7-diazaspiro[3.5]nonan-2-yl)pyrazolo[1,5-a][1,3,5]triazin-4-amine | 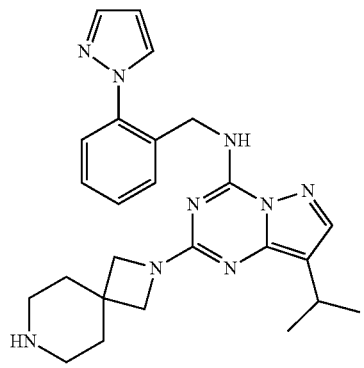 [SMILES: CC(C)c1cnn2c(NCc3ccccc3-n3cccn3)nc(N3CC4(CCNCC4)C3)nc12] |
| (VIII-13) | C25H31N9 | 457.27 | 458.3 | (VI-a) | N-(2-(1H-pyrazol-1-yl)benzyl)-8-isopropyl-2-(1,7-diazaspiro[4.4]nonan-1-yl)pyrazolo[1,5-a][1,3,5]triazin-4-amine | 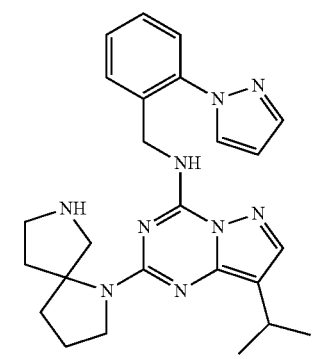 [SMILES: CC(C)c1cnn2c(NCc3ccccc3-n3cccn3)nc(N3CCCC34CCNC4)nc12] |
| (VIII-14) | C27H35N9 | 485.30 | 486.5 | (VI-a) | N-(2-(1H-pyrazol-1-yl)benzyl)-8-isopropyl-2-(2,8-diazaspiro[5.5]undecan-2-yl)pyrazolo[1,5-a][1,3,5]triazin-4-amine | 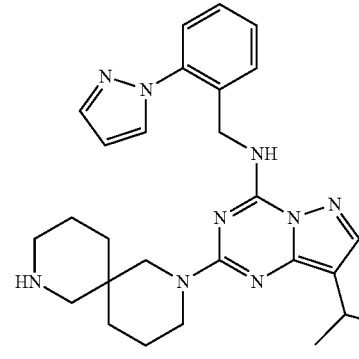 |

-continued

| Compound | formula | calculated | MS(ES) [M + H]+ | starting material | name | structure |
|---|---|---|---|---|---|---|
| (VIII-15) | C27H35N9 | 485.30 | 486.4 | (VI-a) | N-(2-(1H-pyrazol-1-yl)benzyl)-8-isopropyl-2-(1,8-diazaspiro[5.5]undecan-8-yl)pyrazolo[1,5-a][1,3,5]triazin-4-amine | 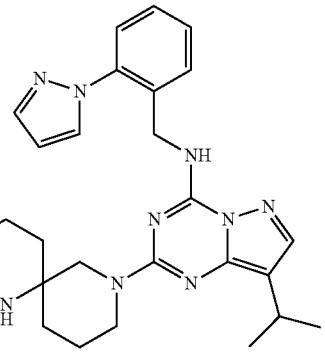 |
| (VIII-16) | C25H31N9 | 457.27 | 458.4 | (VI-a) | N-(2-(1H-pyrazol-1-yl)benzyl)-8-isopropyl-2-(2,7-diazaspiro[3.5]nonan-7-yl)pyrazolo[1,5-a][1,3,5]triazin-4-amine | 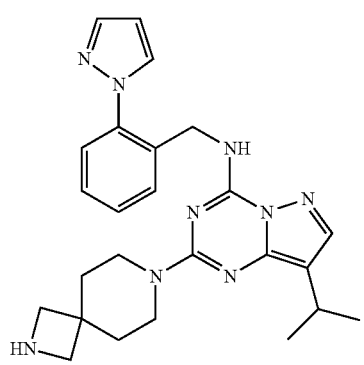 [SMILES: CC(C)c1cnn2c(NCc3ccccc3-n3cccn3)nc(N3CCC4(CC3)CNC4)nc12] |
| (VIII-17) | C25H31N9 | 457.27 | 458.5 | (VI-a) | N-(2-(1H-pyrazol-1-yl)benzyl)-8-isopropyl-2-(1,7-diazaspiro[4.4]nonan-7-yl)pyrazolo[1,5-a][1,3,5]triazin-4-amine | 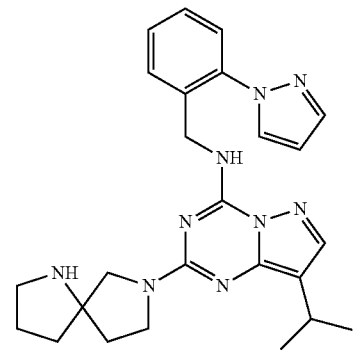 [SMILES: CC(C)c1cnn2c(NCc3ccccc3-n3cccn3)nc(N3CCC4(CCCN4)C3)nc12] |
| (VIII-18) | C25H33N11 | 487.29 | 488.5 | (VI-j) | 8-isopropyl-N-(2-(1-methyl-1H-tetrazol-5-yl)benzyl)-2-(1,8-diazaspiro[4.5]decan-8-yl)pyrazolo[1,5-a][1,3,5]triazin-4-amine | 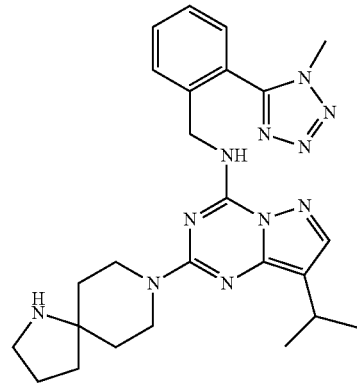 [SMILES: CC(C)c1cnn2c(NCc3ccccc3-c3nnnn3C)nc(N3CCC4(CCCN4)CC3)nc12] |

-continued

| Compound | formula | calculated | MS(ES) [M + H]+ | starting material | name |
|---|---|---|---|---|---|
| (VIII-19) | C25H33N11 | 487.29 | 488.5 | (VI-t) | 8-isopropyl-N-(2-(2-methyl-2H-tetrazol-5-yl)benzyl)-2-(1,8-diazaspiro[4.5]decan-8-yl)pyrazolo[1,5-a][1,3,5]triazin-4-amine |
| (VIII-20) | C25H31N9 | 457.27 | 458.2 | (VI-a) | N-(2-(1H-pyrazol-1-yl)benzyl)-8-isopropyl-2-(1,7-diazaspiro[3.5]nonan-7-yl)pyrazolo[1,5-a][1,3,5]triazin-4-amine |
| (VIII-21) | C27H35N9 | 485.30 | 486.5 | (VI-a) | N-(2-(1H-pyrazol-1-yl)benzyl)-8-isopropyl-2-(2,9-diazaspiro[5.5]undecan-2-yl)pyrazolo[1,5-a][1,3,5]triazin-4-amine |
| (VIII-22) | C26H33N9 | 471.29 | 472.3 | (VI-a) | N-(2-(1H-pyrazol-1-yl)benzyl)-8-isopropyl-2-(1,8-diazaspiro[4.5]decan-1-yl)pyrazolo[1,5-a][1,3,5]triazin-4-amine |

-continued

| Compound | formula | MS(ES) calculated | [M + H]+ | starting material | name | structure |
| --- | --- | --- | --- | --- | --- | --- |
| (VIII-23) | C27H35N9 | 485.30 | 486.4 | (VI-a) | N-(2-(1H-pyrazol-1-yl)benzyl)-8-isopropyl-2-(1,9-diazaspiro[5.5]undecan-9-yl)pyrazolo[1,5-a][1,3,5]triazin-4-amine | 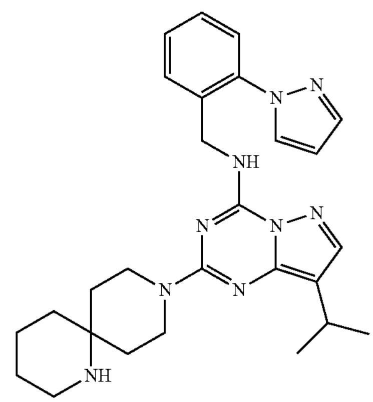 [SMILES: CC(C)c1cnn2c(NCc3ccccc3-n3cccn3)nc(N3CCC4(CCCCN4)CC3)nc12] |
| (VIII-24) | C25H33N9 | 459.29 | 460.3 | (VI-a) | N-(2-(1H-pyrazol-1-yl)benzyl)-2-(4-(dimethylamino)piperidin-1-yl)-8-isopropylpyrazolo[1,5-a][1,3,5]triazin-4-amine | 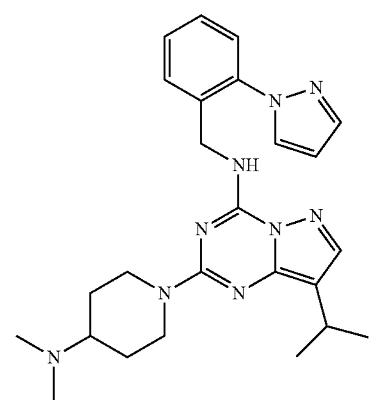 [SMILES: CC(C)c1cnn2c(NCc3ccccc3-n3cccn3)nc(N3CCC(N(C)C)CC3)nc12] |
| (VIII-25) | C24H31N9 | 445.27 | 446.3 | (VI-a) | N-(2-(1H-pyrazol-1-yl)benzyl)-8-isopropyl-2-(4-(methylamino)piperidin-1-yl)pyrazolo[1,5-a][1,3,5]triazin-4-amine | 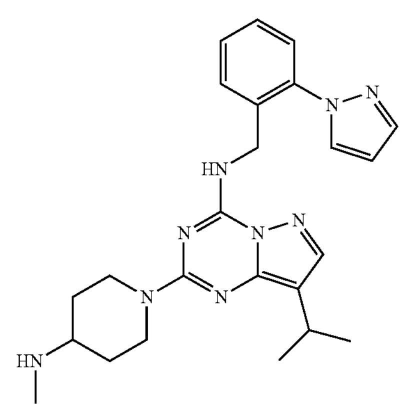 [SMILES: CNC1CCN(c2nc(NCc3ccccc3-n3cccn3)n3ncc(C(C)C)c3n2)CC1] |

-continued

| Compound | formula | calculated | MS(ES) [M + H]+ | starting material | name | structure |
|---|---|---|---|---|---|---|
| (VIII-26) | C27H35N9 | 485.30 | 486.3 | (VI-a) | N-(2-(1H-pyrazol-1-yl)benzyl)-8-isopropyl-2-(3,9-diazaspiro[5.5]undecan-3-yl)pyrazolo[1,5-a][1,3,5]triazin-4-amine | 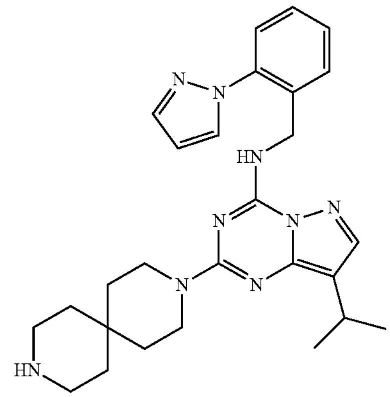 [SMILES: CC(C)c1cnn2c(NCc3ccccc3-n3cccn3)nc(N3CCC4(CCNCC4)CC3)nc12] |
| (VIII-27) | C26H33N9 | 471.29 | 472.3 | (VI-a) | N-(2-(1H-pyrazol-1-yl)benzyl)-8-isopropyl-2-(2,7-diazaspiro[4.5]decan-2-yl)pyrazolo[1,5-a][1,3,5]triazin-4-amine | 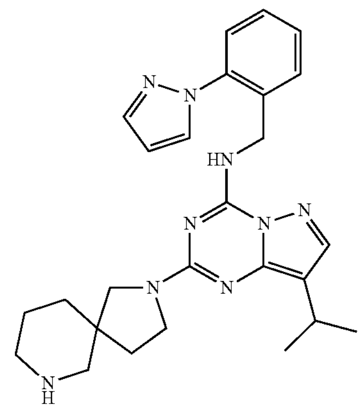 [SMILES: CC(C)c1cnn2c(NCc3ccccc3-n3cccn3)nc(N3CCC4(CCCNC4)C3)nc12] |
| (VIII-28) | C24H29N9 | 443.25 | 444.3 | (VI-a) | N-(2-(1H-pyrazol-1-yl)benzyl)-8-isopropyl-2-(1,6-diazaspiro[3.4]octan-1-yl)pyrazolo[1,5-a][1,3,5]triazin-4-amine | 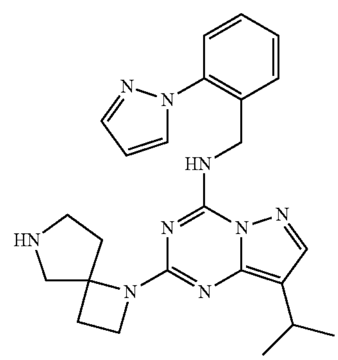 [SMILES: CC(C)c1cnn2c(NCc3ccccc3-n3cccn3)nc(N3CCC34CCNC4)nc12] |
| (VIII-31) | C22H31N7O | 409.26 | 409.9 | (VI-c) | 8-isopropyl-N4-((S)-1-(2-methoxyphenyl)ethyl)-N2-((R)-piperidin-3-yl)pyrazolo[1,5-a][1,3,5]triazine-2,4-diamine | 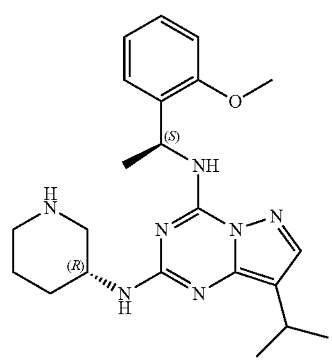 |

-continued

| Compound | formula | MS(ES) calculated | [M + H]+ | starting material | name | structure |
|---|---|---|---|---|---|---|
| (VIII-32) | C23H33N7O | 423.28 | 424.2 | (VI-e) | (R)-N4-(2-isopropoxybenzyl)-8-isopropyl-N2-(piperidin-3-yl)pyrazolo[1,5-a][1,3,5]triazine-2,4-diamine | 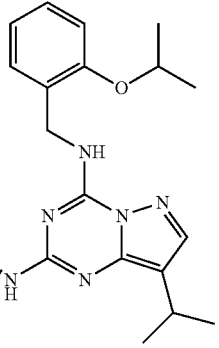 |
| (VIII-33) | C22H28N10 | 432.25 | 433.4 | (VI-g) | (R)-N4-(2-(1H-1,2,4-triazol-1-yl)benzyl)-8-isopropyl-N2-(piperidin-3-yl)pyrazolo[1,5-a][1,3,5]triazine-2,4-diamine | 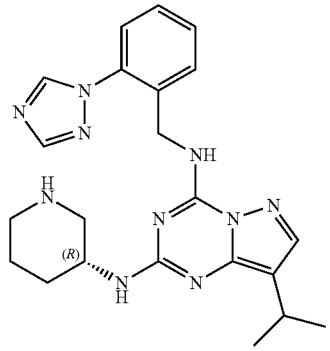 |
| (VIII-34) | C25H31N9 | 457.27 | 458.4 | (VI-a) | N-(2-(1H-pyrazol-1-yl)benzyl)-8-isopropyl-2-(1,7-diazaspiro[3.5]nonan-1-yl)pyrazolo[1,5-a][1,3,5]triazin-4-amine | 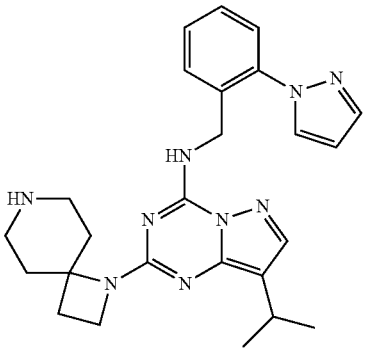 [SMILES: CC(C)c1cnn2c(NCc3ccccc3-n3cccn3)nc(N3CCC34CCNCC4)nc12] |
| (VIII-35) | C25H36N8O2S | 512.26 | 513.4 | (VI-u) | 2-(((8-isopropyl-2-(1,8-diazaspiro[4.5]decan-8-yl)pyrazolo[1,5-a][1,3,5]triazin-4-yl)amino)methyl)-N,N-dimethylbenzene-sulfonamide | 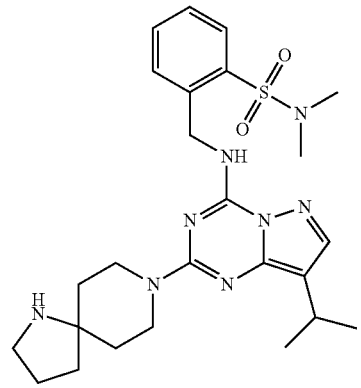 [SMILES: CC(C)c1cnn2c(NCc3ccccc3S(=O)(=O)N(C)C)nc(N3CCC4(CCCN4)CC3)nc12] |

-continued

| Compound | formula | calculated | MS(ES) [M + H]+ | starting material | name | structure |
| --- | --- | --- | --- | --- | --- | --- |
| (VIII-36) | C23H29N9O | 447.25 | 448.4 | (VI-q) | N-(benzo[c][1,2,5]oxadiazol-4-ylmethyl)-8-isopropyl-2-(1,8-diazaspiro[4.5]decan-8-yl)pyrazolo[1,5-a][1,3,5]triazin-4-arinine | 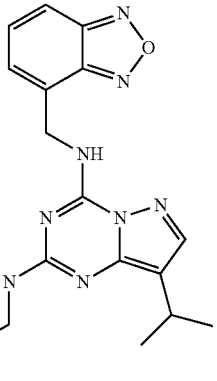 |
| (VIII-37) | C26H33N9 | 471.29 | 472.5 | (VI-a) | N-(2-(1H-pyrazol-1-yl)benzyl)-8-isopropyl-2-(2,8-diazaspiro[4.5]decan-2-yl)pyrazolo[1,5-a][1,3,5]triazin-4-amine | 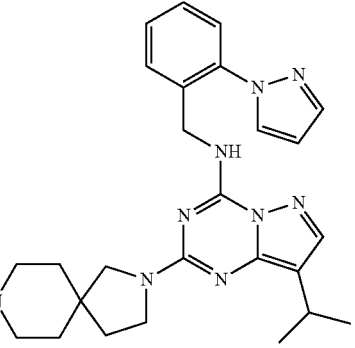 |
| (VIII-38) | C27H36N8O | 488.30 | 489.5 | (VI-s) | 1-(2-(((8-isopropyl-2-(1,8-diazaspiro[4.5]decan-8-yl)pyrazolo[1,5-a][1,3,5]triazin-4-yl)amino)methyl)phenyl)pyrrolidin-2-one | 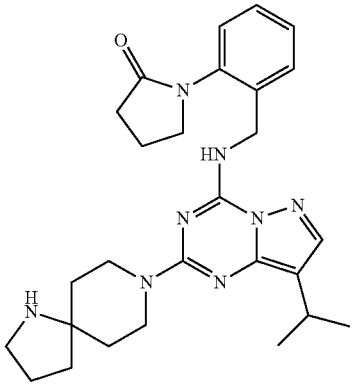 [SMILES: CC(C)c1cnn2c(NCc3ccccc3N3CCCC3=O)nc(N3CCC4(CCCN4)CC3)nc12] |
| (VIII-39) | C21H27N9 | 405.24 | 406.2 | (VI-a) | N4-(2-(1H-pyrazol-1-yl)benzyl)-N2-(3-aminopropyl)-8-isopropylpyrazolo[1,5-a][1,3,5]triazine-2,4-diamine | 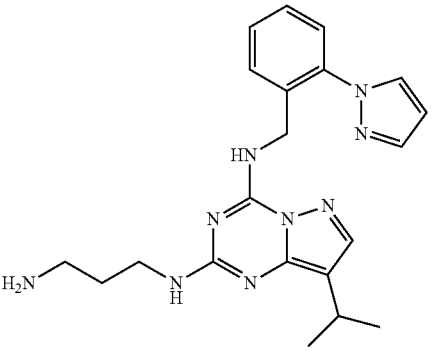 [SMILES: CC(C)c1cnn2c(NCc3ccccc3-n3cccn3)nc(NCCCN)nc12] |

-continued

| Compound | formula | calculated | MS(ES) [M + H]+ | starting material | name | structure |
|---|---|---|---|---|---|---|
| (VIII-40) | C24H31N9 | 445.27 | 446.3 | (VI-a) | N4-(2-(1H-pyrazol-1-yl)benzyl)-8-isopropyl-N2-(2-(pyrrolidin-1-yl)ethyl)pyrazolo[1,5-a][1,3,5]triazine-2,4-diamine | 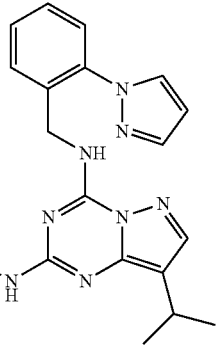 |
| (VIII-41) | C25H29F2N9 | 493.25 | 494.2 | (VI-a) | N-(2-(1H-pyrazol-1-yl)benzyl)-2-(3-(3,3-difluoropyrrolidin-1-yl)azetidin-1-yl)-8-isopropylpyrazolo[1,5-a][1,3,5]triazin-4-amine | 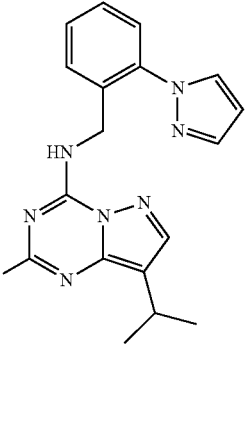 |
| (VIII-42) | C25H33N9O | 475.28 | 476.2 | (VI-a) | N4-(2-(1H-pyrazol-1-yl)benzyl)-8-isopropyl-N2-methyl-N2-(2-morpholinoethyl)pyrazolo[1,5-a][1,3,5]triazine-2,4-diamine | 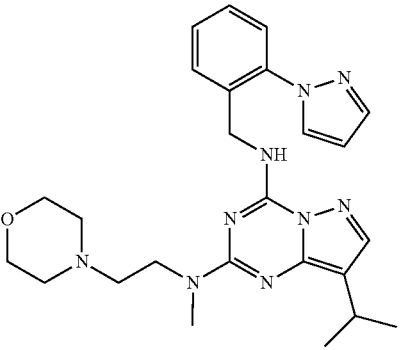 [SMILES: CC(C)c1cnn2c(NCc3ccccc3-n3cccn3)nc(N(C)CCN3CCOCC3)nc12] |
| (VIII-43) | C22H27N9 | 417.24 | 418.2 | (VI-a) | N4-(2-(1H-pyrazol-1-yl)benzyl)-8-isopropyl-N2-(pyrrolidin-3-yl)pyrazolo[1,5-a][1,3,5]triazine-2,4-diamine | 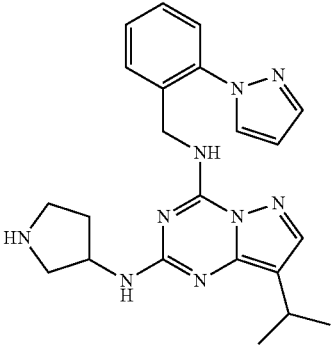 [SMILES: CC(C)c1cnn2c(NCc3ccccc3-n3cccn3)nc(NC3CCNC3)nc12] |

-continued

| Compound | formula | calculated | MS(ES) [M + H]+ | starting material | name | structure |
|---|---|---|---|---|---|---|
| (VIII-44) | C25H33N9O | 475.28 | 476.2 | (VI-a) | N4-(2-(1H-pyrazol-1-yl)benzyl)-8-isopropyl-N2-(3-morpholinopropyl)pyrazolo[1,5-a][1,3,5]triazine-2,4-diamine | 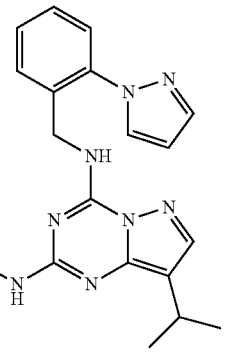 |
| (VIII-45) | C25H33N9 | 459.29 | 460.3 | (VI-a) | N4-(2-(1H-pyrazol-1-yl)benzyl)-8-isopropyl-N2-methyl-N2-(2-(pyrrolidin-1-yl)ethyl)pyrazolo[1,5-a][1,3,5]triazine-2,4-diamine | 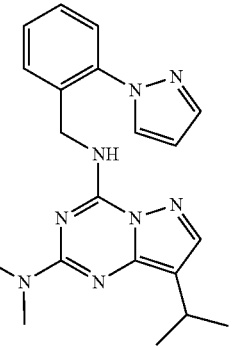 |
| (VIII-46) | C24H31N9O | 461.27 | 462.2 | (VI-a) | N4-(2-(1H-pyrazol-1-yl)benzyl)-8-isopropyl-N2-(2-morpholinoethyl)pyrazolo[1,5-a][1,3,5]triazine-2,4-diamine | 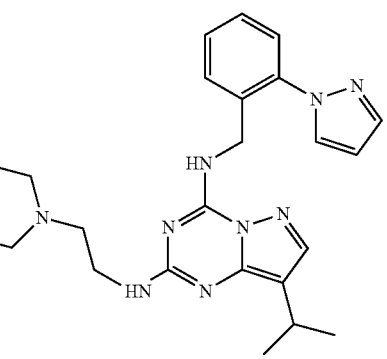 |
| (VIII-47) | C25H29N9O | 471.25 | 472.1 | (VI-a) | 1-(1-(4-((2-(1H-pyrazol-1-yl)benzyl)amino)-8-isopropylpyrazolo[1,5-a][1,3,5]triazin-2-yl)azetidin-3-yl)pyrrolidin-2-one | 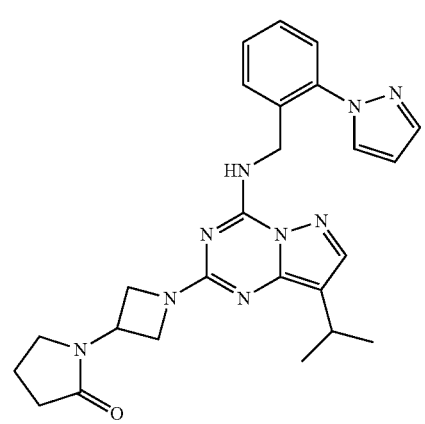 [SMILES: CC(C)c1cnn2c(NCc3ccccc3-n3cccn3)nc(N3CC(N4CCCC4=O)C3)nc12] |

-continued

| Compound | formula | MS(ES) calculated | [M + H]+ | starting material | name | structure |
|---|---|---|---|---|---|---|
| (VIII-48) | C22H29N9O | 435.25 | 436.2 | (VI-a) | N4-(2-(1H-pyrazol-1-yl)benzyl)-N2-(2-(2-aminoethoxy)ethyl)-8-isopropylpyrazolo[1,5-a][1,3,5]triazine-2,4-diamine | 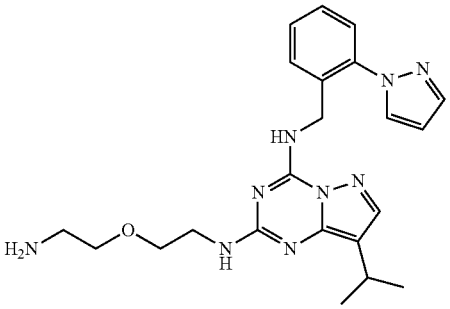 [SMILES: CC(C)c1cnn2c(NCc3ccccc3-n3cccn3)nc(NCCOCCN)nc12] |
| (VIII-49) | C27H37N9 | 487.32 | 488.2 | (VI-a) | N4-(2-(1H-pyrazol-1-yl)benzyl)-8-isopropyl-N2-methyl-N2-(3-(piperidin-1-yl)propyl)pyrazolo[1,5-a][1,3,5]triazine-2,4-diamine | 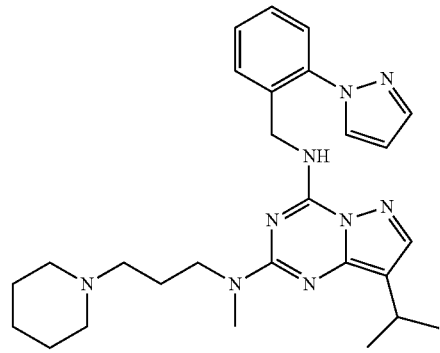 [SMILES: CC(C)c1cnn2c(NCc3ccccc3-n3cccn3)nc(N(C)CCCN3CCCCC3)nc12] |
| (VIII-50) | C24H29N9 | 443.25 | 444.2 | (VI-a) | N-(2-(1H-pyrazol-1-yl)benzyl)-2-(hexahydropyrrolo[3,4-b]pyrrol-5(1H)-yl)-8-isopropylpyrazolo[1,5-a][1,3,5]triazin-4-amine | 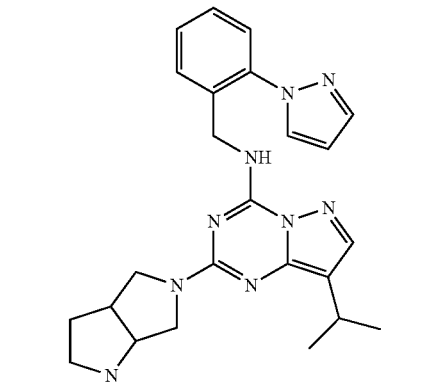 |
| (VIII-51) | C20H25N9 | 391.22 | 392.2 | (VI-a) | N4-(2-(1H-pyrazol-1-yl)benzyl)-N2-(2-aminoethyl)-8-isopropylpyrazolo[1,5-a][1,3,5]triazine-2,4-diamine | 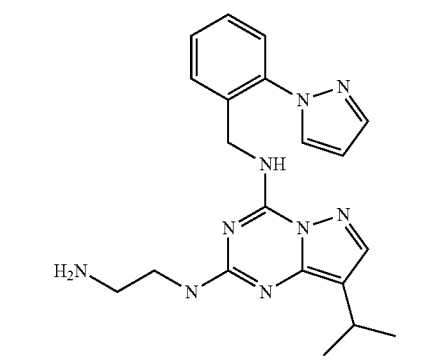 [SMILES: CC(C)c1cnn2c(NCc3ccccc3-n3cccn3)nc(NCCN)nc12] |

-continued

| Compound | formula | calculated | MS(ES) [M + H]+ | starting material | name | structure |
|---|---|---|---|---|---|---|
| (VIII-52) | C23H29N9 | 431.25 | 432.2 | (VI-a) | N4-(2-(1H-pyrazol-1-yl)benzyl)-8-isopropyl-N2-(pyrrolidin-3-ylmethyl)pyrazolo[1,5-a][1,3,5]triazine-2,4-diamine | 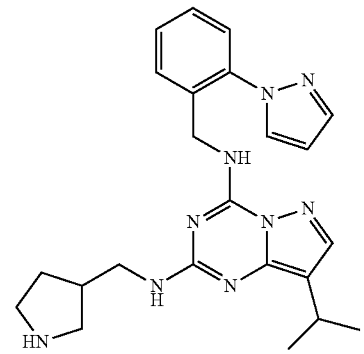 [SMILES: CC(C)c1cnn2c(NCc3ccccc3-n3cccn3)nc(NCC3CCNC3)nc12] |
| (VIII-53) | C23H29N9 | 431.25 | 432.1 | (VI-a) | N-(2-(1H-pyrazol-1-yl)benzyl)-2-(3-aminopiperidin-1-yl)-8-isopropylpyrazolo[1,5-a][1,3,5]triazin-4-amine | 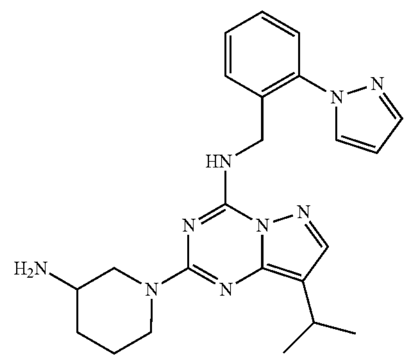 [SMILES: CC(C)c1cnn2c(NCc3ccccc3-n3cccn3)nc(N3CCCC(N)C3)nc12] |
| (VIII-54) | C22H27N9 | 417.24 | 418.2 | (VI-a) | N-(2-(1H-pyrazol-1-yl)benzyl)-2-(3-aminopyrrolidin-1-yl)-8-isopropylpyrazolo[1,5-a][1,3,5]triazin-4-amine | 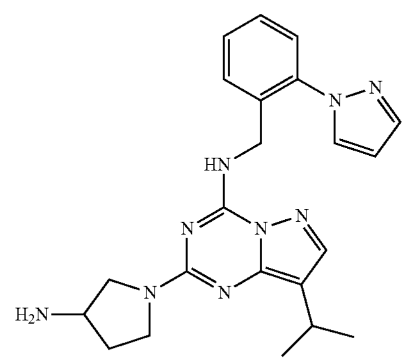 [SMILES: CC(C)c1cnn2c(NCc3ccccc3-n3cccn3)nc(N3CCC(N)C3)nc12] |
| (VIII-55) | C22H27N9O2 | 449.23 | 450.2 | (VI-a) | methyl 2-((4-((2-(1H-pyrazol-1-yl)benzyl)amino)-8-isopropylpyrazolo[1,5-a][1,3,5]triazin-2-yl)amino)-3-aminopropanoate | 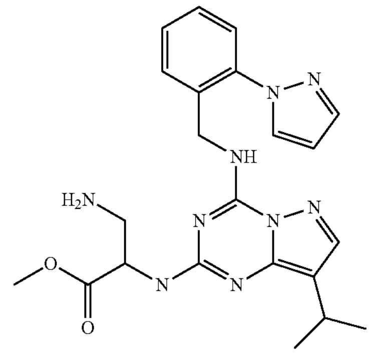 [SMILES: COC(=O)C(CN)Nc1nc(NCc2ccccc2-n2cccn2)n2ncc(C(C)C)c2n1] |

-continued

| Compound | formula | calculated | MS(ES) [M + H]+ | starting material | name | structure |
|---|---|---|---|---|---|---|
| (VIII-56) | C26H29N9 | 467.25 | 468.2 | (VI-a) | N4-(2-(1H-pyrazol-1-yl)benzyl)-N2-(2-amino-1-phenylethyl)-8-isopropylpyrazolo[1,5-a][1,3,5]triazine-2,4-diamine | 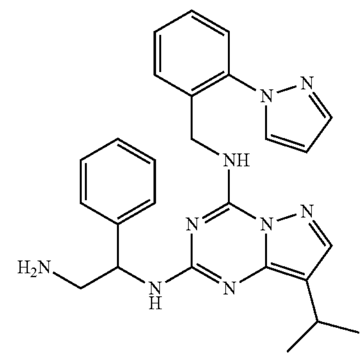 [SMILES: CC(C)c1cnn2c(NCc3ccccc3-n3cccn3)nc(NC(CN)c3ccccc3)nc12] |
| (VIII-57) | C23H29N9 | 431.25 | 432.2 | (VI-a) | N4-(2-(1H-pyrazol-1-yl)benzyl)-N2-(azetidin-3-ylmethyl)-8-isopropyl-N2-methylpyrazolo[1,5-a][1,3,5]triazine-2,4-diamine | 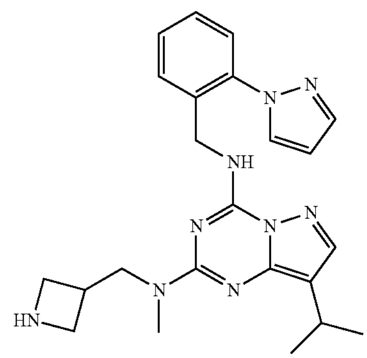 [SMILES: CC(C)c1cnn2c(NCc3ccccc3-n3cccn3)nc(N(C)CC3CNC3)nc12] |
| (VIII-58) | C25H33N9O | 475.28 | 476.2 | (VI-a) | N4-(2-(1H-pyrazol-1-yl)benzyl)-8-isopropyl-N2-methyl-N2-(2-morpholinoethyl)pyrazolo[1,5-a][1,3,5]triazine-2,4-diamine | 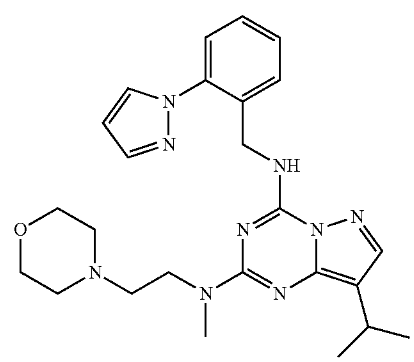 [SMILES: CC(C)c1cnn2c(NCc3ccccc3-n3cccn3)nc(N(C)CCN3CCOCC3)nc12] |
| (VIII-59) | C23H29N9 | 431.25 | 432.2 | (VI-a) | N-(2-(1H-pyrazol-1-yl)benzyl)-2-(4-aminopiperidin-1-yl)-8-isopropylpyrazolo[1,5-a][1,3,5]triazin-4-amine | 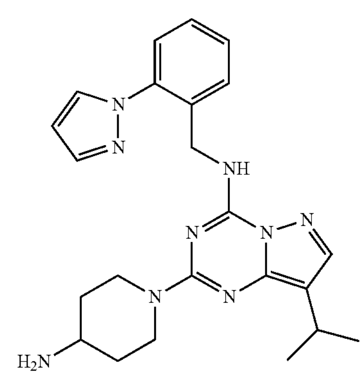 [SMILES: CC(C)c1cnn2c(NCc3ccccc3-n3cccn3)nc(N3CCC(N)CC3)nc12] |

-continued

| Compound | formula | MS(ES) calculated | [M + H]+ | starting material | name | structure |
| --- | --- | --- | --- | --- | --- | --- |
| (VIII-60) | C24H31N9 | 445.27 | 446.2 | (VI-a) | N4-(2-(1H-pyrazol-1-yl)benzyl)-N2-(4-aminocyclohexyl)-8-isopropylpyrazolo[1,5-a][1,3,5]triazine-2,4-diamine | 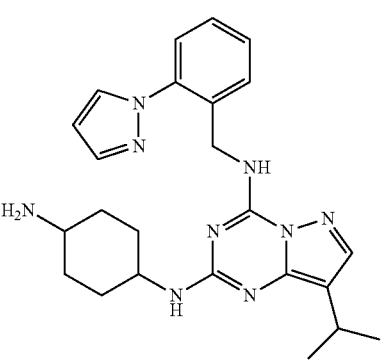 [SMILES: CC(C)c1cnn2c(NCc3ccccc3-n3cccn3)nc(NC3CCC(N)CC3)nc12] |
| (VIII-61) | C28H38N10O2 | 546.32 | 547.2 | (VI-a) | N-(2-(2-((4-((2-(1H-pyrazol-1-yl)benzyl)amino)-8-isopropylpyrazolo[1,5-a][1,3,5]triazin-2-yl)amino)ethoxy)ethyl)-2-(pyrrolidin-1-yl)acetamide | 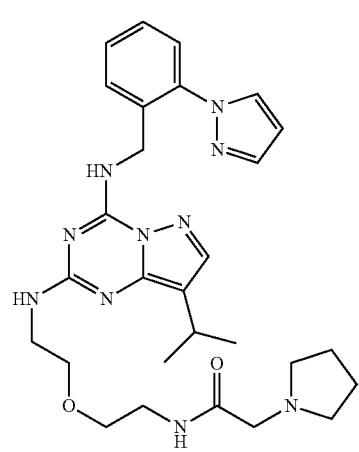 [SMILES: CC(C)c1cnn2c(NCc3ccccc3-n3cccn3)nc(NCCOCCNC(=O)CN3CCCC3)nc12] |
| (VIII-62) | C24H32N10 | 460.28 | 461.2 | (VI-a) | N4-(2-(1H-pyrazol-1-yl)benzyl)-8-isopropyl-N2-(2-(piperazin-1-yl)ethyl)pyrazolo[1,5-a][1,3,5]triazine-2,4-diamine | 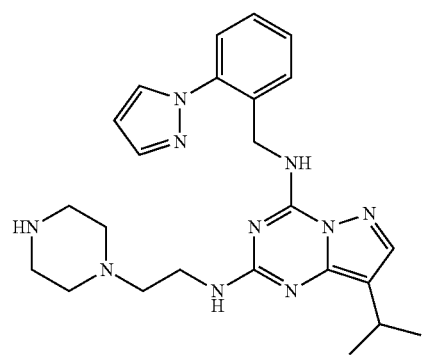 [SMILES: CC(C)c1cnn2c(NCc3ccccc3-n3cccn3)nc(NCCN3CCNCC3)nc12] |

Method E: Substitution of Methylsulfones (VI) with S-nucleophiles

Compound (X-2): 8-isopropyl-2-(piperidin-4-yl-sulfinyl)-N-(2-(thiophen-2-yl)benzyl) pyrazolo[1,5-a][1,3,5]triazin-4-amine

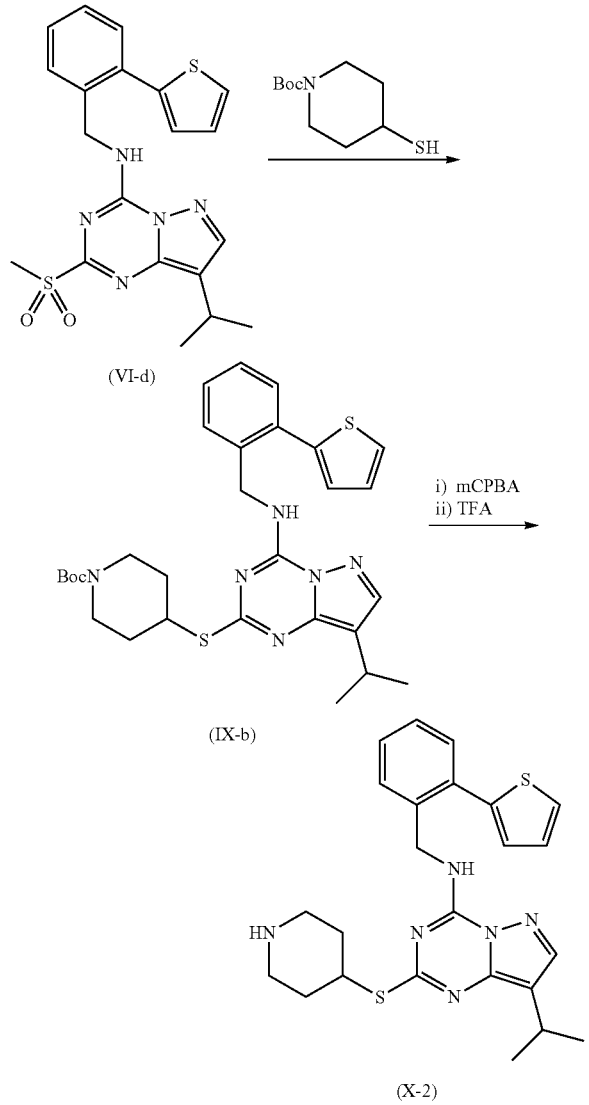

30 mg (0.07 mmol) methylsulfone (VI-d) were added to a solution of tert-butyl 4-mercaptopiperidine-1-carboxylate (46 mg, 0.21 mmol) and KHMDS (29 mg, 0.15 mmol) in DMF. The reaction was stirred at room temperature over night, diluted with ethyl acetate and washed with 10% aqueous NaHCO$_3$ and brine, dried with MgSO$_4$, filtered and concentrated in vacuo. The crude product was dissolved in DCM and cooled in an ice bath. 14 mg mCPBA (0.081 mmol) were added in three portions during 2 h. The reaction mixture was poured into a solution of 2 M aqueous NaOH and extracted with DCM. The organic layer was separated, washed with 2 M aqueous NaOH and brine, dried with MgSO$_4$, filtered and concentrated in vacuo. The protecting group was removed in TFA and the pure title compound (X-2) was obtained after RP-HPLC using a water/acetonitrile (0.1% TFA) gradient.

$^1$H-NMR (400 MHz, d$_6$-DMSO, 300K) δ 1.30 (d, J=6.8 Hz, 3H), 1.31 (d, J=6.8 Hz, 3H), 1.47 (d, broad, J=12.3 Hz, 1H), 1.76 (m, broad, 2H), 2.07 (d, broad, J=12.3 Hz, 1H), 2.62 (m, broad, 1H), 2.80 (m, broad, 1H), 2.99 (m, 1H), 3.14 (h, J=6.8 Hz, 1H), 3.24 (d, broad, 1H). 3.32 (d, broad, 1H), 4.80 (m, 2H), 7.18-7.42 (m, 6H), 7.66 (m, 1H), 8.22 (m, broad, 1H), 8.23 (s, 1H), 8.56 (m, broad, 1H), 9.85 (t, J=5.9 Hz, 1H). MS (ES) C24H28N6OS2 requires 480.18. found 481.7 (M+H)$^+$.

Compounds (X-1)-(X-9)

Title compounds (X-1)-(X-6) were prepared from the related methylsulfones (VI) according to method E. Sulfone (X-7) was prepared similar to (X-1) at elevated temperature using additional equivalents mCPBA. Thioethers (X-8) and (X-9) were prepared from the related intermediates (IX) using TFA to remove the Boc protecting group.

| Compound | formula | calculated | MS(ES) [M + H]+ | starting material | name | structure |
|---|---|---|---|---|---|---|
| (X-1) | C23H28N8OS | 464.21 | 465.1 | (VI-a) | N-(2-(1H-pyrazol-1-yl)benzyl)-8-isopropyl-2-(piperidin-4-ylsulfinyl)pyrazolo[1,5-a][1,3,5]triazin-4-amine | 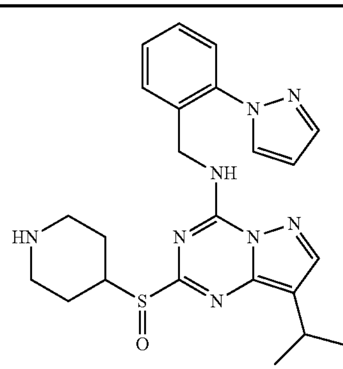 |

-continued

| Compound | formula | MS(ES) calculated | [M + H]+ | starting material | name |
|---|---|---|---|---|---|
| (X-2) | C24H28N6OS2 | 480.18 | 481.7 | (VI-d) | 8-isopropyl-2-(piperidin-4-ylsulfinyl)-N-(2-(thiophen-2-yl)benzyl)pyrazolo[1,5-a][1,3,5]triazin-4-amine |
| (X-3) | C26H30N6OS | 474.22 | 475.3 | (VI-b) | N-([1,1'-biphenyl]-2-ylmethyl)-8-isopropyl-2-(piperidin-4-ylsulfinyl)pyrazolo[1,5-a][1,3,5]triazin-4-amine |
| (X-4) | C22H27N9OS | 465.21 | 466.0 | (VI-g) | N-(2-(1H-1,2,4-triazol-1-yl)benzyl)-8-isopropyl-2-(piperidin-4-ylsulfinyl)pyrazolo[1,5-a][1,3,5]triazin-4-amine |
| (X-5) | C24H30N8OS | 478.23 | 479.2 | (VI-h) | 8-isopropyl-N-(2-(2-methyl-1H-imidazol-1-yl)benzyl)-2-(piperidin-4-ylsulfinyl)pyrazolo[1,5-a][1,3,5]triazin-4-amine |

-continued

| Compound | formula | calculated | MS(ES) [M + H]+ | starting material | name | structure |
|---|---|---|---|---|---|---|
| (X-6) | C23H28N8OS | 464.21 | 465.3 | (VI-a) | N-(2-(1H-pyrazol-1-yl)benzyl)-8-isopropyl-2-((R)-((R)-piperidin-3-yl)sulfinyl)pyrazolo[1,5-a][1,3,5]triazin-4-amine | 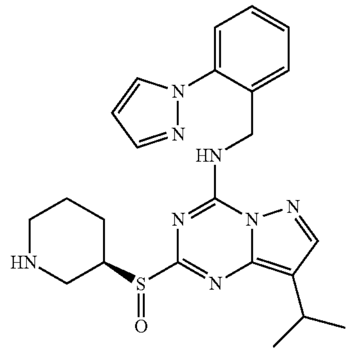 [SMILES: CC(C)c1cnn2c(NCc3ccccc3-n3cccn3)nc(S(=O)[C@@H]3CCCNC3)nc12] |
| (X-7) | C23H28N8O2S | 480.21 | 481.1 | (VI-a) | N-(2-(1H-pyrazol-1-yl)benzyl)-8-isopropyl-2-(piperidin-4-ylsulfonyl)pyrazolo[1,5-a][1,3,5]triazin-4-amine | 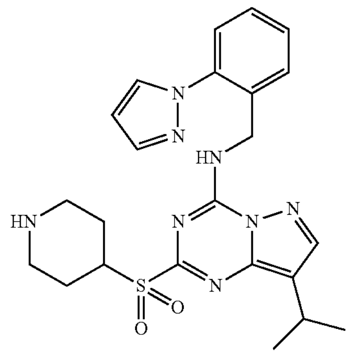 [SMILES: CC(C)c1cnn2c(NCc3ccccc3-n3cccn3)nc(S(=O)(=O)C3CCNCC3)nc12] |
| (X-8) | C23H28N8S | 448.22 | 449.1 | (VI-a) | (R)-N-(2-(1H-pyrazol-1-yl)benzyl)-8-isopropyl-2-(piperidin-3-ylthio)pyrazolo[1,5-a][1,3,5]triazin-4-amine | 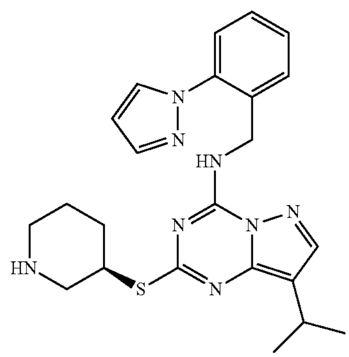 [SMILES: CC(C)c1cnn2c(NCc3ccccc3-n3cccn3)nc(S[C@@H]3CCCNC3)nc12] |
| (X-9) | C23H28N8S | 448.2 | 449.2 | (VI-a) | N-(2-(1H-pyrazol-1-yl)benzyl)-8-isopropyl-2-(piperidin-4-ylthio)pyrazolo[1,5-a][1,3,5]triazin-4-amine | 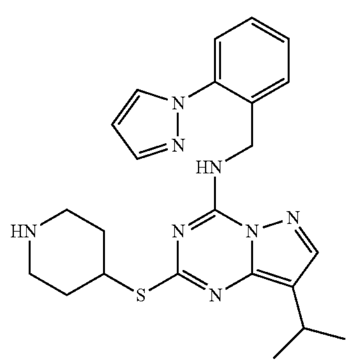 [SMILES: CC(C)c1cnn2c(NCc3ccccc3-n3cccn3)nc(SC3CCNCC3)nc12] |

Intermediate (XI): Ethyl 4-((2-(1H-pyrazol-1-yl)benzyl)amino)-8-isopropylpyrazolo[1,5-a][1,3,5]triazine-2-carbimidate

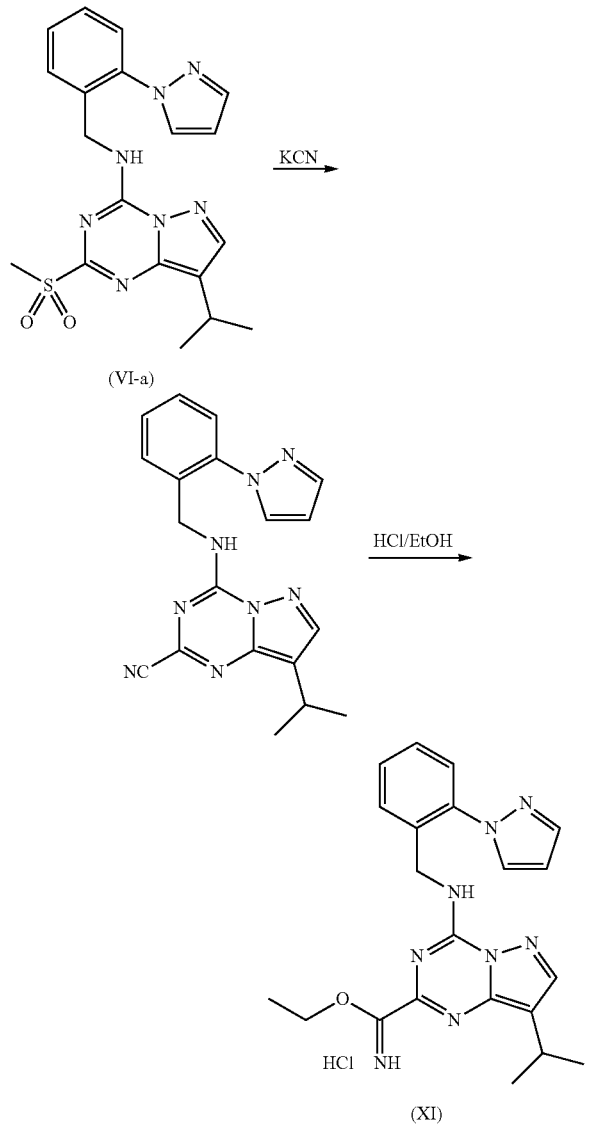

200 mg (0.49 mmol) (VI-a) and 63 mg (0.97 mmol) KCN in 1 ml NMP were heated at 80° C. for 4 h. The reaction mixture was diluted with ethyl acetate and purified on silica (cyclo hexane/ethylacetate) to yield the intermediate nitrile as colorless solid.

$^1$H-NMR (400 MHz, d$_6$-DMSO, 300K) δ 1.30 (d, J=6.8 Hz, 6H), 3.13 (h, J=6.8 Hz, 1H), 4.73 (s, 2H), 6.55 (m, 1H), 7.39-7.45 (m, 4H), 7.80 (m, 1H), 8.19 (m, 1H), 8.28 (s, 1H), 9.67 (s, broad, 1H); MS (ES) C19H18N8 requires 358.17. found 359.1 (M+H)$^+$. This intermediate was dissolved in 3.2 ml 1.25 M HCl/ethanol and stirred at 60° C. over night. The volatiles were removed under reduced pressure and the title compound (XI) was dried. It was used without any further purification.

MS (ES) C21H24N8O requires 404.21. found 406.1 (ester, M+H)$^+$.

Method F: Amides (XII) from Ethyl Carbimidate (XI)

Compound (XII-1): 4-((2-(1H-pyrazol-1-yl)benzyl)amino)-8-isopropyl-N-(piperidin-4-ylmethyl)pyrazolo[1,5-a][1,3,5]triazine-2-carboxamide

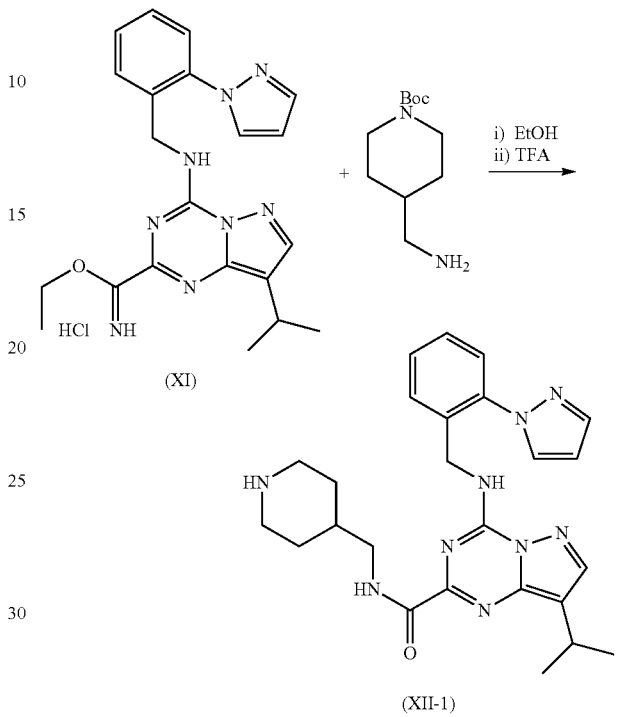

20 mg (0.045 mmol) intermediate (XI) and 0.23 mmol tert-butyl 4-(aminomethyl)piperidine-1-carboxylate in 200 µl ethanol were heated in a sealed tube at 120° C. over night. The reaction mixture was cooled and partitioned between ethyl acetate and brine. The organic phase was dried (MgSO4), filtered and evaporated to dryness. The Boc-protection group was then removed in TFA at room temperature. The pure title compounds (XII-1) was obtained after RP-HPLC using a water acetonitrile (0.1% TFA) gradient.

MS (ES) C25H31N9O requires 473.27. found 474.1 (M+H)$^+$.

Intermediate (XXVI): ethyl 4-((2-(1H-pyrazol-1-yl)benzyl)amino)-8-isopropyl pyrazolo[1,5-a][1,3,5]triazine-2-carboxylate

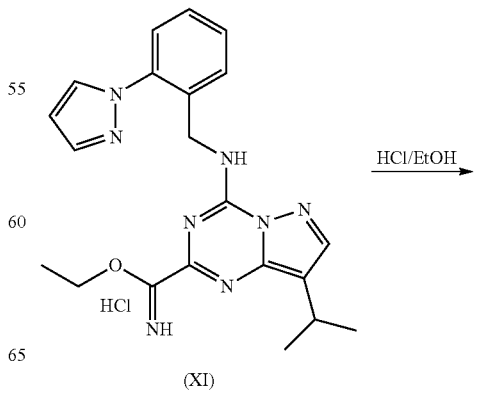

-continued

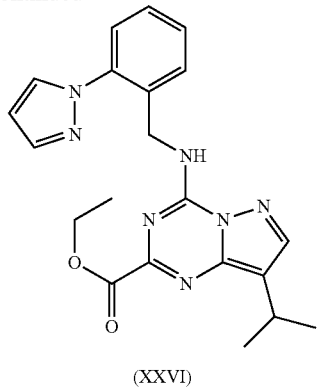

(XXVI)

13.16 g (29.85 mmol) of intermediate (XI) were dissolved in 121 ml ethanol and 97.0 ml 3 M HCl. The reaction mixture was stirred at room temperature over night. The mixture was poured into water and extracted three times with dichloromethane. The organic phase was washed with sodium bicarbonate and brine. The organic phase was dried and evaporated. 8.8 g of the title product were obtained.

MS (ES) C21H23N7O2 requires 405.19. found 406.1 (M+H)$^+$. $^1$H-NMR (300 MHz, CDCl3), δ (ppm): 1.31 (d, J=6.9 Hz, 6H), 1.50 (t, J=7.1 Hz, 3H), 3.35 (m, 1H, 4.51 (q, J=7.0 Hz, 2H), 4.82 (d, J=6.4 Hz, 2H), 6.53 (t, J=2.2 Hz, 1H), 7.30-7.43 (m, 3H), 7.80 (d, J=2.0 Hz, 1H), 7.84-7.90 (m, 2H), 7.94 (s, 1H), 8.54 (t, J=6.4 Hz, 1H).

Intermediate (XXVII): 4-((2-(1H-pyrazol-1-yl)benzyl)amino)-8-isopropylpyrazolo[1,5-a][1,3,5]triazine-2-carboxylic acid

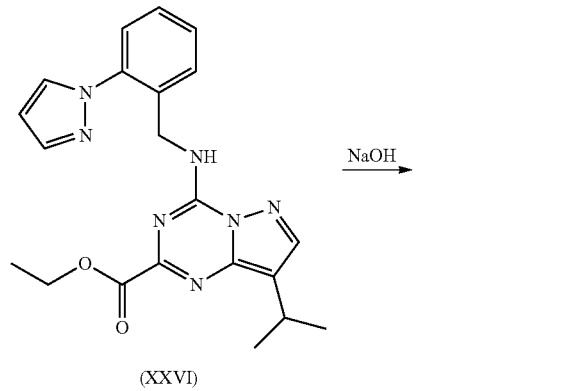

2.5 g (6.17 mmol) of intermediate (XXII) were dissolved in 43 ml THF and 25.6 ml 0.5 M NaOH. The mixture was stirred at room temperature for 5 h. Water was added and the mixture was extracted three times with TBME. The aqueous phase was adjusted to pH 5 using 5% citric acid and extracted with ethyl acetate. The second organic phase was dried and evaporated. 1.72 g (4.56 mmol) of the title product were obtained.

MS (ES) C19H19N7O2 requires 377.16. found 378.1 (M+H)$^+$. $^1$H-NMR (300 MHz, CDCl3), δ (ppm): 1.27 (d, J=6.9 Hz, 6H), 3.13-3-27 (m, 1H), 4.78 (d, J=6.6 Hz, 2H), 6.48 (t, J=2.1 Hz, 1H), 7.25-7.40 (m, 3H), 7.73 (dd, J=5.7/2.3 Hz, 2H), 7.83 (d, J=1.4 Hz, 1H), 7.91 (s, 1H), 8.82 (t, J=6.0 Hz, 1H).

Method L: Amides (XII) from Acid (XXVII)

Compound (XII-7): (4-((2-(1H-pyrazol-1-yl)benzyl)amino)-8-isopropylpyrazolo[1,5-a][1,3,5]triazin-2-yl)(2,6-diazaspiro[3.3]heptan-2-yl)methanone

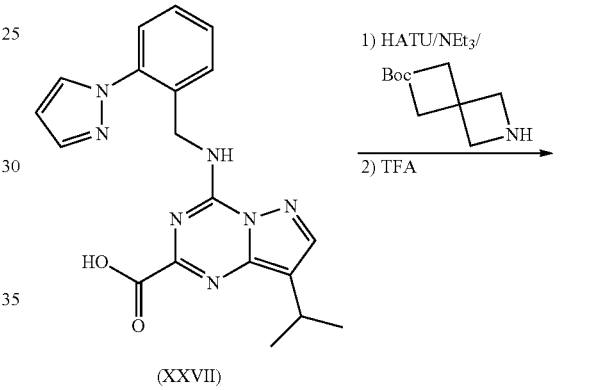

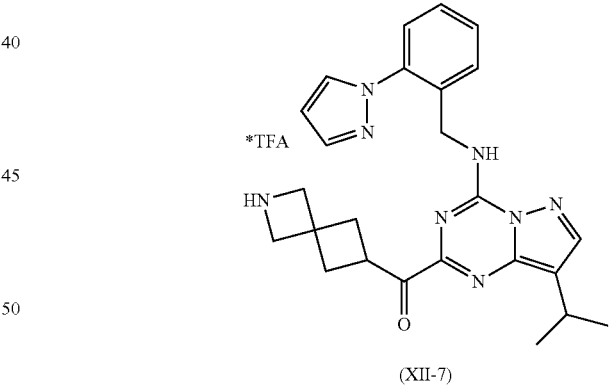

50 mg (132 μmol) 8-Isopropyl-4-(2-pyrazol-1-yl-benzylamino)-pyrazolo[1,5-a][1,3,5]triazine-2-carboxylic acid, 20 mg (141 μmol, 1.07 eq) 6-(tert-butoxycarbonyl)-6-aza-2-azoniaspiro[3.3]heptane oxalate and 64 mg (168 μmol, 1.28 eq) HATU were dissolved in 1.8 ml DMF and cooled to 0° C. 52 mg (512 μmol, 3.89 eq) triethylamine were added. The reaction mixture was stirred over night and allowed to warm to room temperature. The mixture was dissolved in ethyl acetate, washed with saturated sodium bicarbonate solution and brine. The organic phase was dried and evaporated. The residue was purified on silica gel, eluting with 1030 cyclohexaneethyl acetate to give the Boc-protected intermediate of (XII-7).

MS (ES) C29H35N9O3 requires 557.29. found 558 (M+H)+ and 580 (M+Na)+. 45 mg (80.7 μmol) of the Boc-protected intermediate of (XII-7) were dissolved in 1 ml dichloromethane at 0° C. 92 mg (807 μmol, 10 eq) trifluoroacetic acid were added. The reaction mixture was stirred over night. The reaction mixture was evaporated and the residue was purified on silica gel, eluting with 90/10 chloroform/methanol. 34 mg of the title product was obtained.

MS (ES) C24H27N9O requires 457.23. found 458 (M+H)+ and 480 (M+Na)+.

Compounds (XII-1)-(XII-11)

Compounds (XII-1)-(XII-5) were synthesized similar to method F. Compounds (XII-6)-(XII-11) were synthesized similar to method L.

| Compound | formula | calculated | MS(ES) [M + H]+ | from intermediate | name | structure |
|---|---|---|---|---|---|---|
| (XII-1) | C25H31N9O | 473.27 | 474.1 | (XI) | 4-((2-(1H-pyrazol-1-yl)benzyl)amino)-8-isopropyl-N-(piperidin-4-ylmethyl)pyrazolo[1,5-a][1,3,5]triazine-2-carboxamide | 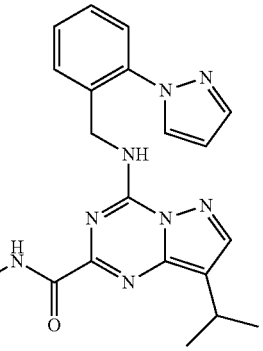 |
| (XII-2) | C23H27N9O | 445.23 | 446.0 | (XI) | 4-((2-(1H-pyrazol-1-yl)benzyl)amino)-N-(azetidin-3-ylmethyl)-8-isopropylpyrazolo[1,5-a][1,3,5]triazine-2-carboxamide | 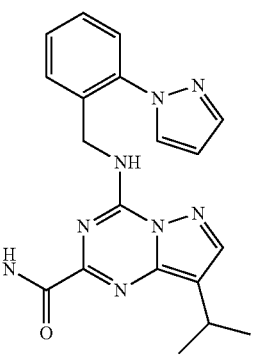 |
| (XII-3) | C24H29N9O | 459.25 | 460.1 | (XI) | 4-((2-(1H-pyrazol-1-yl)benzyl)amino)-8-isopropyl-N-(pyrrolidin-3-ylmethyl)pyrazolo[1,5-a][1,3,5]triazine-2-carboxamide | 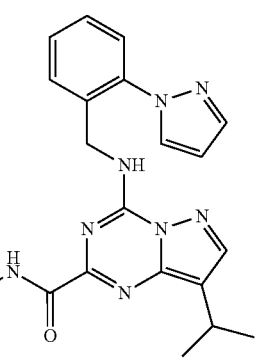 |

-continued

| Compound | formula | calculated | MS(ES) [M + H]+ | from intermediate | name | structure |
|---|---|---|---|---|---|---|
| (XII-4) | C25H31N9O | 473.27 | 474.1 | (XI) | 4-((2-(1H-pyrazol-1-yl)benzyl)amino)-8-isopropyl-N-(piperidin-3-ylmethyl)pyrazolo[1,5-a][1,3,5]triazine-2-carboxamide | 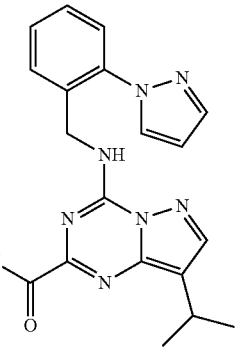 |
| (XII-5) | C23H29N9O | 447.25 | 448.1 | (XI) | 4-((2-(1H-pyrazol-1-yl)benzyl)amino)-N-(4-aminobutyl)-8-isopropylpyrazolo[1,5-a][1,3,5]triazine-2-carboxamide | 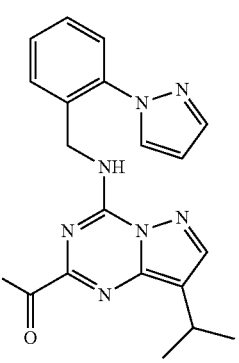 |
| (XII-7) | C24H27N9O | 457.23 | 458.1 | (XXVII) | (4-((2-(1H-pyrazol-1-yl)benzyl)amino)-8-isopropylpyrazolo[1,5-a][1,3,5]triazin-2-yl)(2,6-diazaspiro[3.3]heptan-2-yl)methanone | 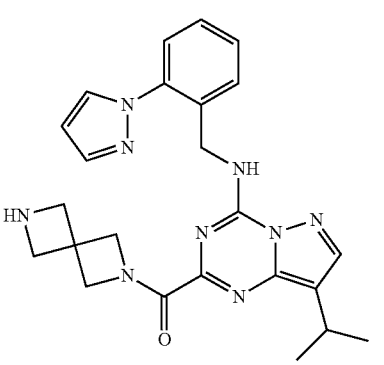 [SMILES: CC(C)c1cnn2c(NCc3ccccc3-n3cccn3)nc(C(=O)N3CC4(CNC4)C3)nc12] |
| (XII-6) | C26H33N9O2 | 503.28 | 504.3 | (XXVII) | 4-((2-(1H-pyrazol-1-yl)benzyl)amino)-8-isopropyl-N-methyl-N-(2-morpholinoethyl)pyrazolo[1,5-a][1,3,5]triazine-2-carboxamide | 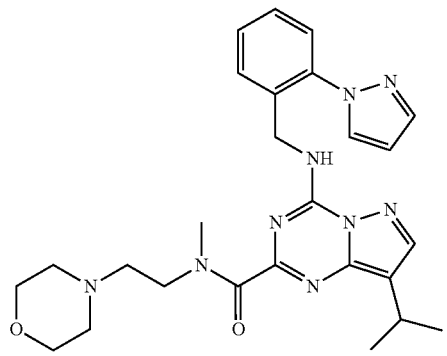 [SMILES: CC(C)c1cnn2c(NCc3ccccc3-n3cccn3)nc(C(=O)N(C)CCN3CCOCC3)nc12] |

-continued

| Compound | formula | calculated | MS(ES) [M + H]+ | from intermediate | name | structure |
|---|---|---|---|---|---|---|
| (XII-8) | C26H33N9O | 487.28 | 488.2 | (XXVII) | 4-((2-(1H-pyrazol-1-yl)benzyl)amino)-8-isopropyl-N-methyl-N-(2-(pyrrolidin-1-yl)ethyl)pyrazolo[1,5-a][1,3,5]triazine-2-carboxamide | 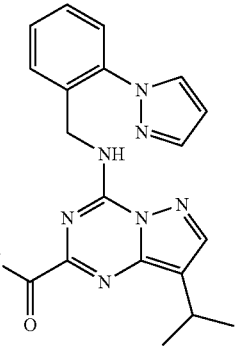 |
| (XII-9) | C23H27N9O | 445.23 | 446.3 | (XXVII) | (4-((2-(1H-pyrazol-1-yl)benzyl)amino)-8-isopropylpyrazolo[1,5-a][1,3,5]triazin-2-yl)(piperazin-1-yl)methanone | 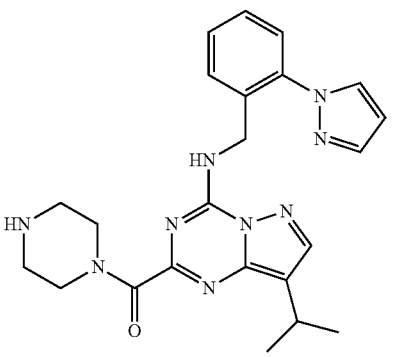 [SMILES: CC(C)c1cnn2c(NCc3ccccc3-n3cccn3)nc(C(=O)N3CCNCC3)nc12] |
| (XII-10) | C22H27N9O | 433.23 | 434.3 | (XXVII) | 4-((2-(1H-pyrazol-1-yl)benzyl)amino)-N-(3-aminopropyl)-8-isopropylpyrazolo[1,5-a][1,3,5]triazine-2-carboxamide | 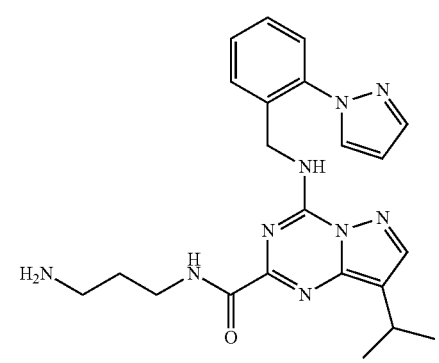 [SMILES: CC(C)c1cnn2c(NCc3ccccc3-n3cccn3)nc(C(=O)NCCCN)nc12] |
| (XII-11) | C24H29N9O | 459.25 | 460.3 | (XXVII) | (4-((2-(1H-pyrazol-1-yl)benzyl)amino)-8-isopropylpyrazolo[1,5-a][1,3,5]triazin-2-yl)(4-aminopiperidin-1-yl)methanone | 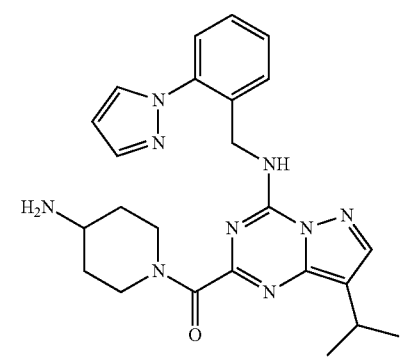 [SMILES: CC(C)c1cnn2c(NCc3ccccc3-n3cccn3)nc(C(=O)N3CCC(N)CC3)nc12] |

Intermediate (XXVIII): (4-((2-(1H-pyrazol-1-yl)benzyl)amino)-8-isopropylpyrazolo[1,5-a][1,3,5]triazin-2-yl)methanol

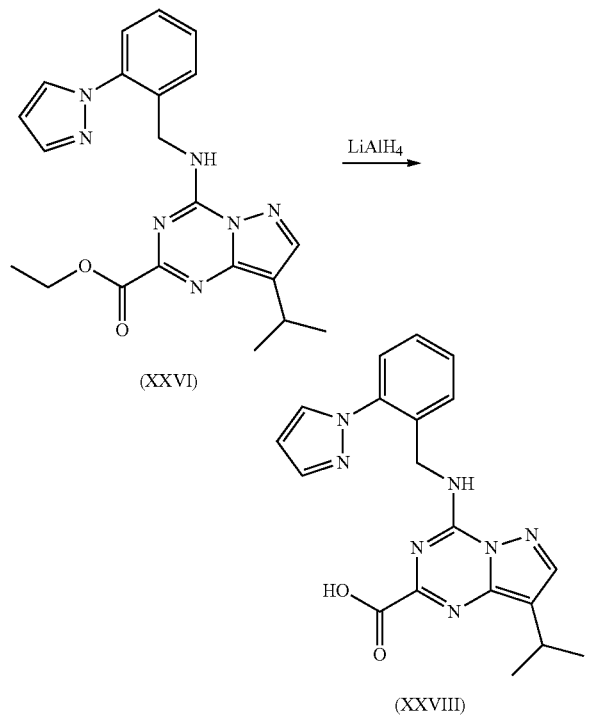

6.0 g (14.8 mmol) of ester (XXVI) were dissolved in 126 ml THF and cooled to 0° C. A suspension of 1.12 g (29.6 mmol) LiAlH₄ in 30 ml THF was added dropwise. The mixture was stirred for 1 h at 0° C. After this time saturated ammonium chloride was added and it was extracted with ethyl acetate. The organic phase was dried and evaporated. The residue was purified on silica gel eluting with 90/10 cyclohexane/ethyl acetate. 2.7 g (7.43 mmol) of the title product were obtained.

MS (ES) C19H21N7O requires 363.18. found 364.2 (M+H)⁺. ¹H-NMR (300 MHz, CDCl3), δ (ppm): 1.32 (d, J=6.7 Hz, 1H), 1.61 (br, 1H), 3.10-3.26 (m, 1H), 3.82 (t, J=4.5 Hz, 1H), 4.65 (d, J=4.3 Hz, 2H), 4.75 (d, J=6.5 Hz, 2H), 6.53 (t, J=2.1 Hz, 1H), 7.30-7.45 (m, 3H), 7.69 (dd, J=7.1/1.6 Hz, 1H), 7.78 (d, J=2.0 Hz, 1H), 7.83 (s, 1H), 7.89 (dd, J=1.4 Hz, 1H), 8.34 (t, J=6.3 Hz, 1H).

Intermediate (XXIX): 4-((2-(1H-pyrazol-1-yl)benzyl)amino)-8-isopropylpyrazolo[1,5-a][1,3,5]triazine-2-carbaldehyde

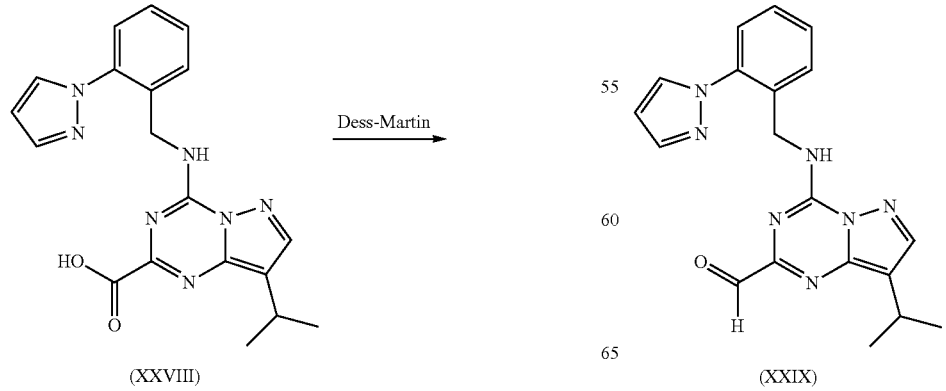

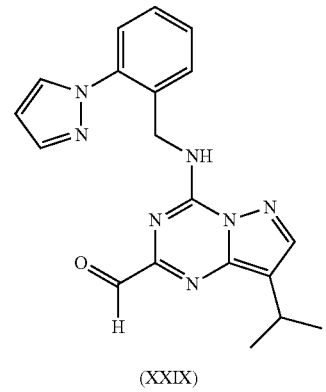

385 mg (908 µmol) Dess-Martin periodinane were dissolved in 1.5 ml dichloromethane and cooled to 0° C. 300 mg (0.825 mmol) of intermediate (XXVIII) in 1.5 ml dichloromethane were added dropwise. The mixture was stirred for 3 h at room temperature. The reaction mixture was neutralized with saturated sodium bicarbonate and extracted with dichloromethane. The organic phase was dried and evaporated. 300 mg of the title product was obtained as crude product and it was used without further purification in the next steps. MS (ES) C19H19N7O requires 361.17. found 362.2 (M+H)⁺. ¹H-NMR (300 MHz, CDCl3), δ (ppm): 1.29 (d, J=6.9 Hz, 6H), 3.16-3.32 (m, 1H), 4.77 (d, J=6.6 Hz, 1H), 6.47 (t, J=2.1 Hz, 1H), 7.23-7.37 (m, 3H), 8.61 (t, J=6.4 Hz, 1H), 9.85 (s, 1H).

Method M: Reductive Aminations with Aldehyde (XXIX)

Compound (XXX-1): N1-((4-((2-(1H-pyrazol-1-yl)benzyl)amino)-8-isopropyl pyrazolo[1,5-a][1,3,5]triazin-2-yl)methyl)ethane-1,2-diamine

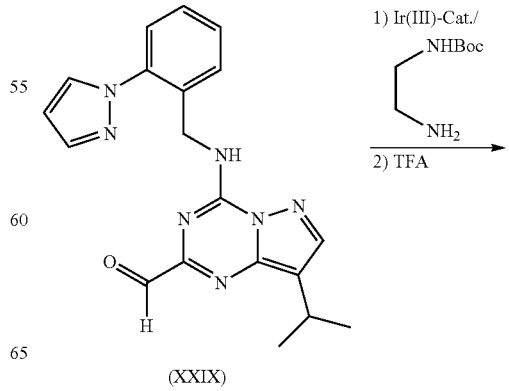

-continued

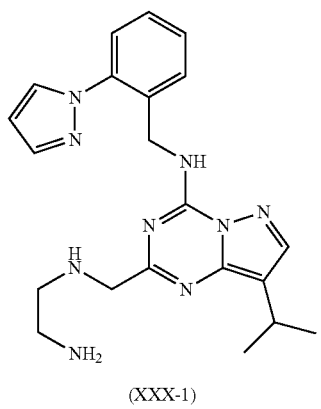

(XXX-1)

21 mg (133 μmol, 1.2 eq) N-Boc-ethylendiamine, 1 mg (1 mol %) Chloro-(pentamethyl-cyclopentadienyl)-{5-methoxy-2-{1-[(4-methoxyphenyl)imino-N]ethyl}phenyl-C}-iridium(III) and 40 mg (111 μmol) 8-Isopropyl-4-(2-pyrazol-1-yl-benzylamino)-pyrazolo[1,5-a][1,3,5]triazine-2-carbaldehyde were dissolved in 1 ml MeOH. 111 μl of formic acid-trimethylamine-complex (5:2) were added and the reaction mixture was stirred for 1 h at 80° C. Water was added and the mixture was extracted with ethyl acetate. The organic phase was washed three times with water, then with brine. The organic phase was dried and the solvent was evaporated off. The residue was purified on silica gel, eluting with 99/1 dichlormethane/methanol. 25 mg of the Boc-protected intermediate were obtained.

MS (ES) C26H35N9O2 requires 505.29. found 506 (M+H)+ and 528 (M+Na)+.

21 mg (42 μmol) of the intermediate were dissolved in 360 μl dichloromethane at 0° C. 48 mg (416 μmol, 10 eq) trifluoroacetic acid was added. The reaction mixture was stirred over night. The reaction mixture was evaporated and the residue was purified on silica gel, eluting with 90/10 chloroform/methanol.

MS (ES) C21H27N9 requires 405.24. found 406 (M+H)+ and 428 (M+Na)+.

Compounds (XXX-1)-(XXX-14)

Compounds (XXX-2)-(XXX-14) were synthesized similar to method M.

| Compound | formula | calculated | MS(ES) [M + H]+ | from intermediate | name | structure |
|---|---|---|---|---|---|---|
| (XXX-1) | C21H27N9 | 405.24 | 406.2 | (XXIX) | N1-((4-((2-(1H-pyrazol-1-yl)benzyl)amino)-8-isopropylpyrazolo[1,5-a][1,3,5]triazin-2-yl)methyl)ethane-1,2-diamine | 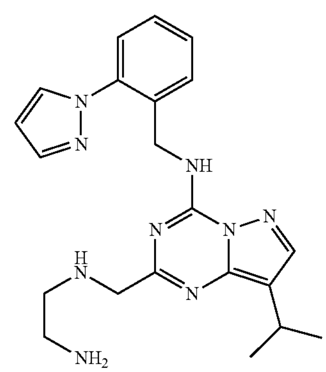 [SMILES: CC(C)c1cnn2c(NCc3ccccc3-n3cccn3)nc(CNCCN)nc12] |
| (XXX-2) | C26H35N9O | 489.30 | 490.2 | (XXIX) | N-(2-(1H-pyrazol-1-yl)benzyl)-8-isopropyl-2-(((3-morpholinopropyl)amino)methyl)pyrazolo[1,5-a][1,3,5]triazin-4-amine | 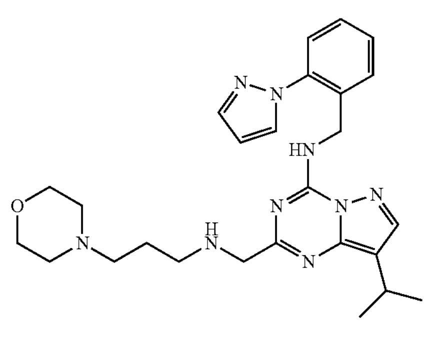 [SMILES: CC(C)c1cnn2c(NCc3ccccc3-n3cccn3)nc(CNCCCN3CCOCC3)nc12] |

-continued

| Compound | formula | calculated | MS(ES) [M + H]+ | from intermediate | name | structure |
|---|---|---|---|---|---|---|
| (XXX-3) | C26H35N9 | 473.30 | 474.3 | (XXIX) | N-(2-(1H-pyrazol-1-yl)benzyl)-8-isopropyl-2-((methyl(2-(pyrrolidin-1-yl)ethyl)amino)methyl)pyrazolo[1,5-a][1,3,5]triazin-4-amine | 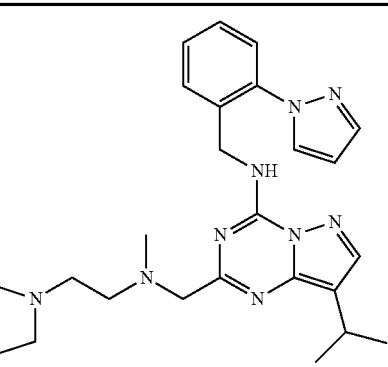 |
| (XXX-4) | C25H33N9 | 459.29 | 460.2 | (XXIX) | N-(2-(1H-pyrazol-1-yl)benzyl)-8-isopropyl-2-(((2-(pyrrolidin-1-yl)ethyl)amino)methyl)pyrazolo[1,5-a][1,3,5]triazin-4-amine | 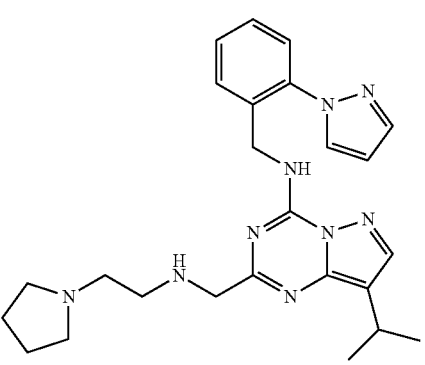 [SMILES: CC(C)c1cnn2c(NCc3ccccc3-n3cccn3)nc(CNCCN3CCCC3)nc12] |
| (XXX-5) | C25H33N9O | 475.28 | 476.2 | (XXIX) | N-(2-(1H-pyrazol-1-yl)benzyl)-8-isopropyl-2-(((2-morpholinoethyl)amino)methyl)pyrazolo[1,5-a][1,3,5]triazin-4-amine | 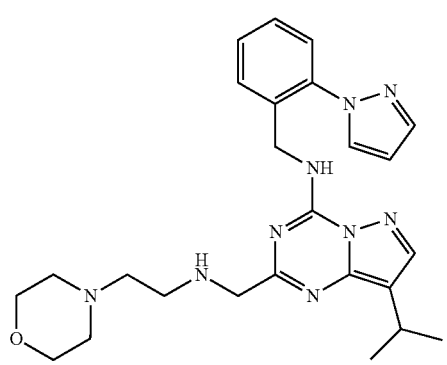 [SMILES: CC(C)c1cnn2c(NCc3ccccc3-n3cccn3)nc(CNCCN3CCOCC3)nc12] |
| (XXX-6) | C28H39N9 | 501.33 | 502.2 | (XXIX) | N-(2-(1H-pyrazol-1-yl)benzyl)-8-isopropyl-2-((methyl(3-(piperidin-1-yl)propyl)amino)methyl)pyrazolo[1,5-a][1,3,5]triazin-4-amine | 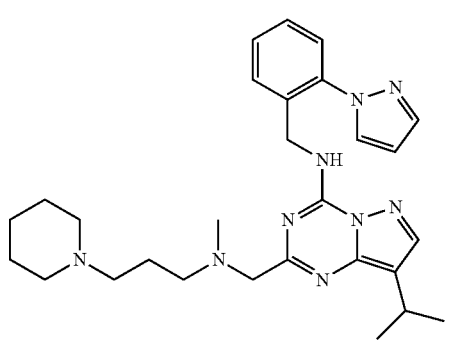 [SMILES: CC(C)c1cnn2c(NCc3ccccc3-n3cccn3)nc(CN(C)CCCN3CCCCC3)nc12] |

-continued

| Compound | formula | calculated | MS(ES) [M + H]+ | from intermediate | name | structure |
|---|---|---|---|---|---|---|
| (XXX-7) | C26H31F2N9 | 507.27 | 508.2 | (XXIX) | N-(2-(1H-pyrazol-1-yl)benzyl)-2-((3-(3,3-difluoropyrrolidin-1-yl)azetidin-1-yl)methyl)-8-isopropylpyrazolo[1,5-a][1,3,5]triazin-4-amine | 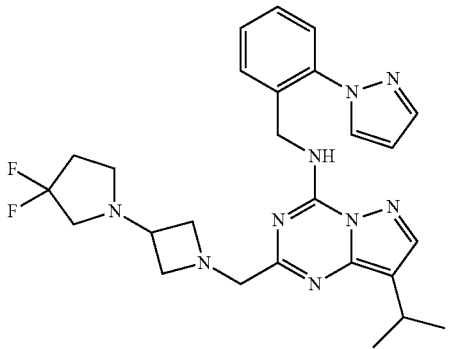 [SMILES: CC(C)c1cnn2c(NCc3ccccc3-n3cccn3)nc(CN3CC(N4CCC(F)(F)C4)C3)nc12] |
| (XXX-8) | C26H31N9O | 485.27 | 486.2 | (XXIX) | 1-(1-((4-((2-(1H-pyrazol-1-yl)benzyl)amino)-8-isopropylpyrazolo[1,5-a][1,3,5]triazin-2-yl)methyl)azetidin-3-yl)pyrrolidin-2-one | 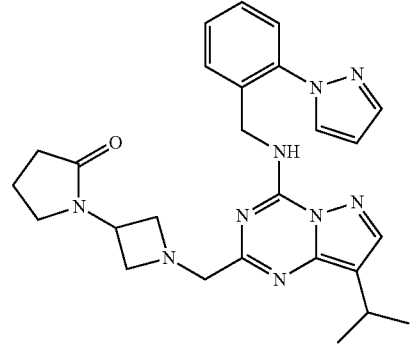 [SMILES: CC(C)c1cnn2c(NCc3ccccc3-n3cccn3)nc(CN3CC(N4CCCC4=O)C3)nc12] |
| (XXX-9) | C26H35N9O | 489.30 | 490.2 | (XXIX) | N-(2-(1H-pyrazol-1-yl)benzyl)-8-isopropyl-2-((4-(2-methoxyethyl)piperazin-1-yl)methyl)pyrazolo[1,5-a][1,3,5]triazin-4-amine | 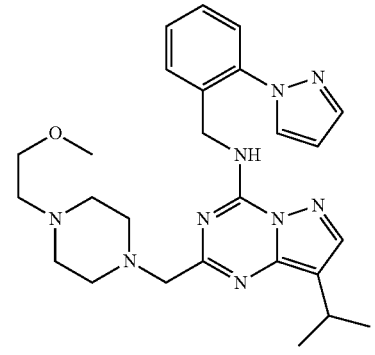 [SMILES: COCCN1CCN(Cc2nc(NCc3ccccc3-n3cccn3)n3ncc(C(C)C)c3n2)CC1] |
| (XXX-10) | C23H29N9 | 431.25 | 432.2 | (XXIX) | N-(2-(1H-pyrazol-1-yl)benzyl)-8-isopropyl-2-((pyrrolidin-3-ylamino)methyl)pyrazolo[1,5-a][1,3,5]triazin-4-amine | 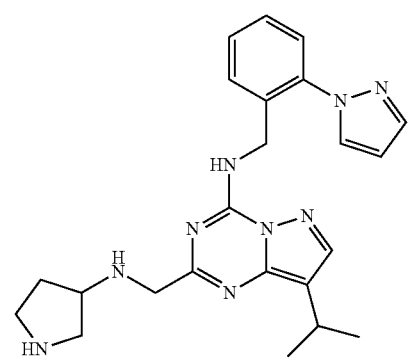 [SMILES: CC(C)c1cnn2c(NCc3ccccc3-n3cccn3)nc(CNC3CCNC3)nc12] |

-continued

| Compound | formula | calculated | MS(ES) [M + H]+ | from intermediate | name | structure |
|---|---|---|---|---|---|---|
| (XXX-11) | C23H29N9 | 431.25 | 432.2 | (XXIX) | N-(2-(1H-pyrazol-1-yl)benzyl)-8-isopropyl-2-(piperazin-1-ylmethyl)pyrazolo[1,5-a][1,3,5]triazin-4-amine | 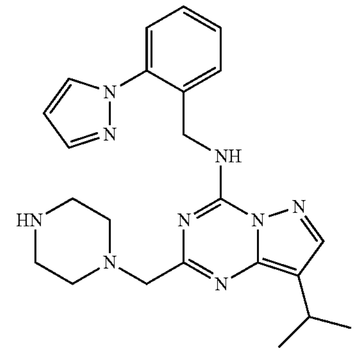 [SMILES: CC(C)c1cnn2c(NCc3ccccc3-n3cccn3)nc(CN3CCNCC3)nc12] |
| (XXX-12) | C24H31N9 | 445.27 | 446.2 | (XXIX) | N-(2-(1H-pyrazol-1-yl)benzyl)-2-(((azetidin-3-ylmethyl)(methyl)amino)methyl)-8-isopropylpyrazolo[1,5-a][1,3,5]triazin-4-amine | 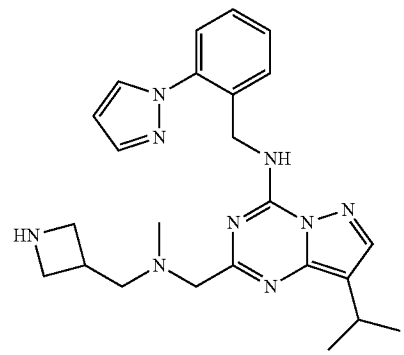 [SMILES: CC(C)c1cnn2c(NCc3ccccc3-n3cccn3)nc(CN(C)CC3CNC3)nc12] |
| (XXX-13) | C29H40N10O2 | 560.33 | 561.3 | (XXIX) | N-(2-(2-(((4-((2-(1H-pyrazol-1-yl)benzyl)amino)-8-isopropylpyrazolo[1,5-a][1,3,5]triazin-2-yl)methyl)amino)ethoxy)ethyl)-2-(pyrrolidin-1-yl)acetamide | 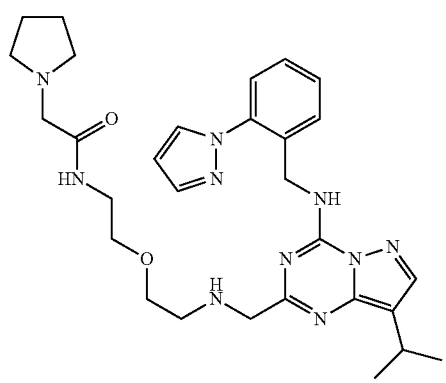 [SMILES: CC(C)c1cnn2c(NCc3ccccc3-n3cccn3)nc(CNCCOCCNC(=O)CN3CCCC3)nc12] |
| (XXX-14) | C24H31N9 | 445.27 | 446.2 | (XXIX) | N-(2-(1H-pyrazol-1-yl)benzyl)-2-((4-aminopiperidin-1-yl)methyl)-8-isopropylpyrazolo[1,5-a][1,3,5]triazin-4-amine | 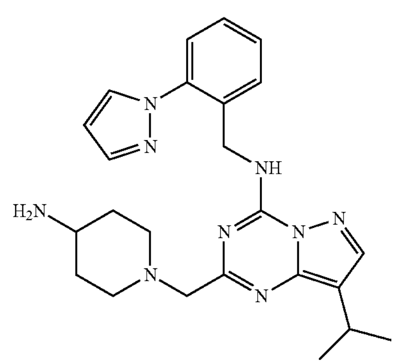 [SMILES: CC(C)c1cnn2c(NCc3ccccc3-n3cccn3)nc(CN3CCC(N)CC3)nc12] |

Method P: Esters (XXXI) from Acid (XXVII)

Compound (XXXI-1): 1-methylpyrrolidin-3-yl 4-((2-(1H-pyrazol-1-yl)benzyl)amino)-8-isopropylpyrazolo[1,5-a][1,3,5]triazine-2-carboxylate

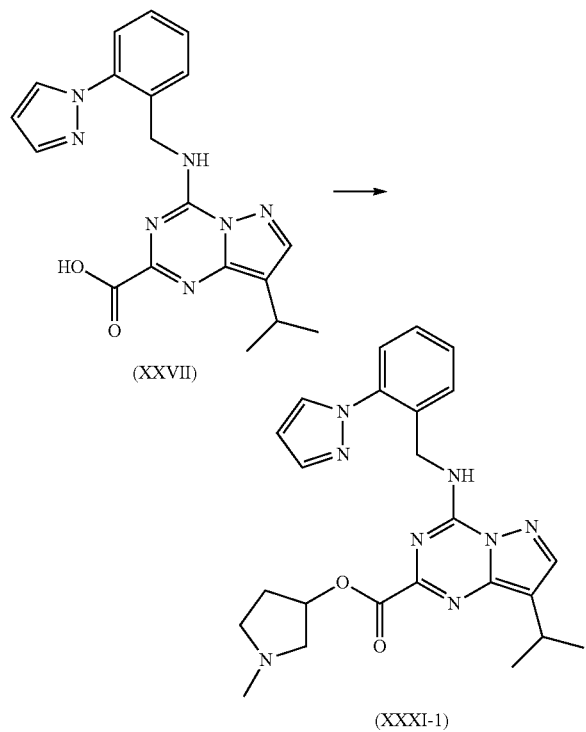

(XXVII)

(XXXI-1)

50 mg (132 µmol) 8-Isopropyl-4-(2-pyrazol-1-yl-benzylamino)-pyrazolo[1,5-a][1,3,5]triazine-2-carboxylic acid were dissolved in 3 ml methanol. 13 mg (132 µmol) triethylamine were added and the reaction mixture was stirred at room temperature. After 30 min the mixture was evaporated to dryness. The residue was dissolved in 3 ml dichloromethane. 16 mg (159 µmol) 3-hydroxy-1-methylpyrrolidine and 76 mg (146 µmol) benzotriazole-1-yl-oxytripyrrolidinophosphonium hexafluorophosphate were added and the reaction mixture was stirred at room temperature over night. The mixture was dissolved in ethyl acetate, washed with saturated sodium bicarbonate solution and brine. The organic phase was dried and evaporated. The residue was purified on silica gel, eluting with 95/5 chloroform/methanol.

MS (ES) C24H28N8O2 requires 460.23. found 461 (M+H)+ and 483 (M+Na)+.

Method Q: Sulfoximines from Thioethers

Compound (XXXII-1): 8-isopropyl-N-(2-(S-methylsulfonimidoyl)benzyl)-2-((R)-piperidin-3-yloxy)pyrazolo[1,5-a][1,3,5]triazin-4-amine

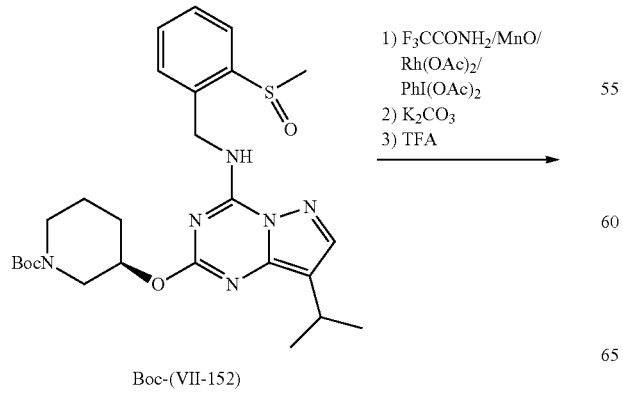

Boc-(VII-152)

1) F₃CCONH₂/MnO/
   Rh(OAc)₂/
   PhI(OAc)₂
2) K₂CO₃
3) TFA

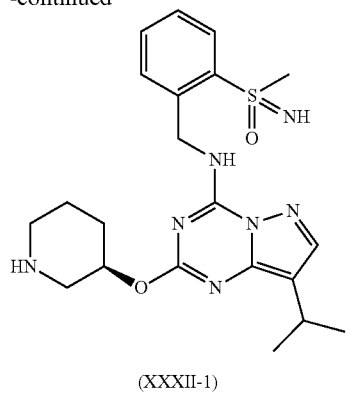

(XXXII-1)

12 mg (0.023 mmol) intermediate Boc-(VII-152), 5.2 mg (0.046 mmol) F₃CCONH₂, 6.4 mg (0.09 mmol) MnO, 1.0 mg (0.0023 mmol) rhodium(II) acetate and 11.1 mg (0.035 mmol) (diacetoxyiodo)benzene were stirred in 0.5 ml DCM at 40° C. After 24 h the mixture was purified on silica gel eluting with a cyclohexane/ethyl acetate gradient. The resulting intermediate was dissolved in methanol and stirred with 20 mg K₂CO₃ at 40° C. for 1 h. The mixture was filtered, and the solvent was removed under reduced pressure. After TFA cleavage of the Boc-protecting group, the crude product was purified by RP-HPLC using a water/acetonitrile (0.1% TFA) gradient.

MS (ES) C21H29N7O2S requires 443.21. found 444.32 (M+H)+.

Intermediate (XXXIII): 4-((2-(1H-pyrazol-1-yl)benzyl)amino)-8-isopropylpyrazolo[1,5-a][1,3,5]triazin-2-ol

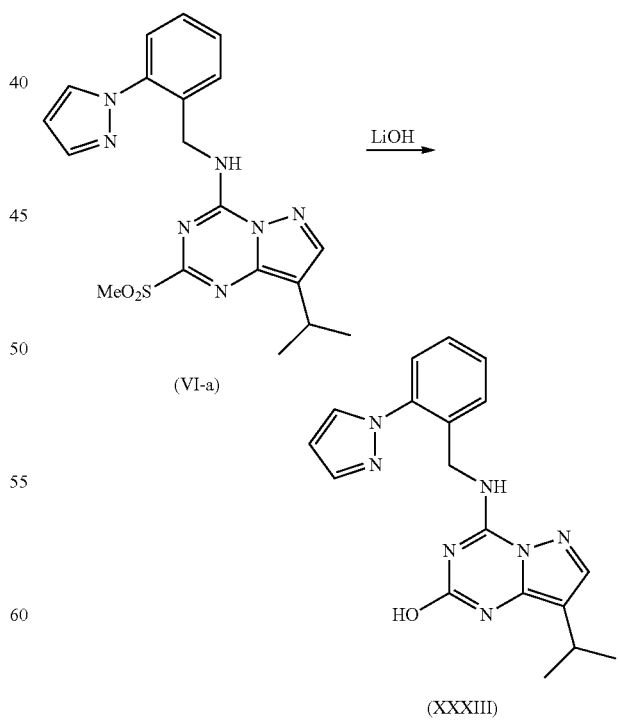

(VI-a)

LiOH (XXXIII)

14.6 g (35.5 mmol) of (8-isopropyl-2-methanesulfonylpyrazolo[1,5-a][1,3,5]triazin-4-yl)-(2-pyrazol-1-yl-benzyl)- amine and lithium hydroxide (2.55 g, 106.4 mmol) were dissolved in 300 mL aqueous 1,4-dioxane (10:1). The mixture was stirred at 60° C. until total consumption of the starting material and then diluted with water. pH was adjusted to 7 by the addition of 6 M hydrochloric acid, and the resulting mixture was extracted with dichloromethane. The combined organic layers were washed with brine, dried (MgSO4) and concentrated. 11.5 g (32.9 mmol) of the title compound were obtained.

1H-NMR (300 MHz, CDCl3) δ (ppm): 1.26 (d, J=6.9 Hz, 6H), 3.00-3.14 (m, 1H), 4.73 (d, J=6.0 Hz, 2H), 6.52 (t, J=2.1 Hz, 1H), 7.33-7.44 (m, 3H), 7.60 (s, 1H), 7.76-7.83 (m, 2H), 7.86 (d, J=1.7 Hz, 1H), 8.61 (t, J=5.6 Hz, 1H), 11.20 (br s, 1H); MS (ES) C18H19N7O requires 349.17. found 350.1 (M+H)+.

Intermediate (XXXIV): N-(2-(1H-pyrazol-1-yl)benzyl)-2-bromo-8-isopropylpyrazolo[1,5-a][1,3,5]triazin-4-amine

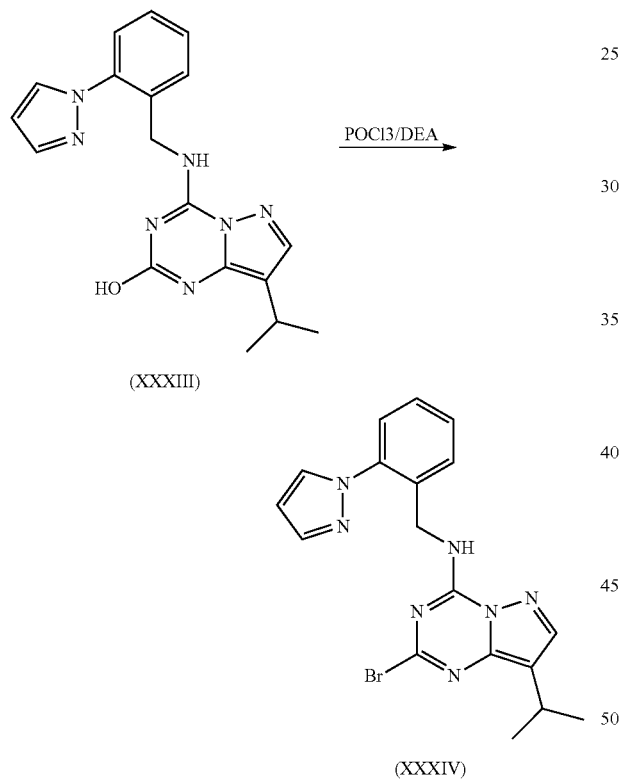

100 mg (286 μmol) 8-Isopropyl-4-(2-pyrazol-1-yl-benzylamino)-pyrazolo[1,5-a][1,3,5]triazin-2-ol were dissolved in 1 ml toluene. 123 mg (429 μmol) phosphorus oxybromide and 85 mg (566 μmol) N,N-diethylaniline were added. The reaction mixture was stirred at 100° C. over night. The mixture was poured in ice. The resulting solution was adjusted to pH 3 with 1 M hydrochloride solution and extracted three times with ethyl acetate. The organic phase was dried and evaporated. The residue was purified on silica gel, eluting with 4010 cyclohexaneethyl acetate. 64 mg of the title product were obtained.

MS (ES) C18H18BrN7 requires 411.08. found 411.9/ 414.4 (M+H)+.

Intermediate (XXXV): tert-butyl 2-(1H-pyrazol-1-yl)benzyl(2-bromo-8-isopropyl pyrazolo[1,5-a][1,3,5]triazin-4-yl)carbamate

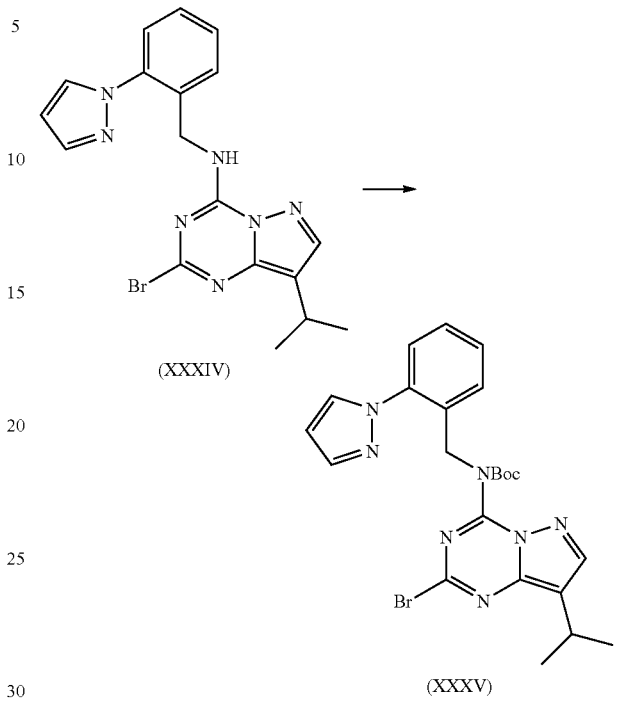

225 mg (546 μmol) of intermediate (XXXIV) were dissolved in 3.5 ml THF. 14 mg (105 μmol) DMAP and 155 mg (708 μmol) di-tert-butyl dicarbonate were added and the mixture was stirred at room temperature over night. The reaction mixture was dissolved in ethyl acetate and washed with water and brine. The organic phase was dried and evaporated. The residue was purified on silica gel, eluting with chloroform. 83 mg of the title product were obtained.

MS (ES) C23H26BrN7O2 requires 511.13. found 512.1/ 514.0 (M+H)+.

Method R: Cross Coupling Reactions with Bromide (XXXV)

Compound (XXXVI-1): N-(2-(1H-pyrazol-1-yl)benzyl)-8-isopropyl-2-(piperidin-3-ylmethyl)pyrazolo[1,5-a][1,3,5]triazin-4-amine

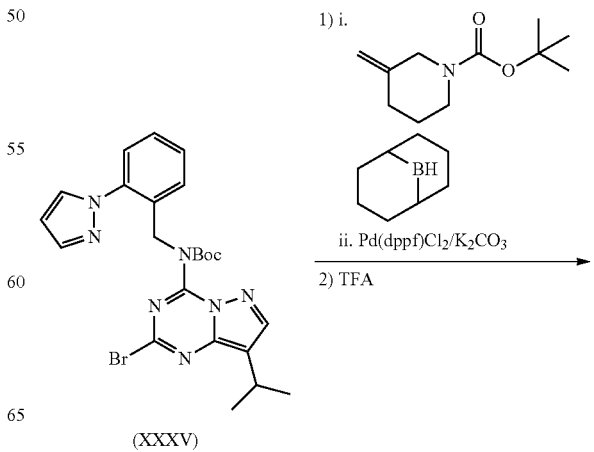

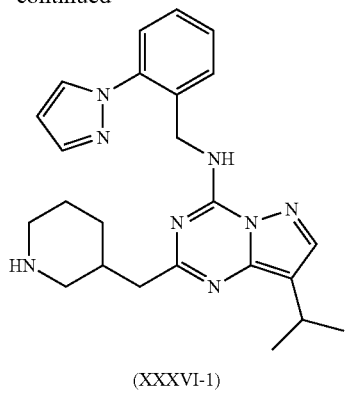

(XXXVI-1)

12 mg (61 μmol) N-Boc-3-methylenepiperidine and 120 μl 9-borabicyclo[3.3.1]-nonane were added into a flask and refluxed for 7 h. 30 mg (59 μmol) of intermediate (XXXV) were dissolved in 1 ml DMF and 50 μl water. 5 mg (3 μmol) 1,1'-bis(diphenylphosphino)ferrocene-palladium(II)dichloride and 11 mg (77 μmol) potassium carbonate were added. To this solution the above prepared solution was added and the mixture was stirred at 60° C. for 2.5 h. The reaction mixture was quenched with water and adjusted to pH 11 with 1 N NaOH. It was extracted three times with ethyl acetate. The organic phase was washed three times with water and once with brine. The organic phase was dried and evaporated. The residue was purified on silica gel, eluting with 50/50 cyclohexane/ethyl acetate. 21 mg of the title compound (XXXVI-1) were obtained.

MS (ES) C34H46N8O4 requires 630.36. found 631.2 (M+H)$^+$.

21 mg of the Boc-protected intermediate were dissolved in 500 μl dichloromethane at 0° C. 10 equivalents trifluoroacetic acid were added. The reaction mixture was stirred over night. The reaction mixture was evaporated and the residue was purified on silica gel, eluting with 19/1 chloroform/methanol.

MS (ES) C24H30N8 requires 430.26. found 431.3 (M+H)$^+$.

Results:
1. Measurement of Binding Affinities to CDKs

This protocol describes how the Lance Kinase Activity Assay was performed to determine IC$_{50}$ values of compounds of general formula (I) against CDK/Cyclin complexes. The principle behind this enzymatic assay is based upon the phosphorylation of the Ulight-Peptide Substrat. It is detected by using a specific EU-labeled anti-phospho peptide antibody. The binding of the Eu labeled anti-phospho peptide antibody to the phosphorylated ULight® labeled peptide gives rise to a FRET-signal.

Binding of an inhibitor to the kinase prevents phosphorylation of the Ulight-MBP Substrat, resulting in a loss of FRET.

CDK2 Enzymatic Activity Assay

TABLE 2

Reagents, stock concentrations and final assay concentrations

| Reagents | Stock concentration | Working concentration | Final assay concentration | Supplier |
|---|---|---|---|---|
| ULight MBP substrate | 5 μM | 83.33 nM | 50 nM | PerkinElmer |
| Eu-Anti-P-MBP Antibody (AB) | 625 nM | 4 nM | 2 nM | PerkinElmer |
| CDK2/CycA (135 kDa) | 2.02 μM | 8.33 nM | 5 nM | Proqinase |
| ATP | 100 mM | 15 μM | 3 μM | Sigma |

The compounds of general formula (I) exemplary summarized in Table 1 were diluted from a 10 mM DMSO stock solution 1:10 in a total volume of 15 μl DMSO. This compound predilution was then serial diluted 1:3 over 8 steps in DMSO and briefly spun down. Each compound solution was now diluted 1:20 in Enzymatic Buffer (HEPES: 50 mM, pH: 7.5; MgCl$_2$: 10 mM; EGTA: 1 mM; DTT: 2 mM; Tween-20: 0.01%), mixed thoroughly and spun down.

For every sample, 2 μl of the diluted compound were mixed with 6 μl CDK2/CycA/substrate working solution (8.33 nM CDK2/CycA; 83.33 nM ULight MBP substrate in enzymatic buffer) and 2 μl ATP working solution (15 μM ATP in enzymatic buffer) in a well of a small volume 384 well plate (Corning Incorporated, Corning, N.Y., USA; order no. 3673). For negative controls, in each well 2 μl of DMSO working solution (5% DMSO diluted in enzymatic buffer) was mixed with 6 μl substrate working solution (83.33 nM ULightMBP substrate in enzymatic buffer) and 2 μl ATP working solution. For positive controls, 2 μl of DMSO working solution were mixed with 6 μl CDK2/CycA/substrate working solution and 2 μl ATP working solution. Positive and negative controls were calculated from at least 8 different wells. The 384 well plates were mixed in a Teleshaker plate mixer (Beckman Coulter, Brea, Calif., USA) at 2000 rpm for 40 sec, and incubated for 1 h at room temperature before addition of 10 μl LANCE Detection Buffer (EDTA: 20 nM; Eu-Anti-P-MBP: 4 nM) per well. Plates were mixed in a Teleshaker plate mixer (Beckman Coulter, Brea, Calif., USA) at 2000 rpm for 40 sec, followed by incubation with Detection Buffer for 1 h, and reading. The FRET signal was measured at 340 nm excitation, 665 nm and 615 nm emission (for the ULight MBP substrate and LanthaScreen Eu-AB, respectively) with an Envision spectrophotometer (Perkin Elmer, Waltham, Mass., USA) with 90 μs delay and 20 μs integration time. IC$_{50}$ values were determined from the sigmoidal dose response curves with the software Quattro Workflow (Quattro GmbH, Munich, Germany). In case of tight binding of the inhibitors to CDK2/CycA, final assay concentrations were adjusted to 0.25 nM Eu-Anti-MBP AB, 2 nM CDK2/CycA and 30 μM ATP, and IC$_{50}$ values were converted according to the Cheng Prusoff equation to the IC$_{50}$ values at the original ATP-concentration.

Results are presented in Tables 5, 6 and 7.

CDK7 Enzymatic Activity Assay

TABLE 3

Reagents, stock concentrations and final assay concentrations

| Reagents | Stock concentration | Working concentration | Final assay concentration | Supplier |
|---|---|---|---|---|
| ULight MBP substrate | 5 μM | 83.33 nM | 50 nM | PerkinElmer |
| Eu-Anti-P-MBP AB | 625 nM | 4 nM | 2 nM | PerkinElmer |

TABLE 3-continued

Reagents, stock concentrations and final assay concentrations

| Reagents | Stock concentration | Working concentration | Final assay concentration | Supplier |
|---|---|---|---|---|
| CDK7/CycH/Mat1 143.2 kDa) | 1.39 µM | 16.66 nM | 10 nM | Carna |
| ATP | 100 mM | 125 µM | 25 µM | Sigma |

The compounds of general formula (I) exemplary summarized in Table 1 were diluted from a 10 mM DMSO stock solution 1:10 in a total volume of 15 µl DMSO. This compound predilution was then serial diluted 1:3 over 8 steps in DMSO and briefly spun down. Each compound solution was now diluted 1:20 in Enzymatic Buffer (HEPES: 50 mM, pH: 7.5; $MgCl_2$: 10 mM; EGTA: 1 mM; DTT: 2 mM; Tween-20: 0.01%), mixed thoroughly and spun down.

For every sample, 2 µl of the diluted compound were mixed with 6 µl CDK7/CycH/Mat1/substrate working solution (16.66 nM CDK7/CycH/Mat1; 83.33 nM ULight MBP substrate in enzymatic buffer) and 2 µl ATP working solution (125 µM ATP in enzymatic buffer) in a well of a small volume 384 well plate (Corning Incorporated, Corning, N.Y., USA; order no. 3673). For negative controls, in each well 2 µl of DMSO working solution (5% DMSO diluted in enzymatic buffer) was mixed with 6 µl substrate working solution (83.33 nM ULightMBP substrate in enzymatic buffer) and 2 µl ATP working solution. For positive controls, 2 µl of DMSO working solution were mixed with 6 µl CDK7/CycH/Mat1/substrate working solution and 2 µl ATP working solution. Positive and negative controls were calculated from at least 8 different wells. The 384 well plates were mixed in a Teleshaker plate mixer (Beckman Coulter, Brea, Calif., USA) at 2000 rpm for 40 sec, and incubated for 1 h at room temperature before addition of 10 µl LANCE Detection Buffer (1×; EDTA: 20 nM; Eu-Anti-P-MBP: 4 nM) per well. Plates were mixed in a Teleshaker plate mixer (Beckman Coulter, Brea, Calif., USA) at 2000 rpm for 40 sec, followed by incubation with Detection Buffer for 1 h, and reading. The FRET signal was measured at 340 nm excitation, 665 nm and 615 nm emission (for the ULight MBP substrate and LanthaScreen Eu-AB, respectively) with an Envision spectrophotometer (Perkin Elmer, Waltham, Mass., USA) with 90 µs delay and 20 µs integration time. $IC_{50}$ values were determined from the sigmoidal dose response curves with the software Quattro Workflow (Quattro GmbH, Munich, Germany). In case of tight binding of the inhibitors to CDK7/CycH/Mat1, final assay concentrations were adjusted to 2 nM Eu-Anti-MBP AB, 10 nM CDK7/CycH/Mat1 and 250 µM ATP; or 2 nM Eu-Anti-MBP AB, 3 nM CDK7/CycH/Mat1 and 2500 µM ATP, and $IC_{50}$ values were converted according to the Cheng Prusoff equation to the $IC_{50}$ values at the original ATP-concentration.

Results are presented in Tables 5, 6 and 7.

CDK9 Enzymatic Activity Assay

TABLE 4

Reagents, stock concentrations and final assay concentrations

| Reagents | Stock concentration | Working concentration | Final assay concentration | Supplier |
|---|---|---|---|---|
| ULight MBP substrate | 5 µM | 83.33 nM | 50 nM | PerkinElmer |
| Eu-Anti-P-MBP AB | 625 nM | 4 nM | 2 nM | PerkinElmer |

TABLE 4-continued

Reagents, stock concentrations and final assay concentrations

| Reagents | Stock concentration | Working concentration | Final assay concentration | Supplier |
|---|---|---|---|---|
| CDK9/Cyclin T1 (131.7 kDa) | 2.67 µM | 16.66 nM | 10 nM | Invitrogen |
| ATP | 100 mM | 125 µM | 25 µM | Sigma |

The compounds of general formula (I) exemplary summarized in Table 1 were diluted from a 10 mM DMSO stock solution 1:10 in a total volume of 15 µl DMSO. This compound predilution was then serial diluted 1:3 over 8 steps in DMSO and briefly spun down. Each compound solution was now diluted 1:20 in Enzymatic Buffer (HEPES: 50 mM, pH: 7.5; $MgCl_2$: 10 mM; EGTA: 1 mM; DTT: 2 mM; Tween-20: 0.01%), mixed thoroughly and spun down.

For every sample, 2 µl of the diluted compound were mixed with 6 µl CDK9/Cyclin T1/substrate working solution (16.66 nM CDK9/cyclin T1; 83.33 nM ULight MBP substrate in enzymatic buffer) and 2 µl ATP working solution (125 µM ATP in enzymatic buffer) in a well of a small volume 384 well plate (Corning Incorporated, Corning, N.Y., USA; order no. 3673). For negative controls, in each well 2 µl of DMSO working solution (5% DMSO diluted in enzymatic buffer) was mixed with 6 µl substrate working solution (83.33 nM ULightMBP substrate in enzymatic buffer) and 2 µl ATP working solution. For positive controls, 2 µl of DMSO working solution were mixed with 6 µl CDK9/cyclin T1/substrate working solution and 2 µl ATP working solution. Positive and negative controls were calculated from at least 8 different wells. The 384 well plates were mixed in a Teleshaker plate mixer (Beckman Coulter, Brea, Calif., USA) at 2000 rpm for 40 sec, and incubated for 1 h at room temperature before addition of 10 µl LANCE Detection Buffer (1×; EDTA: 20 nM; Eu-Anti-P-MBP: 4 nM) per well. Plates were mixed in a Teleshaker plate mixer (Beckman Coulter, Brea, Calif., USA) at 2000 rpm for 40 sec, followed by incubation with Detection Buffer for 1 h, and reading. The FRET signal was measured at 340 nm excitation, 665 nm and 615 nm emission (for the ULight MBP substrate and LanthaScreen Eu-AB, respectively) with an Envision spectrophotometer (Perkin Elmer, Waltham, Mass., USA) with 90 µs delay and 20 µs integration time. $IC_{50}$ values were determined from the sigmoidal dose response curves with the software Quattro Workflow (Quattro GmbH, Munich, Germany). Results are presented in Tables 5A, 5B, 6 and 7.

For evaluating the CDK7 inhibitory activity of the compounds of the present invention the following ranges for the $IC_{50}$ [nM] were applied:

$IC_{50} \leq 5$ nM+++
5 nM$<IC_{50} \leq 10$ nM++
10 nM$<IC_{50} \leq 25$ nM+
$IC_{50}>25$ nM ○

TABLE 5A

CDK7 inhibitory activity of the compounds of general formula (I):

| Comp. | CDK7 | Comp. | CDK7 | Comp. | CDK7 |
|---|---|---|---|---|---|
| (VII-01) | +++ | (VII-26) | +++ | (VIII-055) | ○ |
| (VII-02) | +++ | (VII-27) | +++ | (VIII-06) | +++ |
| (VII-03) | +++ | (VII-28) | +++ | (VIII-07) | +++ |

TABLE 5A-continued

CDK7 inhibitory activity of the compounds of general formula (I):

| Comp. | CDK7 | Comp. | CDK7 | Comp. | CDK7 |
|---|---|---|---|---|---|
| (VII-04) | +++ | (VII-29) | +++ | (VIII-08) | ++ |
| (VII-05) | +++ | (VII-30) | +++ | (VIII-09) | ++ |
| (VII-058) | ○ | (VII-31) | +++ | (VIII-10) | ++ |
| (VII-06) | +++ | (VII-32) | +++ | (VIII-11) | +++ |
| (VII-07) | +++ | (VII-33) | +++ | (VIII-12) | +++ |
| (VII-08) | ++ | (VII-34) | +++ | (VIII-13) | ++ |
| (VII-09) | +++ | (VII-35) | +++ | (VIII-14) | + |
| (VII-092) | + | (VII-36) | +++ | (VIII-15) | + |
| (VII-093) | ○ | (VII-37) | +++ | (VIII-16) | +++ |
| (VII-095) | ○ | (VII-38) | +++ | (VIII-17) | +++ |
| (VII-096) | +++ | (VII-39) | +++ | (VIII-18) | +++ |
| (VII-097) | ○ | (VII-40) | ○ | (VIII-19) | +++ |
| (VII-098) | + | (VII-41) | +++ | (VIII-20) | +++ |
| (VII-099) | +++ | (VII-42) | +++ | (VIII-21) | ++ |
| (VII-10) | +++ | (VII-43) | +++ | (VIII-22) | +++ |
| (VII-100) | +++ | (VII-44) | +++ | (VIII-23) | +++ |
| (VII-103) | + | (VII-45) | +++ | (VIII-24) | +++ |
| (VII-104) | +++ | (VII-46) | +++ | (VIII-25) | +++ |
| (VII-105) | ○ | (VII-47) | +++ | (VIII-26) | ++ |
| (VII-106) | +++ | (VII-48) | +++ | (VIII-27) | ++ |
| (VII-107) | +++ | (VII-49) | +++ | (VIII-28) | +++ |
| (VII-108) | +++ | (VII-50) | +++ | (VIII-31) | ++ |
| (VII-109) | + | (VII-51) | +++ | (VIII-32) | ++ |
| (VII-11) | ++ | (VII-52) | +++ | (VIII-33) | +++ |
| (VII-110) | +++ | (VII-53) | ++ | (VIII-34) | +++ |
| (VII-111) | + | (VII-54) | ++ | (VIII-35) | +++ |
| (VII-112) | ++ | (VII-55) | + | (VIII-36) | +++ |
| (VII-113) | + | (VII-56) | ++ | (VIII-37) | +++ |
| (VII-114) | +++ | (XXX-8) | ○ | (VIII-38) | +++ |
| (VII-115) | ○ | (VII-58) | + | (X-1) | +++ |
| (VII-116) | + | (VII-59) | +++ | (X-2) | +++ |
| (VII-117) | ○ | (VII-60) | ○ | (X-3) | + |
| (VII-118) | ++ | (VII-61) | ++ | (X-4) | +++ |
| (VII-119) | ○ | (VII-62) | + | (X-5) | +++ |
| (VII-12) | +++ | (VII-63) | + | (X-7) | +++ |
| (VII-120) | ++ | (VII-64) | ++ | (X-8) | +++ |
| (VII-121) | +++ | (VII-65) | +++ | (X-9) | + |
| (VII-122) | + | (VII-66) | +++ | (XII-06) | ○ |
| (VII-123) | +++ | (XXX-2) | ○ | (XII-07) | ○ |
| (VII-124) | ○ | (XXX-9) | ○ | (XII-1) | +++ |
| (VII-13) | +++ | (VII-69) | +++ | (XII-10) | ○ |
| (VII-14) | +++ | (VII-70) | +++ | (XII-2) | +++ |
| (VII-141) | + | (XXX-4) | ○ | (XII-3) | +++ |
| (VII-142) | ○ | (VII-72) | +++ | (XXX-7) | ○ |
| (VII-143) | + | (VII-73) | +++ | (XII-5) | +++ |
| (VII-145) | + | (VIII-053) | ○ | (XII-8) | ○ |
| (VII-146) | + | (VII-75) | +++ | (XII-9) | ○ |
| (VII-147) | ++ | (VII-76) | +++ | (VII-71) | +++ |
| (VII-148) | +++ | (VIII-01) | +++ | (XXX-3) | ○ |
| (VII-149) | + | (VIII-052) | ○ | (VII-68) | +++ |
| (VII-15) | +++ | (VIII-039) | ○ | (XXX-5) | ○ |
| (VII-151) | +++ | (VIII-04) | + | (VIII-05) | +++ |
| (VII-152) | + | (VIII-040) | ○ | (XXX-6) | ○ |
| (VII-153) | + | (VIII-041) | ○ | (VII-20) | +++ |
| (VII-154) | +++ | (VIII-043) | ++ | (VIII-054) | ○ |
| (VII-16) | +++ | (VIII-044) | ○ | (VII-57) | +++ |
| (VII-17) | +++ | (VIII-045) | + | (VIII-051) | ++ |
| (VII-18) | +++ | (VIII-046) | ○ | (VIII-02) | +++ |
| (VII-19) | +++ | (VIII-047) | ○ | (VIII-03) | +++ |
| (XXX-4) | ○ | (VIII-048) | + | (VIII-25) | +++ |
| (VII-21) | +++ | (VIII-049) | ○ | (VII-74) | +++ |
| (VII-22) | +++ | (XII-4) | +++ | (VII-67) | +++ |
| (VII-23) | +++ | (VIII-050) | + | (VII-24) | +++ |

Comp.: Compound
CDK7: IC50 [nM] for CDK7 inhibition (the above defined ranges apply)

Correspondingly, for evaluating the simultaneous CDK2 and CDK9 selectivities the following ranges for $IC_{50}$ [nM] were applied:

$IC_{50} \leq 50$ nM ○

50 nM $< IC_{50} \leq 500$ nM +

500 nM $< IC_{50} \leq 2500$ nM ++

$IC_{50} > 2500$ nM +++

TABLE 5B

CDK7 selectivity of the compounds of general formula (I):

| Comp. | CDK2 | CDK9 | Comp. | CDK2 | CDK9 |
|---|---|---|---|---|---|
| (VII-104) | + | +++ | (VII-10) | +++ | ++ |
| (VII-148) | + | + | (VII-11) | ++ | ++ |
| (VII-154) | + | +++ | (VII-12) | ○ | + |
| (VII-100) | + | + | (VII-13) | + | ++ |
| (VII-121) | +++ | +++ | (VII-14) | + | ++ |
| (VII-107) | + | +++ | (VII-15) | +++ | +++ |
| (X-8) | + | +++ | (VII-16) | ++ | +++ |
| (VII-096) | + | ++ | (VII-17) | +++ | +++ |
| (VII-099) | ++ | +++ | (VII-18) | + | ++ |
| (VII-106) | + | +++ | (VII-19) | +++ | ++ |
| (VII-108) | + | +++ | (VII-20) | | ++ |
| (VII-110) | +++ | +++ | (VII-21) | ○ | ++ |
| (VII-114) | +++ | +++ | (VII-22) | + | ++ |
| (VII-151) | ++ | +++ | (VII-23) | ++ | ++++ |
| (X-7) | +++ | +++ | (VII-24) | +++ | +++ |
| (VII-123) | + | +++ | (VII-25) | | +++ |
| (VII-147) | + | +++ | (VII-26) | + | + |
| (VIII-051) | ++ | +++ | (VII-27) | + | + |
| (VIII-043) | + | +++ | (VII-28) | +++ | +++ |
| (VII-112) | +++ | +++ | (VII-29) | + | +++ |
| (VII-120) | + | +++ | (VII-30) | ++ | ○ |
| (VII-118) | + | + | (VII-31) | + | ○ |
| (VII-146) | +++ | +++ | (VII-32) | + | + |
| (VIII-050) | +++ | +++ | (VII-33) | ○ | ○ |
| (VII-145) | ++ | ++ | (VII-34) | + | ++ |
| (VIII-045) | +++ | +++ | (VII-35) | + | + |
| (VIII-048) | +++ | +++ | (VII-36) | ○ | ○ |
| (VII-116) | + | ++ | (VII-37) | ○ | +++ |
| (VII-092) | +++ | +++ | (VII-38) | + | ++ |
| (VII-098) | ++ | +++ | (VII-39) | + | +++ |
| (VII-141) | ++ | +++ | (VII-40) | +++ | +++ |
| (VII-153) | +++ | +++ | (VII-41) | ○ | + |
| (VII-152) | + | ++ | (VII-42) | ○ | + |
| (VII-143) | ++ | ++ | (VII-43) | ○ | + |
| (VII-103) | + | + | (VII-44) | + | +++ |
| (VII-113) | +++ | +++ | (VII-45) | | +++ |
| (VII-111) | +++ | ++ | (VII-46) | | +++ |
| (X-9) | +++ | +++ | (VII-51) | ○ | ++ |
| (VII-109) | +++ | +++ | (VII-52) | + | + |
| (VII-149) | +++ | +++ | (VII-53) | +++ | + |
| (VII-122) | ++ | +++ | (VII-54) | +++ | + |
| (VII-055) | | +++ | (VII-55) | +++ | +++ |
| (XII-07) | +++ | +++ | (VII-56) | ++ | + |
| (VIII-053) | +++ | +++ | (VII-57) | +++ | +++ |
| (VIII-049) | +++ | +++ | (VII-58) | ○ | +++ |
| (VII-117) | +++ | +++ | (VII-59) | +++ | +++ |
| (VII-142) | +++ | +++ | (VII-60) | +++ | +++ |
| (VII-097) | +++ | +++ | (VII-61) | ++ | + |
| (VIII-039) | +++ | +++ | (VII-62) | +++ | +++ |
| (VIII-052) | +++ | +++ | (VII-63) | +++ | +++ |
| (XII-06) | ++ | +++ | (VII-64) | +++ | + |
| (VIII-054) | +++ | +++ | (VII-65) | + | +++ |
| (VIII-046) | +++ | +++ | (VII-66) | +++ | +++ |
| (VII-095) | +++ | +++ | (VII-67) | +++ | +++ |
| (XII-8) | +++ | +++ | (VII-68) | + | + |
| (VII-119) | ++ | +++ | (VII-69) | +++ | +++ |
| (VIII-044) | +++ | +++ | (VII-70) | +++ | +++ |
| (XXX-4) | +++ | +++ | (VII-71) | + | + |
| (VIII-055) | +++ | +++ | (VII-72) | + | + |
| (VIII-040) | +++ | +++ | (VII-73) | ++ | +++ |
| (XXX-3) | +++ | +++ | (VII-74) | + | +++ |
| (XII-10) | +++ | +++ | (VII-75) | +++ | +++ |
| (XXX-9) | +++ | +++ | (VII-76) | +++ | + |
| (VIII-047) | +++ | +++ | (VIII-01) | + | +++ |
| (VII-124) | +++ | +++ | (VIII-02) | +++ | +++ |
| (VII-093) | +++ | +++ | (VIII-03) | +++ | +++ |
| (XXX-6) | +++ | +++ | (VIII-04) | +++ | +++ |
| (XII-9) | +++ | +++ | (VIII-05) | +++ | +++ |
| (XXX-5) | +++ | +++ | (VIII-06) | +++ | +++ |
| (XXX-4) | +++ | +++ | (VIII-07) | +++ | +++ |
| (XXX-2) | +++ | +++ | (VIII-08) | +++ | +++ |
| (XXX-7) | +++ | +++ | (VIII-09) | +++ | +++ |
| (XXX-8) | +++ | +++ | (VIII-10) | +++ | +++ |
| (VII-115) | +++ | +++ | (VIII-11) | ++ | +++ |
| (VII-058) | +++ | +++ | (VIII-12) | +++ | +++ |
| (VIII-041) | +++ | +++ | (VIII-13) | +++ | +++ |

TABLE 5B-continued

CDK7 selectivity of the compounds of general formula (I):

| Comp. | CDK2 | CDK9 | Comp. | CDK2 | CDK9 |
|---|---|---|---|---|---|
| (VII-01) | + | +++ | (VIII-14) | +++ | +++ |
| (VII-02) | o | ++ | (VIII-15) | +++ | +++ |
| (VII-03) | o | + | (VIII-16) | +++ | +++ |
| (VII-05) | +++ | +++ | (VIII-17) | ++ | +++ |
| (VII-06) | +++ | + | (VIII-18) | +++ | +++ |
| (VII-07) | ++ | + | (VIII-19) | +++ | +++ |
| (VII-08) | ++ | ++ | (VIII-20) | +++ | +++ |
| (VII-09) | +++ | +++ | (VIII-21) | ++ | +++ |
| (X-3) | ++ | +++ | (VIII-22) | +++ | +++ |
| (X-4) | + | ++ | (VIII-23) | ++ | ++ |
| (X-5) | ++ | +++ | (VIII-24) | + | ++ |
| (XII-1) | +++ | +++ | (VIII-25) | + | ++ |
| (XII-2) | +++ | +++ | (VIII-26) | +++ | +++ |
| (XII-3) | +++ | +++ | (VIII-27) | +++ | +++ |
| (XII-4) | +++ | +++ | (VIII-28) | +++ | +++ |
| (XII-5) | +++ | +++ | (VIII-31) | +++ | +++ |
| (VIII-36) | +++ | ++ | (VIII-32) | ++ | +++ |
| (VIII-37) | +++ | +++ | (VIII-33) | o | ++ |
| (VIII-38) | +++ | +++ | (VIII-34) | +++ | +++ |
| (X-1) | + | ++ | (VIII-35) | +++ | +++ |
| (X-2) | + | + | | | |

Comp.: Compound
CDK2: Selectivity of CDK7 inhibition over CDK2 inhibition [fold]
CDK9: Selectivity of CDK7 inhibition over CDK9 inhibition [fold]

Comparative Examples

In order to show the surprising effects of the compounds of the present invention the Comparative Examples C-I and C-II, wherein according to the compounds of the general formula (I) $R^3$=H, have been tested in the enzymatic activity assays for CDK2, CDK7 and CDK9 as described above.

C-I and C-II have the following structural formulae:

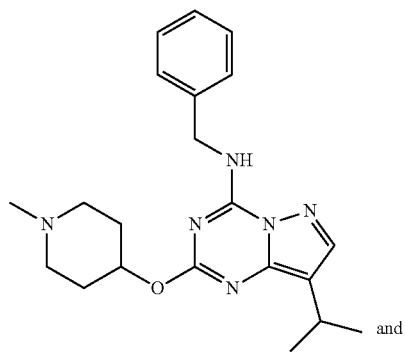

C-I

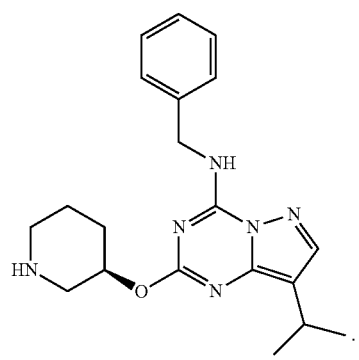

C-II

The selectivity results of Comparable Examples C-I and C-II are directly comparable to the compounds of the present invention as summarized in Table 5. While all compounds show potency against CDK-7, only the compounds of the present invention do not significantly inhibit also CDK-2 and CDK-9. Therefore, the compounds of the present invention can selectively inhibit CDK-7. The degree of selectivity is demonstrated in Table 6 by the multiplicity of the CDK2 and CDK9 activity in terms of the CDK7 activity. For example, while C-I only shows a 9-fold CDK7 activity for CDK2 and a 14-fold CDK7 activity for CDK9 indicating that C-I rather inhibits all three CDK inhibitors, the compounds of the present invention selectively inhibit only CDK7 while the activities for CDK2 and CDK 9 are tremendously higher (up to over the 9000-fold activity of the CDK7 activity).

Also, members of the CDK family have been validated as targets in cancer and inflammatory disease as well as in HIV-1 treatment. However, first generation CDK-inhibitors (Flavopiridol, Roscovitine, SNS-032) do typically inhibit more than one member of the CDK family. Such non specific-CDK inhibitors are meanwhile known for their toxicities and small therapeutic windows in clinical trials. Indeed, knockdown of multiple CDKs is lethal in a variety of model organisms, whereas knockdown of single CDKs is frequently tolerated; indicating that inhibition of single CDKs is less toxic.

Therefore, the main goal in the field of CDK-inhibition is the optimization for selective small-molecule based CDK-inhibitors.

As becomes apparent from Table 7 below first generation CDK-inhibitors generally do not show satisfactory CDK7 inhibition in comparison to the compounds of the present invention, nor do they show any significant effect that CDK 2 or CDK 9 are not inhibited simultaneously. This could at best be addressed for BS-181, however the comparative CDK 7 inhibition is poor and the CDK 2 and CDK 9 inhibition is far below a hundred-fold activity of the CDK 7 activity. In case of SNS-032 and Flavopiridol the CDK 2 and CDK 9 activities are even lower than the CDK 7 activity.

TABLE 6

Comparison of activity and selectivity to Comparative Examples C-I and C-II:

| Compound | Selectivity CDK7 over CDK2 [fold] | IC50 [nM] CDK7 | Selectivity CDK7 over CDK9 [fold] |
|---|---|---|---|
| C-I | 9 | +++ | 14 |
| (VII-70) | 183 | +++ | 992 |
| (VII-57) | 270 | +++ | 909 |
| (VII-59) | 3926 | +++ | 9140 |
| C-II | 14 | +++ | 18 |
| (VII-29) | 394 | +++ | 3255 |

TABLE 7

Comparison of activity and selectivity to state of the art CDK-inhibitors:

| Compound | IC50 [nM] CDK2 | IC50 [nM] CDK7 | IC50 [nM] CDK9 |
|---|---|---|---|
| SNS-032 | o | o | o |
| Flavopiridol | + | o | o |
| BS-181 | +++ | o | +++ |

TABLE 7-continued

Comparison of activity and selectivity to state of the art CDK-inhibitors:

| | | | |
|---|---|---|---|
| (VII-38) | + | +++ | ++ |
| (VII-51) | o | +++ | ++ |

| | Selectivity CDK7 over CDK2 [fold] | IC50 [nM] CDK7 | Selectivity CDK7 over CDK9 [fold] |
|---|---|---|---|
| SNS-032 | 0.1125 | o | 0.089 |
| Flavopiridol | 0.212 | o | 0.064 |
| BS-181 | 56 | o | 33 |
| (VII-38) | 342 | +++ | 2733 |
| (VII-51) | 54 | +++ | 2277 |

The herein tested state of the art compounds have the following structural formulae:

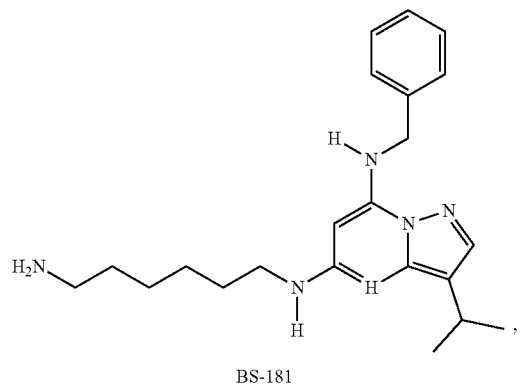

BS-181

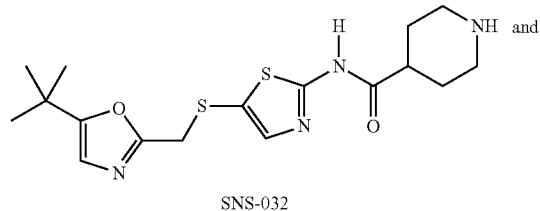

SNS-032

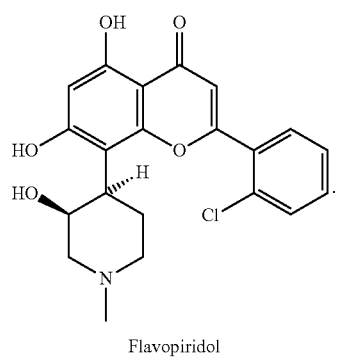

Flavopiridol

The invention claimed is:
1. A compound of the general formula (I)

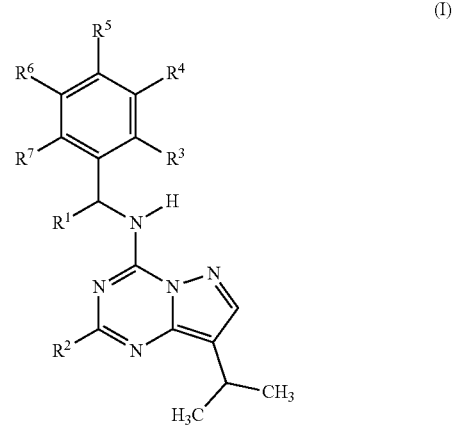

wherein $R^1$ represents —H;

$R^2$ represents —$R^8$, -Q-$R^8$, -Q-$(CH_2)_n$—$R^9$, —$(CH_2)_n$—$R^9$, —$(CH_2)_n$—NH—$R^8$, or —$(CH_2)_m$—NH—$(CH_2)_n$—$R^9$;

$R^3$ represents i) —F, —Cl, —Br, —CN, —$OR^{11}$, —CO—O—$R^{11}$, —$NR^{11}$—CO—$OR^{12}$, —$NHR^{11}$, —$NR^{11}R^{12}$, —$CONR^{11}R^{12}$, —O—CO—$NR^{11}R^{12}$, —O—CO—$OR^{11}$, —$NR^{11}$—CO—$NR^{12}R^{13}$, —$SO_2NR^{11}R^{12}$, —C(=$NR^{11}$)—$NR^{12}R^{13}$, —C($R^{12}$)=$NR^{11}$, —N=$CR^{11}R^{12}$, —N=S(=O)$R^{11}R^{12}$, —$CR^{11}R^{12}R^{13}$, —$CR^{11}$=$CR^{12}R^{13}$, —C≡$CR^{11}$, —$NR^{11}$—C(=$NR^{12}$)—$NR^{13}R^{14}$, —$SR^{11}$, —S(=O)$R^{11}$, —$NR^{11}$—S(=O)$R^{12}$, —O—S(=O)$R^{11}$, —$SO_2$-$R^{11}$, —$NR^{11}$—$SO_2$-$R^{12}$, —O—$SO_2$-$R^{11}$, —SO(=$NR^{11}$)—$R^{12}$, —CO—$R^{11}$, —O—CO—$R^{11}$, —$NR^{11}$—CO—$R^{12}$, or —$CF_3$, ii) 4-membered heterocyclyl, 5-membered heterocyclyl, 6-membered heterocyclyl, 3-membered carbocyclyl, 4-membered carbocyclyl, 5-membered carbocyclyl, 6-membered carbocyclyl, 6-membered aryl, 5-membered heteroaryl, or 6-membered heteroaryl, and wherein all afore-mentioned ring systems can be substituted with 1 to 4 substituents selected from $Z^1$, $Z^2$, $Z^3$ and $Z^4$;

$Z^1$ and $Z^2$ if attached to the same carbon atom can together represent =O to form a carbonyl group with the carbon atom to which $Z^1$ and $Z^2$ are attached; or $R^3$ together with $R^4$ can form a carbocyclic or heterocyclic 4-, 5-, 6- or 7-membered ring with the two carbon atoms of the benzo ring to which $R^3$ and $R^4$ are attached and that 4-, 5-, 6- or 7-membered ring can be partly saturated or unsaturated and can be substituted with 1 to 4 substituents selected from $Z^1$, $Z^2$, $Z^3$ and $Z^4$;

$Z^1$ and $Z^2$ if attached to the same carbon atom can together represent =O to form a carbonyl group with the carbon atom to which $Z^1$ and $Z^2$ are attached;

$R^4$-$R^7$ represent independently of each other —H, —F, —Cl, or —$CH_3$;

$R^8$ represents carbocyclyl, heterocyclyl, spirocarbocyclyl, or spiroheterocyclyl, wherein the afore-mentioned carbocyclyl, heterocyclyl, spirocarbocyclyl and spiroheterocyclyl residues are linked through a ring carbon atom and can be substituted with 1 to 3 substituents selected from $Z^5$, $Z^6$ and $Z^7$;

$Z^5$ and $Z^6$ if attached to the same carbon atom can together represent =O to form a carbonyl group with the carbon atom to which $Z^5$ and $Z^6$ are attached;

$R^9$ represents —$R^8$, nitrogenheterocyclyl, or spironitrogencyclyl, wherein the afore-mentioned nitrogenheterocyclyl and spironitrogencyclyl residues are linked through a ring nitrogen atom and can be substituted with 1 to 3 substituents selected from $Z^5$, $Z^6$ and $Z^7$;

$Z^5$ and $Z^6$ if attached to the same carbon atom can together represent =O to form a carbonyl group with the carbon atom to which $Z^5$ and $Z^6$ are attached;

$R^{11}$, $R^{12}$, $R^{13}$, $R^{14}$ and $R^{15}$ represent independently of each other
—H, linear or branched $C_1$-$C_8$-alkyl, $C_3$-$C_8$-cycloalkyl, $C_1$-$C_9$-heterocyclyl, linear or branched $C_2$-$C_8$-alkenyl, linear or branched $C_2$-$C_8$-alkynyl, $C_6$-$C_{14}$-aryl, or $C_1$-$C_{10}$-heteroaryl,
wherein the afore-mentioned residues can be substituted with 1 to 5 substituents selected from $Z^8$, $Z^9$, $Z^{10}$, $Z^{11}$ and $Z^{12}$; or $R^{11}$ together with $R^{12}$ can form a carbocyclic or heterocyclic 4-, 5- or 6-membered ring and that 4-, 5- or 6-membered ring can be saturated or unsaturated and can be substituted with 1 to 8 substituents selected from $Z^8$, $Z^9$, $Z^{10}$, $Z^{11}$, $Z^{12}$, $Z^{13}$, $Z^{14}$ and $Z^{15}$;

$Z^8$ and $Z^9$ if attached to the same carbon atom can together represent =O to form a carbonyl group with the carbon atom to which $Z^8$ and $Z^9$ are attached;

represents —O—, —S—, —$NR^{15}$—, —SO—, —$SO_2$—CO—, —CO—$NR^{15}$—, or —$NR^{15}$—CO—;

$Z^1$-$Z^{15}$ represent independently of each other

cyclo-$C_3H_5$, cyclo-$C_4H_7$, cyclo-$C_5H_9$, cyclo-$C_6H_{11}$, cyclo-$C_7H_{13}$, —H, —OH, —$OCH_3$, —$OC_2H_5$, —$OC_3H_7$, —O-cyclo-$C_3H_5$, —$OCH(CH_3)_2$, —$OC(CH_3)_3$, —$OC_4H_9$, —OPh, —$OCH_2$-Ph, —$OCPh_3$, —$CH_2$—$OCH_3$, —$C_2H_4$—$OCH_3$, —$C_3H_6$—$OCH_3$, —$CH_2$—$OC_2H_5$, —$C_2H_4$—$OC_2H_5$, —$C_3H_6$—$OC_2H_5$, —$CH_2$—$OC_3H_7$, —$C_2H_4$—$OC_3H_7$, —$C_3H_6$—$OC_3H_7$, —$CH_2$—O-cyclo-$C_3H_5$, —$C_2H_4$—O-cyclo-$C_3H_5$, —$C_3H_6$—O-cyclo-$C_3H_5$, —$CH_2$—$OCH(CH_3)_2$, —$C_2H_4$—$OCH(CH_3)_2$, —$C_3H_6$—$OCH(CH_3)_2$, —$CH_2$—$OC(CH_3)_3$, —$C_2H_4$—$OC(CH_3)_3$, —$C_3H_6$—$OC(CH_3)_3$, —$CH_2$—$OC_4H_9$, —$C_2H_4$—$OC_4H_9$, —$C_3H_6$—$OC_4H_9$, —$CH_2$—OPh, —$C_2H_4$—OPh, —$C_3H_6$—OPh, —$CH_2$—$OCH_2$-Ph, —$C_2H_4$—$OCH_2$-Ph, —$C_3H_6$—$OCH_2$-Ph, —SH, —$SCH_3$, —$SC_2H_5$, —$SC_3H_7$, —S-cyclo-$C_3H_5$, —$SCH(CH_3)_2$, —$SC(CH_3)_3$, —F, —Cl, —Br, —I, —CN, —$COCH_3$, —$COC_2H_5$, —$COC_3H_7$, —CO-cyclo-$C_3H_5$, —$COCH(CH_3)_2$, —$COC(CH_3)_3$, —COOH, —$COOCH_3$, —$COOC_2H_5$, —$COOC_3H_7$, —COO-cyclo-$C_3H_5$, —$COOCH(CH_3)_2$, —$COOC(CH_3)_3$, —OOC—$CH_3$, —OOC—$C_2H_5$, —OOC—$C_3H_7$, —OOC-cyclo-$C_3H_5$, —OOC—$CH(CH_3)_2$, —OOC—$C(CH_3)_3$, —$CONH_2$, —$CONHCH_3$, —$CONHC_2H_5$, —$CONHC_3H_7$, —CONH-cyclo-$C_3H_5$, —$CONH[CH(CH_3)_2]$, —$CONH[C(CH_3)_3]$, —$CON(CH_3)_2$, —$CON(C_2H_5)_2$, —$CON(C_3H_7)_2$, —$CON(cyclo-C_3H_5)_2$, —$CON[CH(CH_3)_2]_2$, —$CON[C(CH_3)_3]_2$, —$NHCOCH_3$, —$NHCOC_2H_5$, —$NHCOC_3H_7$, —NHCO-cyclo-$C_3H_5$, —NHCO—$CH(CH_3)_2$, —NHCO—$C(CH_3)_3$, —NHCO—$OCH_3$, —NHCO—$OC_2H_5$, —NHCO—$OC_3H_7$, —NHCO—O-cyclo-$C_3H_5$, —NHCO—$OCH(CH_3)_2$, —NHCO—$OC(CH_3)_3$, —$NH_2$, —$NHCH_3$, —$NHC_2H_5$, —$NHC_3H_7$, —NH-cyclo-$C_3H_5$, —$NHCH(CH_3)_2$, —$NHC(CH_3)_2$, —$N(CH_3)_2$, —$N(C_2H_5)_2$, —$N(C_3H_7)_2$, —$N(cyclo-C_3H_5)_2$, —$N[CH(CH_3)_2]_2$, —$N[C(CH_3)_3]_2$, —$SOCH_3$, —$SOC_2H_5$, —$SOC_3H_7$, —SO-cyclo-$C_3H_5$, —$SOCH(CH_3)_2$, —$SOC(CH_3)_3$, —$SO_2CH_3$, —$SO_2C_2H_5$, —$SO_2C_3H_7$, —$SO_2$-cyclo-$C_3H_5$, —$SO_2CH(CH_3)_2$, —$SO_2C(CH_3)_3$, —$SO_3H$, —$SO_3CH_3$, —$SO_3C_2H_5$, —$SO_3C_3H_7$, —$SO_3$-cyclo-$C_3H_5$, —$SO_3CH(CH_3)_2$, —$SO_3C(CH_3)_3$, —$SO_2NH_2$, —$SO_2NHCH_3$, —$SO_2NHC_2H_5$, —$SO_2NHC_3H_7$, —$SO_2NH$-cyclo-$C_3H_5$, —$SO_2NHCH(CH_3)_2$, —$SO_2NHC(CH_3)_3$, —$SO_2N(CH_3)_2$, —$SO_2N(C_2H_5)_2$, —$SO_2N(C_3H_7)_2$, —$SO_2N(cyclo-C_3H_5)_2$, —$SO_2N[CH(CH_3)_2]_2$, —$SO_2N[C(CH_3)_3]_2$, —O—S(=O)$CH_3$, —O—S(=O)$C_2H_5$, —O—S(=O)$C_3H_7$, —O—S(=O)-cyclo-$C_3H_5$, —O—S(=O)$CH(CH_3)_2$, —O—S(=O)$C(CH_3)_3$, —S(=O)(=NH)$CH_3$, —S(=O)(=NH)$C_2H_5$, —S(=O)(=NH)$C_3H_7$, —S(=O)(=NH)-cyclo-$C_3H_5$, —S(=O)(=NH)$CH(CH_3)_2$, —S(=O)(=NH)$C(CH_3)_3$, —NH—$SO_2$—$CH_3$, —NH—$SO_2$—$C_2H_5$, —NH—$SO_2$—$C_3H_7$, —NH—$SO_2$-cyclo-$C_3H_5$, —NH—$SO_2$—$CH(CH_3)_2$, —NH—$SO_2$—$C(CH_3)_3$, —O—$SO_2$—$CH_3$, —O—$SO_2$—$C_2H_5$, —O—$SO_2$—$C_3H_7$, —O—$SO_2$-cyclo-$C_3H_5$, —O—$SO_2$—$CH(CH_3)_2$, —O—$SO_2$—$C(CH_3)_3$, —$OCH_2F$, —$OCHF_2$, —$OCF_3$, —$CH_2$—$OCF_3$, —$C_2H_4$—$OCF_3$, —$C_3H_6$—$OCF_3$, —$OC_2F_5$, —$CH_2$—$OC_2F_5$, —$C_2H_4$—$OC_2F_5$, —$C_3H_6$—$OC_2F_5$, —O—$COOCH_3$, —O—$COOC_2H_5$, —O—$COOC_3H_7$, —O—COO-cyclo-$C_3H_5$, —O—$COOCH(CH_3)_2$, —O—$COOC(CH_3)_3$, —NH—CO—$NH_2$, —NH—CO—$NHCH_3$, —NH—CO—$NHC_2H_5$, —NH—CO—$NHC_3H_7$, —NH—CO—$N(C_3H_7)_2$, —NH—CO—$NH[CH(CH_3)_2]$, —NH—CO—$NH[C(CH_3)_3]$, —NH—CO—$N(CH_3)_2$, —NH—CO—$N(C_2H_5)_2$, —NH—CO—NH-cyclo-$C_3H_5$, —NH—CO—N(cyclo-$C_3H_5)_2$, —NH—CO—$N[CH(CH_3)_2]_2$, —NH—C(=NH)—$NH_2$, —NH—C(=NH)—$NHCH_3$, —NH—C(=NH)—$NHC_2H_5$, —NH—C(=NH)—$NHC_3H_7$, —O—CO—NH-cyclo-$C_3H_5$, —NH—C(=NH)—NH-cyclo-$C_3H_5$, —NH—C(=NH)—$NH[CH(CH_3)_2]$, —O—CO—$NH[CH(CH_3)_2]$, —NH—C(=NH)—$NH[C(CH_3)_3]$, —NH—C(=NH)—$N(CH_3)_2$, —NH—C(=NH)—$N(C_2H_5)_2$, —NH—C(=NH)—$N(C_3H_7)_2$, —NH—C(=NH)—N(cyclo-$C_3H_5)_2$, —O—CO—$NHC_3H_7$, —NH—C(=NH)—$N[CH(CH_3)_2]_2$, —NH—C(=NH)—$N[C(CH_3)_3]_2$, —O—CO—$NH_2$, —O—CO—$NHCH_3$, —O—CO—$NHC_2H_5$, —O—CO—$NH[C(CH_3)_3]$, —O—CO—$N(CH_3)_2$, —O—CO—$N(C_2H_5)_2$, —O—CO—$N(C_3H_7)_2$, —O—CO—N(cyclo-$C_3H_5)_2$, —O—CO—$N[CH(CH_3)_2]_2$, —O—CO—$N[C(CH_3)_3]_2$, —O—CO—$OCH_3$, —O—CO—$OC_2H_5$, —O—CO—$OC_3H_7$, —O—CO—O-cyclo-$C_3H_5$, —O—CO—$OCH(CH_3)_2$, —O—CO—$OC(CH_3)_3$, —$CH_2F$, —$CHF_2$, —$CF_3$, —$CH_2$—$CH_2F$, —$CH_2$—$CHF_2$, —$CH_2$—$CF_3$, cyclo-$C_8H_{15}$, -Ph, —$CH_2$-Ph, —$CH_2$—$CH_2$-Ph, —CH=CH-Ph, —$CPh_3$, —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, —$C_5H_{11}$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —CH —(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH—CH₂, —C₃H₆—CH=CH₂, —C₂H₄—CH=CH—CH₃, —CH₂—CH=CH—C₂H₅, —CH=CH—C₃H₇, —CH=CH—CH=CH—CH₃, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C₄H₅—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH=CH—CH₃, —C₂H₄—C(CH₃)=CH—CH₃, —CH₂—CH(CH₃)—CH=CH—CH₃, —CH(CH₃)—CH₂—CH=CH—CH₃, —CH(CH₃)—CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH=CH—C₂H₄—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH=CH—CH₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —C₃H₆—C≡C—CH₃, —CH₂—CH=CH—CH=CH—CH₃, —CH=CH—CH=CH—C₂H₅, —CH(CH₃)—CH₂—C≡CH, —CH(CH₃)—C≡C—CH₃, —C₂H₄—CH(CH₃)—C≡CH, —CH=CH—CH=C(CH₃)₂, —CH₂—CH(CH₃)—CH₂—C≡CH, —CH=CH—C(CH₃)=CH—CH₃, —CH=C(CH₃)—CH=CH—CH₃, —CH₂—CH(CH₃)—C≡CH, —C(CH₃)=CH—CH=CH—CH₃, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—CH₂—CH(CH₃)₂, —CH(CH₃)—C₂H₄—C≡CH, —CH₂—CH(CH₃)—C≡C—CH₃, —C(CH₃)(C₂H₅)—C≡CH, —CH(CH₃)—CH₂—C≡C—CH₃, —C(CH₃)H≡C—C₂H₅, —CH₂—C≡C—CH(CH₃)₂, —C≡C—CH(CH₃)—C₂H₅, —C≡C—CH(CH₃)—C₂H₅, —CH₂—C≡C—CH(CH₃)₂, —C≡C—CH(CH₃)—C₂H₅, —CH(C₂H₅)—C≡C—CH₃,
—C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH(CH₃)—C(CH₃)₂—C≡CH, —CH(C₃H₇)—C≡CH, —CH₂—CH(C₂H₅)—C≡CH, —C(CH₃)(C₃H₇)—C≡CH, —CH₂—CH=C(CH₃)—CH₂—C≡CH, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —C≡C—C(CH₃)₃, —C≡C—CH₂—C≡C—CH₃, or —C≡C—C≡C—C₂H₅;

n is an integer selected from 1, 2, 3, 4, 5, 6, 7 or 8,
m is an integer selected from 0, 1, 2, 3, 4, 5 or 6,
or enantiomers, stereoisomeric forms, mixtures of enantiomers, diastereomers, mixtures of diastereomers, hydrates, solvates, acid salt forms, tautomers, and racemates thereof or pharmaceutically acceptable salts thereof.

2. The compound according to claim 1, wherein
$R^3$ represents —F, —Cl, —Br, —CN, —OR$^{11}$, —CO—O—R$^{11}$, —NR$^{11}$—CO—OR$^{12}$, —NHR$^{11}$, —NR$^{11}$R$^{12}$, —CONR$^{11}$R$^{12}$, —O—CO—NR$^{11}$R$^{12}$, —O—CO—OR$^{11}$, —NR$^{11}$—CO—NR$^{12}$R$^{13}$, —SO₂NR$^{11}$R$^{12}$, —C(=NR$^{11}$)—NR$^{12}$R$^{13}$, —C(R$^{12}$)=NR$^{11}$, —N=CR$^{11}$R$^{12}$, —N=S(=O)R$^{11}$R$^{12}$, —CR$^{11}$R$^{12}$R$^{13}$, —CR$^{11}$=CR$^{12}$R$^{13}$, —C=CR$^{11}$, —NR$^{11}$—C(=NR$^{12}$)—NR$^{13}$R$^{14}$, —SR$^{11}$, —S(=O)R$^{11}$, —NR$^{11}$—S(=O)R$^{12}$, —O—S(=O)R$^{11}$, —SO₂-R$^{11}$, —NR$^{11}$—SO₂-R$^{12}$, —O—SO₂-R$^{11}$, —SO(=NR$^{11}$)R$^{12}$, —CO—R$^{11}$, —O—CO-R$^{11}$, —NR$^{11}$—CO—R$^{12}$, —CF₃, pyridyl, pyrimidinyl, pyrazinyl, pyridazinyl, triazinyl, imidazolyl, furyl, dihydrofuryl, tetrahydrofuryl, thienyl, dihydrothienyl, tetrahydrothienyl, 1,3-oxazolyl, dihydro-1,3-oxazolyl, 1,3-oxazolidinyl, isoxazolyl, dihydro-isoxazolyl, isoxazolidinyl, pyrrolyl, dihydropyrrolyl, pyrrolidinyl, imidazolyl, dihydroimidazolyl, imidazolidinyl, triazolyl, dihydrotriazolyl, triazolidinyl, pyrazolyl, dihydropyrazolyl, pyrazolidinyl, oxadiazolyl, dihydrooxadiazolyl, oxadiazolidinyl, thiadiazolyl, dihydrothiadiazolyl, thiadiazolidinyl, 1,3-thiazolyl, dihydro-1,3-thiazolyl, 1,3-thiazolidinyl, isothiazolyl, dihydroisothiazolyl, isothiazolidinyl, tetrazolyl, dihydrotetrazolyl, tetrazolidinyl, aziridinyl, azirenyl, oxiranyl, thiiranyl, azetidinyl, oxetanyl, thietanyl, cyclopentanonyl, cyclohexanonyl, pyrrolidinonyl, pyrrolidindionyl, piperidinonyl, piperidindionyl, 1-oxidthiopyranyl, 1,1-dioxid-thiopyranyl, dihydro-1-oxidthiopyranyl, dihydro-1,1-dioxid-thiopyranyl, tetrahydro-1-oxid-thiopyranyl, tetrahydro-1,1-dioxidthiopyranyl, morpholinyl, thiomorpholinyl, 1,2-dioxanyl, 1,3-dioxanyl, 1,4-dioxanyl, 1,2-dioxolanyl, 1,3-dioxolanyl, 1,4-dioxolanyl, piperazinyl, 2-oxoazetidinyl, 2-oxo-pyrrolidinyl, 2-oxo-piperidinyl, 2-oxo-oxazolidinyl, 2-oxo-imidazolidinyl, 2-oxo-1,3-oxazinanyl, or 2-oxo-tetrahydropyrimidinyl wherein the afore-mentioned ring systems can be substituted with one to four substituents selected from $Z^1$, $Z^2$, $Z^3$ and $Z^4$;

$R^8$ represents 4-membered heterocyclyl, 5-membered heterocyclyl, 6-membered heterocyclyl, 4-membered carbocyclyl, 5-membered carbocyclyl, 6-membered carbocyclyl, azaspiro[3,3]heptyl, azaspiro[3,4]octyl, azaspiro[3,5]nonyl, azaspiro[3,6]decyl, azaspiro[4,4]nonyl, azaspiro[4,5]decyl, azaspiro[4,6]undecyl, azaspiro[5,5]undecyl, azaspiro[5,6]dodecyl, azaspiro[6,6]tridecyl, diazaspiro[3,3]heptyl, diazaspiro[3,4]octyl, diazaspiro[3,5]nonyl, diazaspiro[3,6]decyl, diazaspiro[4,4]nonyl, diazaspiro[4,5]decyl, diazaspiro[4,6]undecyl, diazaspiro[5,5]undecyl, diazaspiro[5,6]dodecyl, diazaspiro[6,6]tridecyl, triazaspiro[3,5]nonyl, triazaspiro[3,6]decyl, triazaspiro[4,5]decyl, triazaspiro[4,6]undecyl, triazaspiro[5,5]undecyl, triazaspiro[5,6]dodecyl, triazaspiro[6,6]tridecyl, oxazaspiro[3,3]heptyl, oxazaspiro[3,4]octyl, oxazaspiro[3,5]nonyl, oxazaspiro[3,6]decyl, oxazaspiro[4,4]nonyl, oxazaspiro[4,5]decyl, oxazaspiro[4,6]undecyl, oxazaspiro[5,5]undecyl, oxazaspiro[5,6]dodecyl, oxazaspiro[6,6]tridecyl, oxadiazaspiro[3,5]nonyl, oxadiazaspiro[3,6]decyl, oxadiazaspiro[4,5]decyl, oxadiazaspiro[4,6]undecyl, oxadiazaspiro[5,5]undecyl, oxadiazaspiro[5,6]dodecyl, or oxadiazaspiro[6,6]tridecyl, wherein the afore-mentioned carbocyclyl, heterocyclyl, azaspiro, diazaspiro, triazaspiro, oxazaspiro, oxadiazaspiro residues are linked through a ring carbon atom and wherein the afore-mentioned carbocyclyl, heterocyclyl, azaspiro, diazaspiro, triazaspiro, oxazaspiro, oxadiazaspiro residues are substituted with one to three substituents selected from $Z^5$, $Z^6$ and $Z^7$;

$Z^5$ and $Z^6$ if attached to the same carbon atom can together represent =O to form a carbonyl group with the carbon atom to which $Z^5$ and $Z^6$ are attached;

$R^9$ represents 4-membered nitrogenheterocyclyl, 5-membered nitrogenheterocyclyl, 6-membered nitrogenheterocyclyl, 5-membered dinitrogenheterocyclyl, 6-membered dinitrogenheterocyclyl, spiro[2,3]heterohexyl, spiro[2,4]heteroheptyl, spiro[2,5]heterooctyl, spiro[2,7]heterononyl, spiro[3,3]heteroheptyl, spiro[3,4]heterooctyl, spiro[3,5]heterononyl, spiro[3,6]heterodecyl, spiro[4,4]heterononyl, spiro[4,5]heterodecyl, spiro[4,6]heteroundecyl, spiro[5,5]heteroundecyl, spiro[5,6]heterododecyl, or spiro[6,6]heterotridecyl, wherein the afore-mentioned nitrogenheterocyclyl, dinitrogenheterocyclyl and spiro residues are linked through the or a ring nitrogen atom and wherein the afore-mentioned nitrogenheterocyclyl, dinitrogenheterocyclyl and spiro residues are substituted with one to three substituents selected from $Z^5$, $Z^6$ and $Z^7$;

$Z^5$ and $Z^6$ if attached to the same carbon atom can together represent =O to form a carbonyl group with the carbon atom to which $Z^5$ and $Z^6$ are attached;

the residues $R^1$, $R^2$, $R^4$-$R^7$, $R^{11}$-$R^{15}$, m, n, Q, and $Z^1$-$Z^{15}$ have the meanings as defined in claim 1.

3. The compound according to claim 1, wherein
$R^2$ represents —$R^8$, -Q-$R^8$, -Q-$(CH_2)_n$—$R^9$, —$(CH_2)_n$—$R^9$, —$(CH_2)_n$—NH-$R^8$, or —$(CH_2)_m$—NH—$(CH_2)_n$—$R^9$, Q represents —O—, —S—, —$NR^{15}$—, —SO—, or —$SO_2$—;

$R^4$-$R^7$ represent independently of each other —H or —F;

the residues $R^1$, $R^3$, $R^8$, $R^9$, $R^{11}$-$R^{15}$, m, n, and $Z^1$-$Z^{15}$ have the meanings as defined in claim 1.

4. The compound according to claim 1, selected from the group consisting of:

N-(2-(1H-pyrazol-1-yl)benzyl)-8-isopropyl-2-(piperidin-4-yloxy)pyrazolo[1,5-a][1,3,5]triazin-4-amine, (R)—N-(2-(1H-pyrazol-1-yl)benzyl)-8-isopropyl-2-(pyrrolidin-3-yloxy)pyrazolo[1,5-a][1,3,5]triazin-4-amine, (R)—N-(2-(1H-pyrazol-1-yl)benzyl)-8-isopropyl-2-(piperidin-3-yloxy)pyrazolo[1,5-a][1,3,5]triazin-4-amine, N-(2-(1H-pyrazol-1-yl)benzyl)-2-(2-azaspiro[3.3]heptan-6-yloxy)-8-isopropylpyrazolo[1,5-a][1,3,5]triazin-4-amine, 2-(1-oxa-8-azaspiro[4.5]decan-3-yloxy)-N-(2-(1H-pyrazol-1-yl)benzyl)-8-isopropylpyrazolo[1,5-a][1,3,5]triazin-4-amine, (R)—N-([1,1'-biphenyl]-2-ylmethyl)-8-isopropyl-2-(piperidin-3-yloxy)pyrazolo[1,5-a][1,3,5]triazin-4-amine, (R)—N-([1,1'-biphenyl]-2-ylmethyl)-8-isopropyl-2-(pyrrolidin-3-yloxy)pyrazolo[1,5-a][1,3,5]triazin-4-amine, N-([1,1'-biphenyl]-2-ylmethyl)-8-isopropyl-2-(piperidin-4-yloxy)pyrazolo[1,5-a][1,3,5]triazin-4-amine, (R)-8-isopropyl-2-(piperidin-3-yloxy)-N-(2-(thiophen-2-yl)benzyl)pyrazolo[1,5-a][1,3,5]triazin-4-amine, (R)-8-isopropyl-2-(pyrrolidin-3-yloxy)-N-(2-(thiophen-2-yl)benzyl)pyrazolo[1,5-a][1,3,5]triazin-4-amine, 8-isopropyl-2-(piperidin-4-yloxy)-N-(2-(thiophen-2-yl)benzyl)pyrazolo[1,5-a][1,3,5]triazin-4-amine, (R)—N-(2-isopropoxybenzyl)-8-isopropyl-2-(pyrrolidin-3-yloxy)pyrazolo[1,5-a][1,3,5]triazin-4-amine, N-(2-isopropoxybenzyl)-8-isopropyl-2-(piperidin-4-yloxy)pyrazolo[1,5-a][1,3,5]triazin-4-amine, (R)—N-(2-isopropoxybenzyl)-8-isopropyl-2-(piperidin-3-yloxy)pyrazolo[1,5-a][1,3,5]triazin-4-amine, N-(2-(1H-imidazol-1-yl)benzyl)-8-isopropyl-2-(piperidin-4-yloxy)pyrazolo[1,5-a][1,3,5]triazin-4-amine, (R)—N-(2-(1H-1,2,4-triazol-1-yl)benzyl)-8-isopropyl-2-(piperidin-3-yloxy)pyrazolo[1,5-a][1,3,5]triazin-4-amine, (R)—N-(2-(1H-1,2,4-triazol-1-yl)benzyl)-8-isopropyl-2-(pyrrolidin-3-yloxy)pyrazolo[1,5-a][1,3,5]triazin-4-amine, N-(2-(1H-1,2,4-triazol-1-yl)benzyl)-8-isopropyl-2-(piperidin-4-yloxy)pyrazolo[1,5-a][1,3,5]triazin-4-amine, (R)-8-isopropyl-N-(2-(2-methyl-1H-imidazol-1-yl)benzyl)-2-(piperidin-3-yloxy)pyrazolo[1,5-a][1,3,5]triazin-4-amine, 8-isopropyl-N-(2-(2-methyl-1H-imidazol-1-yl)benzyl)-2-(piperidin-4-yloxy)pyrazolo[1,5-a][1,3,5]triazin-4-amine, (R)-8-isopropyl-N-(2-(2-methyl-1H-imidazol-1-yl)benzyl)-2-(pyrrolidin-3-yloxy)pyrazolo[1,5-a][1,3,5]triazin-4-amine, (R)—N-(2-(1H-imidazol-1-yl)benzyl)-8-isopropyl-2-(piperidin-3-yloxy)pyrazolo[1,5-a][1,3,5]triazin-4-amine, (R)—N-(2-(1H-imidazol-1-yl)benzyl)-8-isopropyl-2-(pyrrolidin-3-yloxy)pyrazolo[1,5-a][1,3,5]triazin-4-amine, (R)-8-isopropyl-N-(2-(1-methyl-1H-tetrazol-5-yl)benzyl)-2-(piperidin-3-yloxy)pyrazolo[1,5-a][1,3,5]triazin-4-amine, (R)-5-(((8-isopropyl-2-(piperidin-3-yloxy)pyrazolo[1,5-a][1,3,5]triazin-4-yl)amino)methyl)quinoline 1-oxide, (R)-8-isopropyl-N-(isoquinolin-8-ylmethyl)-2-(piperidin-3-yloxy)pyrazolo[1,5-a][1,3,5]triazin-4-amine, (R)-8-(((8-isopropyl-2-(piperidin-3-yloxy)pyrazolo[1,5-a][1,3,5]triazin-4-yl)amino)methyl)isoquinoline 2-oxide, (R)-8-isopropyl-N-((1-methyl-1H-indazol-4-yl)methyl)-2-(piperidin-3-yloxy)pyrazolo[1,5-a][1,3,5]triazin-4-amine, (R)-8-isopropyl-2-(piperidin-3-yloxy)-N-(2-(pyridin-2-yl)benzyl)pyrazolo[1,5-a][1,3,5]triazin-4-amine, (R)-8-isopropyl-2-(piperidin-3-yloxy)-N-(quinolin-8-ylmethyl)pyrazolo[1,5-a][1,3,5]triazin-4-amine, (R)—N-((1H-indazol-4-yl)methyl)-8-isopropyl-2-(piperidin-3-yloxy)pyrazolo[1,5-a][1,3,5]triazin-4-amine, (R)-8-isopropyl-N-(2-(2-methyl-2H-tetrazol-5-yl)benzyl)-2-(piperidin-3-yloxy)pyrazolo[1,5-a][1,3,5]triazin-4-amine, (R)-2-(((8-isopropyl-2-(piperidin-3-yloxy)pyrazolo[1,5-a][1,3,5]triazin-4-yl)amino)methyl)-N,N-dimethylbenzenesulfonamide, (R)-1-(2-(((8-isopropyl-2-(piperidin-3-yloxy)pyrazolo[1,5-a][1,3,5]triazin-4-yl)amino)methyl)phenyl)pyrrolidin-2-one,
(R)-1-(2-(((8-isopropyl-2-(piperidin-3-yloxy)pyrazolo[1,5-a][1,3,5]triazin-4-yl)amino)methyl)phenyl)azetidin-2-one,
(R)—N-(5-fluoro-2-(1H-pyrazol-1-yl)benzyl)-8-isopropyl-2-(piperidin-3-yloxy)pyrazolo[1,5-a][1,3,5]triazin-4-amine,
(R)—N-(3-fluoro-2-(1H-pyrazol-1-yl)benzyl)-8-isopropyl-2-(piperidin-3-yloxy)pyrazolo[1,5-a][1,3,5]triazin-4-amine,
(R)—N-(4-fluoro-2-(1H-pyrazol-1-yl)benzyl)-8-isopropyl-2-(piperidin-3-yloxy)pyrazolo[1,5-a][1,3,5]triazin-4-amine,
(R)—N-(2-fluoro-6-(1H-pyrazol-1-yl)benzyl)-8-isopropyl-2-(piperidin-3-yloxy)pyrazolo[1,5-a][1,3,5]triazin-4-amine,
8-isopropyl-2-((1-methylpiperidin-4-yl)oxy)-N-(2-(pyridin-3-yl)benzyl)pyrazolo[1,5-a][1,3,5]triazin-4-amine,
(R)-8-isopropyl-2-(piperidin-3-yloxy)-N-(2-(pyridin-3-yl)benzyl)pyrazolo[1,5-a][1,3,5]triazin-4-amine,
8-isopropyl-2-((1-methylpiperidin-4-yl)oxy)-N-(2-phenoxybenzyl)pyrazolo[1,5-a][1,3,5]triazin-4-amine,
(R)-8-isopropyl-N-(2-phenoxybenzyl)-2-(piperidin-3-yloxy)pyrazolo[1,5-a][1,3,5]triazin-4-amine,
(R)-8-isopropyl-N-(2-(oxazol-2-yl)benzyl)-2-(piperidin-3-yloxy)pyrazolo[1,5-a][1,3,5]triazin-4-amine,
(R)—N-(2-(furan-2-yl)benzyl)-8-isopropyl-2-(piperidin-3-yloxy)pyrazolo[1,5-a][1,3,5]triazin-4-amine,
(R)—N-(2-(((8-isopropyl-2-(piperidin-3-yloxy)pyrazolo[1,5-a][1,3,5]triazin-4-yl)amino)methyl)phenyl)acetamide,
(R)—N-(2-(4-chloro-1H-pyrazol-1-yl)benzyl)-8-isopropyl-2-(piperidin-3-yloxy)pyrazolo[1,5-a][1,3,5]triazin-4-amine,
N-(2-(dimethylamino)benzyl)-8-isopropyl-2-((1-methylpiperidin-4-yl)oxy)pyrazolo[1,5-a][1,3,5]triazin-4-amine,
2-(((8-isopropyl-2-((1-methylpiperidin-4-yl)oxy)pyrazolo[1,5-a][1,3,5]triazin-4-yl)amino)methyl)benzonitrile,
N-(2-fluorobenzyl)-8-isopropyl-2-((1-methylpiperidin-4-yl)oxy)pyrazolo[1,5-a][1,3,5]triazin-4-amine,
N-([1,1'-biphenyl]-2-ylmethyl)-8-isopropyl-2-((1-methylpiperidin-4-yl)oxy)pyrazolo[1,5-a][1,3,5]triazin-4-amine,
8-isopropyl-2-((1-methylpiperidin-4-yl)oxy)-N-(2-(trifluoromethyl)benzyl)pyrazolo[1,5-a][1,3,5]triazin-4-amine,
N-(2-(1H-imidazol-1-yl)benzyl)-8-isopropyl-2-((1-methylpiperidin-4-yl)oxy)pyrazolo[1,5-a][1,3,5]triazin-4-amine,
8-isopropyl-2-((1-methylpiperidin-4-yl)oxy)-N-(2-morpholinobenzyl)pyrazolo[1,5-a][1,3,5]triazin-4-amine,
8-isopropyl-2-((1-methylpiperidin-4-yl)oxy)-N-(naphthalen-1-ylmethyl)pyrazolo[1,5-a][1,3,5]triazin-4-amine,
N-(2,6-dichlorobenzyl)-8-isopropyl-2-((1-methylpiperidin-4-yl)oxy)pyrazolo[1,5-a][1,3,5]triazin-4-amine,
N-(2,6-difluorobenzyl)-8-isopropyl-2-((1-methylpiperidin-4-yl)oxy)pyrazolo[1,5-a][1,3,5]triazin-4-amine,
8-isopropyl-2-((1-methylpiperidin-4-yl)oxy)-N-(2-(thiophen-2-yl)benzyl)pyrazolo[1,5-a][1,3,5]triazin-4-amine,
N-(2-isopropoxybenzyl)-8-isopropyl-2-((1-methylpiperidin-4-yl)oxy)pyrazolo[1,5-a][1,3,5]triazin-4-amine,
N-(2-chlorobenzyl)-8-isopropyl-2-((1-methylpiperidin-4-yl)oxy)pyrazolo[1,5-a][1,3,5]triazin-4-amine,
(S)-8-isopropyl-2-((1-methylpiperidin-4-yl)oxy)-N-(1-(naphthalen-1-yl)ethyl)pyrazolo[1,5-a][1,3,5]triazin-4-amine,
N-(2-ethoxybenzyl)-8-isopropyl-2-((1-methylpiperidin-4-yl)oxy)pyrazolo[1,5-a][1,3,5]triazin-4-amine,
8-isopropyl-N-(2-methoxybenzyl)-2-((1-methylpiperidin-4-yl)oxy)pyrazolo[1,5-a][1,3,5]triazin-4-amine,
N-(2-(difluoromethoxy)benzyl)-8-isopropyl-2-((1-methylpiperidin-4-yl)oxy)pyrazolo[1,5-a][1,3,5]triazin-4-amine,
N-(2-(1H-pyrazol-1-yl)benzyl)-8-isopropyl-2-((1-methylpiperidin-4-yl)oxy)pyrazolo[1,5-a][1,3,5]triazin-4-amine,
N-(2-(1H-1,2,4-triazol-1-yl)benzyl)-8-isopropyl-2-((1-methylpiperidin-4-yl)oxy)pyrazolo[1,5-a][1,3,5]triazin-4-amine,
8-isopropyl-N-(2-(2-methyl-1H-imidazol-1-yl)benzyl)-2-((1-methylpiperidin-4-yl)oxy)pyrazolo[1,5-a][1,3,5]triazin-4-amine,
2-((6-aminospiro[3.3]heptan-2-yl)oxy)-8-isopropyl-N-(quinolin-5-ylmethyl)pyrazolo[1,5-a][1,3,5]triazin-4-amine,
8-isopropyl-2-(2-(piperidin-4-yl)ethoxy)-N-(quinolin-5-ylmethyl)pyrazolo[1,5-a][1,3,5]triazin-4-amine,
tert-butyl (2-(((8-isopropyl-2-(2-(piperidin-1-yl)ethoxy)pyrazolo[1,5-a][1,3,5]triazin-4-yl)amino)methyl)phenyl)carbamate,
N4-(2-(1H-pyrazol-1-yl)benzyl)-8-isopropyl-N2-(piperidin-3-yl)pyrazolo[1,5-a][1,3,5]triazine-2,4-diamine,
N-(2-(1H-pyrazol-1-yl)benzyl)-8-isopropyl-2-(2,6-diazaspiro[3.4]octan-2-yl)pyrazolo[1,5-a][1,3,5]triazin-4-amine,
N-(2-(1H-pyrazol-1-yl)benzyl)-8-isopropyl-2-(2,7-diazaspiro[4.4]nonan-2-yl)pyrazolo[1,5-a][1,3,5]triazin-4-amine,
N-(2-(1H-pyrazol-1-yl)benzyl)-8-isopropyl-2-(1,6-diazaspiro[3.5]nonan-1-yl)pyrazolo[1,5-a][1,3,5]triazin-4-amine,
N-(2-(1H-pyrazol-1-yl)benzyl)-8-isopropyl-2-(2,6-diazaspiro[3.5]nonan-2-yl)pyrazolo[1,5-a][1,3,5]triazin-4-amine,
N-(2-(1H-pyrazol-1-yl)benzyl)-8-isopropyl-2-(2,6-diazaspiro[4.5]decan-2-yl)pyrazolo[1,5-a][1,3,5]triazin-4-amine,
N-(2-(1H-pyrazol-1-yl)benzyl)-8-isopropyl-2-(2,6-diazaspiro[3.4]octan-6-yl)pyrazolo[1,5-a][1,3,5]triazin-4-amine,
N-(2-(1H-pyrazol-1-yl)benzyl)-8-isopropyl-2-(1,6-diazaspiro[3.3]heptan-1-yl)pyrazolo[1,5-a][1,3,5]triazin-4-amine,
N-(2-(1H-pyrazol-1-yl)benzyl)-8-isopropyl-2-(2,8-diazaspiro[4.5]decan-8-yl)pyrazolo[1,5-a][1,3,5]triazin-4-amine,
N-(2-(1H-pyrazol-1-yl)benzyl)-8-isopropyl-2-(2,6-diazaspiro[3.3]heptan-2-yl)pyrazolo[1,5-a][1,3,5]triazin-4-amine,
N-(2-(1H-pyrazol-1-yl)benzyl)-8-isopropyl-2-(1,8-diazaspiro[4.5]decan-8-yl)pyrazolo[1,5-a][1,3,5]triazin-4-amine,
N-(2-(1H-pyrazol-1-yl)benzyl)-8-isopropyl-2-(2,7-diazaspiro[3.5]nonan-2-yl)pyrazolo[1,5-a][1,3,5]triazin-4-amine,
N-(2-(1H-pyrazol-1-yl)benzyl)-8-isopropyl-2-(1,7-diazaspiro[4.4]nonan-1-yl)pyrazolo[1,5-a][1,3,5]triazin-4-amine, N-(2-(1H-pyrazol-1-yl)benzyl)-8-isopropyl-2-(2,8-diazaspiro[5.5]undecan-2-yl)pyrazolo[1,5-a][1,3,5]triazin-4-amine,
N-(2-(1H-pyrazol-1-yl)benzyl)-8-isopropyl-2-(1,8-diazaspiro[5.5]undecan-8-yl)pyrazolo[1,5-a][1,3,5]triazin-4-amine,
N-(2-(1H-pyrazol-1-yl)benzyl)-8-isopropyl-2-(2,7-diazaspiro[3.5]nonan-7-yl)pyrazolo[1,5-a][1,3,5]triazin-4-amine,
N-(2-(1H-pyrazol-1-yl)benzyl)-8-isopropyl-2-(1,7-diazaspiro[4.4]nonan-7-yl)pyrazolo[1,5-a][1,3,5]triazin-4-amine,
8-isopropyl-N-(2-(1-methyl-1H-tetrazol-5-yl)benzyl)-2-(1,8-diazaspiro[4.5]decan-8-yl)pyrazolo[1,5-a][1,3,5]triazin-4-amine,
8-isopropyl-N-(2-(2-methyl-2H-tetrazol-5-yl)benzyl)-2-(1,8-diazaspiro[4.5]decan-8-yl)pyrazolo[1,5-a][1,3,5]triazin-4-amine,
N-(2-(1H-pyrazol-1-yl)benzyl)-8-isopropyl-2-(1,7-diazaspiro[3.5]nonan-7-yl)pyrazolo[1,5-a][1,3,5]triazin-4-amine,
N-(2-(1H-pyrazol-1-yl)benzyl)-8-isopropyl-2-(2,9-diazaspiro[5.5]undecan-2-yl)pyrazolo[1,5-a][1,3,5]triazin-4-amine,
N-(2-(1H-pyrazol-1-yl)benzyl)-8-isopropyl-2-(1,8-diazaspiro[4.5]decan-1-yl)pyrazolo[1,5-a][1,3,5]triazin-4-amine,
N-(2-(1H-pyrazol-1-yl)benzyl)-8-isopropyl-2-(1,9-diazaspiro[5.5]undecan-9-yl)pyrazolo[1,5-a][1,3,5]triazin-4-amine,
N-(2-(1H-pyrazol-1-yl)benzyl)-2-(4-(dimethylamino)piperidin-1-yl)-8-isopropylpyrazolo[1,5-a][1,3,5]triazin-4-amine,
N-(2-(1H-pyrazol-1-yl)benzyl)-8-isopropyl-2-(4-(methylamino)piperidin-1-yl)pyrazolo[1,5-a][1,3,5]triazin-4-amine,
N-(2-(1H-pyrazol-1-yl)benzyl)-8-isopropyl-2-(3,9-diazaspiro[5.5]undecan-3-yl)pyrazolo[1,5-a][1,3,5]triazin-4-amine,
N-(2-(1H-pyrazol-1-yl)benzyl)-8-isopropyl-2-(2,7-diazaspiro[4.5]decan-2-yl)pyrazolo[1,5-a][1,3,5]triazin-4-amine,
N-(2-(1H-pyrazol-1-yl)benzyl)-8-isopropyl-2-(1,6-diazaspiro[3.4]octan-1-yl)pyrazolo[1,5-a][1,3,5]triazin-4-amine,
(R)—N4-(2-isopropoxybenzyl)-8-isopropyl-N2-(piperidin-3-yl)pyrazolo[1,5-a][1,3,5]triazine-2,4-diamine,
(R)—N4-(2-(1H-1,2,4-triazol-1-yl)benzyl)-8-isopropyl-N2-(piperidin-3-yl)pyrazolo[1,5-a][1,3,5]triazine-2,4-diamine,
N-(2-(1H-pyrazol-1-yl)benzyl)-8-isopropyl-2-(1,7-diazaspiro[3.5]nonan-1-yl)pyrazolo[1,5-a][1,3,5]triazin-4-amine,
2-(((8-isopropyl-2-(1,8-diazaspiro[4.5]decan-8-yl)pyrazolo[1,5-a][1,3,5]triazin-4-yl)amino)methyl)-N,N-dimethylbenzenesulfonamide,
N-(benzo[c][1,2,5]oxadiazol-4-ylmethyl)-8-isopropyl-2-(1,8-diazaspiro[4.5]decan-8-yl)pyrazolo[1,5-a][1,3,5]triazin-4-amine,
N-(2-(1H-pyrazol-1-yl)benzyl)-8-isopropyl-2-(2, 8-diazaspiro[4.5]decan-2-yl)pyrazolo[1,5-a][1,3,5]triazin-4-amine,
1-(2-(((8-isopropyl-2-(1,8-diazaspiro[4.5]decan-8-yl)pyrazolo[1,5-a][1,3,5]triazin-4-yl)amino)methyl)phenyl)pyrrolidin-2-one,
N-(2-(1H-pyrazol-1-yl)benzyl)-8-isopropyl-2-(piperidin-4-ylsulfinyl)pyrazolo[1,5-a][1,3,5]triazin-4-amine,
8-isopropyl-2-(piperidin-4-ylsulfinyl)-N-(2-(thiophen-2-yl)benzyl)pyrazolo[1,5-a][1,3,5]triazin-4-amine,
N-([1,1'-biphenyl]-2-ylmethyl)-8-isopropyl-2-(piperidin-4-ylsulfinyl)pyrazolo[1,5-a][1,3,5]triazin-4-amine,
N-(2-(1H-1,2,4-triazol-1-yl)benzyl)-8-isopropyl-2-(piperidin-4-ylsulfinyl)pyrazolo[1,5-a][1,3,5]triazin-4-amine,
8-isopropyl-N-(2-(2-methyl-1H-imidazol-1-yl)benzyl)-2-(piperidin-4-ylsulfinyl)pyrazolo[1,5-a][1,3,5]triazin-4-amine,
4-((2-(1H-pyrazol-1-yl)benzyl)amino)-8-isopropyl-N-(piperidin-4-ylmethyl)pyrazolo[1,5-a][1,3,5]triazine-2-carboxamide,
4-((2-(1H-pyrazol-1-yl)benzyl)amino)-N-(azetidin-3-ylmethyl)-8-isopropylpyrazolo[1,5-a][1,3,5]triazine-2-carboxamide,
4-((2-(1H-pyrazol-1-yl)benzyl)amino)-8-isopropyl-N-(pyrrolidin-3-ylmethyl)pyrazolo[1,5-a][1,3,5]triazine-2-carboxamide,
4-((2-(1H-pyrazol-1-yl)benzyl)amino)-8-isopropyl-N-(piperidin-3-ylmethyl)pyrazolo[1,5-a][1,3,5]triazine-2-carboxamide,
(R)—N-(2-bromobenzyl)-8-isopropyl-2-(piperidin-3-yloxy)pyrazolo[1,5-a][1,3,5]triazin-4-amine,
(R)-8-isopropyl-N-(2-(morpholinosulfonyl)benzyl)-2-(piperidin-3-yloxy)pyrazolo[1,5-a][1,3,5]triazin-4-amine,
(R)-8-isopropyl-2-(piperidin-3-yloxy)-N-(2-(pyridin-2-yloxy)benzyl)pyrazolo[1,5-a][1,3,5]triazin-4-amine,
(R)—N-(2-cyclobutoxybenzyl)-8-isopropyl-2-(piperidin-3-yloxy)pyrazolo[1,5-a][1,3,5]triazin-4-amine,
(R)-2-(((8-isopropyl-2-(piperidin-3-yloxy)pyrazolo[1,5-a][1,3,5]triazin-4-yl)amino)methyl)benzamide,
(R)—N-(2-(cyclopentyloxy)benzyl)-8-isopropyl-2-(piperidin-3-yloxy)pyrazolo[1,5-a][1,3,5]triazin-4-amine,
(R)—N-(2,4-dichlorobenzyl)-8-isopropyl-2-(piperidin-3-yloxy)pyrazolo[1,5-a][1,3,5]triazin-4-amine,
8-isopropyl-N-(4-methyl-2-((tetrahydrofuran-3-yl)oxy)benzyl)-2-((R)-piperidin-3-yloxy)pyrazolo[1,5-a][1,3,5]triazin-4-amine,
N-(2-(1H-pyrazol-1-yl)benzyl)-8-isopropyl-2-(2-(piperazin-1-yl)ethoxy)pyrazolo[1,5-a][1,3,5]triazin-4-amine,
N-(2-(1H-pyrazol-1-yl)benzyl)-2-((1R,5S)-3-azabicyclo[3.2.0]heptan-6-yloxy)-8-isopropylpyrazolo[1,5-a][1,3,5]triazin-4-amine,
2-((1,4-oxazepan-6-yl)oxy)-N-(2-(1H-pyrazol-1-yl)benzyl)-8-isopropylpyrazolo[1,5-a][1,3,5]triazin-4-amine,
2-(1-oxa-8-azaspiro[4.5]decan-3-yloxy)-N-(2-(1H-pyrazol-1-yl)benzyl)-8-isopropylpyrazolo[1,5-a][1,3,5]triazin-4-amine,
N-(2-(1H-pyrazol-1-yl)benzyl)-8-isopropyl-2-((1,2,3,6-tetrahydropyridin-3-yl)oxy)pyrazolo[1,5-a][1,3,5]triazin-4-amine,
(R)—N-(2-(cyclopentylthio)benzyl)-8-isopropyl-2-(piperidin-3-yloxy)pyrazolo[1,5-a][1,3,5]triazin-4-amine,
(R)-8-isopropyl-N-(2-(methylthio)benzyl)-2-(piperidin-3-yloxy)pyrazolo[1,5-a][1,3,5]triazin-4-amine,
(R)-8-isopropyl-2-(piperidin-3-yloxy)-N-((2',3',4',5'-tetrahydro-[1,1'-biphenyl]-2-yl)methyl)pyrazolo[1,5-a][1,3,5]triazin-4-amine,
(R)—N-((3,4-dihydro-2H-benzo[b][1,4]dioxepin-6-yl)methyl)-8-isopropyl-2-(piperidin-3-yloxy)pyrazolo[1,5-a][1,3,5]triazin-4-amine,
(R)—N-(2-isobutoxy-4-methylbenzyl)-8-isopropyl-2-(piperidin-3-yloxy)pyrazolo[1,5-a][1,3,5]triazin-4-amine, (R)-1-ethyl-3-(2-(((8-isopropyl-2-(piperidin-3-yloxy) pyrazolo[1,5-a][1,3,5]triazin-4-yl)amino)methyl)phenyl)urea,
(R)-1-benzyl-3-(2-(((8-isopropyl-2-(piperidin-3-yloxy) pyrazolo[1,5-a][1,3,5]triazin-4-yl)amino)methyl)phenyl)urea,
(R)-1-cyclohexyl-3-(2-(((8-isopropyl-2-(piperidin-3-yloxy)pyrazolo[1,5-a][1,3,5]triazin-4-yl)amino) methyl)phenyl)urea,
(R)-1-(2-(((8-isopropyl-2-(piperidin-3-yloxy)pyrazolo[1, 5-a][1,3,5]triazin-4-yl)amino)methyl)phenyl)-3-phenylurea,
(R)-1-(2-(((8-isopropyl-2-(piperidin-3-yloxy)pyrazolo[1, 5-a][1,3,5]triazin-4-yl)amino)methyl)phenyl)-3-propylurea,
N-(but-3-yn-2-yl)-2-(((8-isopropyl-2-((R)-piperidin-3-yloxy)pyrazolo[1,5-a][1,3,5]triazin-4-yl)amino) methyl)benzamide,
(R)-2-(((8-isopropyl-2-(piperidin-3-yloxy)pyrazolo[1,5-a][1,3,5]triazin-4-yl)amino)methyl)-N-methylbenzamide,
(R)-8-isopropyl-N-(2-((4-methylpiperazin-1-yl)sulfonyl) benzyl)-2-(piperidin-3-yloxy)pyrazolo[1,5-a][1,3,5]triazin-4-amine,
(R)-8-isopropyl-2-(piperidin-3-yloxy)-N-(2-(pyrrolidin-1-ylsulfonyl)benzyl)pyrazolo[1,5-a][1,3,5]triazin-4-amine,
(R)—N-isopropyl-2-(((8-isopropyl-2-(piperidin-3-yloxy) pyrazolo[1,5-a][1,3,5]triazin-4-yl)amino)methyl)benzenesulfonamide,
(R)-2-(((8-isopropyl-2-(piperidin-3-yloxy)pyrazolo[1,5-a][1,3,5]triazin-4-yl)amino)methyl)-N-methylbenzenesulfonamide,
(R)—N-(2,3-dichlorobenzyl)-8-isopropyl-2-(piperidin-3-yloxy)pyrazolo[1,5-a][1,3,5]triazin-4-amine,
(R)—N-(4-chloro-2-(trifluoromethyl)benzyl)-8-isopropyl-2-(piperidin-3-yloxy)pyrazolo[1,5-a][1,3,5]triazin-4-amine,
N-(2-(1H-pyrazol-1-yl)benzyl)-2-(2-azabicyclo[2.2.1] heptan-5-yloxy)-8-isopropylpyrazolo[1,5-a][1,3,5]triazin-4-amine,
N-(2-(((8-isopropyl-2-((R)-piperidin-3-yloxy)pyrazolo[1, 5-a][1,3,5]triazin-4-yl)amino)methyl)phenyl)-2-methylpropane-2-sulfinamide,
(R)-isobutyl (2-(((8-isopropyl-2-(piperidin-3-yloxy)pyrazolo[1,5-a][1,3,5]triazin-4-yl)amino)methyl)phenyl) carbamate,
(R)—N-(2,5-dichlorobenzyl)-8-isopropyl-2-(piperidin-3-yloxy)pyrazolo[1,5-a][1,3,5]triazin-4-amine,
(R)-8-isopropyl-2-(piperidin-3-yloxy)-N-(2-(pyrrolidin-1-yl)benzyl)pyrazolo[1,5-a][1,3,5]triazin-4-amine,
(R)-8-isopropyl-N-(2-(piperidin-1-yl)benzyl)-2-(piperidin-3-yloxy)pyrazolo[1,5-a][1,3,5]triazin-4-amine,
azetidin-3-yl (2-((4-((2-(1H-pyrazol-1-yl)benzyl)amino)-8-isopropylpyrazolo[1,5-a][1,3,5]triazin-2-yl)oxy) ethyl)(methyl)carbamate,
N-(2-((4-((2-(1H-pyrazol-1-yl)benzyl)amino)-8-isopropylpyrazolo[1,5-a][1,3,5]triazin-2-yl)oxy)ethyl)-N-methylpiperidine-4-sulfonamide,
2-((4-((2-(1H-pyrazol-1-yl)benzyl)amino)-8-isopropylpyrazolo[1,5-a][1,3,5]triazin-2-yl)oxy)ethyl azetidin-3-ylcarbamate,
2-((4-((2-(1H-pyrazol-1-yl)benzyl)amino)-8-isopropylpyrazolo[1,5-a][1,3,5]triazin-2-yl)oxy)-N-(pyrrolidin-3-yl)ethanesulfonamide,
N-(2-(1H-pyrazol-1-yl)benzyl)-2-(8-azabicyclo[3.2.1]octan-3-yloxy)-8-isopropylpyrazolo[1,5-a][1,3,5]triazin-4-amine,
N-(2-(1H-pyrazol-1-yl)benzyl)-2-(2-azaspiro[3.3]heptan-5-yloxy)-8-isopropylpyrazolo[1,5-a][1,3,5]triazin-4-amine,
N-(2-(1H-pyrazol-1-yl)benzyl)-2-((4-aminocyclohexyl) oxy)-8-isopropylpyrazolo[1,5-a][1,3,5]triazin-4-amine,
(R)—N-(2-cyclobutylbenzyl)-8-isopropyl-2-(piperidin-3-yloxy)pyrazolo[1,5-a][1,3,5]triazin-4-amine,
(R)—N-(2-cyclopentylbenzyl)-8-isopropyl-2-(piperidin-3-yloxy)pyrazolo[1,5-a][1,3,5]triazin-4-amine,
N-(2-cyclopropylbenzyl)-8-isopropyl-2-(piperidin-3-yloxy)pyrazolo[1,5-a][1,3,5]triazin-4-amine,
(R)—N-(2-cyclohexylbenzyl)-8-isopropyl-2-(piperidin-3-yloxy)pyrazolo[1,5-a][1,3,5]triazin-4-amine,
(R)-2-(((8-isopropyl-2-(piperidin-3-yloxy)pyrazolo[1,5-a][1,3,5]triazin-4-yl)amino)methyl)phenyl acetate,
(R)-2-(((8-isopropyl-2-(piperidin-3-yloxy)pyrazolo[1,5-a][1,3,5]triazin-4-yl)amino)methyl)phenyl ethylcarbamate,
(R)-2-(((8-isopropyl-2-(piperidin-3-yloxy)pyrazolo[1,5-a][1,3,5]triazin-4-yl)amino)methyl)phenyl methanesulfonate,
2-(((8-isopropyl-2-((R)-piperidin-3-yloxy)pyrazolo[1,5-a][1,3,5]triazin-4-yl)amino)methyl)phenyl 2-methylpropane-2-sulfinate,
(R)-isobutyl (2-(((8-isopropyl-2-(piperidin-3-yloxy)pyrazolo[1,5-a][1,3,5]triazin-4-yl)amino)methyl)phenyl) carbonate,
(R)-8-isopropyl-N-(2-(methylsulfonyl)benzyl)-2-(piperidin-3-yloxy)pyrazolo[1,5-a][1,3,5]triazin-4-amine,
8-isopropyl-N-(2-(methylsulfinyl)benzyl)-2-((R)-piperidin-3-yloxy)pyrazolo[1,5-a][1,3,5]triazin-4-amine,
N-(2-(cyclopentylsulfinyl)benzyl)-8-isopropyl-2-((R)-piperidin-3-yloxy)pyrazolo[1,5-a][1,3,5]triazin-4-amine,
N4-(2-(1H-pyrazol-1-yl)benzyl)-8-isopropyl-N2-(2-(pyrrolidin-1-yl)ethyl)pyrazolo[1,5-a][1,3,5]triazine-2,4-diamine,
N-(2-(1H-pyrazol-1-yl)benzyl)-2-(3-(3,3-difluoropyrrolidin-1-yl)azetidin-1-yl)-8-isopropylpyrazolo[1,5-a][1,3, 5]triazin-4-amine,
N4-(2-(1H-pyrazol-1-yl)benzyl)-8-isopropyl-N2-methyl-N2-(2-morpholinoethyl)pyrazolo[1,5-a][1,3,5]triazine-2,4-diamine,
N4-(2-(1H-pyrazol-1-yl)benzyl)-8-isopropyl-N2-(pyrrolidin-3-yl)pyrazolo[1,5-a][1,3,5]triazine-2,4-diamine,
N4-(2-(1H-pyrazol-1-yl)benzyl)-8-isopropyl-N2-(3-morpholinopropyl)pyrazolo[1,5-a][1,3,5]triazine-2,4-diamine,
N4-(2-(1H-pyrazol-1-yl)benzyl)-8-isopropyl-N2-methyl-N2-(2-(pyrrolidin-1-yl)ethyl)pyrazolo[1,5-a][1,3,5]triazine-2,4-diamine,
N4-(2-(1H-pyrazol-1-yl)benzyl)-8-isopropyl-N2-(2-morpholinoethyl)pyrazolo[1,5-a][1,3,5]triazine-2,4-diamine,
1-(1-(4-((2-(1H-pyrazol-1-yl)benzyl)amino)-8-isopropylpyrazolo[1,5-a][1,3,5]triazin-2-yl)azetidin-3-yl)pyrrolidin-2-one,
N4-(2-(1H-pyrazol-1-yl)benzyl)-8-isopropyl-N2-methyl-N2-(3-(piperidin-1-yl)propyl)pyrazolo[1,5-a][1,3,5]triazine-2,4-diamine,
N-(2-(1H-pyrazol-1-yl)benzyl)-2-(hexahydropyrrolo[3,4-b]pyrrol-5(1H)-yl)-8-isopropylpyrazolo[1,5-a][1,3,5] triazin-4-amine, N4-(2-(1H-pyrazol-1-yl)benzyl)-8-isopropyl-N2-(pyrrolidin-3-ylmethyl)pyrazolo[1,5-a][1,3,5]triazine-2,4-diamine,
N-(2-(1H-pyrazol-1-yl)benzyl)-2-(3-aminopiperidin-1-yl)-8-isopropylpyrazolo[1,5-a][1,3,5]triazin-4-amine,
N-(2-(1H-pyrazol-1-yl)benzyl)-2-(3-aminopyrrolidin-1-yl)-8-isopropylpyrazolo[1,5-a][1,3,5]triazin-4-amine,
N4-(2-(1H-pyrazol-1-yl)benzyl)-N2-(2-amino-1-phenylethyl)-8-isopropylpyrazolo[1,5-a][1,3,5]triazine-2,4-diamine,
N4-(2-(1H-pyrazol-1-yl)benzyl)-N2-(azetidin-3-ylmethyl)-8-isopropyl-N2-methylpyrazolo[1,5-a][1,3,5]triazine-2,4-diamine,
N4-(2-(1H-pyrazol-1-yl)benzyl)-8-isopropyl-N2-methyl-N2-(2-morpholinoethyl)pyrazolo[1,5-a][1,3,5]triazine-2,4-diamine,
N-(2-(1H-pyrazol-1-yl)benzyl)-2-(4-aminopiperidin-1-yl)-8-isopropylpyrazolo[1,5-a][1,3,5]triazin-4-amine,
N4-(2-(1H-pyrazol-1-yl)benzyl)-N2-(4-aminocyclohexyl)-8-isopropylpyrazolo[1,5-a][1,3,5]triazine-2,4-diamine,
N-(2-(1H-pyrazol-1-yl)benzyl)-8-isopropyl-2-((R)-((R)-piperidin-3-yl)sulfinyl)pyrazolo[1,5-a][1,3,5]triazin-4-amine,
N-(2-(1H-pyrazol-1-yl)benzyl)-8-isopropyl-2-(piperidin-4-ylsulfonyl)pyrazolo[1,5-a][1,3,5]triazin-4-amine,
(R)—N-(2-(1H-pyrazol-1-yl)benzyl)-8-isopropyl-2-(piperidin-3-ylthio)pyrazolo[1,5-a][1,3,5]triazin-4-amine,
N-(2-(1H-pyrazol-1-yl)benzyl)-8-isopropyl-2-(piperidin-4-ylthio)pyrazolo[1,5-a][1,3,5]triazin-4-amine,
(4-((2-(1H-pyrazol-1-yl)benzyl)amino)-8-isopropylpyrazolo[1,5-a][1,3,5]triazin-2-yl)(2,6-diazaspiro[3.3]heptan-2-yl)methanone,
4-((2-(1H-pyrazol-1-yl)benzyl)amino)-8-isopropyl-N-methyl-N-(2-morpholinoethyl)pyrazolo[1,5-a][1,3,5]triazine-2-carboxamide,
4-((2-(1H-pyrazol-1-yl)benzyl)amino)-8-isopropyl-N-methyl-N-(2-(pyrrolidin-1-yl)ethyl)pyrazolo[1,5-a][1,3,5]triazine-2-carboxamide,
(4-((2-(1H-pyrazol-1-yl)benzyl)amino)-8-isopropylpyrazolo[1,5-a][1,3,5]triazin-2-yl)(piperazin-1-yl)methanone,
(4-((2-(1H-pyrazol-1-yl)benzyl)amino)-8-isopropylpyrazolo[1,5-a][1,3,5]triazin-2-yl)(4-aminopiperidin-1-yl)methanone,
N-(2-(1H-pyrazol-1-yl)benzyl)-8-isopropyl-2-(((3-morpholinopropyl)amino)methyl)pyrazolo[1,5-a][1,3,5]triazin-4-amine,
N-(2-(1H-pyrazol-1-yl)benzyl)-8-isopropyl-2-((methyl(2-(pyrrolidin-1-yl)ethyl)amino)methyl)pyrazolo[1,5-a][1,3,5]triazin-4-amine,
N-(2-(1H-pyrazol-1-yl)benzyl)-8-isopropyl-2-(((2-(pyrrolidin-1-yl)ethyl)amino)methyl)pyrazolo[1,5-a][1,3,5]triazin-4-amine,
N-(2-(1H-pyrazol-1-yl)benzyl)-8-isopropyl-2-(((2-morpholinoethyl)amino)methyl)pyrazolo[1,5-a][1,3,5]triazin-4-amine,
N-(2-(1H-pyrazol-1-yl)benzyl)-8-isopropyl-2-((methyl(3-(piperidin-1-yl)propyl)amino)methyl)pyrazolo[1,5-a][1,3,5]triazin-4-amine,
N-(2-(1H-pyrazol-1-yl)benzyl)-2-((3-(3,3-difluoropyrrolidin-1-yl)azetidin-1-yl)methyl)-8-isopropylpyrazolo[1,5-a][1,3,5]triazin-4-amine,
1-(1-((4-((2-(1H-pyrazol-1-yl)benzyl)amino)-8-isopropylpyrazolo[1,5-a][1,3,5]triazin-2-yl)methyl)azetidin-3-yl)pyrrolidin-2-one,
N-(2-(1H-pyrazol-1-yl)benzyl)-8-isopropyl-2-((4-(2-methoxyethyl)piperazin-1-yl)methyl)pyrazolo[1,5-a][1,3,5]triazin-4-amine,
N-(2-(1H-pyrazol-1-yl)benzyl)-8-isopropyl-2-((pyrrolidin-3-ylamino)methyl)pyrazolo[1,5-a][1,3,5]triazin-4-amine,
N-(2-(1H-pyrazol-1-yl)benzyl)-8-isopropyl-2-(piperazin-1-ylmethyl)pyrazolo[1,5-a][1,3,5]triazin-4-amine,
N-(2-(1H-pyrazol-1-yl)benzyl)-2-(((azetidin-3-ylmethyl)(methyl)amino)methyl)-8-isopropylpyrazolo[1,5-a][1,3,5]triazin-4-amine,
N-(2-(2-(((4-((2-(1H-pyrazol-1-yl)benzyl)amino)-8-isopropylpyrazolo[1,5-a][1,3,5]triazin-2-yl)methyl)amino)ethoxy)ethyl)-2-(pyrrolidin-1-yl)acetamide,
N-(2-(1H-pyrazol-1-yl)benzyl)-2-((4-aminopiperidin-1-yl)methyl)-8-isopropylpyrazolo[1,5-a][1,3,5]triazin-4-amine,
1-methylpyrrolidin-3-yl 4-((2-(1H-pyrazol-1-yl)benzyl)amino)-8-isopropylpyrazolo[1,5-a][1,3,5]triazine-2-carboxylate,
N-(2-(1H-pyrazol-1-yl)benzyl)-8-isopropyl-2-(piperidin-3-ylmethyl)pyrazolo[1,5-a][1,3,5]triazin-4-amine,
N4-(2-(1H-pyrazol-1-yl)benzyl)-8-isopropyl-N2-methyl-N2-(2-morpholinoethyl)pyrazolo[1,5-a][1,3,5]triazine-2,4-diamine,
N-(2-(1H-pyrazol-1-yl)benzyl)-2-(4-aminopiperidin-1-yl)-8-isopropylpyrazolo[1,5-a][1,3,5]triazin-4-amine,
N4-(2-(1H-pyrazol-1-yl)benzyl)-N2-(4-aminocyclohexyl)-8-isopropylpyrazolo[1,5-a][1,3,5]triazine-2,4-diamine,
N4-(2-(1H-pyrazol-1-yl)benzyl)-8-isopropyl-N2-(2-(piperazin-1-yl)ethyl)pyrazolo[1,5-a][1,3,5]triazine-2,4-diamine, and
N-(2-(1H-pyrazol-1-yl)benzyl)-2-(azetidin-3-yloxy)-8-isopropylpyrazolo[1,5-a][1,3,5]triazin-4-amine.

5. A method for the treatment of HIV, EBV, HCV, cardiac hypertrophy, bone osteosarcoma, ovarian carcinoma, melanoma, Ewing's sarcoma, colon cancer, acute myeloid leukemia, chronic myelogenous leukemia, T-cell lymphoma, leukemia, neuroblastoma, breast cancer, pancreatic cancer, lung cancer, Burkitt's lymphoma, B cell lymphoma, and inflammation mediated by the cytokines TNF-α, comprising administering to a patient in need thereof a dose-effective amount of a compound according to claim 1.

6. A pharmaceutical composition comprising a dose effective amount of at least one compound according to claim 1 as an active ingredient, together with at least one pharmaceutically acceptable carrier, excipient and/or diluent.

* * * * *